(12) United States Patent
Bregman et al.

(10) Patent No.: US 9,340,549 B2
(45) Date of Patent: May 17, 2016

(54) OXAZOLIDINONE COMPOUNDS AND DERIVATIVES THEREOF

(71) Applicant: AMGEN INC., Thousand Oaks, CA (US)

(72) Inventors: Howard Bregman, Melrose, MA (US); John L. Buchanan, Newton, MA (US); Nagasree Chakka, Lexington, MA (US); Erin F. Dimauro, Cambridge, MA (US); Hakan Gunaydin, Boston, MA (US); Angel Guzman-Perez, Belmont, MA (US); Zihao Hua, Andover, MA (US); Hongbing Huang, Lexington, MA (US); Xin Huang, Wellesley, MA (US); Matthew W. Martin, Arlington, MA (US); Vinod F. Patel, Acton, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/383,432

(22) PCT Filed: Mar. 1, 2013

(86) PCT No.: PCT/US2013/028751
§ 371 (c)(1),
(2) Date: Sep. 5, 2014

(87) PCT Pub. No.: WO2013/134079
PCT Pub. Date: Sep. 12, 2013

(65) Prior Publication Data
US 2015/0045368 A1 Feb. 12, 2015

Related U.S. Application Data

(60) Provisional application No. 61/739,484, filed on Dec. 19, 2012, provisional application No. 61/606,736, filed on Mar. 5, 2012.

(51) Int. Cl.
| | |
|---|---|
| *C07D 413/14* | (2006.01) |
| *C07D 487/04* | (2006.01) |
| *C07D 413/08* | (2006.01) |
| *C07D 413/12* | (2006.01) |
| *C07D 417/12* | (2006.01) |
| *C07D 417/14* | (2006.01) |
| *C07D 471/04* | (2006.01) |
| *C07D 473/00* | (2006.01) |
| *C07D 263/34* | (2006.01) |
| *C07D 519/00* | (2006.01) |
| *C07D 413/10* | (2006.01) |

(52) U.S. Cl.
CPC .......... *C07D 487/04* (2013.01); *C07D 263/34* (2013.01); *C07D 413/08* (2013.01); *C07D 413/10* (2013.01); *C07D 413/12* (2013.01); *C07D 413/14* (2013.01); *C07D 417/12* (2013.01); *C07D 417/14* (2013.01); *C07D 471/04* (2013.01); *C07D 473/00* (2013.01); *C07D 519/00* (2013.01)

(58) Field of Classification Search
CPC ..................................................... C07D 413/14
See application file for complete search history.

(56) References Cited

U.S. PATENT DOCUMENTS

| | | | |
|---|---|---|---|
| 2007/0213356 A1 | 9/2007 | Merrill et al. | |
| 2009/0298834 A1 | 12/2009 | Pajouhesh et al. | |
| 2010/0234365 A1* | 9/2010 | Liu et al. | 514/227.8 |
| 2011/0136813 A1 | 6/2011 | Lum et al. | |
| 2011/0178060 A1 | 7/2011 | Shirai et al. | |
| 2011/0263571 A1 | 10/2011 | Ishibuchi et al. | |
| 2012/0040961 A1 | 2/2012 | Gray et al. | |
| 2012/0165309 A1 | 6/2012 | Takahashi et al. | |
| 2014/0235620 A1* | 8/2014 | Caferro et al. | 514/218 |

FOREIGN PATENT DOCUMENTS

| | | |
|---|---|---|
| WO | 2005/037826 A1 | 4/2005 |
| WO | 2005/074603 A2 | 8/2005 |
| WO | 2005/123080 A2 | 12/2005 |

(Continued)

OTHER PUBLICATIONS

Kumpan et al. (Bioorg. Med. Chem. 23 (2015) 3013-3032).*

(Continued)

*Primary Examiner* — Robert Havlin
(74) *Attorney, Agent, or Firm* — Bernard P. Friedrichsen

(57) ABSTRACT

Compounds of Formula (I) and Formula (II) are useful inhibitors of tankyrase. Compounds of Formula (I) and Formula (II) have the following structure: where the definitions of the variables are provided herein.

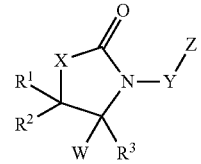

(I)

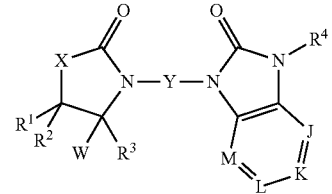

(II)

10 Claims, No Drawings

(56) References Cited

FOREIGN PATENT DOCUMENTS

| WO | 2008/046758 A2 | 4/2008 |
|---|---|---|
| WO | 2008/106128 A2 | 9/2008 |
| WO | 2009/146539 A1 | 12/2009 |
| WO | 2010/032856 A1 | 3/2010 |
| WO | 2010/050461 A1 | 5/2010 |
| WO | 2010/092962 A1 | 8/2010 |
| WO | 2011/068927 A2 | 6/2011 |

OTHER PUBLICATIONS

Kubinyi (3D QSAR in Drug Design: Ligand-Protein Interactions and Molecular Similarity, vol. 2-3, Springer, 1998, 800 pages). p. 243-44 provided.*

Wermuth, The Practice of Medicinal Chemsitry, 2d ed. (2003), 768 pages. Chs 9-10 provided.*

International Search Report for parent PCT Application No. PCT/US2013/028751, mailed on Apr. 22, 2013.

Written Opinion for parent PCT Application No. PCT/US2012/056658.

Hayashi, R. et al., "Torquoselective Ring Closures of Chiral Amido Trienes Derived from Allenamides. A Tandem Allene Isomerization-Pericyclic Ring-Closure-Intramolecular Diels-Alder Cycloaddition," Organic Letters, vol. 12(6), pp. 1152-1155 (2010).

Begis, G. et al, "Asymmetric Synthesis of Aminocyclopropanes and N-Cyclopropylamino Alcohols Through Direct Amidocycloropanation of Alkenes Using Chiral Organozinc Carbenoids," European J. Org. Chem., vol. 10, pp. 1532-1548 (2009).

Aciro, C. et al., "Stereoselective Functionalisation of SuperQuat Enamides: Asymmetric Synthesis of Homochiral 1,2-Diols and α-Benzyloxy Carbonyl Compounds," Tetranderon, vol. 64(39), pp. 9320-9344 (2008).

Davies, S.G. et al., "Oxidative Functionalisation of SuperQuat Enamides" Asymmetric Synmtheis of Homochiral 1,2-Diols, Synthetic Letters, vol. 11, pp. 1659-1662 (2003).

Chen, B. et al., "Small Molecule-Mediated Disruption of Wnt-Dependent Signaling in Tissue Regeneration and Cancer," Nature Chemical Biology, vol. 5(2), pp. 100-107 (2009).

Huang, S.M. et al., "Tankyrase Inhibition Stabilizes Axin and Antagonizes Wnt Signalling," Nature, vol. 461, pp. 614-620 (2009).

Gunaydin, H. et al., "Novel Binding Mode of a Potent and Selective Tankyrase Inhibitor," PLOS One, vol. 7(3) e33740 (2012).

Barker, N, et al., "Mining the Wnt Pathway for Cancer Therapeutics," Nat. Rev. Drug Discovery, vol. 5, pp. 997-1014 (2006).

Hua, Z. et al., "Development of Novel Dual Binders aas Potent, Selective, and Orally Bioavailable Tankyrase Inhibitors," J. Mcd. Chcm., vol. 56(24) pp. 10003-10015 (2013).

Bregman, H, et al., "Discovery of Novel, Induced-Pocket Binding Oxazolidinones as Potent, Selective, and Orally Bioavailable Tankyrase Inhibitors," J. Med. Chem., vol. 56(11), pp. 4320-4342 (2013).

Huang, H. et al., "Structure-Based Design of 2-Aminopyridine Oxazolidinones as Potent and Selective Tankyrase Inhibitors," ACS Med, Chem. Lett., vol. 4(12), pp. 1218-1223 (2013).

Bregman, H. et al., "Discovery of a Class of Novel Tankyrase Inhibitors that Bind to Both the Nicotinamide Pocket and the Inducted Pocket," J. Med. Chem., vol. 56, pp. 1341-1345 (2013).

Schultz, M.D. et al., "[1,2,4]Triazol-3-ylsulfanylmethyl)-3-phenyl-[1,2,4]oxadiazoles: Antagonists of the Wnt Pathway That Inhibit Tankyrases 1 and 2 via Novel Adenosine Pocket Binding," J. Med. Chem., vol. 55, pp. 1127-1136 (2012).

Schultz, M.D. et al., "Identification of NVP-TNKS656: The Use of Structure-Efficiency Relationships to Generate a Highly Potent, Selective, and Orally Active Tankyrase Inhibitor," J. Med. Chem., vol. 56(16), pp. 6495-6511 (2013).

Larsson, E, A, et al., "Fragment-Based Ligand Design of Novel Potent Inhibitors of Tankyrases," J. Med. Chem., vol. 56(11) pp. 4497-4508 (2013).

Lau, T. et al., "A Novel Tankyrase Small-Molecule Inhibitor Suppresses APC Mutation-Driven Colorectal Tumor Growth," Cancer Res., vol. 73(10), pp. 3132-3144 (2013).

Narwal, M. et al., "Structural Basis of Selective Inhibition of Human Tankyrases," J. Med. Chem. vol. 55(3), pp. 1360-1367 (2012).

Voronkov, A. et al., "Structural Basis and SAR for G007-LK, a Lead Stage 1,2,4-Triazole Based Specific Tankyrase ½ Inhibitor,"J. Med. Chem. vol. 56(7), pp. 3012-3023 (2013).

Schultz, M. D. et al., "Structure-Efficiency Relationship of [1,2,4]Triazol-3-ylamines as Novel Nicotimamide Isosteres that Inhibit Tankyrases," J. Med. Chem. vol. 56(17), pp. 7049-7059 (2013).

Haikarainen, T. et al., "Stuctural Basis and Selectivity of Tankyrase Inhibition by a Wnt Signaling Inhibitor WIKI4," PLOS One, vol. 8(6), ee65404 (2013).

* cited by examiner

OXAZOLIDINONE COMPOUNDS AND DERIVATIVES THEREOF

CROSS REFERENCES TO RELATED APPLICATIONS

This application is a 371 National Phase Application of PCT/US2013/028751 filed Mar. 1, 2013, which claims the benefit of U.S. Provisional Application No. 61/606,736 filed Mar. 5, 2012 and U.S. Provisional Application No. 61/739,484 filed Dec. 19, 2012.

FIELD OF THE INVENTION

The present invention relates to compounds capable of inhibiting the kinase activity of tankyrase 1 and/or tankyrase 2, and compositions that include compounds that inhibit tankyrase 1 and/or tankyrase 2. The compounds and compositions may be used to treat diseases or conditions modulated by tankyrase 1 and/or tankyrase 2 such as cancer and are especially useful in treating patients with conditions or diseases related to tankyrase expression.

BACKGROUND OF THE INVENTION

Tankyrase (TNKS) is a member of the poly-ADP-ribose polymerase (PARP) family, which uses NAD+ as a substrate to transfer ADP-ribose polymers onto target proteins, resulting in a post-translational modification referred to as PARsylation. TNKS was first identified as a binding partner for telomerase repeat binding factor 1 (TRF1), which is a key player in the regulation of telomere length at the chromosome ends. Telomere length is maintained by the reverse transcriptase telomerase. The TRF1 and TRF2 proteins are DNA binding proteins that regulate the length and stability of telomeres. Poly-ADP-ribosylation (PARsylation) of TRF1 by TNKS inhibits the ability of TRF1 to bind telomeric DNA thereby allowing telomerase access to telomeric DNA. Thus, TNKS proteins function as positive regulators of telomere length. In addition, it has been reported that TNKS regulates sister chromatid separation during mitosis as well as vesicle trafficking. Additional binding partners of TNKS have recently been identified including CASC3 and BLZF1 (Golgin-45) suggesting roles for TNKS in diverse cellular processes including mRNA metabolism and Golgi structure maintenance.

There are two TNKS genes, TNKS1 and TNKS2, in the human and mouse genomes. Individual and double-knockout of TNKS1 and TNKS2 in mice suggests that they share significant functional redundancy (Chiang Y. J. et. al., "Tankyrase 1 and Tankyrase 2 are Essential but Redundant for Mouse Embryonic Development," PLoS ONE 3(7): e2639. Pp. 1-10 (2008)) as the single homozygous TNKS1 or TNKS2 mice had relatively mild growth phenotypes and no defects in telomere maintenance, whereas the double knockout caused early embryonic lethality.

More recently, TNKS proteins were shown to bind directly to AXIN1 and AXIN2 proteins, which are negative regulators of the Wnt pathway, and regulate their steady state levels by PARsylation and ubiquitination (Huang, S. M. et al. "Tankyrase Inhibition Stabilizes Axin and Antagonizes Wnt Signalling," Nature, 461, pp 614-620 (2009)). Small-molecule inhibitors of tankyrases TNKS1 and TNKS2 can downregulate Wnt signaling (Huang, S. M. et al. "Tankyrase Inhibition Stabilizes Axin and Antagonizes Wnt Signalling," Nature, 461, pp 614-620 (2009); Chen, B. et. al. "Small Molecule-Mediated Disruption of Wnt-Dependent Signaling in Tissue Regeneration and Cancer," Nature Chem. Biol., 5(2), pp 100-107, (2009)) in several immortalized and malignant human cell lines. These inhibitors of TNKS also regulate the Wnt pathway in vivo in a Wnt signaling-dependent zebrafish model of fin regeneration.

Signaling by the Wnt family of secreted proteins plays an essential, evolutionarily conserved role in embryonic development and adult tissue homeostasis in a vast array of organisms including, flies, worms, chickens, frogs and mammals. Wnt signaling is a fundamental morphogenetic pathway that is deployed in diverse settings throughout development to regulate processes such as cell fate specification, tissue patterning, polarity, gastrulation, stem cell maintainence, and cell migration. The Wnt pathway is extraordinarily complex and the binding of Wnt ligands can lead to a variety of biological outcomes depending on the molecular and cellular context. Wnt signaling is often described in terms of either the canonical pathway or one of several non-canonical pathways.

In the canonical or β-catenin-dependent Wnt pathway, specific Wnt ligands regulate the level and sub-cellular localization of β-catenin. In the absence of an activating Wnt signal, glycogen synthase kinase 3β (GSK3β) collaborates with the AXIN and APC (adenomatous polyposis coli) proteins and other factors to phosphorylate β-catenin at its amino (N)-terminal domain. The phosphorylated β-catenin is recognized and ubiquitinated by a complex containing a β-transducin repeat-containing protein (βTrCP), and is then degraded by the proteasome. Wnt binding to the Frizzled-low density lipoprotein-related protein (LRP)-5/6 co-receptor complex on the cell surface leads to the recruitment of disheveled and the inhibition the AXIN/GSK3β complex. This, in turn, leads to the stabilization of the free pools of β-catenin which can enter the nucleus, bind to T cell factor (TCF) transcriptional regulators along with other cofactors and modulate transcription of various genes.

Wnt pathway deregulation has been implicated in many human diseases including cancer as well as many non-oncogenic disorders such as cardiac disease, osteroporosis, osteoarthritis, diabetes, fibrotic/proliferative diseases, Alzheimer's disease and schizophrenia. Wnt/β-catenin signaling is of particular relevance to colorectal cancers (CRC), which are the second leading cause of cancer death in Western societies. Mutations in the tumor suppressor gene, APC, are responsible for Familial Adenomatous Polyposis. Truncating mutations APC are also the most prevalent genetic alterations in sporadic CRC. Inactivating mutations of AXIN1/2 and oncogenic mutations in β-catenin, all of which lead to the stabilization of β-catenin and to altered expression of β-catenin/TCF-regulated genes in the absence of exogenous Wnt signals, have also been identified in human cancers including CRC. Indeed, aberrant activation of Wnt/β-catenin signaling is likely an obligatory step in the initiation of the majority, if not all, human CRC.

There is also good evidence for Wnt pathway hyperactivation in the initiation and/or progression on a variety of other human cancers including gastric, pancreatic, kidney (Wilms), medulloblastoma, melanoma, lung, thyroid, breast and prostate cancer. This pathway activation is achieved by either oncogenic mutations in β-catenin, or loss of function mutations in APC or AXIN. In addition, mutations or epigenetic silencing of extracellular negative regulators such as SFRP's, DKK's and WIF can also lead to abnormal pathway activity and have been widely reported in a large number of different human cancers.

Blocking canonical Wnt signaling in CRC and other Wnt-dependent tumors such as lung, breast and teratocarcinomas has been shown to inhibit tumor growth in human xenografts grown in mice or in transgenic mouse models. Several classes of small molecules have been shown to act as Wnt signaling inhibitors at various "nodes" of the pathway including the disruption of dishevelled activity and b-catenin interaction surfaces with TCF/LEF or pygopus. The efficient assembly of the multi-protein β-catenin destruction complex is dependent on the steady-state levels of its principal constituents. AXIN has been reported to be the concentration-limiting factor in regulating the efficiency of the β-catenin destruction complex and overexpression of AXIN induces β-catenin degradation even in cell lines expressing truncated APC (Hart, M. J. et. al. "Downregulation of Beta-Catenin by Human Axin and its Association with the APC Tumor Suppressor, Beta-Catenin and GSK3 Beta," Curr. Biol., 8(10) pp 573-581 (1998)). Thus, AXIN protein levels need to be tightly regulated to ensure proper Wnt pathway signaling and regulation of AXIN stability by TNKS therefore represents a good therapeutic target.

Cancer stem cells, found in many types of cancer, are rare populations of malignant cells with the capacity for endless self-renewal. They are believed to be responsible for tumor growth, recurrence and metastasis. Also referred to as "tumor-initiating cells," these cells have been identified in many types of solid tumor cancers, including cancer of head and neck, breast, lung, prostate, pancreas and glioblastoma. Cancer stem cells appear to be preferentially resistant to both standard chemotherapy and radiotherapy. One important therapeutic strategy is to specifically target the key biological pathways which are thought to be critical to the activity and survival of cancer stem cells. Since the Wnt pathway has been shown to be critical for cancer stem cells in many types of malignancies (e.g. squamous cancer stem cells), TNKS inhibitors are promising therapeutic compounds for use in treating human disease where cancer stem cells are thought to play a role (i.e. in recurrent or resistant disease). TNKS inhibitors could be either used alone or in combination with current chemotherapies.

Upregulation of telomerase and telomere maintenance is necessary for most cancer cells to replicate indefinitely and thereby enable tumor growth and metastasis. One strategy for the development of anti-cancer therapies is to inhibit telomerase activity in cancer cells. Inhibiting telomerase activity should result in telomere shortening which can cause senescence and death of cancer cells. Another, strategy to inhibit the telomere elongation in cancer cells would be to effectively inhibit telomerase by exclusion by preventing the PARsylation of TRF1 by TNKS. Thus, TNKS inhibitors would be suitable cancer therapies either alone or in combination with telomerase inhibitors by targeting teleomeres and driving cancer cells towards senescence.

A need therefore exists for potent and selective inhibitors of TNKS that may be used to treat cancer. The present application discloses such potent and selective tankyrase inhibitors with good drug-like properties that are suitable for inhibiting the growth of cancer cells. These compounds are especially appropriate for inhibiting CRC or any other human tumor that has evidence of Wnt pathway activation and/or dependence.

SUMMARY OF THE INVENTION

In one aspect, the invention provides a compound of Formula I:

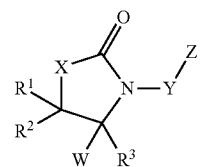

or a pharmaceutically acceptable salt thereof, a tautomer thereof, a pharmaceutically acceptable salt of the tautomer, a stereoisomer of any of the foregoing, or a mixture thereof,
wherein:
$R^1$ and $R^2$ are $(C_1-C_6)$alkyl, $(C_1-C_6)$haloalkyl, or $(C_1-C_6)$ perhaloalkyl; or $R^1$ and $R^2$ join to form a 3 to 7 membered cycloalkyl ring; or $R^1$ and $R^2$ join to form a 4 to 7 membered heterocyclyl ring comprising a heteroatom selected from O, S, or N;
$R^3$ is selected from —H, $(C_1-C_6)$alkyl, $(C_1-C_6)$haloalkyl, $(C_1-C_6)$perhaloalkyl, unsubstituted $(C_6-C_{10})$aryl, substituted $(C_6-C_{10})$aryl, unsubstituted 5 to 10 membered heteroaryl comprising 1, 2, or 3 heteroatoms independently selected from O, S, or N, substituted 5 to 10 membered heteroaryl comprising 1, 2, or 3 heteroatoms independently selected from O, S, or N, unsubstituted $(C_3-C_7)$cycloalkyl, substituted $(C_3-C_7)$cycloalkyl, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or —C(CH$_3$)$_2$—CN, wherein the substituted $(C_6-C_{10})$aryl and the substituted 5 to 10 membered heteroaryl are substituted with 1, 2, or 3 substituents independently selected from —F, —Cl, —Br, —I, —C≡N, —NO$_2$, —OH, —O—$(C_1-C_6)$alkyl, —SH, —S—$(C_1-C_6)$alkyl, —OCF$_3$, —OCHF$_2$, —CF$_3$, —$(C_1-C_6)$alkyl, —NH$_2$, —NH($(C_1-C_4)$alkyl), —N($(C_1-C_4)$alkyl)$_2$, —NHSO$_2$—$(C_1-C_6)$alkyl, —NHC(=O)—$(C_1-C_6)$alkyl, —C(=O)NH$_2$, —C(=O)NH($(C_1-C_6)$alkyl), —C(=O)N($(C_1-C_6)$alkyl)$_2$, —C(=O)NH—OH, —C(=O)NH—O—$(C_1-C_6)$alkyl, —C(=O)—$(C_1-C_6)$alkyl, —CO$_2$H, —C(=O)—O—$(C_1-C_6)$alkyl, —SO$_2$NH$_2$, —SO$_2$NH($(C_1-C_6)$alkyl), —SO$_2$N($(C_1-C_6)$alkyl)$_2$, —SO$_2$—$(C_1-C_6)$alkyl, —SO—$(C_1-C_6)$alkyl, —$(C_1-C_4)$alkylene-OH, or —$(C_1-C_4)$ alkylene-O—$(C_1-C_6)$alkyl, wherein the substituted $(C_3-C_7)$ cycloalkyl, the substituted 5 to 10 membered heterocyclyl, and the substituted 3 or 4 membered heterocyclyl are substituted with 1 or 2 substituents independently selected from —F, —Cl, —Br, —I, —C≡N, —NO$_2$, —OH, —O—$(C_1-C_6)$alkyl, —OCF$_3$, —OCHF$_2$, —CF$_3$, —$(C_1-C_6)$alkyl, —NH$_2$, —NH($(C_1-C_4)$alkyl), —N($(C_1-C_4)$alkyl)$_2$, —C(=O)NH$_2$, —C(=O)NH($(C_1-C_6)$alkyl), —C(=O)N($(C_1-C_6)$alkyl)$_2$, —C(=O)—$(C_1-C_6)$alkyl, —CO$_2$H, or —C(=O)—O—$(C_1-C_6)$alkyl;
W is selected from —H, $(C_1-C_6)$alkyl, $(C_1-C_6)$haloalkyl, $(C_1-C_6)$perhaloalkyl, unsubstituted $(C_6-C_{10})$aryl, substituted $(C_6-C_{10})$aryl, unsubstituted 5 to 10 membered heteroaryl comprising 1, 2, or 3 heteroatoms independently selected from O, S, or N, substituted 5 to 10 membered heteroaryl comprising 1, 2, or 3 heteroatoms independently selected from O, S, or N, unsubstituted $(C_3-C_7)$cycloalkyl, substituted $(C_3-C_7)$cycloalkyl, unsubstituted 5 to 10 membered hetero cyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or —C(CH$_3$)$_2$—CN, wherein the substituted (C$_6$-C$_{10}$)aryl and the substituted 5 to 10 membered heteroaryl are substituted with 1, 2, or 3 substituents independently selected from —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—(C$_1$-C$_6$)alkyl, —(C$_1$-C$_4$)alkylene-OH, or —(C$_1$-C$_4$)alkylene-O—(C$_1$-C$_6$)alkyl, wherein the substituted (C$_3$-C$_7$)cycloalkyl, the substituted 5 to 10 membered heterocyclyl, and the substituted 3 or 4 membered heterocyclyl are substituted with 1 or 2 substituents independently selected from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, or —C(=O)—O—(C$_1$-C$_6$)alkyl;

X is selected from O, S, or NR$^a$, wherein R$^a$ is selected from —H, (C$_1$-C$_6$)alkyl, or —CH$_2$-phenyl;

wherein when X is O at least one of R$^3$ and W is selected from unsubstituted (C$_6$-C$_{10}$)aryl, substituted (C$_6$-C$_{10}$)aryl, unsubstituted 5 to 10 membered heteroaryl, substituted 5 to 10 membered heteroaryl, unsubstituted (C$_3$-C$_7$)cycloalkyl, substituted (C$_3$-C$_7$)cycloalkyl, unsubstituted 5 to 10 membered heterocyclyl, substituted 5 to 10 membered heterocyclyl, unsubstituted 3 or 4 membered heterocyclyl, substituted 3 or 4 membered heterocyclyl or —C(CH$_3$)$_2$—CN;

wherein when X is S or NR$^a$ at least one of R$^3$ and W is selected from unsubstituted (C$_6$-C$_{10}$)aryl, substituted (C$_6$-C$_{10}$)aryl, unsubstituted 5 to 10 membered heteroaryl, substituted 5 to 10 membered heteroaryl, unsubstituted (C$_3$-C$_7$)cycloalkyl, substituted (C$_3$-C$_7$)cycloalkyl, or —C(CH$_3$)$_2$—CN;

Y is selected from unsubstituted (C$_4$-C$_7$)cycloalkyl, substituted (C$_4$-C$_7$)cycloalkyl, unsubstituted (C$_4$-C$_7$)cycloalkenyl, substituted (C$_4$-C$_7$)cycloalkenyl, unsubstituted (C$_6$-C$_{10}$)aryl, substituted (C$_6$-C$_{10}$)aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 4 to 10 membered heterocyclyl comprising 1, 2, or 3 heteroatoms independently selected from O, S, or N, or substituted 4 to 10 membered heterocyclyl comprising 1, 2, or 3 heteroatoms independently selected from O, S, or N, wherein the substituted (C$_4$-C$_7$)cycloalkyl and substituted (C$_4$-C$_7$)cycloalkenyl are substituted with 1 or 2 substituents independently selected from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, or —C(=O)—O—(C$_1$-C$_6$)alkyl, and wherein the substituted (C$_6$-C$_{10}$)aryl, substituted 5 to 10 membered heteroaryl, and substituted 4 to 10 membered heterocyclyl are substituted with 1, 2, or 3 substituents independently selected from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, or —C(=O)—O—(C$_1$-C$_6$)alkyl, and further wherein the substituted 4 to 10 membered heterocyclyl may also be substituted with a =O;

Z is selected from unsubstituted (C$_6$-C$_{10}$)aryl, substituted (C$_6$-C$_{10}$)aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 5 to 10 membered heterocyclyl comprising 1, 2, 3 or 4 heteroatoms independently selected from O, S, or N, or substituted 5 to 10 membered heterocyclyl comprising 1, 2, 3, or 4 heteroatoms independently selected from O, S, or N, or Z is selected from —NR$^b$—Z', —NR$^c$—C(=O)—Z', or —C(=O)—NR$^d$—Z', wherein the substituted (C$_6$-C$_{10}$)aryl, substituted 5 to 10 membered heteroaryl, and the substituted 5 to 10 membered heterocyclyl are substituted with 1, 2, or 3 Q substituents and may additionally be substituted with 0 or 1 of Z' or —NR$^e$—Z', and further wherein the substituted 5 to 10 membered heterocyclyl may also be substituted with a =O;

each Q is independently selected from —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CH$_2$CHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—(C$_1$-C$_6$)alkyl, —(C$_1$-C$_4$)alkylene-OH, —(C$_1$-C$_4$)alkylene-O—(C$_1$-C$_6$)alkyl, unsubstituted (C$_3$-C$_7$)cycloalkyl, unsubstituted 5 to 10 membered heterocyclyl comprising 1, 2, 3, or 4 heteroatoms independently selected from O, S, or N, or unsubstituted 3 or 4 membered heterocyclyl comprising 1 heteroatom selected from O, S, or N;

R$^b$ is selected from —H or (C$_1$-C$_6$)alkyl;
R$^c$ is selected from —H or (C$_1$-C$_6$)alkyl;
R$^d$ is selected from —H or (C$_1$-C$_6$)alkyl;
R$^e$ is selected from —H or (C$_1$-C$_6$)alkyl;

Z' is selected from unsubstituted (C$_6$-C$_{10}$) aryl, substituted (C$_6$-C$_{10}$) aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or unsubstituted (C$_3$-C$_7$)cycloalkyl, wherein, the substituted (C$_6$-C$_{10}$) aryl, the substituted 5 to 10 membered heteroaryl, the substituted 5 to 10 membered heterocyclyl, and the 3 or 4 membered heterocyclyl are substituted with 1, 2, or 3 substituents independently selected from —F, —Cl, —Br, —I, —C≡N, —NO$_2$, —C(=NH)—NH$_2$, —OH, —O—(C$_1$-C$_6$)alkyl, —SH, —S—(C$_1$-C$_6$)alkyl, —OCF$_3$, —OCHF$_2$, —CH$_2$CHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—(C$_1$-C$_6$)alkyl, —(C$_1$-C$_4$)alkylene-OH, or —(C$_1$-C$_4$)alkylene-O—(C$_1$-C$_6$)alkyl, and further wherein the substituted 5 to 10 membered heterocyclyl and the 3 or 4 membered heterocyclyl may also be substituted with a =O.

In another aspect, the invention provides a compound of Formula II:

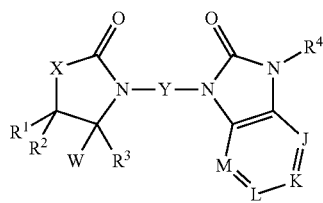

II or a pharmaceutically acceptable salt thereof, a tautomer thereof, a pharmaceutically acceptable salt of the tautomer, a stereoisomer of any of the foregoing, or a mixture thereof, wherein:

R$^1$ and R$^2$ are independently selected from H, (C$_1$-C$_6$)alkyl, (C$_1$-C$_6$)haloalkyl, (C$_1$-C$_6$)perhaloalkyl, unsubstituted (C$_6$-C$_{10}$)aryl, substituted (C$_6$-C$_{10}$)aryl, unsubstituted 5 to 10 membered heteroaryl comprising 1, 2, or 3 heteroatoms independently selected from O, S, or N, substituted 5 to 10 membered heteroaryl comprising 1, 2, or 3 heteroatoms independently selected from O, S, or N, unsubstituted (C$_3$-C$_7$)cycloalkyl, substituted (C$_3$-C$_7$)cycloalkyl, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N; or R$^1$ and R$^2$ join to form a 3 to 7 membered cycloalkyl ring; or R$^1$ and R$^2$ join to form a 4 to 7 membered heterocyclyl ring comprising a heteroatom selected from O, S, or N; wherein the substituted (C$_6$-C$_{10}$)aryl and the substituted 5 to 10 membered heteroaryl are substituted with 1, 2, or 3 substituents independently selected from —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—(C$_1$-C$_6$)alkyl, —(C$_1$-C$_4$)alkylene-OH, or —(C$_1$-C$_4$)alkylene-O—(C$_1$-C$_6$)alkyl, wherein the substituted (C$_3$-C$_7$)cycloalkyl, the substituted 5 to 10 membered heterocyclyl, and the substituted 3 or 4 membered heterocyclyl are substituted with 1 or 2 substituents independently selected from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, or —C(=O)—O—(C$_1$-C$_6$)alkyl;

R$^3$ is selected from —H, (C$_1$-C$_6$)alkyl, (C$_1$-C$_6$)haloalkyl, (C$_1$-C$_6$)perhaloalkyl, unsubstituted (C$_6$-C$_{10}$)aryl, substituted (C$_6$-C$_{10}$)aryl, unsubstituted 5 to 10 membered heteroaryl comprising 1, 2, or 3 heteroatoms independently selected from O, S, or N, substituted 5 to 10 membered heteroaryl comprising 1, 2, or 3 heteroatoms independently selected from O, S, or N, unsubstituted (C$_3$-C$_7$)cycloalkyl, substituted (C$_3$-C$_7$)cycloalkyl, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or —C(CH$_3$)$_2$—CN, wherein the substituted (C$_6$-C$_{10}$)aryl and the substituted 5 to 10 membered heteroaryl are substituted with 1, 2, or 3 substituents independently selected from —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—(C$_1$-C$_6$)alkyl, —(C$_1$-C$_4$)alkylene-OH, or —(C$_1$-C$_4$)alkylene-O—(C$_1$-C$_6$)alkyl, wherein the substituted (C$_3$-C$_7$)cycloalkyl, the substituted 5 to 10 membered heterocyclyl, and the substituted 3 or 4 membered heterocyclyl are substituted with 1 or 2 substituents independently selected from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, or —C(=O)—O—(C$_1$-C$_6$)alkyl;

W is selected from —H, (C$_1$-C$_6$)alkyl, (C$_1$-C$_6$)haloalkyl, (C$_1$-C$_6$)perhaloalkyl, unsubstituted (C$_6$-C$_{10}$)aryl, substituted (C$_6$-C$_{10}$)aryl, unsubstituted 5 to 10 membered heteroaryl comprising 1, 2, or 3 heteroatoms independently selected from O, S, or N, substituted 5 to 10 membered heteroaryl comprising 1, 2, or 3 heteroatoms independently selected from O, S, or N, unsubstituted (C$_3$-C$_7$)cycloalkyl, substituted (C$_3$-C$_7$)cycloalkyl, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or —C(CH$_3$)$_2$—CN, wherein the substituted (C$_6$-C$_{10}$)aryl and the substituted 5 to 10 membered heteroaryl are substituted with 1, 2, or 3 substituents independently selected from —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—($C_1$-$C_6$)alkyl, —($C_1$-$C_4$)alkylene-OH, or —($C_1$-$C_4$)alkylene-O—($C_1$-$C_6$)alkyl, wherein the substituted ($C_3$-$C_7$)cycloalkyl, the substituted 5 to 10 membered heterocyclyl, and the substituted 3 or 4 membered heterocyclyl are substituted with 1 or 2 substituents independently selected from —F, —Cl, —Br, —I, —C≡N, —$NO_2$, —OH, —O—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —C(=O)$NH_2$, —C(=O)NH(($C_1$-$C_6$)alkyl), —C(=O)N(($C_1$-$C_6$)alkyl)$_2$, —C(=O)—($C_1$-$C_6$)alkyl, —$CO_2$H, or —C(=O)—O—($C_1$-$C_6$)alkyl;

X is selected from O, S, or $NR^a$, wherein $R^a$ is selected from —H, ($C_1$-$C_6$)alkyl, or —$CH_2$-phenyl;

J is N or $CR^5$;
K is N or $CR^6$;
L is N or $CR^7$;
M is N or $CR^8$;

wherein 0, 1, or 2 of J, K, L, and M are N;

$R^4$ is selected from —H, —($C_1$-$C_6$)alkyl, ($C_1$-$C_6$)haloalkyl, or ($C_1$-$C_6$)perhaloalkyl;

$R^5$ is selected from —H, —F, —Cl, —Br, —I, —C≡N, —$NO_2$, —OH, —O—($C_1$-$C_6$)alkyl, —SH, —S—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —$NHSO_2$—($C_1$-$C_6$)alkyl, —NHC(=O)—($C_1$-$C_6$)alkyl, —C(=O)$NH_2$, —C(=O)NH(($C_1$-$C_6$)alkyl), —C(=O)N(($C_1$-$C_6$)alkyl)$_2$, —C(=O)NH—OH, —C(=O)NH—O—($C_1$-$C_6$)alkyl, —C(=O)—($C_1$-$C_6$)alkyl, —$CO_2$H, —C(=O)—O—($C_1$-$C_6$)alkyl, —$SO_2NH_2$, —$SO_2$NH(($C_1$-$C_6$)alkyl), —$SO_2$N(($C_1$-$C_6$)alkyl)$_2$, —$SO_2$—($C_1$-$C_6$)alkyl, —SO—($C_1$-$C_6$)alkyl, —($C_1$-$C_4$)alkylene-OH, or —($C_1$-$C_4$)alkylene-O—($C_1$-$C_6$)alkyl;

$R^6$ is selected from —H, —F, —Cl, —Br, —I, —C≡N, —$NO_2$, —OH, —O—($C_1$-$C_6$)alkyl, —SH, —S—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —$NHSO_2$—($C_1$-$C_6$)alkyl, —NHC(=O)—($C_1$-$C_6$)alkyl, —C(=O)$NH_2$, —C(=O)NH(($C_1$-$C_6$)alkyl), —C(=O)N(($C_1$-$C_6$)alkyl)$_2$, —C(=O)NH—OH, —C(=O)NH—O—($C_1$-$C_6$)alkyl, —C(=O)—($C_1$-$C_6$)alkyl, —$CO_2$H, —C(=O)—O—($C_1$-$C_6$)alkyl, —$SO_2NH_2$, —$SO_2$NH(($C_1$-$C_6$)alkyl), —$SO_2$N(($C_1$-$C_6$)alkyl)$_2$, —$SO_2$—($C_1$-$C_6$)alkyl, —SO—($C_1$-$C_6$)alkyl, —($C_1$-$C_4$)alkylene-OH, or —($C_1$-$C_4$)alkylene-O—($C_1$-$C_6$)alkyl;

$R^7$ is selected from —H, —F, —Cl, —Br, —I, —C≡N, —$NO_2$, —OH, —O—($C_1$-$C_6$)alkyl, —SH, —S—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —$NHSO_2$—($C_1$-$C_6$)alkyl, —NHC(=O)—($C_1$-$C_6$)alkyl, —C(=O)$NH_2$, —C(=O)NH(($C_1$-$C_6$)alkyl), —C(=O)N(($C_1$-$C_6$)alkyl)$_2$, —C(=O)NH—OH, —C(=O)NH—O—($C_1$-$C_6$)alkyl, —C(=O)—($C_1$-$C_6$)alkyl, —$CO_2$H, —C(=O)—O—($C_1$-$C_6$)alkyl, —$SO_2NH_2$, —$SO_2$NH(($C_1$-$C_6$)alkyl), —$SO_2$N(($C_1$-$C_6$)alkyl)$_2$, —$SO_2$—($C_1$-$C_6$)alkyl, —SO—($C_1$-$C_6$)alkyl, —($C_1$-$C_4$)alkylene-OH, or —($C_1$-$C_4$)alkylene-O—($C_1$-$C_6$)alkyl;

$R^8$ is selected from —H, —F, —Cl, —Br, —I, —C≡N, —$NO_2$, —OH, —O—($C_1$-$C_6$)alkyl, —SH, —S—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —$NHSO_2$—($C_1$-$C_6$)alkyl, —NHC(=O)—($C_1$-$C_6$)alkyl, —C(=O)$NH_2$, —C(=O)NH(($C_1$-$C_6$)alkyl), —C(=O)N(($C_1$-$C_6$)alkyl)$_2$, —C(=O)NH—OH, —C(=O)NH—O—($C_1$-$C_6$)alkyl, —C(=O)—($C_1$-$C_6$)alkyl, —$CO_2$H, —C(=O)—O—($C_1$-$C_6$)alkyl, —$SO_2NH_2$, —$SO_2$NH(($C_1$-$C_6$)alkyl), —$SO_2$N(($C_1$-$C_6$)alkyl)$_2$, —$SO_2$—($C_1$-$C_6$)alkyl, —SO—($C_1$-$C_6$)alkyl, —($C_1$-$C_4$)alkylene-OH, or —($C_1$-$C_4$)alkylene-O—($C_1$-$C_6$)alkyl;

wherein one of $R^5$, $R^6$, $R^7$, and $R^8$ may optionally be unsubstituted ($C_3$-$C_7$)cycloalkyl, unsubstituted 3 membered heterocycle comprising 1 heteroatom selected from O, S, or N, unsubstituted 4 membered heterocycle comprising 1 or 2 heteroatoms independently selected from O, S, or N, or unsubstituted 5 to 10 membered heterocyclyl comprising 1, 2, 3 or 4 heteroatoms independently selected from O, S, or N; and Y is selected from unsubstituted ($C_4$-$C_7$)cycloalkyl, substituted ($C_4$-$C_7$)cycloalkyl, unsubstituted ($C_4$-$C_7$)cycloalkenyl, substituted ($C_4$-$C_7$)cycloalkenyl, unsubstituted ($C_6$-$C_{10}$)aryl, substituted ($C_6$-$C_{10}$)aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 4 to 10 membered heterocyclyl comprising 1, 2, or 3 heteroatoms independently selected from O, S, or N, or substituted 4 to 10 membered heterocyclyl comprising 1, 2, or 3 heteroatoms independently selected from O, S, or N, wherein the substituted ($C_4$-$C_7$)cycloalkyl and substituted ($C_4$-$C_7$)cycloalkenyl are substituted with 1 or 2 substituents independently selected from —F, —Cl, —Br, —I, —C≡N, —$NO_2$, —OH, —O—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —C(=O)$NH_2$, —C(=O)NH(($C_1$-$C_6$)alkyl), —C(=O)N(($C_1$-$C_6$)alkyl)$_2$, —C(=O)—($C_1$-$C_6$)alkyl, —$CO_2$H, or —C(=O)—O—($C_1$-$C_6$)alkyl, and wherein the substituted ($C_6$-$C_{10}$)aryl, substituted 5 to 10 membered heteroaryl, and substituted 4 to 10 membered heterocyclyl are substituted with 1, 2, or 3 substituents independently selected from —F, —Cl, —Br, —I, —C≡N, —$NO_2$, —OH, —O—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —C(=O)$NH_2$, —C(=O)NH(($C_1$-$C_6$)alkyl), —C(=O)N(($C_1$-$C_6$)alkyl)$_2$, —C(=O)—($C_1$-$C_6$)alkyl, —$CO_2$H, or —C(=O)—O—($C_1$-$C_6$)alkyl, and further wherein the substituted 4 to 10 membered heterocyclyl may also be substituted with a =O.

In some embodiments, the compound is a salt. Such salts may be anhydrous or associated with water as a hydrate.

Also provided are pharmaceutical compositions that include at least one pharmaceutically acceptable excipient, carrier or diluent and the compound or the pharmaceutically acceptable salt thereof, the tautomer thereof, the pharmaceutically acceptable salt of the tautomer, the stereoisomer of any of the foregoing, or the mixture thereof according to any one of the embodiments. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of cancer or for inhibiting tankyrase 1 and or tankyrase 2.

In other embodiments, the invention provides a method of treating cancer. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the cancer os colon cancer and in still other such embodiments is APC colon cancer. In some embodiments, the subject is a human cancer patient, and the cancer is selected from colon cancer. In still other embodiments, the cancer is selected from colon, pancreatic, ovarian, gastric, lung, or leukemia. In still other embodiments the cancer is any other cancer that relies on the Wnt pathway for growth or survival.

In still other embodiments, the invention provides a method of treating a condition where it is desired to inhibit tankyrase 1 or tankyrase 2 activity. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of any of the embodiments.

In some embodiments, the compound or the pharmaceutically acceptable salt thereof, the tautomer thereof, the pharmaceutically acceptable salt of the tautomer, the stereoisomer of any of the foregoing, or the mixture thereof according to any one of any of the embodiments is used in the preparation of a medicament. In some such embodiments, the medicament is for use in treating cancer. In some such embodiments, a medicament is for use in inhibiting tankyrase 1 or tankyrase 2. In still other such embodiments, the medicament is for use in treating a cancer in a human cancer patient such as a human with colon cancer.

In some such embodiments, the compound or the pharmaceutically acceptable salt thereof, the tautomer thereof, the pharmaceutically acceptable salt of the tautomer, the stereoisomer of any of the foregoing, or the mixture thereof according to any one of any of the embodiments is provided for use in treating cancer. In some such embodiments, the cancer is colon cancer. In still other embodiments the use is for treating cancer in a human patient.

Other objects, features and advantages of the invention will become apparent to those skilled in the art from the following description and claims.

DETAILED DESCRIPTION OF THE INVENTION

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula.

Compounds of the present disclosure include, but are not limited to, compounds of Formula I and Formula II and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as ($C_1$-$C_4$) alkyl esters. In other embodiments, the term "compound" encompasses the compound itself, pharmaceutically acceptable salts thereof, tautomers of the compound, pharmaceutically acceptable salts of the tautomers.

The term "solvate" refers to the compound formed by the interaction of a solvent and a compound. Suitable solvates are pharmaceutically acceptable solvates, such as hydrates, including monohydrates and hemi-hydrates.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention. For example, if a variable is said to be H, this means that variable may also be deuterium (D) or tritium (T).

"Alkyl" refers to a saturated branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl and propan-2-yl, butyls such as butan-1-yl, butan-2-yl, 2-methyl-propan-1-yl, 2-methyl-propan-2-yl, tert-butyl, and the like. In certain embodiments, an alkyl group comprises 1 to 20 carbon atoms. In some embodiments, alkyl groups include 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a ($C_1$-$C_6$) alkyl group and an alkyl group having 1 to 4 carbon atoms may be referred to as a ($C_1$-$C_4$)alkyl. This nomenclature may also be used for alkyl groups with differing numbers of carbon atoms.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl(allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a ($C_2$-$C_6$) alkenyl group.

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —($C_2$-$C_6$)alkynyl group.

"Alkoxy" refers to a radical —OR where R represents an alkyl group as defined herein. Representative examples include, but are not limited to, methoxy, ethoxy, propoxy, butoxy, cyclohexyloxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O($C_{1-6}$)alkyl or as —O—($C_{1-6}$) alkyl groups. In some embodiments, an alkoxy group may include 1 to 4 carbon atoms and may be designated as —O($C_{1-4}$) alkyl or as an —O—($C_{1-4}$) alkyl group.

"Alkylene" refers to a divalent saturated hydrocarbon group derived from a parent alkane by removal of two hydrogen atoms. Examples of alkylene group include, but are not limited to, —$CH_2$—, —$CH_2CH_2$—, —$CH(CH_3)$—, —$CH_2CH_2CH_2$—, —$CH_2C(CH_3)(H)$—, and the like. In some embodiments an alkylene may include 1 to 6 carbon atoms and in other embodiments may include 1 to 4 carbon atoms. Such groups may be designated as —($C_1$-$C_6$)alkylene- and —($C_1$-$C_4$)alkylene-groups.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene. Aryl also encompasses bicyclic carbocyclic aromatic ring systems where each of the rings is aromatic, for example, naphthalene. Aryl groups may thus include fused ring systems where each ring is a carbocyclic aromatic ring. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with an aromatic ring that includes at least one heteroatom, the resulting ring system is heteroaryl, not aryl, as defined herein.

"Carbonyl" refers to the radical —C(O) or —C(=O) group.

"Carboxy" refers to the radical —C(O)OH.

"Cyano" refers to the radical —CN.

"Cycloalkyl" refers to a saturated cyclic alkyl group derived by the removal of one hydrogen atom from a single carbon atom of a parent cycloalkane. Typical cycloalkyl groups include, but are not limited to, groups derived from cyclopropane, cyclobutane, cyclopentane, cyclohexane, cycloheptane, cyclooctane, and the like. Cycloalkyl groups may be described by the number of carbon atoms in the ring. For example a cycloalkyl group having 3 to 7 ring members may be referred to as a ($C_3$-$C_7$)cycloalkyl and a cycloalkyl group having 4 to 7 ring members may be referred to as a ($C_4$-$C_7$)cycloalkyl. In certain embodiments, the cycloalkyl group can be a ($C_3$-$C_{10}$)cycloalkyl, a ($C_3$-$C_7$)cycloalkyl, a ($C_3$-$C_6$)cycloalkyl, or a ($C_4$-$C_7$)cycloalkyl group.

"Cycloalkenyl" refers to a cyclic alkyl group having at least one carbon-carbon double bond derived by the removal of one hydrogen atom from a single carbon atom of a parent cycloalkene. Typical cycloalkenyl groups include, but are not limited to, groups derived from cyclobutene, cyclopentene, cyclohexene, cycloheptene, cyclooctene, and the like. Cycloalkenyl groups may be described by the number of carbon atoms in the ring. For example a cycloalkenyl group having 4 to 7 ring members may be referred to as a ($C_4$-$C_7$)

cycloalkenyl. In certain embodiments, the cycloalkenyl group can be ($C_4$-$C_{10}$)cycloalkenyl, such as, for example, a ($C_4$-$C_7$)cycloalkenyl or ($C_4$-$C_6$)cycloalkenyl group.

"Heterocyclyl" refers to a cyclic group that includes at least one saturated or unsaturated, but non-aromatic, cyclic ring. Heterocyclyl groups include at least one heteroatom as a ring member. Typical heteroatoms include, but are not limited to, O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring.

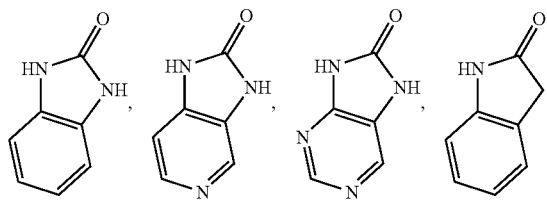 [SMILES: O=c1[nH]c2ccccc2[nH]1 ; O=c1[nH]c2ccncc2[nH]1 ; O=c1[nH]c2cncnc2[nH]1 ; O=C1Cc2ccccc2N1]

In some embodiments, a heterocyclyl group includes 3 to 10 ring members of which 1, 2, or 3 ring members are independently selected from O, S, or N. In other embodiments, a heterocyclyl group includes 4 to 10 ring members of which 1, 2, or 3 are heteroatoms independently selected from O, S, or N. In other embodiments, a heterocyclyl group includes 5 to 10 ring members of which 1, 2, 3 or 4 are heteroatoms independently selected from O, S, or N. In other embodiments, a heterocyclyl group includes 4 to 7 ring members comprising 1 heteroatom selected from O, S, or N. In still other embodiments, a heterocyclyl group includes 3 or 4 ring members of which 1 is a heteroatom selected from O, S, or N. In still other embodiments, a heterocyclyl group includes rings with 5 to 10 ring members of which 1, 2, 3, or 4 are heteroatoms selected from O, S, or N and rings with 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Substituted heterocyclyl also includes ring systems substituted with one or more oxo (=O) or oxide (—O⁻) substituents, such as piperidinyl N-oxide, morpholinyl-N-oxide, 1-oxo-1-thiomorpholinyl, pyridinonyl, benzimidazolonyl, benzo[d]oxazol-2(3H)-only, 3,4-dihydroisoquinolin-1 (2H)-only, indolin-only, 1H-imidazo[4,5-c]pyridin-2(3H)-only, 7H-purin-8(9H)-only, imidazolidin-2-only, 1H-imidazol-2 (3H)-only, 1,1-dioxo-1-thiomorpholinyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). Representative "haloalkyl" groups include difluoromethyl, 2,2,2-trifluoroethyl, 2,2,2-trichloroethyl, and the like. The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 14-membered, but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, and N, with the remaining ring atoms being carbon. In monocyclic heteroaryl groups, the single ring is aromatic and includes at least one heteroatom. In bicyclic aromatic rings, both rings are aromatic. In bicyclic heteroaryl groups, at least one of the rings must include a heteroatom, but it is not necessary that both rings include a heteroatom although it is permitted for them to do so. For example, heteroaryl includes a 5- to 7-membered heteroaromatic ring fused to a carbocyclic aromatic ring or fused to a heteroaromatic ring. In tricyclic aromatic rings, all three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

"Sulfonyl" refers to a radical —$S(O)_2R$ where R is an alkyl, substituted alkyl, substituted cycloalkyl, substituted heterocyclyl, substituted aryl, or substituted heteroaryl group as defined herein. Representative examples include, but are not limited to, methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocyclyl, substituted aryl, or substituted heteroaryl group as defined herein that may be optionally substituted as defined herein.

Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In one aspect, the invention provides a compound of Formula I:

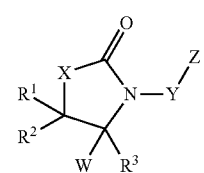

or a pharmaceutically acceptable salt thereof, a tautomer thereof, a pharmaceutically acceptable salt of the tautomer, a stereoisomer of any of the foregoing, or a mixture thereof, wherein:

$R^1$ and $R^2$ are $(C_1-C_6)$alkyl, $(C_1-C_6)$haloalkyl, or $(C_1-C_6)$perhaloalkyl; or $R^1$ and $R^2$ join to form a 3 to 7 membered cycloalkyl ring; or $R^1$ and $R^2$ join to form a 4 to 7 membered heterocyclyl ring comprising a heteroatom selected from O, S, or N;

$R^3$ is selected from —H, $(C_1-C_6)$alkyl, $(C_1-C_6)$haloalkyl, $(C_1-C_6)$perhaloalkyl, unsubstituted $(C_6-C_{10})$aryl, substituted $(C_6-C_{10})$aryl, unsubstituted 5 to 10 membered heteroaryl comprising 1, 2, or 3 heteroatoms independently selected from O, S, or N, substituted 5 to 10 membered heteroaryl comprising 1, 2, or 3 heteroatoms independently selected from O, S, or N, unsubstituted $(C_3-C_7)$cycloalkyl, substituted $(C_3-C_7)$cycloalkyl, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or —$C(CH_3)_2$—CN, wherein the substituted $(C_6-C_{10})$aryl and the substituted 5 to 10 membered heteroaryl are substituted with 1, 2, or 3 substituents independently selected from —F, —Cl, —Br, —I, —C≡N, —$NO_2$, —OH, —O—$(C_1-C_6)$alkyl, —SH, —S—$(C_1-C_6)$alkyl, —$OCF_3$, —$OCHF_2$, —$CF_3$, —$(C_1-C_6)$alkyl, —$NH_2$, —NH$((C_1-C_4)$alkyl$)$, —N$((C_1-C_4)$alkyl$)_2$, —$NHSO_2$—$(C_1-C_6)$alkyl, —NHC(=O)—$(C_1-C_6)$alkyl, —C(=O)$NH_2$, —C(=O)NH$((C_1-C_6)$alkyl$)$, —C(=O)N$((C_1-C_6)$alkyl$)_2$, —C(=O)NH—OH, —C(=O)NH—O—$(C_1-C_6)$alkyl, —C(=O)—$(C_1-C_6)$alkyl, —$CO_2H$, —C(=O)—O—$(C_1-C_6)$alkyl, —$SO_2NH_2$, —$SO_2NH((C_1-C_6)$alkyl$)$, —$SO_2N((C_1-C_6)$alkyl$)_2$, —$SO_2$—$(C_1-C_6)$alkyl, —SO—$(C_1-C_6)$alkyl, —$(C_1-C_4)$alkylene-OH, or —$(C_1-C_4)$ alkylene-O—($C_1$-$C_6$)alkyl, wherein the substituted ($C_3$-$C_7$) cycloalkyl, the substituted 5 to 10 membered heterocyclyl, and the substituted 3 or 4 membered heterocyclyl are substituted with 1 or 2 substituents independently selected from —F, —Cl, —Br, —I, —C≡N, —$NO_2$, —OH, —O—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —C(=O)$NH_2$, —C(=O)NH(($C_1$-$C_6$)alkyl), —C(=O)N(($C_1$-$C_6$)alkyl)$_2$, —C(=O)—($C_1$-$C_6$)alkyl, —$CO_2$H, or —C(=O)—O—($C_1$-$C_6$)alkyl;

W is selected from —H, ($C_1$-$C_6$)alkyl, ($C_1$-$C_6$)haloalkyl, ($C_1$-$C_6$)perhaloalkyl, unsubstituted ($C_6$-$C_{10}$)aryl, substituted ($C_6$-$C_{10}$)aryl, unsubstituted 5 to 10 membered heteroaryl comprising 1, 2, or 3 heteroatoms independently selected from O, S, or N, substituted 5 to 10 membered heteroaryl comprising 1, 2, or 3 heteroatoms independently selected from O, S, or N, unsubstituted ($C_3$-$C_7$)cycloalkyl, substituted ($C_3$-$C_7$)cycloalkyl, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or —C(CH$_3$)$_2$—CN, wherein the substituted ($C_6$-$C_{10}$)aryl and the substituted 5 to 10 membered heteroaryl are substituted with 1, 2, or 3 substituents independently selected from —F, —Cl, —Br, —I, —C≡N, —$NO_2$, —OH, —O—($C_1$-$C_6$)alkyl, —SH, —S—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —$NHSO_2$—($C_1$-$C_6$)alkyl, —NHC(=O)—($C_1$-$C_6$)alkyl, —C(=O)$NH_2$, —C(=O)NH(($C_1$-$C_6$)alkyl), —C(=O)N(($C_1$-$C_6$)alkyl)$_2$, —C(=O)NH—OH, —C(=O)NH—O—($C_1$-$C_6$)alkyl, —C(=O)—($C_1$-$C_6$)alkyl, —$CO_2$H, —C(=O)—O—($C_1$-$C_6$)alkyl, —$SO_2NH_2$, —$SO_2$NH(($C_1$-$C_6$)alkyl), —$SO_2$N(($C_1$-$C_6$)alkyl)$_2$, —$SO_2$—($C_1$-$C_6$)alkyl, —SO—($C_1$-$C_6$)alkyl, —($C_1$-$C_4$)alkylene-OH, or —($C_1$-$C_4$)alkylene-O—($C_1$-$C_6$)alkyl, wherein the substituted ($C_3$-$C_7$)cycloalkyl, the substituted 5 to 10 membered heterocyclyl, and the substituted 3 or 4 membered heterocyclyl are substituted with 1 or 2 substituents independently selected from —F, —Cl, —Br, —I, —C≡N, —$NO_2$, —OH, —O—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —C(=O)$NH_2$, —C(=O)NH(($C_1$-$C_6$)alkyl), —C(=O)N(($C_1$-$C_6$)alkyl)$_2$, —C(=O)—($C_1$-$C_6$)alkyl, —$CO_2$H, or —C(=O)—O—($C_1$-$C_6$)alkyl;

X is selected from O, S, or NR$^a$, wherein R$^a$ is selected from —H, ($C_1$-$C_6$)alkyl, or —CH$_2$-phenyl;

wherein when X is O at least one of R$^3$ and W is selected from unsubstituted ($C_6$-$C_{10}$)aryl, substituted ($C_6$-$C_{10}$)aryl, unsubstituted 5 to 10 membered heteroaryl, substituted 5 to 10 membered heteroaryl, unsubstituted ($C_3$-$C_7$)cycloalkyl, substituted ($C_3$-$C_7$)cycloalkyl, unsubstituted 5 to 10 membered heterocyclyl, substituted 5 to 10 membered heterocyclyl, unsubstituted 3 or 4 membered heterocyclyl, substituted 3 or 4 membered heterocyclyl or —C(CH$_3$)$_2$—CN;

wherein when X is S or NR$^a$ at least one of R$^3$ and W is selected from unsubstituted ($C_6$-$C_{10}$)aryl, substituted ($C_6$-$C_{10}$)aryl, unsubstituted 5 to 10 membered heteroaryl, substituted 5 to 10 membered heteroaryl, unsubstituted ($C_3$-$C_7$)cycloalkyl, substituted ($C_3$-$C_7$)cycloalkyl, or —C(CH$_3$)$_2$—CN;

Y is selected from unsubstituted ($C_4$-$C_7$)cycloalkyl, substituted ($C_4$-$C_7$)cycloalkyl, unsubstituted ($C_4$-$C_7$)cycloalkenyl, substituted ($C_4$-$C_7$)cycloalkenyl, unsubstituted ($C_6$-$C_{10}$)aryl, substituted ($C_6$-$C_{10}$)aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 4 to 10 membered heterocyclyl comprising 1, 2, or 3 heteroatoms independently selected from O, S, or N, or substituted 4 to 10 membered heterocyclyl comprising 1, 2, or 3 heteroatoms independently selected from O, S, or N, wherein the substituted ($C_4$-$C_7$)cycloalkyl and substituted ($C_4$-$C_7$)cycloalkenyl are substituted with 1 or 2 substituents independently selected from —F, —Cl, —Br, —I, —C≡N, —$NO_2$, —OH, —O—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —C(=O)$NH_2$, —C(=O)NH(($C_1$-$C_6$)alkyl), —C(=O)N(($C_1$-$C_6$)alkyl)$_2$, —C(=O)—($C_1$-$C_6$)alkyl, —$CO_2$H, or —C(=O)—O—($C_1$-$C_6$)alkyl, and wherein the substituted ($C_6$-$C_{10}$)aryl, substituted 5 to 10 membered heteroaryl, and substituted 4 to 10 membered heterocyclyl are substituted with 1, 2, or 3 substituents independently selected from —F, —Cl, —Br, —I, —C≡N, —$NO_2$, —OH, —O—($C_1$-$C_6$)alkyl, —$OCF_3$, —$OCHF_2$, —$CF_3$, —($C_1$-$C_6$)alkyl, —$NH_2$, —NH(($C_1$-$C_4$)alkyl), —N(($C_1$-$C_4$)alkyl)$_2$, —C(=O)$NH_2$, —C(=O)NH(($C_1$-$C_6$)alkyl), —C(=O)N(($C_1$-$C_6$)alkyl)$_2$, —C(=O)—($C_1$-$C_6$)alkyl, —$CO_2$H, or —C(=O)—O—($C_1$-$C_6$)alkyl, and further wherein the substituted 4 to 10 membered heterocyclyl may also be substituted with a =O;

Z is selected from unsubstituted ($C_6$-$C_{10}$)aryl, substituted ($C_6$-$C_{10}$)aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 5 to 10 membered heterocyclyl comprising 1, 2, 3 or 4 heteroatoms independently selected from O, S, or N, or substituted 5 to 10 membered heterocyclyl comprising 1, 2, 3, or 4 heteroatoms independently selected from O, S, or N, or Z is selected from —NR$^b$—Z', —NR$^c$—C(=O)—Z', or —C(=O)—NR$^d$—Z', wherein the substituted ($C_6$-$C_{10}$)aryl, substituted 5 to 10 membered heteroaryl, and the substituted 5 to 10 membered heterocyclyl are substituted with 1, 2, or 3 Q substituents and may additionally be substituted with 0 or 1 of Z' or —NR$^e$—Z', and further wherein the substituted 5 to 10 membered heterocyclyl may also be substituted with a =O;

each Q is independently selected from —F, —Cl, —Br, —I, —C≡N, —$NO_2$, —OH, —O—($C_1$-$C_6$)alkyl, —SH, —S—($C_1$-$C_6$)alkyl, —$OCF_3$, —$OCHF_2$, —$CH_2CHF_2$, —$CF_3$, —($C_1$-$C_6$)alkyl, —$NH_2$, —NH(($C_1$-$C_4$)alkyl), —N(($C_1$-$C_4$)alkyl)$_2$, —$NHSO_2$—($C_1$-$C_6$)alkyl, —NHC(=O)—($C_1$-$C_6$)alkyl, —C(=O)$NH_2$, —C(=O)NH(($C_1$-$C_6$)alkyl), —C(=O)N(($C_1$-$C_6$)alkyl)$_2$, —C(=O)NH—OH, —C(=O)NH—O—($C_1$-$C_6$)alkyl, —C(=O)—($C_1$-$C_6$)alkyl, —$CO_2$H, —C(=O)—O—($C_1$-$C_6$)alkyl, —$SO_2NH_2$, —$SO_2$NH(($C_1$-$C_6$)alkyl), —$SO_2$N(($C_1$-$C_6$)alkyl)$_2$, —$SO_2$—($C_1$-$C_6$)alkyl, —SO—($C_1$-$C_6$)alkyl, —($C_1$-$C_4$)alkylene-OH, —($C_1$-$C_4$)alkylene-O—($C_1$-$C_6$)alkyl, unsubstituted ($C_3$-$C_7$)cycloalkyl, unsubstituted 5 to 10 membered heterocyclyl comprising 1, 2, 3, or 4 heteroatoms independently selected from O, S, or N, or unsubstituted 3 or 4 membered heterocyclyl comprising 1 heteroatom selected from O, S, or N;

R$^b$ is selected from —H or ($C_1$-$C_6$)alkyl;
R$^c$ is selected from —H or ($C_1$-$C_6$)alkyl;
R$^d$ is selected from —H or ($C_1$-$C_6$)alkyl;
R$^e$ is selected from —H or ($C_1$-$C_6$)alkyl;

Z' is selected from unsubstituted ($C_6$-$C_{10}$) aryl, substituted ($C_6$-$C_{10}$) aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or unsubstituted ($C_3$-$C_7$)cycloalkyl, wherein, the substituted ($C_6$-$C_{10}$) aryl, the substituted 5 to 10 membered heteroaryl, the substituted 5 to 10 membered heterocyclyl, and the 3 or 4 membered heterocyclyl are substituted with 1, 2, or 3 substituents independently selected from —F, —Cl, —Br, —I, —C≡N, —$NO_2$, —C(=NH)—$NH_2$, —OH, —O—($C_1$-$C_6$)alkyl, —SH, —S—($C_1$-$C_6$)alkyl, —$OCF_3$, —$OCHF_2$, —$CH_2CHF_2$, —$CF_3$, —($C_1$-$C_6$)alkyl, —$NH_2$, —NH(($C_1$-$C_4$)alkyl), —N(($C_1$-$C_4$)alkyl)$_2$, —$NHSO_2$—($C_1$-$C_6$)alkyl, —NHC(=O)—($C_1$-$C_6$)alkyl, —C(=O)$NH_2$, —C(=O)NH(($C_1$-$C_6$)alkyl), —C(=O)N(($C_1$-$C_6$)alkyl)$_2$, —C(=O)NH—OH, —C(=O)NH—O—($C_1$-$C_6$)alkyl, —C(=O)—($C_1$-$C_6$)alkyl, —$CO_2$H, —C(=O)—O—($C_1$-$C_6$)alkyl, —$SO_2NH_2$, —$SO_2$NH(($C_1$-$C_6$)alkyl), —$SO_2$N(($C_1$-$C_6$)alkyl)$_2$, —$SO_2$—($C_1$-$C_6$)alkyl, —SO—($C_1$-$C_6$)alkyl, —($C_1$-$C_4$)alkylene-OH, or —($C_1$-$C_4$)alkylene-O—($C_1$-$C_6$)alkyl, and further wherein the substituted 5 to 10 membered heterocyclyl and the 3 or 4 membered heterocyclyl may also be substituted with a =O.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, X is O.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, X is S.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, X is $NR^a$ and $R^a$ is H.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, $R^1$ and $R^2$ are ($C_1$-$C_6$)alkyl; or $R^1$ and $R^2$ join to form a 3 to 7 membered cycloalkyl ring; or $R^1$ and $R^2$ join to form a 4 to 7 membered heterocyclyl ring comprising a heteroatom selected from O, S, or N.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, $R^1$ and $R^2$ are independently selected from —$CH_3$ or —$CH_2CH_3$.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, $R^1$ and $R^2$ are both —$CH_3$.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, $R^1$ and $R^2$ join to form a cyclobutyl, cyclopentyl, or cyclohexyl ring.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, Y is selected from cyclohexyl, cyclohexenyl, phenyl, tolyl, pyridyl, [1,2,4]triazolo[4,3-a]pyridinyl, or 3,4-dihydroisoquinolin-1(2H)-onyl. In some such embodiments, Y is cyclohexyl. In other such embodiments, Y is cyclohexenyl. In still other such embodiments, Y is phenyl. In still further such embodiments, Y is tolyl. In still other such embodiments, Y is pyridyl. In still other such embodiments, Y is [1,2,4]triazolo[4,3-a]pyridinyl. In still other embodiments, Y is 3,4-dihydroisoquinolin-1(2H)-onyl.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is selected from

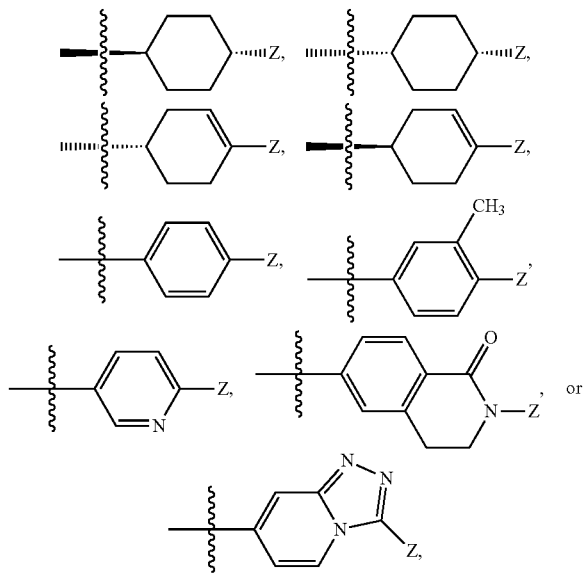

where the symbol ∿, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is

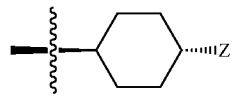

where the symbol ∿, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is

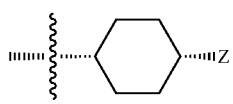

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is selected from

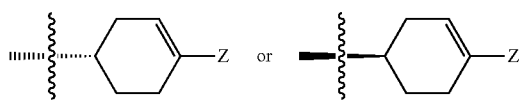

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is

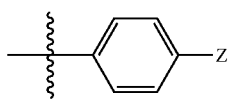

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is

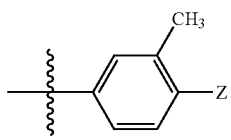

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is

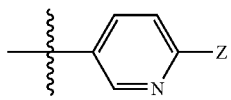

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is

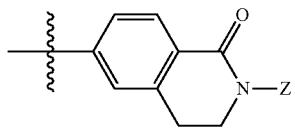

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is

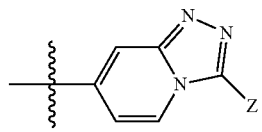

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is selected from

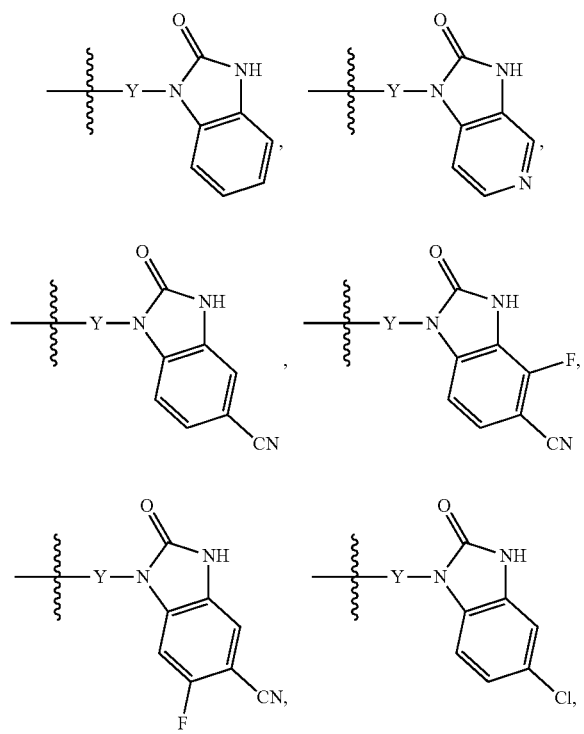

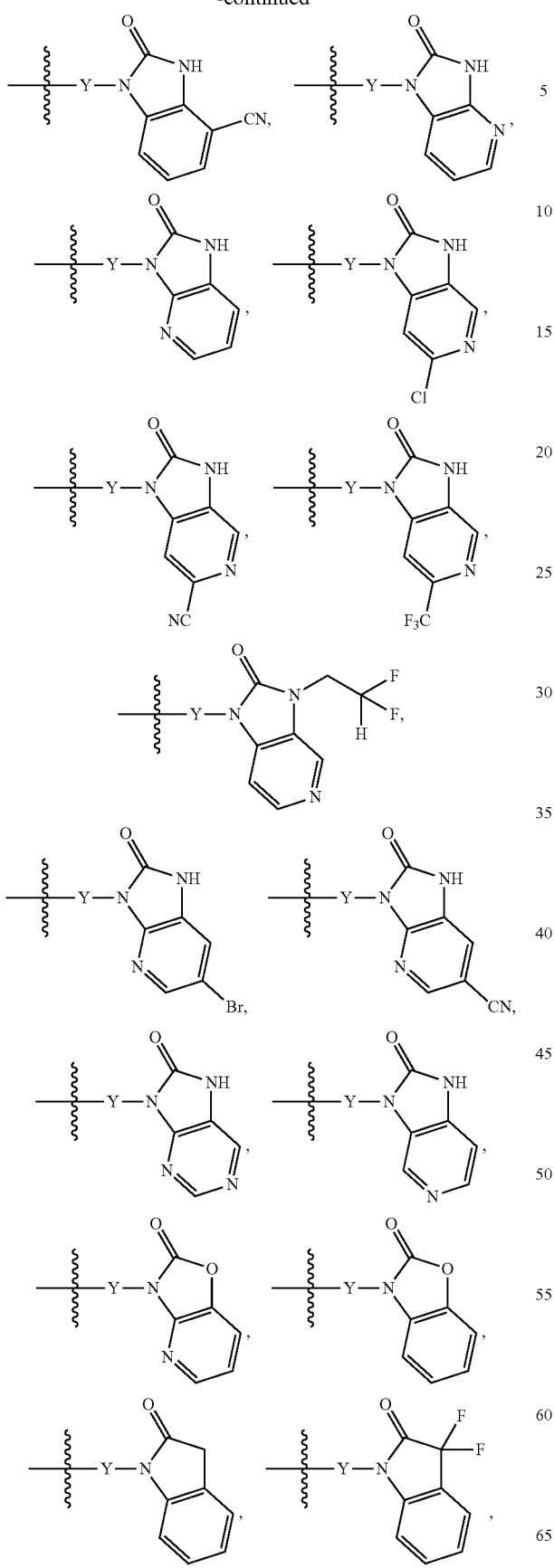
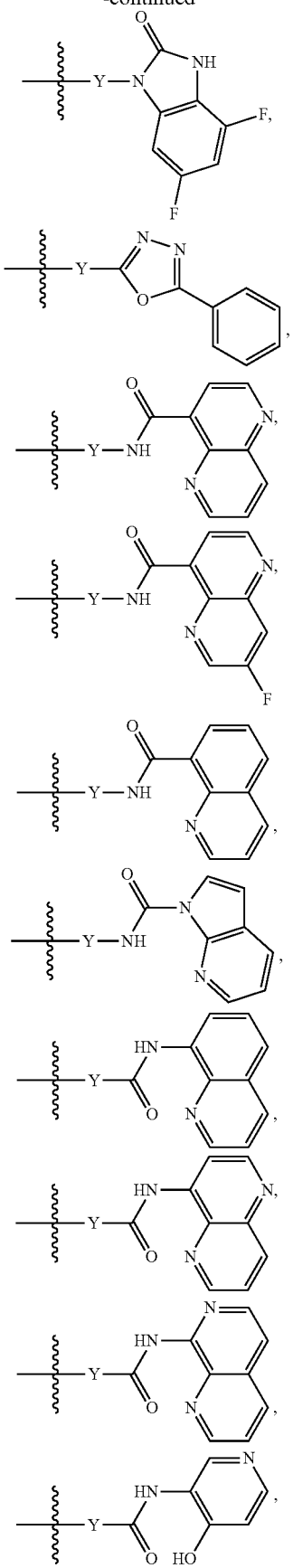

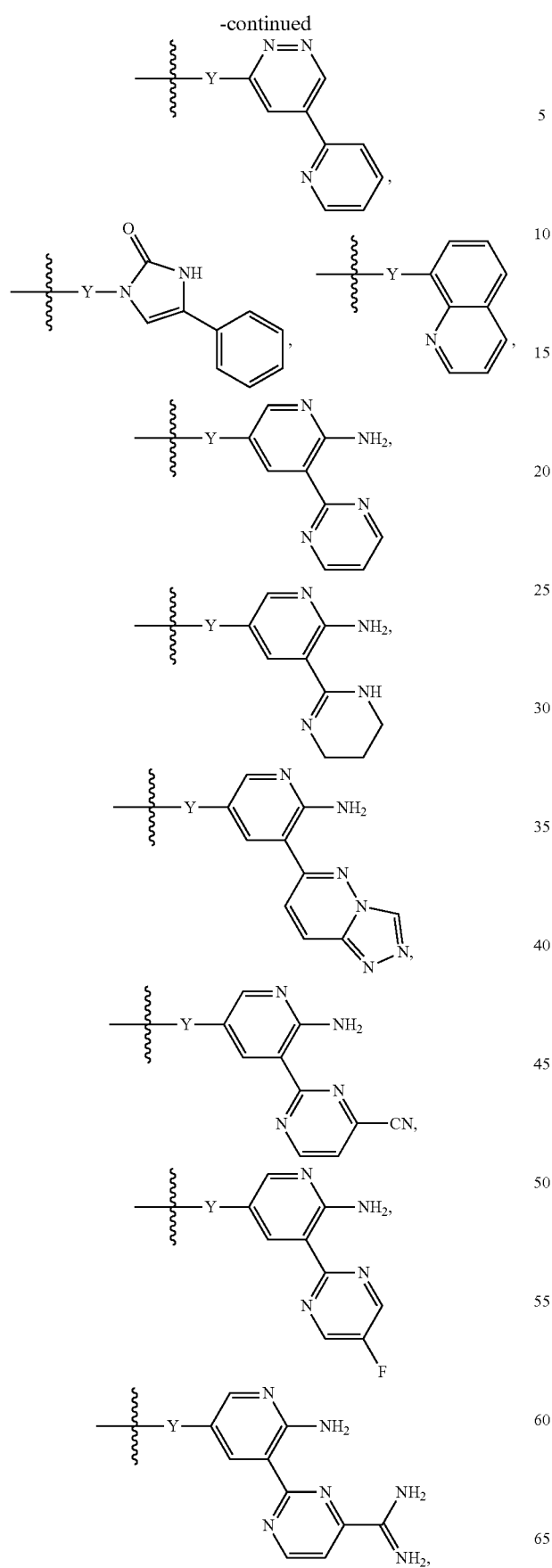
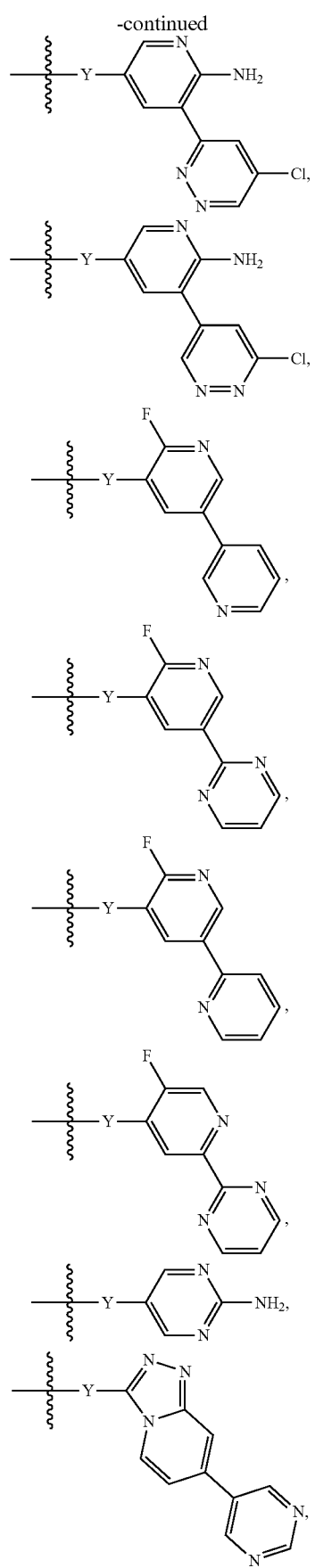

-continued

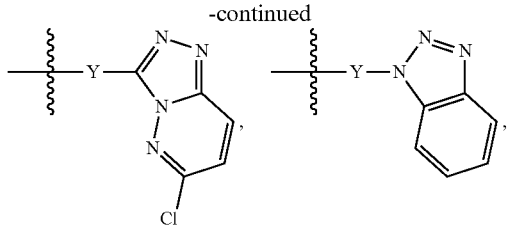

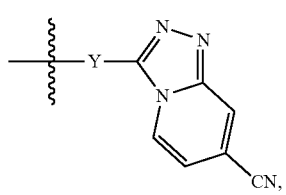

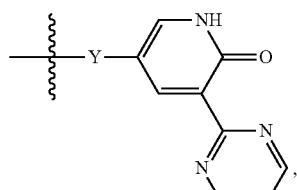

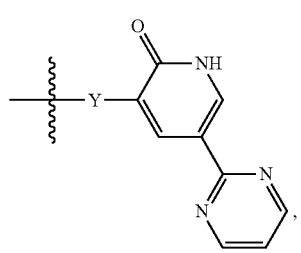

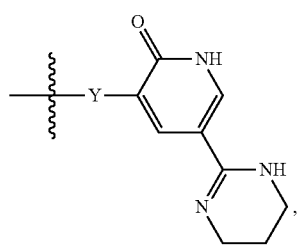

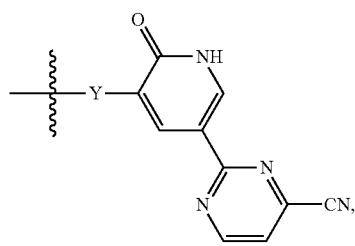

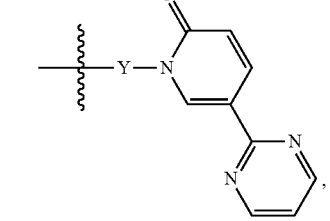

-continued

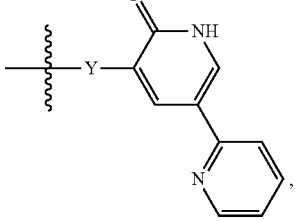

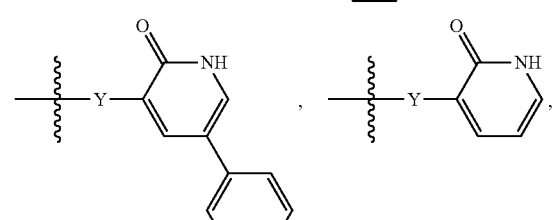

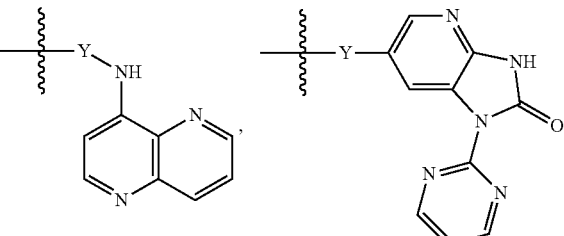

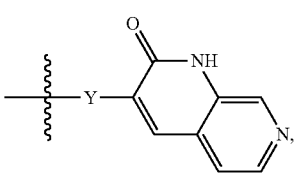

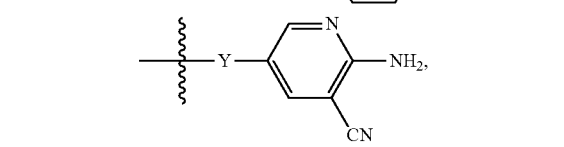

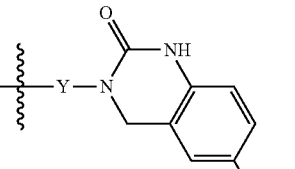

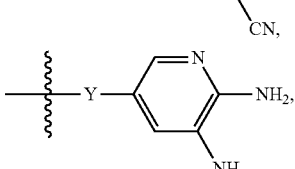

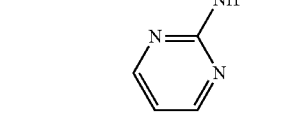

where the symbol ~~, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is selected from

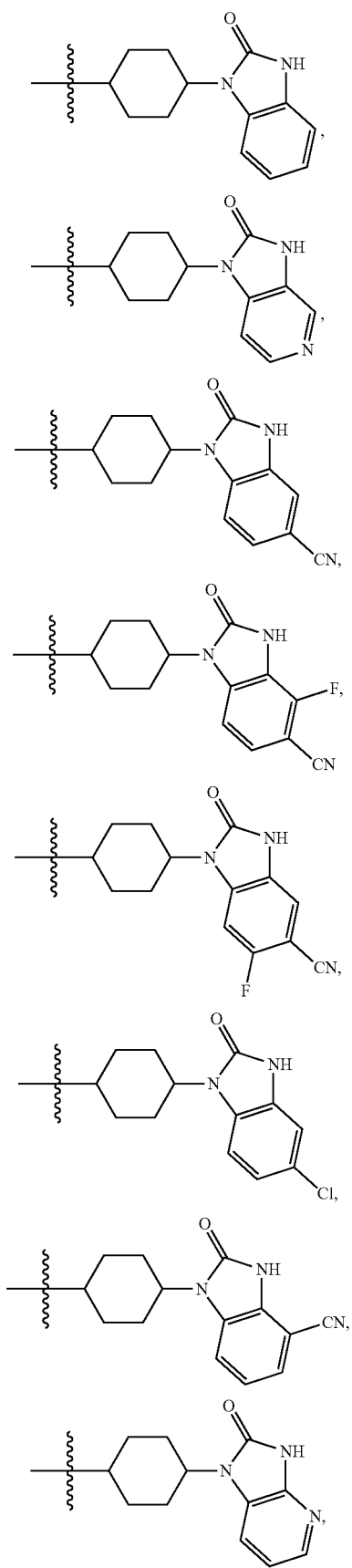
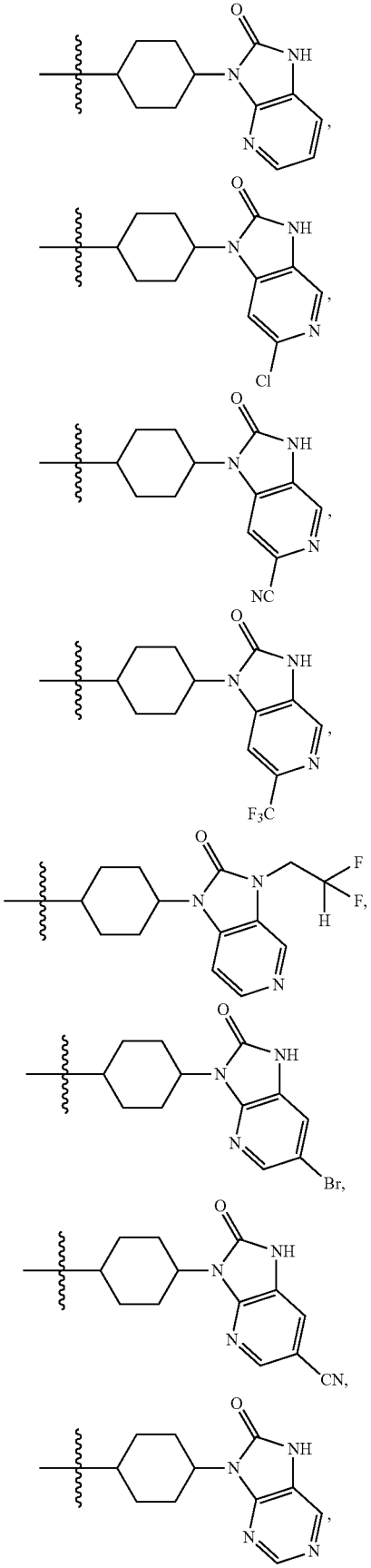

33
-continued
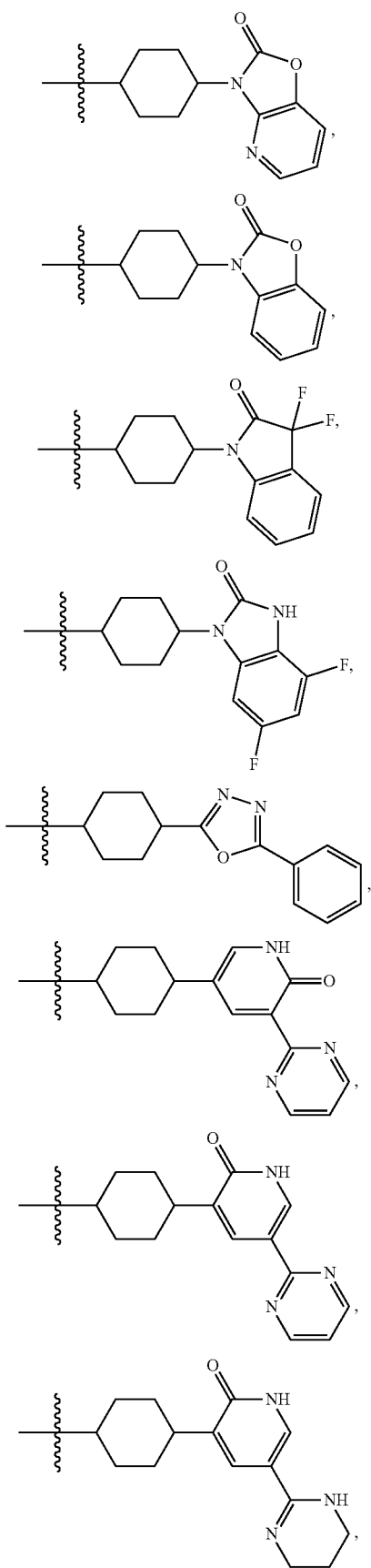
34
-continued
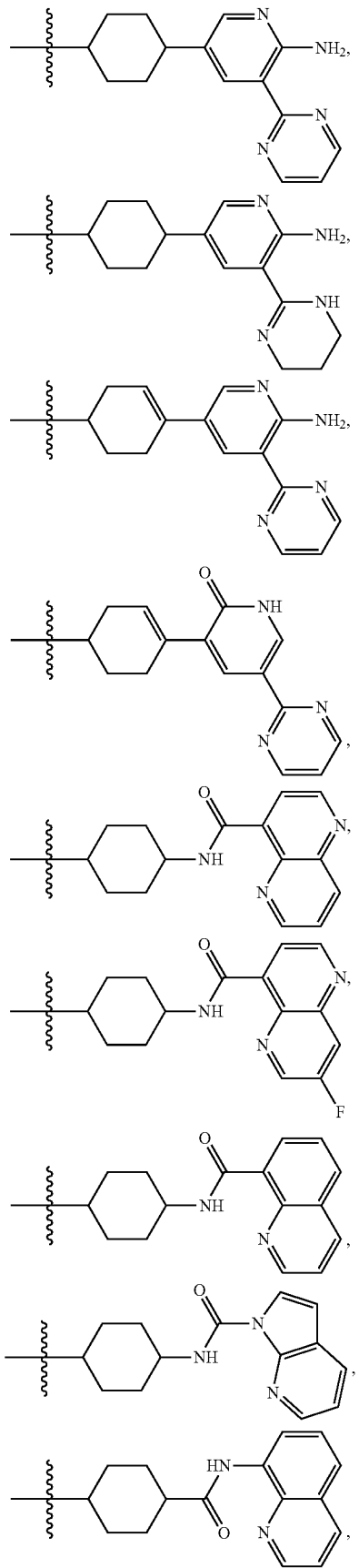

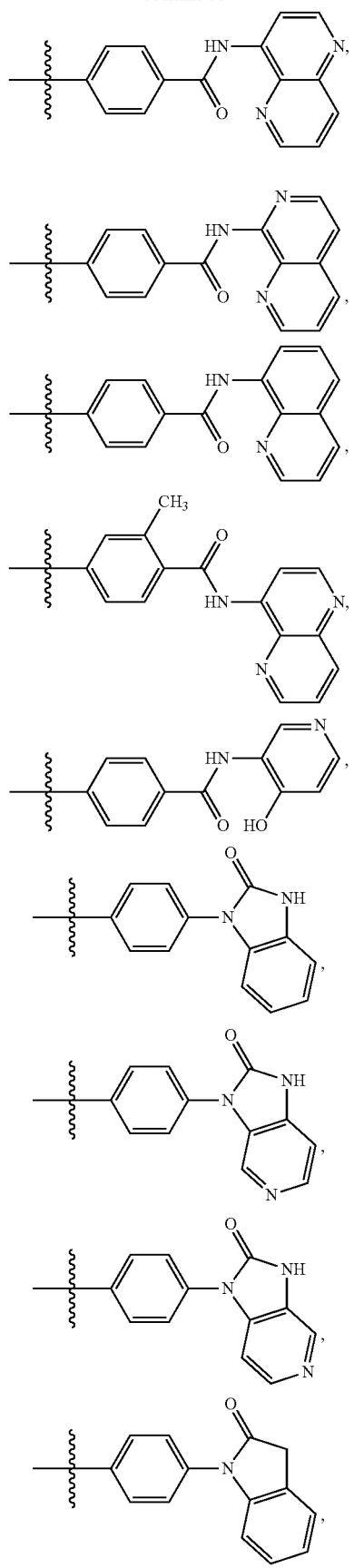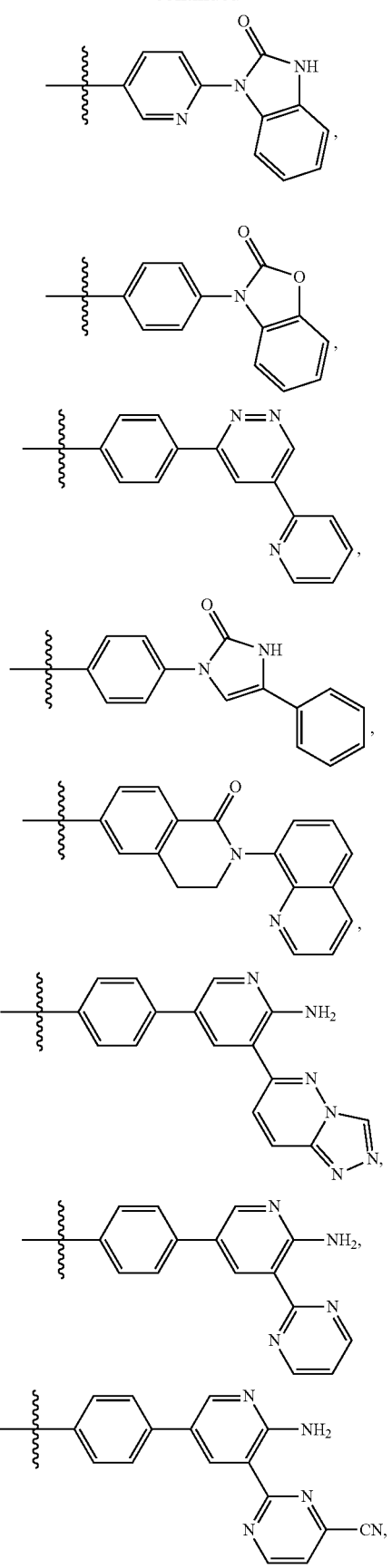

37
-continued
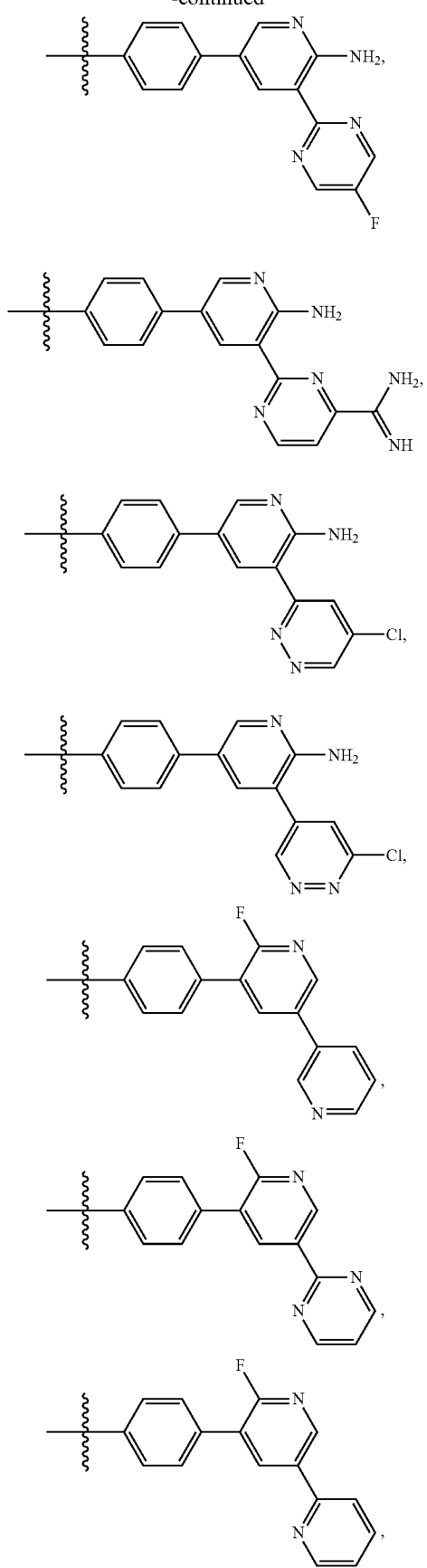
38
-continued
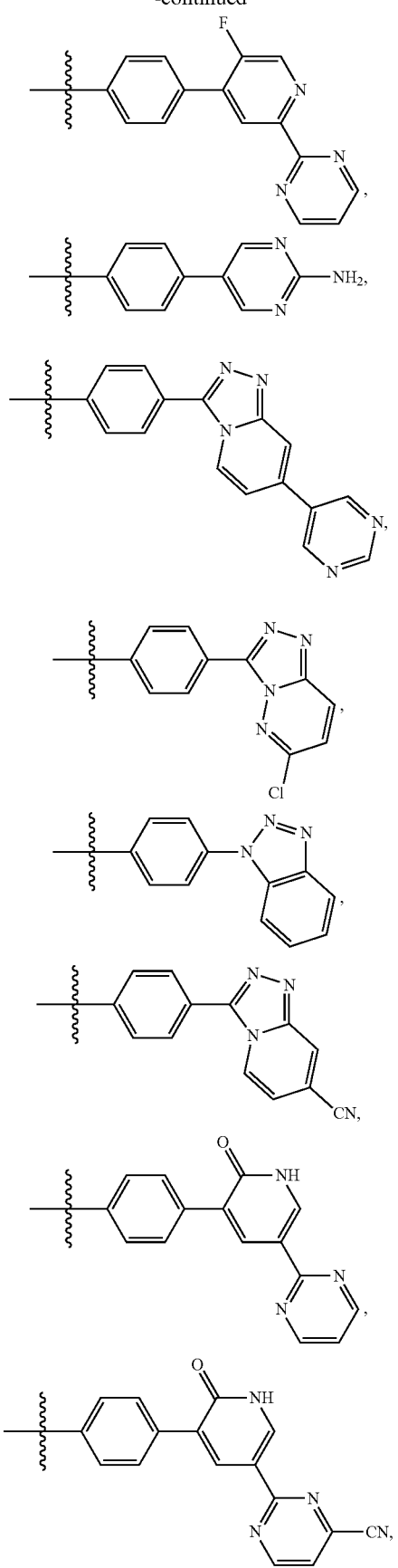

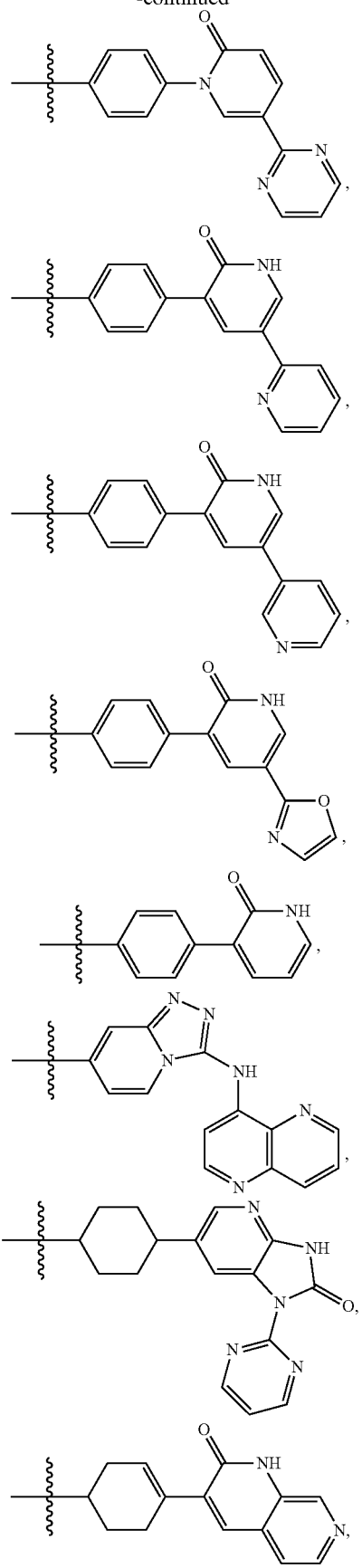

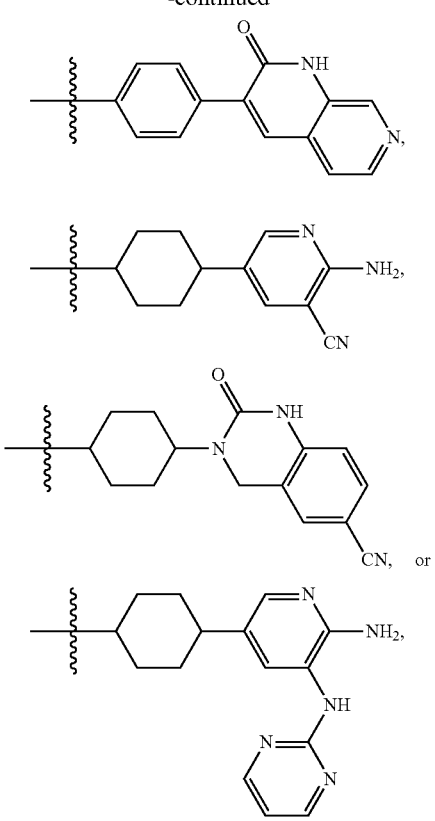

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is selected from

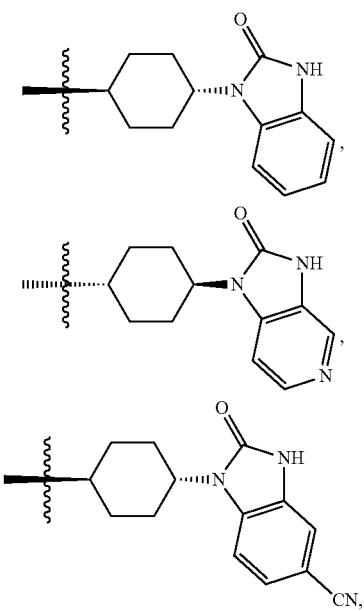

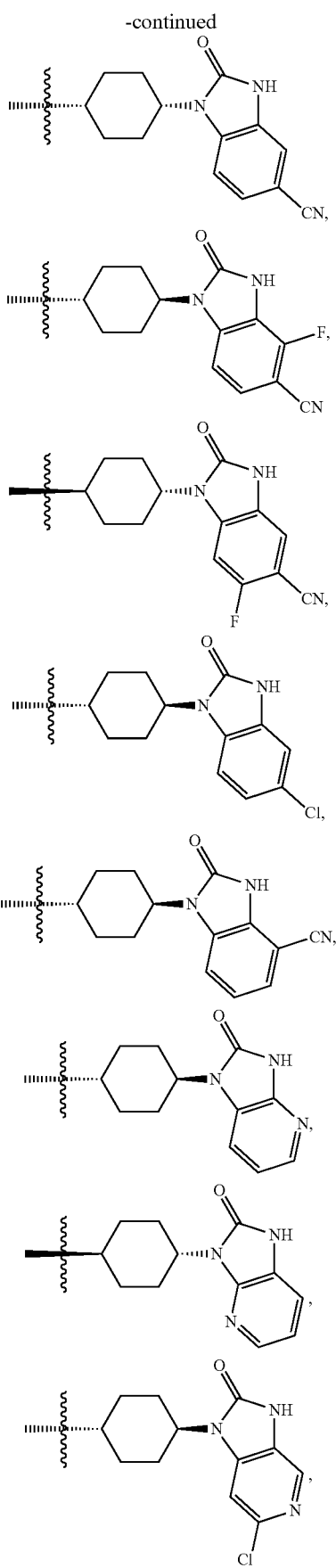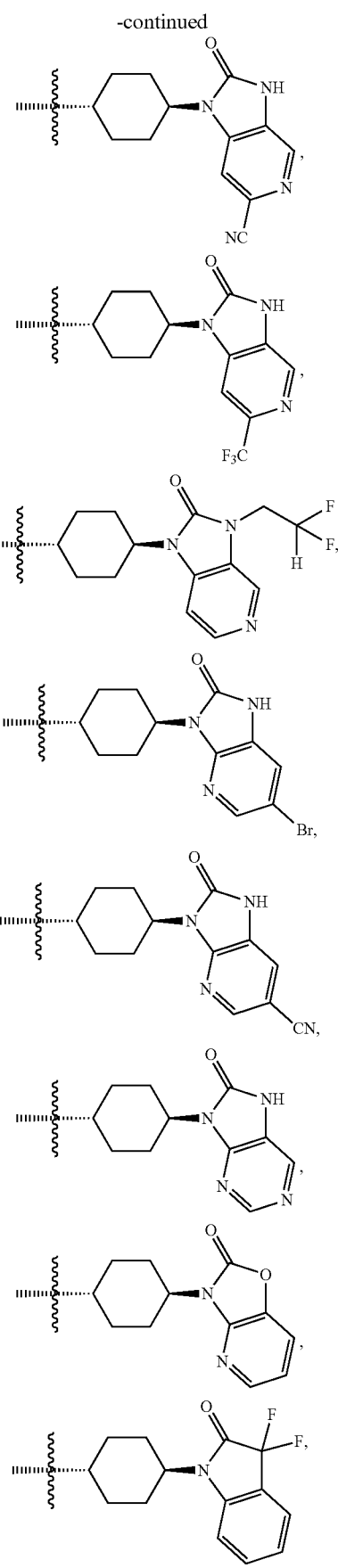

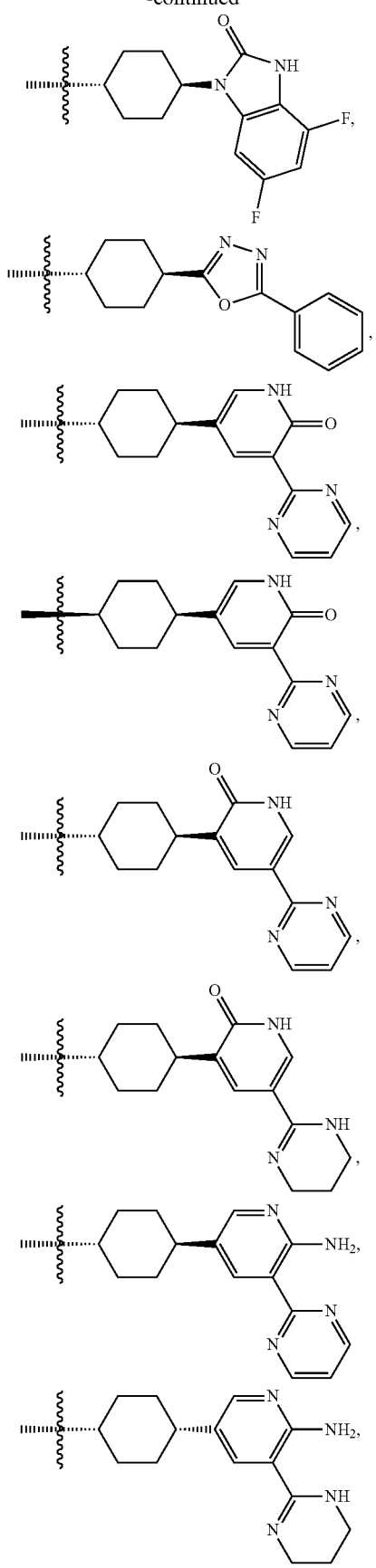
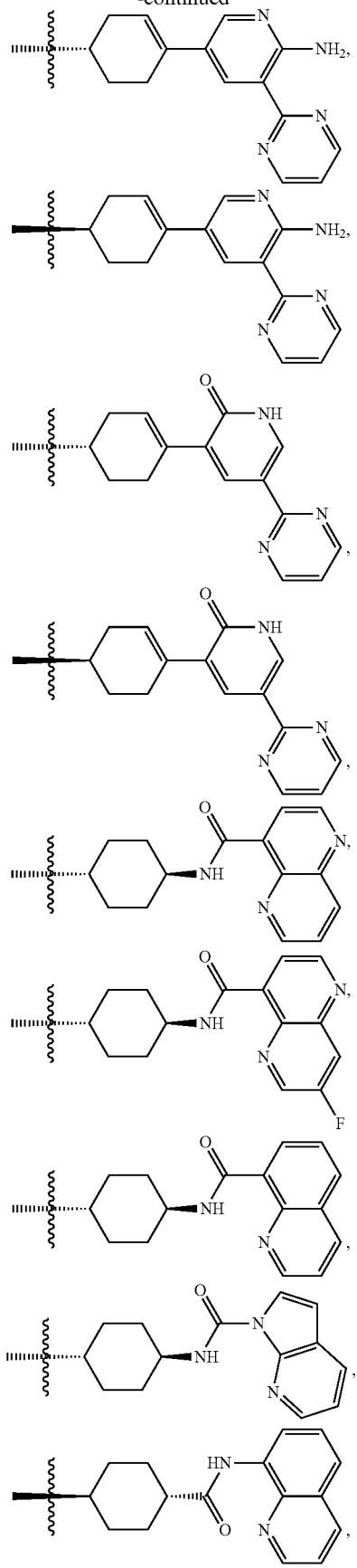

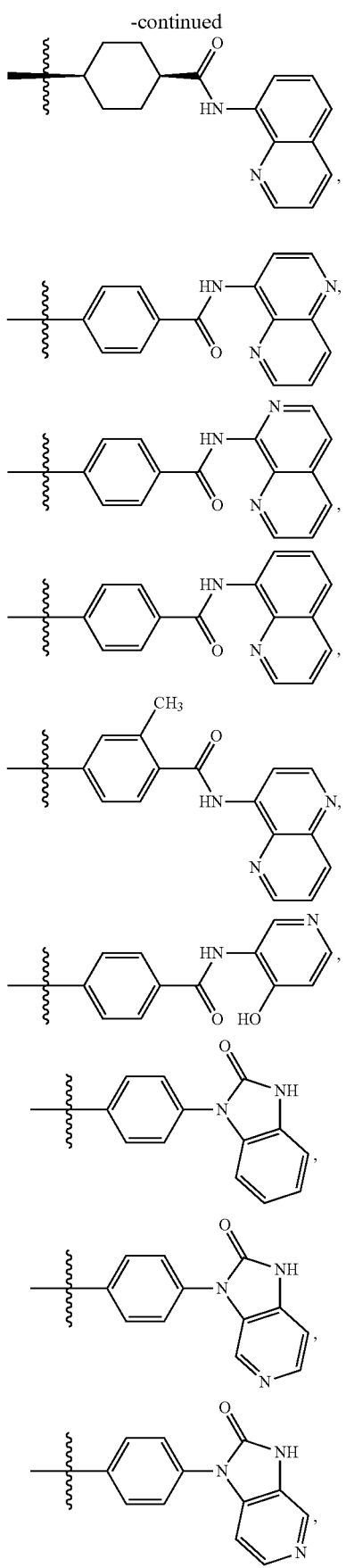
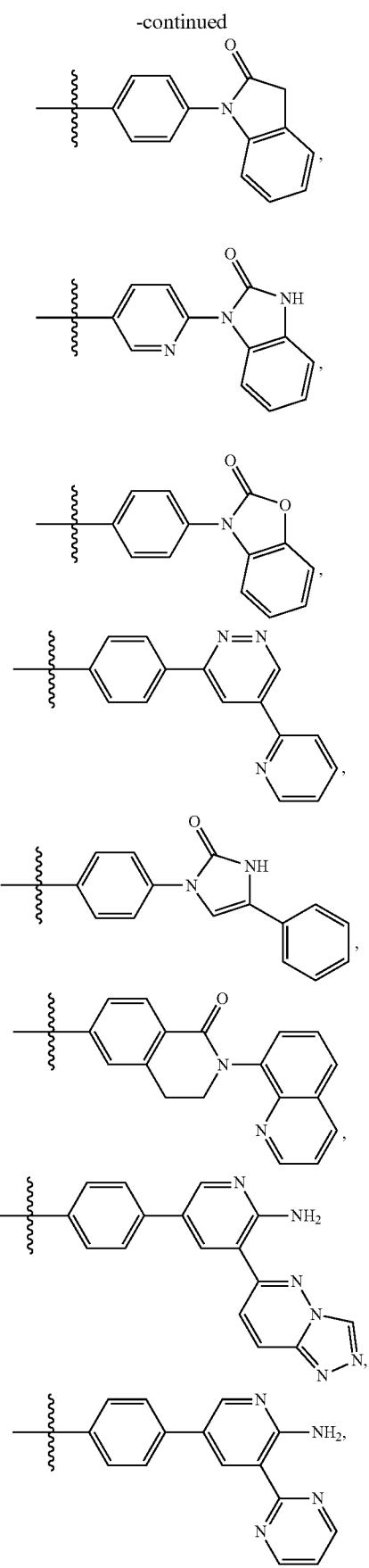

-continued
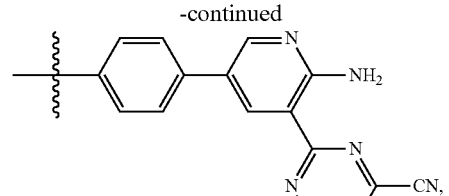
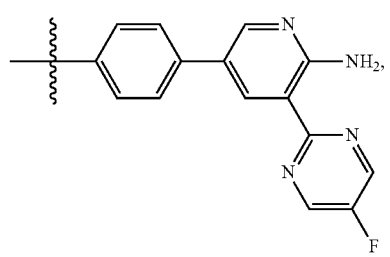
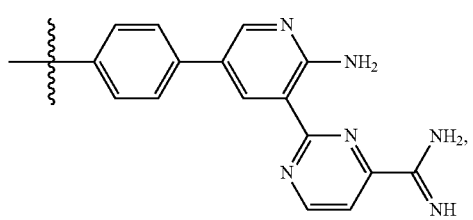
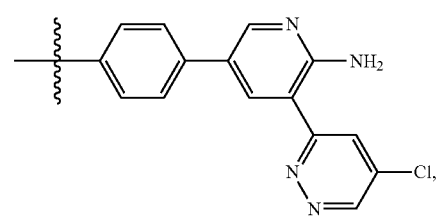
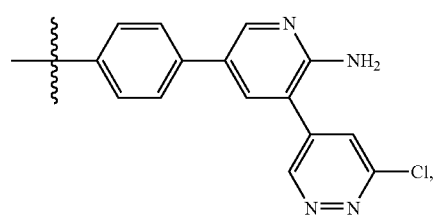
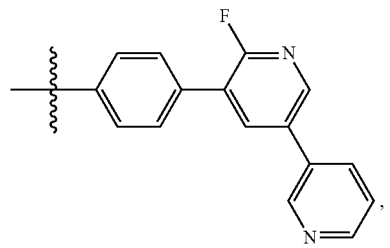
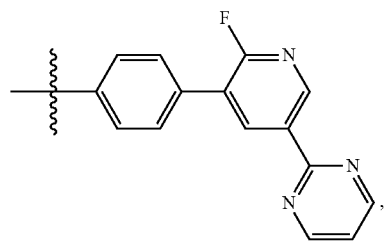
-continued
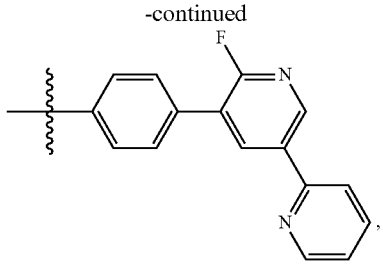
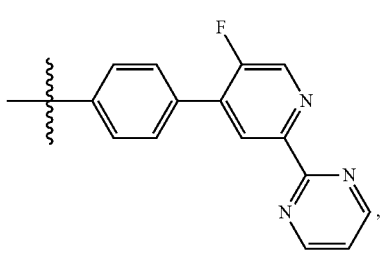
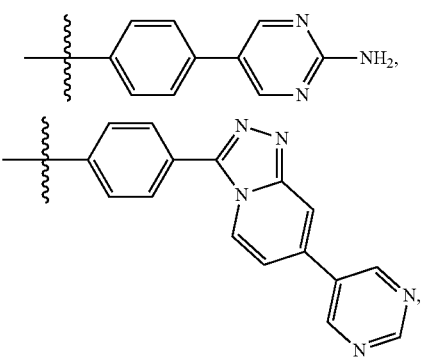
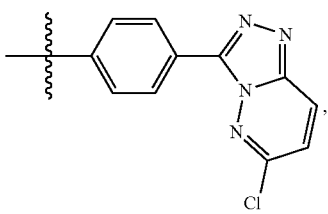
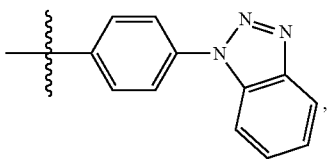
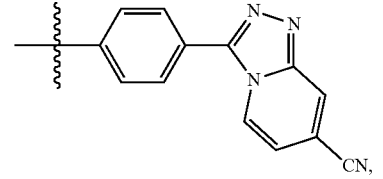
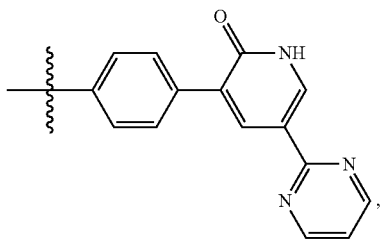

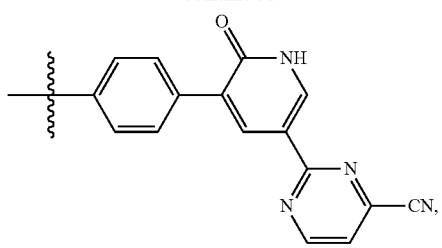

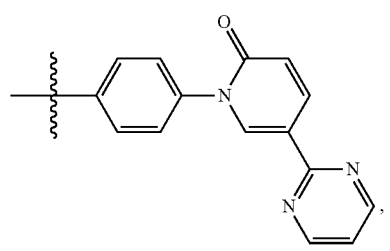

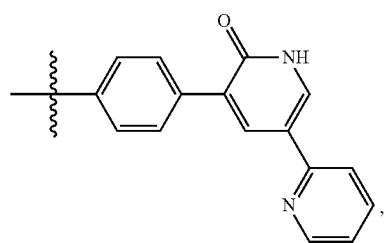

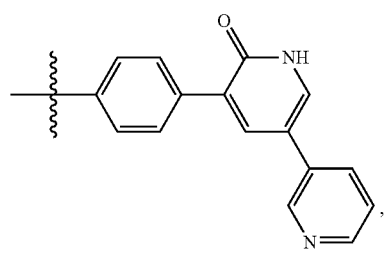

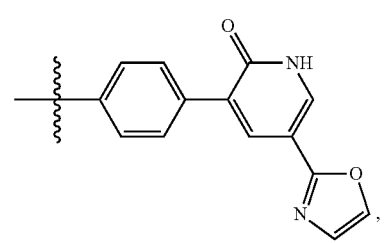

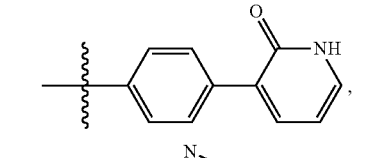

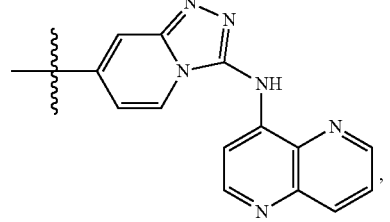

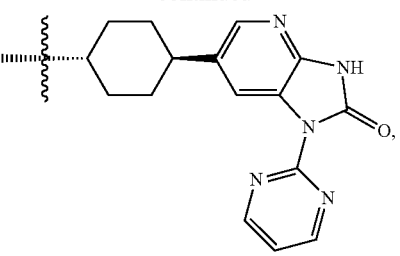

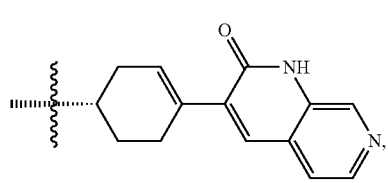

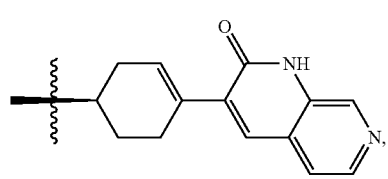

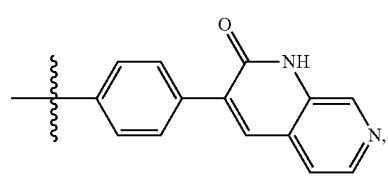

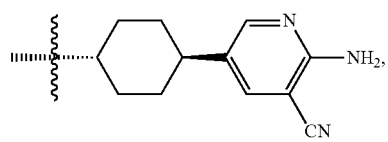

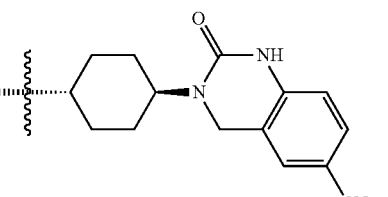

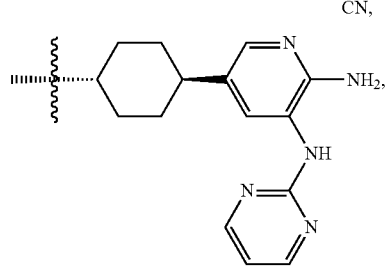

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, —Y—Z is selected from

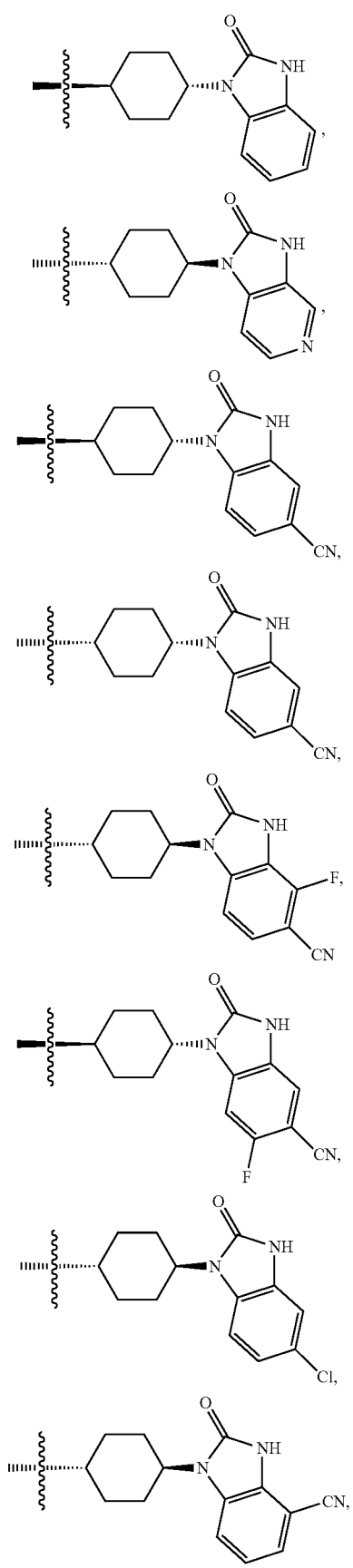
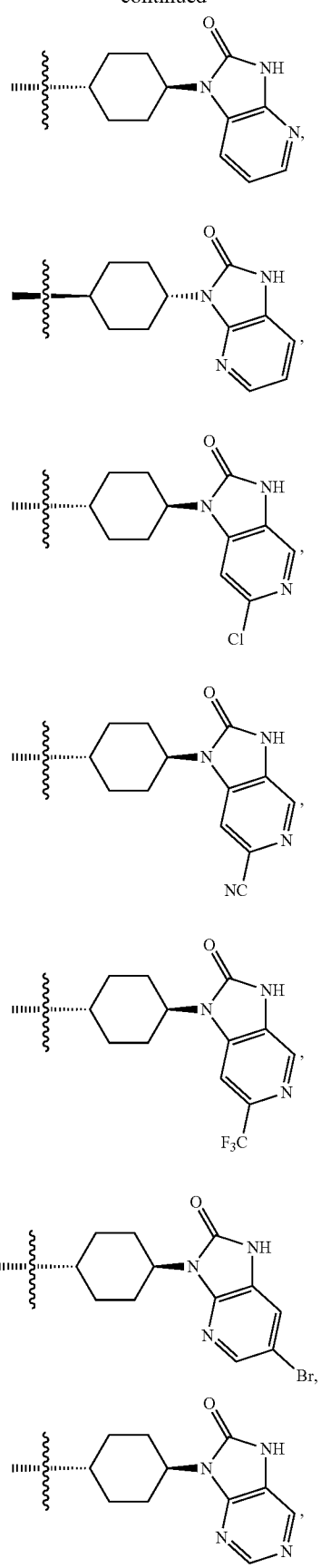

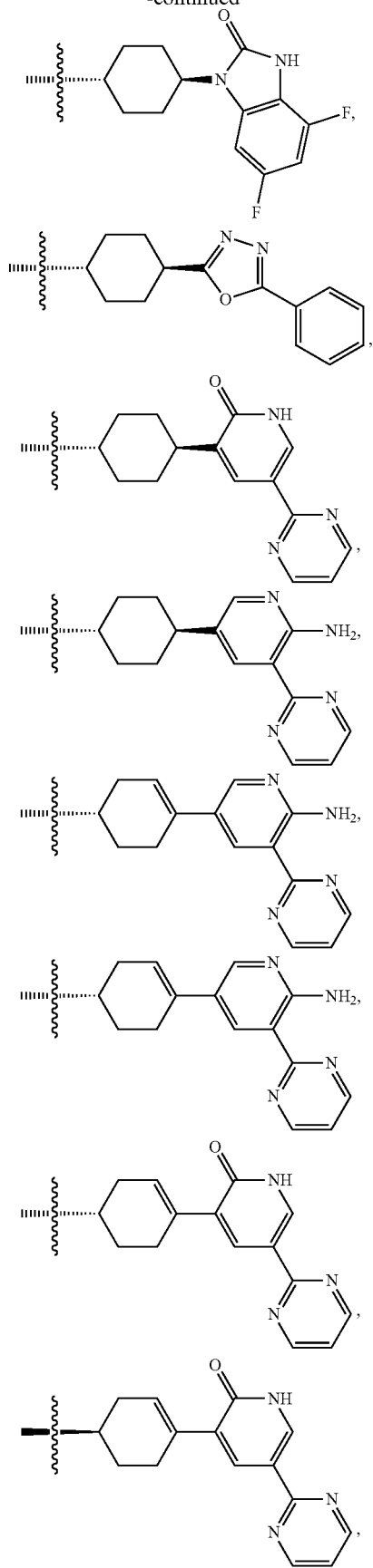
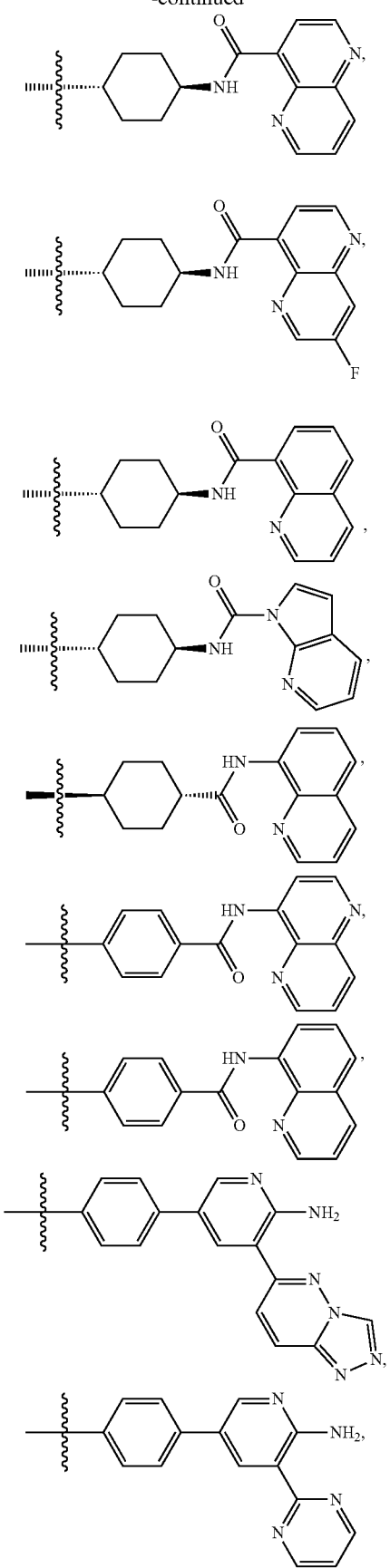

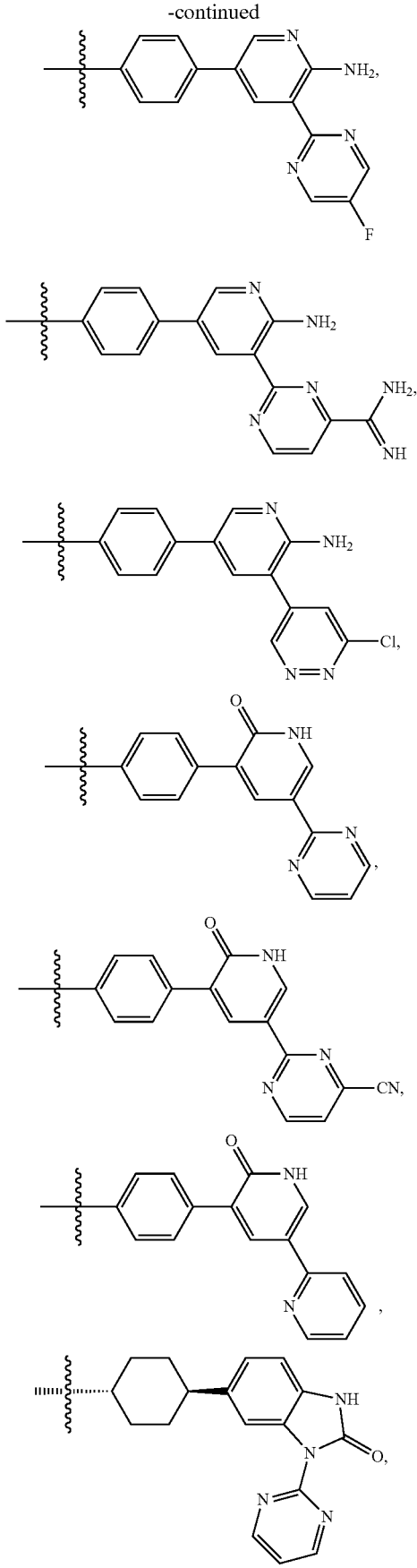
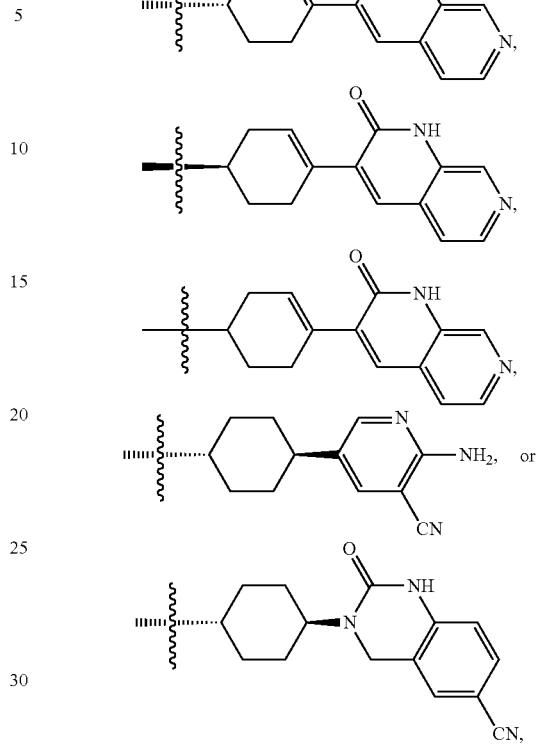

where the symbol ~~~, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, one of $R^3$ and W is selected from —H or $(C_1-C_6)$ alkyl. In some such embodiments, one of $R^3$ and W is —H.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, one of $R^3$ and W is selected from pyridyl, phenyl, or phenyl substituted with 1, 2, or 3 substituents independently selected from —F, —Cl, —Br, —I, —C≡N, —$NO_2$, —OH, —O—$(C_1-C_6)$alkyl, —$OCF_3$, —$OCHF_2$, —$CF_3$, —$(C_1-C_6)$alkyl, —$NH_2$, —NH$((C_1-C_4)$alkyl), —N$((C_1-C_4)$alkyl$)_2$, —$NHSO_2$—$(C_1-C_6)$alkyl, —NHC(=O)—$(C_1-C_6)$alkyl, —C(=O)$NH_2$, —C(=O)NH$((C_1-C_6)$alkyl), —C(=O)N$((C_1-C_6)$alkyl$)_2$, —C(=O)—$(C_1-C_6)$alkyl, —$CO_2$H, —C(=O)—O—$(C_1-C_6)$alkyl, —$SO_2NH_2$, —$SO_2$NH$((C_1-C_6)$alkyl), —$SO_2$N$((C_1-C_6)$alkyl$)_2$, —$SO_2$—$(C_1-C_6)$alkyl, or —SO—$(C_1-C_6)$alkyl. In some such embodiments, one of $R^3$ and W is selected from pyridyl, phenyl, or phenyl substituted with 1, 2, or 3 substituents independently selected from —F, —Cl, —Br, —O—$(C_1-C_6)$alkyl, or —$(C_1-C_6)$alkyl. In other such embodiments, one of $R^3$ and W is selected from pyridyl, phenyl, or phenyl substituted with 1 substituent selected from —F, —Cl, —$OCH_3$, or —$CH_3$. In still other such embodiments, one of $R^3$ and W is phenyl.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, one of $R^3$ and W is selected from

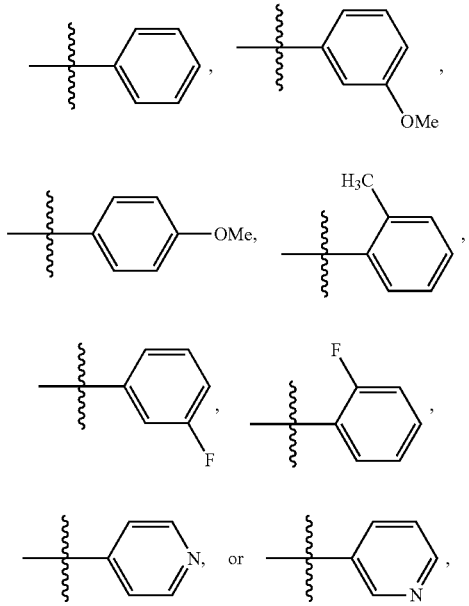

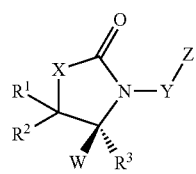

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, the compound of Formula I is a compound of Formula IA

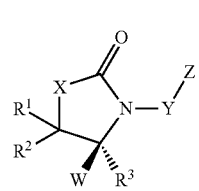

IA and W is selected from pyridyl, phenyl, or phenyl substituted with 1, 2, or 3 substituents independently selected from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, or —SO—(C$_1$-C$_6$)alkyl. In some such embodiments, W is selected from pyridyl, phenyl, or phenyl substituted with 1, 2, or 3 substituents independently selected from —F, —Cl, —Br, —O—(C$_1$-C$_6$)alkyl, or —(C$_1$-C$_6$)alkyl. In other such embodiments, W is selected from pyridyl, phenyl, or phenyl substituted with 1 substituent selected from —F, —Cl, —OCH$_3$, or —CH$_3$. In still other such embodiments, W is phenyl. In still other embodiments, W is selected from

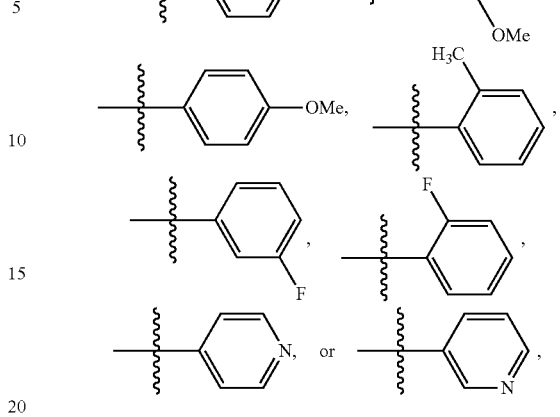

where the symbol ⌇, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, the compound of Formula I is a compound of Formula IA

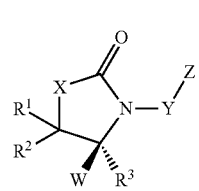

IA and $R^3$ is selected from pyridyl, phenyl, or phenyl substituted with 1, 2, or 3 substituents independently selected from from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, or —SO—(C$_1$-C$_6$)alkyl. In some such embodiments, $R^3$ is selected from pyridyl, phenyl, or phenyl substituted with 1, 2, or 3 substituents independently selected from —F, —Cl, —Br, —O—(C$_1$-C$_6$)alkyl, or —(C$_1$-C$_6$)alkyl. In other such embodiments, $R^3$ is selected from pyridyl, phenyl, or phenyl substituted with 1 substituent selected from —F, —Cl, —OCH$_3$, or —CH$_3$. In still other such embodiments, $R^3$ is phenyl. In still other embodiments, $R^3$ is selected from

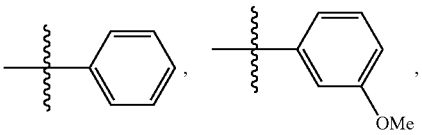

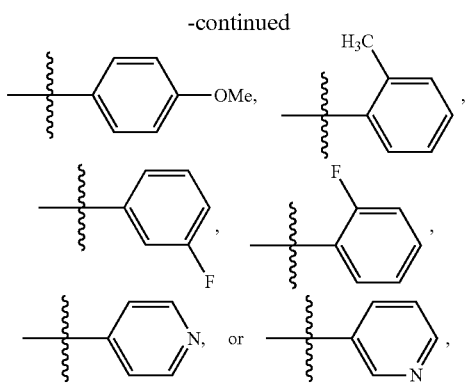

where the symbol ~~~, when drawn across a bond, indicates the point of attachment to the rest of the molecule.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, one of $R^3$ and W is —$C(CH_3)_2$—CN.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, one of $R^3$ and W is an unsubstituted 5 to 10 membered heterocyclyl or is a substituted 5 to 10 membered heterocyclyl. In some such embodiments, one of $R^3$ and W is a 4-, 5-, or 6-membered heterocyclyl. In still other such embodiments, one of $R^3$ and W is a 4-, 5-, or 6-membered heterocyclyl that includes one O atom.

In some embodiments of the compound of Formula I, or the pharmaceutically acceptable salt thereof, the tautomer thereof, the pharmaceutically acceptable salt of the tautomer, the stereoisomer of any of the foregoing, or the mixture thereof, the compound of Formula I is one of the compounds of Examples 1-131.

In another aspect, the invention provides a compound of Formula II:

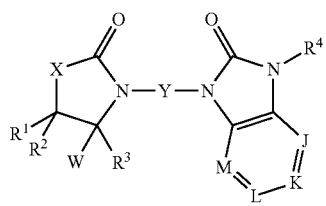

or a pharmaceutically acceptable salt thereof, a tautomer thereof, a pharmaceutically acceptable salt of the tautomer, a stereoisomer of any of the foregoing, or a mixture thereof,
wherein:
$R^1$ and $R^2$ are independently selected from H, $(C_1-C_6)$ alkyl, $(C_1-C_6)$haloalkyl, $(C_1-C_6)$perhaloalkyl, unsubstituted $(C_6-C_{10})$aryl, substituted $(C_6-C_{10})$aryl, unsubstituted 5 to 10 membered heteroaryl comprising 1, 2, or 3 heteroatoms independently selected from O, S, or N, substituted 5 to 10 membered heteroaryl comprising 1, 2, or 3 heteroatoms independently selected from O, S, or N, unsubstituted $(C_3-C_7)$ cycloalkyl, substituted $(C_3-C_7)$cycloalkyl, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N; or $R^1$ and $R^2$ join to form a 3 to 7 membered cycloalkyl ring; or $R^1$ and $R^2$ join to form a 4 to 7 membered heterocyclyl ring comprising a heteroatom selected from O, S, or N; wherein the substituted $(C_6-C_{10})$aryl and the substituted 5 to 10 membered heteroaryl are substituted with 1, 2, or 3 substituents independently selected from —F, —Cl, —Br, —I, —C≡N, —$NO_2$, —OH, —O—$(C_1-C_6)$alkyl, —SH, —S—$(C_1-C_6)$ alkyl, —$OCF_3$, —$OCHF_2$, —$CF_3$, —$(C_1-C_6)$alkyl, —$NH_2$, —NH$((C_1-C_4)$alkyl), —N$((C_1-C_4)$alkyl$)_2$, —$NHSO_2$—$(C_1-C_6)$alkyl, —NHC(═O)—$(C_1-C_6)$alkyl, —C(═O)$NH_2$, —C(═O)NH$((C_1-C_6)$alkyl), —C(═O)N$((C_1-C_6)$alkyl$)_2$, —C(═O)NH—OH, —C(═O)NH—O—$(C_1-C_6)$alkyl, —C(═O)—$(C_1-C_6)$alkyl, —$CO_2H$, —C(═O)—O—$(C_1-C_6)$alkyl, —$SO_2NH_2$, —$SO_2$NH$((C_1-C_6)$alkyl), —$SO_2$N$((C_1-C_6)$alkyl$)_2$, —$SO_2$—$(C_1-C_6)$alkyl, —SO—$(C_1-C_6)$ alkyl, —$(C_1-C_4)$alkylene-OH, or —$(C_1-C_4)$alkylene-O—$(C_1-C_6)$alkyl, wherein the substituted $(C_3-C_7)$cycloalkyl, the substituted 5 to 10 membered heterocyclyl, and the substituted 3 or 4 membered heterocyclyl are substituted with 1 or 2 substituents independently selected from —F, —Cl, —Br, —I, —C≡N, —$NO_2$, —OH, —O—$(C_1-C_6)$alkyl, —$OCF_3$, —$OCHF_2$, —$CF_3$, —$(C_1-C_6)$alkyl, —$NH_2$, —NH$((C_1-C_4)$ alkyl), —N$((C_1-C_4)$alkyl$)_2$, —C(═O)$NH_2$, —C(═O)NH $((C_1-C_6)$alkyl), —C(═O)N$((C_1-C_6)$alkyl$)_2$, —C(═O)—$(C_1-C_6)$alkyl, —$CO_2H$, or —C(═O)—O—$(C_1-C_6)$alkyl;

$R^3$ is selected from —H, $(C_1-C_6)$alkyl, $(C_1-C_6)$haloalkyl, $(C_1-C_6)$perhaloalkyl, unsubstituted $(C_6-C_{10})$aryl, substituted $(C_6-C_{10})$aryl, unsubstituted 5 to 10 membered heteroaryl comprising 1, 2, or 3 heteroatoms independently selected from O, S, or N, substituted 5 to 10 membered heteroaryl comprising 1, 2, or 3 heteroatoms independently selected from O, S, or N, unsubstituted $(C_3-C_7)$cycloalkyl, substituted $(C_3-C_7)$cycloalkyl, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or —$C(CH_3)_2$—CN, wherein the substituted $(C_6-C_{10})$aryl and the substituted 5 to 10 membered heteroaryl are substituted with 1, 2, or 3 substituents independently selected from —F, —Cl, —Br, —I, —C≡N, —$NO_2$, —OH, —O—$(C_1-C_6)$alkyl, —SH, —S—$(C_1-C_6)$alkyl, —$OCF_3$, —$OCHF_2$, —$CF_3$, —$(C_1-C_6)$alkyl, —$NH_2$, —NH$((C_1-C_4)$alkyl), —N$((C_1-C_4)$alkyl$)_2$, —$NHSO_2$—$(C_1-C_6)$alkyl, —NHC(═O)—$(C_1-C_6)$alkyl, —C(═O)$NH_2$, —C(═O)NH$((C_1-C_6)$alkyl), —C(═O)N $((C_1-C_6)$alkyl$)_2$, —C(═O)NH—OH, —C(═O)NH—O—$(C_1-C_6)$alkyl, —C(═O)—$(C_1-C_6)$alkyl, —$CO_2H$, —C(═O)—O—$(C_1-C_6)$alkyl, —$SO_2NH_2$, —$SO_2$NH$((C_1-C_6)$alkyl), —$SO_2$N$((C_1-C_6)$alkyl$)_2$, —$SO_2$—$(C_1-C_6)$alkyl, —SO—$(C_1-C_6)$alkyl, —$(C_1-C_4)$alkylene-OH, or —$(C_1-C_4)$ alkylene-O—$(C_1-C_6)$alkyl, wherein the substituted $(C_3-C_7)$ cycloalkyl, the substituted 5 to 10 membered heterocyclyl, and the substituted 3 or 4 membered heterocyclyl are substituted with 1 or 2 substituents independently selected from —F, —Cl, —Br, —I, —C≡N, —$NO_2$, —OH, —O—$(C_1-C_6)$alkyl, —$OCF_3$, —$OCHF_2$, —$CF_3$, —$(C_1-C_6)$alkyl, —$NH_2$, —NH$((C_1-C_4)$alkyl), —N$((C_1-C_4)$alkyl$)_2$, —C(═O)$NH_2$, —C(═O)NH$((C_1-C_6)$alkyl), —C(═O)N ((C$_1$-C$_6$)alkyl)$_2$, —C(=O)—(C$_1$-C$_6$)alkyl, —CO$_2$H, or —C(=O)—O—(C$_1$-C$_6$)alkyl;

W is selected from —H, (C$_1$-C$_6$)alkyl, (C$_1$-C$_6$)haloalkyl, (C$_1$-C$_6$)perhaloalkyl, unsubstituted (C$_6$-C$_{10}$)aryl, substituted (C$_6$-C$_{10}$)aryl, unsubstituted 5 to 10 membered heteroaryl comprising 1, 2, or 3 heteroatoms independently selected from O, S, or N, substituted 5 to 10 membered heteroaryl comprising 1, 2, or 3 heteroatoms independently selected from O, S, or N, unsubstituted (C$_3$-C$_7$)cycloalkyl, substituted (C$_3$-C$_7$)cycloalkyl, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or —C(CH$_3$)$_2$—CN, wherein the substituted (C$_6$-C$_{10}$)aryl and the substituted 5 to 10 membered heteroaryl are substituted with 1, 2, or 3 substituents independently selected from —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—(C$_1$-C$_6$)alkyl, —(C$_1$-C$_4$)alkylene-OH, or —(C$_1$-C$_4$)alkylene-O—(C$_1$-C$_6$)alkyl, wherein the substituted (C$_3$-C$_7$)cycloalkyl, the substituted 5 to 10 membered heterocyclyl, and the substituted 3 or 4 membered heterocyclyl are substituted with 1 or 2 substituents independently selected from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, or —C(=O)—O—(C$_1$-C$_6$)alkyl;

X is selected from O, S, or NR$^a$, wherein R$^a$ is selected from —H, (C$_1$-C$_6$)alkyl, or —CH$_2$-phenyl;

J is N or CR$^5$;
K is N or CR$^6$;
L is N or CR$^7$;
M is N or CR$^8$;
wherein 0, 1, or 2 of J, K, L, and M are N;

R$^4$ is selected from —H, —(C$_1$-C$_6$)alkyl, (C$_1$-C$_6$)haloalkyl, or (C$_1$-C$_6$)perhaloalkyl;

R$^5$ is selected from —H, —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—(C$_1$-C$_6$)alkyl, —(C$_1$-C$_4$)alkylene-OH, or —(C$_1$-C$_4$)alkylene-O—(C$_1$-C$_6$)alkyl;

R$^6$ is selected from —H, —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—(C$_1$-C$_6$)alkyl, —(C$_1$-C$_4$)alkylene-OH, or —(C$_1$-C$_4$)alkylene-O—(C$_1$-C$_6$)alkyl;

R$^7$ is selected from —H, —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—(C$_1$-C$_6$)alkyl, —(C$_1$-C$_4$)alkylene-OH, or —(C$_1$-C$_4$)alkylene-O—(C$_1$-C$_6$)alkyl;

R$^8$ is selected from —H, —F, —Cl, —Br, —I, —C≡N, —NO$_2$, —OH, —O—(C$_1$-C$_6$)alkyl, —SH, —S—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)NH—OH, —C(=O)NH—O—(C$_1$-C$_6$)alkyl, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, —SO—(C$_1$-C$_6$)alkyl, —(C$_1$-C$_4$)alkylene-OH, or —(C$_1$-C$_4$)alkylene-O—(C$_1$-C$_6$)alkyl;

wherein one of R$^5$, R$^6$, R$^7$, and R$^8$ may optionally be unsubstituted (C$_3$-C$_7$)cycloalkyl, unsubstituted 3 membered heterocycle comprising 1 heteroatom selected from O, S, or N, unsubstituted 4 membered heterocycle comprising 1 or 2 heteroatoms independently selected from O, S, or N, or unsubstituted 5 to 10 membered heterocyclyl comprising 1, 2, 3 or 4 heteroatoms independently selected from O, S, or N; and Y is selected from unsubstituted (C$_4$-C$_7$)cycloalkyl, substituted (C$_4$-C$_7$)cycloalkyl, unsubstituted (C$_4$-C$_7$)cycloalkenyl, substituted (C$_4$-C$_7$)cycloalkenyl, unsubstituted (C$_6$-C$_{10}$)aryl, substituted (C$_6$-C$_{10}$)aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 4 to 10 membered heterocyclyl comprising 1, 2, or 3 heteroatoms independently selected from O, S, or N, or substituted 4 to 10 membered heterocyclyl comprising 1, 2, or 3 heteroatoms independently selected from O, S, or N, wherein the substituted (C$_4$-C$_7$)cycloalkyl and substituted (C$_4$-C$_7$)cycloalkenyl are substituted with 1 or 2 substituents independently selected from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, or —C(=O)—O—(C$_1$-C$_6$)alkyl, and wherein the substituted (C$_6$-C$_{10}$)aryl, substituted 5 to 10 membered heteroaryl, and substituted 4 to 10 membered heterocyclyl are substituted with 1, 2, or 3 substituents independently selected from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, or —C(=O)—O—(C$_1$-

$C_6$)alkyl, and further wherein the substituted 4 to 10 membered heterocyclyl may also be substituted with a =O.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, X is O.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, X is S.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, X is $NR^a$ and $R^a$ is H.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, $R^1$ and $R^2$ are ($C_1$-$C_6$)alkyl; or $R^1$ and $R^2$ join to form a 3 to 7 membered cycloalkyl ring; or $R^1$ and $R^2$ join to form a 4 to 7 membered heterocyclyl ring comprising a heteroatom selected from O, S, or N.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, $R^1$ and $R^2$ are independently selected from —$CH_3$ or —$CH_2CH_3$.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, $R^1$ and $R^2$ are both —$CH_3$.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, one of $R^1$ and $R^2$ is —$CH_3$.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, $R^1$ and $R^2$ join to form a cyclobutyl, cyclopentyl, or cyclohexyl ring.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, one of $R^1$ and $R^2$ is —H.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, one of $R^1$ and $R^2$ is substituted ($C_6$-$C_{10}$)aryl or unsubstituted ($C_6$-$C_{10}$)aryl and the other of $R^1$ and $R^2$ is —H or —$CH_3$.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, one of $R^1$ and $R^2$ is substituted ($C_6$-$C_{10}$)aryl or unsubstituted ($C_6$-$C_{10}$)aryl and the other of $R^1$ and $R^2$ is —$CH_3$.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, one of $R^1$ and $R^2$ is substituted ($C_6$-$C_{10}$)aryl or unsubstituted ($C_6$-$C_{10}$)aryl.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, Y is selected from cyclohexyl, cyclohexenyl, phenyl, tolyl, pyridyl, [1,2,4]triazolo[4,3-a]pyridinyl, or 3,4-dihydroisoquinolin-1(2H)-onyl. In some such embodiments, Y is cyclohexyl. In other such embodiments, Y is cyclohexenyl. In still other such embodiments, Y is phenyl. In still further such embodiments, Y is tolyl. In still other such embodiments, Y is pyridyl. In still other such embodiments, Y is [1,2,4]triazolo[4,3-a]pyridinyl. In still other embodiments, Y is 3,4-dihydroisoquinolin-1(2H)-onyl.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, Y is selected from

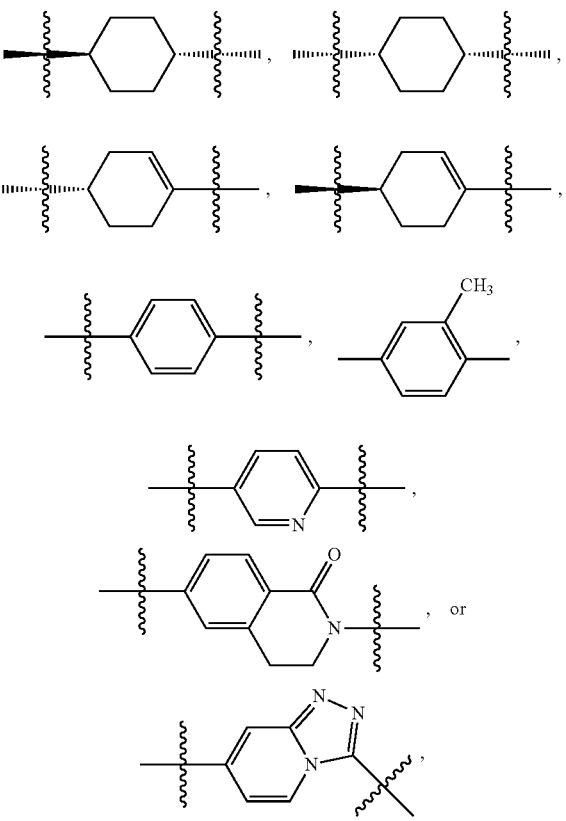

where the symbol ~~~, when drawn across a bond, indicates the point of attachment to the rest of the molecule.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, the compound of Formula II is a compound of Formula IIA

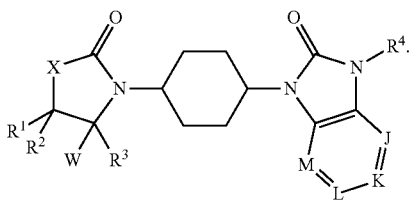

IIA

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, the compound of Formula II is a compound of Formula IIB

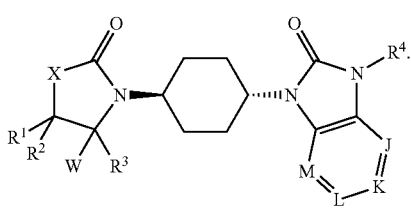

IIB

In some embodiments of the compound of Formula II, IIA, or IIB, or the pharmaceutically acceptable salt thereof, the tautomer thereof, the pharmaceutically acceptable salt of the tautomer, the stereoisomer of any of the foregoing, or the mixture thereof, 0 of J, K, L, and M is N.

In some embodiments of the compound of Formula II, IIA, or IIB, or the pharmaceutically acceptable salt thereof, the tautomer thereof, the pharmaceutically acceptable salt of the tautomer, the stereoisomer of any of the foregoing, or the mixture thereof, 1 of J, K, L, and M is N. In some such embodiments, J is N. In other such embodiments, K is N. In still other such embodiments, L is N. In still other such embodiments, M is N.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, 2 of J, K, L, and M are N. In some such embodiments, J and K are N. In other such embodiments, J and L are N. In still other such embodiments, J and M are N. In other such embodiments, K and L are N. In still further such embodiments, K and M are N. In still further such embodiments, L and M are N.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, at least one of $R^5$, $R^6$, $R^7$ or $R^8$ is selected from —F, —Cl, —Br, —C≡N, —CF$_3$, or —(C$_1$-C$_6$)alkyl. In some such embodiments, at least one of $R^5$, $R^6$, $R^7$ or $R^8$ is —F. In still further such embodiments, at least one of $R^5$, $R^6$, $R^7$ or $R^8$ is —C≡N. In still other such embodiments, at least one of $R^5$, $R^6$, $R^7$ or $R^8$ is —CF$_3$.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, one of $R^3$ and W is selected from —H or (C$_1$-C$_6$)alkyl.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, one of $R^3$ and W is —H.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, one of $R^3$ and W is selected from pyridyl, phenyl, or phenyl substituted with 1, 2, or 3 substituents independently selected from —F, —Cl, —Br, —I, —C≡N, —NO$_2$, —OH, —O—(C$_1$-C$_6$)alkyl, —OCF$_3$, —OCHF$_2$, —CF$_3$, —(C$_1$-C$_6$)alkyl, —NH$_2$, —NH((C$_1$-C$_4$)alkyl), —N((C$_1$-C$_4$)alkyl)$_2$, —NHSO$_2$—(C$_1$-C$_6$)alkyl, —NHC(=O)—(C$_1$-C$_6$)alkyl, —C(=O)NH$_2$, —C(=O)NH((C$_1$-C$_6$)alkyl), —C(=O)N((C$_1$-C$_6$)alkyl)$_2$, —C(=O)—(C$_1$-C$_6$)alkyl, —CO$_2$H, —C(=O)—O—(C$_1$-C$_6$)alkyl, —SO$_2$NH$_2$, —SO$_2$NH((C$_1$-C$_6$)alkyl), —SO$_2$N((C$_1$-C$_6$)alkyl)$_2$, —SO$_2$—(C$_1$-C$_6$)alkyl, or —SO—(C$_1$-C$_6$)alkyl. In some such embodiments, one of $R^3$ and W is selected from pyridyl, phenyl, or phenyl substituted with 1, 2, or 3 substituents independently selected from —F, —Cl, —Br, —O—(C$_1$-C$_6$)alkyl, or —(C$_1$-C$_6$)alkyl. In still other such embodiments, one of $R^3$ and W is selected from pyridyl, phenyl, or phenyl substituted with 1 substituent selected from —F, —Cl, —OCH$_3$, or —CH$_3$. In still further such embodiments, one of $R^3$ and W is phenyl.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, one of $R^3$ and W is selected from

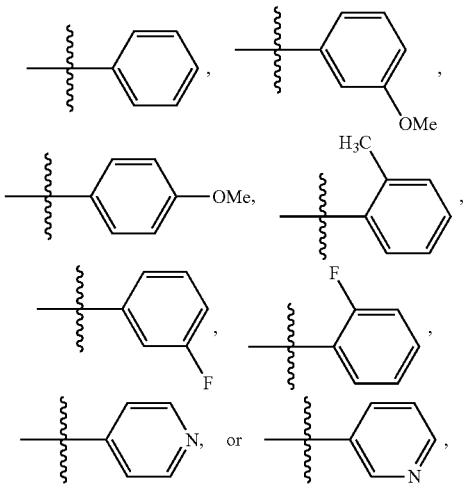

where the symbol , when drawn across a bond, indicates the point of attachment to the rest of the molecule.

In some embodiments of the compound of Formula II, or the pharmaceutically acceptable salt thereof, the tautomer thereof, the pharmaceutically acceptable salt of the tautomer, the stereoisomer of any of the foregoing, or the mixture thereof, $R^4$ is —H or —CH$_3$. In still other such embodiments, $R^4$ is —H. In still further embodiments, $R^4$ is —CH$_2$CF$_3$.

In some embodiments, the compound is a salt. Such salts may be anhydrous or associated with water as a hydrate.

Also provided are pharmaceutical compositions that include the compound or the pharmaceutically acceptable salt thereof, the tautomer thereof, the pharmaceutically acceptable salt of the tautomer, the stereoisomer of any of the foregoing, or the mixture thereof according to any one of the embodiments and at least one pharmaceutically acceptable excipient, carrier or diluent. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of cancer or, in some embodiments, for inhibiting tankyrase 1 and or tankyrase 2.

In other embodiments, the invention provides a method of treating cancer. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the cancer os colon cancer and in still other such embodiments is APC colon cancer. In some embodiments, the subject is a human cancer patient, and the cancer is selected from colon cancer. In still other embodiments, the cancer is selected from colon, pancreatic, ovarian, gastric, lung, or leukemia. In still other embodiments the cancer is any other cancer that relies on the Wnt pathway for growth or survival.

In still other embodiments, the invention provides a method of treating a condition where it is desired to inhibit tankyrase 1 or tankyrase 2 activity. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of any of the embodiments.

In some embodiments, the compound or the pharmaceutically acceptable salt thereof, the tautomer thereof, the pharmaceutically acceptable salt of the tautomer, the stereoisomer of any of the foregoing, or the mixture thereof according to any one of any of the embodiments is used in the preparation of a medicament. In some such embodiments, the medicament is for use in treating cancer. In some such embodiments, a medicament is for use in inhibiting tankyrase 1 or tankyrase 2. In still other such embodiments, the medicament is for use in treating a cancer in a human cancer patient such as a human with colon cancer.

In some such embodiments, the compound or the pharmaceutically acceptable salt thereof, the tautomer thereof, the pharmaceutically acceptable salt of the tautomer, the stereoisomer of any of the foregoing, or the mixture thereof according to any one of any of the embodiments is provided for use in treating cancer. In some such embodiments, the cancer is colon cancer. In still other embodiments the use is for treating cancer in a human patient.

In one embodiment, the invention provides a method of treating a proliferation-related disorder in a mammal in need thereof. Such methods include administering to the mammal a therapeutically effective amount of a compound of any of the embodiments described herein or a pharmaceutical composition comprising the compound. Another embodiment of the invention comprises treating abnormal cell growth by administering a therapeutically effective amount of a compound of the invention or a pharmaceutical composition of the invention to a subject in need thereof. In some embodiments, the invention provides the use of a compound of any of the embodiments or a pharmaceutical composition of the invention for treating abnormal cell growth. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer wherein the cancer is selected from the group consisting of small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment of said method, said abnormal cell growth is a benign proliferative disease, including, but not limited to, psoriasis, benign prostatic hypertrophy or restenosis.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention may be used to treat or prevent various kinase-related disorders. Thus, the present invention provides methods for treating or preventing such disorders. In some embodiments, the invention provides a method for treating a kinase-mediated disorder in a subject that includes administering a therapeutically effective amount of a compound of any of the embodiments of the invention or a pharmaceutical composition to the subject. In some embodiments, the subject is a mammal, and in some such embodiments is a human. In some embodiments the disorder is mediated by IGF-1R, Insulin Receptor, tankyrase 1, tankyrase 2, ALK, KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some such embodiments, the disorder is mediated by tankyrase 1 or tankyrase 2. In some such embodiments, the administration of the compound or pharmaceutical composition produces selective inhibition of tankyrase 1 and or tankyrase 2. In some embodiments, the disorder is cancer. The present invention thus provides methods for treating or preventing tankyrase 1 and or tankyrase 2 mediated disease states, such as cancer. In some embodiments, the cancer is a tumor such as a solid tumor.

The compounds of the invention may also be used to treat proliferation-related disorders. Thus, the invention further provides methods for treating such proliferation-related disorders in a subject. Such methods include administering to a subject in need thereof a therapeutically effective amount of the compound or pharmaceutical composition of any of the embodiments. In some embodiments, the subject is a mammal. In some such embodiments, the mammal is a human. In some embodiments, the proliferation-related disorder is abnormal cell growth. In other embodiments, the disorder is inflammation or an inflammation-related disorder. In still other embodiments, the disorder is a metabolic disease such as diabetes. In still other embodiments, the disorder is cancer. In some such embodiments, the cancer is a solid tumor.

The magnitude of a prophylactic or therapeutic dose of a compound of any of the embodiments or a pharmaceutically acceptable salt, solvate, hydrate, or stereoisomer thereof in the acute or chronic treatment or prevention of a cancer or other disease or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

The compounds of the invention can be administered to provide systemic distribution of the compound within the patient. Therefore, in some embodiments, the compounds of the invention are administered to produce a systemic effect in the body.

The compounds of the invention may also be administered directly to a site affected by a condition, as, for example, an in the treatment of an accessible area of skin or an esophageal cancer.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that demonstrates anti-cancer activity. In another embodiment, an additional therapeutic agent that demonstrates cytotoxic activity is administered to a subject such as a cancer patient.

The compounds of the invention and the other therapeutics agent can act additively or, preferably, synergistically. In some embodiments, a composition comprising a compound of the invention is administered concurrently with the administration of another therapeutic agent, which can be part of the same composition or can be in a different composition from the one that comprises the compound of the invention. In other embodiments, a compound of the invention is administered prior to, or subsequent to, administration of another therapeutic agent. In still other embodiments, a compound of the invention is administered to a patient who has not previously undergone or is not currently undergoing treatment with another therapeutic agent. A compound of the invention may be administered to a subject that has had, is currently undergoing, or is scheduled to receive radiation therapy. In some such embodiments, the subject is a cancer patient.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of any of the embodiments described herein may also be administered sequentially with known anticancer or cytotoxic agents when a combination formulation is inappropriate. The invention is not limited in the sequence of administration as compounds of the invention may be administered either prior to, simultaneous with, or after administration of a known anticancer or cytotoxic agent.

There are large numbers of antineoplastic agents available in commercial use, in clinical evaluation and in pre-clinical development, which may be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from, but are not limited to, the group consisting of 5-FU-fibrinogen, acanthifolic acid, aminothiadiazole, brequinar sodium, carmofur, Ciba-Geigy CGP- 30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT, and uricytin.

A second family of antineoplastic agents which may be used in combination with compounds of the present invention consists of alkylating-type antineoplastic agents. Suitable alkylating-type antineoplastic agents may be selected from, but are not limited to, the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, and trimelamol.

A third family of antineoplastic agents which may be used in combination with compounds of the present invention consists of antibiotic-type antineoplastic agents. Suitable antibiotic-type antineoplastic agents may be selected from, but are not limited to, the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from, but not limited to, the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969, 110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, c-met inhibitors, KDR inhibitors, EGF inhibitors and CDK inhibitors, TNF inhibitors, matrix metalloproteinases (MMP) inhibitors, COX-2 inhibitors including celecoxib, NSAID's, or $\alpha_v\beta_3$ inhibitors.

The invention is further described by reference to the following examples, which are intended to exemplify the claimed invention but not to limit it in any way.

EXAMPLES

Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen or argon atmosphere. Purity was measured using Agilent 1100 Series high performance liquid chromatography (HPLC) systems with UV detection at 254 nm and 215 nm (System A: Agilent Zorbax Eclipse XDB-C8 4.6×150 mm, 5 micron, 5 to 100% ACN in $H_2O$ with 0.1% TFA for 15 minutes at 1.5 mL/minute; System B: Zorbax SB-C8, 4.6×75 mm, 10 to 90% ACN in $H_2O$ with 0.1% formic acid for 12 minutes at 1.0 mL/minute). Silica gel chromatography was generally performed with prepacked silica gel cartridges (Biotage or Teledyne-Isco). $^1$H NMR spectra were recorded on a Bruker AV-400 (400 MHz) spectrometer or a Varian 400 MHz spectrometer at ambient temperature, or the NMR spectra were collected with a Bruker Avance III spectrometer operating at a proton frequency of 500.13 MHz using a 10 μL Protasis CapNMR flow probe. NMR samples were delivered to the flow probe using a Protasis One-Minute NMR™ Automation system comprised of a Discovery Tower™ Sample Manager and a Waters Liquid Handler made by CTC, Switzerland (Model 2777). All observed protons are reported as parts per million (ppm) downfield from tetramethylsilane (TMS) or another internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series LC-MS with UV detection at 254 nm and 215 nm and a low resonance electrospray mode (ESI).

The following Abbreviations are used to refer to various reagents and solvents:

ACN Acetonitrile
AcOH Acetic Acid
CDI 1,1'-Carbonyldiimidazole
DCE 1,2-Dichloroethane
DCM Dichloromethane
DIEA N,N-Diisopropylethylamine
DMF N,N-Dimethylformamide
DMSO Dimethylsulfoxide
EtOAc Ethyl Acetate
EtOH Ethanol
HATU O-(7-Azabenzotriazol-1-yl)-N,N,N',N'-tetramethyluronium hexafluorophosphate
iPrOH Isopropanol
MeOH Methanol
NBS N-Bromosuccinimide
PPTS Pyridinium p-toluenesulfonate
RT Room temperature
TEA Triethylamine
TFA Trifluoroacetic acid
THF Tetrahydrofuran
TsCl p-Toluenesulfonyl chloride
TLC Thin Layer Chromatography

SYNTHESIS OF INTERMEDIATES

Intermediate A

4-Iodo-N-(quinolin-8-yl)benzamide

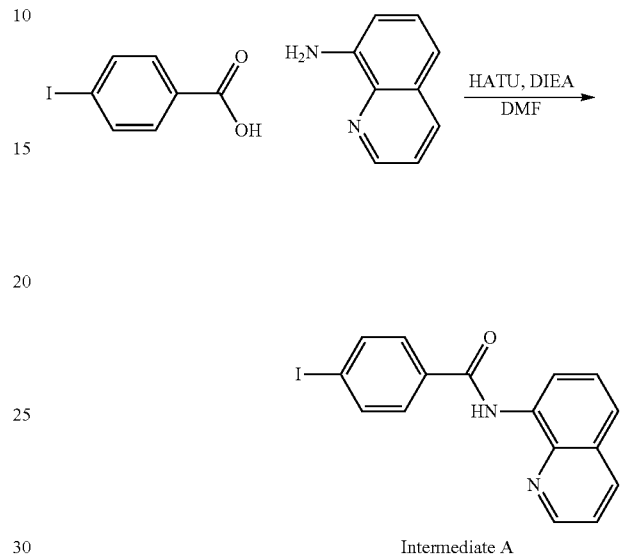

Intermediate A

A mixture of 4-iodobenzoic acid (commercially available from Sigma-Aldrich, Milwaukee, Wis.) (9.26 g, 37.3 mmol), DIEA (13.05 mL, 74.7 mmol), HATU (7.10 g, 18.67 mmol) and quinolin-8-amine (commercially available from Sigma-Aldrich, Milwaukee, Wis.) (7 g, 48.6 mmol) in DMF (124 mL) was stirred under nitrogen overnight at room temperature. The reaction mixture was diluted with saturated $NaHCO_3$ (100 mL) and water (300 mL) yielding a yellow/brown precipitate which was filtered, washed with water (100 mL) and dried on high vacuum to obtain 4-iodo-N-(quinolin-8-yl)benzamide (9 g, 24.05 mmol, 64.4% yield) as a yellow brown solid. $^1$H NMR (400 MHz, DMSO-$d_6$) δ=10.65 (s, 1H), 8.98 (dd, J=1.6, 4.3 Hz, 1H), 8.70 (dd, J=1.4, 7.6 Hz, 1H), 8.47 (dd, J=1.7, 8.3 Hz, 1H), 8.03-7.98 (m, 2H), 7.83-7.79 (m, 2H), 7.76 (dd, J=1.3, 8.2 Hz, 1H), 7.71-7.62 (m, 2H).

Intermediate B (S)-3-(4-Bromophenyl)-5,5-dimethyl-4-phenyloxazolidin-2-one

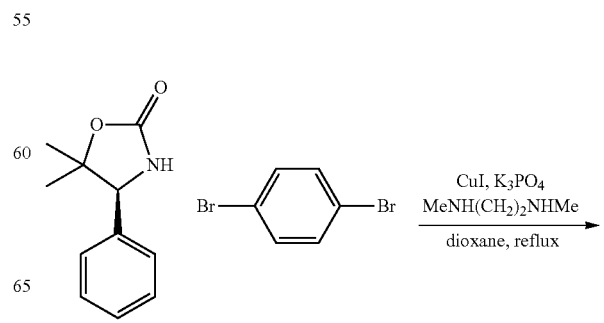

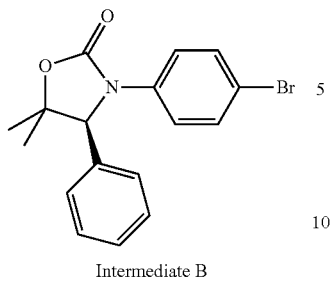

Intermediate B

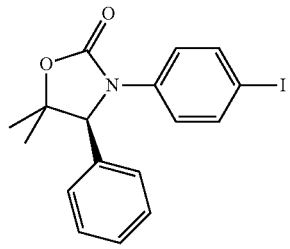

Intermediate C

To a round bottom flask were added (S)-5,5-dimethyl-4-phenyloxazolidin-2-one (2.00 g, 10.46 mmol)(commercially available from Sigma-Aldrich, Milwaukee, Wis.), 1,4-dibromobenzene (commercially available from Sigma-Aldrich, Milwaukee, Wis.) (4.93 g), 1,4-dioxane (41.8 mL) and tribasic potassium phosphate (11.10 g, 52.3 mmol). The vessel was purged with nitrogen and then N,N'-dimethylethylenediamine (2.251 mL, 20.92 mmol) and copper (I) iodide (1.992 g, 10.46 mmol) were added. The vessel was heated at reflux overnight providing an orange suspension containing product along with two other major impurities according to LC-MS. To the mixture was added water, and the resulting slurry was transferred to a separatory funnel and extracted with EtOAc (2×). The combined organic layers were back extracted with water, separated, dried with $Na_2SO_4$, filtered, and dried under reduced pressure. The residue was purified twice using a 50 g SNAP column ramping EtOAc in heptane from 0-30% leading to coelution of product with impurity. Another run using DCM:MeOH:$NH_4$OH (90:10:1) in DCM afforded (S)-3-(4-bromophenyl)-5,5-dimethyl-4-phenyloxazolidin-2-one (1.85 g, 5.34 mmol, 51.1% yield) as a white solid. Minor amounts of (S)-5,5-dimethyl-4-phenyloxazolidin-2-one was still present after the second purification, but the material was used as is. $^1$H NMR (400 MHz, DMSO-$d_6$) δ=7.50-7.41 (m, 4H), 7.40-7.34 (m, 2H), 7.33-7.28 (m, 2H), 7.26-7.20 (m, 1H), 5.46 (s, 1H), 1.62 (s, 3H), 0.89 (s, 3H).

Intermediate C (S)-3-(4-Iodophenyl)-5,5-dimethyl-4-phenyloxazolidin-2-one

A resealable tube was charged with (S)-5,5-dimethyl-4-phenyloxazolidin-2-one (commercially available from Sigma-Aldrich, Milwaukee, Wis.) (1.01 g, 5.28 mmol), 1,4-diiodobenzene (commercially available from Sigma-Aldrich, Milwaukee, Wis.) (3.48 g, 10.56 mmol), tribasic potassium phosphate (5.61 g, 26.4 mmol) and dioxane (20.0 mL). The mixture was purged with argon and then copper (I) iodide (1.006 g, 5.28 mmol) and N,N'-dimethylethylenediamine (1.137 mL, 10.56 mmol) were added. The system was purged with argon, the tube was sealed, and the reaction mixture was heated at 100° C. for 12 hours. The reaction mixture was filtered through Celite® brand filter aid and concentrated to afford a purple solid. This material was purified via column chromatography on silica gel (RediSep 80 g column, gradient elution with 0-25% EtOAc-hexane) to afford (S)-3-(4-iodophenyl)-5,5-dimethyl-4-phenyloxazolidin-2-one (1.271 g, 3.23 mmol, 61.2% yield) as a white solid. $^1$H NMR (400 MHz, DMSO-$d_6$) δ=7.64-7.59 (m, 2H), 7.39-7.33 (m, 2H), 7.33-7.27 (m, 3H), 7.26-7.20 (m, 2H), 5.43 (s, 1H), 1.61 (s, 3H), 0.89 (s, 3H).

Intermediate D (S)-4-(5,5-Dimethyl-2-oxo-4-phenyloxazolidin-3-yl)benzoic acid

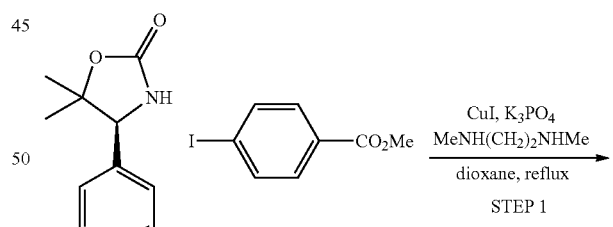

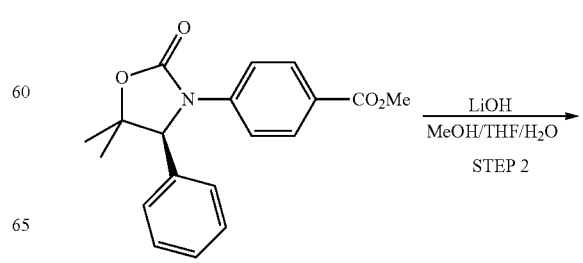

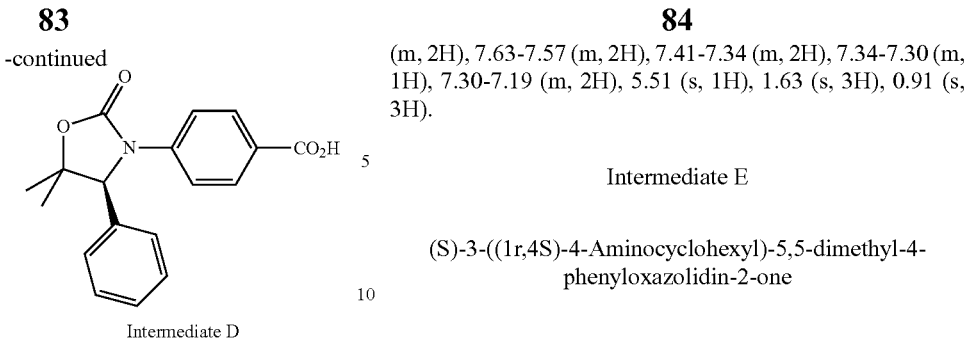

Intermediate D

Step 1

(S)-Methyl 4-(5,5-dimethyl-2-oxo-4-phenyloxazolidin-3-yl)benzoate

To a round bottom flask were added (S)-5,5-dimethyl-4-phenyloxazolidin-2-one (commercially available from Sigma-Aldrich, Milwaukee, Wis.) (1.717 g, 8.98 mmol), methyl 4-iodobenzoate (commercially available from Sigma-Aldrich, Milwaukee, Wis.) (2.353 g, 8.98 mmol), and dioxane (90 mL). Tribasic potassium phosphate (9.53 g, 44.9 mmol), and copper (I) iodide (1.710 g, 8.98 mmol) were then added to the flask. The vessel was purged with nitrogen and N,N'-dimethylethylenediamine (1.933 mL, 17.96 mmol) was added. The suspension was heated at reflux overnight yielding a tan suspension. The mixture was filtered through Celite® brand filter aid, and the filtrate was dried under reduced pressure providing (S)-methyl 4-(5,5-dimethyl-2-oxo-4-phenyloxazolidin-3-yl)benzoate (2.72 g, 8.36 mmol, 93% yield) as a light green oil which was used in the next step. $^1$H NMR (400 MHz, CDCl$_3$) δ=7.94-7.90 (m, 2H), 7.55-7.51 (m, 2H), 7.39-7.32 (m, 3H), 7.21-7.16 (m, 2H), 5.04 (s, 1H), 3.86 (s, 3H), 1.70 (s, 3H), 1.02 (s, 3H).

Step 2

(S)-4-(5,5-Dimethyl-2-oxo-4-phenyloxazolidin-3-yl)benzoic acid

To a flask charged with (S)-methyl 4-(5,5-dimethyl-2-oxo-4-phenyloxazolidin-3-yl)benzoate (2.70 g, 8.30 mmol) were added THF (48.5 mL), MeOH (48.5 mL) and water (48.5 mL) respectively. To the resulting turbid solution was added LiOH (0.994 g, 41.5 mmol), and the resulting mixture was heated at 50° C. overnight. The resulting mixture was cooled in an ice water bath and brought to pH~2 by the addition of 2N HCl (~15 mL) leading to a light yellow solution to which water was added (~100 mL). This lead to the formation of a white precipitate which was collected by vacuum filtration and washed with excess water. After drying under high vacuum overnight, (S)-4-(5,5-dimethyl-2-oxo-4-phenyloxazolidin-3-yl)benzoic acid (1.25 g, 4.02 mmol, 48.4% yield) was obtained as a white solid. NMR indicated that the product formed as a THF adduct with a 3:2 product to THF ratio. $^1$H NMR (400 MHz, DMSO-d$_6$) δ=12.76 (br. s., 1H), 7.87-7.81 (m, 2H), 7.63-7.57 (m, 2H), 7.41-7.34 (m, 2H), 7.34-7.30 (m, 1H), 7.30-7.19 (m, 2H), 5.51 (s, 1H), 1.63 (s, 3H), 0.91 (s, 3H).

Intermediate E

(S)-3-((1r,4S)-4-Aminocyclohexyl)-5,5-dimethyl-4-phenyloxazolidin-2-one

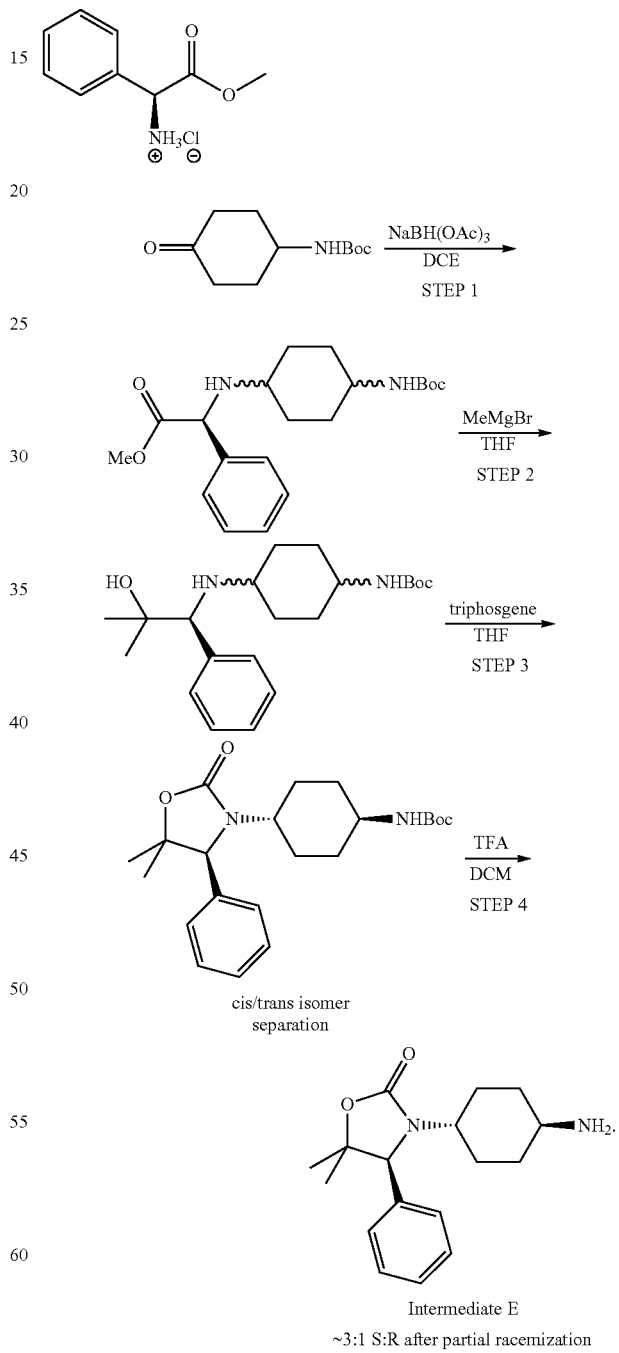

Intermediate E
~3:1 S:R after partial racemization

Note: partial racemization may ocur in steps 1 or 2

Step 1

(S)-Methyl 2-((4-((tert-butoxycarbonyl)amino)-cyclohexyl)amino)-2-phenylacetate To a flask charged with 4-N-boc-aminocyclohexanone (commercially available from Combi-Blocks, San Diego, Calif.) (11.00 g, 51.6 mmol) was added DCE (206 mL) followed by (S)-(+)-2-phenylglycine methyl ester hydrochloride (commercially available from Sigma-Aldrich, Milwaukee, Wis.) (10.40 g, 51.6 mmol). The resulting mixture was stirred at room temperature for 15 minutes prior to the addition of sodium triacetoxyborohydride (21.86 g, 103 mmol). The resulting suspension was stirred overnight at room temperature leading to conversion to desired product (~1:1 cis: trans). To the mixture was added water, and the resulting mixture was transferred to a separatory funnel. The mixture was extracted with EtOAc (2x). The combined organics were dried with $Na_2SO_4$, filtered, and dried under reduced pressure. The crude material was purified with a 100 g SNAP column ramping DCM:MeOH (90:10) in DCM (0-25%), then isocratic at 25% (monitoring at 215 nm) to yield (S)-methyl 2-(((1 r,4S)-4-((tert-butoxycarbonyl)amino)cyclohexyl)amino)-2-phenylacetate (12.43 g, 34.3 mmol, 66.5% yield) as a mixture of isomers and as a yellow solid.

Step 2

(S)-tert-Butyl (4-((2-hydroxy-2-methyl-1-phenylpropyl)amino)cyclohexyl)carbamate A flask charged with (S)-methyl 2-(((1r,4S)-4-((tert-butoxycarbonyl)amino)cyclohexyl)amino)-2-phenylacetate (12.4 g, 34.2 mmol) was dried under high vacuum and placed under nitrogen. Then, THF (98 mL) was added, and the resulting solution was cooled in an ice water bath prior to the addition of methylmagnesium bromide (16.32 g, 137 mmol) over 15 minutes. The mixture was allowed to slowly warm to room temp overnight providing a yellow suspension. The mixture was carefully added to a mixture of ice, saturated aqueous $NH_4Cl$, and EtOAc with stirring. Much of the solid was difficult to remove and was transferred with the aid of MeOH. The mixture was transferred to a separatory funnel and extracted with EtOAc (2x). The combined organic layers were dried with $MgSO_4$, filtered, and dried under reduced pressure. The residue was purified with a 100 g SNAP column ramping DCM:MeOH (90:10) in DCM from 0-30%, then isocratic at 30% (monitoring at 215 nm) providing a mixture of isomers of tert-butyl ((1 S,4r)-4-(((S)-2-hydroxy-2-methyl-1-phenylpropyl)amino)cyclohexyl)carbamate (5.28 g, 14.57 mmol, 42.6% yield) as a yellow solid as. NMR indicated about a 3:1 mixture of isomers. A later assessment of intermediate 4 established a 3:1 mixture of enantiomers implying partial racemization had occurred in this step.

Step 3 tert-Butyl ((1 S,4r)-4-((S)-5,5-dimethyl-2-oxo-4-phenyloxazolidin-3-yl)cyclohexyl)carbamate To a flask charged with tert-butyl ((1S,4r)-4-(((S)-2-hydroxy-2-methyl-1-phenylpropyl)amino)cyclohexyl)carbamate (5.2 g, 14.34 mmol) were added THF (57.4 mL), and DIEA (12.53 mL, 71.7 mmol). The mixture was cooled in an ice water bath prior to the addition of triphosgene (4.26 g, 14.34 mmol). The resulting yellow suspension was allowed to stir and warm slowly to room temperature overnight. LC-MS of the yellow suspension indicated the desired product as the main peak (observed as carbamic acid, with t-butyl lost) with consumption of starting material. To the mixture was added water, and the resulting orange solution was transferred to a separatory funnel, diluted with brine, and extracted with EtOAc (2x). The combined organic layers were dried under reduced pressure and purified with a 200 g (15 μm spherical silica, Interchim) column, flow rate 65 mL/min ramping DCM:MeOH (90:10) in DCM, from 0-30%, then isocratic at 30% (monitoring at 215 nm) providing some separation of regioisomers with peak slicing yielding the trans:cis product in 50% yield (~4:1).

Step 4

(S)-3-((1r,4S)-4-Aminocyclohexyl)-5,5-dimethyl-4-phenyloxazolidin-2-one

To a flask charged with tert-butyl ((1S,4r)-4-((S)-5,5-dimethyl-2-oxo-4-phenyloxazolidin-3-yl)cyclohexyl)carbamate (2.81 g, 7.23 mmol) was added DCM (28.9 mL) followed by TFA (5.57 mL, 72.3 mmol). The resulting mixture was stirred for 3 hours at room temperature. The mixture was dried under reduced pressure and purified with a 40 g HP spherical silica column (Interchim) ramping DCM:MeOH (90:10) in DCM (0-100%) (monitoring at 215 nm) to provide product as a white foam (quantitative conversion). Chiral purification: Column: Chiralpak AD-H, 5×30 cm; Mobile Phase: 20% MeOH w/0.2% diethylamine/80% $CO_2$; Flowrate: 350 mL/min; Sample dissolution: 72 mg/mL in 1:1 DCM/MeOH, processed with 1.25 mL injections. $^1$H NMR (400 MHz, DMSO-$d_6$) δ=7.79-7.64 (m, 2H), 7.45-7.38 (m, 2H), 7.38-7.32 (m, 1H), 7.32-7.10 (m, 2H), 4.59 (s, 1H), 3.41-3.32 (m, 1H), 2.84 (tt, J=3.8, 11.6 Hz, 1H), 1.94 (td, J=3.2, 12.5 Hz, 1H), 1.86-1.74 (m, 3H), 1.59-1.52 (m, 1H), 1.45 (s, 3H), 1.37-1.07 (m, 3H), 0.78 (s, 3H). m/z (ESI) 289.2 (M+H)$^+$. The material could be obtained and used as a TFA salt with direct drying of the reaction mixture.

Intermediate F

1-((1r,4r)-4-Aminocyclohexyl)-1H-benzo[d]imidazol-2(3H)-one hydrochloride

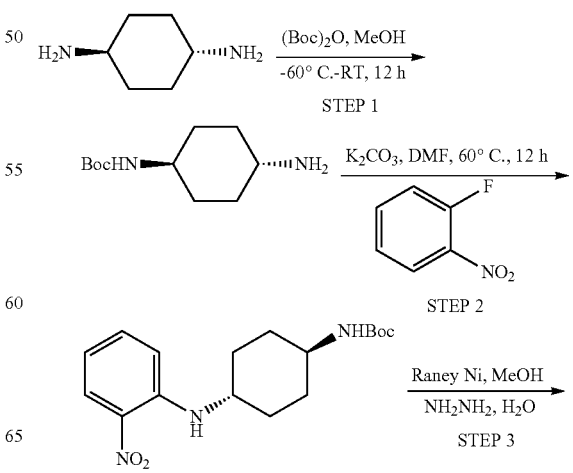

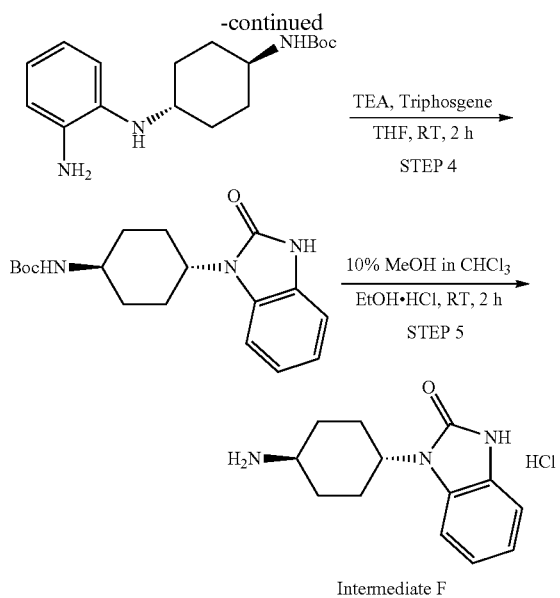

Intermediate F

Step 1 tert-Butyl ((1r,4r)-4-aminocyclohexyl)carbamate

To a solution of trans-1,4-diaminocyclohexane (commercially available from Sigma-Aldrich, Milwaukee, Wis.) (5 g, 43.78 mmol) in MeOH (100 mL) was added di-tert-butyl dicarbonate (4.77 g, 21.89 mmol) with MeOH (50 mL) at −60° C. over 90 minutes. The temperature was slowly allowed to warm to ambient temperature. The reaction mixture was stirred for 12 hours at ambient temperature. After completion of the reaction, monitored by TLC (TLC eluent: 10% MeOH in CHCl$_3$, Ninhydrin stain active), the reaction mixture was concentrated to remove MeOH. Water was added to form a white precipitate. The resulting mixture was stirred for 10 minutes and then the precipitate was filtered and washed with water. The filtrate (aqueous layer) was extracted with EtOAc (2×150 mL). The extract was washed with saturated aqueous NaCl solution and separated and further dried on anhydrous Na$_2$SO$_4$. Following filtration, the organic layer was concentrated under reduced pressure to afford tert-butyl ((1r,4r)-4-aminocyclohexyl)carbamate as a white solid (2.6 g, 27.70%). The filtered solid (3 g) product was bisboc protected compound and unreacted starting material remained in the aqueous layer. $^1$H NMR (400 MHz, DMSO-d$_6$): δ 6.67 (d, J=7.6 Hz, 1H), 3.12 (m, 1H), 2.44 (m, 1H), 1.71 (m, 4H), 1.36 (s, 9H), 1.17 (m, 2H), 1.04 (m, 2H).

Step 2 tert-Butyl ((1r,4r)-4-((2-nitrophenyl)amino)cyclohexyl)-carbamate

To a solution of tert-butyl ((1r,4r)-4-aminocyclohexyl)carbamate (1 g, 4.66 mmol) and 1-fluoro-2-nitrobenzene (commercially available from Sigma-Aldrich, Milwaukee, Wis.) (0.658 g, 4.66 mmol) in DMF (5 mL) was added K$_2$CO$_3$ (1.28 g, 9.32 mmol) at ambient temperature. The resulting reaction mixture was stirred for 12 hours at 60° C. After completion of reaction (monitored by TLC (TLC eluent: 30% EtOAc in petroleum ether)), the reaction mixture was cooled to ambient temperature and water was added to obtain a yellow precipitate. After stirring for 10 minutes, the mixture was filtered and washed with water and then dried under vacuum to afford tert-butyl ((1r,4r)-4-((2-nitrophenyl)amino)cyclohexyl)carbamate as a yellow solid (1.5 g, 95.84%). $^1$H NMR (300 MHz, DMSO-d$_6$) δ 8.03 (d, J=8.6 Hz, 1H), 7.87 (d, J=7.6 Hz, 1H), 7.52-7.43 (m, 1H), 7.11 (d, J=8.7 Hz, 1H), 6.83 (d, J=7.6 Hz, 1H), 6.71-6.57 (m, 1H), 3.42 (m, 1H), 1.99 (s, 2H), 1.81 (s, 2H), 1.45-1.20 (m, 2H+2H+1H+9H=14H). m/z (ESI) 336.3 (M+H)$^+$.

Step 3 tert-Butyl ((1r,4r)-4-((2-aminophenyl)amino)-cyclohexyl)carbamate

To a stirred suspension of Raney Nickel (1.5 g) in MeOH (30 mL) was added tert-butyl ((1r,4r)-4-((2-nitrophenyl)amino)cyclohexyl)carbamate (1.5 g, 4.47 mmol) at ambient temperature. The temperature was then raised to 56° C. Hydrazine hydrate (1.5 mL) was added very slowly over 10 minutes (exothermic reaction). The resulting mixture was stirred for 10 minutes at the same temperature. After completion of reaction (monitored by TLC (TLC eluent: 50% EtOAc in petroleum ether)), the reaction mixture was cooled to ambient temperature. The reaction mixture was then filtered through Celite® brand filter aid and concentrated. High vacuum was applied to remove excess hydrazine hydrate. The residue was washed with petroleum ether providing tert-butyl ((1r,4r)-4-((2-aminophenyl)amino)cyclohexyl)carbamate as a grey solid (1.1 g, 80.58%). $^1$H NMR (300 MHz, DMSO-d$_6$): 6.85 (d, J=4.5 Hz, 1H), 6.52-6.34 (m, 3H), 4.45 (br s, 2H), 7.08 (d, J=7.5 Hz, 1H), 3.21-3.06 (m, 2H), 2.00-1.96 (m, 2H), 1.81-1.77 (m, 2H), 1.37 (s, 9H), 1.28-1.15 (m, 3H). m/z (ESI) 306.2 (M+H)$^+$.

Step 4 tert-Butyl ((1r,4r)-4-(2-oxo-2,3-dihydro-1H-benzo[d]imidazol-1-yl)cyclohexyl)carbamate To a solution of tert-butyl ((1r,4r)-4-((2-aminophenyl)amino)cyclohexyl)carbamate (24.8 g, 81.20 mmol) in THF (250 mL) were added TEA (8.21 g, 81.20 mmol) and triphosgene (24 g, 81.20 mmol) at 0° C. The reaction mixture was stirred for 2 hours at ambient temperature. After completion of reaction (monitored by TLC (TLC eluent: 50% EtOAc in petroleum ether)), the reaction mixture was quenched with saturated NaHCO$_3$ solution and extracted with 20% THF in EtOAc (3×200 mL). The extract was washed with brine and dried on anhydrous Na$_2$SO$_4$. After filtration, the organic layer was concentrated under vacuum to afford tert-butyl ((1r,4r)-4-(2-oxo-2,3-dihydro-1H-benzo[d]imidazol-1-yl)cyclohexyl)carbamate as an off-white solid (16 g+8 g, 89.18%). The insoluble aqueous layer was filtered and washed with water and dried under vacuum (8 g). $^1$H NMR (400 MHz, DMSO-d$_6$): δ 7.31 (m, 1H), 6.97 (m, 4H), 6.81 (d, J=8 Hz, 1H), 4.13 (m, 1H), 2.25 (m, 2H), 1.91 (d, J=11.2 Hz, 2H), 1.67 (d, J=10.8 Hz, 2H), 1.39 (s, 9H), 1.35 (m, 2H). m/z (ESI) 276.1 (NHCOOH).

Step 5

1-((1r,4r)-4-Aminocyclohexyl)-1H-benzo[d]imidazol-2(3H)-one hydrochloride

To a solution of tert-butyl ((1r,4r)-4-(2-oxo-2,3-dihydro-1H-benzo[d]imidazol-1-yl)cyclohexyl)carbamate (12.5 g, 37.71 mmol) in 10% MeOH in CHCl₃ (125 mL) was added saturated ethanolic HCl (125 mL) at ambient temperature. The reaction mixture was stirred for 2 hours at the same temperature. After completion of reaction (monitored by TLC (TLC eluent: 100% EtOAc)), the reaction mixture was concentrated and diethyl ether (50 mL) was added. The resulting mixture was stirred for 10 minutes. The resulting precipitate was filtered, and the solid was washed with diethyl ether to afford 1-(4-amino-cyclohexyl)-1,3-dihydro-benzoimidazol-2-one hydrochloride as a tan solid (9.1 g, 90.18%). ¹H NMR (400 MHz, DMSO-d₆): δ 10.90 (bs, 1H), 8.19 (bs, 3H), 7.38 (q, J=5.6 Hz & J=2.4 Hz, 1H), 6.97 (m, 3H), 4.18 (m, 1H), 3.23 (m, 1H), 2.30 (m, 2H), 2.11 (d, J=11.6 Hz, 2H), 1.75 (d, J=10.8 Hz, 2H), 1.59 (m, 2H). m/z (ESI) 232.1.

Intermediate G (S)-3-(4-(7-Iodo-[1,2,4]triazolo[4,3-a]pyridin-3-yl) phenyl)-5,5-dimethyl-4-phenyloxazolidin-2-one

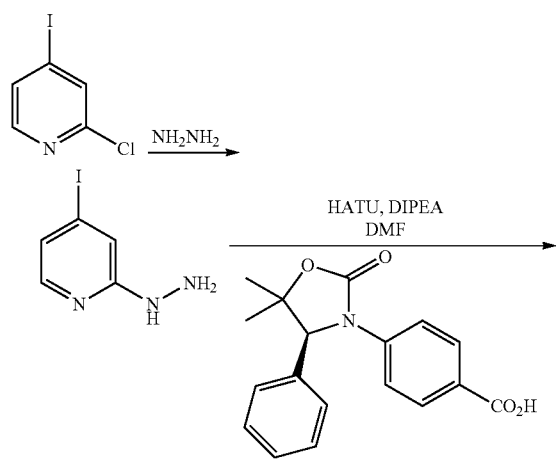

Intermediate G

Step 1

2-Hydrazinyl-4-iodopyridine

A mixture of 2-chloro-4-iodopyridine (5000 mg, 20.88 mmol) (commercially available from Frontier Scientific, Inc., Logan Utah) and anhydrous hydrazine (32.8 mL, 1045 mmol, commercially available from Sigma-Aldrich, Milwaukee, Wis.) was heated at 70° C. for 30 minutes. LC-MS indicated complete conversion to desired product. The reaction mixture was concentrated under vacuum, and the solid was washed with water (3×15 mL) and air dried. The gray colored solid was used directly without further purification. m/z (ESI) 236.0 (M+H)⁺.

Step 2

(S)-4-(5,5-Dimethyl-2-oxo-4-phenyloxazolidin-3-yl)-N'-(4-iodopyridin-2-yl)benzohydrazide (S)-4-(5,5-Dimethyl-2-oxo-4-phenyloxazolidin-3-yl)benzoic acid (1500 mg, 4.82 mmol) was dissolved in DMF (9.636 mL) at room temperature. To the reaction mixture were added N-ethyl-N-isopropylpropan-2-amine (2.514 mL, 14.45 mmol), 2-(3H-[1,2,3]triazolo[4,5-b]pyridin-3-yl)-1,1,3,3-tetramethylisouronium hexafluorophosphate(V) (1.832 g, 4.82 mmol, commercially available from Sigma-Aldrich, Milwaukee, Wis.) and 2-hydrazinyl-4-iodopyridine (1.132 g, 4.82 mmol). The vial was sealed and immersed in a 55° C. oil bath. After stirring overnight, LC-MS indicated complete conversion. After cooling to room temperature, the reaction mixture was transferred to water in a flask in an ice/water bath. The solution was washed with DCM (3×50 mL). The combined organic layers were then washed with water (2×50 mL) and brine (50 mL). The organic extract was dried over Na₂SO₄. The residual material was absorbed onto a plug of silica gel and purified by chromatography through a Redi-Sep pre-packed silica gel column (40 g), eluting with a gradient of 0% to 10% MeOH in DCM, to provide (S)-4-(5,5-dimethyl-2-oxo-4-phenyloxazolidin-3-yl)-N'-(4-iodopyridin-2-yl) benzohydrazide (1.53 g, 2.90 mmol, 60.1% yield) as an off-white solid. m/z (ESI) 529.0 (M+H)⁺.

Step 3

(S)-3-(4-(7-Iodo-[1,2,4]triazolo[4,3-a]pyridin-3-yl) phenyl)-5,5-dimethyl-4-phenyloxazolidin-2-one A heterogeneous mixture of (S)-4-(5,5-dimethyl-2-oxo-4-phenyloxazolidin-3-yl)-N'-(4-iodopyridin-2-yl)benzohydrazide (1.53 g, 2.90 mmol) in glacial AcOH (11.70 mL, 203 mmol) was heated at 180° C. for 1 hour. LC-MS indicated clean and complete conversion to the desired product. The reaction mixture was concentrated under vacuum to give the product as a yellow solid. The material was carried on to next step without purification. m/z (ESI) 511.0 (M+H)⁺.

Intermediate H 2-(2-Fluoro-5-(4,4,5,5-tetramethyl-1,3,2-dioxaborolan-2-yl)pyridin-3-yl)pyrimidine

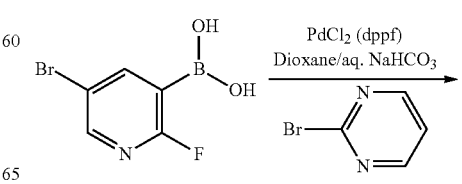

Step 1

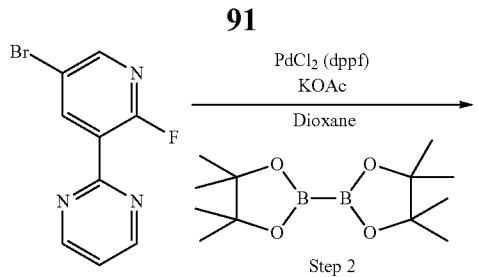

mmol, 79% yield). ¹H NMR (400 MHz, DMSO-d₆) δ 9.00 (d, J=4.89 Hz, 2H), 8.82 (dd, J=1.96, 10.37 Hz, 1H), 8.55 (br. s, 1H), 7.57 (t, J=4.89 Hz, 1H), 1.34 (s, 12H). m/z (ESI) 219.9 (M-C₆H₉).

Intermediate I (S)-3-((1r,4S)-4-Aminocyclohexyl)-4-(4-fluorophenyl)-5,5-dimethyloxazolidin-2-one

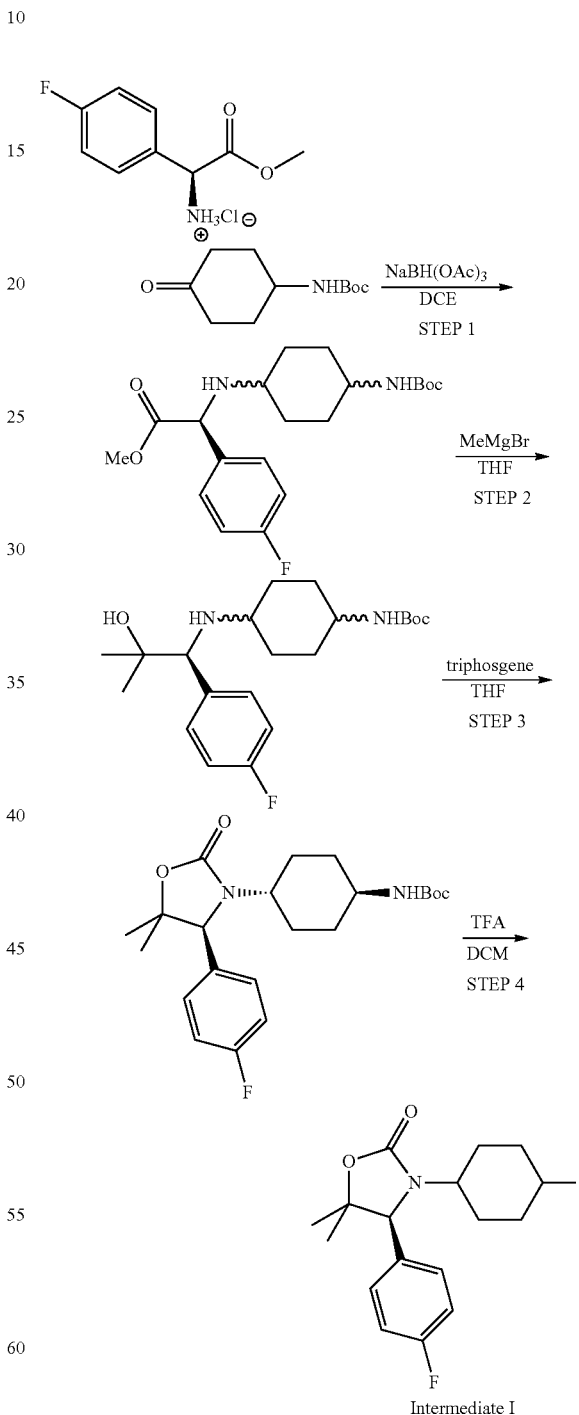

Intermediate I

~85:15 S:R, cis/trans mixture

Note: partial racemization may ocur in steps 1 or 2

Step 1

2-(5-Bromo-2-fluoropyridin-3-yl)pyrimidine

2-Bromopyrimidine (5.42 g, 34.1 mmol), sodium carbonate (22.75 mL, 45.5 mmol), 5-bromo-2-fluoropyridine-3-boronic acid (5 g, 22.75 mmol, commercially available from Frontier Scientific, Inc., Logan Utah), and dichloro(1,1-bis(diphenylphosphinoferrocene))palladium(II) (1.858 g, 2.275 mmol, commercially available from Sigma-Aldrich, Milwaukee, Wis.) were combined in dioxane (32.5 mL) and stirred at 100° C. overnight. LC-MS indicated good conversion to desired product. The material thus obtained was absorbed onto a plug of silica gel and purified by chromatography through a Redi-Sep pre-packed silica gel column (12 g), eluting with a gradient of 0% to 10% MeOH in DCM, to provide 2-(5-bromo-2-fluoropyridin-3-yl)pyrimidine (4.37 g, 17.20 mmol, 76% yield) as yellow solid. m/z (ESI) 253.8.

Step 2

2-(2-Fluoro-5-(4,4,5,5-tetramethyl-1,3,2-dioxaborolan-2-yl)pyridin-3-yl)pyrimidine To a solution of 2-(5-bromo-2-fluoropyridin-3-yl)pyrimidine (1.7 g, 6.69 mmol) and dioxane (13.38 mL) were added potassium acetate (3.28 g, 33.5 mmol, commercially available from Sigma-Aldrich, Milwaukee, Wis.), 4,4,4',4',5,5,5',5'-octamethyl-2,2'-bi(1,3,2-dioxaborolane) (1.869 g, 7.36 mmol, commercially available from Sigma-Aldrich, Milwaukee, Wis.) and 1,1'-bis(diphenylphosphino)ferrocene-palladium (II)dichloride DCM complex (0.546 g, 0.669 mmol, commercially available from Sigma-Aldrich, Milwaukee, Wis.). The reaction vessel was flushed with argon, sealed, and heated at 130° C. for 1 hour in a microwave oven. LC-MS showed complete conversion to the desired product. The reaction mixture was then cooled to room temperature and filtered through Celite® brand filter aid. After removal of solvent, the residue was absorbed onto a plug of silica gel and purified by chromatography through a Redi-Sep pre-packed silica gel column (40 g), eluting with a gradient of 0% to 50% EtOAc in hexane, to provide 2-(2-fluoro-5-(4,4,5,5-tetramethyl-1,3,2-dioxaborolan-2-yl)pyridin-3-yl)pyrimidine (1.6 g, 5.31

Step 1

(S)-Methyl 2-((4-((tert-butoxycarbonyl)amino)cyclohexyl)amino)-2-(4-fluorophenyl)acetate To a flask charged with 4-N-boc-aminocyclohexanone (commercially available from Beta Pharma Inc., Branford, Conn.) (2.500 g, 11.72 mmol) was added DCE (46.9 mL) followed by (S)-methyl 2-amino-2-(4-fluorophenyl)acetate hydrochloride (commercially available from Astatech Inc., Bristol, Pa.) (2.57 g, 11.72 mmol). The resulting mixture was stirred at room temperature for 15 minutes prior to the addition of sodium triacetoxyborohydride (4.97 g, 23.44 mmol). The resulting suspension was stirred overnight at room temperature. To the mixture was added water, the resulting mixture transferred to a separatory funnel. Water was added to the mixture, and the product was extracted with DCM (2×). The combined organic layers were dried with $Na_2SO_4$, filtered, and dried under reduced pressure. The residue was purified with a 100 g SNAP column ramping DCM:MeOH (90:10) in DCM (0-30%), detection at 215 nm, then isocratic at 30% to yield (S)-methyl 2-(((1r,4S)-4-((tert-butoxycarbonyl)amino)cyclohexyl)amino)-2-(4-fluorophenyl)acetate (3.93 g, 10.33 mmol, 88% yield) as a light yellow oil and as a mixture of isomers, m/z (ESI) 381.0 $(M+H)^+$.

Step 2

(S)-tert-Butyl (4-((1-(4-fluorophenyl)-2-hydroxy-2-methylpropyl)amino)cyclohexyl)carbamate To a flask charged with (S)-methyl 2-(((1r,4S)-4-((tert-butoxycarbonyl)amino)cyclohexyl)amino)-2-(4-fluorophenyl)acetate (3.90 g, 10.25 mmol) was added diethyl ether (29.3 mL). The mixture was cooled in an ice water bath and methylmagnesium bromide 3.0 M in diethyl ether (10.93 mL, 32.8 mmol) was added dropwise. The resulting white slurry was allowed to slowly warm to room temperature overnight. The resulting mixture was carefully added to an ice/water/$NH_4Cl$ mixture and was then transferred to a separatory funnel and extracted with EtOAc (2×). The combined organic layers were dried with $Na_2SO_4$, filtered, and dried under reduced pressure. The crude residue was purified with a 50 g SNAP column ramping DCM:MeOH (90:10) in DCM (0-100%, detection at 215 nm) providing tert-butyl ((1S,4r)-4-(((S)-1-(4-fluorophenyl)-2-hydroxy-2-methylpropyl)amino)cyclohexyl)carbamate (2.68 g, 7.04 mmol, 68.7% yield) as a yellow oil. LC-MS indicated the product as the main peak with minor impurities present (215 nm). The material was used in the next step without further purification. m/z (ESI) 381.0 $(M+H)^+$.

Step 3 tert-Butyl ((1S,4r)-4-((S)-4-(4-fluorophenyl)-5,5-dimethyl-2-oxooxazolidin-3-yl)cyclohexyl)carbamate To a flask charged with tert-butyl ((1S,4r)-4-(((S)-1-(4-fluorophenyl)-2-hydroxy-2-methylpropyl)amino)cyclohexyl)carbamate (2.68 g, 7.04 mmol) were added THF (28.2 mL), and DIEA (6.15 mL, 35.2 mmol). The resulting solution was cooled in an ice water bath and triphosgene (2.090 g, 7.04 mmol) was added in one batch. After 90 minutes of stirring (slow warming, ice melt), LC-MS indicated near complete conversion to the desired product (observed as the carbamic acid (t-butyl group removed)). The mixture was carefully added to a stirred slurry of ice/water/$NH_4Cl$, and the resulting mixture was transferred to a separatory funnel and extracted with EtOAc (2×). The combined organic layers were dried under reduced pressure and purified with a 40 HP spherical silica column (15 m, Interchim) ramping DCM:MeOH (90:10) in DCM (0-25%, then isocratic at 25%, detection at 215 nm) yielding tert-butyl ((1S,4r)-4-((S)-4-(4-fluorophenyl)-5,5-dimethyl-2-oxooxazolidin-3-yl)cyclohexyl)carbamate (1.91 g, 4.70 mmol, 66.7% yield) as a mixture of diastereomers and as a yellow foam. m/z (ESI) 351.0 $(M-tBu)^+$.

Step 4

(S)-3-((1r,4S)-4-Aminocyclohexyl)-4-(4-fluorophenyl)-5,5-dimethyloxazolidin-2-one To a flask charged with tert-butyl ((1R,4s)-4-((S)-4-(4-fluorophenyl)-5,5-dimethyl-2-oxooxazolidin-3-yl)cyclohexyl)carbamate (1.9 g, 4.67 mmol) were added DCM (18.70 mL) and TFA (3.60 mL, 46.7 mmol) respectively. The vessel was stirred for 3 hours at room temperature leading to conversion to the desired product. The orange/brown solution was dried under reduced pressure and the residue was purified/free based with a 10 g SCX-2 column washing with MeOH, then 2 M $NH_3$ in MeOH. The basic wash was dried under reduced pressure providing (S)-3-((1s,4R)-4-aminocyclohexyl)-4-(4-fluorophenyl)-5,5-dimethyloxazolidin-2-one (1.2 g, 3.92 mmol, 84% yield) as a mixture of cis and trans isomers as a sticky orange/brown oil. Subsequent analyses on final compounds indicated that ~15% racemization had occurred. m/z (ESI) 307.1 $(M+H)^+$.

Intermediate J (S)-5,5-Dimethyl-4-phenyl-3-(4-(4,4,5,5-tetramethyl-1,3,2-dioxaborolan-2-yl)phenyl)oxazolidin-2-one

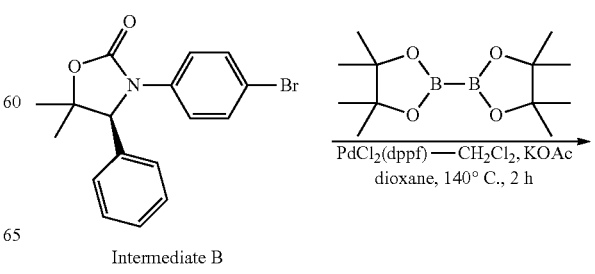

Intermediate B

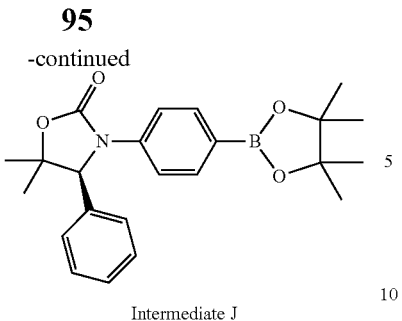

Intermediate J

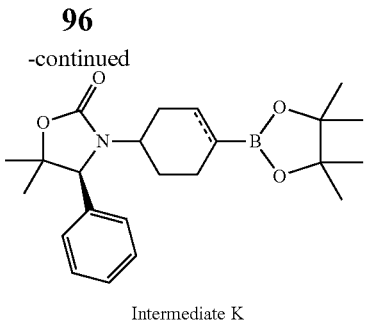

Intermediate K

To a 10-20 mL microwave vial charged with (S)-3-(4-bromophenyl)-5,5-dimethyl-4-phenyloxazolidin-2-one (Intermediate B)(0.75 g, 2.166 mmol) was added dioxane (10.83 mL). The mixture was sparged with nitrogen during the respective additions of bis(pinacolato)diboron (1.100 g, 4.33 mmol), potassium acetate (0.638 g, 6.50 mmol), and PdCl$_2$(dppf)-CH$_2$Cl$_2$ adduct (0.177 g, 0.217 mmol). The vessel was then sealed and irradiated at 140° C. for 2 hours. After cooling to room temperature, the product was adsorbed onto a plug of silica gel and purified by chromatography through a Redi-Sep pre-packed silica gel column (40 g, ISCO), eluting with a gradient of 0% to 50% Et$_2$O in hexane, to provide (S)-5,5-dimethyl-4-phenyl-3-(4-(4,4,5,5-tetramethyl-1,3,2-dioxaborolan-2-yl)phenyl)oxazolidin-2-one (720 mg, 1.831 mmol, 85% yield) as tan solid. m/z (ESI) 394.2 (M+H)$^+$.

Intermediate K (4S)-5,5-Dimethyl-4-phenyl-3-(4-(4,4,5,5-tetramethyl-1,3,2-dioxaborolan-2-yl)cyclohex-3-en-1-yl)oxazolidin-2-one

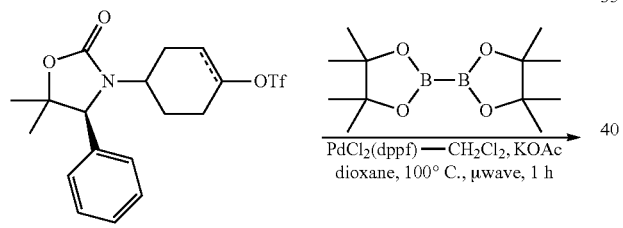

Intermediate MM1

A microwave vial was charged with 4-((S)-5,5-dimethyl-2-oxo-4-phenyloxazolidin-3-yl)cyclohex-1-en-1-yl trifluoromethanesulfonate (0.100 g, 0.238 mmol), bis(pinacolato) diboron (0.067 g, 0.262 mmol), potassium acetate (0.117 g, 1.192 mmol), and dioxane (2.0 mL). Dichloro[1,1'-bis(diphenylphosphino)-ferrocene]palladium (II) DCM adduct (0.019 g, 0.024 mmol) was added, the vial was purged with argon, and the tube was sealed. The mixture was irradiated at 100° C. in the microwave for 1 hour. The reaction mixture was filtered through Celite® brand filter aid and the filtrate was concentrated to afford a brown solid. The residual oil was purified via column chromatography on silica gel (RediSep 40 g column, gradient elution with 0-50% EtOAc-hexane) and provided (4S)-5,5-dimethyl-4-phenyl-3-(4-(4,4,5,5-tetramethyl-1,3,2-dioxaborolan-2-yl)cyclohex-3-en-1-yl)oxazolidin-2-one (0.032 g, 0.081 mmol, 33.8% yield) as a white solid. m/z (ESI) 398.4 (M+H)$^+$.

Intermediate L (R)-3-((1r,4R)-4-(6-Amino-5-bromopyridin-3-yl)cyclohexyl)-5,5-dimethyl-4-phenyloxazolidin-2-one

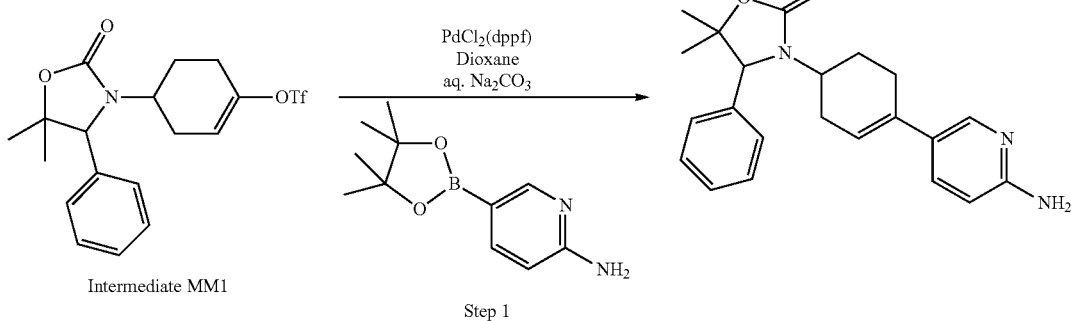

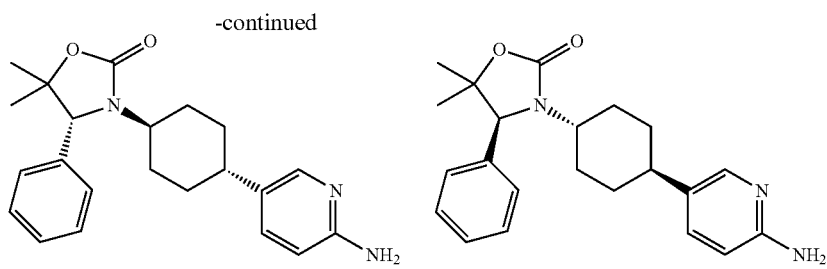

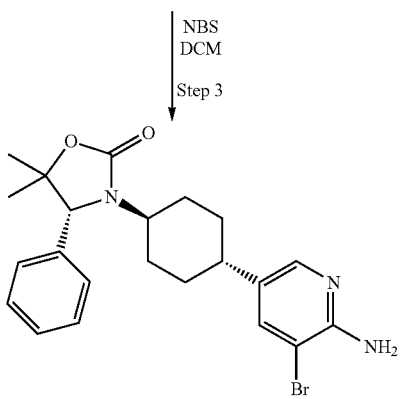

Intermediate L

Step 1

3-(4-(6-Aminopyridin-3-yl)cyclohex-3-en-1-yl)-5,5-dimethyl-4-phenyloxazolidin-2-one A microwave vial was charged with 5,5-dimethyl-2-oxo-4-phenyloxazolidin-3-yl)cyclohex-1-en-1-yl trifluoromethanesulfonate (500 mg, 1.192 mmol), 2-amino-5-(4,4,5,5-tetramethyl-1,3,2-dioxaborolan-2-yl)pyridine (262 mg, 1.192 mmol, commercially available from Sigma-Aldrich, Milwaukee, Wis.), and sodium carbonate (1.788 mL, 3.58 mmol, commercially available from Sigma-Aldrich, Milwaukee, Wis.), tetrakis(triphenylphosphine)palladium(0) (138 mg, 0.119 mmol, Strem) and dioxane (3.974 mL) were added. The system was purged with argon, and the tube was sealed. The mixture was stirred at 100° C. in the microwave for 1 hour. LC-MS indicated clean and good conversion to desired product. The reaction mixture was filtered through Celite® brand filter aid and the filtrate was concentrated to afford a yellow oil. The residual oil was purified via column chromatography on silica gel (RediSep 40 g column, gradient elution with 0 to 100% EtOAc-heptane) and provided 3-(4-(6-aminopyridin-3-yl)cyclohex-3-en-1-yl)-5,5-dimethyl-4-phenyloxazolidin-2-one (450 mg, 1.238 mmol, 104% yield) as a white solid. m/z (ESI) 364.2 (M+H)$^+$.

Step 2

(R)-3-((1r,4R)-4-(6-Aminopyridin-3-yl)cyclohexyl)-5,5-dimethyl-4-phenyloxazolidin-2-one and (S)-3-((1r,4S)-4-(6-aminopyridin-3-yl)cyclohexyl)-5,5-dimethyl-4-phenyloxazolidin-2-one To a 50 mL high pressure round-bottomed flask were added 3-(4-(6-aminopyridin-3-yl)cyclohex-3-en-1-yl)-5,5-dimethyl-4-phenyloxazolidin-2-one (11 g, 30.3 mmol) and palladium (10% wt. on activated carbon) (3.22 g, 3.03 mmol, commercially available from Sigma-Aldrich, Milwaukee, Wis.) in MeOH. The reaction mixture was stirred at 50° C. under 45 psi of hydrogen overnight. LC-MS indicated good conversion to desired product. After cooling to room temperature, the reaction mixture was filtered and concentrated under reduced pressure. The reaction mixture was subject to chiral separation (purified using SFC Column: Chiralpak AD, 5 micron, 5 cm id×15 cm length; Mobile Phase: 35% MeOH w/0.2% diethylamine/65% $CO_2$, Flowrate: 350 mL/min; Back pressure regulator setting: 100 bar), which provided (S)-3-((1r,4S)-4-(6-aminopyridin-3-yl)cyclohexyl)-5,5-dimethyl-4-phenyloxazolidin-2-one, m/z (ESI) 366.2 (M+H)$^+$ and (R)-3-((1r,4R)-4-(6-aminopyridin-3-yl)cyclohexyl)-5,5-dimethyl-4-phenyloxazolidin-2-one m/z (ESI) 366.2 (M+H)$^+$ in good optical purity (>97% ee).

Step 3

(R)-3-((1 r,4R)-4-(6-Amino-5-bromopyridin-3-yl)cyclohexyl)-5,5-dimethyl-4-phenyloxazolidin-2-one To a solution of (R)-3-((1r,4R)-4-(6-aminopyridin-3-yl)cyclohexyl)-5,5-dimethyl-4-phenyloxazolidin-2-one (250 mg, 0.684 mmol) in DCM (3.420 mL) at 0° C., was added NBS (134 mg, 0.752 mmol, commercially available from Sigma-Aldrich, Milwaukee, Wis.). The reaction mixture was stirred for 1 hour at the same temperature, and LC-MS indicated clean and complete conversion to desired product. The solution was then concentrated and water was added. The solid was filtered and washed three times with water. The solid was air-dried which provided (R)-3-((1r,4R)-4-(6-amino-5-bromopyridin-3-yl)cyclohexyl)-5,5-dimethyl-4- phenyloxazolidin-2-one (357 mg, 0.803 mmol) as yellow solid. m/z (ESI) 444.0. The material was used without further purification.

Intermediate M (R)-4-((S)-5,5-Dimethyl-2-oxo-4-phenyloxazolidin-3-yl)cyclohex-1-en-1-yl trifluoromethanesulfonate and (S)-4-((S)-5,5-dimethyl-2-oxo-4-phenyloxazolidin-3-yl)cyclohex-1-en-1-yl trifluoromethanesulfonate

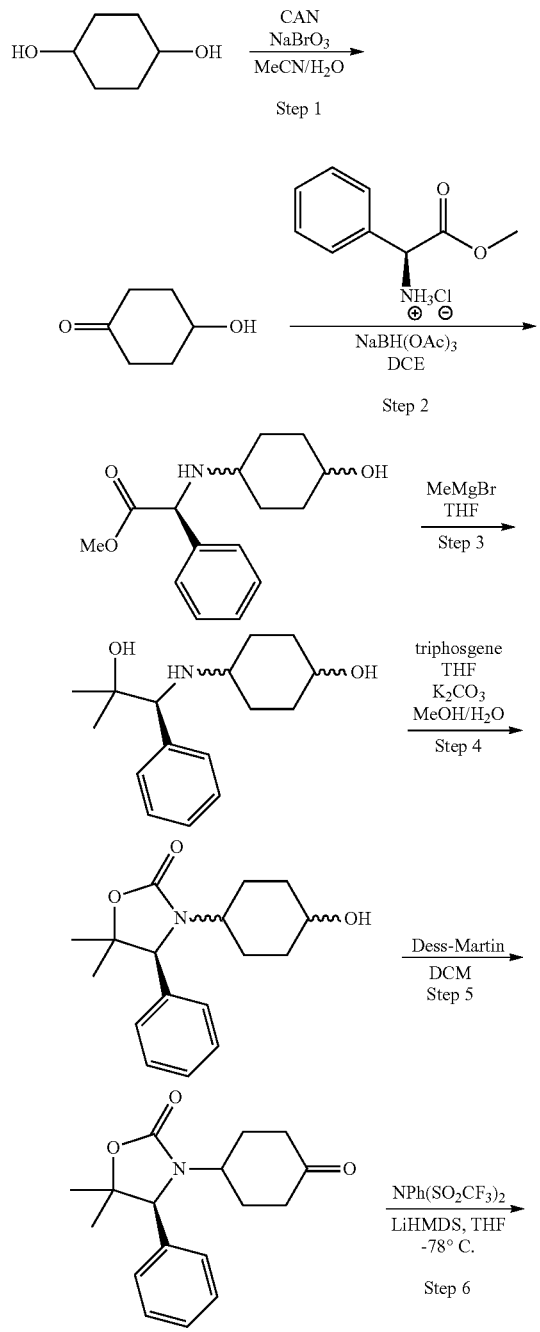

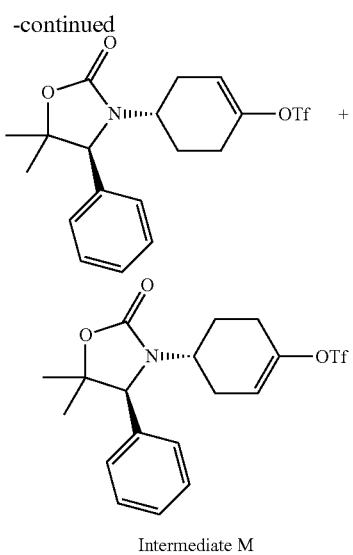

Intermediate M

Step 1

4-Hydroxycyclohexanone

Cerium (IV) ammonium nitrate (45.4 g, 82.85 mmol) and sodium bromate (125 g, 0.828 mol) were added to a solution of 1,4-cyclohexanediol (commercially available from Sigma-Aldrich, Milwaukee, Wis., 278 g, 2.393 mol) in ACN (2.7 L) and water (1.15 L). The resulting mixture was heated at reflux for 2.5 hours and then cooled to room temperature. The resulting solution was extracted with chloroform (1 L×3), and the combined organic extracts were dried, filtered and concentrated to afford 4-hydroxycyclohexanone (245 g, 91%). m/z (ESI) 115 (M+H)$^+$.

Step 2

(S)-Methyl 2-((4-hydroxycyclohexyl)amino)-2-phenylacetate (S)-(+)-2-Phenylglycine methyl ester (commercially available from Sigma-Aldrich, Milwaukee, Wis., 433 g, 2.146 mol) was added to a solution of 4-hydroxycyclohexanone (245 g, 2.146 mol) in DCE (8.5 L). Sodium triacetoxyborohydride was added (910 g, 4.292 mol), and the mixture was stirred at room temperature under nitrogen for 23 hours. Water (3 L) was added to quench the reaction, and the organic layer was separated. The aqueous phase was extracted with DCM (4 L×2) and the organic layers were combined, dried, filtered and concentrated. The residue was purified by column chromatography (gradient elution with 100% DCM to DCM/MeOH=25:1) to afford (S)-methyl 2-((4-hydroxycyclohexyl)amino)-2-phenylacetate (197 g, 35%) (mixture of cis and trans). m/z (ESI) 264 (M+H)$^+$.

Step 3

(S)-4-((2-Hydroxy-2-methyl-1-phenylpropyl)amino)cyclohexanol

A solution of methylmagnesium bromide in 2-methyltetrahydrofuran (3.2 M, 935 mL, 2.992 mol) was added over 1 hour to an ice-cooled solution of (S)-methyl 2-((4-hydroxycyclohexyl)amino)-2-phenylacetate (197 g, 0.748 mol) in anhydrous THF (2 L). The resulting mixture was allowed to warm to room temperature slowly under nitrogen and stirred for 2.5 hours. The mixture was poured into a well stirred mixture of ice water and saturated aqueous ammonium chloride. The mixture was extracted with EtOAc (3 L×3), and the organic layers were combined, dried, filtered and concentrated to give (S)-4-((2-hydroxy-2-methyl-1-phenylpropyl)amino)cyclohexanol (184 g, 93%). m/z (ESI) 264 (M+H)$^+$.

Step 4 cis- and trans-(S)-3-(4-Hydroxycyclohexyl)-5,5-dimethyl-4-phenyloxazolidin-2-one A 12 L three-neck flask was charged with (S)-4-((2-hydroxy-2-methyl-1-phenylpropyl)amino)cyclohexanol (184 g, 0.699 mol), DIEA (609 mL, 3.495 mol) and anhydrous THF (2.8 L) under nitrogen. The solution was cooled using an ice-water bath. Triphosgene (207.4 g, 0.699 mol) was then added over 10 minutes (Caution: the reaction was very exothermic and the temperature went up to ~50° C.), and the mixture was stirred under nitrogen for 2.75 hours at ~0° C. MeOH (850 mL) was added very carefully over 5 minutes, and the mixture was stirred for 15 minutes. The mixture was then concentrated, and the oily residue was transferred to 12 L flask. MeOH (2.75 L) and water (2.75 L) were added, followed by potassium carbonate (965 g, 6.99 mol), and the mixture was heated at reflux for 4 hours. The mixture was cooled to room temperature and MeOH was removed under reduced pressure. The resulting aqueous phase was extracted with EtOAc (3 L×3). The organic layers were combined, dried and concentrated. The resulting residue was purified by column chromatography (eluting with DCM/MeOH=200:1 to 50:1) to give the cis and trans compounds. A mixture of the cis and trans compounds (84 g, 42%) was also obtained.

cis-(S)-3-(4-Hydroxycyclohexyl)-5,5-dimethyl-4-phenyloxazolidin-2-one (25 g, 12%). $^1$H NMR (300 MHz, CDCl$_3$) δ ppm 7.40-7.20 (m, 4H), 7.15-7.05 (m, 1H), 4.38 (s, 1H), 3.95 (br, 1H), 3.75-3.65 (m, 1H), 2.15-1.95 (m, 1H), 1.90-1.80 (m, 1H), 1.75-1.55 (m, 3H), 1.52 (s, 3H), 1.50-1.30 (m, 3H), 1.21 (d, J=3.0 Hz, 1H), 0.90 (s, 3H). m/z (ESI) 290 (M+H)$^+$.

trans-(S)-3-(4-Hydroxycyclohexyl)-5,5-dimethyl-4-phenyloxazolidin-2-one (13.2 g, 7%). $^1$H NMR (300 MHz, CDCl$_3$) δ ppm 7.40-7.20 (m, 4H), 7.15-7.05 (m, 1H), 4.33 (s, 1H), 3.60-3.40 (m, 2H), 2.05-1.95 (m, 1H), 1.90-1.80 (m, 3H), 1.70-1.60 (m, 1H), 1.55 (br, 1H), 1.52 (s, 3H), 1.40-1.20 (m, 3H), 0.90 (s, 3H). m/z (ESI) 290 (M+H)$^+$.

Step 5

(S)-5,5-Dimethyl-3-(4-oxocyclohexyl)-4-phenyloxazolidin-2-one

Dess-Martin periodinane (500 mL, 0.3 M in DCM, 0.15 mol) was added over 15 minutes to an ice-cooled solution of (S)-3-(4-hydroxycyclohexyl)-5,5-dimethyl-4-phenyloxazolidin-2-one (39.5 g, 0.136 mol) in DCM (1 L). The resulting mixture was stirred at room temperature under nitrogen for 22.5 hours. Saturated aqueous Na$_2$S$_2$O$_3$ (300 mL) and saturated aqueous NaHCO$_3$ (300 mL) were added, and the mixture was stirred at room temperature for 1 hour. The organic layer was separated, washed with brine (300 mL), dried, filtered and concentrated. The resulting residue was purified by column chromatography (eluting with 100% DCM to DCM/MeOH=100:1) to afford (S)-5,5-dimethyl-3-(4-oxocyclohexyl)-4-phenyloxazolidin-2-one (25 g, 64%). $^1$H NMR (300 MHz, d$_6$-DMSO) δ ppm 7.45-7.20 (m, 5H), 4.67 (s, 1H), 4.0-3.90 (m, 1H), 2.60-2.35 (m, 2H), 2.25-1.95 (m, 4H), 1.85-1.70 (m, 1H), 1.55-1.40 (m, 1H), 1.47 (s, 3H), 0.80 (s, 3H). m/z (ESI) 288 (M+H)$^+$.

Step 6

(R)-4-((S)-5,5-Dimethyl-2-oxo-4-phenyloxazolidin-3-yl)cyclohex-1-en-1-yl trifluoromethanesulfonate and (S)-4-((S)-5,5-Dimethyl-2-oxo-4-phenyloxazolidin-3-yl)cyclohex-1-en-1-yl trifluoromethanesulfonate A solution of (S)-5,5-dimethyl-3-(4-oxocyclohexyl)-4-phenyloxazolidin-2-one (24 g, 83.5 mmol) in anhydrous THF (450 mL) was cooled to −78° C. using a dry ice-acetone bath. Lithium bis(trimethylsilyl)amide (1.0 M in THF)(96 mL, 96 mmol) was added over 5 minutes, and the resulting mixture was stirred at −78° C. for 45 minutes. N-Phenyltrifluoromethanesulfonimide (47.3 g, 0.132 mol) was added, and the mixture was stirred at room temperature under nitrogen for 16.5 hours. Water (250 mL) was added to quench the reaction, and the mixture was concentrated. The resulting aqueous phase was extracted with EtOAc (250 mL×3). The organic layers were combined, washed with saturated aqueous NaHCO$_3$ solution (100 mL×2), water (100 mL×2), and brine (100 mL). The organic layer was then dried, filtered and concentrated. The residue was purified by column chromatography (eluting with hexanes/EtOAc=20:1 to 5:1) to afford a mixture of (R)-4-((S)-5,5-dimethyl-2-oxo-4-phenyloxazolidin-3-yl)cyclohex-1-en-1-yl trifluoromethanesulfonate and (S)-4-((S)-5,5-dimethyl-2-oxo-4-phenyloxazolidin-3-yl)cyclohex-1-en-1-yl trifluoromethanesulfonate (25 g, 71%). $^1$H NMR (300 MHz, d$_6$-DMSO) δ ppm 7.50-7.20 (m, 5H), 5.90-5.75 (m, 1H), 4.68 (d, J=9 Hz, 1H), 3.70-3.50 (m, 1H), 2.85-2.70 (m, 1H), 2.50-2.10 (m, 3H), 2.05-1.90 (m, 1H), 1.80-1.55 (m, 1H), 1.47 (s, 3H), 0.80 (s, 3H). m/z (ESI) 420 (M+H)$^+$.

General Schemes

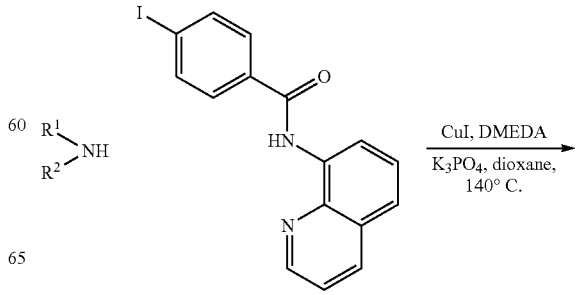

General Scheme A

-continued

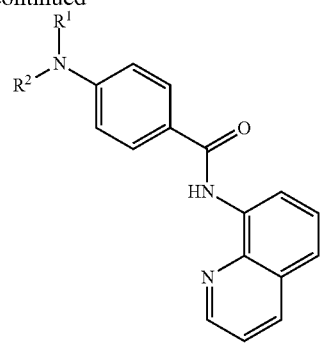

Representative Method

4-Iodo-N-(quinolin-8-yl)benzamide (0.20 g, 0.535 mmol), the selected amine/amide/urea (0.535 mmol), and potassium phosphate (0.567 g, 2.67 mmol) were taken up in dioxane (5 mL), and the mixture was purged with nitrogen prior to the addition of copper (I) iodide (0.102 g, 0.535 mmol) and $N^1,N^2$-dimethylethane-1,2-diamine (0.115 mL, 1.069 mmol). The mixture was re-purged with nitrogen and then heated in a microwave at 140° C. for 2 hours. The resulting reaction mixture was filtered through a frit and washed with MeOH and dried under reduced pressure. The resulting residue was purified by either MPLC or RP-HPLC to obtain product.

General Scheme B

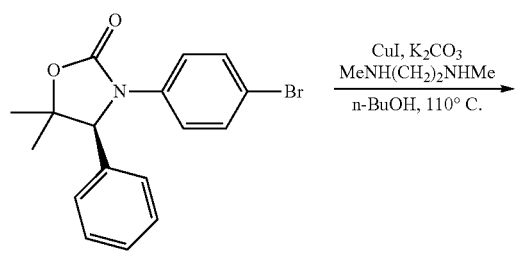

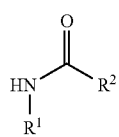

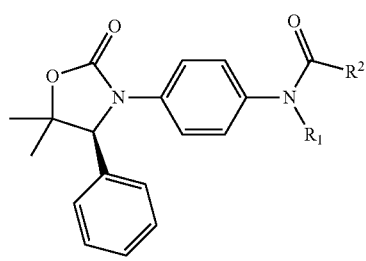

Representative Method

To a flask charged with (S)-3-(4-bromophenyl)-5,5-dimethyl-4-phenyloxazolidin-2-one (0.100 mg, 0.289 µmol), potassium carbonate (0.120 mg, 0.867 mol), copper (I) iodide (0.055 mg, 0.289 µmol), and the selected amine/amide/urea (0.289 µmol) were added n-butanol (solvent volume was 1.155 µL) and $N^1,N^2$-dimethylethane-1,2-diamine (0.051 mg, 0.578 µmol). The resulting suspension was purged with nitrogen, then sealed and shaken overnight at 110° C. The resulting mixture was cooled to room temperature and filtered through Celite® brand filter aid. The filtrate was dried under reduced pressure and the resulting purified by either MPLC or RP-HPLC to obtain product.

General Scheme C

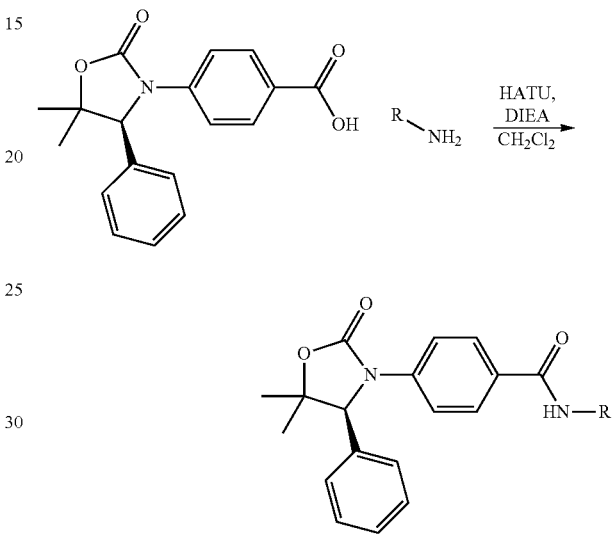

Representative Method

To a vial charged with (S)-4-(5,5-dimethyl-2-oxo-4-phenyloxazolidin-3-yl)benzoic acid (0.250 mg, 0.803 µmol) was added 2-(3H-[1,2,3]triazolo[4,5-b]pyridin-3-yl)-1,1,3,3-tetramethylisouronium hexafluorophosphate(V) (0.336 mg, 0.883 µmol) followed by DCM (solvent volume was 3.21 µL) and N-ethyl-N-isopropylpropan-2-amine (0.420 µL, 2.409 µmol). The mixture was shaken for 15 minutes yielding a yellow solution to which the selected amine (0.883 µmol) was added. The resulting mixture was stirred (varying temperatures) overnight. The reaction mixture was dried under reduced pressure, and the resulting residue was purified by either MPLC or RP-HPLC to obtain product.

General Scheme D Example 1. Synthesis of (S)-4-(5,5-dimethyl-2-oxo-4-phenyloxazolidin-3-yl)-N-(1,5-naphthyridin-4-yl)benzamide

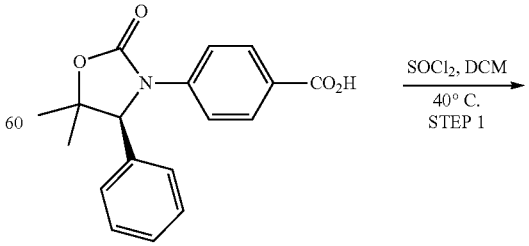

Intermediate D

-continued

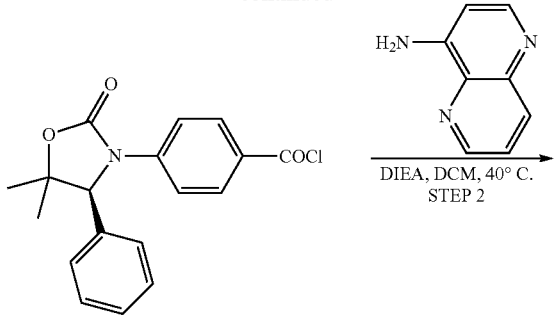

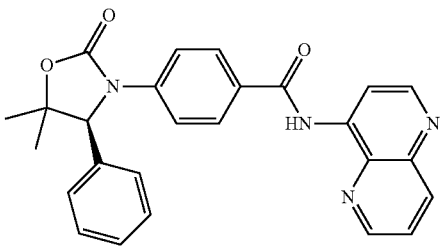

Example 1

Step 1

(S)-4-(5,5-Dimethyl-2-oxo-4-phenyloxazolidin-3-yl) benzoyl chloride

To a vial charged with (S)-4-(5,5-dimethyl-2-oxo-4-phenyloxazolidin-3-yl)benzoic acid (0.200 g, 0.642 mmol) was added DCM (2.57 mL) followed by thionyl chloride (0.469 mL, 6.42 mmol). The vial containing the resulting mixture was sealed and shaken at 40° C. for 2 hours. LC-MS indicated near complete conversion to desired product (primarily methyl ester peak identified). The mixture was dried under reduced pressure providing the product as a light yellow solid. Mass of product not obtained. m/z (ESI) 326.2 (M+H)+ (methyl ester ionization observed).

Step 2

(S)-4-(5,5-Dimethyl-2-oxo-4-phenyloxazolidin-3-yl)-N-(1,5-naphthyridin-4-yl)benzamide To a vessel charged with (S)-4-(5,5-dimethyl-2-oxo-4-phenyloxazolidin-3-yl)benzoyl chloride (50 mg, 0.152 mmol) were added DCM (606 µL), 1,5-naphthyridin-4-amine (commercially available from Astatech Inc., Bristol, Pa.) (24 mg, 0.167 mmol), and DIEA (55.6 µL, 0.318 mmol) respectively. The vessel was sealed and shaken overnight at 40° C. The mixture was dried under reduced pressure and purified using a 25 g, 15 m spherical silica column (Interchim) ramping 0-100% EtOAc in heptane from 0-100% to elute product, which was lyophilized from MeOH/H$_2$O to yield (S)-4-(5,5-dimethyl-2-oxo-4-phenyloxazolidin-3-yl)-N-(1,5-naphthyridin-4-yl)benzamide (64 mg, 96%) as an off-white powder. $^1$H NMR (400 MHz, DMSO-d$_6$) δ=10.63 (s, 1H), 9.01 (dd, J=1.6, 4.2 Hz, 1H), 8.93 (d, J=5.0 Hz, 1H), 8.54 (d, J=5.1 Hz, 1H), 8.46 (dd, J=1.6, 8.5 Hz, 1H), 8.01-7.96 (m, 2H), 7.89 (dd, J=4.3, 8.6 Hz, 1H), 7.76-7.70 (m, 2H), 7.43-7.37 (m, 2H), 7.36-7.22 (m, 3H), 5.57 (s, 1H), 1.67 (s, 3H), 0.94 (s, 3H). m/z (ESI) 439.2 (M+H)+.

General Method MM-1

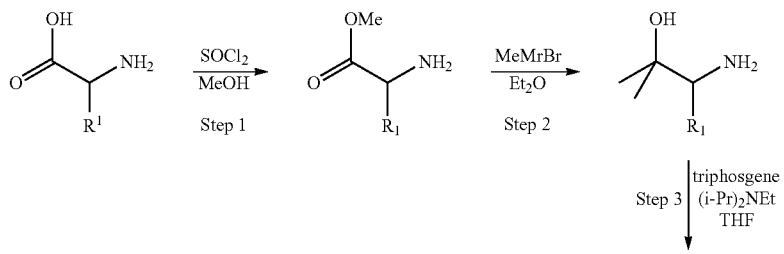

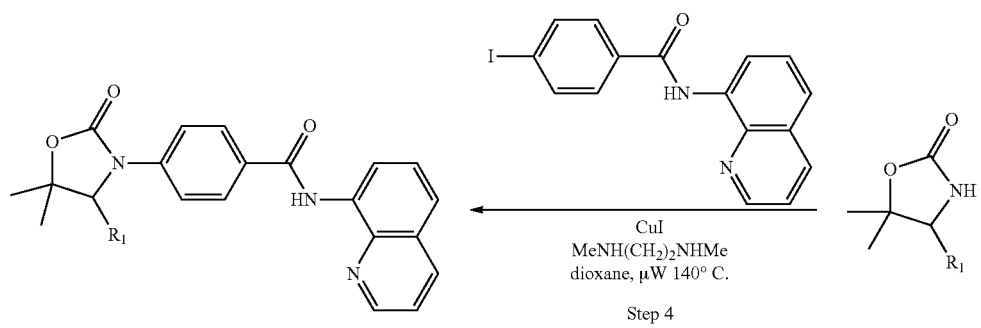

Step 4

Example 2

Synthesis of (S)-4-(4-(4-fluorophenyl)-5,5-dimethyl-2-oxooxazolidin-3-yl)-N-(quinolin-8-yl)benzamide

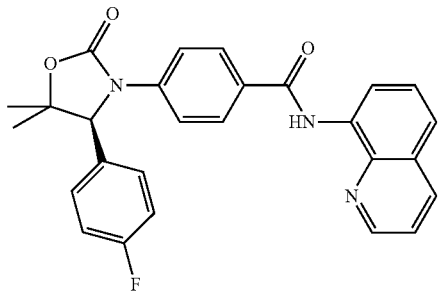 [SMILES: CC1(C)OC(=O)N(c2ccc(C(=O)Nc3cccc4cccnc34)cc2)[C@H]1c1ccc(F)cc1]

Step 1

(S)-Methyl 2-amino-2-(4-fluorophenyl)acetate

Thionyl chloride (0.475 mL, 6.50 mmol) was added dropwise to a solution of (S)-4-fluorophenylglycine (commercially available from Sigma-Aldrich, Milwaukee, Wis.)(1.00 g, 5.91 mmol) in MeOH (25.0 mL), and the mixture was stirred at reflux for 2 hours. The reaction mixture was then concentrated to afford a brown oil. The residue was dissolved in EtOAc, and the solution was partitioned between EtOAc and saturated aqueous NaHCO₃ solution. The aqueous phase was separated and extracted with EtOAc. The combined organic phases were washed with brine, dried over anhydrous Na₂SO₄, filtered, and concentrated to afford (S)-methyl 2-amino-2-(4-fluorophenyl)acetate (1.1 g, 6.0 mmol, 100% yield) as a brown oil. $^1$H NMR (400 MHz, DMSO-d$_6$) δ ppm 2.28 (br. s., 2H), 3.59 (s, 3H), 4.55 (s, 1H), 7.05-7.23 (m, 2H), 7.31-7.53 (m, 2H). m/z (ESI) 184 (M+H)$^+$.

Step 2

(S)-1-Amino-1-(4-fluorophenyl)-2-methylpropan-2-ol

A solution of (S)-methyl 2-amino-2-(4-fluorophenyl)acetate (0.500 g, 2.73 mmol) in diethyl ether (2.0 mL) was added dropwise to a 0° C. solution of methylmagnesium bromide (3.0 M in diethyl ether) (commercially available from Sigma-Aldrich, Milwaukee, Wis., 5.46 mL, 16.38 mmol). The ice bath was then removed, and the mixture was stirred at room temperature for 2 hours. The reaction mixture was cooled to 0° C., diluted with EtOAc, and quenched by the addition of saturated aqueous ammonium chloride solution. The solution was partitioned between EtOAc and saturated aqueous NaHCO₃ solution. The aqueous phase was separated and extracted with EtOAc. The combined organic phases were washed with brine, dried over anhydrous Na₂SO₄, filtered, and concentrated to afford a yellow-brown oil. The residual oil was dissolved in DCM and passed through a Silycycle SCX column washing with MeOH and then with 7 N ammonia in MeOH. The ammonia solution was concentrated to afford (S)-1-amino-1-(4-fluorophenyl)-2-methylpropan-2-ol (0.365 g, 1.992 mmol, 73% yield) as a yellow-brown oil. $^1$H NMR (400 MHz, DMSO-d$_6$) δ ppm 0.94 (s, 3H), 1.00 (s, 3H), 1.99 (s, 2H), 3.69 (s, 1H), 4.38 (s, 1H), 7.07 (t, J=8.95 Hz, 2H), 7.37 (dd, J=8.41, 5.77 Hz, 2H). m/z (ESI) 184 (M+H)$^+$.

Step 3

(S)-4-(4-Fluorophenyl)-5,5-dimethyloxazolidin-2-one

Triphosgene (0.591 g, 1.992 mmol) was added to a 0° C. solution of (S)-1-amino-1-(4-fluorophenyl)-2-methylpropan-2-ol (0.365 g, 1.992 mmol) and N,N-diisopropylethylamine (0.347 mL, 1.992 mmol) in THF (20 mL), and the mixture was stirred at 0° C. for 1.5 hours. The reaction mixture was next partitioned between DCM and saturated aqueous NaHCO₃ solution. The aqueous phase was separated and extracted with DCM. The combined organic phases were washed with brine, dried over anhydrous Na₂SO₄, filtered, and concentrated to afford an orange oil. The residual oil was purified using column chromatography on silica gel (RediSep 40 g column, gradient elution with 0-50% EtOAc-hexane) to afford (S)-4-(4-fluorophenyl)-5,5-dimethyloxazolidin-2-one (0.215 g, 1.028 mmol, 52% yield) as a white solid. $^1$H NMR (400 MHz, DMSO-d$_6$) δ ppm 0.78 (s, 3H), 1.50 (s, 3H), 4.66 (s, 1H), 7.19-7.27 (m, 2H), 7.29-7.37 (m, 2H), 8.04 (s, 1H). m/z (ESI) 210 (M+H)$^+$.

Step 4

(S)-4-(4-(4-Fluorophenyl)-5,5-dimethyl-2-oxooxazolidin-3-yl)-N-(quinolin-8-yl)benzamide A microwave vial was charged with (S)-4-(4-fluorophenyl)-5,5-dimethyloxazolidin-2-one (0.050 g, 0.239 mmol), 4-iodo-N-(quinolin-8-yl)benzamide (0.098 g, 0.263 mmol), tribasic potassium phosphate (0.254 g, 1.195 mmol) and dioxane (2.50 mL). The mixture was purged with argon and then copper (I) iodide (0.046 g, 0.239 mmol) and N,N'-dimethylethylenediamine (0.051 mL, 0.478 mmol) were added. The system was purged with argon, the tube was sealed, and the reaction mixture was heated at 140° C. for 2 hours in the microwave. The reaction mixture was filtered through Celite® brand filter aid, and the filtrate was concentrated to afford an orange brown solid. The residual material was purified using column chromatography on silica gel (RediSep 40 g column, gradient elution with 0-50% EtOAc-hexane) to afford (S)-4-(4-(4-fluorophenyl)-5,5-dimethyl-2-oxooxazolidin-3-yl)-N-(quinolin-8-yl)benzamide (0.097 g, 0.213 mmol, 89% yield) as a white solid. $^1$H NMR (400 MHz, DMSO-d$_6$) δ ppm 0.95 (s, 3H) 1.66 (s, 3H) 5.60 (s, 1H) 7.16-7.29 (m, 2H) 7.36 (br. s., 2H) 7.58-7.81 (m, 5H) 7.97 (d, J=8.80 Hz, 2H) 8.45 (dd, J=8.31, 1.66 Hz, 1H) 8.67 (dd, J=7.68, 1.32 Hz, 1H) 8.95 (dd, J=4.21, 1.66 Hz, 1H) 10.55 (s, 1H). m/z (ESI) 456 (M+H)$^+$.

General Method MM-2

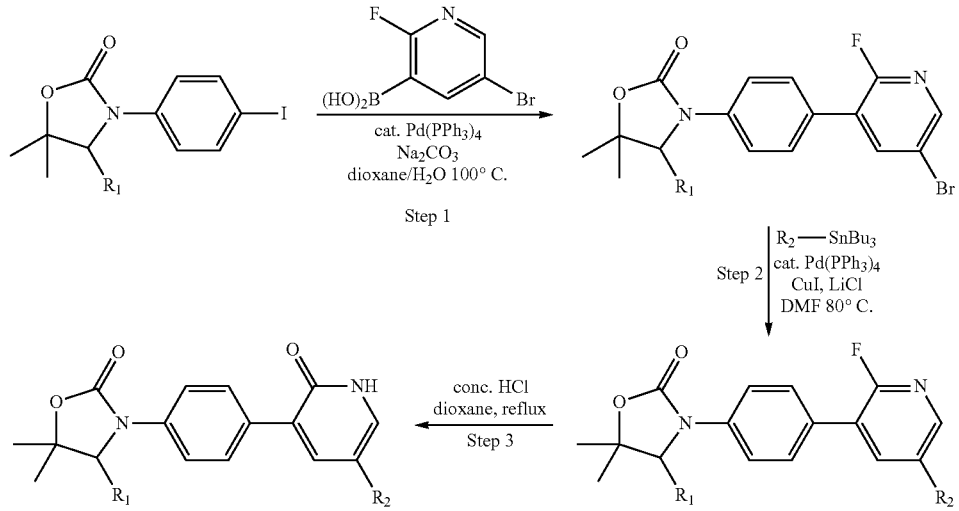

Examples 3 and 4

Synthesis of (S)-3-(4-(2-fluoro-5-(pyrimidin-2-yl)pyridin-3-yl)phenyl)-5,5-dimethyl-4-phenyloxazolidin-2-one and (S)-5,5-dimethyl-3-(4-(2-oxo-5-(pyrimidin-2-yl)-1,2-dihydropyridin-3-yl)phenyl)-4-phenyloxazolidin-2-one Example 3

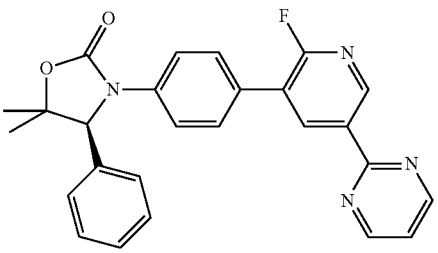

Example 4

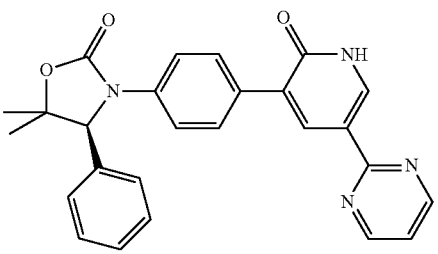

Step 1

(S)-3-(4-(5-Bromo-2-fluoropyridin-3-yl)phenyl)-5,5-dimethyl-4-phenyloxazolidin-2-one A microwave vial was charged with (S)-3-(4-iodophenyl)-5,5-dimethyl-4-phenyloxazolidin-2-one (Intermediate C)(0.200 g, 0.509 mmol), 5-bromo-2-fluoropyridine-3-boronic acid (0.224 g, 1.017 mmol)(commercially available from Alfa Aesar, Ward Hill, Mass.), sodium carbonate (0.162 g, 1.526 mmol), dioxane (3.0 mL), and water (0.600 mL). Tetrakis(triphenylphosphine)palladium(0) (0.059 g, 0.051 mmol) was added, the system was purged with argon, and the tube was sealed. The mixture was then stirred at 100° C. in the microwave for 1 hour. The resulting reaction mixture was filtered through Celite® brand filter aid and the filtrate was concentrated to afford a yellow oil. The residual oil was purified by column chromatography on silica gel (RediSep 40 g column, gradient elution with 0-25% EtOAc-hexane) to afford (S)-3-(4-(5-bromo-2-fluoropyridin-3-yl)phenyl)-5,5-dimethyl-4-phenyloxazolidin-2-one (0.104 g, 0.236 mmol, 46% yield) as a pale tan solid. $^1$H NMR (400 MHz, DMSO-d$_6$) δ ppm 0.92 (s, 3H), 1.64 (s, 3H), 5.52 (s, 1H), 7.07-7.47 (m, 5H), 7.51-7.75 (m, 4H), 8.15-8.44 (m, 2H). m/z (ESI) 441, 443 (M+H)$^+$.

Step 2

(S)-3-(4-(2-Fluoro-5-(pyrimidin-2-yl)pyridin-3-yl)phenyl)-5,5-dimethyl-4-phenyloxazolidin-2-one (Example 3)

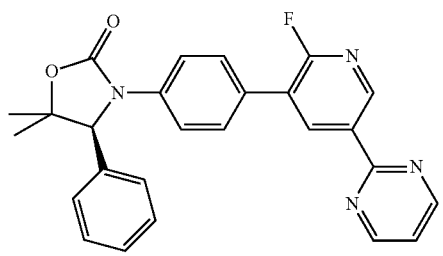 [SMILES: CC1(C)OC(=O)N(c2ccc(-c3cc(-c4ncccn4)cnc3F)cc2)[C@H]1c1ccccc1]

A resealable tube was charged with (S)-3-(4-(5-bromo-2-fluoropyridin-3-yl)phenyl)-5,5-dimethyl-4-phenyloxazolidin-2-one (0.050 g, 0.113 mmol), 2-(tributylstannyl)pyrimidine (commercially available from Frontier Scientific, Inc., Logan Utah) (0.056 mL, 0.170 mmol), lithium chloride (9.61 mg, 0.227 mmol), copper (I) iodide (2.158 mg, 0.011 mmol), and DMF (1.0 mL). Tetrakis(triphenylphosphine)palladium (0) (0.013 g, 0.011 mmol) was added, the system was purged with argon, and the tube was sealed. The mixture was then stirred at 100° C. for 12 hours. The reaction mixture was next concentrated to afford a brown oil. The residual oil was purified by column chromatography on silica gel (RediSep 40 g column, gradient elution with 0-50% EtOAc-hexane) to afford (S)-3-(4-(2-fluoro-5-(pyrimidin-2-yl)pyridin-3-yl)phenyl)-5,5-dimethyl-4-phenyloxazolidin-2-one (0.021 g, 0.048 mmol, 42% yield) as a white solid. $^1$H NMR (400 MHz, DMSO-$d_6$) δ ppm 0.90-1.00 (m, 3H), 1.66 (s, 3H), 5.53 (s, 1H), 7.21-7.46 (m, 5H), 7.54 (t, J=4.89 Hz, 1H), 7.60-7.74 (m, 4H), 8.81 (dd, J=9.78, 2.35 Hz, 1H), 8.96 (d, J=4.89 Hz, 2H), 9.09 (dd, J=2.25, 1.08 Hz, 1H). m/z (ESI) 441 (M+H)$^+$.

Step 3

(S)-5,5-Dimethyl-3-(4-(2-oxo-5-(pyrimidin-2-yl)-1,2-dihydropyridin-3-yl)phenyl)-4-phenyloxazolidin-2-one (Example 4)

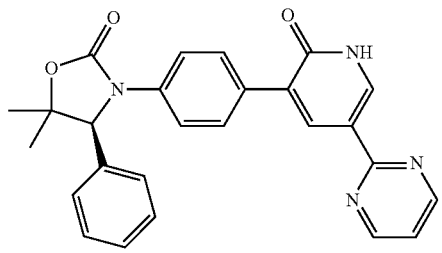

A resealable tube was charged with (S)-3-(4-(2-fluoro-5-(pyrimidin-2-yl)pyridin-3-yl)phenyl)-5,5-dimethyl-4-phenyloxazolidin-2-one (0.034 g, 0.077 mmol), dioxane (2.0 mL), and water (0.667 mL). Concentrated HCl (37%) (0.167 mL) was added, the system was flushed with argon, the tube was sealed, and the reaction mixture was stirred at 100° C. for 1.5 hours. The reaction mixture was next partitioned between EtOAc and saturated aqueous NaHCO$_3$ solution. The aqueous phase was extracted with EtOAc. The combined organic phases were washed with brine, dried over anhydrous Na$_2$SO$_4$, filtered, and concentrated to afford (S)-5,5-dimethyl-3-(4-(2-oxo-5-(pyrimidin-2-yl)-1,2-dihydropyridin-3-yl)phenyl)-4-phenyloxazolidin-2-one (0.034 g, 0.078 mmol, 100% yield) as a white solid. $^1$H NMR (400 MHz, DMSO-$d_6$) δ ppm 0.92 (s, 3H), 1.65 (s, 3H), 5.48 (s, 1H), 7.18-7.45 (m, 6H), 7.48-7.59 (m, 2H), 7.65-7.75 (m, 2 H), 8.32 (d, J=2.45 Hz, 1H), 8.43 (d, J=2.54 Hz, 1H), 8.80 (d, J=4.89 Hz, 2H), 12.13 (br. s., 1H). m/z (ESI) 439 (M+H)$^+$.

General Method MM-3

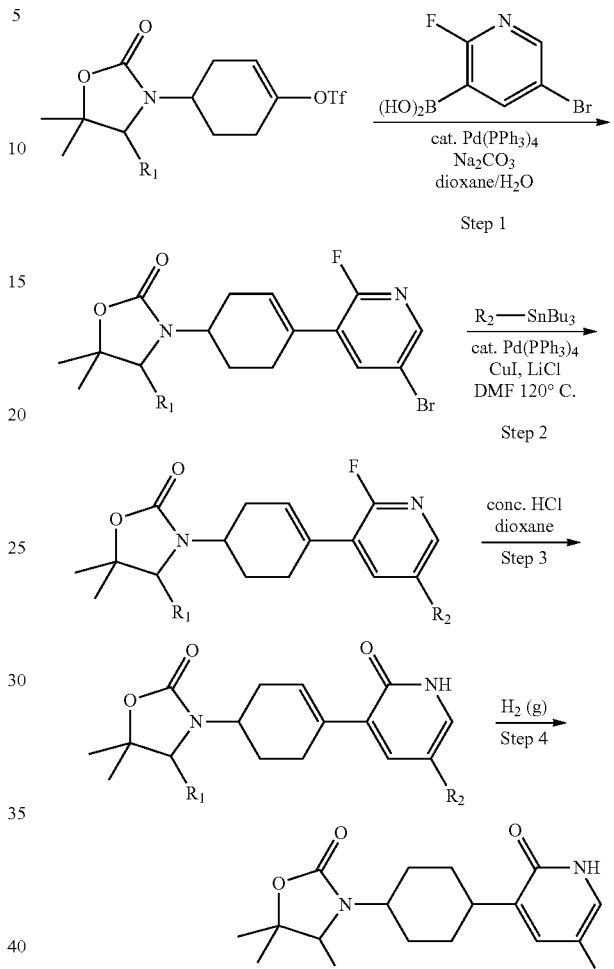

Examples 5, 6, 7, and 8

Synthesis of (+/−)-3-(trans-4-((4S/R)-5,5-dimethyl-2-oxo-4-phenyl-1,3-oxazolidin-3-yl)cyclohexyl)-5-(2-pyrimidinyl)-2(1H)-pyridinone and (+/−)-3-(cis-4-((4S/R)-5,5-dimethyl-2-oxo-4-phenyl-1,3-oxazolidin-3-yl)cyclohexyl)-5-(2-pyrimidinyl)-2(1H)-pyridinone Examples 5 and 6

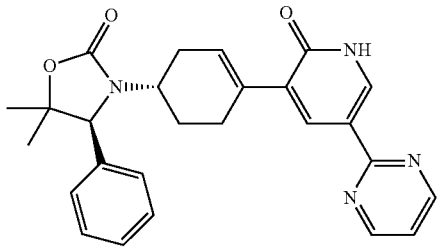

113

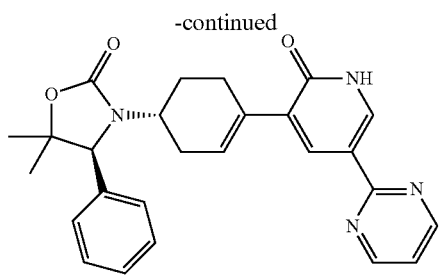

Example 7

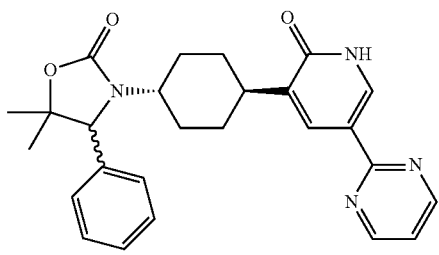

Example 8

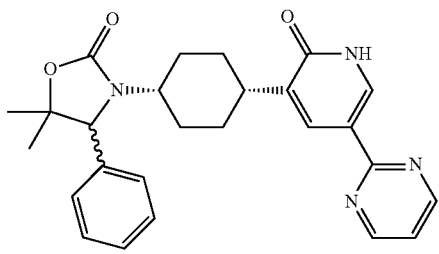

Step 1

(S)-3-((R)-4-(5-Bromo-2-fluoropyridin-3-yl)cyclo-hex-3-en-1-yl)-5,5-dimethyl-4-phenyloxazolidin-2-one and (S)-3-((S)-4-(5-bromo-2-fluoropyridin-3-yl)cyclohex-3-en-1-yl)-5,5-dimethyl-4-phenyloxazolidin-2-one A microwave vial was charged with a mixture of (R)-4-((S)-5,5-dimethyl-2-oxo-4-phenyloxazolidin-3-yl)cyclohex-1-en-1-yl trifluoromethanesulfonate and (S)-4-((S)-5,5-dimethyl-2-oxo-4-phenyloxazolidin-3-yl)cyclohex-1-en-1-yl trifluoromethanesulfonate (1.00 g, 2.384 mmol), 5-bromo-2-fluoropyridine-3-boronic acid (0.786 g, 3.58 mmol) (commercially available from Alfa Aesar, Ward Hill, Mass.), sodium carbonate (0.758 g, 7.15 mmol), dioxane (10.0 mL) and water (2.000 mL). Tetrakis(triphenylphosphine)palladium(0) (0.276 g, 0.238 mmol) was added, the system was purged with argon, and the tube was sealed. The mixture was then stirred at 100° C. in the microwave for 1 hour. The reaction mixture was filtered through Celite® brand filter aid and the filtrate was concentrated to afford a yellow oil. The residual yellow oil was purified by column chromatography on silica gel (RediSep 40 g column, gradient elution with 0 to 25 to 50% EtOAc-heptane) to afford a mixture of (S)-3-((R)-4-(5-bromo-2-fluoropyridin-3-yl)cyclohex-3-en-1-yl)-5,5-dimethyl-4-phenyloxazolidin-2-one and (S)-3-((S)-4-(5-bromo-2-fluoropyridin-3-yl)cyclohex-3-en-1-yl)-5,5-dimethyl-4-phenyloxazolidin-2-one (0.659 g, 1.480 mmol, 62.1% yield) as a white solid. $^1$H NMR (400 MHz, DMSO-d$_6$) δ ppm 0.82 (s, 3H), 1.49 (s, 3H), 1.50-1.58 (m, 1H), 1.65-2.48 (m, 4H), 2.61-2.89 (m, 1H), 3.51-3.82 (m, 1H), 4.70 (d, J=11.64 Hz, 1H), 5.83-6.14 (m, 1H), 7.11-7.62 (m, 5H), 8.05 (ddd, J=8.78, 6.63, 2.49 Hz, 1H), 8.17-8.32 (m, 1H). m/z (ESI) 445, 447 (M+H)⁺.

Step 2

(S)-3-((R)-4-(2-Fluoro-5-(pyrimidin-2-yl)pyridin-3-yl)cyclohex-3-en-1-yl)-5,5-dimethyl-4-phenyloxazolidin-2-one and (S)-3-((S)-4-(2-fluoro-5-(pyrimidin-2-yl)pyridin-3-yl)cyclohex-3-en-1-yl)-5,5-dimethyl-4-phenyloxazolidin-2-one A microwave vial was charged with a mixture of (S)-3-((R)-4-(5-bromo-2-fluoropyridin-3-yl)cyclohex-3-en-1-yl)-5,5-dimethyl-4-phenyloxazolidin-2-one and (S)-3-((S)-4-(5-bromo-2-fluoropyridin-3-yl)cyclohex-3-en-1-yl)-5,5-dimethyl-4-phenyloxazolidin-2-one (0.037 g, 0.083 mmol), 2-(tributylstannyl)pyrimidine (commercially available from Frontier Scientific, Inc., Logan Utah) (0.041 mL, 0.125 mmol), lithium chloride (7.04 mg, 0.166 mmol), copper (I) iodide (1.582 mg, 8.31 mol), and DMF (1.0 mL). Tetrakis(triphenylphosphine)palladium(0) (9.60 mg, 8.31 mol) was added, the system was purged with argon, and the tube was sealed. The mixture was then stirred at 120° C. in a microwave for 2 hours. The reaction mixture was concentrated to afford a brown oil. The residual brown oil was purified by column chromatography on silica gel (RediSep 40 g column, gradient elution with 0-50% EtOAc-heptane) to afford a mixture of (S)-3-((R)-4-(2-fluoro-5-(pyrimidin-2-yl)pyridin-3-yl)cyclohex-3-en-1-yl)-5,5-dimethyl-4-phenyloxazolidin-2-one and (S)-3-((S)-4-(2-fluoro-5-(pyrimidin-2-yl)pyridin-3-yl)cyclohex-3-en-1-yl)-5,5-dimethyl-4-phenyloxazolidin-2-one (0.027 g, 0.061 mmol, 73.1% yield) as an off-white solid. $^1$H NMR (400 MHz, DMSO-d$_6$) δ ppm 0.83 (s, 3H), 1.50 (s, 3H), 1.53-1.65 (m, 1H), 1.67-1.83 (m, 1H), 1.94-2.46 (m, 3H), 2.69-2.85 (m, 1H), 3.63-3.84 (m, 1H), 4.67-4.78 (m, 1H), 5.89-6.14 (m, 1H), 7.23-7.49 (m, 5H), 7.52 (t, J=4.89 Hz, 1H), 8.62 (dt, J=9.66, 2.85 Hz, 1H), 8.93 (d, J=4.89 Hz, 2H), 8.97-9.02 (m, 1H). m/z (ESI) 445 (M+H)⁺.

Step 3

(S)-5,5-Dimethyl-3-((S)-4-(2-oxo-5-(pyrimidin-2-yl)-1,2-dihydropyridin-3-yl)cyclohex-3-en-1-yl)-4-phenyloxazolidin-2-one and (S)-5,5-dimethyl-3-((R)-4-(2-oxo-5-(pyrimidin-2-yl)-1,2-dihydropyridin-3-yl)cyclohex-3-en-1-yl)-4-phenyloxazolidin-2-one (structures have been arbitrarily assigned)

Examples 5 and 6

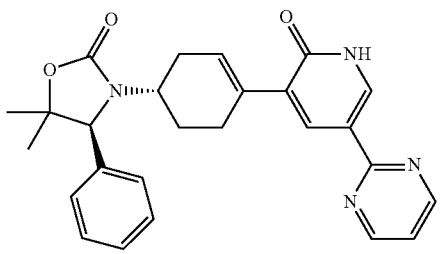 [SMILES: CC1(C)OC(=O)N(c2ccc(-c3cc(-c4ncccn4)c[nH]c3=O)cc2)[C@H]1c1ccccc1]

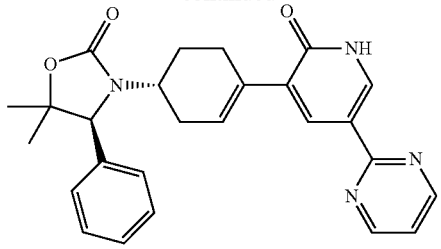

A resealable tube was charged with a mixture of (S)-3-((R)-4-(2-fluoro-5-(pyrimidin-2-yl)pyridin-3-yl)cyclohex-3-en-1-yl)-5,5-dimethyl-4-phenyloxazolidin-2-one and (S)-3-((S)-4-(2-fluoro-5-(pyrimidin-2-yl)pyridin-3-yl)cyclohex-3-en-1-yl)-5,5-dimethyl-4-phenyloxazolidin-2-one (0.090 g, 0.202 mmol), dioxane (3.0 mL), and water (1.0 mL). Concentrated HCl (37%) (0.25 mL) was added, the system was flushed with argon, the tube was sealed, and the reaction mixture was stirred at 100° C. for 2 hours. The reaction mixture was partitioned between EtOAc and saturated aqueous NaHCO$_3$ solution. The aqueous phase was washed and extracted with EtOAc. The combined organic phases were washed with brine, dried over anhydrous Na$_2$SO$_4$, filtered, and concentrated to afford an off-white solid. This material was purified via SFC separation (Chiralpak AD-H column (2×15 cm), eluting with 25% MeOH (0.2% DEA)/CO$_2$, 100 bar, 70 mL/min, 220 nM. Injection volume 0.5 mL, 9 mg/mL MeOH) to afford (S)-5,5-dimethyl-3-((S)-4-(2-oxo-5-(pyrimidin-2-yl)-1,2-dihydropyridin-3-yl)cyclohex-3-en-1-yl)-4-phenyloxazolidin-2-one (0.026 g, 0.059 mmol, 29% yield) as a white solid (first eluting peak, structure arbitrarily assigned). $^1$H NMR (400 MHz, DMSO-d$_6$) δ ppm 0.82 (s, 3H), 1.50 (s, 3H), 1.86-2.23 (m, 4H), 2.27-2.48 (m, 1H), 2.54-2.70 (m, 1H), 3.56-3.84 (m, 1H), 4.51-4.89 (m, 1H), 6.35 (br. s., 1H), 7.14-7.62 (m, 6H), 8.05-8.36 (m, 2H), 8.67-8.90 (m, 2H), 11.96 (br. s., 1H). m/z (ESI) 443 (M+H)$^+$.

Purification also afforded (S)-5,5-dimethyl-3-((R)-4-(2-oxo-5-(pyrimidin-2-yl)-1,2-dihydropyridin-3-yl)cyclohex-3-en-1-yl)-4-phenyloxazolidin-2-one (0.028 g, 0.063 mmol, 62.2% yield) as a white solid (second eluting peak, structure arbitrarily assigned). $^1$H NMR (400 MHz, DMSO-d$_6$) δ ppm 0.82 (s, 3H), 1.38-1.49 (m, 1H), 1.50 (s, 3H), 1.70 (d, J=12.52 Hz, 1H), 2.10-2.46 (m, 3H), 2.60-2.86 (m, 1H), 3.46-3.95 (m, 1H), 4.71 (s, 1H), 6.46 (br. s., 1H), 7.07-7.71 (m, 6H), 8.00-8.42 (m, 2H), 8.77 (d, J=4.89 Hz, 2H), 11.95 (br. s., 1H). m/z (ESI) 443 (M+H)$^+$.

Step 4

(+/−)-3-(trans-4-((4S/R)-5,5-Dimethyl-2-oxo-4-phenyl-1,3-oxazolidin-3-yl)cyclohexyl)-5-(2-pyrimidinyl)-2(1H)-pyridinone and AMG2716737: (+/−)-3-(cis-4-((4S/R)-5,5-dimethyl-2-oxo-4-phenyl-1,3-oxazolidin-3-yl)cyclohexyl)-5-(2-pyrimidinyl)-2(1H)-pyridinone 1,1'-Bis(di-i-propylphosphino)ferrocene(1,5-cyclooctadiene)rhodium(I)tetrafluoroborate (commercially available from Strem Chemicals Inc., Newburyport, Mass.) (0.089 g, 0.124 mmol) was added to a mixture of (S)-5,5-dimethyl-3-((S)-4-(2-oxo-5-(pyrimidin-2-yl)-1,2-dihydropyridin-3-yl)cyclohex-3-en-1-yl)-4-phenyloxazolidin-2-one and (S)-5,5-dimethyl-3-((R)-4-(2-oxo-5-(pyrimidin-2-yl)-1,2-dihydropyridin-3-yl)cyclohex-3-en-1-yl)-4-phenyloxazolidin-2-one (0.550 g, 1.243 mmol) in MeOH (8.0 mL) and DCM (2.00 mL). The system was evacuated and purged with H$_2$ (g), and then stirred at room temperature under a H$_2$ (g) atmosphere for 2 days. A second portion of 1,1'-bis(di-i-propylphosphino)ferrocene(1,5-cyclooctadiene)rhodium(I)tetrafluoroborate (0.089 g, 0.124 mmol) was added, the system was evacuated and purged with H$_2$ (g), and then stirred at room temperature under a H$_2$ (g) atmosphere for 2 hours. The material was purified via reverse-phase preparative HPLC using a Phenomenex Luna column, 5 micron, C18(2), 100 Å, 150×30 mm, 0.1% TFA in ACN/H$_2$O, gradient 35% to 85% over 20 minutes to afford (+/−)-3-(trans-4-((4S/R)-5,5-dimethyl-2-oxo-4-phenyl-1,3-oxazolidin-3-yl)cyclohexyl)-5-(2-pyrimidinyl)-2(1H)-pyridinone (0.100 g, 0.225 mmol, 18% yield) as an off-white solid (second eluting peak). $^1$H NMR (400 MHz, DMSO-d$_6$) δ ppm 0.81 (s, 3H), 1.06-1.45 (m, 4H), 1.48 (s, 3H), 1.53-1.96 (m, 5H), 3.46-3.69 (m, 1H), 4.66 (s, 1H), 7.08-7.54 (m, 6H), 7.99-8.34 (m, 2H), 8.76 (d, J=4.89 Hz, 2H), 11.84 (br. s., 1H). m/z (ESI) 445 (M+H)$^+$. (+/−)-3-(cis-4-((4S/R)-5,5-Dimethyl-2-oxo-4-phenyl-1,3-oxazolidin-3-yl)cyclohexyl)-5-(2-pyrimidinyl)-2(1H)-pyridinone (0.245 g, 0.551 mmol, 44.3% yield) (first eluting peak) was also obtained. $^1$H NMR (400 MHz, DMSO-d$_6$) δ ppm 0.79 (s, 3H), 1.34-1.50 (m, 2H), 1.50-1.55 (m, 3H), 1.56-1.81 (m, 4H), 1.85-2.04 (m, 1H), 2.18-2.45 (m, 1H), 2.72-2.97 (m, 1H), 3.47-3.64 (m, 1H) 4.65 (s, 1H), 6.97-7.60 (m, 6H), 7.97-8.36 (m, 2H), 8.82 (d, J=4.89 Hz, 2H), 11.57-12.05 (m, 1H). m/z (ESI) 445 (M+H)$^+$ General Method MM-4

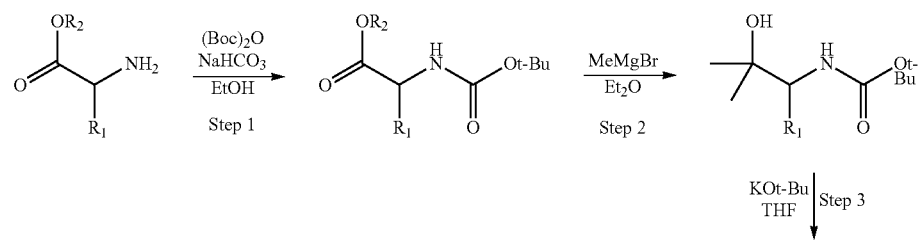

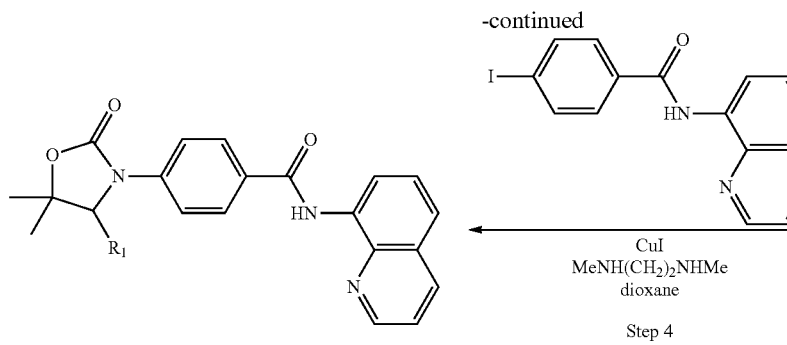

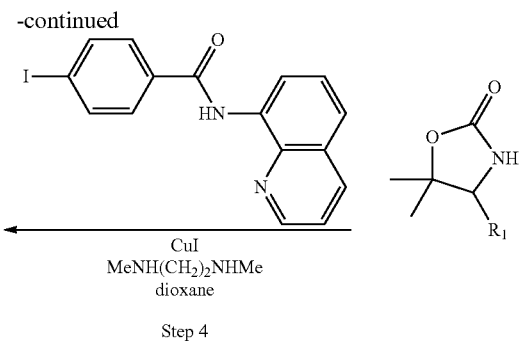

Step 4

Example 9

Synthesis of (+/−)-(R/S)-4-(5,5-dimethyl-2-oxo-4-(pyridin-3-yl)oxazolidin-3-yl)-N-(quinolin-8-yl)benzamide

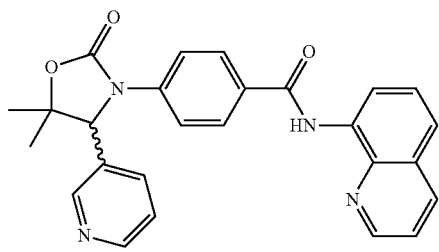

Step 1

Methyl 2-((tert-butoxycarbonyl)amino)-2-(pyridin-3-yl)acetate

NaHCO$_3$ (0.665 g, 7.91 mmol) was added to a 0° C. solution of (+/−)-methyl 2-amino-2-(pyridin-3-yl)acetate dihydrochloride (commercially available from Enamine Building Blocks, Kiev, Ukraine) (0.541 g, 2.261 mmol) in EtOH (11.3 mL). Di-tert-butyl dicarbonate (0.503 g, 2.306 mmol) was added, and the mixture was stirred at room temperature for 16 hours. The reaction mixture was then partitioned between DCM and water. The aqueous phase was separated and extracted with DCM. The combined organic phases were washed with brine, dried over anhydrous Na$_2$SO$_4$, filtered, and concentrated to afford methyl 2-((tert-butoxycarbonyl)amino)-2-(pyridin-3-yl)acetate (0.584 g, 2.193 mmol, 97% yield) as an orange brown oil. $^1$H NMR (400 MHz, DMSO-d$_6$) δ ppm 1.39 (s, 9H), 3.63 (s, 3H), 5.31 (d, J=8.12 Hz, 1H), 7.39 (dd, J=7.78, 4.74 Hz, 1H), 7.79 (d, J=7.92 Hz, 1H), 7.87-8.01 (m, 1H), 8.52 (dd, J=4.79, 1.56 Hz, 1H), 8.59 (d, J=2.05 Hz, 1H). m/z (ESI) 267 (M+H)$^+$.

Step 2 tert-Butyl (2-hydroxy-2-methyl-1-(pyridin-3-yl)propyl)carbamate

A solution of methyl 2-((tert-butoxycarbonyl)amino)-2-(pyridin-3-yl)acetate (0.584 g, 2.193 mmol) in diethyl ether (2.0 mL) was added dropwise to a 0° C. solution of methylmagnesium bromide (3.0 M in diethyl ether) (4.39 mL, 13.16 mmol). The reaction was diluted with additional diethyl ether (3.0 mL). The ice bath was removed, and the mixture was stirred at room temperature for 16 hours. The reaction mixture was then quenched by pouring onto a solution of ice, EtOAc, and saturated aqueous ammonium chloride solution and stirring for 10 minutes. The aqueous phase was separated and extracted with EtOAc. The combined organic phases were washed with brine, dried over anhydrous Na$_2$SO$_4$, filtered, and concentrated to afford a yellow solid. The residual yellow material was purified by column chromatography on silica gel (RediSep 40 g column, gradient elution with 50-100% EtOAc-hexane) to afford afford tert-butyl (2-hydroxy-2-methyl-1-(pyridin-3-yl)propyl)carbamate (0.388 g, 1.457 mmol, 66% yield) as an off-white solid. $^1$H NMR (400 MHz, DMSO-d$_6$) δ ppm 0.99 (s, 3H), 1.08 (s, 3H), 1.36 (s, 9H), 4.46 (d, J=9.49 Hz, 1H), 4.55 (s, 1H), 7.22 (d, J=9.00 Hz, 1H), 7.30 (dd, J=7.87, 4.74 Hz, 1H), 7.73 (d, J=7.83 Hz, 1H), 8.41 (dd, J=4.79, 1.66 Hz, 1H), 8.49 (s, 1H). m/z (ESI) 267 (M+H)$^+$.

Step 3

5,5-Dimethyl-4-(pyridin-3-yl)oxazolidin-2-one

Potassium tert-butoxide (0.093 g, 0.826 mmol) was added to a 0° C. solution of tert-butyl (2-hydroxy-2-methyl-1-(pyridin-3-yl)propyl)carbamate (0.200 g, 0.751 mmol) in THF (5.0 mL). The ice bath was removed and the reaction mixture was stirred at room temperature for 16 hours. The reaction mixture was concentrated to afford a yellow oil. The residual yellow oil was dissolved in DCM and passed through a Silycycle SCX column washing with MeOH and then with 7 N ammonia in MeOH. The ammonia solution was concentrated to afford 5,5-dimethyl-4-(pyridin-3-yl)oxazolidin-2-one (0.150 g, 0.780 mmol, 100% yield) as a pale yellow oil. $^1$H NMR (400 MHz, DMSO-d$_6$) δ ppm 0.82 (s, 3H), 1.53 (s, 3H), 4.74 (s, 1H), 7.44 (ddd, J=7.90, 4.77, 0.64 Hz, 1H), 7.64-7.78 (m, 1H), 8.08 (s, 1H), 8.51 (d, J=2.35 Hz, 1H), 8.55 (dd, J=4.79, 1.66 Hz, 1H). m/z (ESI) 193 (M+H)$^+$.

Step 4

(+/−)-(R/S)-4-(5,5-Dimethyl-2-oxo-4-(pyridin-3-yl)oxazolidin-3-yl)-N-(quinolin-8-yl)benzamide A microwave vial was charged with 5,5-dimethyl-4-(pyridin-3-yl)oxazolidin-2-one (0.072 g, 0.376 mmol), 4-iodo-N-(quinolin-8-yl)benzamide (0.155 g, 0.414 mmol), tribasic potassium phosphate (0.399 g, 1.880 mmol) and dioxane (3.50 mL). The mixture was purged with argon and then copper (I) iodide (0.072 g, 0.376 mmol) and N,N'-dimethylethylenediamine (0.081 mL, 0.752 mmol) were added. The system was purged with argon, the tube was sealed, and the reaction mixture was heated at 140° C. for 1 hour in a microwave. The reaction mixture was filtered through Celite® brand filter aid and the filtrate was concentrated to afford an orange brown solid. This residual material was purified by column chromatography on silica gel (RediSep 40 g column, gradient elution with 50-100% EtOAc-hexane) to afford (+/−)-(R/S)-4-(5,5-dimethyl-2-oxo-4-(pyridin-3-yl)oxazolidin-3-yl)-N-(quinolin-8-yl)benzamide (0.092 g, 0.210 mmol, 56% yield) as an off-white solid. $^1$H NMR (400 MHz, DMSO-$d_6$) δ ppm 0.98 (s, 3H), 1.69 (s, 3H), 5.69 (s, 1H), 7.40 (dd, J=8.02, 4.79 Hz, 1H), 7.57-7.79 (m, 6H), 7.90-8.04 (m, 2H), 8.45 (dd, J=8.31, 1.66 Hz, 1H), 8.54 (dd, J=4.74, 1.61 Hz, 1H), 8.60 (br. s., 1H), 8.67 (dd, J=7.63, 1.27 Hz, 1H), 8.95 (dd, J=4.25, 1.71 Hz, 1H), 10.56 (s, 1H). m/z (ESI) 439 (M+H)$^+$.

Examples 10 and 11

Synthesis of (R)-4-(5,5-dimethyl-2-oxo-4-(pyridin-3-yl)oxazolidin-3-yl)-N-(quinolin-8-yl)benzamide and (S)-4-(5,5-dimethyl-2-oxo-4-(pyridin-3-yl)oxazolidin-3-yl)-N-(quinolin-8-yl)benzamide Example 10

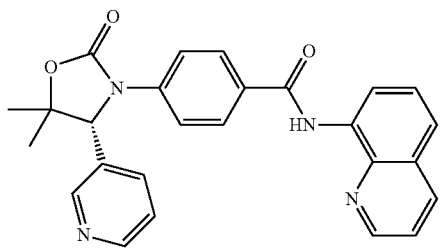 [SMILES: CC1(C)OC(=O)N(c2ccc(C(=O)Nc3cccc4cccnc34)cc2)C1c1cccnc1]

Example 11

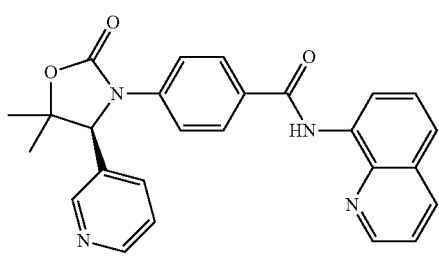

A racemic mixture of (+/−)-(R/S)-4-(5,5-dimethyl-2-oxo-4-(pyridin-3-yl)oxazolidin-3-yl)-N-(quinolin-8-yl)benzamide (0.070 g, 0.160 mmol) was purified by SFC separation (Chiralpak AD-H column (2×15 cm), eluting with 50/50 CO$_2$/MeOH with 0.2% DEA; flow rate: 80 mL/min; 13 mg sample/injection) to afford (R)-4-(5,5-dimethyl-2-oxo-4-(pyridin-3-yl)oxazolidin-3-yl)-N-(quinolin-8-yl)benzamide (0.030 g, 0.068 mmol, 86% yield) as an off-white solid (first eluting peak). $^1$H NMR (400 MHz, DMSO-$d_6$) δ ppm 0.98 (s, 3H), 1.69 (s, 3H), 5.69 (s, 1H), 7.40 (dd, J=7.73, 4.69 Hz, 1H), 7.57-7.82 (m, 6H), 7.91-8.05 (m, 2H), 8.45 (dd, J=8.36, 1.61 Hz, 1H), 8.54 (dd, J=4.74, 1.61 Hz, 1H), 8.60 (br. s., 1H), 8.67 (dd, J=7.63, 1.37 Hz, 1H), 8.95 (dd, J=4.21, 1.66 Hz, 1H), 10.56 (s, 1H). m/z (ESI) 439 (M+H)$^+$. (S)-4-(5,5-Dimethyl-2-oxo-4-(pyridin-3-yl)oxazolidin-3-yl)-N-(quinolin-8-yl)benzamide (0.030 g, 0.068 mmol, 86% yield) was also obtained as an off-white solid (second eluting peak). $^1$H NMR (400 MHz, DMSO-$d_6$) δ ppm 0.98 (s, 3H), 1.69 (s, 3H), 5.69 (s, 1H), 7.40 (dd, J=7.68, 4.94 Hz, 1H), 7.57-7.81 (m, 6H), 7.90-8.06 (m, 2H), 8.45 (dd, J=8.41, 1.66 Hz, 1H), 8.54 (dd, J=4.74, 1.61 Hz, 1H), 8.60 (br. s., 1H), 8.67 (dd, J=7.63, 1.27 Hz, 1H), 8.95 (dd, J=4.30, 1.66 Hz, 1H), 10.56 (s, 1H). m/z (ESI) 439 (M+H)$^+$.

General Method HH-1

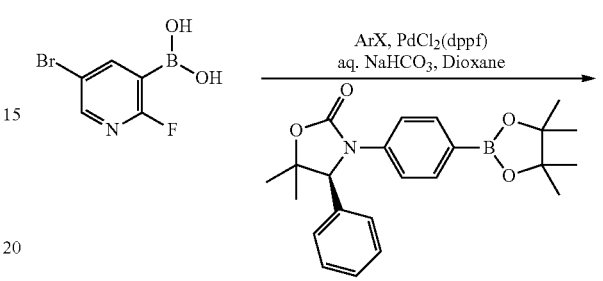

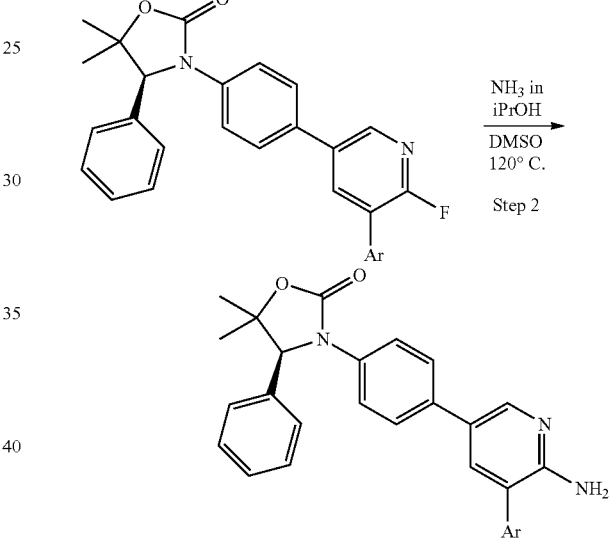

Example 12

Synthesis of (S)-3-(4-(5-([1,2,4]triazolo[4,3-b]pyridazin-6-yl)-6-aminopyridin-3-yl)phenyl)-5,5-dimethyl-4-phenyloxazolidin-2-one Example 12

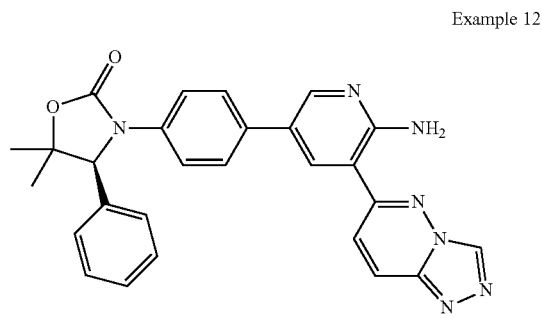 [SMILES: CC1(C)OC(=O)N(c2ccc(-c3cnc(N)c(-c4ccc5nncn5n4)c3)cc2)[C@H]1c1ccccc1]

Step 1

(S)-3-(4-(5-([1,2,4]Triazolo[4,3-b]pyridazin-6-yl)-6-fluoropyridin-3-yl)phenyl)-5,5-dimethyl-4-phenyloxazolidin-2-one 6-Chloro-1,2,4-triazolo[4,3-b]pyridazine (141 mg, 0.910 mmol, commercially available from Synthonix, Wake Forest, N.C.), sodium carbonate (910 µL, 1.820 mmol), 5-bromo-2-fluoropyridine-3-boronic acid (200 mg, 0.910 mmol), and dichloro(1,1-bis(diphenylphosphinoferrocene))palladium (II) (74.3 mg, 0.091 mmol, commercially available from Sigma-Aldrich, Milwaukee, Wis.) were combined in dioxane (3033 µL) and stirred at 130° C. in a microwave oven for 1 hour. LC-MS indicated good conversion to the desired product 6-(5-bromo-2-fluoropyridin-3-yl)-[1,2,4]triazolo[4,3-b]pyridazine. (S)-5,5-dimethyl-4-phenyl-3-(4-(4,4,5,5-tetramethyl-1,3,2-dioxaborolan-2-yl)phenyl)oxazolidin-2-one (179 mg, 0.455 mmol) and dichloro(1,1-bis(diphenylphosphinoferrocene))palladium(II) (74.3 mg, 0.091 mmol, commercially available from Sigma-Aldrich, Milwaukee, Wis.) were then added to the reaction mixture. The reaction was stirred for another hour at 130° C. in a microwave oven. LC-MS indicated good conversion to desired product. The material thus obtained was absorbed onto a plug of silica gel and purified by chromatography through a Redi-Sep pre-packed silica gel column (40 g), eluting with a gradient of 0% to 10% MeOH in DCM, to provide (S)-3-(4-(5-([1,2,4]triazolo[4,3-b]pyridazin-6-yl)-6-fluoropyridin-3-yl)phenyl)-5,5-dimethyl-4-phenyloxazolidin-2-one (40 mg, 0.083 mmol, 9.15% yield).

Step 2

(S)-3-(4-(5-([1,2,4]Triazolo[4,3-b]pyridazin-6-yl)-6-aminopyridin-3-yl)phenyl)-5,5-dimethyl-4-phenyloxazolidin-2-one A 2-mL glass microwave reaction vessel was charged with ammonia (2 M solution in 2-propanol) (63.2 µL, 2.91 mmol) (commercially available from Sigma-Aldrich, Milwaukee, Wis.) and (S)-3-(4-(5-([1,2,4]triazolo[4,3-b]pyridazin-6-yl)-6-fluoropyridin-3-yl)phenyl)-5,5-dimethyl-4-phenyloxazolidin-2-one (14 mg, 0.029 mmol) in DMSO (291 µL). The reaction mixture was stirred and heated at 120° C. overnight. LC-MS indicated clean and complete conversion to desired product. After cooling to room temperature, the reaction mixture was diluted with water and extracted with EtOAc (3×). The combined organic layers were washed with water (2×) and brine and dried over MgSO$_4$. The solution was filtered and concentrated under reduced pressire. The residue was purified by reverse-phase preparative HPLC using 0.1% TFA in ACN/H$_2$O, gradient 15% to 90% over 20 minutes to provide (S)-3-(4-(5-([1,2,4]triazolo[4,3-b]pyridazin-6-yl)-6-aminopyridin-3-yl)phenyl)-5,5-dimethyl-4-phenyloxazolidin-2-one as yellow solid. $^1$H NMR (500 MHz, DMSO-d$_6$) δ 9.67 (s, 1H), 8.44 (d, J=2.24 Hz, 1H), 8.39 (d, J=9.72 Hz, 1H), 8.27 (d, J=2.56 Hz, 1H), 8.03 (d, J=9.94 Hz, 1H), 7.67 (d, J=8.76 Hz, 2H), 7.55 (d, J=8.87 Hz, 2H), 7.35-7.41 (m, 2H), 7.27-7.34 (m, 3H), 7.23 (s, 2H), 5.47-5.53 (m, 1H), 1.66 (s, 3H), 0.92 (s, 3H). m/z (ESI) 478.2 (M+H)$^+$.

General Method HH-2

Examples 13 and 14

Synthesis of (S)-3-((1r,4S)-4-(6-amino-5-(pyrimidin-2-ylamino)pyridin-3-yl)cyclohexyl)-5,5-dimethyl-4-phenyloxazolidin-2-one and (R)-5,5-dimethyl-3-((1r,4R)-4-(2-oxo-1-(pyrimidin-2-yl)-2,3-dihydro-1H-imidazo[4,5-b]pyridin-6-yl)cyclohexyl)-4-phenyloxazolidin-2-one

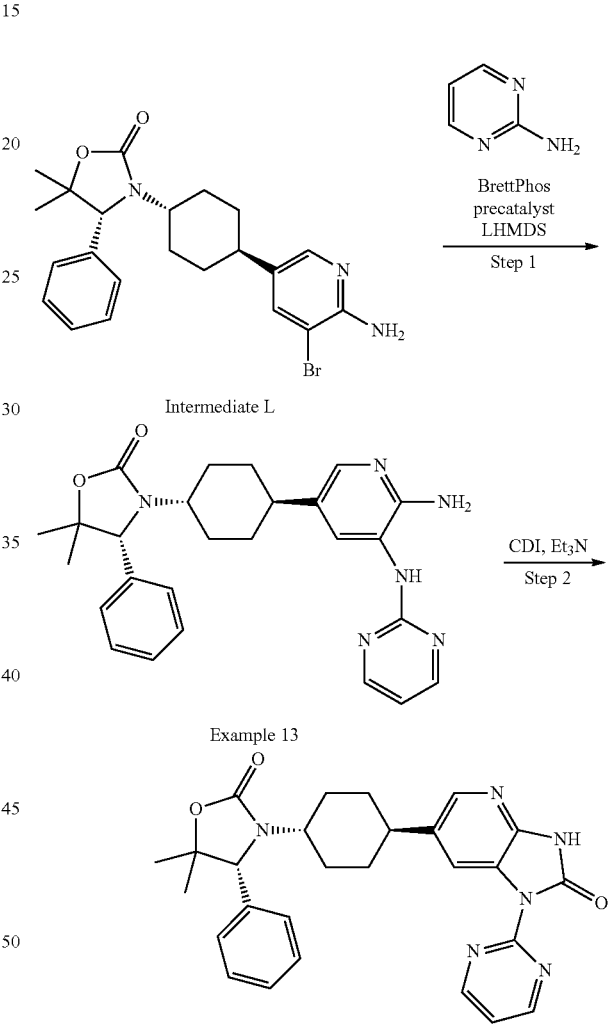

Step 1

(S)-3-((1r,4S)-4-(6-Amino-5-(pyrimidin-2-ylamino)pyridin-3-yl)cyclohexyl)-5,5-dimethyl-4-phenyloxazolidin-2-one (Example 13)

A glass microwave reaction vessel was charged with (S)-3-((1r,4S)-4-(6-amino-5-bromopyridin-3-yl)cyclohexyl)-5,5-dimethyl-4-phenyloxazolidin-2-one (100 mg, 0.225 mmol), 2-aminopyrimidine (42.8 mg, 0.450 mmol), BrettPhos Precatalyst (17.98 mg, 0.023 mmol) and dicyclohexyl(2',4',6'-triisopropyl-3,6-dimethoxy-[1,1'-biphenyl]-2-yl)phosphine (12.08 mg, 0.023 mmol). The vessel was capped and evacuated and refilled with argon three times. Dioxane (450 µL) and lithium bis(trimethylsilyl)amide (1.0 M solution in THF) (563 µL, 0.563 mmol) were then added to the reaction mixture. The mixture was stirred and heated at 65° C. over the weekend. LC-MS indicated clean conversion to desired product. The material thus obtained was absorbed onto a plug of silica gel and purified by chromatography through a Redi-Sep pre-packed silica gel column (12 g), eluting with a gradient of 0% to 10% MeOH in DCM, to provide (S)-3-((1r,4S)-4-(6-amino-5-(pyrimidin-2-ylamino)pyridin-3-yl)cyclohexyl)-5,5-dimethyl-4-phenyloxazolidin-2-one. $^1$H NMR (500 MHz, DMSO-$d_6$) δ 8.48-8.56 (m, 1H), 8.37 (d, J=4.70 Hz, 2H), 7.58 (s, 2H), 7.32-7.46 (m, 4H), 7.22 (br. s, 2H), 6.74 (t, J=4.49 Hz, 1H), 5.40-5.51 (m, 2H), 4.62 (s, 1H), 3.45-3.58 (m, 1H), 2.15-2.26 (m, 1H), 1.75-1.90 (m, 3H), 1.53-1.70 (m, 2H), 1.40-1.52 (m, 4H), 1.28-1.39 (m, 1H), 1.11-1.25 (m, 1H), 0.75-0.84 (m, 3H). m/z (ESI) 459.3 (M+H)$^+$.

Step 2

(R)-5,5-Dimethyl-3-((1r,4R)-4-(2-oxo-1-(pyrimidin-2-yl)-2,3-dihydro-1H-imidazo[4,5-b]pyridin-6-yl)cyclohexyl)-4-phenyloxazolidin-2-one (Example 14)

To a flask charged with (R)-3-((1r,4R)-4-(6-amino-5-(pyrimidin-2-ylamino)pyridin-3-yl)cyclohexyl)-5,5-dimethyl-4-phenyloxazolidin-2-one (18 mg, 0.039 mmol) were added THF (157 µL) and DIEA (24.00 µL, 0.137 mmol). The resulting solution was cooled in an ice water bath prior to the addition of CDI (22.28 mg, 0.137 mmol). The resulting mixture was stirred for 3 hours and allowed to slowly warm to room temperature. The reaction mixture was then stirred over the weekend. LC-MS indicated good conversion to product. The material thus obtained was absorbed onto a plug of silica gel and purified by chromatography through a Redi-Sep pre-packed silica gel column (12 g), eluting with a gradient of 0% to 10% MeOH in DCM, to provide (R)-5,5-dimethyl-3-((1r,4R)-4-(2-oxo-1-(pyrimidin-2-yl)-2,3-dihydro-1H-imidazo[4,5-b]pyridin-6-yl)cyclohexyl)-4-phenyloxazolidin-2-one as yellow solid. $^1$H NMR (500 MHz, DMSO-$d_6$) δ 11.74 (br. s, 1H), 8.94 (d, J=6.20 Hz, 2H), 7.86 (dd, J=1.50, 13.68 Hz, 2H), 7.49 (t, J=4.81 Hz, 1H), 7.34-7.46 (m, 4H), 7.25 (br. s, 2H), 4.63 (s, 1H), 3.45-3.63 (m, 1H), 2.36-2.47 (m, 1H), 1.78-1.92 (m, 3H), 1.59-1.72 (m, 2H), 1.52-1.59 (m, 1H), 1.47 (s, 3H), 1.38-1.46 (m, 1H), 1.16-1.28 (m, 1H), 0.80 (s, 3H). m/z (ESI) 485.2 (M+H)$^+$.

Example 15 and 16

Synthesis of (S)-5,5-dimethyl-3-(4-(2-oxo-1H-imidazo[4,5-c]pyridin-3(2H)-yl)phenyl)-4-phenyloxazolidin-2-one and (S)-5,5-dimethyl-3-(4-(2-oxo-2,3-dihydro-1H-imidazo[4,5-c]pyridin-1-yl)phenyl)-4-phenyloxazolidin-2-one

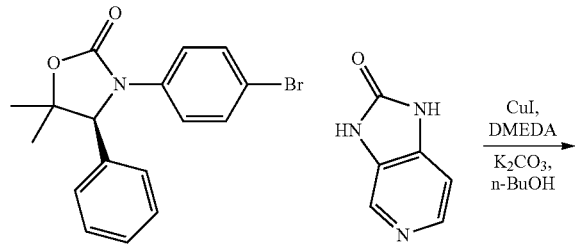

Intermediate B

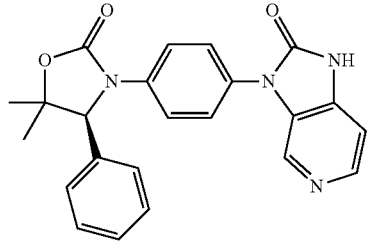

Product A

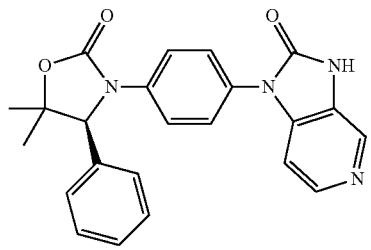

Product B

Examples 15 and 16

To a vial charged with (S)-3-(4-bromophenyl)-5,5-dimethyl-4-phenyloxazolidin-2-one (0.100 mg, 0.289 µmol), potassium carbonate (0.120 mg, 0.867 mol), copper (I) iodide (0.055 mg, 0.289 µmol), and 1H-imidazo[4,5-c]pyridin-2(3H)-one (commercially available from Prime Organics Inc. Woburn, Mass.) (117 mg, 0.867 µmol) were added n-butanol (1.155 µL) and $N^1,N^2$-dimethylethane-1,2-diamine (0.051 mg, 0.578 µmol). The suspension was purged with nitrogen, and then sealed and shaken overnight at 110° C. The resulting suspension was cooled to room temperature and filtered through Celite® brand filter aid. The filtrate was dried under reduced pressure and the residue was dissolved in DMSO and purified using RP-HPLC ramping ACN in H$_2$O (10-90%, 0.1% TFA throughout). Separation of isomers was accomplished and the respective product containing eluents were dried under reduced pressure providing products which were lyophilized from MeOH/H$_2$O providing (S)-5,5-dimethyl-3-(4-(2-oxo-1H-imidazo[4,5-c]pyridin-3(2H)-yl)phenyl)-4-phenyloxazolidin-2-one (5 mg, 4%) as a yellow solid and (S)-5,5-dimethyl-3-(4-(2-oxo-2,3-dihydro-1H-imidazo[4,5-c]pyridin-1-yl)phenyl)-4-phenyloxazolidin-2-one (5 mg, 4%) as a light brown solid. Structures were assigned arbitrarily. Data for product A: $^1$H NMR (500 MHz, DMSO-$d_6$) δ=8.22 (d, J=5.2 Hz, 1H), 8.14 (s, 1H), 7.69-7.64 (m, 2H), 7.51 (d, J=9.0 Hz, 2H), 7.42-7.38 (m, 2H), 7.35-7.28 (m, 3H), 7.12 (d, J=5.2 Hz, 1H), 5.51 (s, 1H), 1.66 (s, 3H), 0.93 (s, 3H). m/z (ESI) 401.2 (M+H)$^+$. Data for product B: $^1$H NMR (500 MHz, DMSO-$d_6$) δ=8.29 (s, 1H), 8.18 (s, 1H), 7.67 (d, J=9.0 Hz, 2H), 7.47 (d, J=8.9 Hz, 2H), 7.42-7.38 (m, 2H), 7.35-7.28 (m, 3H), 6.99 (d, J=5.4 Hz, 1H), 5.51 (s, 1H), 1.66 (s, 3H), 0.93 (s, 3H). m/z (ESI) 401.2 (M+H)$^+$.

Example 17

Synthesis of (S)-3-(4-(5,5-dimethyl-2-oxo-4-phenyloxazolidin-3-yl)phenyl)benzo[d]oxazol-2(3H)-one

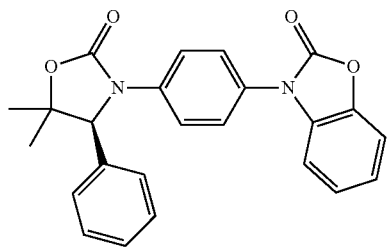 [SMILES: CC1(C)OC(=O)N(c2ccc(-n3c(=O)oc4ccccc43)cc2)[C@H]1c1ccccc1]

The title compound was prepared as described in General Scheme B using benzo[d]oxazol-2(3H)-one. The residue was dissolved in DMSO and purified using RP-HPLC ramping ACN in H$_2$O (10-90%, 0.1% TFA throughout) and the product containing eluents were dried under reduced pressure and lyophilized from MeOH/H$_2$O providing (S)-3-(4-(5,5-dimethyl-2-oxo-4-phenyloxazolidin-3-yl)phenyl)benzo[d]oxazol-2(3H)-one (12 mg, 10%). $^1$H NMR (500 MHz, DMSO-d$_6$) δ=7.71-7.67 (m, 2H), 7.57-7.53 (m, 2H), 7.43-7.37 (m, 3H), 7.35-7.28 (m, 3H), 7.21-7.16 (m, 2H), 7.04-6.99 (m, 1H), 5.52 (s, 1H), 1.66 (s, 3H), 0.93 (s, 3H). m/z (ESI) 401.2 (M+H)$^+$.

Example 18

Synthesis of (S)-5,5-dimethyl-3-(4-(2-oxoindolin-1-yl)phenyl)-4-phenyloxazolidin-2-one

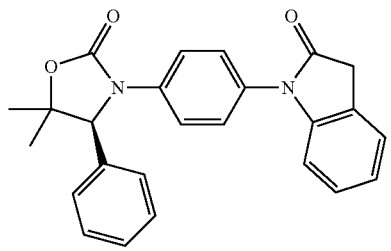 [SMILES: CC1(C)OC(=O)N(c2ccc(N3C(=O)Cc4ccccc43)cc2)[C@H]1c1ccccc1]

The title compound was prepared as described in General Scheme B using indolin-2-one. The residue was dissolved in DMSO and purified using RP-HPLC ramping ACN in H$_2$O (10-90%, 0.1% TFA throughout) and the product containing eluents were dried under reduced pressure and lyophilized from MeOH/H$_2$O providing (S)-5,5-dimethyl-3-(4-(2-oxoindolin-1-yl)phenyl)-4-phenyloxazolidin-2-one (12 mg, 10%). $^1$H NMR (500 MHz, DMSO-d$_6$) δ=7.65 (d, J=9.0 Hz, 2H), 7.42-7.38 (m, 2H), 7.37-7.28 (m, 6H), 7.20-7.15 (m, 1H), 7.06-7.01 (m, 1H), 6.62 (d, J=8.1 Hz, 1H), 5.49 (s, 1H), 3.70 (s, 2H), 1.65 (s, 3H), 0.92 (s, 3H). m/z (ESI) 399.2 (M+H)$^+$.

Example 19

Synthesis of (S)-5,5-dimethyl-3-(4-(2-oxo-2,3-dihydro-1H-benzo[d]imidazol-1-yl)phenyl)-4-phenyloxazolidin-2-one

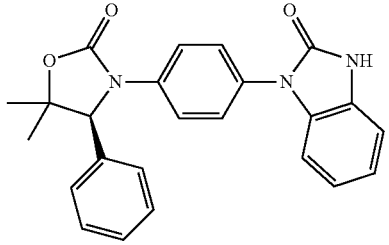 [SMILES: CC1(C)OC(=O)N(c2ccc(-n3c(=O)[nH]c4ccccc43)cc2)[C@H]1c1ccccc1]

The title compound was prepared as described in General Scheme B using 1H-benzo[d]imidazol-2(3H)-one. The residue was dissolved in DMSO and purified using RP-HPLC ramping ACN in H$_2$O (20-90%, 0.1% TFA throughout). The product containing eluents were diluted with saturated aqueous NaHCO$_3$ and extracted with EtOAc. The combined organic layers were dried with Na$_2$SO$_4$, filtered and dried under reduced pressure providing a film which was dried under reduced pressure and lyophilized from MeOH/H$_2$O providing (S)-5,5-dimethyl-3-(4-(2-oxo-2,3-dihydro-1H-benzo[d]imidazol-1-yl)phenyl)-4-phenyloxazolidin-2-one as an off-white solid (57 mg, 33%). $^1$H NMR (400 MHz, DMSO-d$_6$) δ=11.08 (s, 1H), 7.69-7.62 (m, 2H), 7.47-7.42 (m, 2H), 7.42-7.37 (m, 2H), 7.36-7.28 (m, 3H), 7.05-7.02 (m, 2H), 7.00-6.94 (m, 1H), 6.92-6.88 (m, 1H), 5.50 (s, 1H), 1.66 (s, 3H), 0.93 (s, 3H). m/z (ESI) 400.2 (M+H)$^+$.

Example 20

Synthesis of (S)-4-(5,5-dimethyl-2-oxo-4-phenyloxazolidin-3-yl)-N-(1,7-naphthyridin-8-yl)benzamide

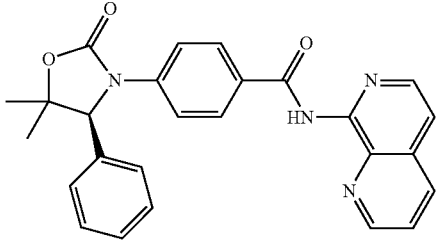 [SMILES: CC1(C)OC(=O)N(c2ccc(C(=O)Nc3nccc4cccnc34)cc2)[C@H]1c1ccccc1]

The title compound was prepared as described in General Scheme D using 1,7-naphthyridin-8-amine (commercially available from Ellanova Laboratories, Hamden, Conn.). The mixture was dried under reduced pressure and purified using a 25 g, 15 m spherical silica column (Interchim) ramping 0-100% EtOAc in heptane from 0-100% to elute product, which was lyophilized from MeOH/H$_2$O to yield (S)-4-(5,5-dimethyl-2-oxo-4-phenyloxazolidin-3-yl)-N-(1,7-naphthyridin-8-yl)benzamide (23 mg, 35%) as an off-white powder. $^1$H NMR (500 MHz, DMSO-d$_6$) δ=10.68 (s, 1H), 8.99 (dd, J=1.6, 4.2 Hz, 1H), 8.45 (dd, J=1.5, 8.4 Hz, 1H), 8.39 (d, J=5.7 Hz, 1H), 7.97 (d, J=8.9 Hz, 2H), 7.82 (dd, J=4.2, 8.3 Hz, 1H), 7.71 (d, J=5.7 Hz, 1H), 7.68 (d, J=8.9 Hz, 2H), 7.42-7.37 (m, 2H), 7.35-7.25 (m, 3H), 5.57 (s, 1H), 1.67 (s, 3H), 0.94 (s, 3H). m/z (ESI) 439.2 (M+H)+.

Example 21

Synthesis of (S)-4-(5,5-dimethyl-2-oxo-4-phenyloxazolidin-3-yl)-N-(4-hydroxypyridin-3-yl)benzamide

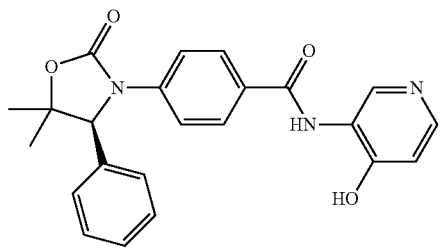 [SMILES: CC1(C)OC(=O)N(c2ccc(C(=O)Nc3cnccc3O)cc2)[C@H]1c1ccccc1]

The title compound was prepared as described in General Scheme D using 3-aminopyridin-4-ol (commercially available from Matrix Scientific, Columbia, S.C.) in place of 1,5-naphthyridin-4-amine. The mixture was dried under reduced pressure and purified using a 25 g, 15 μm spherical silica column (Interchim) ramping DCM:MeOH:NH₄OH (90:10:1) in DCM from 0-100% to elute product, which was lyophilized from MeOH/H₂O to yield (S)-4-(5,5-dimethyl-2-oxo-4-phenyloxazolidin-3-yl)-N-(4-hydroxypyridin-3-yl)benzamide (49 mg, 80%). ¹H NMR (500 MHz, DMSO-d₆) δ=11.56 (br. s., 1H), 9.21 (br. s., 1H), 8.71 (d, J=1.5 Hz, 1H), 7.82 (d, J=8.9 Hz, 2H), 7.69 (dd, J=1.3, 7.1 Hz, 1H), 7.65 (d, J=8.9 Hz, 2H), 7.40-7.34 (m, 2H), 7.31 (t, J=7.3 Hz, 1H), 7.27 (br. s., 2H), 6.28 (d, J=7.1 Hz, 1H), 5.53 (s, 1H), 1.65 (s, 3H), 0.92 (s, 3H). m/z (ESI) 404.1 (M+H)+.

Example 22

Synthesis of (S)-5,5-dimethyl-3-(6-(2-oxo-2,3-dihydro-1H-benzo[d]imidazol-1-yl)pyridin-3-yl)-4-phenyloxazolidin-2-one

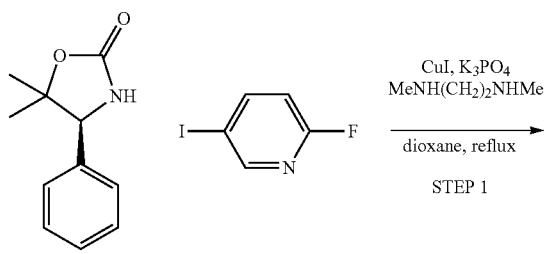

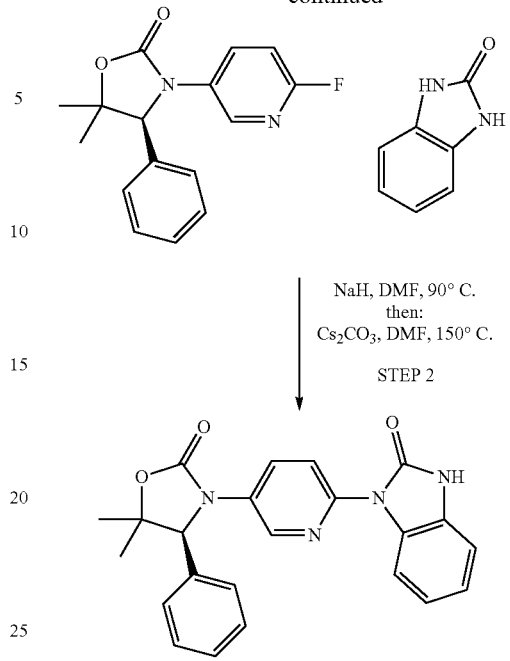

Example 22

Step 1

(S)-3-(6-Fluoropyridin-3-yl)-5,5-dimethyl-4-phenyloxazolidin-2-one

To a round bottom flask were added (S)-5,5-dimethyl-4-phenyloxazolidin-2-one (commercially available from Sigma-Aldrich, Milwaukee, Wis.) (0.750 g, 3.92 mmol), 2-fluoro-5-iodopyridine (commercially available from Sigma-Aldrich, Milwaukee, Wis.) (1.749 g, 7.84 mmol), and dioxane (15.69 mL). Tribasic potassium phosphate (4.16 g, 19.61 mmol) was then added to the mixture. The vessel was purged with nitrogen followed by the addition of N,N'-dimethylethylenediamine (0.844 mL, 7.84 mmol) and copper (I) iodide (0.747 g, 3.92 mmol). The vessel was heated to reflux overnight providing an orange suspension. To the mixture was added water (~10 mL), and the resulting slurry was filtered through Celite® brand filter aid. The yellow filtrate was transferred to a separatory funnel, diluted with water and extracted with EtOAc (2×). The combined organic layers were dried with Na₂SO₄, filtered, and dried under reduced pressure. The residue was purified with a 50 g SNAP column (Biotage) ramping EtOAc in heptane (0-35%, then isocratic at 35%) to elute (S)-3-(6-fluoropyridin-3-yl)-5,5-dimethyl-4-phenyloxazolidin-2-one (0.815 g, 2.85 mmol, 72.6% yield) which was obtained as a white solid upon drying. ¹H NMR (400 MHz, CDCl₃) δ=8.21 (ddd, J=3.0, 6.8, 9.0 Hz, 1H), 8.02-7.99 (m, 1H), 7.41-7.34 (m, 3H), 7.20-7.16 (m, 2H), 6.88 (ddd, J=0.6, 3.5, 8.9 Hz, 1H), 5.00 (s, 1H), 1.71 (s, 3H), 1.04 (s, 3H). m/z (ESI) 287.1 (M+H)+.

Step 2

(S)-5,5-Dimethyl-3-(6-(2-oxo-2,3-dihydro-1H-benzo[d]imidazol-1-yl)pyridin-3-yl)-4-phenyloxazolidin-2-one To a flask charged with 2-hydroxybenzimidazole (commercially available from Sigma-Aldrich, Milwaukee, Wis.)

(0.094 g, 0.699 mmol) was added dry DMF (1.8 mL). The resulting light brown solution was cooled in an ice water bath prior to the addition of sodium hydride (60% suspension in mineral oil) (29 mg, 0.733 mmol). The resulting slurry was stirred at 0° C. for 5 minutes and then at room temperature for 1.25 hours providing a peach suspension to which a solution of (S)-3-(6-fluoropyridin-3-yl)-5,5-dimethyl-4-phenyloxazolidin-2-one (0.200 g, 0.699 mmol) in DMF (1 mL) was added. The resulting solution was heated at 90° C. for 18 hours. LC-MS indicated product formation (~20% conversion according, 215 nm) with significant starting material present. The orange solution was transferred to a microwave vial, and one equivalent of cesium carbonate (0.228 g, 0.699 mmol) was added. The mixture was then irradiated at 150° C. for 30 minutes leading to further conversion (~50%). The mixture was irradiated for another 90 minutes leading to slightly further conversion (~60%). Additional 2-hydroxybenzimidazole (0.094 g, 0.699 mmol) and cesium carbonate (0.228 g, 0.699 mmol) were added, and the mixture was irradiated at 150° C. for 30 minutes leading to additional conversion. The mixture was dried under reduced pressure and purified with a 25 g HP spherical silica (15 um) column ramping EtOAc in heptane from 0-100% leading to elution of product along with a minor impurity (10-20%). The material was dried under reduced pressure, dissolved in MeOH, filtered through an HPLC frit and purified ramping ACN in H₂O (10-90%, 0.1% TFA throughout) providing separation of product from impurity. The combined product eluents were transferred to a separatory funnel, diluted with saturated aqueous NaHCO₃, and extracted with EtOAc (2×). The combined organic layers were dried with Na₂SO₄, filtered, and dried under reduced pressure providing a white solid, which after drying under high vacuum over the weekend still contained EtOAc. The material was lyophilized from MeOH/H₂O providing (S)-5,5-dimethyl-3-(6-(2-oxo-2,3-dihydro-1H-benzo[d]imidazol-1-yl)pyridin-3-yl)-4-phenyloxazolidin-2-one (65 mg, 23%) as a white solid. $^1$H NMR (400 MHz, DMSO-d₆) δ=8.62 (dd, J=0.7, 2.8 Hz, 1H), 8.10 (dd, J=2.8, 9.0 Hz, 1H), 8.00 (dd, J=0.6, 9.0 Hz, 1H), 7.74 (qd, J=0.6, 8.0 Hz, 1H), 7.42-7.36 (m, 2H), 7.35-7.29 (m, 3H), 7.09-6.95 (m, 3H), 5.58 (s, 1H), 1.67 (s, 3H), 0.95 (s, 3H). m/z (ESI) 401.2 (M+H)⁺.

Examples 23 and 24

Synthesis of (S)-5,5-dimethyl-3-((1r,4S)-4-(2-oxo-2,3-dihydro-1H-imidazo[4,5-c]pyridin-1-yl)cyclohexyl)-4-phenyloxazolidin-2-one and (R)-5,5-dimethyl-3-((1r,4R)-4-(2-oxo-2,3-dihydro-H-imidazo[4,5-c]pyridin-1-yl)cyclohexyl)-4-phenyloxazolidin-2-one Example 23

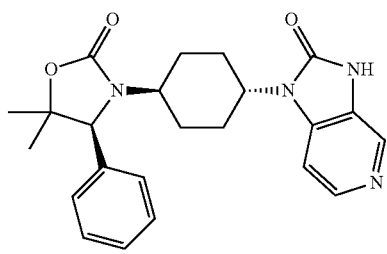

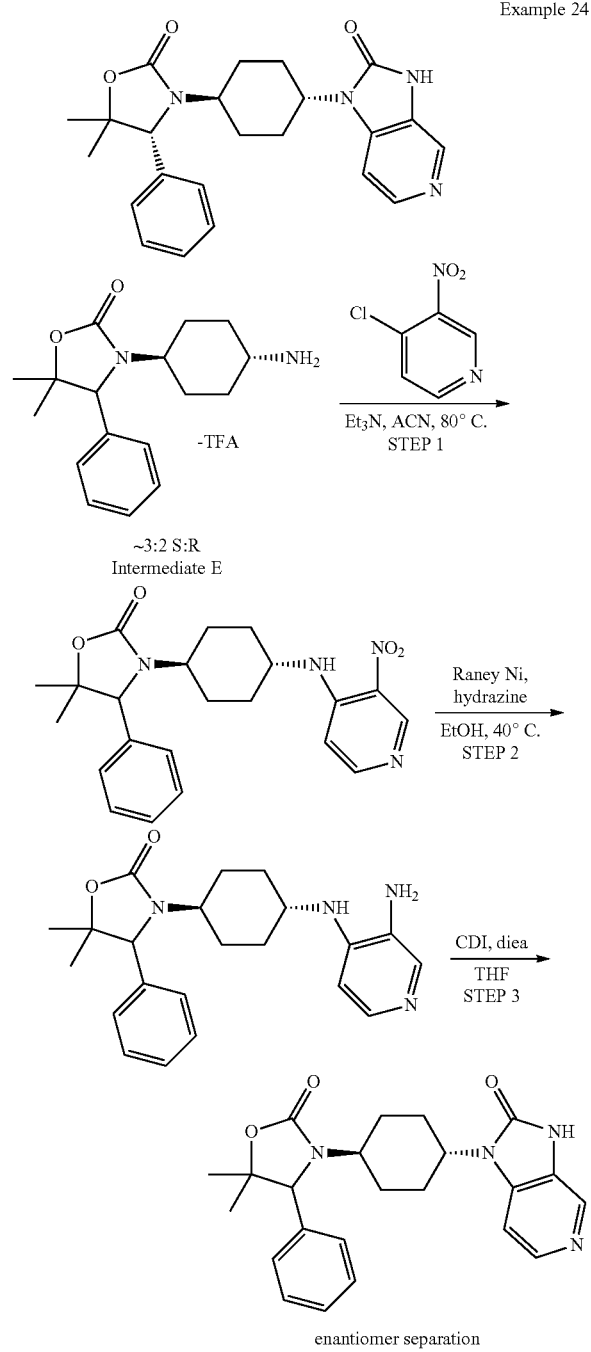

Step 1

5,5-Dimethyl-3-((1r,4r)-4-((3-nitropyridin-4-yl)amino)cyclohexyl)-4-phenyloxazolidin-2-one To a flask charged with 3-((1r,4r)-4-aminocyclohexyl)-5,5-dimethyl-4-phenyloxazolidin-2-one 2,2,2-trifluoroacetate (3.00 g, 7.46 mmol) were added ACN (24.85 mL), TEA (2.078 mL, 14.91 mmol) and 4-chloro-3-nitropyridine (commercially available from Sigma-Aldrich, Milwaukee, Wis.) (1.206 g, 7.60 mmol) respectively. The resulting orange solution was shaken at 80° C. overnight. Additional 4-chloro-3- nitropyridine was added (0.4 eq, 480 mg), and stirring and heating was continued. After 30 minutes, no additional conversion had occurred. Additional TEA (2.078 mL, 14.91 mmol) was added and heating and stirring was continued at 80° C. After 1 hour, LC-MS of the red/orange solution indicated consumption of starting material. The mixture was cooled in an ice water bath and stirred at 0° C. and saturated aqueous NH₄Cl was added. The mixture was transferred to a separatory funnel and extracted with EtOAc (2×). The combined organic layers were dried with Na₂SO₄, filtered, and dried under reduced pressure. The residue thus obtained was purified with an 80 HP spherical silica column (15 μm spherical) ramping EtOAc in heptane (0-100%, 5% DCM throughout) leading to the isolation of 5,5-dimethyl-3-((1r,4r)-4-((3-nitropyridin-4-yl)amino)cyclohexyl)-4-phenyloxazolidin-2-one (1.83 g, 4.46 mmol, 59.8% yield) as a yellow solid. ¹H NMR (400 MHz, CDCl₃) δ=9.19 (s, 1H), 8.25 (d, J=6.3 Hz, 1H), 8.00 (d, J=7.2 Hz, 1H), 7.49-7.29 (m, 4H), 7.23-7.06 (m, 1H), 6.64 (d, J=6.3 Hz, 1H), 4.39 (s, 1H), 3.50-3.34 (m, 2H), 2.24-2.05 (m, 3H), 2.04-1.95 (m, 1H), 1.91-1.80 (m, 1H), 1.63-1.56 (m, 1H), 1.46-1.26 (m, 2H), 0.94 (s, 3H). m/z (ESI) 411.2 (M+H)⁺.

Step 2

3-((1r,4r)-4-((3-Aminopyridin-4-yl)amino)cyclohexyl)-5,5-dimethyl-4-phenyloxazolidin-2-one To a flask charged with (S)-5,5-dimethyl-3-((1r,4S)-4-((3-nitropyridin-4-yl)amino)cyclohexyl)-4-phenyloxazolidin-2-one (1.82 g, 4.43 mmol) were added EtOH (89 mL), Raney nickel (slurry, in water) (4.88 mL, 740 mmol) (added roughly using pipette). The flask was sealed, placed under nitrogen, and heated at 40° C. To the resulting yellow solution was added hydrazine hydrate solution (2.071 mL, 66.5 mmol) dropwise. The resulting mixture was stirred for 3 hours at 40° C. LC-MS indicated conversion to desired product with complete consumption of starting material. The mixture was filtered through Celite® brand filter aid which was washed with MeOH. The filtrate was dried under reduced pressure providing an off-white foam after drying under high vacuum overnight which was used directly in the next step. m/z (ESI) 381.4 (M+H)⁺.

Step 3

5,5-Dimethyl-3-((1r,4r)-4-(2-oxo-2,3-dihydro-1H-imidazo[4,5-c]pyridin-1-yl)cyclohexyl)-4-phenyloxazolidin-2-one To a flask charged with 3-((1r,4r)-4-((3-aminopyridin-4-yl)amino)cyclohexyl)-5,5-dimethyl-4-phenyloxazolidin-2-one (1.60 g, 4.21 mmol) were added THF (16.82 mL), and DIEA (2.57 mL, 14.72 mmol). The mixture was cooled in an ice water bath prior to the addition of CDI (2.387 g, 14.72 mmol). The resulting mixture was allowed to stir and warm slowly to room temperature as the ice melted. After 2 hours, LC-MS indicated complete conversion to the desired product. To the yellow solution was added saturated aqueous NH₄Cl and the mixture was transferred to a separatory funnel and extracted with EtOAc (2×). The combined organic layers were washed with brine, dried with Na₂SO₄, filtered and dried under reduced pressure. The residue thus obtained was purified with a 40 g HP spherical silica column (Interchim) ramping DCM:MeOH (90:10) in DCM from 0-35%, then isocratic at 35%, then ramping to 100% providing product in 3 peaks, the first eluting had a bright yellow/green impurity coelute with the product (300 mg), then a clean fraction (1 g as a white foam), then a fraction which had coeluted with imidazole (400 mg). The impure fractions were combined repurified using a 40 g HP spherical silica column (Interchim) ramping DCM:MeOH:NH₄OH (90:10:1) in DCM from 0-45%, then isocratic at 45%, then ramping to 100% leading to some separation of impurities, which were combined with the clean fraction from the first run yielding product cleanly as a mixture of enantiomers (S:R~3:2, 1.3 g) as a white solid. Enantiomers were separated with the following method: Column: Chiralpak OD, 5 micron, 5 cm i.d.×25 cm length; Mobile phase: 25% iPrOH w/0.2% diethylamine/75% CO₂; Flow-rate: 325 mL/minute; Detection: 275 nm; Injection size: 35 mg in 2.0 mL of 1:1 DCM:MeOH. Example 23 ((S)-5,5-dimethyl-3-((1r,4S)-4-(2-oxo-2,3-dihydro-1H-imidazo[4,5-c]pyridin-1-yl)cyclohexyl)-4-phenyloxazolidin-2-one) was the first eluting enantiomer (major peak). Example 24 ((R)-5,5-dimethyl-3-((1 r,4R)-4-(2-oxo-2,3-dihydro-1H-imidazo[4,5-c]pyridin-1-yl)cyclohexyl)-4-phenyloxazolidin-2-one) was the second eluting isomer. ¹H NMR (400 MHz, DMSO-d₆) δ=8.15 (d, J=0.6 Hz, 1H), 8.08 (d, J=5.4 Hz, 1H), 7.46-7.39 (m, 3H), 7.39-7.35 (m, 1H), 7.28 (br. s., 2H), 4.66 (s, 1H), 4.04 (tt, J=3.8, 12.4 Hz, 1H), 3.68 (tt, J=3.9, 11.6 Hz, 1H), 2.25-2.03 (m, 2H), 2.02-1.83 (m, 2H), 1.77-1.68 (m, J=12.4 Hz, 1H), 1.61 (s, 3H), 1.48 (s, 3H), 1.29 (dq, J=3.1, 12.7 Hz, 1H), 0.80 (s, 3H). m/z (ESI) 407.2 (M+H)⁺.

Example 25

Synthesis of N-((1S,4r)-4-((S)-5,5-dimethyl-2-oxo-4-phenyloxazolidin-3-yl)cyclohexyl)-1,5-naphthyridine-4-carboxamide

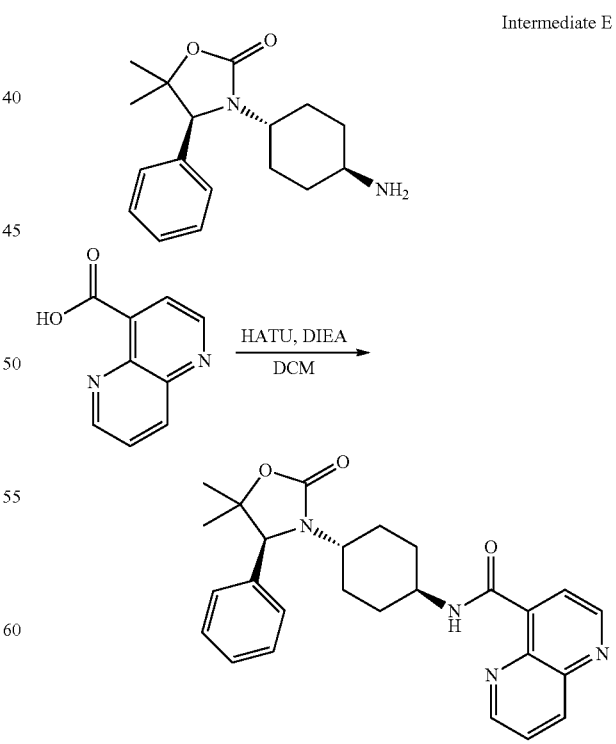

Intermediate E

Example 25

To a vial charged with (S)-3-((1r,4S)-4-aminocyclohexyl)-5,5-dimethyl-4-phenyloxazolidin-2-one (0.052 g, 0.180 mmol) were added DCM (0.721 mL), DIEA (0.094 mL, 0.541 mmol), 1,5-naphthyridine-4-carboxylic acid (commercially available from Life Chemicals Building Blocks, Orange, Conn.) (0.031 g, 0.180 mmol) and HATU (0.069 g, 0.180 mmol) respectively. The resulting suspension was shaken overnight at room temperature leading to conversion to desired product according to LC-MS along with a more major and polar impurity peak along with consumption of starting amine. The mixture was dried under reduced pressure and purified using a 25 g HP-spherical silica column (15 μm) ramping DCM in MeOH (90:10) in DCM from 0-30%, then isocratic at 30% providing separation of impurities and isolation of product, isolated as a white powder upon lyophilization (32 mg). However, NMR reflected a major impurity with aliphatic peaks (not observed in LC-MS). The material was repurified using a 2 g SCX-2 column washing with MeOH and then 2 M $NH_3$ in MeOH. The basic wash was dried under reduced pressure and lyophilized from $MeOH/H_2O$ to yield N-((1 S,4r)-4-((S)-5,5-dimethyl-2-oxo-4-phenyloxazolidin-3-yl)cyclohexyl)-1,5-naphthyridine-4-carboxamide (0.009 g, 0.020 mmol, 11.23% yield) as a white powder. $^1$H NMR (500 MHz, DMSO-$d_6$) δ=10.25 (d, J=7.7 Hz, 1H), 9.13 (d, J=4.4 Hz, 1H), 9.07 (dd, J=1.7, 4.2 Hz, 1H), 8.57 (dd, J=1.7, 8.5 Hz, 1H), 8.20 (d, J=4.4 Hz, 1H), 7.89 (dd, J=4.2, 8.5 Hz, 1H), 7.46-7.40 (m, 2H), 7.39-7.16 (m, 3H), 4.66 (s, 1H), 3.77-3.67 (m, 1H), 3.56-3.45 (m, 1H), 2.10-2.03 (m, 1H), 1.94-1.83 (m, 3H), 1.62-1.55 (m, 1H), 1.48 (s, 3H), 1.47-1.42 (m, 1H), 1.34 (dq, J=3.2, 12.5 Hz, 1H), 1.26-1.16 (m, 1H), 0.81 (s, 3H). m/z (ESI) 445.3 (M+H)$^+$.

Example 26

Synthesis of N-((1S,4r)-4-((S)-5,5-dimethyl-2-oxo-4-phenyloxazolidin-3-yl)cyclohexyl)quinoline-8-carboxamide Intermediate E

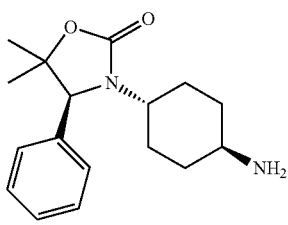

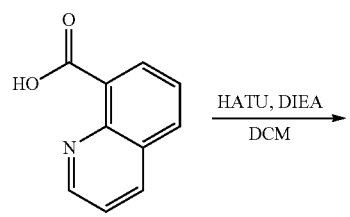

-continued

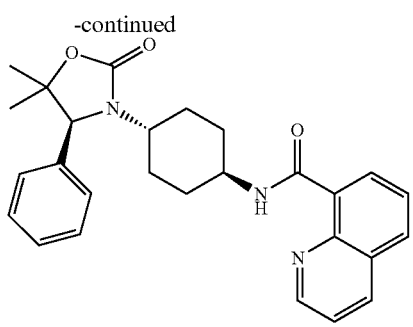

Example 26

To a vial charged with (S)-3-((1r,4S)-4-aminocyclohexyl)-5,5-dimethyl-4-phenyloxazolidin-2-one (0.750 g, 2.60 mmol) were added DCM (10.40 mL), DIEA (1.363 mL, 7.80 mmol), 8-quinoline carboxylic acid (commercially available from Sigma-Aldrich, Milwaukee, Wis.) (0.450 g, 2.60 mmol) and HATU (0.989 g, 2.60 mmol) respectively. The resulting suspension was shaken overnight at room temperature leading to conversion to desired product according to LC-MS with more minor and polar impurities visible. The resulting brown solution was dried under reduced pressure and purified with a 40 g HP spherical silica column (15 μm spherical, Interchim) ramping DCM:MeOH (90:10) in DCM (0-30%, then isocratic at 30%, monitoring at 215 nm) providing product along with impurity coelution. The material was repurified (same column type) with a ramp of EtOAc in heptane (10% DCM throughout) (0-100%) leading to separation of some minor impurities. However, NMR revealed ~10% starting quinoline carboxylic acid. The white solid was dissolved in DCM and extracted with 1 M $Na_2CO_3$ (3×). The organic phase was dried with $Na_2SO_4$, filtered and dried under reduced pressure providing N-((1 S,4r)-4-((S)-5,5-dimethyl-2-oxo-4-phenyloxazolidin-3-yl)cyclohexyl)quinoline-8-carboxamide (0.846 g, 1.907 mmol, 73.3% yield) as a white solid. $^1$H NMR (400 MHz, DMSO-$d_6$) δ=10.80 (d, J=7.6 Hz, 1H), 9.00 (dd, J=1.9, 4.3 Hz, 1H), 8.53 (ddd, J=1.7, 7.7, 8.9 Hz, 2H), 8.17 (dd, J=1.6, 8.2 Hz, 1H), 7.72 (t, J=7.7 Hz, 1H), 7.66 (dd, J=4.3, 8.3 Hz, 1H), 7.48-7.40 (m, 2H), 7.40-7.12 (m, 3H), 4.67 (s, 1H), 3.71 (s, 1H), 3.58-3.46 (m, 1H), 2.08 (td, J=3.0, 12.4 Hz, 1H), 1.96-1.82 (m, 3H), 1.62-1.53 (m, 1H), 1.51-1.37 (m, 4H), 1.37-1.27 (m, 1H), 1.26-1.14 (m, 1H), 0.81 (s, 3H). m/z (ESI) 444.2 (M+H)$^+$.

Example 27

Synthesis of (R+S)N-((1S,4r)-4-((S)-5,5-dimethyl-2-oxo-4-phenyloxazolidin-3-yl)cyclohexyl)quinoline-8-carboxamide

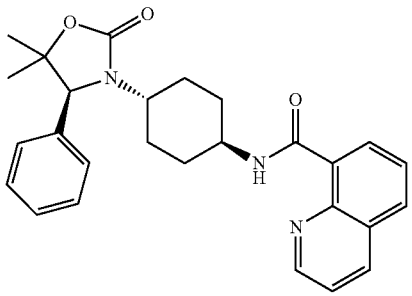

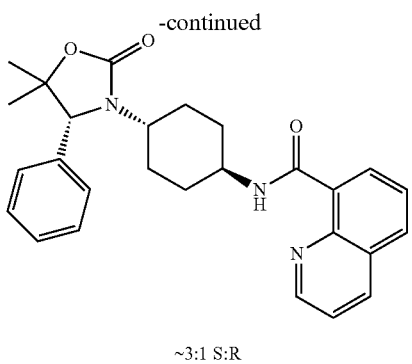

~3:1 S:R

This mixture of compounds was prepared using the procedure of Example 26 using partially racemized Intermediate E. See Example 26 for analytical data.

Example 28

Synthesis of N-((1R,4r)-4-((R)-5,5-dimethyl-2-oxo-4-phenyloxazolidin-3-yl)cyclohexyl)quinoline-8-carboxamide

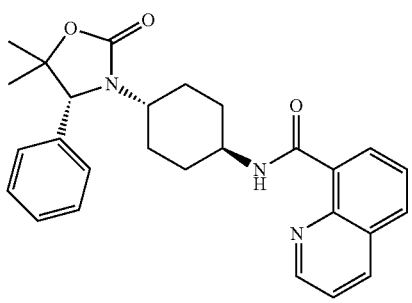 [SMILES: CC1(C)OC(=O)N([C@H]2CC[C@H](NC(=O)c3cccc4cccnc34)CC2)[C@@H]1c1ccccc1]

The title compound was isolated after chiral chromatography of an enantiomeric mixture. Conditions: Chiralpak OZ-H (2×25 cm); 35% MeOH (0.1% diethyl amine)/$CO_2$; 100 bar; 70 mL/min, 220 nm detection; injection volume 1.5 mL, 9 mg/mL MeOH. The second eluting isomer was assigned as (R) arbitrarily and not elucidated experimentally but assigned in analogy to known (R) isomers. See Example 26 for analytical data.

Example 29

Synthesis of (S)-3-((1r,4S)-4-(5-chloro-2-oxo-2,3-dihydro-1H-benzo[d]imidazol-1-yl)cyclohexyl)-5,5-dimethyl-4-phenyloxazolidin-2-one

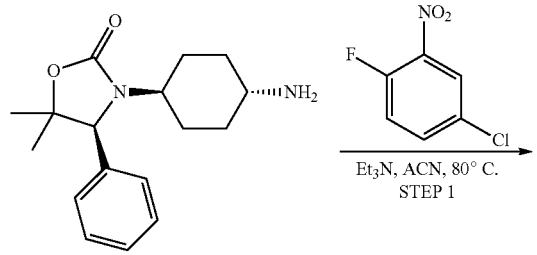

Intermediate E

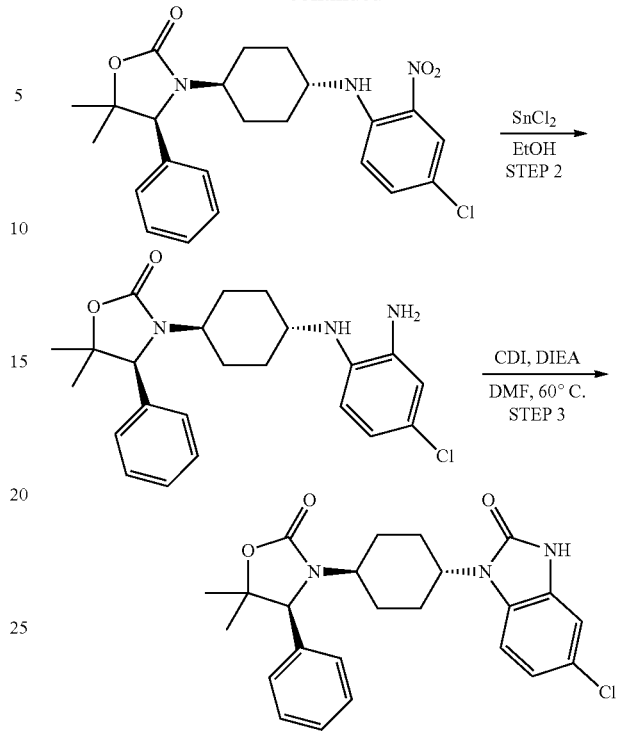

Example 29

Step 1

(S)-3-((1r,4S)-4-((4-Chloro-2-nitrophenyl)amino)cyclohexyl)-5,5-dimethyl-4-phenyloxazolidin-2-one To a vial charged with (S)-3-((1r,4S)-4-aminocyclohexyl)-5,5-dimethyl-4-phenyloxazolidin-2-one (0.182 g, 0.631 mmol) were added ACN (2.104 mL), TEA (0.176 mL, 1.262 mmol) and 4-chloro-1-fluoro-2-nitrobenzene (commercially available from ArkPharm, Inc., Chicago, Ill.) (0.111 g, 0.631 mmol) respectively. The resulting orange solution was shaken at 80° C. for 4 hours leading to conversion to desired product as the major species according to LC-MS. The bright orange solution was dried under reduced pressure and purified with a 25 g SNAP column ramping EtOAc in heptane (0-100%, with 10% DCM throughout) providing isolation of product (227 mg, 81%) as an orange solid. $^1$H NMR (400 MHz, $CDCl_3$) δ=8.11 (d, J=2.4 Hz, 3H), 7.88 (d, J=7.5 Hz, 1H), 7.46-7.36 (m, 3H), 7.34-7.29 (m, 1H), 7.14 (br. s., 1H), 6.75 (d, J=9.3 Hz, 1H), 4.39 (s, 1H), 3.45 (tt, J=3.9, 12.0 Hz, 1H), 3.34 (tdt, J=3.7, 7.5, 11.3 Hz, 1H), 2.22-2.12 (m, 1H), 2.12-2.02 (m, 2H), 2.02-1.92 (m, 1H), 1.82 (dquin, J=3.2, 12.8 Hz, 1H), 1.58-1.44 (m, 4H), 1.42-1.20 (m, 2H), 0.92 (s, 3H). m/z (ESI) 444.3 $(M+H)^+$.

Step 2

(S)-3-((1r,4S)-4-((2-Amino-4-chlorophenyl)amino)cyclohexyl)-5,5-dimethyl-4-phenyloxazolidin-2-one To a flask charged with (S)-3-((1r,4S)-4-((4-chloro-2-nitrophenyl)amino)cyclohexyl)-5,5-dimethyl-4-phenyloxazolidin-2-one (0.235 g, 0.529 mmol) was added EtOH (1.512 mL) followed by tin(II) chloride (0.301 g, 1.588 mmol). The resulting yellow suspension was heated overnight at 80° C. under nitrogen providing an orange solution containing product as the primary species according to LC-MS, observed as a double peak. The orange solution was purified directly with a 5 g SCX-2 column washing with MeOH and then with 2 M NH₃ in MeOH which provided product as a red solid (152 mg, 69%) which will be directly used in a subsequent step. m/z (ESI) 414.2 (M+H)⁺.

Step 3

(S)-3-((1r,4S)-4-(5-Chloro-2-oxo-2,3-dihydro-1H-benzo[d]imidazol-1-yl)cyclohexyl)-5,5-dimethyl-4-phenyloxazolidin-2-one To a flask charged with (S)-3-((1r,4S)-4-((2-amino-4-chlorophenyl)amino)cyclohexyl)-5,5-dimethyl-4-phenyloxazolidin-2-one (0.220 g, 0.531 mmol) were added DMF (2.126 mL), DIEA (0.139 mL, 0.797 mmol) and CDI (0.129 g, 0.797 mmol). After 1 hour of shaking at 60° C., LC-MS indicated about 20% conversion to product. Additional CDI (3 eq) was added and shaking at 60° C. was continued overnight. LC-MS indicated product as the major species. The mixture was dried under reduced pressure and purified with a 25 g column (15 um spherical, Interchim) ramping DCM:MeOH (90:10) in DCM from 0-30%, then isocratic at 30% (monitoring at 215 nm) providing product with a minor impurity according to LC-MS. Upon drying, the material had a pinkish color. The material was dissolved in MeOH and passed through a 2 g SCX-2 column. The pink material was retained on the column and product eluted through. After drying, the material was lyophilized from MeOH/H₂O providing (S)-3-((1r,4S)-4-(5-chloro-2-oxo-2,3-dihydro-1H-benzo[d]imidazol-1-yl)cyclohexyl)-5,5-dimethyl-4-phenyloxazolidin-2-one (129 mg, 0.293 mmol, 55.2% yield) as a white solid. ¹H NMR (400 MHz, DMSO-d₆) δ=10.96 (d, J=8.7 Hz, 1H), 7.50-7.39 (m, 3H), 7.39-7.16 (m, 3H), 7.00-6.89 (m, 2H), 4.65 (d, J=4.0 Hz, 1H), 4.02 (ddd, J=3.7, 8.2, 16.2 Hz, 1H), 3.77-3.60 (m, 1H), 2.29-2.04 (m, 2H), 2.03-1.83 (m, 2H), 1.75-1.50 (m, 3H), 1.48 (s, 3H), 1.36-1.19 (m, 1H), 0.83-0.77 (m, 3H). m/z (ESI) 440.1 (M+H)⁺.

Examples 30 and 31

Synthesis of (S)-5,5-dimethyl-3-((1r,4S)-4-(2-oxo-2,3-dihydro-1H-imidazo[4,5-b]pyridin-1-yl)cyclohexyl)-4-phenyloxazolidin-2-one and (R)-5,5-dimethyl-3-((1r,4R)-4-(2-oxo-2,3-dihydro-1H-imidazo[4,5-b]pyridin-1-yl)cyclohexyl)-4-phenyloxazolidin-2-one

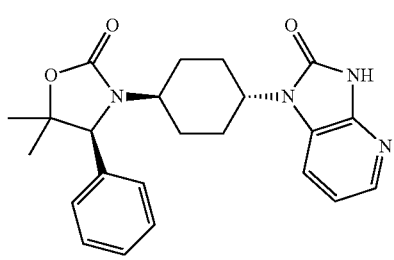

Example 30

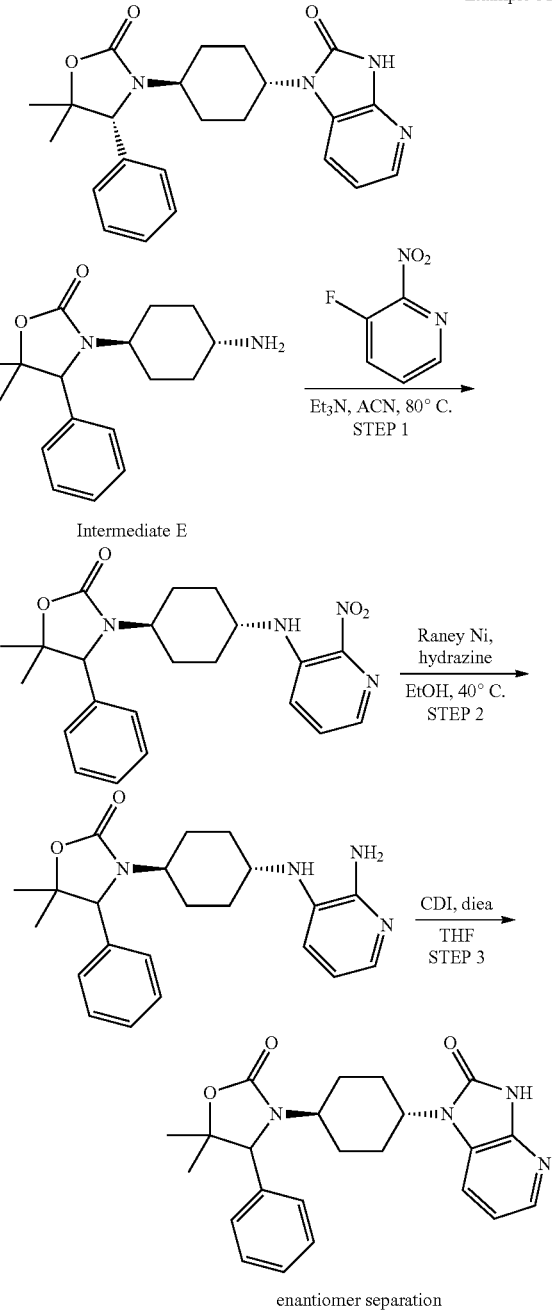

Step 1

5,5-Dimethyl-3-((1r,4r)-4-((2-nitropyridin-3-yl)amino)cyclohexyl)-4-phenyloxazolidin-2-one To a vial charged with (S)-3-((1r,4S)-4-aminocyclohexyl)-5,5-dimethyl-4-phenyloxazolidin-2-one (0.560 g, 1.942 mmol) were added ACN (6.47 mL), TEA (0.541 mL, 3.88 mmol) and 3-fluoro-2-nitropyridine (commercially available from Matrix Scientific, Columbia, S.C.) (276 mg, 1.94 mmol) respectively. The resulting orange solution was shaken at 80° C. for 4 hours leading to conversion to desired product as the major species according to LC-MS with about 50% conversion. The mixture was shaken for 48 hours at 80° C. providing complete conversion to desired product according to LC-MS. The mixture was dried under reduced pressure and purified using a 25 g SNAP column (Biotage) ramping EtOAc in heptane (0-100%, with 10% DCM throughout) providing (S)-5,5-dimethyl-3-((1r,4S)-4-((2-nitropyridin-3-yl)amino) cyclohexyl)-4-phenyloxazolidin-2-one (0.714 g, 1.739 mmol, 90% yield) as a yellow foam. $^1$H NMR (400 MHz, DMSO-$d_6$) δ=7.78 (dd, J=1.3, 3.9 Hz, 1H), 7.66 (dd, J=1.2, 8.9 Hz, 1H), 7.53 (dd, J=4.0, 8.7 Hz, 1H), 7.46-7.39 (m, 2H), 7.38-7.15 (m, 3H), 4.60 (s, 1H), 3.53-3.41 (m, 2H), 2.02 (td, J=3.1, 12.8 Hz, 1H), 1.98-1.79 (m, 3H), 1.58 (d, J=10.5 Hz, 1H), 1.47 (s, 3H), 1.46-1.37 (m, 1H), 1.37-1.25 (m, 2H), 0.78 (s, 3H). m/z (ESI) 411.2 (M+H)$^+$.

Step 2

3-((1r,4r)-4-((2-Aminopyridin-3-yl)amino)cyclo-hexyl)-5,5-dimethyl-4-phenyloxazolidin-2-one To a flask charged with (S)-5,5-dimethyl-3-((1r,4S)-4-((2-nitropyridin-3-yl)amino)cyclohexyl)-4-phenyloxazolidin-2-one (0.702 g, 1.710 mmol) was added EtOH (34.2 mL) and Raney nickel (slurry in water) (1.884 mL, 286 mmol) (added using pipette). The flask was sealed, placed under nitrogen, and heated to 40° C. To the resulting yellow solution was added hydrazine hydrate solution (0.799 mL, 25.7 mmol) dropwise. The resulting mixture was stirred overnight at 40° C. LC-MS indicated conversion to desired product with consumption of starting material. The mixture was filtered through Celite® brand filter aid which was washed with MeOH. The filtrate was dried under reduced pressure and the material purified with SCX-2 (5 g) washing with MeOH, then 2 M NH$_3$ in MeOH. The washes were combined and dried under reduced pressure. The residue was purified with a 50 g SNAP column (Biotage) ramping MeOH in DCM from 0-25%, leading to isolation of (S)-3-((1r,4S)-4-((2-aminopyridin-3-yl)amino)cyclohexyl)-5,5-dimethyl-4-phenyloxazolidin-2-one (0.580 g, 1.524 mmol, 89% yield) as a purple film. $^1$H NMR (400 MHz, DMSO-$d_6$) δ=7.45-7.38 (m, 2H), 7.38-7.23 (m, 3H), 7.21 (dd, J=1.5, 4.9 Hz, 1H), 6.52 (d, J=6.8 Hz, 1H), 6.38 (dd, J=4.9, 7.6 Hz, 1H), 5.36 (s, 2H), 4.61 (s, 1H), 4.38 (d, J=7.4 Hz, 1H), 3.53-3.42 (m, 1H), 3.06-2.95 (m, 1H), 2.03 (td, J=3.2, 12.9 Hz, 1H), 1.92-1.76 (m, 3H), 1.58-1.49 (m, 1H), 1.46 (s, 3H), 1.26-1.03 (m, 3H), 0.78 (s, 3H). m/z (ESI) 381.4 (M+H)$^+$.

Step 3

(S)-5,5-Dimethyl-3-((1r,4S)-4-(2-oxo-2,3-dihydro-1H-imidazo[4,5-b]pyridin-1-yl)cyclohexyl)-4-phenyloxazolidin-2-one To a flask charged with (S)-3-((1r,4S)-4-((2-aminopyridin-3-yl)amino)cyclohexyl)-5,5-dimethyl-4-phenyloxazolidin-2-one (0.560 g, 1.472 mmol) were added THF (5.89 mL), DIEA (0.566 mL, 3.24 mmol) and CDI (0.525 g, 3.24 mmol) respectively. The dark mixture was stirred at 45° C. overnight providing ~70% conversion according to LC-MS with clean conversion and starting material remaining. An additional 1 equivalent of DIEA and CDI were added and heating was continued. An additional 2 hours of heating at 45° C. led to complete conversion according to LC-MS. The dark purple solution was dried under reduced pressure and purified with a 50 g SNAP column (Biotage) ramping DCM:MeOH (90:10) in DCM from 0-30%, then isocratic at 30% providing elution of product. Using the following conditions the enantiomers were successfully separated (AD-H (2×20 cm) column, 25% MeOH (0.1% DEA)/CO$_2$, 100 bar, 70 mL/min, 220 nm detection, injection volume: 1 mL, 18 mg/mL, 4:1 MeOH:DCM). The NMR showed the presence of substantial diethyl amine. Each of the enantiomers were dissolved in DCM/trace MeOH and extracted with H$_2$O (2×). The organics were dried with Na$_2$SO$_4$, filtered, and dried under reduced pressed, then lyophilized from MeOH/H$_2$O. The NMRs revealed that this washing protocol was successful and the solids (light pink) were obtained ((S enantiomer, peak 2, 235 mg, 39%, Example 30 ((S)-5,5-dimethyl-3-((1r,4S)-4-(2-oxo-2,3-dihydro-1H-imidazo[4,5-b]pyridin-1-yl)cyclohexyl)-4-phenyloxazolidin-2-one) and (R enantiomer, peak 1, 85 mg, 14%, Example 31 ((R)-5,5-dimethyl-3-((1r,4R)-4-(2-oxo-2,3-dihydro-1H-imidazo[4,5-b]pyridin-1-yl)cyclohexyl)-4-phenyloxazolidin-2-one)). Starting amine (intermediate) was a partially racemized mixture which had been obtained from a pure S enantiomer (during step 2 of intermediate E synthesis), proving that the major enantiomer is S. $^1$H NMR (400 MHz, DMSO-$d_6$) δ=11.47 (br. s., 1H), 7.86 (d, J=3.9 Hz, 1H), 7.67 (d, J=7.9 Hz, 1H), 7.42 (d, J=6.5 Hz, 2H), 7.39-7.13 (m, 3H), 6.97-6.88 (m, 1H), 4.66 (s, 1H), 4.11-3.98 (m, 1H), 3.74-3.60 (m, 1H), 2.24-1.86 (m, 4H), 1.74 (d, J=11.2 Hz, 1H), 1.60 (t, J=12.6 Hz, 2H), 1.48 (s, 3H), 1.28 (q, J=11.3 Hz, 1H), 0.80 (s, 3H). m/z (ESI) 381.4 (M+H)$^+$.

Example 32

Synthesis of (1S,4r)-4-((S)-5,5-dimethyl-2-oxo-4-phenyloxazolidin-3-yl)-N-(quinolin-8-yl)cyclohex-anecarboxamide

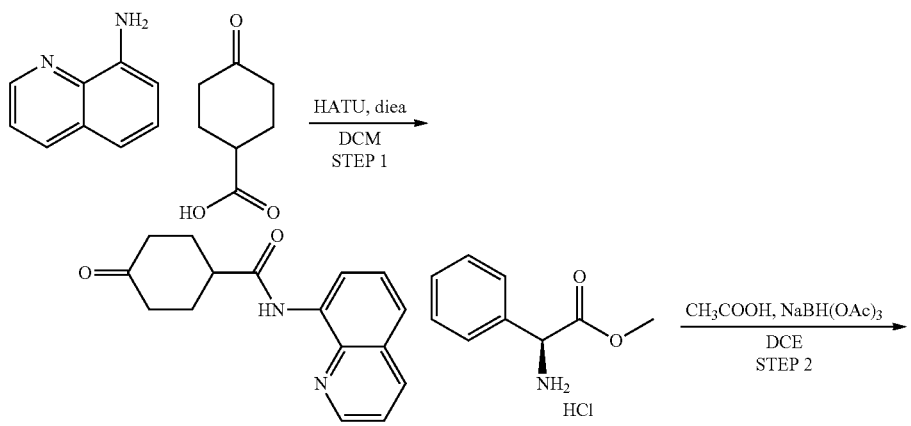

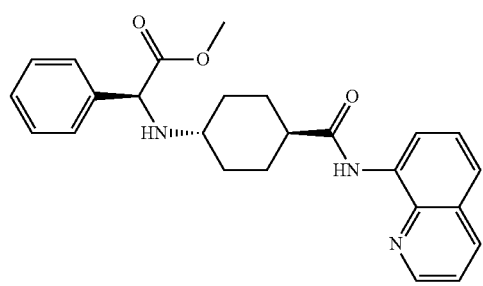

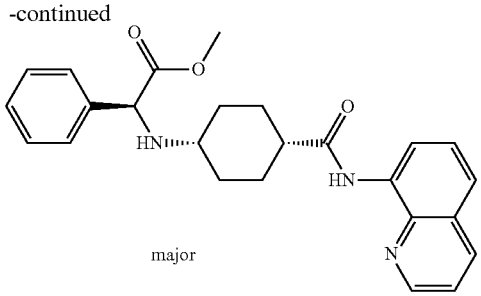

major

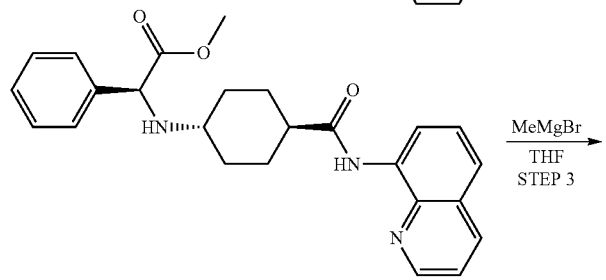

MeMgBr
THF
STEP 3

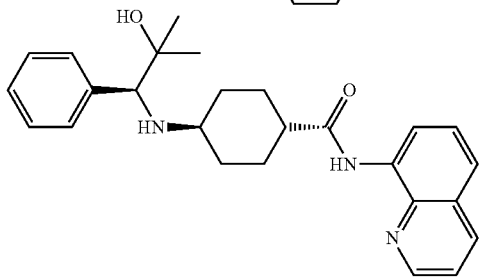

triphosgene
DIEA, DCM
STEP 4

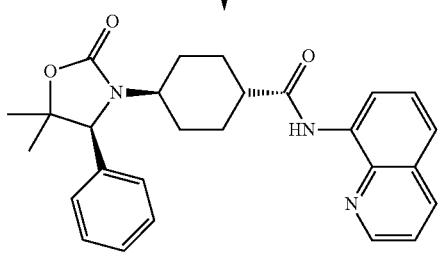

Example 32

Step 1

4-Oxo-N-(quinolin-8-yl)cyclohexanecarboxamide

To a flask charged with 4-oxocyclohexane carboxylic acid (commercially available from Alfa Aesar, Ward Hill, Mass.) (2.000 mL, 14.07 mmol) were added DCM (56.3 mL), DIEA (5.16 mL, 29.5 mmol), HATU (5.35 g, 14.07 mmol) and 8-aminoquinoline (commercially available from Sigma-Aldrich, Milwaukee, Wis.) (2.130 g, 14.77 mmol) respectively. The resulting light brown suspension was stirred overnight at room temperature without much color change but complete dissolution of materials. LC-MS indicated product as the primary species. The solution was dried under reduced pressure and purified ramping with EtOAc in heptane from 0-50%, then isocratic at 50% which led to the system clogging up a bit due to precipitation of product. Product eluted following a less polar impurity and the system was flushed with DCM:MeOH:NH$_4$OH (90:10:1) to elute the remainder of the product. Solid 4-oxo-N-(quinolin-8-yl)cyclohexanecarboxamide (1.900 g, 7.08 mmol, 50.3% yield) was obtained as a tan. $^1$H NMR (400 MHz, CDCl$_3$) δ=10.02 (br. s., 1H), 8.83 (dd, J=1.7, 4.2 Hz, 1H), 8.78 (dd, J=2.2, 6.7 Hz, 1H), 8.20 (dd, J=1.7, 8.3 Hz, 1H), 7.60-7.53 (m, 2H), 7.49 (dd, J=4.3, 8.3 Hz, 1H), 2.97 (tt, J=3.8, 10.5 Hz, 1H), 2.67-2.63 (m, 1H), 2.63-2.59 (m, 1H), 2.54-2.35 (m, 4H), 2.29-2.16 (m, 2H). m/z (ESI) 269.1 (M+H)$^+$.

Step 2

(S)-Methyl 2-phenyl-2-(((1r,4S)-4-(quinolin-8-ylcarbamoyl)cyclohexyl)amino)acetate & (S)-methyl 2-phenyl-2-(((1s,4R)-4-(quinolin-8-ylcarbamoyl)cyclohexyl)amino)acetate To a flask charged with 4-oxo-N-(quinolin-8-yl)cyclohexanecarboxamide (1.43 g, 5.33 mmol) were added DCE (26.6 mL), AcOH (0.305 mL, 5.33 mmol), (S)-(+)-2-phenylglycine methyl ester hydrochloride (commercially available from Sigma-Aldrich, Milwaukee, Wis.) (1.182 g, 5.86 mmol) and sodium triacetoxyborohydride (1.581 g, 7.46 mmol) respectively. The resulting orange suspension was stirred at room temperature overnight. After overnight stirring, LC-MS indicated about 50% conversion with two higher molecular weight minor impurities present. Additional (S)-(+)-2-phenylglycine methyl ester hydrochloride (1.182 g, 5.86 mmol) was added and the mixture was stirred for 15 minutes at room temp followed by addition of sodium triacetoxyborohydride (1.581 g, 7.46 mmol). The resulting mixture was stirred at room temperature for 1 hour. LC-MS indicated complete conversion after this additional reaction time. To the mixture was added 1 N NaOH (~100 mL), and the resulting suspension was transferred to a separatory funnel with some DCM dilution. The organic layer was separated and the aqueous phase extracted with DCM (2×). The combined organic layers were dried with Na$_2$SO$_4$, filtered, and dried under reduced pressure. The residue obtained was purified with a 100 g SNAP column (Biotage) ramping EtOAc in heptane (0-35%, then isocratic at 35%) leading to isolation of (S)-methyl 2-phenyl-2-(((1 s,4R)-4-(quinolin-8-ylcarbamoyl)cyclohexyl)amino)acetate (1.45 g, 3.47 mmol, 65.2% yield) as a yellow sticky foam. Further ramping of the gradient to 100% EtOAc led to elution of trans isomer (S)-methyl 2-phenyl-2-(((1r,4S)-4-(quinolin-8-ylcarbamoyl)cyclohexyl)amino)acetate (0.333 g, 0.798 mmol, 14.97% yield). The cis/trans relationship was determined after the fact by x-ray crystal structure analysis of the final compound in this scheme. The minor and correct trans isomer was used for the rest of the reaction sequence. m/z (ESI) 418.2 (M+H)$^+$.

Step 3

(1 S,4r)-4-(((S)-2-Hydroxy-2-methyl-1-phenylpropyl)amino)-N-(quinolin-8-yl)cyclohexanecarboxamide To a flask charged with (S)-methyl 2-phenyl-2-(((1r,4S)-4-(quinolin-8-ylcarbamoyl)cyclohexyl)amino)acetate (0.333 g, 0.798 mmol) was added dry THF (3.19 mL). The resulting dark yellow solution was cooled in an ice water bath and then methylmagnesium bromide (3.0 M in diethyl ether) (commercially available from Sigma-Aldrich, Milwaukee, Wis.) (1.595 mL, 4.79 mmol) was added dropwise leading to the formation of a tan precipitate. After 15 minutes, the ice bath was removed and the resulting suspension stirred at room temperature for 3 hours providing a red colored mixture. The suspension was added to an Erlenmeyer containing ice cold aqueous NH$_4$Cl and EtOAc. The resulting mixture was transferred to a separatory funnel, the organic layer separated and the aqueous phase extracted once more with EtOAc. The combined organic layers were dried with Na$_2$SO$_4$, filtered, and dried under reduced pressure providing (1S,4r)-4-(((S)-2-hydroxy-2-methyl-1-phenylpropyl)amino)-N-(quinolin-8-yl)cyclohexanecarboxamide (0.366 g, 0.877 mmol, 110% yield) as a yellow oil. The material obtained was used in the next step without further purification. m/z (ESI) 418.3 (M+H)$^+$.

Step 4

(1 S,4r)-4-((S)-5,5-Dimethyl-2-oxo-4-phenyloxazolidin-3-yl)-N-(quinolin-8-yl)cyclohexanecarboxamide To a vial charged with (1S,4r)-4-(((S)-2-hydroxy-2-methyl-1-phenylpropyl)amino)-N-(quinolin-8-yl)cyclohexanecarboxamide (366 mg, 0.877 mmol) were added THF (3097 µL), and DIEA (168 µL, 0.964 mmol). The resulting mixture was cooled in an ice water bath giving a yellow solution. To the solution was added triphosgene (286 mg, 0.964 mmol) which lead to the formation of a yellow/white precipitate within 10 minutes. The mixture was stirred overnight at room temperature. The orange suspension was quenched by the addition of saturated aqueous NaHCO$_3$. The mixture was transferred to a separatory funnel and extracted with EtOAc (2×). The combined organic layers were dried with Na$_2$SO$_4$, filtered, and dried under reduced pressure. The residue thus obtained was purified with a 25 g silica (15 m spherical silica, Interchim) column ramping EtOAc in heptane from 0-30%, then isocratic at 30% to provide (1 S,4r)-4-((S)-5,5-dimethyl-2-oxo-4-phenyloxazolidin-3-yl)-N-(quinolin-8-yl)cyclohexanecarboxamide (166 mg, 0.374 mmol, 42.7% yield) as an off-white solid upon drying. $^1$H NMR (400 MHz, DMSO-d$_6$) δ=10.02 (s, 1H), 8.90 (dd, J=1.7, 4.3 Hz, 1H), 8.57 (dd, J=1.3, 7.7 Hz, 1H), 8.39 (dd, J=1.7, 8.4 Hz, 1H), 7.66-7.59 (m, 2H), 7.57-7.50 (m, 1H), 7.46-7.40 (m, 2H), 7.40-7.15 (m, 3H), 4.62 (s, 1H), 3.51-3.41 (m, 1H), 2.58-2.52 (m, 1H), 2.03-1.95 (m, 1H), 1.92-1.75 (m, 3H), 1.64 (d, J=10.9 Hz, 1H), 1.59-1.50 (m, 1H), 1.50-1.47 (m, 3H), 1.47-1.36 (m, 1H), 1.27-1.13 (m, 1H), 0.81 (s, 3H). m/z (ESI) 444.3 (M+H)$^+$.

Example 33

Synthesis of (1R,4s)-4-((S)-5,5-dimethyl-2-oxo-4-phenyloxazolidin-3-yl)-N-(quinolin-8-yl)cyclohexanecarboxamide

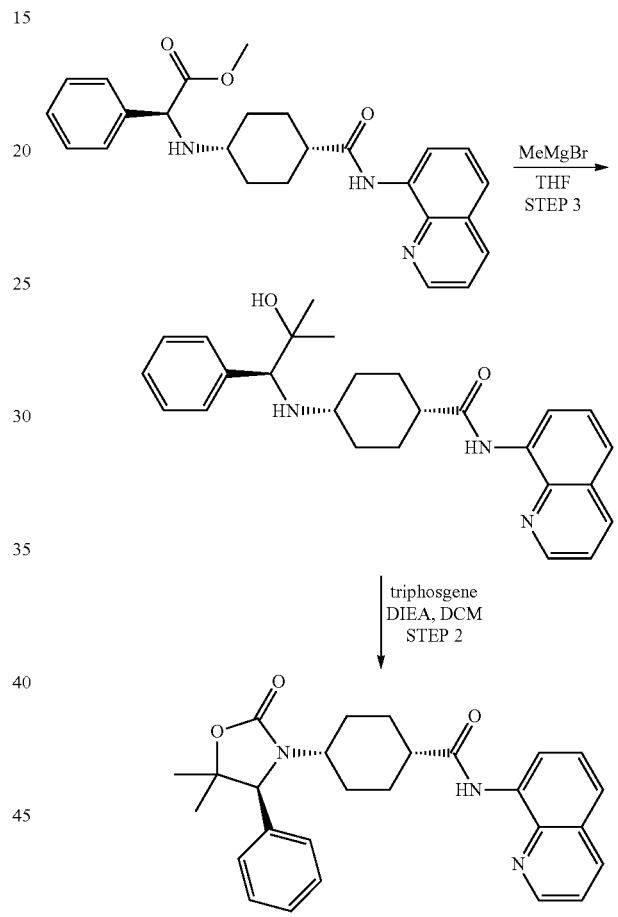

Example 33

Step 1

(1R,4s)-4-(((S)-2-Hydroxy-2-methyl-1-phenylpropyl)amino)-N-(quinolin-8-yl)cyclohexanecarboxamide (See preparation of Example 32 for the synthesis of the starting material)

A round bottom flask with a stir bar was dried under high vacuum and placed under nitrogen prior to the addition of methylmagnesium bromide (3.0 M in diethyl ether) (commercially available from Sigma-Aldrich, Milwaukee, Wis.) (2.381 mL, 7.14 mmol). The solution was cooled in an ice water bath. In a separate flask, (S)-methyl 2-phenyl-2-(((1r, 4S)-4-(quinolin-8-ylcarbamoyl)cyclohexyl)amino)acetate (0.497 g, 1.190 mmol) was dried under reduced pressure, placed under nitrogen and dissolved in Et₂O (1.7 mL). The solution was added dropwise to the cooled Grignard solution. This lead to the initial formation of a precipitate which then formed a red solution followed by eventual precipitation. The vial containing starting material was washed with another 1 mL of Et₂O, and this was transferred to the cooled reaction mixture. The ice bath was removed and the mixture was stirred at room temperature overnight. After this time, the solvent had evaporated despite only using a needle for nitrogen flow. To the mixture was added THF (2 mL) leading to near complete solubilization. The thick red mixture was poured carefully into cold NH₄Cl (ice present) with EtOAc (~25 mL). The transfer was aided by an EtOAc wash. The resulting mixture was separated in a separatory funnel. The organic layer was dried with Na₂SO₄, filtered and dried under reduced pressure. The crude brown oil was purified with a 50 g SNAP column (Biotage) ramping EtOAc in heptane (0-35%, then isocratic at 35%) to provide (1S,4r)-4-(((S)-2-hydroxy-2-methyl-1-phenylpropyl)amino)-N-(quinolin-8-yl)cyclohexanecarboxamide (0.190 g, 0.455 mmol, 38.2% yield) as a pale yellow foam upon drying. m/z (ESI) 418.2 (M+H)⁺.

Step 2

(1R,4s)-4-((S)-5,5-Dimethyl-2-oxo-4-phenyloxazolidin-3-yl)-N-(quinolin-8-yl)cyclohexanecarboxamide To a vial charged with (1R,4s)-4-(((S)-2-hydroxy-2-methyl-1-phenylpropyl)amino)-N-(quinolin-8-yl)cyclohexanecarboxamide (185 mg, 0.443 mmol) were added THF (1566 µL), and DIEA (77 µL, 0.443 mmol). The resulting mixture was cooled in an ice water bath giving a yellow solution. To the solution was added triphosgene (131 mg, 0.443 mmol) leading to the formation of a yellow/white precipitate within 10 minutes. The mixture was stirred overnight at room temperature, although after 1 hour the reaction looked to be near completion according to LC-MS. The orange suspension was quenched by the addition of saturated aqueous NaHCO₃. The mixture was then transferred to a separatory funnel and extracted with EtOAc (2×). The combined organic layers were dried with Na₂SO₄, filtered, and dried under reduced pressure. The residue thus obtained was purified with a 25 g HP silica (15 m spherical silica, Interchim) column ramping EtOAc in heptane from 0-30%, then isocratic at 30% to provide product which had coeluted with starting material (~5% impurity according to HPLC, 108 mg obtained). The material was repurified using a DCM:MeOH:NH₄OH (90:10:1) in DCM (0-30%) using the same type of column as previous to provide pure (1R,4s)-4-((S)-5,5-dimethyl-2-oxo-4-phenyloxazolidin-3-yl)-N-(quinolin-8-yl)cyclohexanecarboxamide (0.058 g, 0.131 mmol, 29.5% yield) with peak slicing as a white solid. ¹H NMR (400 MHz, DMSO-d₆) δ=9.99 (s, 1H), 8.89 (dd, J=1.7, 4.2 Hz, 1H), 8.57 (dd, J=1.2, 7.5 Hz, 1H), 8.41 (dd, J=1.5, 8.3 Hz, 1H), 7.70-7.61 (m, 2H), 7.61-7.53 (m, 1H), 7.42-7.03 (m, 5H), 4.56 (s, 1H), 3.58-3.46 (m, 1H), 2.92-2.83 (m, 1H), 2.20-2.07 (m, 2H), 1.97 (d, J=10.6 Hz, 1H), 1.75-1.52 (m, 3H), 1.46 (s, 3H), 1.43-1.34 (m, 2H), 0.76 (s, 3H). m/z (ESI) 444.2 (M+H)⁺.

Example 34

Synthesis of (R+S) 5-methyl-3-((1r,4r)-4-(2-oxo-2,3-dihydro-1H-benzo[d]imidazol-1-yl)cyclohexyl)-5-phenyloxazolidin-2-one

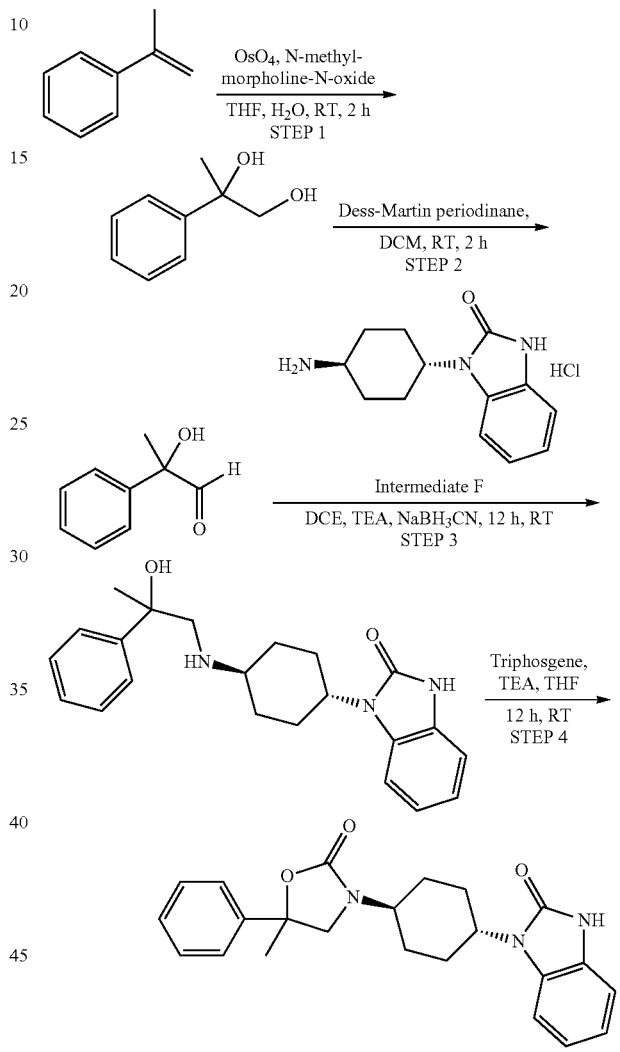

Example 34

Step 1

2-Phenylpropane-1,2-diol

To a solution of in prop-1-en-2-ylbenzene (commercially available from Sigma-Aldrich, Milwaukee, Wis.) (2 g, 16.9 mmol) in a THF (20 mL): H₂O (10 mL) mixture were added N-methylmorpholine N-oxide (1.98 g, 16.9 mmol) and osmium tetroxide (429.90 mg, 1.6 mmol) at 0° C. The resulting reaction mixture was stirred for 2 hours at ambient temperature. After completion of reaction (monitored by TLC (TLC eluent: 30% EtOAc in petroleum ether)), the reaction mixture was diluted with water and extracted with EtOAc.

The organic layers were combined and washed with water, washed with saturated NaCl solution, and dried on anhydrous $Na_2SO_4$. Then the organic layer was filtered under vacuum to provide a residue which was purified by column chromatography eluting with 50-60% EtOAc in hexane to afford 2-phenylpropane-1,2-diol, 1.5 g (58.25%) as a colorless liquid. $^1$H NMR (400 MHz, DMSO-$d_6$): δ 7.45-7.43 (m, 2H), 7.30-7.26 (m, 2H), 7.20-7.16 (m, 1H), 4.86 (s, 1H), 4.68 (t, J=6 Hz, 1H), 3.39 (d, J=6 Hz, 1H), 1.38 (s, 3H). (no MS ionization).

Step 2

2-Hydroxy-2-phenylpropanal

To a solution of 2-phenylpropane-1,2-diol (3 g, 19.7 mmol) in DCM (60 mL) was added Dess-Martin periodinane (8.36 g, 19.7 mmol) at 0° C. The reaction mixture was stirred for 2 hours at ambient temperature. After completion of the reaction (monitored by TLC (TLC eluent: 30% EtOAc in petroleum ether)), the reaction mixture was quenched with saturated $NaHCO_3$ solution and extracted with EtOAc. The organic layers were combined and washed with water, washed with saturated NaCl solution, and dried on anhydrous $Na_2SO_4$. The organic layer was then filtered and concentrated under vacuum to yield intermediate 2-hydroxy-2-phenylpropanal (2 g unpurified) as a colorless liquid. The intermediate thus obtained was used in the next step without any further purification. $^1$H NMR (400 MHz, $CDCl_3$): δ 9.50 (s, 1H). The $^1$H NMR spectrum was not completely clean, but since the aldehyde peak at 9.50 ppm was observed, this intermediate was used in the next step without purification.

Step 3

1-((1r,4r)-4-((2-Hydroxy-2-phenylpropyl)amino) cyclohexyl)-1H-benzo[d]imidazol-2(3H)-one To a suspension of 2-hydroxy-2-phenylpropanal (1 g, 6.6 mmol) and 1-(4-amino-cyclohexyl)-1,3-dihydro-benzoimidazol-2-one hydrochloride (1.78 g, 6.6 mmol) in DCE (20 mL) was added TEA (2.03 g, 19.9 mmol). The reaction mixture was stirred for 1 hour at ambient temperature. Then, $NaBH_3CN$ (836.91 mg, 13.3 mmol) was added, and the reaction mixture was stirred for 12 hours at ambient temperature. After completion of the reaction (monitored by TLC (TLC eluent: 10% MeOH in DCM)), the reaction mixture was quenched with saturated $NaHCO_3$ solution and extracted with EtOAc. The organic layers were combined and then washed with water, washed with saturated NaCl solution, and dried on anhydrous $Na_2SO_4$. The organic layer was filtered and concentrated under vacuum providing a residue which was purified by column chromatography using silica gel eluting with 2-5% MeOH in DCM to afford 1-((1r,4r)-4-((2-hydroxy-2-phenylpropyl)amino)cyclohexyl)-1H-benzo[d]imidazol-2(3H)-one (400 mg) as an off-white solid. $^1$H NMR (300 MHz, DMSO-$d_6$): δ 10.95 (s, 1H), 7.50-7.48 (m, 2H), 7.41-7.32 (m, 2H), 7.28-7.21 (m, 2H), 7.19-6.91 (m, 3H), 4.14 (m, 1H), 2.9-2.65 (m, 2H), 2.4-2.1 (m, 2H), 2.1-1.9 (m, 2H), 1.7-1.6 (m, 3H), 1.45 (s, 3H), 0.96-0.86 (m, 2H). m/z (ESI) 365.9 (M+H)$^+$.

Step 4

(R+S) 5-Methyl-3-((1r,4r)-4-(2-oxo-2,3-dihydro-1H-benzo[d]imidazol-1-yl)cyclohexyl)-5-phenyloxazolidin-2-one To a solution of 1-((1r,4r)-4-((2-hydroxy-2-phenylpropyl) amino)cyclohexyl)-1H-benzo[d]imidazol-2(3H)-one (300 mg, 0.82 mmol) in THF (9 mL) were added TEA (166.12 mg, 1.64 mmol) and triphosgene (243.58 mg, 0.82 mmol) at 0° C. The reaction mixture was stirred for 12 hours at ambient temperature. After completion of reaction (monitored by TLC (TLC eluent: 10% MeOH in DCM)), the reaction mixture was quenched with saturated $NaHCO_3$ solution and extracted with EtOAc. The organic layers were combined and washed with water, washed with saturated NaCl solution, and dried on anhydrous $Na_2SO_4$. The organic layer was then filtered and concentrated under vacuum providing a residue which was purified by preparative HPLC (column: 21.2×150×5 m Zorbax XDB C-18 (#026), mobile phase: 10 mM $NH_4OAc$ (A): 1:1/MeOH:ACN (B), flow rate 20 mL/min, 0-2 minutes 40-50% B, 2-10 minutes 50-80% B) to afford (R+S) 5-methyl-3-((1r,4r)-4-(2-oxo-2,3-dihydro-1H-benzo[d]imidazol-1-yl)cyclohexyl)-5-phenyloxazolidin-2-one, 85 mg (26.45%) as an off-white solid. $^1$H NMR (400 MHz, DMSO-$d_6$): δ 10.85 (s, 1H), 7.43 (d, J=4.4 Hz, 4H), 7.38-7.30 (m, 2H), 7.00-6.91 (m, 3H), 4.23-4.11 (m, 1H), 3.81-3.75 (m, 2H), 3.64 (d, J=8.8 Hz, 1H), 2.41-2.22 (m, 2H), 1.88-1.82 (m, 1H), 1.80-1.57 (m, 8H). m/z (ESI) 391.9 (M+H)$^+$.

Example 35

Synthesis of (R+S) 5,5-dimethyl-3-((1r,4r)-4-(2-oxo-2,3-dihydro-1H-benzo[d]imidazol-1-yl)cyclohexyl)-4-phenyloxazolidin-2-one

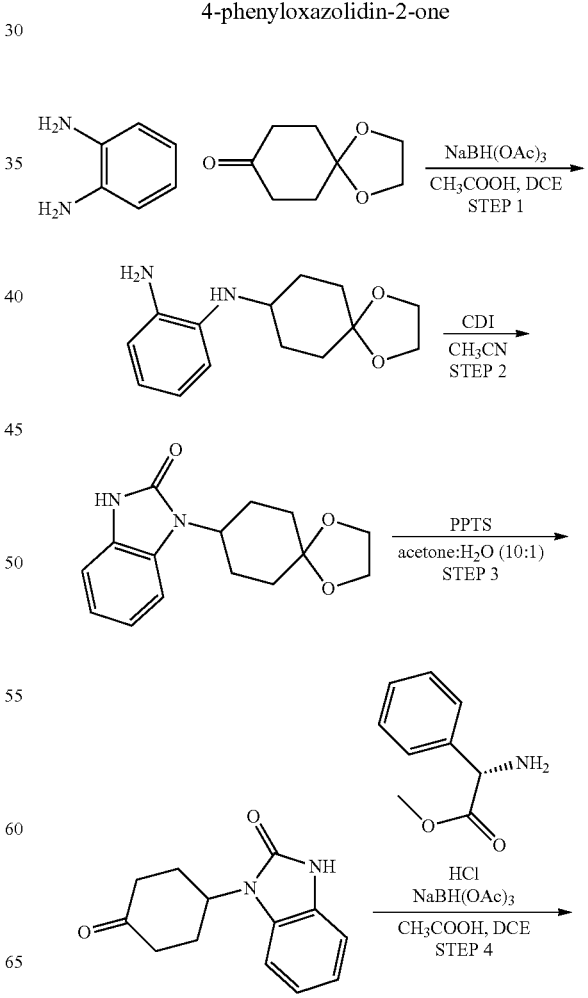

149

-continued

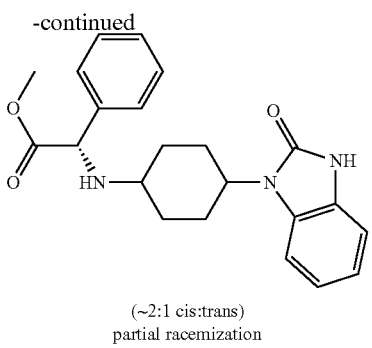

(~2:1 cis:trans)
partial racemization

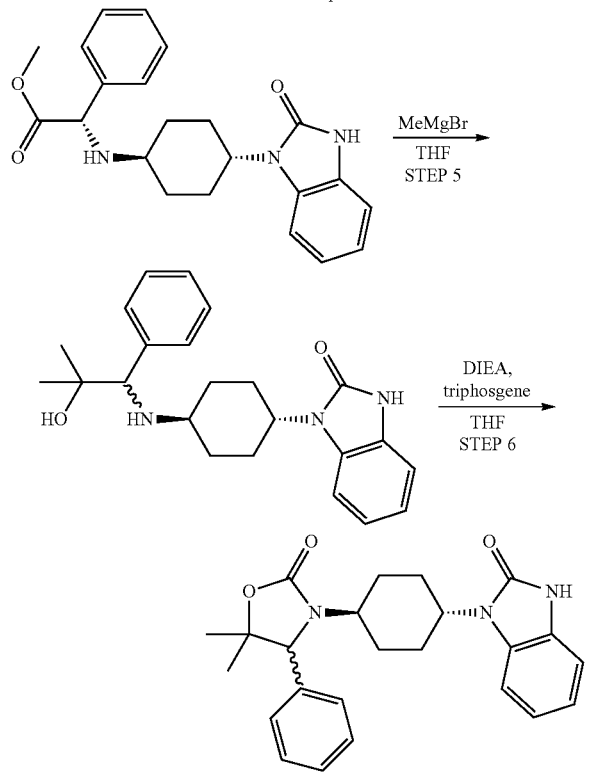

Example 35

Steps 1 and 2

N¹-(1,4-Dioxaspiro[4.5]decan-8-yl)benzene-1,2-diamine and 1-(1,4-dioxaspiro[4.5]decan-8-yl)-1H-benzo[d]imidazol-2(3H)-one The compounds N¹-(1,4-dioxaspiro[4.5]decan-8-yl)benzene-1,2-diamine and 1-(1,4-dioxaspiro[4.5]decan-8-yl)-1H-benzo[d]imidazol-2(3H)-one were prepared using the method described in U.S. Pat. No. 6,867,222 and PCT Publication No. WO 2002/085357 both of which are hereby incorporated by reference herein.

Step 3

1-(4-Oxocyclohexyl)-1H-benzo[d]imidazol-2(3H)-one

To a flask charged with 1-(1,4-dioxaspiro[4.5]decan-8-yl)-1H-benzo[d]imidazol-2(3H)-one (1.100 g, 4.01 mmol) were added acetone (7.29 mL) and water (0.729 mL) followed by PPTS (1.310 g, 5.21 mmol). The resulting light brown solution was heated at reflux overnight. Water was then added to the mixture leading to an oiling out of the organics. The mixture was transferred to a separatory funnel and extracted with EtOAc (2×). The combined organic layers were dried with $Na_2SO_4$, filtered, and dried under reduced pressure. The oil thus obtained was purified with a 50 g SNAP column (Biotage) ramping DCM:MeOH:$NH_4$OH (90:10:1) in DCM from 0-35% leading to coelution of product and starting material. The mixture was used in the next step without further purification. The mixture containing 1-(4-oxocyclohexyl)-1H-benzo[d]imidazol-2(3H)-one (0.685 g, 2.97 mmol, 74.2% yield) was obtained as a brown foam. m/z (ESI) 231.2 $(M+H)^+$.

150

Step 4

(S)-Methyl 2-(((1r,4S)-4-(2-oxo-2,3-dihydro-1H-benzo[d]imidazol-1-yl)cyclohexyl)amino)-2-phenylacetate and (S)-methyl 2-(((1s,4R)-4-(2-oxo-2,3-dihydro-1H-benzo[d]imidazol-1-yl)cyclohexyl)amino)-2-phenylacetate To a flask charged with 1-(4-oxocyclohexyl)-1H-benzo[d]imidazol-2(3H)-one (0.685 g, 2.97 mmol) were added DCE (14.87 mL), AcOH (0.221 mL, 3.87 mmol), (S)-(+)-2-phenylglycine methyl ester hydrochloride (commercially available from Sigma-Aldrich, Milwaukee, Wis.) (0.660 g, 3.27 mmol) and sodium triacetoxyborohydride (0.883 g, 4.16 mmol) respectively. The resulting orange suspension was stirred at room temperature for 4 hours leading to consumption of starting ketone. To the mixture was added 1 N NaOH. The resulting mixture was transferred to a separatory funnel and extracted with DCM (2×). The combined organic layers were dried with $Na_2SO_4$, filtered, and dried under reduced pressure. The residue was purified with a 5 g SCX-2 column washing first with MeOH (eluents dried to give 300 mg of ketal, from prior experiment), then with 2 M $NH_3$ in MeOH to provide a residue containing the product. This residue thus obtained was purified with silica gel chromatography, leading to isolation of two isomers, one major, but the major material still had impurity present. This material was repurified using Gilson RP-HPLC ramping ACN in $H_2O$ (10-90%, 0.1% TFA throughout) leading to isolation of product (cis) as a TFA salt (S)-methyl 2-(((1r,4S)-4-(2-oxo-2,3-dihydro-1H-benzo[d]imidazol-1-yl)cyclohexyl)amino)-2-phenylacetate (0.078 g, 0.164 mmol, 5.50% yield). Note: partial racemization likely occurred in this step, but the extent of which was not determined. The minor isomer (trans) was obtained directly from regular phase chromatography (S)-methyl 2-(((1s,4R)-4-(2-oxo-2,3-dihydro-1H-benzo[d]imidazol-1-yl)cyclohexyl)amino)-2-phenylacetate (0.037 g, 0.098 mmol, 3.28% yield). m/z (ESI) 380.2 $(M+H)^+$.

Step 5

1-((1r,4r)-4-((2-Hydroxy-2-methyl-1-phenylpropyl)amino)cyclohexyl)-1H-benzo[d]imidazol-2(3H)-one To a flask containing a stir bar was added (S)-methyl 2-(((1r,4S)-4-(2-oxo-2,3-dihydro-1H-benzo[d]imidazol-1-yl)cyclohexyl)amino)-2-phenylacetate (0.035 g, 0.092 mmol) which had been dried under high vacuum and placed under nitrogen. Dry THF (0.419 mL) was then added to the reaction vessel. The resulting suspension was cooled in an ice water bath prior to the dropwise addition of methylmagnesium bromide 3.0 M in diethyl ether (0.066 mL, 0.553 mmol) leading to solubilization. The solution was stirred at 0° C. for 15 minutes and then the ice bath was removed and stirring was continued for 1 hour leading to a turbid brown mixture. The mixture was added to an Erlenmeyer flask containing ice cold NH₄Cl and EtOAc. The resulting mixture was transferred to a separatory funnel, the organic layer separated and the aqueous layer was extracted with EtOAc. The combined organic layers were dried under reduced pressure and purified with a 2 g SCX-2 column loading with MeOH and washing with MeOH, followed by 2 M NH₃ in MeOH. The basic wash was dried under reduced pressure. The material thus obtained was used in the next step without further purification. 1-((1S,4r)-4-(((S)-2-Hydroxy-2-methyl-1-phenylpropyl)amino)cyclohexyl)-1H-benzo[d]imidazol-2(3H)-one (0.029 g, 0.076 mmol, 83% yield) was obtained as a light yellow solid. m/z (ESI) 380.2 (M+H)⁺.

Step 6

(R+S) 5,5-Dimethyl-3-((1r,4r)-4-(2-oxo-2,3-dihydro-1H-benzo[d]imidazol-1-yl)cyclohexyl)-4-phenyloxazolidin-2-one To a flask charged with 1-((1S,4r)-4-(((S)-2-hydroxy-2-methyl-1-phenylpropyl)amino)cyclohexyl)-1H-benzo[d]imidazol-2(3H)-one (0.029 g, 0.076 mmol) were added THF (0.273 mL) and DIEA (0.015 mL, 0.084 mmol). The resulting solution was cooled in an ice water bath prior to the addition of triphosgene (0.025 g, 0.084 mmol). After 15 minutes, the ice bath was removed and the mixture was stirred for 1 hour at room temperature. LC-MS indicated product and starting material (~3:2 product:starting material) were both present. Additional DIEA (0.015 mL, 0.084 mmol) and triphosgene (0.025 g, 0.084 mmol) were added, and the mixture was stirred at room temperature overnight. MeOH was carefully added to the mixture to quench remaining triphosgene. The resulting solution was dried under reduced pressure and purified using a 25 g HP, 15 m spherical silica column (Interchim) ramping EtOAc in heptane from 0-35%, then isocratic at 35% leading to isolation of product as a film which was lyophilized from MeOH:H₂O providing (S)-5,5-dimethyl-3-((1r,4S)-4-(2-oxo-2,3-dihydro-1H-benzo[d]imidazol-1-yl)cyclohexyl)-4-phenyloxazolidin-2-one (6.00 mg, 0.015 mmol, 19.36% yield) as a white solid. The cis/trans identification was not elucidated experimentally, but was defined based on analogy to known structures with trans>>cis in potency. ¹H NMR (500 MHz, DMSO-d₆) δ=10.75 (s, 1H), 7.46-7.40 (m, 2H), 7.38-7.34 (m, 1H), 7.33-7.18 (m, 3H), 6.95-6.90 (m, 3H), 4.66 (s, 1H), 4.03 (tt, J=3.9, 12.4 Hz, 1H), 3.65 (tt, J=4.0, 11.8 Hz, 1H), 2.22 (dq, J=4.3, 12.6 Hz, 1H), 2.14 (dq, J=3.6, 12.8 Hz, 1H), 2.00-1.86 (m, 2H), 1.74-1.52 (m, 3H), 1.48 (s, 3H), 1.34-1.22 (m, 1H), 0.80 (s, 3H). m/z (ESI) 406.2 (M+H)⁺.

Example 36

Synthesis of (R+S) 5,5-dimethyl-3-((1r,4r)-4-(2-oxo-1H-imidazo[4,5-b]pyridin-3(2H)-yl)cyclohexyl)-4-phenyloxazolidin-2-one

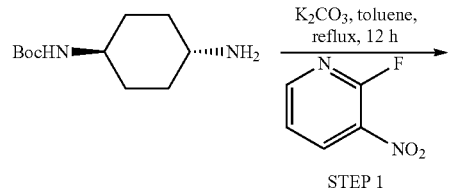

STEP 1

Step 1 tert-Butyl ((1r,4r)-4-((3-nitropyridin-2-yl)amino)cyclohexyl)carbamate

To a flask charged with toluene (37.3 mL) were added trans-N-boc-1,4-cyclohexanediamine (2.00 g, 9.33 mmol), potassium carbonate (1.290 g, 9.33 mmol) and 2-fluoro-3-nitropyridine (commercially available from Matrix Scientific, Columbia, S.C.) (1.326 mL, 9.33 mmol). The resulting bright yellow solution was heated overnight at 120° C. leading to conversion to the desired product as the primary species along with a more polar impurity according to LC-MS. The mixture was diluted with water, transferred to a separatory funnel and extracted with EtOAc (2×). The combined organic layers were dried with Na$_2$SO$_4$, filtered, and dried under reduced pressure providing a bright yellow solid which was triturated with DCM providing tert-butyl ((1r,4r)-4-((3-nitro-pyridin-2-yl)amino)cyclohexyl)carbamate (1.51 g, 4.49 mmol, 48.1% yield) as a bright yellow solid. $^1$H NMR (400 MHz, DMSO-d$_6$) δ=8.49 (dd, J=1.8, 4.5 Hz, 1H), 8.41 (dd, J=1.8, 8.4 Hz, 1H), 8.06 (d, J=7.7 Hz, 1H), 6.79-6.69 (m, 2H), 4.13-4.00 (m, J=3.9, 7.4, 7.4, 11.3 Hz, 1H), 3.29-3.20 (m, 1H), 2.01-1.92 (m, 2H), 1.82 (d, J=10.6 Hz, 2H), 1.55-1.41 (m, 2H), 1.38 (s, 9H), 1.35-1.21 (m, 2H). m/z (ESI) 281.2 (M+H)$^+$.

Step 2 tert-Butyl ((1r,4r)-4-((3-aminopyridin-2-yl)amino) cyclohexyl)carbamate

To a flask charged with tert-butyl ((1r,4r)-4-((3-nitropyridin-2-yl)amino)cyclohexyl)carbamate (1.500 g, 4.46 mmol) were added EtOH (12.74 mL) and tin(II) chloride (2.54 g, 13.38 mmol). The resulting yellow suspension was heated at 80° C. under nitrogen overnight providing a light brown solution containing primarily product according to LC-MS. The mixture was dried under reduced pressure and purified with a 50 g SNAP column (Biotage) ramping DCM:MeOH (90:10) in DCM from 0-100% (215 nm detection) yielding product as an orange foam. TLC indicated a starting spot present along with product indicating some potential salt coelution. NMR analysis showed the product along with minor impurities in the aliphatic region. The material was purified with a 10 g SCX-2 column washing with MeOH, then with NH$_3$ in MeOH providing tert-butyl ((1r,4r)-4-((3-aminopyridin-2-yl)amino)cyclohexyl)carbamate (0.840 g, 2.74 mmol, 61.5% yield) as a brown flaky solid. $^1$H NMR (400 MHz, DMSO-d$_6$) δ=7.31 (dd, J=1.6, 5.2 Hz, 1H), 6.71 (dd, J=7.8, 12.8 Hz, 2H), 6.36 (t, J=6.2 Hz, 1H), 4.87 (br. s., 2H), 3.73 (s, 1H), 3.23 (br. s., 1H), 1.97 (d, J=8.2 Hz, 2H), 1.80 (d, J=7.7 Hz, 2H), 1.38 (s, 9H), 1.35-1.17 (m, 4H). m/z (ESI) 307.2 (M+H)$^+$.

Step 3 tert-Butyl ((1r,4r)-4-(2-oxo-1H-imidazo[4,5-b]pyridin-3(2H)-yl)cyclohexyl)carbamate To a flask charged with tert-butyl ((1r,4r)-4-((3-aminopyridin-2-yl)amino)cyclohexyl)carbamate (0.830 g, 2.71 mmol) were added THF (10.84 mL) and TEA (0.793 mL, 5.69 mmol). The resulting suspension was cooled in an ice water bath prior to the addition of triphosgene (0.804 g, 2.71 mmol) leading to the immediate formation of a precipitate product. To the solid were added additional THF (~15 mL) and a small amount of water. The resulting solid was collected by vacuum filtration and washed with water followed by diethyl ether and dried under high vacuum providing product as a white solid (420 mg). The filtrate was analyzed by LC-MS which indicated the presence of additional solid. The mixture was transferred to a separatory funnel and extracted with EtOAc (2×). The combined organic layers were dried with Na$_2$SO$_4$, filtered, and dried under reduced pressure providing additional product (180 mg) as a light tan solid with slightly lower purity than the precipitated material (total—600 mg, 67%). $^1$H NMR (400 MHz, DMSO-d$_6$) δ=11.04 (s, 1H), 7.93 (dd, J=1.4, 5.2 Hz, 1H), 7.26 (dd, J=1.3, 7.7 Hz, 1H), 6.97 (dd, J=5.2, 7.7 Hz, 1H), 6.77 (d, J=7.3 Hz, 1H), 4.18 (tt, J=4.0, 12.4 Hz, 1H), peak under H$_2$O in DMSO (1H), 2.47-2.27 (m, 2H), 1.90 (d, J=11.6 Hz, 2H), 1.68 (d, J=10.8 Hz, 2H), 1.39 (s, 9H), 1.36-1.25 (m, 2H). m/z (ESI) 355.2 (M+Na)$^+$.

Step 4

3-((1r,4r)-4-Aminocyclohexyl)-1H-imidazo[4,5-b] pyridin-2(3H)-one

To a vial charged with tert-butyl ((1r,4r)-4-(2-oxo-1H-imidazo[4,5-b]pyridin-3(2H)-yl)cyclohexyl)carbamate (0.600 g, 1.805 mmol) were added DCM (7.22 mL) and TFA (1.391 mL, 18.05 mmol) providing a light peach solution which was stirred at room temperature. After 1 hour, LC-MS indicated product as the primary species. The solution was dried under reduced pressure, and the residue thus obtained was purified with a 5 g SCX-2 column washing with MeOH followed by 2 M NH$_3$ in MeOH. The basic wash was dried under reduced pressure to provide 3-((1r,4r)-4-aminocyclohexyl)-1H-imidazo[4,5-b]pyridin-2(3H)-one (0.343 g, 1.477 mmol, 82% yield) as a white solid. $^1$H NMR (400 MHz, DMSO-d$_6$) δ=7.92 (dd, J=1.5, 5.2 Hz, 1H), 7.26 (dd, J=1.5, 7.6 Hz, 1H), 6.96 (dd, J=5.2, 7.7 Hz, 1H), 4.19 (tt, J=3.9, 12.3 Hz, 1H), 2.70-2.60 (m, 1H), 2.41 (dq, J=3.3, 12.8 Hz, 2H), 1.88 (d, J=11.5 Hz, 2H), 1.64 (d, J=11.2 Hz, 2H), 1.25-1.11 (m, 2H). m/z (ESI) 233.2 (M+H)$^+$.

Step 5

3-((1r,4r)-4-((2-Hydroxy-2-methyl-1-phenylpropyl) amino)cyclohexyl)-1H-imidazo[4,5-b]pyridin-2(3H)-one To a flask charged with 3-((1r,4r)-4-aminocyclohexyl)-1H-imidazo[4,5-b]pyridin-2(3H)-one (0.335 g, 1.442 mmol) were added DMF (5.77 mL), 1-phenyl-2-hydroxy-2-methyl-1-propanone (commercially available from Sigma-Aldrich, Milwaukee, Wis.) (0.219 mL, 1.442 mmol), and AcOH (0.091 mL, 1.586 mmol) respectively. The resulting suspension was stirred for 15 minutes prior to the addition of sodium triacetoxyborohydride (0.611 g, 2.88 mmol). The resulting suspension was then stirred overnight at 60° C. leading to formation of product along with significant reduced alcohol and starting amine still remaining. Additional ketone (2 eq) and sodium triacetoxyborohydride (0.611 g, 2.88 mmol) were added, and the resulting mixture was stirred at 60° C. After 2 hours of stirring, LC-MS indicated starting material consumption and additional product present. Water was added to the mixture which was then transferred to a separatory funnel and extracted with EtOAc (2×). The combined organic layers were dried with Na$_2$SO$_4$, filtered, and dried under reduced pressure providing a residue. The residue was purified with a 25 g SNAP column (Biotage) ramping DCM:MeOH (90:10) in DCM from 0-30%, then isocratic at 30% providing impurity elution, then ramping to 100% polar eluent to provide 3-((1r,4r)-4-((2-hydroxy-2-methyl-1-phenylpropyl)amino)cyclohexyl)-1H-imidazo[4,5-b]pyridin-2 (3H)-one (0.255 g, 0.670 mmol, 46.5% yield). m/z (ESI) 381.2 (M+H)$^+$.

Step 6

(R+S) 5,5-Dimethyl-3-((1r,4r)-4-(2-oxo-1H-imidazo [4,5-b]pyridin-3 (2H)-yl)cyclohexyl)-4-phenyloxazolidin-2-one A vial charged with 3-((1 r,4r)-4-((2-hydroxy-2-methyl-1-phenylpropyl)amino)cyclohexyl)-1H-imidazo[4,5-b]pyridin-2(3H)-one (0.245 g, 0.644 mmol) and a stir bar was dried under reduced pressure and placed under nitrogen. Next, THF (2.58 mL) and DIEA (0.236 mL, 1.352 mmol) were added. The resulting suspension was cooled in an ice water bath prior to the addition of triphosgene (0.065 g, 0.219 mmol). The resulting suspension was stirred at 0° C. and allowed to slowly warm to room temperature. The mixture was then cooled in an ice water bath and additional triphosgene was added (130 mg) while stirring continued. After 15 minutes, LC-MS indicated cyclization had occurred along with over-acylation as indicated by the masses of the over-acylated acid and ester. After 20 minutes of stirring at room temperature, no additional conversion was observed. Therefore, an additional 0.5 eq of triphosgene was added (98 mg) and stirring at room temperature was continued. After another hour, only minor additional conversion was observed. To the mixture was added MeOH and the mixture dried under reduced pressure. The material thus obtained was purified with a 25 g HP spherical silica column (15 um) ramping DCM:MeOH (90:10) in DCM from 0-30%, then isocratic at 30%, then to 100% providing product (38 mg, 15%) along with over-acylated material. $^1$H NMR (500 MHz, DMSO-$d_6$) δ=11.02 (br. s., 1H), 7.91-7.87 (m, 1H), 7.46-7.40 (m, 2H), 7.40-7.34 (m, 1H), 7.34-7.19 (m, 3H), 6.95 (dd, J=5.2, 7.7 Hz, 1H), 4.68 (s, 1H), 4.14-4.06 (m, 1H), 3.48 (t, J=11.6 Hz, 1H), 2.46-2.36 (m, 1H), 2.35-2.24 (m, 1H), 1.99-1.85 (m, 2H), 1.74 (d, J=12.6 Hz, 1H), 1.68-1.54 (m, 2H), 1.48 (s, 3H), 1.31-1.21 (m, 1H), 0.82 (s, 3H). m/z (ESI) 407.1 (M+H)$^+$.

Examples 37 and 38

Synthesis of (S)-5,5-dimethyl-3-((1r,4S)-4-(2-oxo-1H-imidazo[4,5-b]pyridin-3(2H)-yl)cyclohexyl)-4-phenyloxazolidin-2-one and (R)-5,5-dimethyl-3-((1r,4R)-4-(2-oxo-1H-imidazo[4,5-b]pyridin-3(2H)-yl)cyclohexyl)-4-phenyloxazolidin-2-one

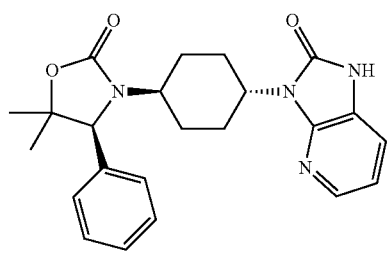

Example 37

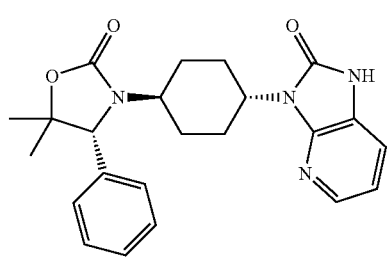

Example 38

Example compounds 37 and 38 were obtained from Example 36 using chiral chromatography. Column: Chiralpak AS, 5 micron, 2 cm i.d.×40 cm length; Mobile phase: 35% MeOH w/0.2% diethylamine/65% CO$_2$; Flowrate: 65 mL/minute; Detection: 293 nm; Injection size: 3 mg in 400 µL of 1:1 DCM: MeOH. The first eluting isomer (Example 37: (S)-5,5-dimethyl-3-((1r,4S)-4-(2-oxo-1H-imidazo[4,5-b]pyridin-3(2H)-yl)cyclohexyl)-4-phenyloxazolidin-2-one) was assigned as (S), and the second eluting isomer (Example 38: (R)-5,5-dimethyl-3-((1r,4R)-4-(2-oxo-1H-imidazo[4,5-b] pyridin-3(2H)-yl)cyclohexyl)-4-phenyloxazolidin-2-one) assigned (R) arbitrarily and not elucidated experimentally but assigned in analogy to known (S) isomers, which are more potent than (R) isomers.

Example 39

Synthesis of (S)-3-((1r,4S)-4-(3-(2,2-difluoroethyl)-2-oxo-2,3-dihydro-1H-imidazo[4,5-c]pyridin-1-yl)cyclohexyl)-5,5-dimethyl-4-phenyloxazolidin-2-one

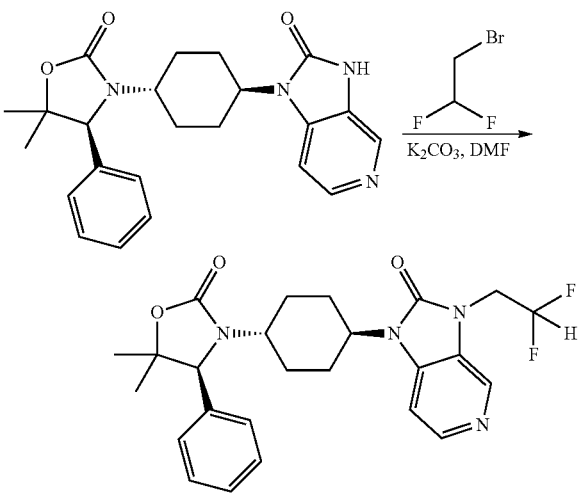

Example 39

To a vial of (S)-5,5-dimethyl-3-((1r,4S)-4-(2-oxo-2,3-dihydro-1H-imidazo[4,5-c]pyridin-1-yl)cyclohexyl)-4-phenyloxazolidin-2-one (0.023 g, 0.057 mmol) were added potassium carbonate (0.023 g, 0.170 mmol) and DMF (0.226 mL). 2-Bromo-1,1-difluoroethane (commercially available from Activate Scientific, Prien, Germany) (5.39 µL, 0.068 mmol) was then added dropwise from a pipette tip. The vial was sealed and heated to 80° C. with stirring. After 2 hours, LC-MS indicated the formation of product (~70%) with starting material present. Heating and stirring was continued overnight yielding consumption of starting material with product as the main species according to LC-MS. The mixture was dried under reduced pressure and purified with a 25 g HP spherical silica column (Interchim) ramping DCM:MeOH (90:10) in DCM from 0-20%, then isocratic at 20%, then ramping to 50% polar eluent, leading to product elution. The product was obtained as a colorless oil which was lyophilized from MeOH/H$_2$O to yield (S)-3-((1r,4S)-4-(3-(2,2-difluoroethyl)-2-oxo-2,3-dihydro-1H-imidazo[4,5-c]pyridin-1-yl)cyclohexyl)-5,5-dimethyl-4-phenyloxazolidin-2-one (21 mg, 0.045 mmol, 79% yield) as a white solid. $^1$H NMR (500 MHz, DMSO-$d_6$) δ=8.41 (s, 1H), 8.19 (d, J=5.3 Hz, 1H), 7.51 (d, J=5.3 Hz, 1H), 7.47-7.40 (m, 2H), 7.39-7.20 (m, 3H), 6.34 (tt, J=3.2, 57.0 Hz ($^2$JHF), 1H), 4.66 (s, 1H), 4.33 (dt, J=2.9, 15.9 Hz, 2H), 4.11 (tt, J=3.8, 12.4 Hz, 1H), 3.68 (tt, J=3.6, 11.8 Hz, 1H), 2.25-2.07 (m, 2H), 2.02-1.87 (m, 2H), 1.77 (td, J=2.7, 12.6 Hz, 1H), 1.68-1.58 (m, 2H), 1.48 (s, 3H), 1.32 (dq, J=3.9, 12.8 Hz, 1H), 0.80 (s, 3H). m/z (ESI) 471.3 (M+H)$^+$.

Example 40

Synthesis of (S)-5,5-dimethyl-4-phenyl-3-(4-(5-(pyridin-2-yl)pyridazin-3-yl)phenyl)oxazolidin-2-one

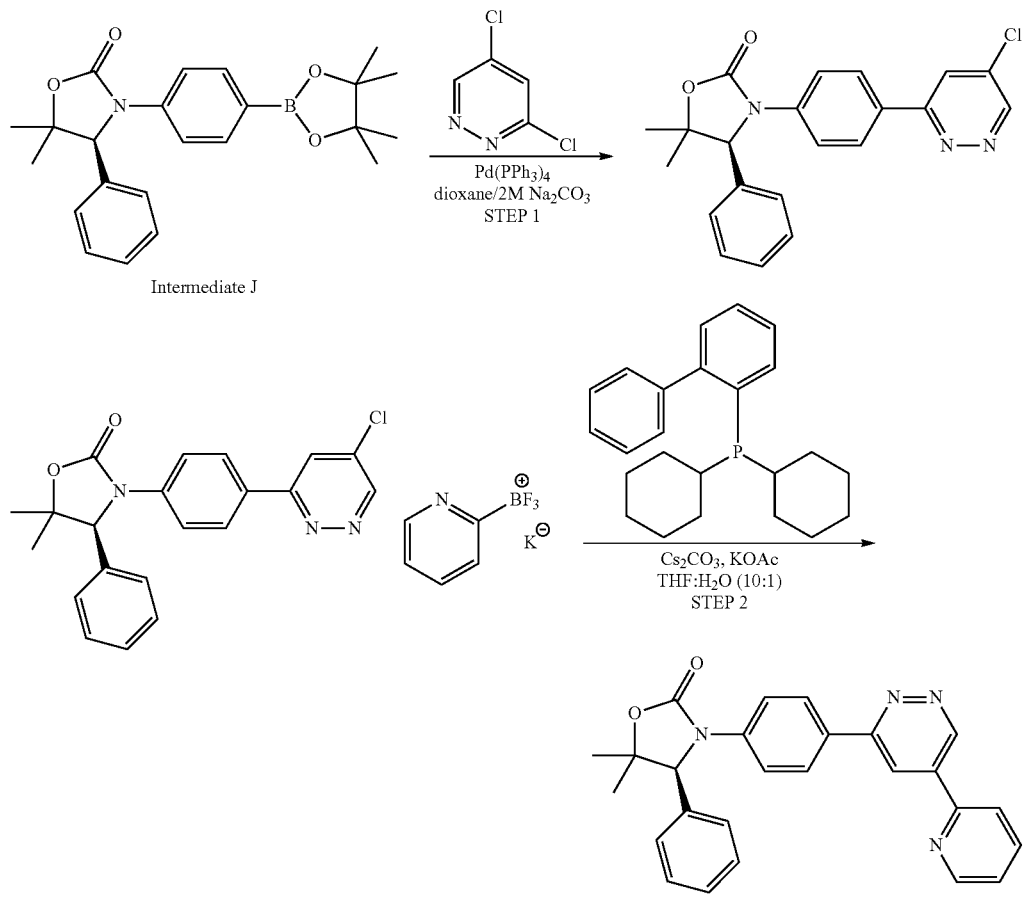

Example 40

Step 1

(S)-3-(4-(5-Chloropyridazin-3-yl)phenyl)-5,5-dimethyl-4-phenyloxazolidin-2-one To a 0.5-2.0 mL microwave vial charged with (S)-5,5-dimethyl-4-phenyl-3-(4-(4,4,5,5-tetramethyl-1,3,2-dioxaborolan-2-yl)phenyl)oxazolidin-2-one (Intermediate J) (0.240 g, 0.610 mmol) and 3,5-dichloropyridazine (commercially available from ACES Pharma, Princeton, N.J.) (0.100 g, 0.671 mmol) were added dioxane (1.220 mL), and 2 M Na$_2$CO$_3$ (1.220 mL). Nitrogen was bubbled through the resulting suspension and then Pd(PPh$_3$)$_4$ (0.071 g, 0.061 mmol) was added. The resulting mixture was irradiated at 100° C. for 30 minutes. LC-MS indicated the formation of product as a major species (two close peaks with product mass, likely isomers) along with other impurities with consumption of starting material. The dark suspension was diluted with water, transferred to a separatory funnel, and extracted with EtOAc (2×). The combined organic layers were dried with Na$_2$SO$_4$, filtered, and dried under reduced pressure. The residual material was purified with a 40 g HP 15 µm spherical silica column (Interchim) ramping EtOAc in heptane from 0-100% leading to isolation of product (primarily one isomer) as the major species with 10-15% impurity. (S)-3-(4-(5-Chloropyridazin-3-yl)phenyl)-5,5-dimethyl-4-phenyloxazolidin-2-one (0.058 g, 0.153 mmol, 25.02% yield) was obtained as a white solid. Note: the regiochemistry of the product was not confirmed, but it was assumed that the major product would result from the more reactive chloride). m/z (ESI) 380.1 (M+H)$^+$.

Step 2

(S)-5,5-Dimethyl-4-phenyl-3-(4-(5-(pyridin-2-yl)pyridazin-3-yl)phenyl)oxazolidin-2-one To a microwave vial charged with (S)-3-(4-(5-chloropyridazin-3-yl)phenyl)-5,5-dimethyl-4-phenyloxazolidin-2-one (0.058 g, 0.153 mmol) were added THF (0.522 mL), water (0.052 mL), potassium pyrido-2-trifluoroborate (commercially available from Combi-Blocks, San Diego, Calif.) (0.034 g, 0.183 mmol), cesium carbonate (0.149 g, 0.458 mmol), potassium acetate (0.749 mg, 7.63 µmol), and (2-biphenyl)dicyclohexylphosphine (5.35 mg, 0.015 mmol). The resulting mixture was purged with nitrogen and then irradiated at 135° C. for 20 minutes. Additional potassium pyrido-2-trifluoroborate (0.034 g, 0.183 mmol), potassium acetate (0.749 mg, 7.63 µmol) and (2-biphenyl)dicyclohexylphosphine (5.35 mg, 0.015 mmol) were added and the resulting suspension was heated over two nights at 130° C. in a sealed vial leading to additional conversion to desired product. Additional major species were also present. The dark mixture was then cooled to room temperature, diluted with water and extracted with EtOAc (2×). The combined organic layers were dried with Na$_2$SO$_4$, filtered, and dried under reduced pressure. The residue was purified with MPLC ramping EtOAc in heptane (0-100%). The product mixture was purified using the Gilson RP-HPLC ramping ACN in H$_2$O (10-90%, 0.1% TFA throughout). The product containing eluents were dried under reduced pressure and free-based using a 500 mg SCX-2 column washing with MeOH and then with 2 M NH$_3$ in MeOH. The oil obtained upon drying of the basic wash was lyophilized from MeOH/H$_2$O providing (S)-5,5-dimethyl-4-phenyl-3-(4-(5-(pyridin-2-yl)pyridazin-3-yl) phenyl)oxazolidin-2-one (0.003 g, 7.10 μmol, 4.65% yield) as a white solid. Analytical data is consistent with desired product. $^1$H NMR (500 MHz, DMSO-d$_6$) δ=9.82 (d, J=2.1 Hz, 1H), 8.81 (d, J=4.1 Hz, 1H), 8.66 (d, J=2.0 Hz, 1H), 8.38 (d, J=7.9 Hz, 1H), 8.21 (d, J=8.9 Hz, 2H), 8.04 (dt, J=1.7, 7.7 Hz, 1H), 7.71 (d, J=9.0 Hz, 2H), 7.56 (dd, J=5.2, 7.2 Hz, 1H), 7.42-7.36 (m, 2H), 7.32 (t, J=7.2 Hz, 3H), 5.58 (s, 1H), 1.67 (s, 3H), 0.94 (s, 3H). m/z (ESI) 423.3 (M+H)$^+$.

Example 41

Synthesis of (S)-4-(5,5-dimethyl-2-oxo-4-(o-tolyl) oxazolidin-3-yl)-N-(quinolin-8-yl)benzamide

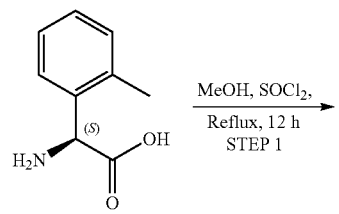

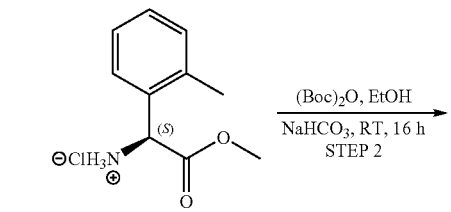

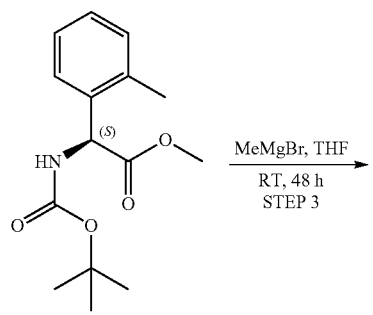

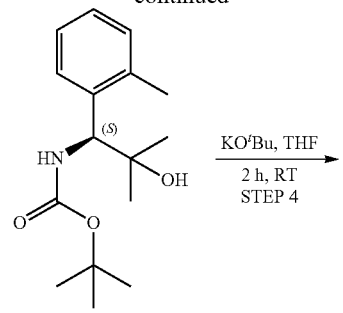

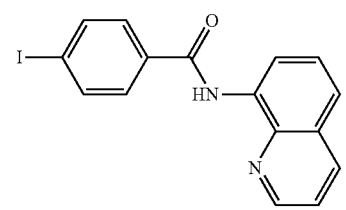

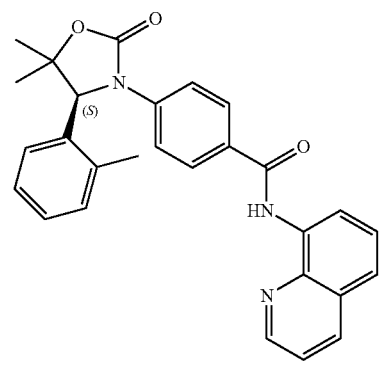

Example 41

Step 1

(S)-2-Methoxy-2-oxo-1-(o-tolyl)ethanaminium chloride

To a suspension of (S)-2-amino-2-(o-tolyl)acetic acid (commercially available from ACES Pharma, Princeton, N.J.) (800 mg, 4.84 mmol) in MeOH (20 mL) was added thionyl chloride (633.77 mg, 5.32 mmol) dropwise at −10° C. The resulting reaction mixture was stirred for 12 hours at reflux. After completion of the reaction (Reaction monitored by TLC, TLC system: 50% EtOAc in hexane), the reaction mixture was cooled to ambient temperature and then concentrated under reduced pressure. The residue was crystallized with MeOH and diethyl ether to afford (S)-2-methoxy-2-oxo-1-(o-tolyl)ethanaminium chloride, (1 g, 95.78%) as a white solid. $^1$H NMR (400 MHz, DMSO-d$_6$): δ 8.97 (s, 3H), 7.39-7.28 (m, 4H), 5.34 (s, 1H), 3.70 (s, 3H), 2.43 (s, 3H). m/z (ESI) 180.1 (M+H)$^+$.

Step 2

(S)-Methyl 2-((tert-butoxycarbonyl)amino)-2-(o-tolyl)acetate

To a solution of (S)-2-methoxy-2-oxo-1-(o-tolyl)ethanaminium chloride (1 g, 4.6 mmol) in EtOH (10 mL) were added NaHCO$_3$ (1.558 g, 18.5 mmol) and di-tert-butyl dicarbonate (1.51 g, 6.9 mmol). The resulting reaction mixture was stirred for 12 hours at ambient temperature. After completion of the reaction (monitored by TLC, TLC system: 30% EtOAc in hexane), the reaction mixture was filtered through Celite® brand filter aid and the filtrate was concentrated. The residue was purified by column chromatography using silica gel and eluting with 20% EtOAc in hexane to afford (S)-methyl 2-((tert-butoxycarbonyl)amino)-2-(o-tolyl)acetate, 1.29 g (99.61%Y) as a white solid. $^1$H NMR (400 MHz, DMSO-d$_6$): δ 7.74 (d, J=8.3 Hz, 1H), 7.21-7.18 (m, 4H), 5.42 (d, J=8.3 Hz, 1H), 3.62 (s, 3H), 2.33 (s, 3H), 1.38 (s, 9H).

Step 3

(S)-tert-Butyl (2-hydroxy-2-methyl-1-(o-tolyl)propyl)carbamate

To a solution of (S)-methyl 2-((tert-butoxycarbonyl)amino)-2-(o-tolyl)acetate (1.3 g, 4.6 mmol) in dry THF (13 mL) was slowly added MeMgBr (3 M in diethyl ether) (3.32 g, 27.9 mmol) at ambient temperature. The reaction mixture was stirred for 24 hours at ambient temperature. After completion of the reaction (Reaction monitor by TLC, TLC system: 30% EtOAc in hexane), the reaction mixture was quenched with saturated NH$_4$Cl solution and extracted with EtOAc. The combined organic layers were washed with water, with saturated NaCl solution, dried with Na$_2$SO$_4$, filtered and evaporated. The residue was purified by column chromatography eluting with 30% EtOAc in hexane to afford (S)-tert-butyl (2-hydroxy-2-methyl-1-(o-tolyl)propyl)carbamate, 1.2 g (92.30%Y) as an off-white solid. $^1$H NMR (400 MHz, DMSO-d$_6$): δ 7.44 (d, J=7.1 Hz, 1H), 7.17-7.11 (m, 3H), 7.00 (d, J=9.2 Hz, 1H), 4.76 (d, J=9.2 Hz, 1H), 4.46 (s, 1H), 2.39 (s, 3H), 1.38 (s, 9H), 1.20 (s, 3H), 0.98 (s, 3H).

Step 4

(S)-5,5-Dimethyl-4-(o-tolyl)oxazolidin-2-one

To a solution of (S)-tert-butyl (2-hydroxy-2-methyl-1-(o-tolyl)propyl)carbamate (1 g, 3.5 mmol) in THF (20 mL) was added potassium tert-butoxide (803.37 mg, 7.1 mmol) at 0-5° C. The resulting reaction mixture was stirred for 2 hours at ambient temperature. After completion of the reaction (monitored by TLC, TLC system: 50% EtOAc in hexane), the reaction mixture was quenched with ice water and extracted with EtOAc. The combined organic layers were washed with, water, washed with saturated NaCl solution, dried with Na$_2$SO$_4$, filtered and evaporated to afford (S)-5,5-dimethyl-4-(o-tolyl)oxazolidin-2-one, 0.7 g (95.28%Y) as an off-white solid. $^1$H NMR (400 MHz, DMSO-d$_6$): δ 7.96 (s, 1H), 7.27-7.25 (m, 1H), 7.22-7.19 (m, 3H), 4.83 (s, 1H), 2.29 (s, 3H), 1.55 (s, 3H), 0.81 (s, 3H). m/z (ESI) 206.1 (M+H)$^+$.

Step 5

(S)-4-(5,5-Dimethyl-2-oxo-4-(o-tolyl)oxazolidin-3-yl)-N-(quinolin-8-yl)benzamide To a nitrogen purged solution of 4-iodo-N-(quinolin-8-yl)benzamide (Intermediate A) (250 mg, 0.66 mmol) in 1,4-dioxane (3 mL) were added cesium carbonate (435.37 mg, 1.33 mmol), xantphos (77.31 mg, 0.13 mmol), Pd$_2$(dba)$_3$ (61.18 mg, 0.06 mmol) and (S)-5,5-dimethyl-4-(o-tolyl)oxazolidin-2-one (164.55 mg, 0.80 mmol). The mixture was purged with nitrogen for 5-10 minutes and then stirred for 3 hours at 100° C. After completion of the reaction (monitored by TLC, TLC system: 30% EtOAc in hexane), the reaction mixture was allowed to cool to ambient temperature and filtered through Celite® brand filter aid. The filtrate was concentrated and purified by column chromatography using silica gel and eluting with 30-40% EtOAc in hexane to afford (S)-4-(5,5-dimethyl-2-oxo-4-(o-tolyl)oxazolidin-3-yl)-N-(quinolin-8-yl)benzamide (80 mg, 26.51%) as an off-white solid. $^1$H NMR (400 MHz, DMSO-d$_6$): δ 10.55 (s, 1H), 8.95 (dd, J=4.2, 1.6 Hz, 1H), 8.68-8.66 (m, 1H), 8.46 (dd, J=8.3, 1.5 Hz, 1H), 7.97 (d, J=8.8 Hz, 2H), 7.73-7.61 (m, 5H), 7.31 (d, J=7.2 Hz, 1H), 7.23-7.15 (m, 2H), 6.96 (d, J=6.7 Hz, 1H), 5.68 (s, 1H), 1.71 (s, 3H), 0.95 (s, 3H). In CD$_3$OD: the singlet appeared for 3H at δ 2.52 (s, 3H). m/z (ESI) 452.2 (M+H)$^+$.

Example 42

Synthesis of (R+S) 4-(4-(2-fluorophenyl)-5,5-dimethyl-2-oxooxazolidin-3-yl)-N-(quinolin-8-yl)benzamide

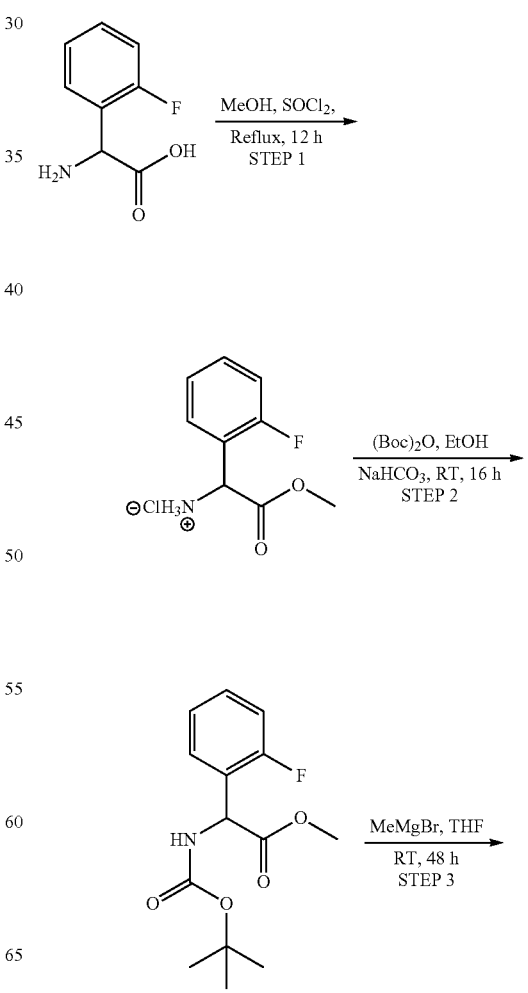

163

-continued

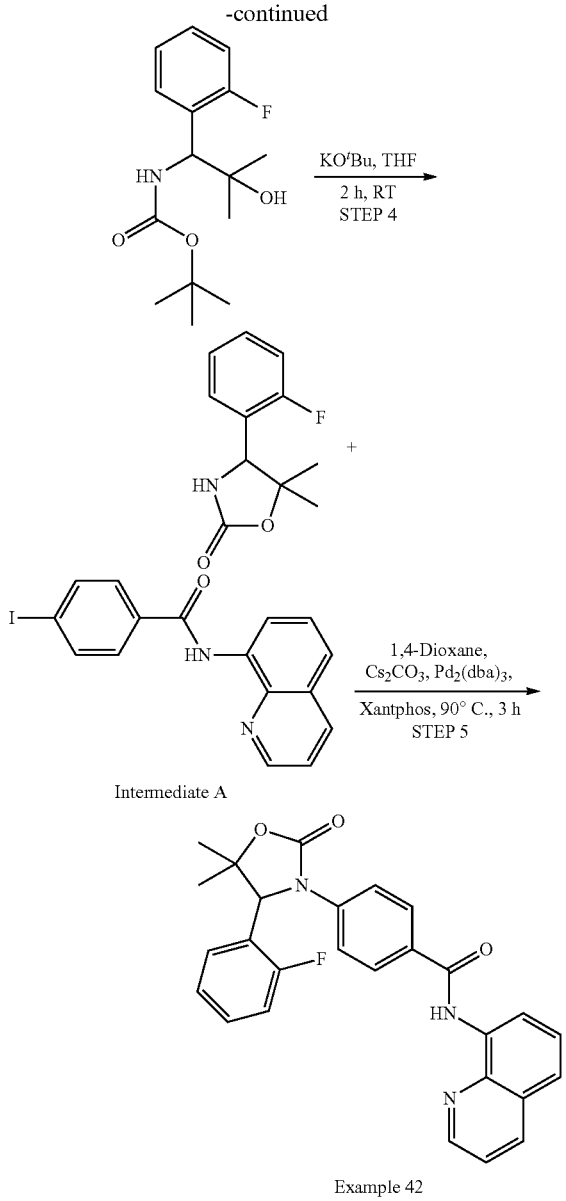

Intermediate A

Example 42

Step 1

1-(2-Fluorophenyl)-2-methoxy-2-oxoethanaminium chloride

To a suspension of 2-amino-2-(2-fluorophenyl)acetic acid (commercially available from Sigma-Aldrich, Milwaukee, Wis.) (2 g, 11.8 mmol) in MeOH (40 mL) was added thionyl chloride (1.54 g, 13 mmol) dropwise at −10° C. The resulting reaction mixture was stirred for 12 hours at reflux. After completion of the reaction (monitored by TLC, TLC system: 50% EtOAc in hexane), the reaction mixture was cooled to ambient temperature and then concentrated under reduced pressure. The residue was recrystallized with MeOH and diethyl ether to afford 1-(2-fluorophenyl)-2-methoxy-2-oxoethanaminium chloride, 2.5 g (96.30%) as a white solid. $^1$H NMR (400 MHz, DMSO-$d_6$): δ 9.12 (s, 3H), 7.60-7.50 (m, 2H), 7.36-7.29 (m, 2H), 5.45 (s, 1H), 3.73 (s, 3H). m/z (ESI) 184.2 (M+H)$^+$.

164

Step 2

Methyl 2-((tert-butoxycarbonyl)amino)-2-(2-fluorophenyl)acetate

To a solution of 1-(2-fluorophenyl)-2-methoxy-2-oxoethanaminium chloride (2.6 g, 11.8 mmol) in EtOH (26 mL) were added NaHCO$_3$ (3.97 g, 47.3 mmol) and di tert-butyl dicarbonate (3.87 g, 17.7 mmol). The resulting reaction mixture was stirred for 12 hours at ambient temperature. After completion of the reaction (reaction monitored by TLC, TLC system: 30% EtOAc in hexane), the reaction mixture was filtered through Celite® brand filter aid and the filtrate was concentrated. The residue was purified by column chromatography using silica gel eluting with 20% EtOAc in hexane to afford methyl 2-((tert-butoxycarbonyl)amino)-2-(2-fluorophenyl)acetate (3 g, 89.47%) as a white solid. $^1$H NMR (300 MHz, DMSO-$d_6$): δ 7.91 (d, J=8.7 Hz, 1H), 7.44-7.35 (m, 2H), 7.25-7.17 (m, 2H), 5.50 (d, J=8.6 Hz, 1H), 3.63 (s, 3H), 1.39 (s, 9H).

Step 3 tert-Butyl (1-(2-fluorophenyl)-2-hydroxy-2-methylpropyl)carbamate

To a solution of methyl 2-((tert-butoxycarbonyl)amino)-2-(2-fluorophenyl)acetate (500 mg, 1.76 mmol) in dry THF (10 mL) was slowly added MeMgBr (3 M in diethyl ether) (1.05 g, 8.83 mmol) at ambient temperature. The reaction mixture was stirred for 24 hours at ambient temperature. After completion of the reaction (monitored by TLC, TLC system: 30% EtOAc in hexane), the reaction mixture was quenched with saturated NH$_4$Cl solution and extracted with EtOAc. The combined organic layers were washed with water, saturated NaCl solution, dried with Na$_2$SO$_4$, filtered and concentrated. The residue was purified by column chromatography using silica gel eluting with 30% EtOAc in hexane to afford tert-butyl (1-(2-fluorophenyl)-2-hydroxy-2-methylpropyl)carbamate (500 mg, 99.98%) as an off-white solid. $^1$H NMR (400 MHz, DMSO-$d_6$): δ 7.52-7.48 (m, 1H), 7.32-7.28 (m, 1H), 7.20-7.12 (m, 3H), 4.85 (d, J=9.6 Hz, 1H), 4.52 (s, 1H), 1.41 (s, 9H), 1.20 (s, 3H), 0.99 (s, 3H).

Step 4

4-(2-Fluorophenyl)-5,5-dimethyloxazolidin-2-one

To a solution of tert-butyl (1-(2-fluorophenyl)-2-hydroxy-2-methylpropyl)carbamate (400 mg, 1.41 mmol) in THF (8 mL) was added potassium tert-butoxide (316.87 mg, 2.82 mmol) at 0-5° C. The resulting reaction mixture was stirred for 2 hours at ambient temperature. After completion of the reaction (monitored by TLC, TLC system: 50% EtOAc in hexane), the reaction mixture was quenched with ice water and extracted with EtOAc. The combined organic layers were washed with, water, saturated NaCl solution and dried on Na$_2$SO$_4$, filtered, and concentrated under reduced pressure to afford 4-(2-fluorophenyl)-5,5-dimethyloxazolidin-2-one (290 mg, 98.18%) as an off-white solid. $^1$H NMR (400 MHz, DMSO-$d_6$): δ 8.05 (s, 1H), 7.44-7.35 (m, 2H), 7.30-7.22 (m, 2H), 4.88 (s, 1H), 1.53 (s, 3H), 0.88 (s, 3H). m/z (ESI) 210.1 (M+H)$^+$.

Step 5

4-(4-(2-Fluorophenyl)-5,5-dimethyl-2-oxooxazolidin-3-yl)-N-(quinolin-8-yl)benzamide To a nitrogen purged solution of 4-iodo-N-(quinolin-8-yl) benzamide (250 mg, 0.66 mmol) in 1,4-dioxane (5 mL) were added cesium carbonate (435.37 mg, 1.33 mmol), xantphos (77.31 mg, 0.13 mmol), Pd$_2$(dba)$_3$ (61.18 mg, 0.06 mmol) and 4-(2-fluorophenyl)-5,5-dimethyloxazolidin-2-one (167.73 mg, 0.80 mmol). The mixture was purged with nitrogen for 5-10 minutes. The reaction mixture was then stirred for 3 hours at 100° C. After completion of the reaction (monitored by TLC, TLC system: 30% EtOAc in hexane), the reaction mixture was cooled to ambient temperature and filtered through Celite® brand filter aid. The filtrate was concentrated and purified by column chromatography using silica gel and eluting with 30% EtOAc in hexane to afford (R+S) 4-(4-(2-fluorophenyl)-5,5-dimethyl-2-oxooxazolidin-3-yl)-N-(quinolin-8-yl)benzamide (60 mg, 19.71%) as an off-white solid. $^1$H NMR (400 MHz, DMSO-d$_6$): δ 10.57 (s, 1H), 8.95 (dd, J=1.2 Hz, 1H), 8.68 (d, J=7.6 Hz, 1H), 8.46 (d, J=8.3 Hz, 1H), 8.00-7.95 (m, 2H), 7.82-7.62 (m, 5H), 7.41-7.35 (m, 2H), 7.19-7.08 (m, 2H), 5.84 (s, 1H), 1.69 (s, 3H), 1.03 (s, 3H). m/z (ESI) 456.1 (M+H)$^+$.

Example 43

Synthesis of (S)-4-(5,5-diethyl-2-oxo-4-phenyloxazolidin-3-yl)-N-(quinolin-8-yl)benzamide

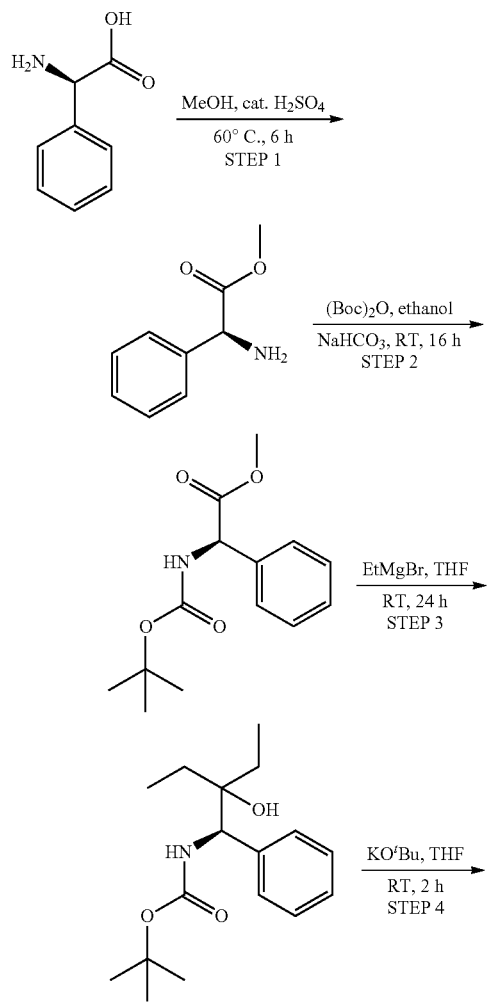

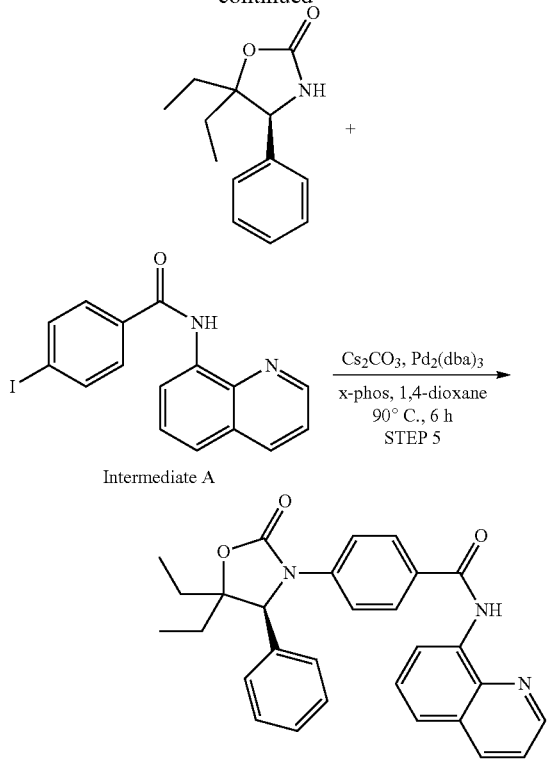

Example 43

Step 1

(S)-Methyl 2-amino-2-phenylacetate

A catalytic amount of concentrated sulfuric acid (0.1 mL) was added to a 50 mL round bottom flask containing a solution of (S)-2-amino-2-phenylacetic acid (commercially available from Sigma-Aldrich, Milwaukee, Wis.) (1.0 g, 6.6 mmol) in MeOH (10 mL). The resulting mixture was heated at 65° C. for 6 hours. The solvent was removed under reduced pressure, and the mixture was quenched with aqueous NaHCO$_3$ and extracted with EtOAc. The organic layer was dried over Na$_2$SO$_4$, filtered, and concentrated to afford (S)-methyl 2-amino-2-phenylacetate (0.8 g, 74.0%) as a white solid. $^1$H NMR (300 MHz, CDCl$_3$) δ: 7.37-7.32 (m, 5H), 4.62 (s, 1H), 3.70 (s, 3H).

Step 2

(R)-Methyl 2-((tert-butoxycarbonyl)amino)-2-phenylacetate

NaHCO$_3$ (1.7 g, 19.4 mmol) and (Boc)$_2$O (2.1 g, 9.7 mmol) were added to a 50 mL round bottom flask containing a solution of (S)-methyl 2-amino-2-phenylacetate (0.8 g, 4.9 mmol) in EtOH (20 mL). The resulting mixture was stirred at ambient temperature for 16 hours. After completion of reaction (monitored by TLC, TLC eluent: 20% EtOAc in hexane), the mixture was filtered and the filtrate concentrated to afford 1.2 g (94.0%) of (R)-methyl 2-((tert-butoxycarbonyl)amino)-2-phenylacetate colorless oil. $^1$H NMR (400 MHz, CDCl$_3$) δ: 7.36-7.31 (m, 5H), 5.55 (m, 1H), 5.31 (d, J=7.4 Hz, 1H), 3.72 (s, 3H), 1.43 (s, 9H).

Step 3

(R)-tert-Butyl (2-ethyl-2-hydroxy-1-phenylbutyl) carbamate

To a two-necked 50 mL round bottom flask were added (R)-methyl 2-((tert-butoxycarbonyl)amino)-2-phenylacetate (1.2 g, 5.68 mmol) and dry THF (30 mL). The resulting mixture was cooled to 0° C. Ethyl magnesium bromide (3.02 g, 22.72 mmol) (3M solution in diethyl ether) was added dropwise, and the mixture was slowly allowed to warm to ambient temperature. The mixture was then stirred at ambient temperature for 24 hours. After completion of reaction (monitored by TLC, TLC eluent: 30% EtOAc in hexane), the mixture was quenched in $NH_4Cl$ solution and extracted with EtOAc. The combined organic layers were dried over $Na_2SO_4$, filtered, and concentrated to yield 1.2 g (90.0%) of (R)-tert-butyl (2-ethyl-2-hydroxy-1-phenylbutyl)carbamate as a white solid. $^1H$ NMR (300 MHz, $CDCl_3$) δ: 7.35-7.26 (m, 5H), 5.56 (d, J=9.1 Hz, 1H), 4.61 (d, J=9.4 Hz, 1H), 1.68-1.63 (m, 2H), 1.39 (s, 9H), 1.32-1.22 (m, 2H), 0.92 (t, J=7.4 Hz, 3H), 0.80 (t, J=7.4 Hz, 3H).

Step 4

(S)-5,5-Diethyl-4-phenyloxazolidin-2-one

A solution of (R)-tert-butyl (2-ethyl-2-hydroxy-1-phenyl-butyl)carbamate (1.2 g, mmol) in dry THF (5 mL) in a 25 mL round bottom flas was cooled to 0° C. To the solution was added potassium t-butoxide (1.46 g, 13.04 mmol) in one portion, and the mixture was allowed to slowly warm to room temperature and stirred for 2 hours. After completion of reaction (monitored by TLC, TLC eluent: 30% EtOAc in hexane), the solvent was removed under reduced pressure, the reaction was quenched in saturated $NH_4Cl$ solution. The product was extracted with EtOAc. The organic layer was dried over $Na_2SO_4$, filtered and concentrated to afford 0.6 g (66.6%) of (S)-5,5-diethyl-4-phenyloxazolidin-2-one colorless oil. $^1H$ NMR (300 MHz, $CDCl_3$) δ: 7.38-7.33 (m, 3H), 7.28-7.25 (m, 2H), 5.63 (s, 1H), 4.71 (s, 1H), 1.80-1-2 (m, 2H), 1.38-1.28 (m, 1H), 1.06 (t, J=7.2 Hz, 3H), 0.72 (t, J=7.4 Hz, 3H).

Step 5

(S)-4-(5,5-Diethyl-2-oxo-4-phenyloxazolidin-3-yl)-N-(quinolin-8-yl)benzamide To a 25 mL round bottom flask were added (S)-5,5-diethyl-4-phenyloxazolidin-2-one (0.3 g, 1.36 mmol), 4-iodo-N-(quinolin-8-yl)benzamide (0.560 g, 1.5 mmol), $Cs_2CO_3$ (0.972 g, 3.0 mmol), X-Phos (35 mg, 0.068 mmol), $Pd_2(dba)_3$ (62 mg, 0.068 mmol) and 1,4-dioxane (2 mL). The mixture was purged with $N_2$ gas for 15 minutes. The reaction mixture was then heated at 90° C. for 6 hours. After completion of reaction (monitored by TLC, TLC eluent: 30% EtOAc in hexane), the reaction mixture was cooled to ambient temperature and treated with water (5 mL) and the mixture extracted with EtOAc (5 mL). The aqueous layer was back extracted with EtOAc (5 mL). The combined organic layers were dried over anhydrous $Na_2SO_4$ and concentrated. The crude material was purified with HPLC (column: AG/AD/C18-027, ramping ACN in $H_2O$, 40-50% B, 0-2 minutes, 50-90% B, 2-10 minutes, flow rate 20 mL/min) to afford 50 mg of (S)-4-(5,5-diethyl-2-oxo-4-phenyloxazolidin-3-yl)-N-(quinolin-8-yl) benzamide as a brown solid. $^1H$ NMR (300 MHz, $CDCl_3$) δ: 10.67 (s, 1H), 8.96-8.80 (m, 2H), 8.20 (dd, J=8.3, 1.6 Hz, 1H), 7.99 (d, J=9 Hz, 2H), 7.68 (d, J=8.7 Hz, 2H), 7.62-7.56 (m, 2H), 7.57-7.47 (m, 1H), 7.40-7.36 (m, 3H), 7.28-7.24 (m, 2H), 5.15 (s, 1H), 2.04-1.96 (m, 2H), 1.39-1.20 (m, 2H), 1.12 (t, J=7.5 Hz, 3H), 0.85 (t, J=7.4 Hz, 3H). m/z (ESI) 466.2 $(M+H)^+$.

Example 44

Synthesis of (R+S) 4-(6-oxo-8-phenyl-5-oxa-7-aza-spiro[3.4]octan-7-yl)-N-(quinolin-8-yl)benzamide

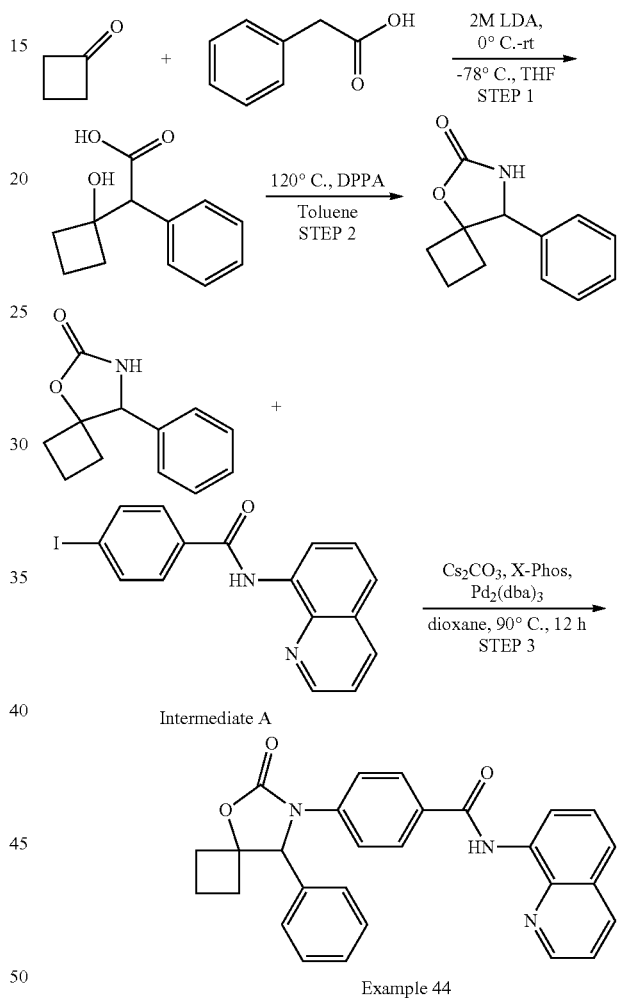

Example 44

Step 1

2-(1-Hydroxycyclobutyl)-2-phenylacetic acid

To a dried 250 mL round bottom flask containing 2 M lithium diisopropyl amide in THF (2 eq.) in THF (60 mL) at 0° C., was added phenyl acetic acid (1.0 g, 7.35 mmol, 1 eq). The resulting mixture was stirred at ambient temperature for 30 minutes. The reaction mixture was then cooled to −78° C. and a mixture of cyclobutanone (commercially available from Sigma-Aldrich, Milwaukee, Wis.) (0.617 g, 8.82 mmol, 1.2 eq.) in THF (20 mL) was added dropwise. The resulting mixture was then stirred at −78° C. and then at ambient temperature for 3 hours. Reaction progress was monitored by TLC (TLC eluent: 30% EtOAc in hexane). The reaction mixture was poured into an EtOAc/water mixture and the aqueous layer was extracted with EtOAc. The aqueous layer was then acidified with dilute hydrochloric acid and extracted with DCM. The DCM solution was washed with brine and concentrated. The residue was purified by column chromatography using silica gel eluting with 15% EtOAc in hexane to yield 2-(1-hydroxycyclobutyl)-2-phenylacetic acid (1.1 g, 73%). $^1$H NMR (300 MHz, CDCl$_3$) δ: 7.42-7.26 (m, 5H), 3.88 (s, 1H), 2.24-2.19 (m, 2H), 2.10-2.05 (m, 2H), 1.93-1.87 (m, 3H). m/z (ESI) 189 (M+H)$^+$ (-Dehydroxy mass observed).

Step 2

8-Phenyl-5-oxa-7-azaspiro[3.4]octan-6-one

Into a 100 mL round bottom flask charged with 2-(1-hydroxycyclobutyl)-2-phenylacetic acid (0.5 g, 2.42 mmol, 1 eq.) in toluene (30 mL) were added TEA (2.5 eq) and diphenyl phosphoryl azide (2 eq). The resulting mixture was stirred at 120° C. for 12 hours. Reaction progress was monitored by TLC (TLC eluent: 30% EtOAc in hexane). The reaction mixture was cooled and toluene was evaporated under reduced pressure to afford the initial product. The initial product was purified by column chromatography using silica gel eluting with 10% EtOAc in hexane to afford 8-phenyl-5-oxa-7-azaspiro[3.4]octan-6-one (0.5 g, 73%). $^1$H NMR (300 MHz, CDCl$_3$) δ: 7.52-7.23 (m, 5H), 5.72 (s, 1H), 4.74 (s, 1H), 2.69-2.50 (m, 1H), 2.30-2.40 (m, 1H), 2.10-2.20 (m, 1H), 1.94-1.66 (m, 1H), 1.75-1.64 (m, 1H), 1.43-1.35 (m, 1H).

Step 3

(R+S) 4-(6-Oxo-8-phenyl-5-oxa-7-azaspiro[3.4]octan-7-yl)-N-(quinolin-8-yl)benzamide A mixture of 8-phenyl-5-oxa-7-azaspiro[3.4]octan-6-one (0.3 g, 1.57 mmol), 4-iodo-N-(quinolin-8-yl)benzamide, (0.650 g, 1.73 mmol), Cs$_2$CO$_3$ (1.125 g, 3.47 mmol), X-Phos (40 mg, 0.07 mmol) and Pd$_2$(dba)$_3$ (73 mg, 0.07 mmol) in 1,4-dioxane (2 mL) in a 50 mL round bottom flask was purged with N$_2$ gas for 15 minutes. The reaction mixture was then heated at 90° C. for 12 hours. After completion of reaction (monitored by TLC, TLC eluent: 30% EtOAc in hexane), the reaction mixture was cooled, and 1,4-dioxane was evaporated under reduced pressure to afford initial product. The initial product was purified by column chromatography using silica gel eluting with 20% EtOAc in hexane to yield (R+S) 4-(6-oxo-8-phenyl-5-oxa-7-azaspiro[3.4]octan-7-yl)-N-(quinolin-8-yl)benzamide (70 mg, 12%) as a brown solid. $^1$H NMR (400 MHz, CDCl$_3$) δ: 10.65 (s, 1H), 8.88 (dd, J=7.2, 1.6 Hz, 1H), 8.83-8.81 (m, 1H), 8.18 (dd, J=8.4, 1.6 Hz, 1H), 7.99-7.96 (m, 2H), 7.67-7.64 (m, 2H), 7.59-7.51 (m, 2H), 7.49-7.45 (m, 1H), 7.43-7.34 (m, 3H), 7.29-7.26 (m, 2H), 5.23 (s, 1H), 2.68-2.63 (m, 1H), 2.48-2.43 (m, 1H), 2.22-2.18 (m, 1H), 1.96-1.91 (m, 1H), 1.76-1.71 (m, 1H), 1.62-1.57 (m, 1H). m/z (ESI) 450.1 (M+H)$^+$.

Example 45

Synthesis of (R+S) 4-(2-oxo-4-phenyl-1-oxa-3-azaspiro[4.4]nonan-3-yl)-N-(quinolin-8-yl)benzamide

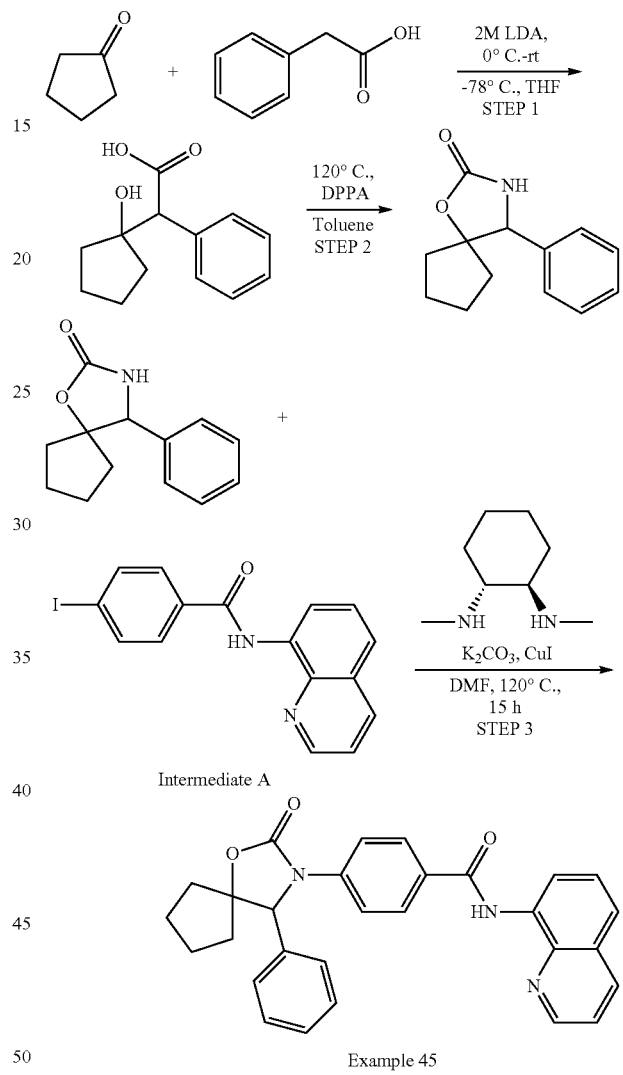

Example 45

Step 1

2-(1-Hydroxycyclopentyl)-2-phenylacetic acid

To a dry 250 mL round bottom flask containing 2 M lithium diisopropyl amide in THF (2 eq.) in THF (164 mL) at 0° C., was added phenyl acetic acid (3.5 g, 25.71 mmol). The mixture was then stirred at ambient temperature for 30 minutes. The reaction mixture was cooled to −78° C. and cyclopentanone (commercially available from Sigma-Aldrich, Milwaukee, Wis.) (2.73 mL, 30.85 mmol, 1.2 eq.) in THF (90 mL) was added dropwise. The mixture was then stirred at −78° C. and allowed to warm to ambient temperature over 3 hours. The progress of the reaction was monitored by TLC (TLC eluent: 30% EtOAc in hexane). The reaction mixture was poured into an EtOAc/water mixture and the aqueous layer was extracted with EtOAc. The aqueous layer was then acidified with dilute hydrochloric acid and extracted with DCM. The DCM solution was washed with brine and then concentrated to provide the product. The product (3.5 g) thus obtained was used in the next step without any further purification.

Step 2

4-Phenyl-1-oxa-3-azaspiro[4.4]nonan-2-one

To a 100 mL round bottom flask charged with 2-(1-hydroxycyclopentyl)-2-phenylacetic acid (3.5 g, 16.13 mmol, 1 eq.) in toluene (70 mL) were added TEA (2.5 eq) and diphenyl phosphoryl azide (2 eq). The resulting mixture was stirred at 120° C. for 12 hours. Reaction progress was monitored by TLC (TLC eluent: 30% EtOAc in hexane). The reaction mixture was cooled and toluene was removed under reduced pressure. The product thus obtained was purified by column chromatography using silica gel and eluting with 10% EtOAc in hexane to afford 4-phenyl-1-oxa-3-azaspiro[4.4]nonan-2-one (2 g, 31%). $^1$H NMR (300 MHz, CDCl$_3$) δ: 8.06 (s, 1H), 7.28-7.41 (m, 5H), 4.78 (s, 1H), 1.88-2.03 (m, 2H), 1.23-1.70 (m, 5H), 0.97-1.03 (m, 1H). m/z (ESI) 218.3 (M+H)$^+$.

Step 3

(R+S) 4-(2-Oxo-4-phenyl-1-oxa-3-azaspiro[4.4]nonan-3-yl)-N-(quinolin-8-yl)benzamide To a 50 mL dried round bottom flask containing a degassed solution of 4-phenyl-1-oxa-3-azaspiro[4.4]nonan-2-one (1 eq., 1.73 mmol) and 4-iodo-N-(quinolin-8-yl)benzamide (1.2 eq.) in DMF (15 mL), potassium carbonate (2.5 eq.) and trans (N,N)-dimethyl cyclohexanediamine (0.5 eq.) was added CuI (0.1 eq). The resulting mixture was stirred at 120° C. for 15 hours. Reaction progress was monitored by TLC (TLC eluent: 10% MeOH in DCM). The reaction mixture was cooled and poured into crushed ice (5 g). The solid thus obtained was filtered, washed with water (25 mL) and dissolved in DCM. The DCM solution was then washed with water (100 mL), washed brine (50 mL) and dried over anhydrous Na$_2$SO$_4$, filtered, concentrated and purified by column chromatography using silica gel and DCM as eluting solvent to yield (R+S) 4-(2-oxo-4-phenyl-1-oxa-3-azaspiro[4.4]nonan-3-yl)-N-(quinolin-8-yl)benzamide (90 mg, 11%) as a white solid. $^1$H NMR (400 MHz, DMSO-d$_6$) δ: 10.55 (s, 1H), 8.94 (d, J=4 Hz, 1H), 8.65 (d, J=7.2 Hz, 1H), 8.44 (d, J=8.4 Hz, 1H), 7.95 (d, J=8.4 Hz, 1H), 7.75-7.63 (m, 5H), 7.39-7.32 (m, 5H), 5.75 (s, 1H), 2.10-2.20 (m, 2H), 1.50-1.78 (s, 4H), 1.30-1.40 (m, 1H), 1.10-1.20 (m, 1H). m/z (ESI) 464.3 (M+H)$^+$.

Example 46

Synthesis of (R+S) 4-(2-oxo-4-phenyl-1-oxa-3-azaspiro[4.5]decan-3-yl)-N-(quinolin-8-yl)benzamide

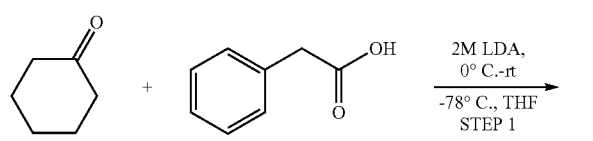

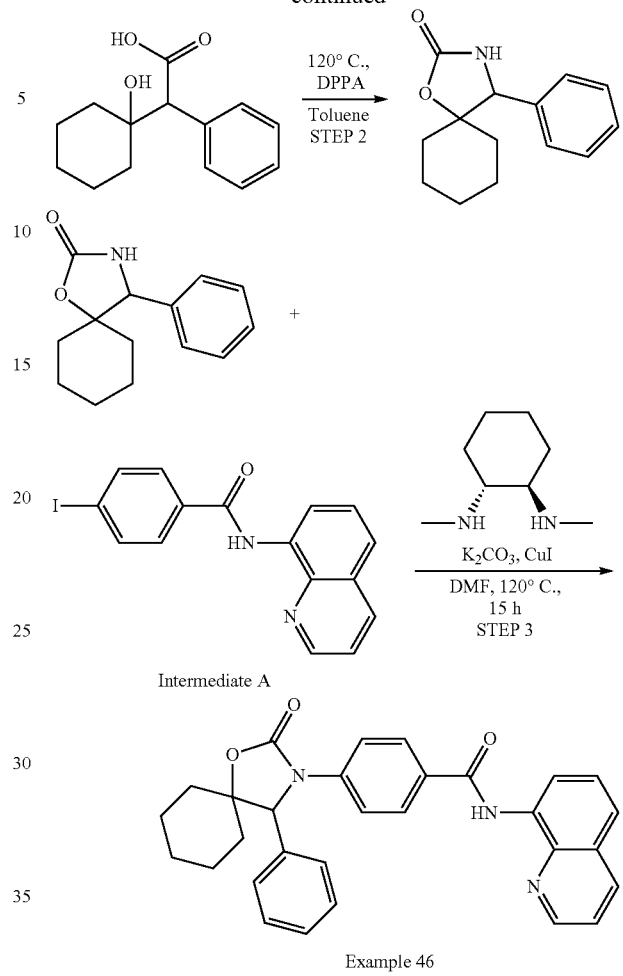

Example 46

Step 1

2-(1-Hydroxycyclohexyl)-2-phenylacetic acid

To a dried 250 mL round bottom flask containing 2 M lithium diisopropyl amide in THF (2 eq.) in THF (329 mL) at 0° C., was added phenyl acetic acid (6 g, 44.07 mmol). The resulting mixture was then stirred at ambient temperature for 30 minutes. The reaction mixture was cooled to −78° C. and cyclohexanone (commercially available from Sigma-Aldrich, Milwaukee, Wis.) (5.49 mL, 52.88 mmol, 1.2 eq.) in THF (181 mL) was added dropwise. The resulting mixture was stirred at −78° C. and allowed to warm to ambient temperature over 3 hours. Reaction progress was monitored by TLC (TLC eluent: 30% EtOAc in hexane). The reaction mixture was then poured into a EtOAc/water mixture, and the aqueous layer was extracted with EtOAc. The aqueous layer was then acidified with dilute hydrochloric acid and extracted with DCM. The DCM solution was washed with brine and concentrated. The product (6.5 g) thus obtained was used without any further purification.

Step 2

4-Phenyl-1-oxa-3-azaspiro[4.5]decan-2-one

To a 100 mL round bottom flask charged with 2-(1-hydroxycyclohexyl)-2-phenylacetic acid (6.5 g, 28.14 mmole, 1 eq.) in toluene (100 mL) were added TEA (2.5 eq) and diphenyl phosphoryl azide (2 eq). The resulting mixture was then stirred at 120° C. for 12 hours. Reaction progress was monitored by TLC (TLC eluent: 30% EtOAc in hexane). The reaction mixture was then cooled and toluene was removed under reduced pressure to afford the product. The product thus obtained was purified by column chromatography using silica gel and eluting with 10% EtOAc in hexane to afford 4-phenyl-1-oxa-3-azaspiro[4.5]decan-2-one (2 g, 31%). $^1$H NMR (400 MHz, DMSO-$d_6$) δ: 8.04 (s, 1H), 7.26-7.41 (m, 5H), 4.54 (s, 1H), 1.93-1.97 (m, 1H), 1.48-1.78 (m, 4H), 1.12-1.33 (m, 5H). m/z (ESI) 232.1 (M+H)$^+$.

Step 3

(R+S) 4-(2-Oxo-4-phenyl-1-oxa-3-azaspiro[4.5]decan-3-yl)-N-(quinolin-8-yl)benzamide To a 50 mL dried round bottom flask containing a degassed solution of 4-phenyl-1-oxa-3-azaspiro[4.5]decan-2-one (1 eq., 1.73 mmol) and 4-iodo-N-(quinolin-8-yl)benzamide (1.2 eq.) in DMF (15 mL), potassium carbonate (2.5 eq.) and trans (N,N)-dimethyl cyclohexanediamine (0.5 eq.), was added CuI (0.1 eq). The resulting mixture was then stirred at 120° C. for 15 hours. Reaction progress was monitored by TLC (TLC eluent: 10% MeOH in DCM). The reaction mixture was cooled and poured into crushed ice (5 g). The solid thus obtained was filtered, washed with water (25 mL) and dissolved in DCM. The DCM solution was then washed with water (100 mL), brine (50 mL) and dried over anhydrous $Na_2SO_4$, filtered, concentrated and purified by column chromatography using silica gel and DCM as eluting solvent to yield (R+S) 4-(2-oxo-4-phenyl-1-oxa-3-azaspiro[4.5]decan-3-yl)-N-(quinolin-8-yl)benzamide (90 mg, 11%) as a white solid. $^1$H NMR (400 MHz, DMSO-$d_6$) δ: 10.46 (s, 1H), 8.95 (dd, J=4.4, 1.6 Hz, 1H), 8.66 (d, J=6.4 Hz, 1H), 8.44 (dd, J=8.4, 1.6 Hz, 1H), 7.94 (d, J=8.0 Hz, 2H), 7.75-7.72 (m, 3H), 7.68-7.61 (m, 3H), 7.32-7.39 (m, 4H), 5.52 (s, 1H), 2.08-2.11 (m, 1H), 1.83-1.89 (m, 1H), 1.74-1.53 (m, 3H), 1.35-1.42 (m, 2H), 1.20-1.23 (m, 3H). m/z (ESI) 478.2 (M+H)$^+$.

Example 47

Synthesis of 1-((1S,4r)-4-((S)-5,5-dimethyl-2-oxo-4-phenyloxazolidin-3-yl)cyclohexyl)-2-oxo-2,3-dihydro-1H-benzo[d]imidazole-5-carbonitrile

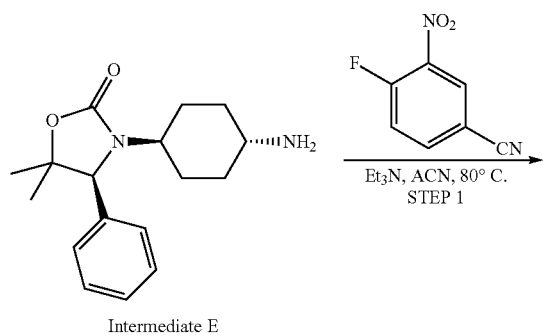

Intermediate E

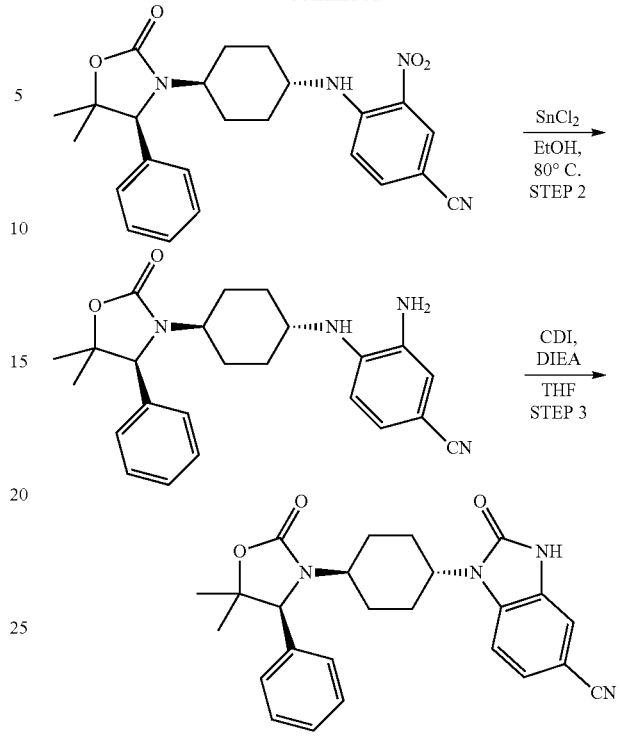

Example 47

Step 1

4-(((1r,4r)-4-(5,5-Dimethyl-2-oxo-4-phenyloxazolidin-3-yl)cyclohexyl)amino)-3-nitrobenzonitrile The intermediate E lot used in this Example existed as ~3:1 S:R mixture of phenyl chirality. To a vial charged with (S)-3-((1r,4S)-4-aminocyclohexyl)-5,5-dimethyl-4-phenyloxazolidin-2-one (0.150 g, 0.520 mmol) were added ACN (1.734 mL), TEA (0.145 mL, 1.040 mmol) and 4-fluoro-3-nitrobenzonitrile (commercially available from Alfa Aesar, Ward Hill, Mass.) (0.086 g, 0.520 mmol) respectively. The resulting orange solution was shaken at 80° C. overnight. The resulting mixture was dried under reduced pressure and the material thus obtained was purified with a 25 g SNAP column ramping EtOAc in heptane from 0-100% with 10% DCM throughout providing 4-(((1S,4r)-4-((S)-5,5-dimethyl-2-oxo-4-phenyloxazolidin-3-yl)cyclohexyl)amino)-3-nitrobenzonitrile (0.172 g, 0.396 mmol, 76% yield) as a yellow solid. $^1$H NMR (400 MHz, CDCl$_3$) δ=8.47 (d, J=2.0 Hz, 1H), 8.25 (d, J=7.4 Hz, 1H), 7.58-7.51 (m, 1H), 7.47-7.28 (m, 4H), 7.14 (br. s., 1H), 6.85 (d, J=9.2 Hz, 1H), 4.39 (s, 1H), 3.50-3.33 (m, 2H), 2.24-2.06 (m, 3H), 2.02-1.93 (m, 1H), 1.90-1.79 (m, 1H), 1.62-1.49 (m, 4H), 1.47-1.26 (m, 2H), 0.92 (s, 3H). m/z (ESI) 435.2 (M+H)$^+$.

Step 2

3-Amino-4-(((1r,4r)-4-(5,5-dimethyl-2-oxo-4-phenyloxazolidin-3-yl)cyclohexyl)amino)benzonitrile To a flask charged with 4-(((1S,4r)-4-((S)-5,5-dimethyl-2-oxo-4-phenyloxazolidin-3-yl)cyclohexyl)amino)-3-nitrobenzonitrile (0.172 g, 0.396 mmol) was added EtOH (2.64 mL) followed by tin (II) chloride (0.225 g, 1.188 mmol). The resulting yellow suspension was heated overnight at 80° C.

LC-MS of the resulting yellow solution indicated the product as the major species along with minor impurities which were close to the product with respect to retention time. The solution was cooled to room temperature and filtered through a Si-thiol column. The filtrate was dried under reduced pressure and purified with a 25 g SNAP column ramping DCM:MeOH (90:10) in DCM from 0-30%, then isocratic at 30% to provide the product along with minor impurities which had coeluted. The material thus obtained was used without further purification. 3-Amino-4-(((1S,4r)-4-((S)-5,5-dimethyl-2-oxo-4-phenyloxazolidin-3-yl)cyclohexyl)amino)benzonitrile (0.117 g, 0.289 mmol, 73.1% yield) was obtained as a yellow oil. m/z (ESI) 405.2 (M+H)$^+$.

Step 3

1-((1S,4r)-4-((S)-5,5-Dimethyl-2-oxo-4-phenyloxazolidin-3-yl)cyclohexyl)-2-oxo-2,3-dihydro-1H-benzo[d]imidazole-5-carbonitrile To a flask charged with 3-amino-4-(((1 S,4r)-4-((S)-5,5-dimethyl-2-oxo-4-phenyloxazolidin-3-yl)cyclohexyl) amino)benzonitrile (0.878 g, 2.171 mmol) were added THF (8.68 mL) and DIEA (1.327 mL, 7.60 mmol). The resulting solution was cooled in an ice water bath prior to the addition of CDI (1.232 g, 7.60 mmol). The resulting mixture was stirred for 3 hours and allowed to slowly warm (ice melt) providing a greenish suspension. LC-MS indicated complete conversion to product. The mixture was dried under reduced pressure and purified with a 40 g HP spherical silica column (15 m spherical, Interchim) ramping DCM:MeOH (90:10) in DCM from 0-30%, then isocratic at 30% yielding partial separation of clean product obtained as a white film as well as a darker eluting mixture primarily containing product. The dark mixture was purified with an SCX-2 column (5 g) washing with MeOH leading to elution of a yellow solution containing product. The dark material stuck on the column. After drying, the pale yellow solid was triturated with diethyl ether and the off-white solid thus obtained was combined with the clean material from the initial column. NMR revealed some very minor impurities in the aliphatic region. The solid was ground up with a spatula and triturated again with ether providing a white solid with some yellow filtrate indicating removal of the impurities, providing 1-((1S,4r)-4-((S)-5,5-dimethyl-2-oxo-4-phenyloxazolidin-3-yl)cyclohexyl)-2-oxo-2,3-dihydro-1H-benzo[d]imidazole-5-carbonitrile (790 mg, 85%). $^1$H NMR (500 MHz, DMSO-d$_6$) δ=7.53 (d, J=8.3 Hz, 1H), 7.49-7.34 (m, 4H), 7.29 (d, J=8.3 Hz, 3H), 4.65 (s, 1H), 4.12-4.04 (m, 1H), 3.70-3.61 (m, 1H), 2.27-2.07 (m, 2H), 2.02-1.85 (m, 2H), 1.73 (d, J=11.6 Hz, 1H), 1.68-1.54 (m, 2H), 1.48 (s, 3H), 1.36-1.25 (m, 1H), 0.82-0.77 (m, 3H). m/z (ESI) 431.1 (M+H)$^+$.

Example 48

Synthesis of (S)-3-((1s,4R)-4-(3,3-difluoro-2-oxoindolin-1-yl)cyclohexyl)-5,5-dimethyl-4-phenyloxazolidin-2-one

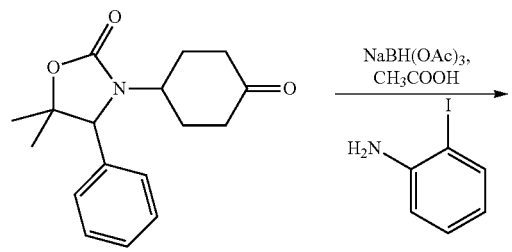

See Intermediate M synthesis

STEP 1

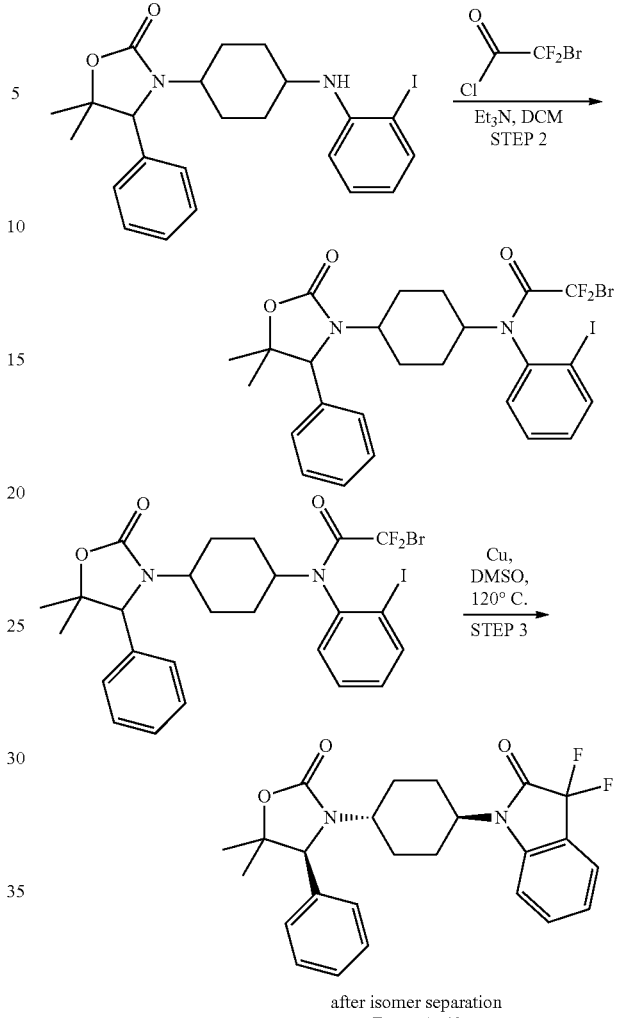

after isomer separation
Example 48

Step 1

(S)-3-(4-((2-Iodophenyl)amino)cyclohexyl)-5,5-dimethyl-4-phenyloxazolidin-2-one

The starting material (see Intermediate M synthesis) was a mixture of S:R stereoisomers (~3:1). To a vial charged with 2-iodoaniline (commercially available from Sigma-Aldrich, Milwaukee, Wis.) (0.100 g, 0.457 mmol) were added (S)-5,5-dimethyl-3-(4-oxocyclohexyl)-4-phenyloxazolidin-2-one (0.131 g, 0.457 mmol), DCE (1.826 mL) and AcOH (0.039 mL, 0.685 mmol). The mixture was stirred at room temperature for 15 minutes prior to the addition of sodium triacetoxyborohydride (0.213 g, 1.004 mmol). The pale yellow suspension was then stirred overnight at room temperature. Water was added to the mixture and the resulting mixture was transferred to a separatory funnel and extracted with DCM (2×). The combined organic layers were dried with Na$_2$SO$_4$, filtered, and dried under reduced pressure. The material thus obtained was purified with a 25 g SNAP column (Biotage) ramping EtOAc in heptane (10% DCM throughout, 0-50%) providing the desired product as a mixture of isomers according to LC-MS (2:1 cis:trans). m/z (ESI) 491.1 (M+H)$^+$.

Step 2

3-Amino-4-(((1r,4r)-4-(5,5-dimethyl-2-oxo-4-phenyloxazolidin-3-yl)cyclohexyl)amino)benzonitrile A flask charged with (S)-3-((1r,4S)-4-((2-iodophenyl)amino)cyclohexyl)-5,5-dimethyl-4-phenyloxazolidin-2-one (850 mg, 1.733 mmol) and containing a stir bar was dried under high vacuum and then placed under nitrogen. DCM (9370 μL) and TEA (483 μL, 3.47 mmol) were then added to the flask. The resulting pale yellow solution was cooled in an ice water bath prior to the dropwise addition of bromodifluoroacetyl chloride (commercially available from Matrix Scientific, Columbia, S.C.)(369 μL, 1.907 mmol). The resulting yellow solution was stirred for 1 hour at 0° C. and then at room temperature overnight. LC-MS indicated complete conversion to desired product. The mixture was dried under reduced pressure and purified with a 50 g SNAP column (Biotage) eluting with EtOAc in heptane from 0-100% with 5% DCM throughout providing 2-bromo-N-((1S,4r)-4-((S)-5,5-dimethyl-2-oxo-4-phenyloxazolidin-3-yl)cyclohexyl)-2,2-difluoro-N-(2-iodophenyl)acetamide (1243 mg, 1.920 mmol, 99% yield) as a mixture of isomers. m/z (ESI) 647.2 (M+H)+.

Step 3

(S)-3-((1s,4R)-4-(3,3-Difluoro-2-oxoindolin-1-yl)cyclohexyl)-5,5-dimethyl-4-phenyloxazolidin-2-one To a vial charged with 2-bromo-N-((1 S,4r)-4-((S)-5,5-dimethyl-2-oxo-4-phenyloxazolidin-3-yl)cyclohexyl)-2,2-difluoro-N-(2-iodophenyl)acetamide (0.95 g, 1.468 mmol) were added DMSO (7.34 mL) and copper (nanopowder) (0.026 mL, 3.67 mmol). The vial was sealed, and the mixture was heated at 120° C. overnight. LC-MS indicated conversion to desired product as the main species which was directly purified with a 40 g HP spherical silica column (15 μm) ramping DCM:MeOH (90:10) in DCM (0-20%), but the DMSO pushed everything through towards the solvent front, except the copper metal. The combined eluents were dried under reduced pressure and the material was repurified with Gilson RP-HPLC (50-90% ACN in H2O, 0.1% TFA modifier) which did not yield separation of isomers. The mixture (cis:trans (2:1) S:R (3:1)) was purified with chiral HPLC: ChiralPak IC (2×15 cm), 30% iPrOH (0.1% DEA)/CO2, 100 bar, 65 mL/min, 220 nm detection, inj. vol. 1.6 mL, 18 mg/mL, 1:1 DCM:MeOH. The desired product was the third eluted peak and was lyophilized from MeOH:H2O yielding (S)-3-((1 s,4R)-4-(3,3-difluoro-2-oxoindolin-1-yl)cyclohexyl)-5,5-dimethyl-4-phenyloxazolidin-2-one as a white solid (264 mg, 41%). Cis and trans isomers were identified by NMR spectroscopy (the two sets of equally wide tt at 3.95 and 3.62 are indicative of trans), the major of each being S based on the starting reagent. $^1$H NMR (400 MHz, DMSO-$d_6$) δ=7.67 (dd, J=1.1, 7.3 Hz, 1H), 7.59-7.51 (m, 1H), 7.51-7.46 (m, 1H), 7.46-7.39 (m, 2H), 7.39-7.33 (m, 1H), 7.33-7.13 (m, 3H), 4.64 (s, 1H), 3.95 (tt, J=3.6, 12.3 Hz, 1H), 3.61 (tt, J=3.6, 11.9 Hz, 1H), 2.23-2.01 (m, 2H), 2.01-1.83 (m, 2H), 1.78 (d, J=12.4 Hz, 1H), 1.68-1.55 (m, 2H), 1.47 (s, 3H), 1.37-1.25 (m, 1H), 0.79 (s, 3H). m/z (ESI) 441.2 (M+H)+.

Example 49

Synthesis of '3-(trans-4-((4S)-5,5-dimethyl-2-oxo-4-phenyl-1,3-oxazolidin-3-yl)cyclohexyl)[1,3]oxazolo[4,5-b]pyridin-2(3H)-one

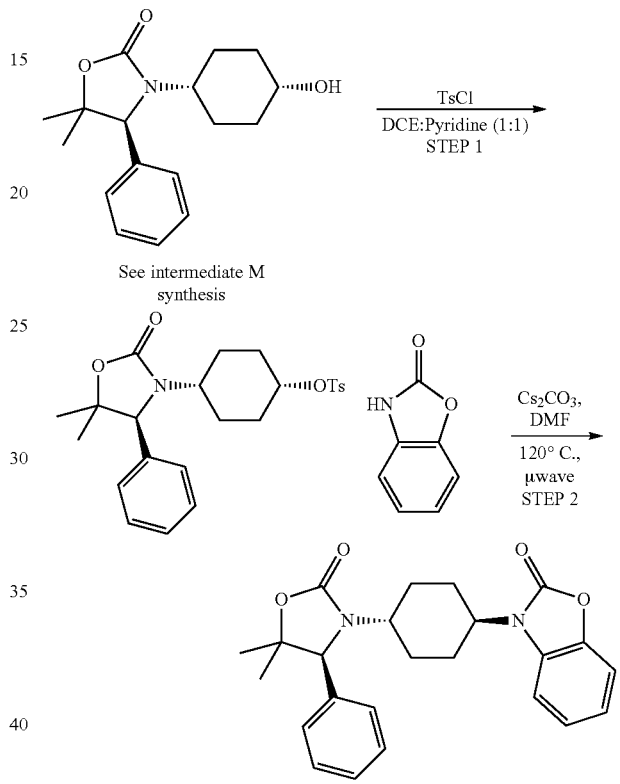

Example 49

Step 1

(1R,4s)-4-((S)-5,5-Dimethyl-2-oxo-4-phenyloxazolidin-3-yl)cyclohexyl 4-methylbenzenesulfonate To a vial charged with 3-((1s,4s)-4-hydroxycyclohexyl)-5,5-dimethyl-4-phenyloxazolidin-2-one (0.985 g, 3.40 mmol) were added DCE (6.81 mL), and pyridine (6.81 mL). The solution was cooled in an ice water bath prior to the addition of TsCl (0.681 g, 3.57 mmol). The resulting solution was allowed to slowly warm to room temperature (ice melt). After 3 hours of stirring, only minor conversion was observed according to LC-MS (~20%). Additional TsCl was added (4 eq) and stirring was continued overnight. The light brown solution was dried under reduced pressure, and the crude oil was purified with a 25 g spherical silica (15 m, Interchim) column ramping DCM:MeOH (90:10) in DCM (0-15%), then isocratic at 15% providing the title product (1.325 g, 2.99 mmol, 88% yield) as a white solid. m/z (ESI) 444.2 (M+H)+.

Step 2

'3-(trans-4-((4S)-5,5-Dimethyl-2-oxo-4-phenyl-1,3-oxazolidin-3-yl)cyclohexyl)[1,3]oxazolo[4,5-b]pyridin-2(3H)-one To a microwave vial charged with (1R,4s)-4-((S)-5,5-dimethyl-2-oxo-4-phenyloxazolidin-3-yl)cyclohexyl 4-methylbenzenesulfonate (0.250 g, 0.564 mmol) were added oxazolo[4,5-b]pyridin-2(3H)-one (commercially available from Sigma-Aldrich, Milwaukee, Wis.) (0.192 g, 1.409 mmol), cesium carbonate (0.184 g, 0.564 mmol) and DMF (2.255 mL) respectively. The vessel was sealed and irradiated at 120° C. for 30 minutes. LC-MS indicated primarily elimination product with trace product present. The mixture was purified with a 5 g SCX-2 column washing with MeOH, then 2M $NH_3$ in MeOH. The basic wash was dried under reduced pressure and purified with a 25 g spherical silica column (15 m, Interchim) ramping DCM:MeOH (90:10) in DCM from 0-30%, then isocratic at 30% leading to coelution of product with impurities. The material was purified using a Gilson RP-HPLC ramping ACN in $H_2O$ (10-90%, 0.1% TFA throughout) providing isolation of a small amount of product. The eluents were dried under reduced pressure and free-based with a 500 mg SCX-2 column washing with MeOH, then 2M $NH_3$ in MeOH. The basic wash was dried under reduced pressure and lyophilized from MeOH/$H_2O$ providing the title product as a white powder (1 mg, 2.454 mol, 0.435% yield). $^1$H NMR (500 MHz, DMSO-$d_6$) δ=7.87 (d, J=6.8 Hz, 1H), 7.49-7.16 (m, 6H), 6.88 (d, J=14.5 Hz, 1H), 4.68 (s, 1H), 4.57-4.46 (m, 1H), 3.61 (br. s., 1H), 2.11-1.89 (m, 5H), 1.83 (d, J=12.2 Hz, 1H), 1.68 (d, J=12.8 Hz, 1H), 1.48 (s, 3H), 1.38-1.25 (m, 1H), 0.85-0.78 (m, 3H). m/z (ESI) 408.2 $(M+H)^+$.

Example 50

Synthesis of (S)-5,5-dimethyl-3-((1r,4S)-4-(8-oxo-7H-purin-9(8H)-yl)cyclohexyl)-4-phenyloxazolidin-2-one

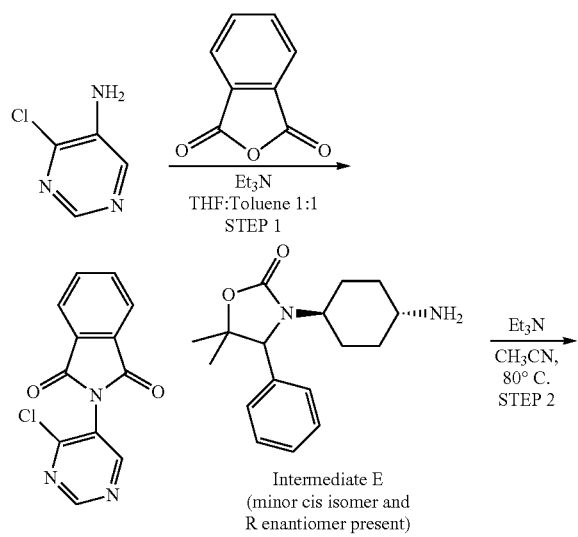

Intermediate E
(minor cis isomer and R enantiomer present)

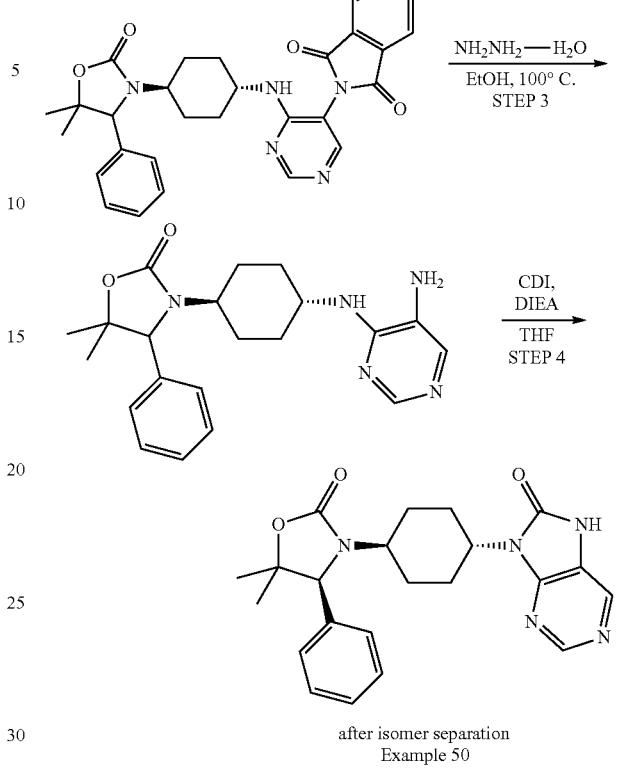

after isomer separation
Example 50

Step 1

2-(4-Chloropyrimidin-5-yl)isoindoline-1,3-dione

To a vial charged with 4-chloropyrimidin-5-amine (commercially available from Frontier Scientific, Inc., Logan Utah) (0.500 g, 3.86 mmol) were added THF (6.43 mL), toluene (6.43 mL), TEA (1.345 mL, 9.65 mmol) and phthalic anhydride (1.310 mL, 13.51 mmol). The mixture was heated to 100° C. for 72 hours. The mixture was then dried under reduced pressure and purified with a 50 g SNAP column (Biotage) ramping EtOAc in heptane from 0-45%, then isocratic at 45% to elute 2-(4-chloropyrimidin-5-yl)isoindoline-1,3-dione (0.773 g, 2.98 mmol, 77% yield) as a yellow solid. $^1$H NMR (400 MHz, DMSO-$d_6$) δ=9.23 (d, J=0.4 Hz, 1H), 9.09 (d, J=0.4 Hz, 1H), 8.12-8.05 (m, 2H), 8.04-7.96 (m, 2H). m/z (ESI) 260.1 $(M+H)^+$.

Step 2

2-(4-(((1r,4r)-4-(5,5-Dimethyl-2-oxo-4-phenyloxazolidin-3-yl)cyclohexyl)amino)pyrimidin-5-yl)isoindoline-1,3-dione To a vial charged with 2-(4-chloropyrimidin-5-yl)isoindoline-1,3-dione (0.327 g, 1.259 mmol) were added ACN (4.20 mL), TEA (0.369 mL, 2.64 mmol) and 3-((1r,4r)-4-aminocyclohexyl)-5,5-dimethyl-4-phenyloxazolidin-2-one 2,2,2-trifluoroacetate (0.507 g, 1.259 mmol) (Intermediate E which was a mixture of S:R enantiomers~3:2) respectively. The vessel was sealed and shaken overnight at 80° C. providing a dark solution containing the title compound as the primary species according to LC-MS. The solution was dried under reduced pressure and purified with a 40 g HP spherical silica column (Interchim) ramping EtOAc in heptane (0-100%, 5% DCM throughout) leading to isolation of 2-(4-(((1 r,4r)-4-(5,5-dimethyl-2-oxo-4-phenyloxazolidin-3-yl)cyclohexyl)amino)pyrimidin-5-yl)isoindoline-1,3-dione (0.435 g, 0.850 mmol, 67.5% yield) as a mixture of trans:cis isomers with minor impurities and as a light yellow foam. m/z (ESI) 512.3 (M+H)+.

Step 3

3-((1r,4r)-4-((5-Aminopyrimidin-4-yl)amino)cyclohexyl)-5,5-dimethyl-4-phenyloxazolidin-2-one To a vial charged with 2-(4-(((1 r,4r)-4-(5,5-dimethyl-2-oxo-4-phenyloxazolidin-3-yl)cyclohexyl)amino)pyrimidin-5-yl)isoindoline-1,3-dione (0.435 g, 0.850 mmol) were added EtOH (3.40 mL) and hydrazine hydrate (0.132 mL, 4.25 mmol). The vial was sealed and heated at 100° C. for 2 hours yielding a white suspension. LC-MS indicated complete conversion to clean product. The solid was collected via vacuum filtration and washed with DCM/MeOH. The precipitate was primarily 2,3-dihydrophthalazine-1,4-dione. The filtrate contained product along with phthalazine dione. The filtrate was purified with a 5 g SCX-2 column washing with MeOH and then with 2 M $NH_3$ in MeOH. The basic wash was dried under reduced pressure providing 2-(4-(((1r,4r)-4-(5,5-dimethyl-2-oxo-4-phenyloxazolidin-3-yl)cyclohexyl)amino)pyrimidin-5-yl)isoindoline-1,3-dione (0.435 g, 0.850 mmol, 72.8%) as a white foam. m/z (ESI) 382.3 (M+H)+.

Step 4

(S)-5,5-Dimethyl-3-((1r,4S)-4-(8-oxo-7H-purin-9(8H)-yl)cyclohexyl)-4-phenyloxazolidin-2-one To a vial charged with 3-((1r,4r)-4-((5-aminopyrimidin-4-yl)amino)cyclohexyl)-5,5-dimethyl-4-phenyloxazolidin-2-one (0.330 g, 0.865 mmol) were added THF (3.46 mL), DIEA (0.529 mL, 3.03 mmol) and CDI (0.491 g, 3.03 mmol) respectively. The mixture was shaken at room temperature for 2 hours providing a yellow solution which primarily contained product according to LC-MS. The material was loaded directly onto a load column and purified with a 25 g HP spherical silica gel column (Interchim) ramping DCM:MeOH:$NH_4OH$ (90:10:1) in DCM from 0-35%, then isocratic at 35% yielding product as a white foam after drying. The $^1H$ NMR spectrum was consistent with a product as a mixture of isomers. The material was repurified twice more as follows: Column: Chiralpak OD-H (2×15 cm), gradient: 20% MeOH (0.2% DEA)/$CO_2$, 100 bar, flow: 65 mL/min, detection: 220 nm, injection volume: 0.75 mL, 12 mg/mL, dissolution: 1:1 DCM:MeOH. The desired enantiomer (major product) was the first eluting material. Second purification: Column: Chiralpak AD-H, 2×15 cm, Mobile Phase: 75% $CO_2$/25% MeOH w/0.2% DEA, Flow rate: 80 mL/min, detection: 279 nm, injection volume: 0.5 mL, dissolution: 5 mL 1:1 DCM:MeOH. The product was lyophilized from MeOH/$H_2O$ yielding (S)-5,5-dimethyl-3-((1r,4S)-4-(8-oxo-7H-purin-9(8H)-yl)cyclohexyl)-4-phenyloxazolidin-2-one (0.069 g, 0.169 mmol, 19.58% yield) as a white powder. $^1H$ NMR (400 MHz, DMSO-$d_6$) δ=11.20 (br. s., 1H), 8.56-8.48 (m, 1H), 8.21 (s, 1H), 7.51-7.41 (m, 2H), 7.40-7.10 (m, 3H), 4.68 (s, 1H), 4.07 (tt, J=3.6, 12.3 Hz, 1H), 3.54-3.43 (m, 1H), 2.41-2.17 (m, 2H), 2.02-1.86 (m, 2H), 1.79 (d, J=12.4 Hz, 1H), 1.64 (d, J=10.6 Hz, 2H), 1.48 (s, 3H), 1.35-1.17 (m, 1H), 0.81 (s, 3H). m/z (ESI) 408.0 (M+H)+.

Example 51

Synthesis of 1-((1S,4r)-4-((S)-5,5-dimethyl-2-oxo-4-phenyloxazolidin-3-yl)cyclohexyl)-2-oxo-2,3-dihydro-1H-benzo[d]imidazole-4-carbonitrile

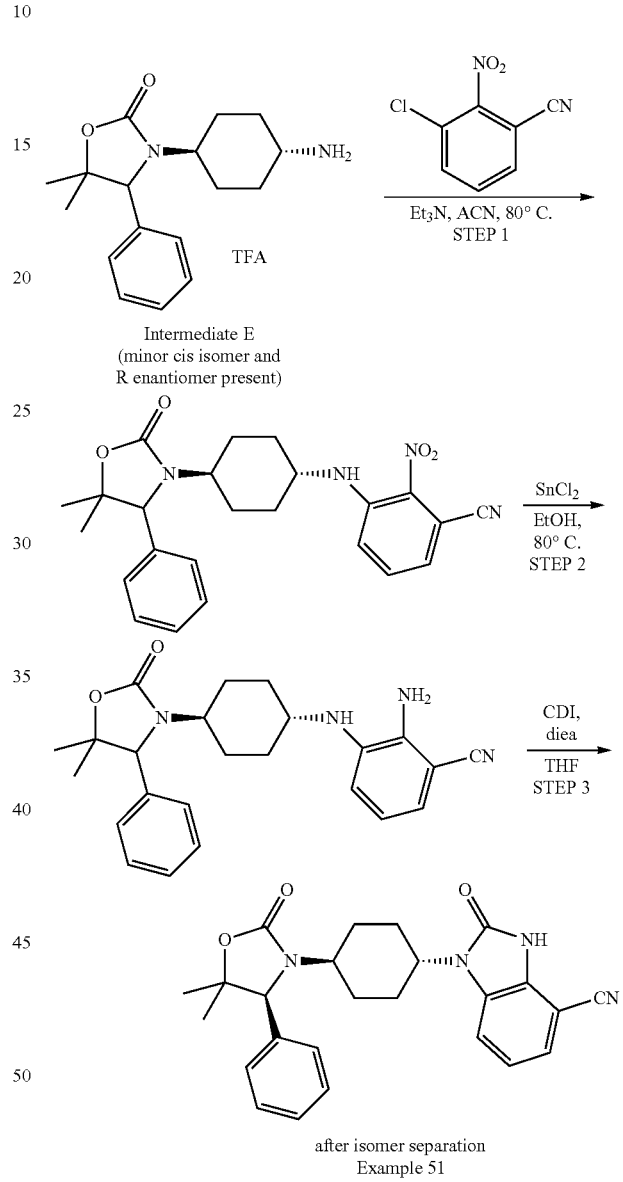

Step 1

3-(((1r,4r)-4-(5,5-Dimethyl-2-oxo-4-phenyloxazolidin-3-yl)cyclohexyl)amino)-2-nitrobenzonitrile To a vial charged with 3-((1r,4r)-4-aminocyclohexyl)-5,5-dimethyl-4-phenyloxazolidin-2-one 2,2,2-trifluoroacetate (0.300 g, 0.746 mmol) were added ACN (2.485 mL), DIEA (0.260 mL, 1.491 mmol) and 3-chloro-2-nitrobenzonitrile (commercially available from Biogene Organics, Inc., Spring Tex.) (0.136 g, 0.746 mmol) respectively. The vial was sealed and heated at 80° C. overnight providing an orange/brown solution and about 50% conversion according to LC-MS. Additional DIEA (0.260 mL, 1.491 mmol) was added and heating and shaking continued. After 1 additional hour at 80° C. no additional conversion was observed and the presence of starting nitrobenzene was confirmed by LC-MS. The mixture was then heated at 110° C. overnight leading to conversion to product along with two major impurities which had similar retention times to that of the product. The mixture was dried under reduced pressure and purified with a 25 g column ramping DCM:MeOH:NH4OH (90:10:1) in DCM from 0-15%, then 15% isocratic which yielded some separation of impurities, but not complete separation. The material (~50% purity) was used in the next step without further purification. 3-(((1r,4r)-4-(5,5-Dimethyl-2-oxo-4-phenyloxazolidin-3-yl) cyclohexyl)amino)-2-nitrobenzonitrile (0.180 g, 0.414 mmol, 55.6% yield) was isolated as an orange/brown solid. m/z (ESI) 435.0 (M+H)+.

Step 2

2-Amino-3-(((1r,4r)-4-(5,5-dimethyl-2-oxo-4-phenyloxazolidin-3-yl)cyclohexyl)amino)benzonitrile To a flask charged with 3-(((1S,4r)-4-((S)-5,5-dimethyl-2-oxo-4-phenyloxazolidin-3-yl)cyclohexyl)amino)-2-nitrobenzonitrile (0.180 g, 0.414 mmol) was added EtOH (2.76 mL) followed by tin (II) chloride (0.236 g, 1.243 mmol). The resulting yellow suspension was heated at 80° C. for 2 hours providing an orange brown solution. LC-MS indicated the product as the major species. The solution was cooled to room temperature and filtered through a Si-thiol column. The filtrate was dried under reduced pressure and purified with a 25 g SNAP column ramping DCM:MeOH (90:10) in DCM from 0-50%, to yield product along with the impurities which coeluted (most impurities present from crude). The material was further purified with a 2 g SCX-2 column washing with MeOH, then 2 M NH3 in MeOH to yield 2-amino-3-(((1 S,4r)-4-((S)-5,5-dimethyl-2-oxo-4-phenyloxazolidin-3-yl) cyclohexyl)amino)benzonitrile (0.124 g, 0.307 mmol, 74.0% yield) as a brown oil which had been enriched in purity relative to after MPLC (~75% pure). The material was used in the next step without further purification. m/z (ESI) 405.0 (M+H)+.

Step 3

1-((1S,4r)-4-((S)-5,5-Dimethyl-2-oxo-4-phenyloxazolidin-3-yl)cyclohexyl)-2-oxo-2,3-dihydro-1H-benzo[d]imidazole-4-carbonitrile To a vial charged with 2-amino-3-(((1 S,4r)-4-((S)-5,5-dimethyl-2-oxo-4-phenyloxazolidin-3-yl)cyclohexyl) amino)benzonitrile (0.124 g, 0.307 mmol) were added THF (1.226 mL), DIEA (0.187 mL, 1.073 mmol) and CDI (0.174 g, 1.073 mmol) respectively. The dark mixture was stirred for 1 hour at room temperature yielding no conversion according to LC-MS. The mixture was then heated to 60° C. After 2 hours LC-MS indicated about 30% conversion. Heating and shaking at 60° C. was continued overnight. LC-MS indicated that the product was the main species. The dark solution was dried under reduced pressure and purified with RP-HPLC ramping ACN in H2O (10-90%, 0.1% TFA) affording incomplete purification. The product containing eluents was dried under reduced pressure and repurified: Separation No. 1-Chiralpak OJ-H, 2×25 cm, 80% CO2/20% MeOH w/0.2% DEA, 80 mL/min, 254 nm, Dissolution: 20 mL 3:1 MeOH: DCM, Sample processed with 0.25 mL injections and 2.75 minute cycle time. Separation No. 2-Chiralpak Iowa, 2×25 cm, 75% CO2/25% MeOH w/0.2% DEA, 80 mL/min, 215 nm, Dissolution: 10 mL 1:1 MeOH:DCM, Sample processed with 0.15 mL injections and 5.25 minute cycle time. The desired major enantiomer eluted first. The resulting material was passed through a 2 g SCX-2 column and the initial wash was dried under reduced pressure and lyophilized from MeOH/H2O providing 1-((1S,4r)-4-((S)-5,5-dimethyl-2-oxo-4-phenyloxazolidin-3-yl)cyclohexyl)-2-oxo-2,3-dihydro-1H-benzo[d]imidazole-4-carbonitrile (17 mg, 0.039 mmol, 12.88% yield) as a white solid. 1H NMR (500 MHz, DMSO-d6) d=11.90 (s, 1H), 7.66 (d, J=7.8 Hz, 1H), 7.46-7.39 (m, 2H), 7.39-7.15 (m, 4H), 7.07 (t, J=8.0 Hz, 1H), 4.65 (s, 1H), 4.11-4.02 (m, 1H), 3.66 (d, J=11.8 Hz, 1H), 2.26-2.06 (m, 2H), 2.03-1.84 (m, 2H), 1.80-1.69 (m, 1H), 1.67-1.55 (m, 2H), 1.48 (s, 3H), 1.30 (dq, J=3.7, 12.8 Hz, 1H), 0.80 (s, 3H). m/z (ESI) 431.1 (M+H)+.

Example 52

Synthesis of (S)-5,5-dimethyl-3-((1r,4S)-4-(2-oxo-6-(trifluoromethyl)-2,3-dihydro-1H-imidazo[4,5-c] pyridin-1-yl)cyclohexyl)-4-phenyloxazolidin-2-one

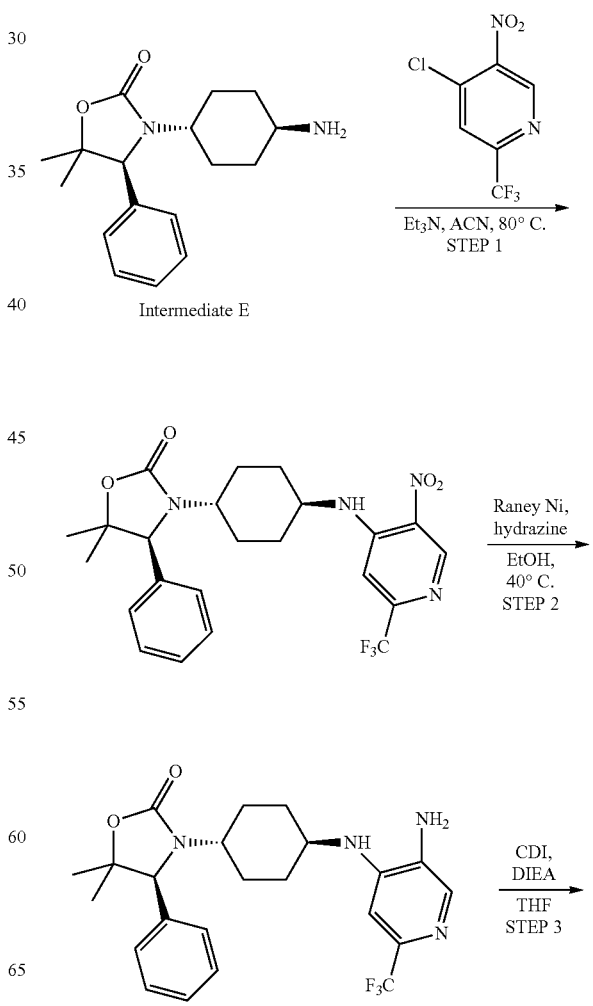

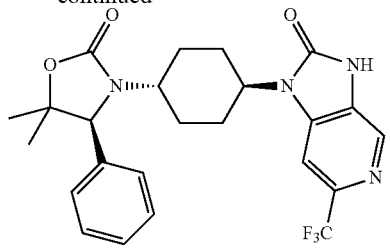

Example 52

Step 1

(S)-5,5-Dimethyl-3-((1r,4S)-4-((5-nitro-2-(trifluoromethyl)pyridin-4-yl)amino)cyclohexyl)-4-phenyloxazolidin-2-one To a vial charged with (S)-3-((1r,4S)-4-aminocyclohexyl)-5,5-dimethyl-4-phenyloxazolidin-2-one (0.094 g, 0.326 mmol) were added ACN (1.087 mL), DIEA (0.114 mL, 0.652 mmol) and 4-chloro-5-nitro-2-(trifluoromethyl)pyridine (commercially available from Abby Pharmatech, LLC, Newark, N.J.) (0.078 g, 0.342 mmol) respectively. The vial was sealed and heated at 80° C. for 2 hours providing a brown solution with product as the main species according to LC-MS. The solution was dried under reduced pressure and purified with a 25 g SNAP column (Biotage) ramping DCM:MeOH (90:10) in DCM (0-25%, then isocratic at 25%, 215 nm detection) providing (S)-5,5-dimethyl-3-((1r,4S)-4-((5-nitro-2-(trifluoromethyl)pyridin-4-yl)amino)cyclohexyl)-4-phenyloxazolidin-2-one (0.150 g, 0.314 mmol, 96% yield) as a yellow solid. m/z (ESI) 479.0 (M+H)$^+$.

Step 2

(S)-3-((1r,4S)-4-((5-Amino-2-(trifluoromethyl)pyridin-4-yl)amino)cyclohexyl)-5,5-dimethyl-4-phenyloxazolidin-2-one To a flask charged with (S)-5,5-dimethyl-3-((1r,4S)-4-((5-nitro-2-(trifluoromethyl)pyridin-4-yl)amino)cyclohexyl)-4-phenyloxazolidin-2-one (0.150 g, 0.314 mmol) was added EtOH (6.27 mL). Raney 3202 nickel (slurry in water) (0.345 mL, 52.4 mmol) was then added using a pipette. The flask was sealed, placed under nitrogen, and heated at 40° C. To the resulting yellow solution was added hydrazine hydrate solution (0.146 mL, 4.70 mmol) dropwise. The resulting mixture was stirred for 90 minutes at 40° C. LC-MS indicated complete conversion to the desired product. The mixture was filtered through Celite® brand filter aid which was washed with MeOH. The filtrate was dried under reduced pressure and then purified using a 5 g SCX-2 column washing with MeOH, then 2 M NH$_3$ in MeOH. The basic mixture was dried under reduced pressure providing (S)-3-((1r,4S)-4-((5-amino-2-(trifluoromethyl)pyridin-4-yl)amino)cyclohexyl)-5,5-dimethyl-4-phenyloxazolidin-2-one (0.128 g, 0.285 mmol, 91% yield) was a tan sticky solid. $^1$H NMR (400 MHz, CDCl$_3$) δ=7.92 (s, 1H), 7.48-7.29 (m, 4H), 7.24-7.08 (m, 1H), 6.72 (s, 1H), 4.39 (s, 1H), 4.03 (d, J=7.4 Hz, 1H), 3.72-3.58 (m, 1H), 3.33-3.15 (m, 3H), 2.25-2.16 (m, 1H), 2.09-1.87 (m, 3H), 1.82-1.73 (m, 1H), 1.55 (s, 3H), 1.38-1.16 (m, 3H), 0.93 (s, 3H). m/z (ESI) 449.0 (M+H)$^+$.

Step 3

(S)-5,5-Dimethyl-3-((1r,4S)-4-(2-oxo-6-(trifluoromethyl)-2,3-dihydro-1H-imidazo[4,5-c]pyridin-1-yl)cyclohexyl)-4-phenyloxazolidin-2-one To a flask charged with (S)-3-(4-((5-amino-2-(trifluoromethyl)pyridin-4-yl)amino)cyclohexyl)-5,5-dimethyl-4-phenyloxazolidin-2-one (0.120 g, 0.268 mmol) were added THF (1.070 mL), DIEA (0.164 mL, 0.936 mmol) and CDI (0.152 g, 0.936 mmol) respectively. The mixture was shaken at room temperature for 3 hours. LC-MS indicated complete reaction. The mixture was dried under reduced pressure and purified with a 25 g HP spherical silica column (Interchim) ramping DCM:MeOH (90:10) in DCM from 0-20%, then isocratic at 20% to provide product as an off white filmy solid which was lyophilized from MeOH/H$_2$O to yield (S)-5,5-dimethyl-3-((1 s,4R)-4-(2-oxo-6-(trifluoromethyl)-2,3-dihydro-1H-imidazo[4,5-c]pyridin-1-yl)cyclohexyl)-4-phenyloxazolidin-2-one (0.111 g, 0.234 mmol, 87% yield) as an off-white solid. $^1$H NMR (400 MHz, DMSO-d$_6$) δ=11.57 (br. s., 1H), 8.28 (s, 1H), 7.93 (s, 1H), 7.53-7.11 (m, 6H), 4.65 (s, 1H), 4.19-4.09 (m, 1H), 3.76-3.65 (m, 1H), 2.35-2.09 (m, 2H), 2.03-1.83 (m, 2H), 1.75 (d, J=11.8 Hz, 1H), 1.67-1.55 (m, 2H), 1.48 (s, 3H), 1.38-1.25 (m, 1H), 0.80 (s, 3H). m/z (ESI) 475.0 (M+H)$^+$.

Examples 53 and 54

Synthesis of (S)-3-((1r,4S)-4-(6-chloro-2-oxo-2,3-dihydro-1H-imidazo[4,5-c]pyridin-1-yl)cyclohexyl)-5,5-dimethyl-4-phenyloxazolidin-2-one and 1-((1S,4r)-4-((S)-5,5-dimethyl-2-oxo-4-phenyloxazolidin-3-yl)cyclohexyl)-2-oxo-2,3-dihydro-1H-imidazo[4,5-c]pyridine-6-carbonitrile

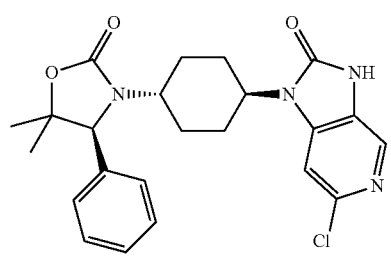

Example 53

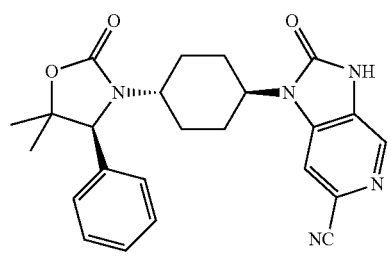

Example 54

187

-continued

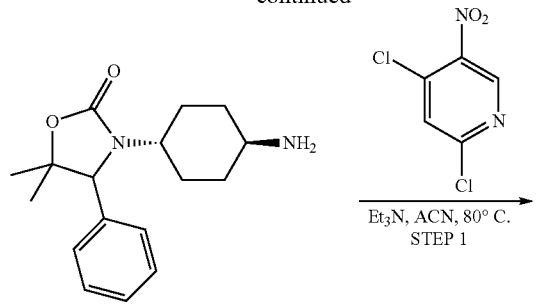

Intermediate E
(minor cis isomer and R enantiomer present)

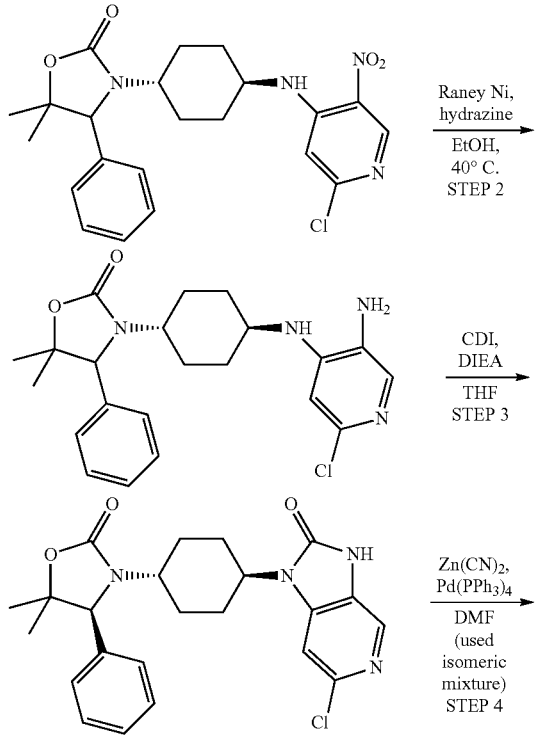

after isomer separation

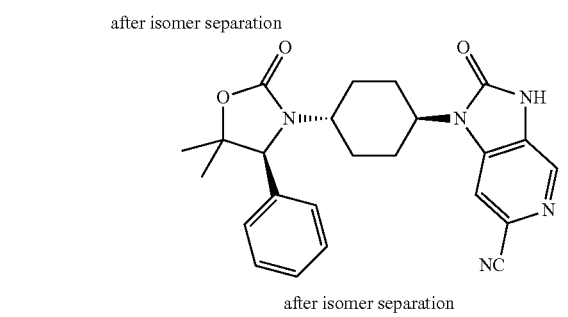

after isomer separation

Step 1

(S)-3-((1r,4S)-4-((2-Chloro-5-nitropyridin-4-yl) amino)cyclohexyl)-5,5-dimethyl-4-phenyloxazolidin-2-one To a vial charged with 3-((1r,4r)-4-aminocyclohexyl)-5,5-dimethyl-4-phenyloxazolidin-2-one 2,2,2-trifluoroacetate (0.35 g, 0.870 mmol) (amine contained minor amounts of cis cyclohexyl impurity and was partially racemized at phenyl) were added ACN (2.90 mL), TEA (0.364 mL, 2.61 mmol) and 2,4-dichloro-5-nitropyridine (0.201 g, 1.044 mmol) respectively. The resulting orange solution was shaken at 80° C. overnight. The mixture was dried under reduced pressure and purified with a 25 g SNAP column ramping DCM:MeOH (90:10) in DCM from 0-100% (215 nm detection) leading to the isolation of 3-((1r,4r)-4-((2-chloro-5-nitropyridin-4-yl) amino)cyclohexyl)-5,5-dimethyl-4-phenyloxazolidin-2-one (0.365 g, 0.820 mmol, 94% yield) as a yellow solid. m/z (ESI) 445.0 (M+H)$^+$.

Step 2

2: (S)-3-((1r,4S)-4-((5-Amino-2-chloropyridin-4-yl) amino)cyclohexyl)-5,5-dimethyl-4-phenyloxazolidin-2-one To a flask charged with (S)-3-((1r,4S)-4-((2-chloro-5-nitropyridin-4-yl)amino)cyclohexyl)-5,5-dimethyl-4-phenyloxazolidin-2-one (0.350 g, 0.787 mmol) was added EtOH (15.73 mL). Raney 3202 nickel (slurry in water) (0.866 mL, 131 mmol) was added using pipette. The flask was sealed, placed under nitrogen, and heated at 40° C. To the resulting yellow solution was added hydrazine hydrate solution (0.367 mL, 11.80 mmol) dropwise. The resulting mixture was stirred for 3 hours at 40° C. LC-MS indicated all starting material with no conversion. An additional aliquot of Raney 3202 nickel (slurry in water) (0.866 mL, 131 mmol) and hydrazine hydrate solution (0.367 mL, 11.80 mmol) were added, and the mixture was heated at 60° C. under nitrogen. Within 10 minutes, the yellow suspension had become a colorless heterogenous mixture. LC-MS indicated complete conversion to the desired product. The resulting mixture was filtered through Celite® brand filter aid which was washed with MeOH. The filtrate was dried under reduced pressure and then purified using a 5 g SCX-2 column washing with MeOH, then 2 M NH$_3$ in MeOH. The basic wash was dried under reduced pressure providing a brown oil which solidified after being pumped on under high vacuum overnight to yield (S)-3-((1r,4S)-4-((5-amino-2-chloropyridin-4-yl)amino)cyclohexyl)-5,5-dimethyl-4-phenyloxazolidin-2-one (0.306 g, 0.737 mmol, 94% yield) as a light brown solid. m/z (ESI) 415.0 (M+H)$^+$.

Step 3

(S)-3-((1r,4S)-4-(6-Chloro-2-oxo-2,3-dihydro-1H-imidazo[4,5-c]pyridin-1-yl)cyclohexyl)-5,5-dimethyl-4-phenyloxazolidin-2-one To a flask charged with 3-((1r,4r)-4-((5-amino-2-chloropyridin-4-yl)amino)cyclohexyl)-5,5-dimethyl-4-phenyloxazolidin-2-one (0.300 g, 0.723 mmol) were added THF (2.89 mL), DIEA (0.442 mL, 2.53 mmol) and CDI (0.410 g, 2.53 mmol) respectively. The resulting mixture was stirred at room temperature for 1 hour providing a brown solution with product as the major species and consumption of starting material. The mixture was dried under reduced pressure and purified with a 25 g column ramping DCM:MeOH (90:10) in DCM from 0-50% leading to isolation of product as a mixture of isomers. Purification 1: Column: Chiralcel OD-H, 2×25 cm Mobile Phase: 35% MeOH w/0.2% diethylamine/65% CO$_2$, Flowrate: 80 mL/min, Sample dissolved at 14 mg/mL in 1:1 DCM/MeOH, processed with 0.5 mL injections. This purification generated 91 mg of major peak at ~90%. Purification 2: Column: Chiralpak AS-H, 2×15 cm, Mobile Phase: 25% MeOH w/0.2% diethylamine/75% CO$_2$, Flowrate: 80 mL/min, Sample dissolved at 11 mg/mL in 1:1 DCM/MeOH, processed with 0.2 mL injections. This purification generated 65 mg of major peak at >99% de and achiral purity. The $^1$H NMR revealed minor impurities. The material was repurified with a 2 g SCX-2 column washing with MeOH, then 2 M NH$_3$ in MeOH. The basic wash was dried under reduced pressure and lyophilized from MeOH/H$_2$O to provide Example 53 ((S)-3-((1r,4S)-4-(6-chloro-2-oxo-2,3-dihydro-1H-imidazo[4,5-c]pyridin-1-yl)cyclohexyl)-5,5-dimethyl-4-phenyloxazolidin-2-one) (49 mg, 15%) as a white powder. $^1$H NMR (400 MHz, DMSO-d$_6$) δ=7.91 (s, 1H), 7.61 (s, 1H), 7.51-6.97 (m, 5H), 4.64 (s, 1H), 4.12-3.96 (m, 1H), 3.81-3.65 (m, 1H), 2.27-2.03 (m, 2H), 2.03-1.82 (m, 1H), 1.71 (d, J=12.0 Hz, 1H), 1.67-1.51 (m, 2H), 1.48 (s, 3H), 1.35-1.18 (m, 1H), 1.01 (dt, J=3.0, 7.1 Hz, 1H), 0.79 (s, 3H). m/z (ESI) 441.0 (M+H)$^+$.

Step 4

1-((1S,4r)-4-((S)-5,5-Dimethyl-2-oxo-4-phenyloxazolidin-3-yl)cyclohexyl)-2-oxo-2,3-dihydro-1H-imidazo[4,5-c]pyridine-6-carbonitrile To a vial charged with 3-((1r,4r)-4-(6-chloro-2-oxo-2,3-dihydro-1H-imidazo[4,5-c]pyridin-1-yl)cyclohexyl)-5,5-dimethyl-4-phenyloxazolidin-2-one (0.128 g, 0.290 mmol) were added zinc cyanide (0.018 mL, 0.290 mmol) and DMF (1.161 mL). The resulting mixture was purged with argon prior to the addition of Pd(PPh$_3$)$_4$ (0.034 g, 0.029 mmol). The vessel was then sealed and heated at 120° C. After 3 hours, LC-MS indicated ~40% conversion to product with starting material present as well. Additional Pd(PPh$_3$)$_4$ (0.034 g, 0.029 mmol) was added, and the mixture was purged with nitrogen. The vessel was then sealed and heated at 120° C. overnight. The resulting mixture was diluted with MeOH (~1 mL), filtered through an HPLC filtered and purified by Gilson RP-HPLC ramping ACN in H$_2$O (25-75%, 0.1% TFA throughout). The product had partially coeluted with starting material, but was separated from the other impurities. The product eluents were dried under reduced pressure, then purified with a 15 m spherical silica column (Interchim) ramping DCM:MeOH (90:10) in DCM (0-50%). Product (white solid, 34 mg), a mixture of isomers, was purified as follows: Purification 1:Column: Chiralcel OD-H, 2×25 cm, Mobile Phase: 35% MeOH w/0.2% diethylamine/65% CO$_2$, Flowrate: 80 mL/min, Sample dissolved at 9 mg/mL in 1:1 DCM/MeOH, processed with 0.25 mL injections. This purification generated 19 mg of major peak at ~80%. Purification 2: Column: Chiralpak AS-H, 2×15 cm, Mobile Phase: 25% MeOH w/0.2% diethylamine/75% CO$_2$, Flowrate: 80 mL/min, Sample dissolved at 4 mg/mL in 1:1 DCM/MeOH, processed with 0.25 mL injections. This purification generated 8.5 mg of major peak at >99% de and achiral purity. The material was re-purified with a 2 g SCX-2 column washing with MeOH, then 2 M NH$_3$ in MeOH. The basic wash was dried under reduced pressure and lyophilized from MeOH/H$_2$O to provide Example 54 (1-((1S,4r)-4-((S)-5,5-dimethyl-2-oxo-4-phenyloxazolidin-3-yl)cyclohexyl)-2-oxo-2,3-dihydro-1H-imidazo[4,5-c]pyridine-6-carbonitrile) (8 mg, 0.019 mmol, 6.39% yield) as a light yellow powder. $^1$H NMR (500 MHz, DMSO-d$_6$) δ=8.28 (s, 1H), 8.24 (s, 1H), 7.48-7.16 (m, 5H), 4.65 (s, 1H), 4.13-4.03 (m, 1H), 3.80-3.70 (m, 1H), 2.27-2.08 (m, 2H), 2.01-1.85 (m, 2H), 1.73 (d, J=9.5 Hz, 1H), 1.67-1.54 (m, 2H), 1.48 (s, 3H), 1.35-1.21 (m, 1H), 0.80 (s, 3H). m/z (ESI) 432.0 (M+H)$^+$.

Example 55

Synthesis of (S)-4-(4-fluorophenyl)-5,5-dimethyl-3-((1 r,4S)-4-(2-oxo-2,3-dihydro-1H-imidazo[4,5-c]pyridin-1-yl)cyclohexyl)oxazolidin-2-one

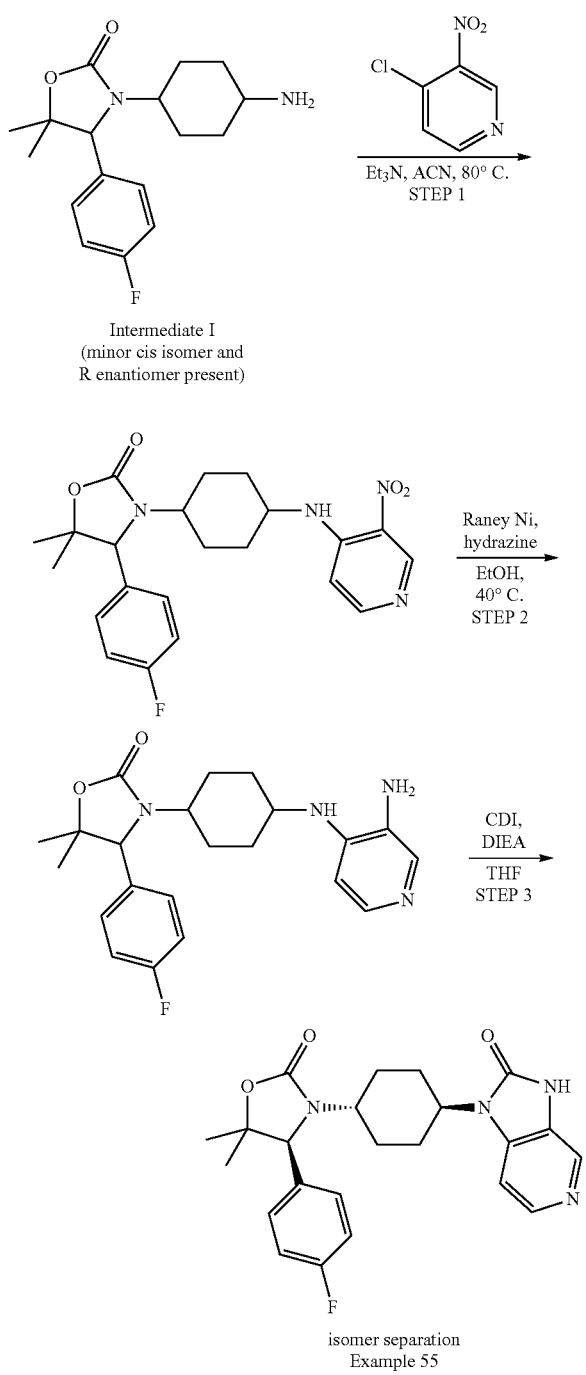

Step 1

(S)-4-(4-Fluorophenyl)-5,5-dimethyl-3-(4-((3-nitro-pyridin-4-yl)amino)cyclohexyl)oxazolidin-2-one To a vial charged with (S)-3-(4-aminocyclohexyl)-4-(4-fluorophenyl)-5,5-dimethyloxazolidin-2-one (0.320 g, 1.044 mmol) were added ACN (3.48 mL), DIEA (0.365 mL, 2.089 mmol) and 4-chloro-3-nitropyridine (commercially available from Sigma-Aldrich, Milwaukee, Wis.) (0.166 g, 1.044 mmol) respectively. The vial was sealed and heated at 80° C. for 2 hours leading to ~90% conversion to the desired product with starting amine present. Additional chloropyridine (0.2 eq) and DIEA (0.2 eq) were added, and the mixture was heated at 80° C. for an additional 15 hours. The dark mixture was dried under reduced pressure and purified with a 25 g HP spherical silica column ramping DCM:MeOH (90:10) in DCM from 0-50%, then isocratic at 50% (detection at 215 nm) leading to isolation of (S)-4-(4-fluorophenyl)-5,5-dimethyl-3-(4-((3-nitropyridin-4-yl)amino)cyclohexyl)oxazolidin-2-one (0.286 g, 0.668 mmol, 63.9% yield) as an orange/brown oil and as a mixture of cis/trans isomers. m/z (ESI) 429.0 (M+H)$^+$.

Step 2

(S)-3-(4-((3-Aminopyridin-4-yl)amino)cyclohexyl)-4-(4-fluorophenyl)-5,5-dimethyloxazolidin-2-one To a flask charged with (S)-4-(4-fluorophenyl)-5,5-dimethyl-3-(4-((3-nitropyridin-4-yl)amino)cyclohexyl)oxazolidin-2-one (0.285 g, 0.665 mmol) was added EtOH (13.30 mL). Raney 3202 nickel (slurry in water) (0.733 mL, 111 mmol) was then added using a pipette. The flask was sealed, placed under nitrogen, and heated at 40° C. To the resulting yellow solution was added hydrazine hydrate solution (0.311 mL, 9.98 mmol) dropwise. The resulting mixture was stirred for 90 minutes at 40° C. LC-MS indicated complete conversion to the desired product. The mixture was cooled to room temperature, filtered through Celite® brand filter aid, and washed with MeOH. The filtrate was dried under reduced pressure and was then purified using a 5 g SCX-2 column washing with MeOH and then with 2 M NH$_3$ in MeOH. The basic wash was dried under reduced pressure providing a brown oil which solidified after overnight under high vacuum to yield (S)-3-(4-((3-aminopyridin-4-yl)amino)cyclohexyl)-4-(4-fluorophenyl)-5,5-dimethyloxazolidin-2-one (0.213 g, 0.535 mmol, 80% yield) as a yellow solid. m/z (ESI) 399.0 (M+H)$^+$.

Step 3

(S)-4-(4-Fluorophenyl)-5,5-dimethyl-3-((1r,4S)-4-(2-oxo-2,3-dihydro-1H-imidazo[4,5-c]pyridin-1-yl)cyclohexyl)oxazolidin-2-one To a flask charged with (S)-3-(4-((3-aminopyridin-4-yl)amino)cyclohexyl)-4-(4-fluorophenyl)-5,5-dimethyloxazolidin-2-one (0.210 g, 0.527 mmol) were added THF (2.108 mL) and DIEA (0.322 mL, 1.845 mmol). The mixture was cooled in an ice water bath prior to the addition of CDI (0.299 g, 1.845 mmol). The resulting mixture was stirred and slowly warmed to room temperature by allowing the ice to melt. After 2 hours, LC-MS indicated complete conversion to desired product. The mixture was dried under reduced pressure and purified with a 25 g HP spherical silica column (Interchim) ramping DCM:MeOH (90:10) in DCM (0-20%, then extended isocratic at 20%, then after the first peak eluted ramped to 50%, detection at 215 nm) yielding separation of cis/trans isomers, the first eluted compound, (S)-4-(4-fluorophenyl)-5,5-dimethyl-3-((1s,4R)-4-(2-oxo-2,3-dihydro-1H-imidazo[4,5-c]pyridin-1-yl)cyclohexyl)oxazolidin-2-one (152 mg, 0.358 mmol, 67.9% yield), was obtained as a yellow oil with impurity coelution according to $^1$H NMR. The second peak was obtained as a white solid with a minor impurity present and a large impurity peak in the aromatic region according to $^1$H NMR. The methine proton splittings suggested the trans product. The material was purified with a 5 g SCX-2 column washing with MeOH and then with 2 M NH$_3$ in MeOH. The basic wash was dried under reduced pressure yielding a product as a white solid with minor impurities (LC-MS) still present. Chiral purification: Column: Chiralpak AS-H, 2×25 cm, Mobile Phase: 20% MeOH w/0.2% diethylamine/80% CO$_2$, Flowrate: 65 mL/min, Sample dissolved at 11 mg/mL in 1:2 DCM/MeOH, processed with 1.5 mL injections. Example 55 ((S)-4-(4-fluorophenyl)-5,5-dimethyl-3-((1s,4R)-4-(2-oxo-2,3-dihydro-1H-imidazo[4,5-c]pyridin-1-yl)cyclohexyl)oxazolidin-2-one (51 mg, 0.120 mmol, 22.80% yield)) was the first eluting peak and after lyophilization from MeOH/H$_2$O was obtained as a fluffy white solid. $^1$H NMR (400 MHz, DMSO-d$_6$) δ=8.15 (s, 1H), 8.10 (d, J=5.4 Hz, 1H), 7.47-7.18 (m, 5H), 4.70 (s, 1H), 4.10-3.99 (m, 1H), 3.69 (tt, J=3.8, 11.8 Hz, 1H), 2.26-2.03 (m, 2H), 2.00-1.84 (m, 2H), 1.73 (d, J=11.9 Hz, 1H), 1.60 (br. s., 2H), 1.47 (s, 3H), 1.27 (dq, J=4.0, 12.7 Hz, 1H), 0.81 (s, 3H). m/z (ESI) 425.1 (M+H)$^+$.

Examples 56 and 57

Synthesis of (S)-3-((1r,4S)-4-(6-bromo-2-oxo-1H-imidazo[4,5-b]pyridin-3(2H)-yl)cyclohexyl)-5,5-dimethyl-4-phenyloxazolidin-2-one and 3-((1S,4r)-4-((S)-5,5-dimethyl-2-oxo-4-phenyloxazolidin-3-yl)cyclohexyl)-2-oxo-2,3-dihydro-1H-imidazo[4,5-b]pyridine-6-carbonitrile

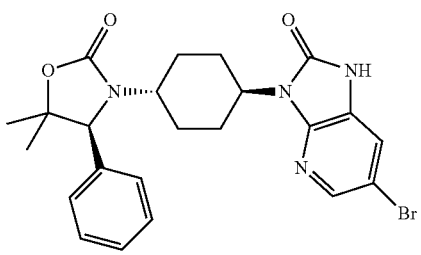

Example 56

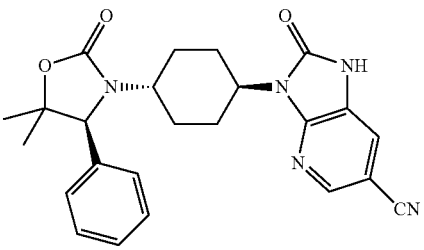

Example 57

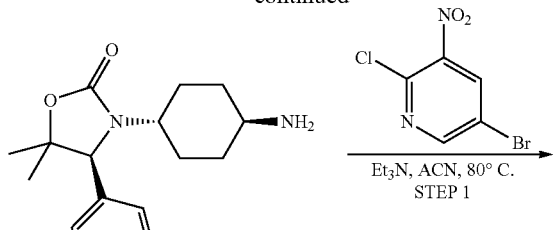

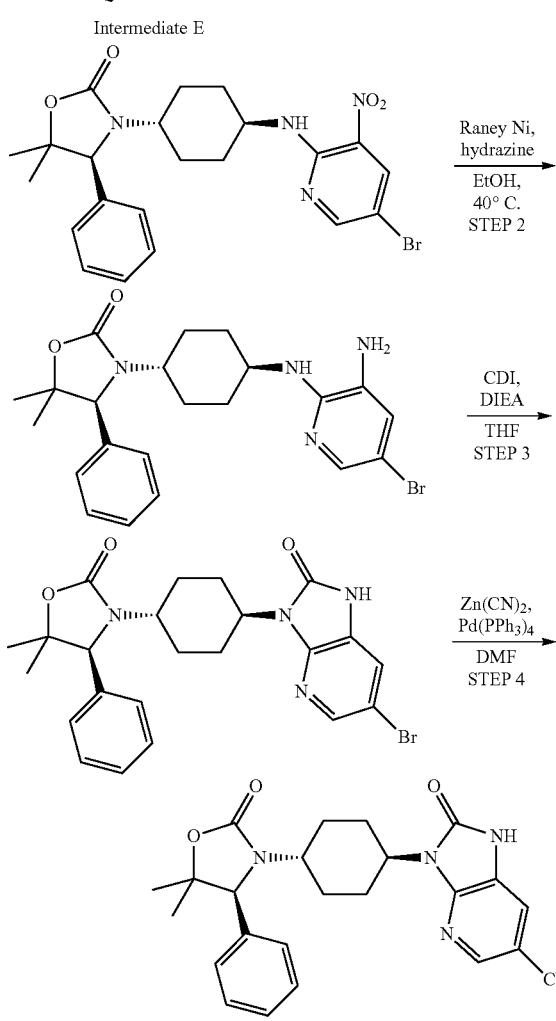

Step 1

(S)-3-((1r,4S)-4-((5-Bromo-3-nitropyridin-2-yl)amino)cyclohexyl)-5,5-dimethyl-4-phenyloxazolidin-2-one To a vial charged with (S)-3-((1r,4S)-4-aminocyclohexyl)-5,5-dimethyl-4-phenyloxazolidin-2-one (0.194 g, 0.673 mmol) were added ACN (2.242 mL), DIEA (0.235 mL, 1.345 mmol) and 5-bromo-2-chloro-3-nitropyridine (commercially available from Matrix Scientific, Columbia, S.C.) (0.168 g, 0.706 mmol) respectively. The vial was sealed and heated at 90° C. for 2 hours providing a brown solution with product as the main species according to LC-MS. The solution was dried under reduced pressure and purified with a 25 g SNAP column ramping DCM:MeOH (90:10) in DCM (0-30%, then isocratic at 30%, detection at 215 nm) providing (S)-3-((1r,4S)-4-((5-bromo-3-nitropyridin-2-yl)amino)cyclohexyl)-5,5-dimethyl-4-phenyloxazolidin-2-one (0.315 g, 0.644 mmol, 96% yield) as a yellow/orange solid. m/z (ESI) 490.1 (M+H)$^+$.

Step 2

(S)-3-((1r,4S)-4-((3-Amino-5-bromopyridin-2-yl)amino)cyclohexyl)-5,5-dimethyl-4-phenyloxazolidin-2-one To a flask charged with (S)-3-((1r,4S)-4-((5-bromo-3-nitropyridin-2-yl)amino)cyclohexyl)-5,5-dimethyl-4-phenyloxazolidin-2-one (0.310 g, 0.633 mmol) was added EtOH (12.67 mL). Raney 3202 nickel (slurry in water) (0.698 mL, 106 mmol) was then added using a pipette. The flask was sealed, placed under nitrogen, and heated at 40° C. To the resulting yellow solution was added hydrazine hydrate solution (0.296 mL, 9.50 mmol) dropwise. The resulting mixture was stirred at 40° C. overnight. LC-MS of the cloudy white suspension indicated complete conversion to the desired product. The mixture was cooled to room temperature and filtered through Celite® brand filter aid which was washed with MeOH. The filtrate was dried under reduced pressure and then purified using a 5 g SCX-2 column washing with MeOH and then with 2 M NH$_3$ in MeOH. The basic wash was dried under reduced pressure providing (S)-3-((1 r,4S)-4-((3-amino-5-bromopyridin-2-yl)amino)cyclohexyl)-5,5-dimethyl-4-phenyloxazolidin-2-one (0.270 g, 0.588 mmol, 93% yield) as a purple film. m/z (ESI) 459.1 (M+H)$^+$.

Step 3

(S)-3-((1 r,4S)-4-(6-Bromo-2-oxo-1H-imidazo[4,5-b]pyridin-3(2H)-yl)cyclohexyl)-5,5-dimethyl-4-phenyloxazolidin-2-one To a flask charged with (S)-3-(4-((3-amino-5-bromopyridin-2-yl)amino)cyclohexyl)-5,5-dimethyl-4-phenyloxazolidin-2-one (0.270 g, 0.588 mmol) were added THF (2.351 mL), DIEA (0.359 mL, 2.057 mmol) and CDI (0.334 g, 2.057 mmol) respectively. The mixture was shaken at room temperature overnight. LC-MS of the dark solution indicated complete reaction. The mixture was dried under reduced pressure and purified with a 25 g HP 15 m spherical silica column (Interchim) ramping DCM:MeOH (90:10) in DCM (0-30%, then isocratic at 30%, detection at 215 nm) yielding, after drying, Example 56 ((S)-3-((1s,4R)-4-(6-bromo-2-oxo-1H-imidazo[4,5-b]pyridin-3(2H)-yl)cyclohexyl)-5,5-dimethyl-4-phenyloxazolidin-2-one (0.230 g, 0.474 mmol, 81% yield)) as an off-white solid. $^1$H NMR (400 MHz, DMSO-d$_6$) δ=11.27 (br. s., 1H), 8.00 (d, J=2.0 Hz, 1H), 7.52-7.14 (m, 6H), 4.67 (s, 1H), 4.12-4.01 (m, 1H), 3.52-3.40 (m, 1H), 2.42-2.17 (m, 2H), 2.01-1.83 (m, 2H), 1.75 (d, J=12.0 Hz, 1H), 1.61 (t, J=13.2 Hz, 2H), 1.47 (s, 3H), 1.33-1.16 (m, 1H), 0.81 (s, 3H). m/z (ESI) 485.1 (M+H)$^+$.

Step 4

3-((1S,4r)-4-((S)-5,5-Dimethyl-2-oxo-4-phenyloxazolidin-3-yl)cyclohexyl)-2-oxo-2,3-dihydro-1H-imidazo[4,5-b]pyridine-6-carbonitrile To a 0.5-2.0 mL microwave vial charged with (S)-3-((1 s,4R)-4-(6-bromo-2-oxo-1H-imidazo[4,5-b]pyridin-3(2H)- yl)cyclohexyl)-5,5-dimethyl-4-phenyloxazolidin-2-one (0.200 g, 0.412 mmol) was added DMF (1.648 mL) followed by zinc cyanide (0.026 mL, 0.412 mmol) and [1,1-bis(diphenylphosphino)ferrocene]palladium(II) chloride (complex with DCM (1:1)) (0.034 g, 0.041 mmol). The resulting mixture was purged with argon, sealed and irradiated for 30 minutes at 160° C. LC-MS indicated that no conversion had occurred. To the mixture was added Pd(PPh$_3$)$_4$ (0.048 g, 0.041 mmol) and 2 eq of Zn(CN)$_2$. The vessel was purged with argon and the mixture was heated at 120° C. for 90 minutes providing complete conversion according to LC-MS. The suspension was cooled to room temperature and filtered through a 5 g SCX-2 column washing with MeOH and then with 2 M NH$_3$ in MeOH. The product eluted during the initial MeOH wash. This wash was dried under reduced pressure, and the residual brown oil was purified with a 25 g HP spherical silica column (15 m, Interchim) ramping DCM:MeOH (90:10) in DCM (0-30%, then isocratic at 30%, detection at 215 nm) yielding an off-white solid with a minor yellow discoloration (168 mg). The material thus obtained was triturated with MeOH and washed with a small volume of MeOH to provide Example 57 (3-((1 S,4r)-4-((S)-5,5-dimethyl-2-oxo-4-phenyloxazolidin-3-yl)cyclohexyl)-2-oxo-2,3-dihydro-1H-imidazo[4,5-b]pyridine-6-carbonitrile) as a white solid (56 mg. 31%). $^1$H NMR (400 MHz, DMSO-d$_6$) δ=11.56 (br. s., 1H), 8.38 (d, J=1.9 Hz, 1H), 7.67 (d, J=1.9 Hz, 1H), 7.47-7.17 (m, 5H), 4.67 (s, 1H), 4.13 (tt, J=3.8, 12.3 Hz, 1H), 3.53-3.41 (m, 1H), 2.41-2.17 (m, 2H), 2.01-1.84 (m, 2H), 1.83-1.73 (m, 1H), 1.71-1.58 (m, 2H), 1.47 (s, 3H), 1.35-1.20 (m, 1H), 0.81 (s, 3H). m/z (ESI) 432.0 (M+H)$^+$.

Example 58

Synthesis of N-(trans-4-((4S)-5,5-dimethyl-2-oxo-4-phenyl-1,3-oxazolidin-3-yl)cyclohexyl)-1H-pyrrolo[2,3-b]pyridine-1-carboxamide

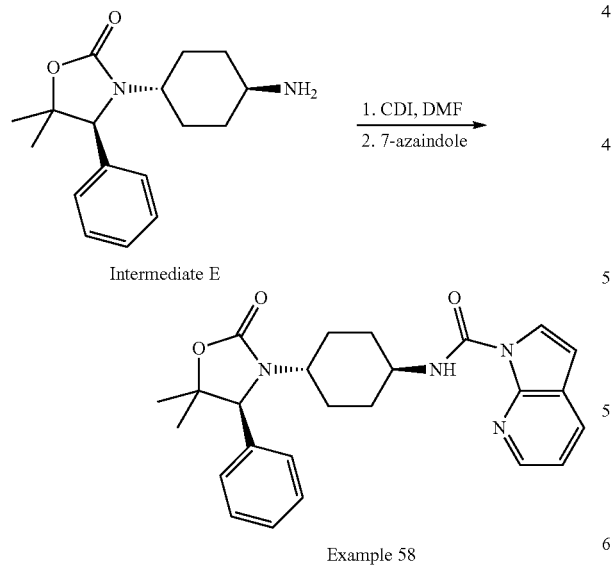

Intermediate E

Example 58

To a vial charged with (S)-3-((1r,4S)-4-aminocyclohexyl)-5,5-dimethyl-4-phenyloxazolidin-2-one (0.135 g, 0.468 mmol) were added DMF (1.872 mL), TEA (0.196 mL, 1.404 mmol) and CDI (0.076 g, 0.468 mmol). The resulting mixture was stirred at room temperature for 2 hours yielding a white suspension. To the mixture was added 1H-pyrrolo[2,3-b]pyridine (0.066 g, 0.562 mmol), and the mixture was heated at 90° C. overnight. The light brown suspension was dried under reduced pressure, and the residue was purified with a 25 g HP spherical silica column (15 m, Interchim) ramping DCM:MeOH in DCM (0-30%) providing product which was subsequently lyophilized from MeOH/H$_2$O providing N-((1 S,4r)-4-((S)-5,5-dimethyl-2-oxo-4-phenyloxazolidin-3-yl)cyclohexyl)-1H-pyrrolo[2,3-b]pyridine-1-carboxamide (0.056 g, 0.129 mmol, 27.7% yield) as a white solid. $^1$H NMR (400 MHz, DMSO-d$_6$) δ=9.45 (d, J=7.5 Hz, 1H), 8.36 (dd, J=1.5, 4.9 Hz, 1H), 8.14 (dd, J=1.6, 7.8 Hz, 1H), 7.92 (d, J=4.0 Hz, 1H), 7.47-7.38 (m, 2H), 7.38-7.09 (m, 4H), 6.69 (d, J=3.9 Hz, 1H), 4.66 (s, 1H), 3.63-3.49 (m, 2H), 2.12-2.04 (m, 1H), 1.96-1.81 (m, 3H), 1.60-1.52 (m, 1H), 1.52-1.42 (m, 4H), 1.36 (dq, J=3.4, 12.5 Hz, 1H), 1.26-1.13 (m, 1H), 0.80 (s, 3H). m/z (ESI) 433.4 (M+H)$^+$.

Example 59

Synthesis of N-((1S,4r)-4-((S)-5,5-dimethyl-2-oxo-4-phenyloxazolidin-3-yl)cyclohexyl)-7-fluoro-1,5-naphthyridine-4-carboxamide

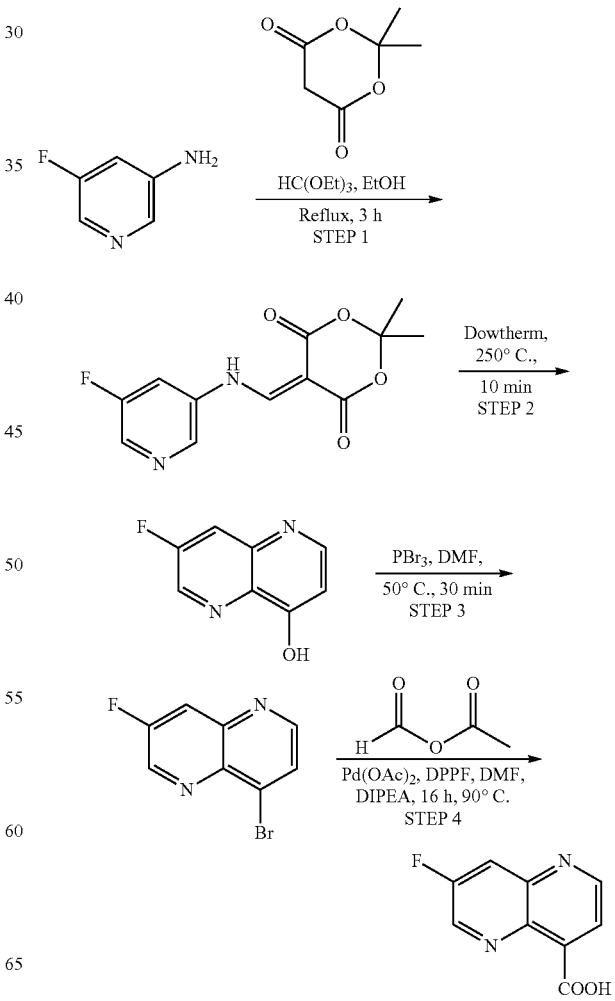

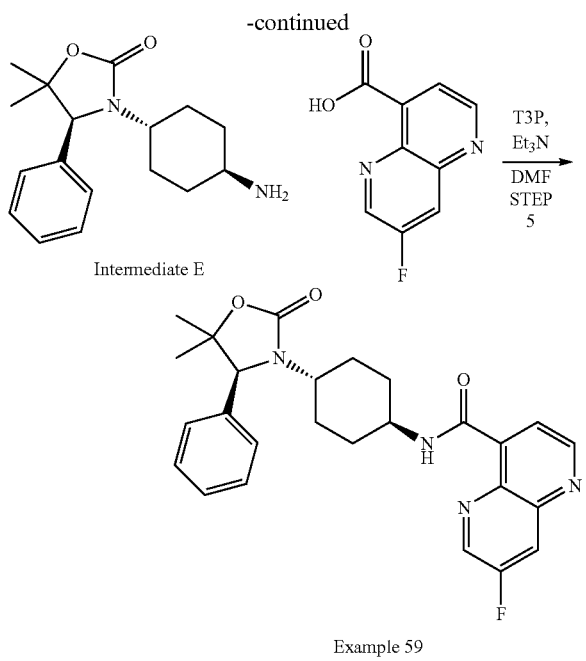

Example 59

Step 1

5-(((5-Fluoropyridin-3-yl)amino)methylene)-2,2-dimethyl-1,3-dioxane-4,6-dione To a solution of 5-fluoropyridin-3-amine (2 g, 0.01 mol) in EtOH (20 mL), were added 2,2'-dimethyl-1,3-dioxane-4,6-dione (Meldrum's acid) (2.44 g, 0.02 mol) and triethyl orthoformate CH(OEt)$_3$ (2.64 g, 0.01 mol). The resulting mixture was heated at reflux for 3 hours with constant stirring. The reaction was monitored by TLC (TLC eluent: 40% EtOAc in petroleum ether, UV active). After completion of reaction, the mixture was allowed to cool to ambient temperature yielding a white colored precipitate. The precipitate was filtered, washed with EtOH (20 mL) and dried under vacuum to afford 5-(((5-fluoropyridin-3-yl)amino)methylene)-2,2-dimethyl-1,3-dioxane-4,6-dione as an off white solid (1.2 g, 25%). $^1$H NMR (400 MHz, DMSO-d$_6$): δ 11.33 (d, J=14.4 Hz, 1H), 8.71 (s, 1H), 8.65 (d, J=14.4 Hz, 1H), 8.47 (d, J=2.4 Hz, 1H), 8.17-8.13 (m, 1H), 1.68 (s, 6H).

Step 2: 7-Fluoro-1,5-naphthyridin-4-ol

To a stirred solution of Dowtherm A at 250° C., was added 5-(((5-fluoropyridin-3-yl)amino)methylene)-2,2-dimethyl-1,3-dioxane-4,6-dione (1 g, 0.003 mol) portionwise over a period of 10 minutes. The reaction was monitored by TLC (TLC eluent: 50% EtOAc in petroleum ether, uv active). After completion of reaction, the mixture was cooled to ambient temperature and treated with diethyl ether to obtain a grey precipitate. The precipitate was stirred for 5-10 minutes and filtered, washed with diethyl ether and dried under vacuum to obtain 7-fluoro-1,5-naphthyridin-4-ol as a tan colored solid, (0.4 g, 64.93%). $^1$H NMR (400 MHz, DMSO-d$_6$): δ 12.68 (bs, 1H), 9.43 (s, 1H), 8.75 (t, J=6.4 Hz, 1H), 8.59 (d, J=8, 1H), 6.99 (d, J=17.2 Hz, 1H). m/z (ESI) 165.1 (M+H)$^+$.

Step 3

8-Bromo-3-fluoro-1,5-naphthyridine

To a suspension of 7-fluoro-1,5-naphthyridin-4-ol (400 mg, 2.43 mmol) in DMF (8 mL), was added PBr$_3$ (659.65 mg, 2.43 mmol) dropwise at 50° C. for 10 minutes. After complete addition of PBr$_3$, the suspension became homogeneous and a brown precipitate was obtained over a period of 30 minutes. The reaction was monitored by TLC (TLC eluent: 50% EtOAc in petroleum ether). After completion of reaction, the mixture was cooled to ambient temperature to generate more precipitate. The precipitate was filtered and washed with Et$_2$O (15 mL) and dried under vacuum to afford a brown colored hydro bromide salt of 8-bromo-2-methoxy-[1,5]naphthyridine which was free-based using saturated bicarbonate solution (10 mL) and product was extracted into EtOAc (2×25 mL). The organic layer was dried over anhydrous Na$_2$SO$_4$ and concentrated under reduced pressure to afford 8-bromo-3-fluoro-1,5-naphthyridine as a brown solid, (200 mg, 36%). $^1$H NMR (300 MHz, DMSO-d$_6$): δ 9.19 (d, J=2.4 Hz, 1H), 8.84 (d, J=4.8 Hz, 1H), 8.44 (dd, J=2.8 & 9.2 Hz, 1H), 8.23 (d, J=4.8 Hz, 1H). m/z (ESI) 227.1 (M+H)$^+$.

Step 4

7-Fluoro-1,5-naphthyridine-4-carboxylic acid

To a solution of 8-bromo-3-fluoro-1,5-naphthyridine (1.7 g, 0.0074 mol) in DMF (17 mL) in a reaction tube were added dppf (207.44 mg, 0.0003 mol) and palladium acetate (84.25 mg, 0.0003 mol). The mixture was then purged with argon for 5-10 minutes. Then, DIPEA (3.4 mL, 2 times) and acetic formic anhydride (3.4 mL, 2 times) were added slowly at room temperature. The reaction mixture was stirred for 16 hours at 90° C. After completion of reaction (monitored by TLC (TLC eluent: 50% EtOAc in petroleum ether, UV active)), the mixture was cooled to ambient temperature and concentrated. The mixture was taken in 20% NaOH solution and extracted with EtOAc. Then the aqueous layer was acidified with 1 N HCl at 0-5° C. and extracted with EtOAc. The extract was washed with water and then with saturated NaCl solution. The organic layer was then dried over Na$_2$SO$_4$. The organic solvent was removed under reduced pressure to afford 7-fluoro-1,5-naphthyridine-4-carboxylic acid (950 mg, 66%). $^1$H NMR (400 MHz, DMSO-d$_6$): δ 14.2 (bs, 1H), 9.20 (d, J=2.8 Hz, 1H), 9.16 (d, J=4.4 Hz, 1H), 8.49 (dd, J=2.8 Hz&9.6 Hz, 1H), 7.98 (d, J=4 Hz, 1H). m/z (ESI) 193.2 (M+H)$^+$.

Step 5

N-((1S,4r)-4-((S)-5,5-Dimethyl-2-oxo-4-phenyloxazolidin-3-yl)cyclohexyl)-7-fluoro-1,5-naphthyridine-4-carboxamide To a vial charged with (S)-3-((1r,4S)-4-aminocyclohexyl)-5,5-dimethyl-4-phenyloxazolidin-2-one (0.073 g, 0.253 mmol) were added DMF (1.013 mL), TEA (0.039 mL, 0.278 mmol), 7-fluoro-1,5-naphthyridine-4-carboxylic acid (0.049 g, 0.253 mmol) and 1-propanephosphonic acid cyclic anhydride (0.161 mL, 0.253 mmol) respectively. The resulting light brown solution was shaken at room temperature. After 4 hours of stirring, LC-MS showed product as the major species with acid and amine still present (~60% conversion). Additional 1-propanephosphonic acid cyclic anhydride (0.161 mL, 0.253 mmol) was added and the mixture was shaken overnight at room temperature. Minimal additional conversion was observed. The mixture was dried under reduced pressure and purified using a 25 g HP spherical silica column (15 µm, Interchim) ramping DCM:MeOH (90:10) in DCM from 0-100% with product elution occurring towards the 100% polar eluent along with a minor impurity (10-20%)

which was more polar and visible by TLC and LC-MS. The material was repurified by dissolving in MeOH and using RP-HPLC (Gilson) ramping ACN in H₂O (10-90%, 0.1% TFA) affording separation of impurities. The product containing eluents were transferred to a separatory funnel, diluted with EtOAc and washed with saturated aqueous NaHCO₃. The organic layer was dried with Na₂SO₄, filtered, and dried under reduced pressure. The film obtained was lyophilized from MeOH/H₂O providing N-((1 S,4r)-4-((S)-5,5-dimethyl-2-oxo-4-phenyloxazolidin-3-yl)cyclohexyl)-7-fluoro-1,5-naphthyridine-4-carboxamide (0.041 g, 0.089 mmol, 35.0% yield) as an off-white solid. ¹H NMR (400 MHz, DMSO-d₆) δ=9.57 (d, J=7.7 Hz, 1H), 9.15 (d, J=2.8 Hz, 1H), 9.13 (d, J=4.4 Hz, 1H), 8.44 (dd, J=2.8, 9.5 Hz, 1H), 8.05 (d, J=4.4 Hz, 1H), 7.46-7.15 (m, 5H), 4.66 (s, 1H), 3.70 (tdt, J=3.9, 7.6, 11.5 Hz, 1H), 3.53-3.41 (m, 1H), 2.08-1.99 (m, 1H), 1.92-1.81 (m, 2H), 1.61-1.53 (m, 1H), 1.47 (s, 3H), 1.45-1.13 (m, 4H), 0.80 (s, 3H). m/z (ESI) 463.3 (M+H)⁺.

Example 60

Synthesis of 1-((1S,4r)-4-((S)-5,5-dimethyl-2-oxo-4-phenyloxazolidin-3-yl)cyclohexyl)-4-fluoro-2-oxo-2,3-dihydro-1H-benzo[d]imidazole-5-carbonitrile

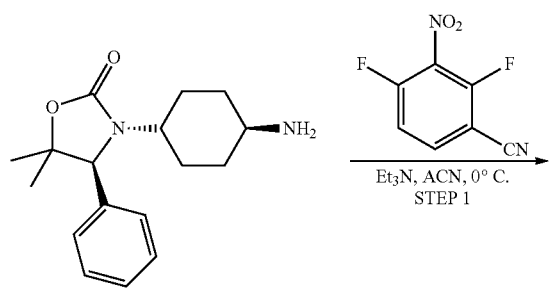

Intermediate E

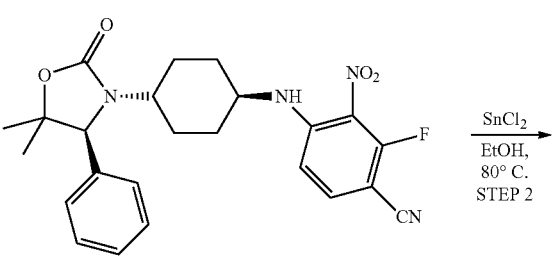

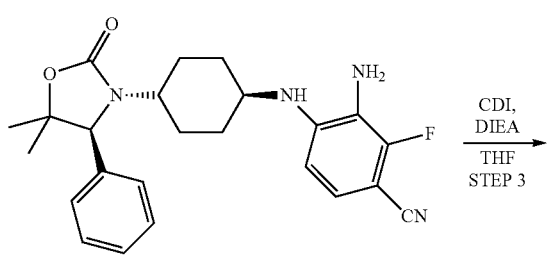

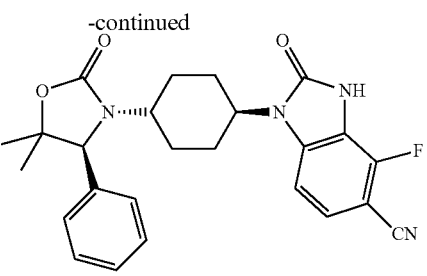

Example 60

Step 1

4-(((1S,4r)-4-((S)-5,5-Dimethyl-2-oxo-4-phenyloxazolidin-3-yl)cyclohexyl)amino)-2-fluoro-3-nitrobenzonitrile To a vial charged with (S)-3-((1r,4S)-4-aminocyclohexyl)-5,5-dimethyl-4-phenyloxazolidin-2-one (0.114 g, 0.395 mmol) were added ACN (1.318 mL) and TEA (0.110 mL, 0.791 mmol). The resulting solution was cooled in an ice water bath. To a separate vial were added 2,4-difluoro-3-nitrobenzonitrile (0.076 g, 0.415 mmol) and ACN (200 µL). The mixture of 2,4-difluoro-3-nitrobenzonitrile dissolved in ACN was added slowly to the cooled solution of the amine. The mixture was allowed to slowly warm to room temperature overnight. The resulting orange solution was dried under reduced pressure and purified with a 25 g SNAP column ramping DCM:MeOH (90:10) in DCM from 0-30%, then isocratic at 30% (detection at 215 nm) to provide 4-(((1 S,4r)-4-((S)-5,5-dimethyl-2-oxo-4-phenyloxazolidin-3-yl)cyclohexyl)amino)-2-fluoro-3-nitrobenzonitrile (0.161 g, 0.356 mmol, 90% yield) as a yellow solid with about 20% impurity present. The material was used in the next step without further purification. m/z (ESI) 453.4 (M+H)⁺.

Step 2

3-Amino-4-(((1S,4r)-4-((S)-5,5-dimethyl-2-oxo-4-phenyloxazolidin-3-yl)cyclohexyl)amino)-2-fluorobenzonitrile To a vial charged with 4-(((1 S,4r)-4-((S)-5,5-dimethyl-2-oxo-4-phenyloxazolidin-3-yl)cyclohexyl)amino)-2-fluoro-3-nitrobenzonitrile (0.161 g, 0.356 mmol) were added EtOH (1.423 mL) and tin (II) chloride (0.202 g, 1.067 mmol) respectively. The suspension was heated at 80° C. for 3 hours yielding an orange solution. The resulting mixture was dried under reduced pressure and the residue thus obtained was purified with a 25 g SNAP column ramping DCM:MeOH (90:10) in DCM (0-30%, then isocratic at 30%, detection at 215 nm) leading to isolation of the product as an orange oil (145 mg, 96%). m/z (ESI) 423.4 (M+H)⁺.

Step 3

1-((1S,4r)-4-((S)-5,5-Dimethyl-2-oxo-4-phenyloxazolidin-3-yl)cyclohexyl)-4-fluoro-2-oxo-2,3-dihydro-1H-benzo[d]imidazole-5-carbonitrile To a flask charged with 3-amino-4-(((1S,4r)-4-((S)-5,5-dimethyl-2-oxo-4-phenyloxazolidin-3-yl)cyclohexyl)amino)-2-fluorobenzonitrile (0.145 g, 0.343 mmol) were added THF (1.373 mL), DIEA (0.210 mL, 1.201 mmol) and CDI (0.195 g, 1.201 mmol) respectively. The mixture was shaken at room temperature for 90 minutes. The mixture was then dried under reduced pressure, and the residue was purified with a 25 g HP spherical silica column (15 m spherical silica, Interchim) ramping DCM:MeOH (90:10) in DCM from 0-25%, then isocratic at 25%, detection at 215 nm providing product as a white solid (118 mg, 77%). $^1$H NMR (400 MHz, DMSO-$d_6$) δ=11.94 (br. s., 1H), 7.52-7.13 (m, 7H), 4.67-4.62 (m, 1H), 4.09 (tt, J=3.4, 12.4 Hz, 1H), 3.66 (tt, J=3.8, 11.7 Hz, 1H), 2.40-2.05 (m, 2H), 2.03-1.84 (m, 2H), 1.81-1.55 (m, 3H), 1.48 (s, 3H), 1.36-1.21 (m, 1H), 0.80 (s, 3H). m/z (ESI) 449.1 (M+H)$^+$.

Example 61

Synthesis of 1-((1S,4r)-4-((S)-4-(4-fluorophenyl)-5,5-dimethyl-2-oxooxazolidin-3-yl)cyclohexyl)-2-oxo-2,3-dihydro-1H-benzo[d]imidazole-5-carbonitrile

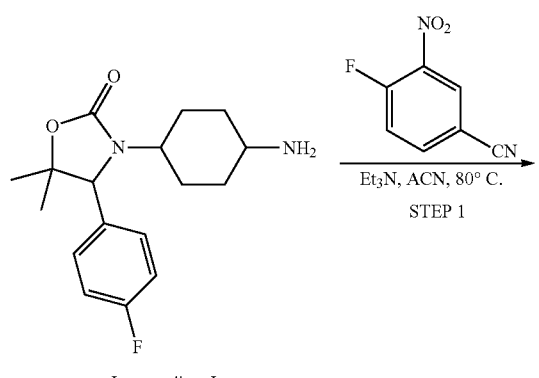

Intermediate I

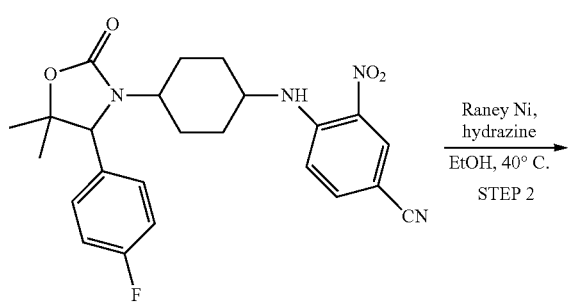

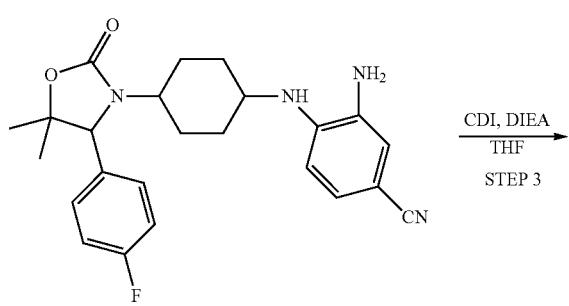

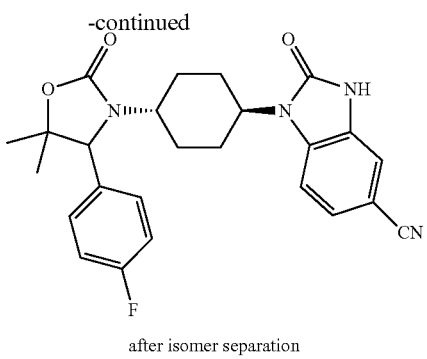

after isomer separation

Example 61

Step 1

(S)-4-((4-(4-(4-Fluorophenyl)-5,5-dimethyl-2-oxooxazolidin-3-yl)cyclohexyl)amino)-3-nitrobenzonitrile To a vial charged with (S)-3-(4-aminocyclohexyl)-4-(4-fluorophenyl)-5,5-dimethyloxazolidin-2-one (0.353 g, 1.152 mmol) were added ACN (3.84 mL), DIEA (0.402 mL, 2.304 mmol) and 4-fluoro-3-nitrobenzonitrile (commercially available from J & W Pharmlab, Levittown, Pa.) (0.191 g, 1.152 mmol) respectively. After completion of reaction, the dark mixture was dried under reduced pressure and purified with a 25 g HP spherical silica column ramping DCM:MeOH (90:10) in DCM from 0-50%, then isocratic at 50% (detection at 215 nm) leading to isolation of product which was obtained as an orange/brown oil as a mixture of cis/trans isomers of (S)-4-((4-(4-(4-fluorophenyl)-5,5-dimethyl-2-oxooxazolidin-3-yl)cyclohexyl)amino)-3-nitrobenzonitrile (0.490 g, 1.083 mmol, 94% yield). m/z (ESI) 453.2 (M+H)$^+$.

Step 2

(S)-3-Amino-4-((4-(4-(4-fluorophenyl)-5,5-dimethyl-2-oxooxazolidin-3-yl)cyclohexyl)amino)benzonitrile To a flask charged with (S)-4-((4-(4-(4-fluorophenyl)-5,5-dimethyl-2-oxooxazolidin-3-yl)cyclohexyl)amino)-3-nitrobenzonitrile (0.490 g, 1.083 mmol) was added EtOH (4.33 mL) followed by tin (II) chloride (0.616 g, 3.25 mmol). The resulting yellow suspension was heated overnight at 80° C. LC-MS analysis of the resulting suspension indicated about 90% conversion to the desired product (215 nm). Additional EtOH (4 mL) was added to aid solubilization and additional SnCl$_2$ was added (300 mg). The resulting mixture was heated at 80° C. After 1 hour, LC-MS indicated complete conversion. The yellow suspension was dried under reduced pressure and the residue was purified with a 50 g SNAP column ramping DCM:MeOH (90:10) in DCM (0-30%, then isocratic at 30%, detection at 215 nm) to provide (S)-3-amino-4-((4-(4-(4-fluorophenyl)-5,5-dimethyl-2-oxooxazolidin-3-yl)cyclohexyl)amino)benzonitrile (0.156 g, 0.369 mmol, 34.1% yield) as a brown oil and as a mixture of isomers with impurities present (~20% based on LC-MS). The material was used in the next step without further purification. m/z (ESI) 423.2 (M+H)$^+$.

Step 3

1-((1S,4r)-4-((S)-4-(4-Fluorophenyl)-5,5-dimethyl-2-oxooxazolidin-3-yl)cyclohexyl)-2-oxo-2,3-dihydro-1H-benzo[d]imidazole-5-carbonitrile To a flask charged with (S)-3-amino-4-((4-(4-(4-fluorophenyl)-5,5-dimethyl-2-oxooxazolidin-3-yl)cyclohexyl)amino)benzonitrile (0.156 g, 0.369 mmol) were added THF (1.477 mL) and DIEA (0.226 mL, 1.292 mmol). The resulting solution was cooled in an ice water bath prior to addition of CDI (0.210 g, 1.292 mmol). The resulting mixture was stirred for 3 hours and allowed to slowly warm to room temperature (ice melt) providing a greenish suspension. The resulting mixture was dried under reduced pressure and the residue was purified with a 25 g HP spherical silica column (15 μm, Interchim) ramping DCM:MeOH (90:10) in DCM (0-30%, isocratic at 30%, detection at 215 nm) providing the product as a mixture of isomers. Purification 1: Chiralpak AD-H, 2×15 cm, Mobile Phase: 30% iPrOH w/0.1% diethylamine/70% $CO_2$, Flowrate: 60 mL/min, detection 220 nm. Sample dissolved at 8 mg/mL with 0.5 mL injections. Purification 2: Chiralpak AD-H, 2×15 cm, Mobile Phase: 15% iPrOH w/0.1% diethylamine/85% $CO_2$, Flowrate: 60 mL/min, detection 220 nm with 1.0 mL injections providing the desired product as the major isomer (first eluting peak) (41 mg, 25%). $^1$H NMR (400 MHz, DMSO-$d_6$) δ=11.25 (br. s., 1H), 7.94 (d, J=1.0 Hz, 1H), 7.54-7.14 (m, 5H), 7.08 (d, J=8.0 Hz, 1H), 4.69 (s, 1H), 4.14-4.01 (m, 1H), 3.82-3.69 (m, 1H), 2.35-2.10 (m, 2H), 2.04-1.82 (m, 2H), 1.75-1.65 (m, 1H), 1.58 (t, J=16.4 Hz, 2H), 1.47 (s, 3H), 1.36-1.18 (m, 1H), 0.86-0.76 (m, 3H). m/z (ESI) 449.1 (M+H)$^+$.

Example 62

Synthesis of 3-((1S,4r)-4-((S)-5,5-dimethyl-2-oxo-4-phenyloxazolidin-3-yl)cyclohexyl)-2-oxo-1,2,3,4-tetrahydroquinazoline-6-carbonitrile

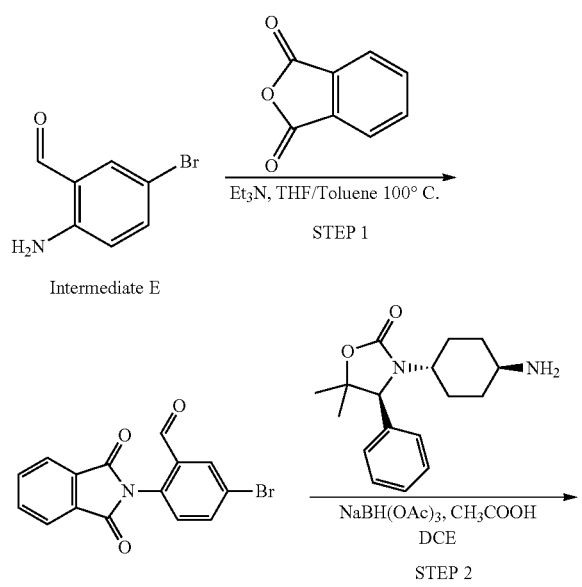

Example 62

Step 1

5-Bromo-2-(1,3-dioxoisoindolin-2-yl)benzaldehyde

To a vial charged with 2-amino-5-bromobenzaldehyde (commercially available from Matrix Scientific, Columbia, S.C.) (0.500 g, 2.500 mmol) were added THF (4.17 mL), toluene (4.17 mL), TEA (0.871 mL, 6.25 mmol) and phthalic anhydride (0.849 mL, 8.75 mmol). The mixture was heated at 100° C. overnight. LC-MS indicated that the product was present as a component of a complex mixture. The resulting mixture was passed through a 10 g SCX-2 column with much solid sticking to the top of the column and some product eluting through indicating a solubility issue in MeOH. The solid and filtrate were dissolved in DCM:MeOH and the crude residue was adsorbed onto silica gel with drying under reduced pressure. The adsorbed material was purified with a 50 g SNAP column ramping EtOAc in heptane from 0-45%, then isocratic at 45% to elute 5-bromo-2-(1,3-dioxoisoindolin-2-yl)benzaldehyde (0.290 g, 0.878 mmol, 35.1% yield) as a yellow solid. m/z (ESI) 330.0/332.0 (M+H)$^+$.

Step 2

2-(4-Bromo-2-((((1S,4r)-4-((S)-5,5-dimethyl-2-oxo-4-phenyloxazolidin-3-yl)cyclohexyl)amino)methyl)phenyl)isoindoline-1,3-dione To a flask charged with 5-bromo-2-(1,3-dioxoisoindolin-2-yl)benzaldehyde (0.275 g, 0.833 mmol) were added DCE (3.33 mL), AcOH (0.048 mL, 0.833 mmol) and (S)-3-((1r,4S)-4-aminocyclohexyl)-5,5-dimethyl-4-phenyloxazolidin-2-one (0.240 g, 0.833 mmol) followed by sodium triacetoxyborohydride (0.353 g, 1.666 mmol). The vessel was shaken at room temperature overnight. LC-MS indicated product formation along with another major impurity. To the mixture was added water (~3 mL) and the resulting mixture was purified with a 10 g SCX-2 column washing with MeOH and then with 2 M $NH_3$ in MeOH. The basic wash was dried under reduced pressure and purified with a 25 g SNAP column ramping EtOAc in heptane (0-100%), then DCM:MeOH (90:10) in DCM (0-30%, then isocratic at 30%) to provide product (188 mg, 37%). m/z (ESI) 602.0/604.0 $(M+H)^+$.

Step 3

(S)-3-((1 r,4S)-4-((2-Amino-5-bromobenzyl)amino)cyclohexyl)-5,5-dimethyl-4-phenyloxazolidin-2-one To a flask charged with 2-(4-bromo-2-((((1 S,4r)-4-((S)-5,5-dimethyl-2-oxo-4-phenyloxazolidin-3-yl)cyclohexyl)amino)methyl)phenyl)isoindoline-1,3-dione (0.184 g, 0.305 mmol) were added EtOH (1.222 mL) and hydrazine hydrate solution (0.048 mL, 1.527 mmol). The vessel was sealed and heated at 80° C. for 90 minutes leading to conversion to the desired product seen as a broad peak in the LC-MS. The mixture was dried under reduced pressure and purified with a 25 g SNAP column ramping DCM:MeOH (90:10) in DCM (0-30%, then isocratic at 30%, detection at 215 nm). The product eluted as the second peak. LC-MS indicated the presence of ~20% impurity, although the molecular weight was the same as the product. The product ((S)-3-((1 r,4S)-4-((2-amino-5-bromobenzyl)amino)cyclohexyl)-5,5-dimethyl-4-phenyloxazolidin-2-one) (0.078 g, 0.165 mmol, 54.1% yield) was obtained as a colorless oil. The mixture was used as is for the subsequent step. m/z (ESI) 472.0/474.0 $(M+H)^+$.

Step 4

(S)-3-((1r,4S)-4-(6-Bromo-2-oxo-1,2-dihydroquinazolin-3(4H)-yl)cyclohexyl)-5,5-dimethyl-4-phenyloxazolidin-2-one To a vial charged with (S)-3-((1r,4S)-4-((2-amino-5-bromobenzyl)amino)cyclohexyl)-5,5-dimethyl-4-phenyloxazolidin-2-one (0.078 g, 0.165 mmol) were added ACN (0.660 mL) and CDI (0.080 g, 0.495 mmol). The resulting solution was stirred at room temperature for 1 hour. LC-MS indicated complete conversion to the desired product. The mixture was dried under reduced pressure and purified with a 25 g SNAP column ramping DCM:MeOH (90:10) in DCM (0-30%, isocratic at 30%, detection at 215 nm). The product eluted sharply during the gradient along with ~20% impurity according to LC-MS. The product mixture was obtained as a yellow oil and was used in the next step without further purification (97 mg, 118%). m/z (ESI) 498.2/500.2 $(M+H)^+$.

Step 5

3-((1S,4r)-4-((S)-5,5-Dimethyl-2-oxo-4-phenyloxazolidin-3-yl)cyclohexyl)-2-oxo-1,2,3,4-tetrahydroquinazoline-6-carbonitrile To a flask charged with (S)-3-((1r,4S)-4-(6-bromo-2-oxo-1,2-dihydroquinazolin-3 (4H)-yl)cyclohexyl)-5,5-dimethyl-4-phenyloxazolidin-2-one (0.085 g, 0.171 mmol) were added zinc cyanide (0.032 mL, 0.512 mmol), $Pd(PPh_3)_4$ (0.039 g, 0.034 mmol), and DMF (0.682 mL). The vessel was purged with argon, sealed, and heated at 120° C. for 30 minutes. After 30 minutes a yellow orange suspension was present and LC-MS showed a complex mixture. Heating and shaking at 120° C. was continued overnight. An LC-MS of the resulting orange suspension indicated a complex mixture with product present. The mixture was dried under reduced pressure and purified with a 25 g HP spherical silica column (15 m, Interchim) ramping DCM:MeOH (90:10) in DCM (0-25%, then isocratic at 25%, detection at 215 nm). The desired product eluted last, and was cleanly, obtained as a white film upon drying. The film was lyophilized from $MeOH:H_2O$ providing the title compound as a fluffy white powder (15 mg, 20%). $^1$H NMR (500 MHz, DMSO-$d_6$) δ=9.66 (s, 1H), 7.56 (dd, J=1.8, 8.3 Hz, 1H), 7.51 (s, 1H), 7.45-7.15 (m, 5H), 6.85 (d, J=8.2 Hz, 1H), 4.64 (s, 1H), 4.34-4.25 (m, 2H), 4.00-3.90 (m, 1H), 3.48-3.38 (m, 1H), 1.89-1.82 (m, 2H), 1.72-1.52 (m, 4H), 1.46 (s, 4H), 1.22-1.12 (m, 1H), 0.80 (s, 3H). m/z (ESI) 445.4 $(M+H)^+$.

Example 63

Synthesis of (S)-5,5-dimethyl-3-(1-oxo-2-(quinolin-8-yl)-1,2,3,4-tetrahydroisoquinolin-6-yl)-4-phenyloxazolidin-2-one

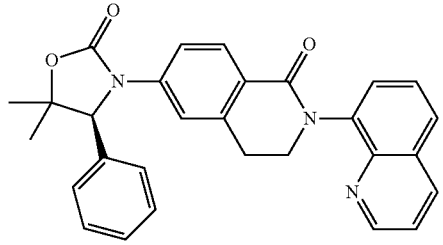 [SMILES: CC1(C)OC(=O)N(c2ccc3c(c2)CCN(c2cccc4cccnc24)C3=O)[C@H]1c1ccccc1]

Step 1

(S)-5,5-Dimethyl-3-(1-oxo-1,2,3,4-tetrahydroisoquinolin-6-yl)-4-phenyloxazolidin-2-one

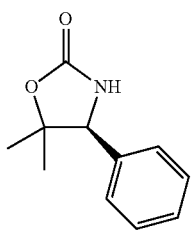

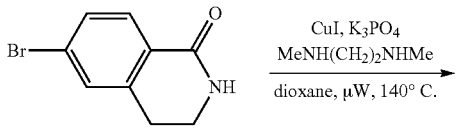

-continued

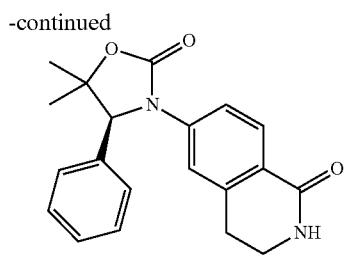

The title compound was prepared as described in General Scheme A substituting (S)-5,5-dimethyl-4-phenyloxazolidin-2-one (commercially available from Sigma-Aldrich, Milwaukee, Wis.) and 6-bromo-3,4-dihydroisoquinolin-1(2H)-one (commercially available from Astatech Inc., Bristol, Pa.). The final reaction mixture was filtered through Celite® brand filter aid with MeOH and DCM, concentrated, and purified (ISCO: 5 g cartridge, 12 g column, 0 to 35 to 100%, 90/10 DCM-MeOH in DCM). Fractions with product were repurified (ISCO: 5 g cartridge, 12 g column, 0 to 100% EtOAc-heptanes) giving (S)-5,5-dimethyl-3-(1-oxo-1,2,3,4-tetrahydroisoquinolin-6-yl)-4-phenyloxazolidin-2-one (79.7 mg, 0.237 mmol, 53.6% yield). $^1$H NMR (400 MHz, DMSO-$d_6$) δ 7.76-7.80 (m, 1H), 7.70 (d, J=8.51 Hz, 1H), 7.53-7.56 (m, 1H), 7.36 (m, 6H), 5.49 (s, 1H), 3.30 (s, 2H), 2.73-2.88 (m, 2H), 1.62 (s, 3H), 0.90 (s, 3H). m/z (ESI) 337.2 (M+H)$^+$.

Step 2

(S)-5,5-Dimethyl-3-(1-oxo-2-(quinolin-8-yl)-1,2,3,4-tetrahydroisoquinolin-6-yl)-4-phenyloxazolidin-2-one

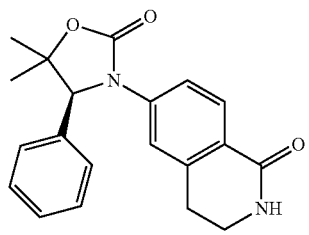

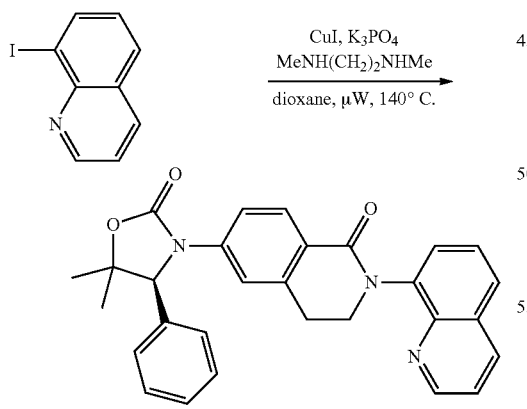

The title compound was prepared as described in General Scheme A substituting (S)-5,5-dimethyl-3-(1-oxo-1,2,3,4-tetrahydroisoquinolin-6-yl)-4-phenyloxazolidin-2-one and 8-iodoquinoline (commercially available from Synthonix, Wake Forest, N.C.). The final reaction mixture was filtered through Celite® brand filter aid with MeOH and DCM, concentrated, and purified (ISCO: 5 g cartridge, 12 g column, 0 to 40 to 80 to 100% EtOAc-heptanes) giving (S)-5,5-dimethyl-3-(1-oxo-2-(quinolin-8-yl)-1,2,3,4-tetrahydroisoquinolin-6-yl)-4-phenyloxazolidin-2-one (68.1 mg, 0.147 mmol, 68.6% yield). $^1$H NMR (400 MHz, DMSO-$d_6$) δ 8.85-8.89 (m, 1H), 8.41-8.46 (m, 1H), 7.96-8.01 (m, 1H), 7.77-7.81 (m, 1H), 7.71-7.76 (m, 1H), 7.62-7.69 (m, 2H), 7.52-7.59 (m, 1H), 7.37-7.46 (m, 3H), 7.22-7.36 (m, 3H), 5.54-5.58 (m, 1H), 3.80-4.09 (m, 2H), 3.10-3.18 (m, 2H), 1.66 (s, 3H), 0.93 (s, 3H). m/z (ESI) 464.2 (M+H)$^+$.

Example 64

Synthesis of (S)-3-(4-(6-amino-5-(5-fluoropyrimidin-2-yl)pyridin-3-yl)phenyl)-5,5-dimethyl-4-phenyloxazolidin-2-one

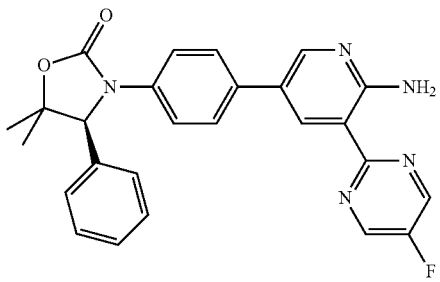 [SMILES: CC1(C)OC(=O)N(c2ccc(-c3cnc(N)c(-c4ncc(F)cn4)c3)cc2)[C@H]1c1ccccc1]

The title compound was prepared from 2-bromo-5-fluoropyrimidine (commercially available from Sigma-Aldrich, Milwaukee, Wis.) according to the procedure described in General Method HH-1 to afford (S)-3-(4-(6-amino-5-(5-fluoropyrimidin-2-yl)pyridin-3-yl)phenyl)-5,5-dimethyl-4-phenyloxazolidin-2-one as a light-yellow solid. $^1$H NMR (500 MHz, DMSO-$d_6$) δ 9.01 (s, 2H), 8.76 (d, J=2.35 Hz, 1H), 8.43 (d, J=2.56 Hz, 1H), 7.56 (s, 4H), 7.35-7.41 (m, 2H), 7.26-7.34 (m, 3H), 5.47 (s, 1H), 1.65 (s, 3H), 0.92 (s, 3H). m/z (ESI) 456.2 (M+H)$^+$.

Example 65

Synthesis of (S)-3-(4-(6-amino-5-(pyrimidin-2-yl)pyridin-3-yl)phenyl)-5,5-dimethyl-4-phenyloxazolidin-2-one

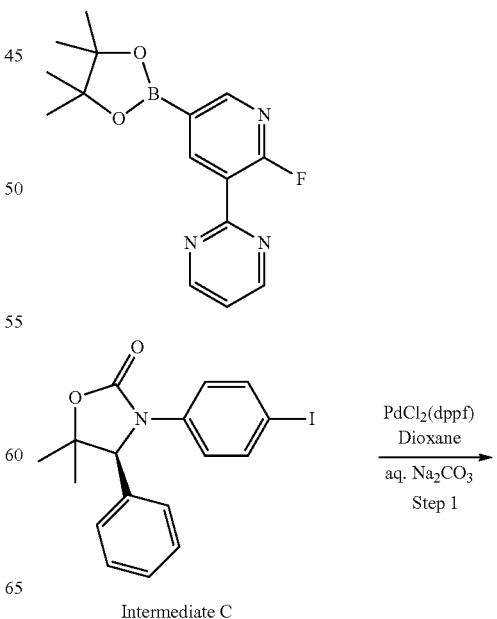

Intermediate C

-continued

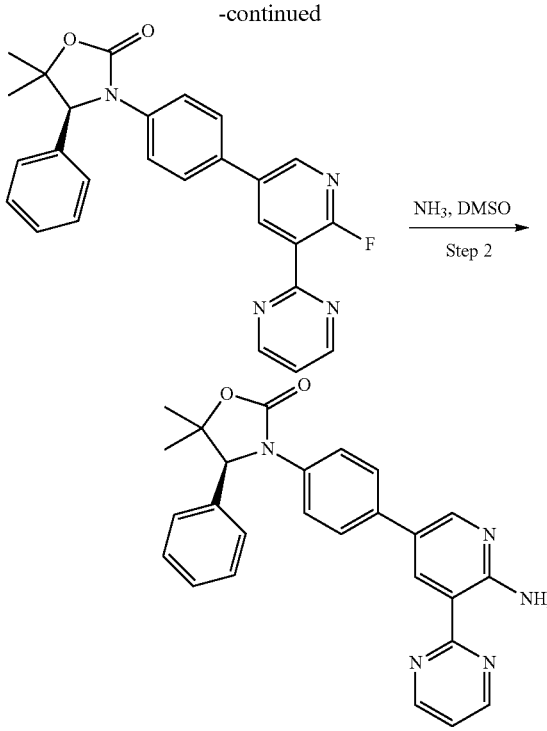

Example 65

Step 1

(S)-3-(4-(6-Fluoro-5-(pyrimidin-2-yl)pyridin-3-yl)phenyl)-5,5-dimethyl-4-phenyloxazolidin-2-one (S)-3-(4-Iodophenyl)-5,5-dimethyl-4-phenyloxazolidin-2-one (Intermediate C)(2.61 g, 6.64 mmol), sodium carbonate (6.64 mL, 13.28 mmol), 2-(2-fluoro-5-(4,4,5,5-tetramethyl-1,3,2-dioxaborolan-2-yl)pyridin-3-yl)pyrimidine (Intermediate H) (2 g, 6.64 mmol), and dichloro(1,1-bis(diphenylphosphinoferrocene))palladium(II) (0.542 g, 0.664 mmol, commercially available from Sigma-Aldrich, Milwaukee, Wis.) were combined in dioxane (16.60 mL) and stirred at 110° C. overnight. LC-MS indicated that there was complete conversion to the desired product. The final reaction material was adsorbed onto a plug of silica gel and purified by chromatography through a Redi-Sep pre-packed silica gel column (12 g), eluting with a gradient of 0% to 50% EtOAc in hexane, to provide (S)-3-(4-(6-fluoro-5-(pyrimidin-2-yl)pyridin-3-yl)phenyl)-5,5-dimethyl-4-phenyloxazolidin-2-one as yellow solid. m/z (ESI) 441.3 (M+H)$^+$.

Step 2

(S)-3-(4-(6-Amino-5-(pyrimidin-2-yl)pyridin-3-yl)phenyl)-5,5-dimethyl-4-phenyloxazolidin-2-one A 2-mL glass microwave reaction vessel was charged with ammonia (2 M solution in 2-propanol) (123 µL, 5.68 mmol, commercially available from Sigma-Aldrich, Milwaukee, Wis.) and (S)-3-(4-(6-fluoro-5-(pyrimidin-2-yl)pyridin-3-yl)phenyl)-5,5-dimethyl-4-phenyloxazolidin-2-one (25 mg, 0.057 mmol) in DMSO (568 µL). The reaction mixture was stirred and heated at 100° C. in a heating block overnight. LC-MS indicated clean and complete conversion to the desired product. The material thus obtained was purified by reverse-phase preparative HPLC using 0.1% TFA in ACN/H$_2$O, gradient 15% to 90% over 20 minutes to provide (S)-3-(4-(6-amino-5-(pyrimidin-2-yl)pyridin-3-yl)phenyl)-5,5-dimethyl-4-phenyloxazolidin-2-one as a yellow solid. $^1$H NMR (500 MHz, DMSO-d$_6$) δ 8.93 (d, J=5.02 Hz, 2H), 8.84 (d, J=2.46 Hz, 1H), 8.42 (d, J=2.56 Hz, 1H), 7.56 (s, 4H), 7.43 (t, J=4.81 Hz, 1H), 7.34-7.41 (m, 2H), 7.25-7.34 (m, 3H), 5.48 (s, 1H), 1.65 (s, 3H), 0.91 (s, 3H). m/z (ESI) 438.2 (M+H)$^+$.

Example 66

Synthesis of (S)-5,5-dimethyl-4-phenyl-3-(4-(7-(pyrimidin-5-yl)-[1,2,4]triazolo[4,3-a]pyridin-3-yl)phenyl)oxazolidin-2-one

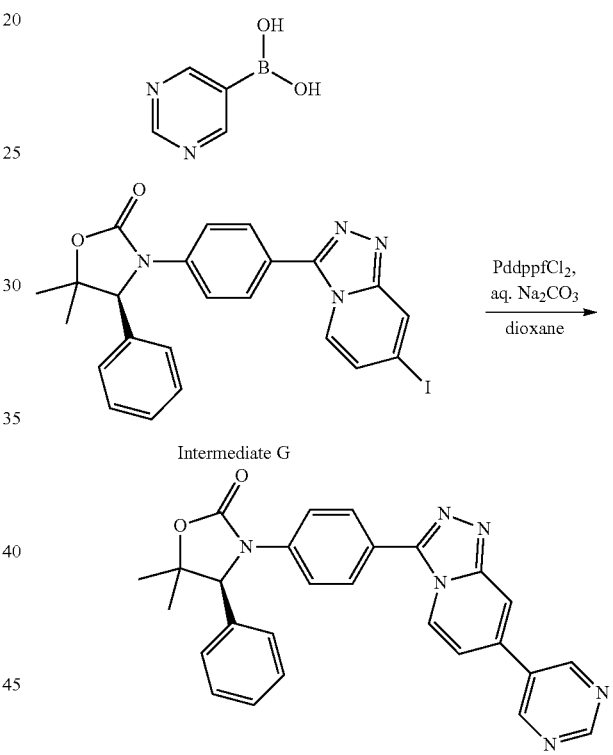

Example 66

(S)-3-(4-(7-Iodo-[1,2,4]triazolo[4,3-a]pyridin-3-yl)phenyl)-5,5-dimethyl-4-phenyloxazolidin-2-one (70 mg, 0.137 mmol), sodium carbonate (2 M, 137 µL, 0.274 mmol), 5-pyrimidinylboronic acid (17.00 mg, 0.137 mmol) (commercially available from Sigma-Aldrich, Milwaukee, Wis.), and dichloro(1,1-bis(diphenylphosphinoferrocene))palladium (II) (11.20 mg, 0.014 mmol) (commercially available from Sigma-Aldrich, Milwaukee, Wis.) were combined in dioxane (457 µL) and stirred at 130° C. for 1 hour. LC-MS indicated that there was complete conversion to the desired product. The final reaction mixture was passed through a syringe filter, and the material thus obtained was purified by reverse-phase preparative HPLC using 0.1% TFA in ACN/H$_2$O, gradient 15% to 90% over 20 minutes to provide (S)-5,5-dimethyl-4-phenyl-3-(4-(7-(pyrimidin-5-yl)-[1,2,4]triazolo[4,3-a]pyridin-3-yl)phenyl)oxazolidin-2-one (15 mg, 0.032 mmol, 23.64% yield) as a tan solid. $^1$H NMR (400 MHz, DMSO-$d_6$) δ 9.35 (s, 2H), 9.27 (s, 1H), 8.66-8.66 (m, 1H), 8.68 (dd, J=0.88, 6.36 Hz, 1H), 8.45 (dd, J=1.17, 1.86 Hz, 1H), 7.86-7.96 (m, 2H), 7.71-7.81 (m, 2H), 7.51 (dd, J=2.15, 7.43 Hz, 1H), 7.37-7.46 (m, 2H), 7.28-7.37 (m, 3H), 5.57 (s, 1H), 1.67 (s, 3H), 0.94 (s, 3H). m/z (ESI) 463.2 (M+H)$^+$.

Example 67

Synthesis of (S)-3-(4-(5,5-dimethyl-2-oxo-4-phenyloxazolidin-3-yl)phenyl)-[1,2,4]triazolo[4,3-a]pyridine-7-carbonitrile

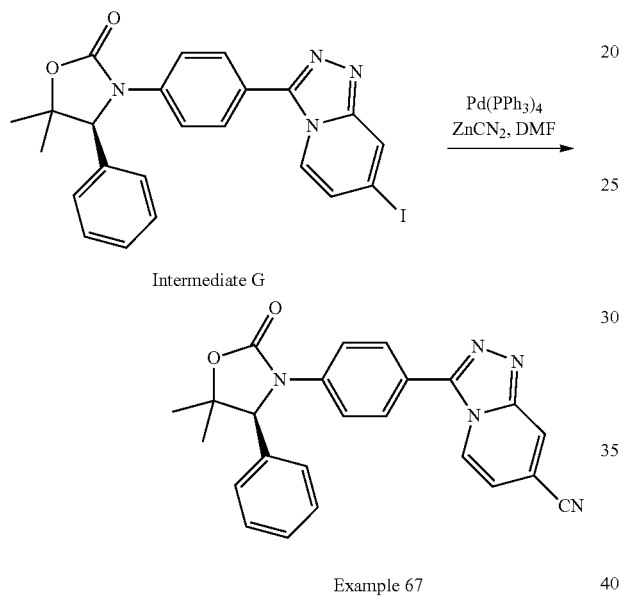

Example 67

To a 2 mL sealable tube were added (S)-3-(4-(7-iodo-[1,2,4]triazolo[4,3-a]pyridin-3-yl)phenyl)-5,5-dimethyl-4-phenyloxazolidin-2-one (70 mg, 0.137 mmol), dicyanozinc (16.11 mg, 0.137 mmol, commercially available from Sigma-Aldrich, Milwaukee, Wis.) and Pd(Ph$_3$P)$_4$ (15.85 mg, 0.014 mmol, commercially available from Sigma-Aldrich, Milwaukee, Wis.) in DMF (457 μL). The mixture was purged with nitrogen for 5 minutes and then the tube was sealed. The vessel was heated to 85° C. in a microwave oven for 1 hour. LC-MS indicated complete conversion to the desired product. The final reaction mixture was passed through a syringe filter, and the material thus obtained was purified by reverse-phase preparative HPLC using 0.1% TFA in ACN/H$_2$O, gradient 15% to 90% over 20 minutes to provide (S)-3-(4-(5,5-dimethyl-2-oxo-4-phenyloxazolidin-3-yl)phenyl)-[1,2,4]triazolo[4,3-a]pyridine-7-carbonitrile (20 mg, 0.049 mmol, 35.6% yield) as a tan solid. $^1$H NMR (400 MHz, DMSO-$d_6$) δ 8.71 (t, J=1.37 Hz, 1H), 8.66 (dd, J=1.17, 7.34 Hz, 1H), 7.84-7.90 (m, 2H), 7.72-7.78 (m, 2H), 7.37-7.44 (m, 2H), 7.28-7.37 (m, 3H), 7.22 (dd, J=1.56, 7.34 Hz, 1H), 5.56 (s, 1H), 1.67 (s, 3H), 0.94 (s, 3H). m/z (ESI) 410.2 (M+H)$^+$.

Example 68

Synthesis of (S)-3-(4-(6-chloro-[1,2,4]triazolo[4,3-b]pyridazin-3-yl)phenyl)-5,5-dimethyl-4-phenyloxazolidin-2-one

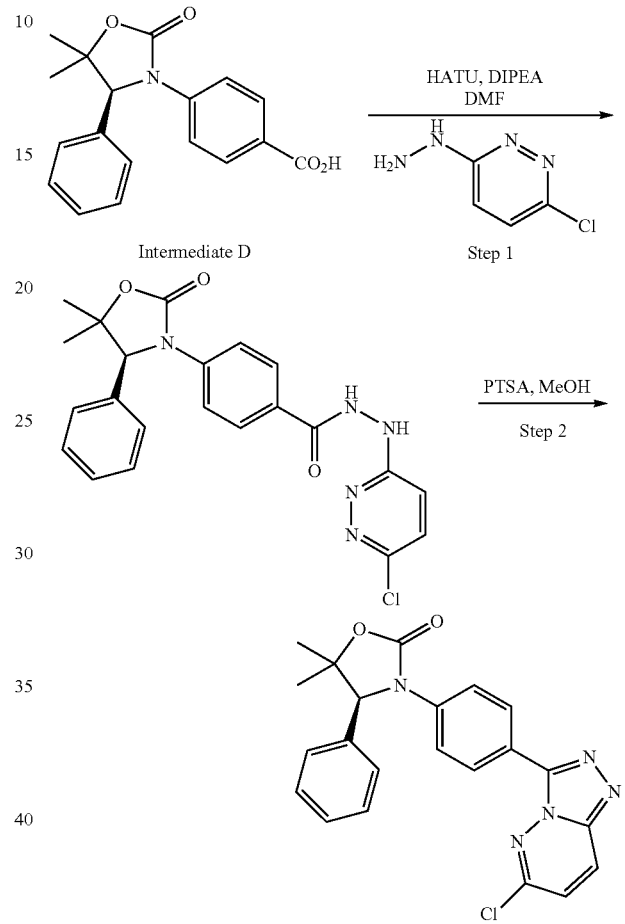

Example 68

Step 1

(S)—N'-(6-Chloropyridazin-3-yl)-4-(5,5-dimethyl-2-oxo-4-phenyloxazolidin-3-yl)benzohydrazide (S)-4-(5,5-Dimethyl-2-oxo-4-phenyloxazolidin-3-yl)benzoic acid (400 mg, 1.285 mmol) was dissolved in DMF (2.57 mL) at room temperature. To the reaction mixture, was successively added N-ethyl-N-isopropylpropan-2-amine (670 μL, 3.85 mmol), 2-(3H-[1,2,3]triazolo[4,5-b]pyridin-3-yl)-1,1,3,3-tetramethylisouronium hexafluorophosphate(V) (489 mg, 1.285 mmol, commercially available from Sigma-Aldrich, Milwaukee, Wis.) and 3-chloro-6-hydrazinylpyridazine (186 mg, 1.285 mmol). The vial was sealed and immersed in a 55° C. oil bath. After stirring overnight, LC-MS indicated complete conversion to the product. After cooling to room temperature, the reaction mixture was transferred to water in a flask in an ice/water bath. The solution was extracted w with DCM (3×50 mL). The combined organic layers were then washed with water (2×50 mL) and brine (50 mL). The organic layer was dried over Na$_2$SO$_4$. The solution was then filtered and concentrated under reduced pressure to give the product as a yellow solid. The product thus obtained was was used in the next step without further purification. m/z (ESI) 438.0 (M+H)$^+$.

Step 2

(S)-3-(4-(6-Chloro-[1,2,4]triazolo[4,3-b]pyridazin-3-yl)phenyl)-5,5-dimethyl-4-phenyloxazolidin-2-one (S)—N'-(6-Chloropyridazin-3-yl)-4-(5,5-dimethyl-2-oxo-4-phenyloxazolidin-3-yl)benzohydrazide (100 mg, 0.228 mmol) was dissolved in MeOH (2.284 mL). To the reaction mixture was added 4-methylbenzenesulfonic acid hydrate (43.4 mg, 0.228 mmol, commercially available from Sigma-Aldrich, Milwaukee, Wis.). The mixture was heated at 55° C. and was stirred overnight. LC-MS indicated incomplete conversion. The mixture was then heated at 100° C. in a microwave for 1 hour. LC-MS indicated complete and clean conversion to the desired product. The reaction mixture was then concentrated under reduced pressure and providing a yellow residue. The residue was dissolved in 2 mL of MeOH and 1 mL of NH$_4$OH, and the mixture was purified by reverse-phase preparative HPLC using 0.1% TFA in ACN/H$_2$O, gradient 20% to 90% over 20 minutes. The pure fractions were combined and diluted with 30% ammonium hydroxide, and the aqueous layer was extracted with DCM (3×20 mL) to provide (S)-3-(4-(6-chloro-[1,2,4]triazolo[4,3-b]pyridazin-3-yl)phenyl)-5,5-dimethyl-4-phenyloxazolidin-2-one (30 mg, 0.071 mmol, 31.3% yield) as a yellow solid. $^1$H NMR (500 MHz, DMSO-d$_6$) δ 8.50 (d, J=9.40 Hz, 1H), 8.20 (d, J=8.33 Hz, 2H), 7.74 (d, J=9.19 Hz, 2H), 7.52 (d, J=9.62 Hz, 1H), 7.36-7.42 (m, 2H), 7.26-7.35 (m, 3H), 5.55 (s, 1H), 1.67 (s, 3H), 0.94 (s, 3H). m/z (ESI) 420.0 (M+H)$^+$.

Example 69

Synthesis of (S)-3-(4-(1H-benzo[d][1,2,3]triazol-1-yl)phenyl)-5,5-dimethyl-4-phenyloxazolidin-2-one

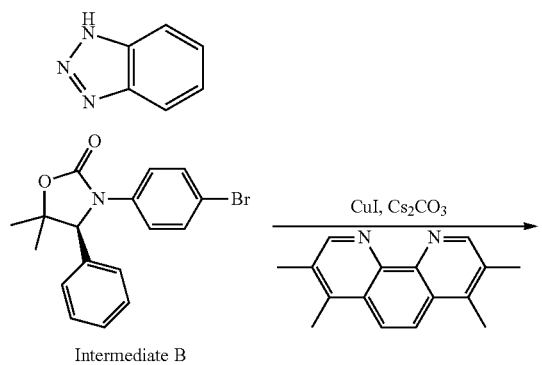

Intermediate B

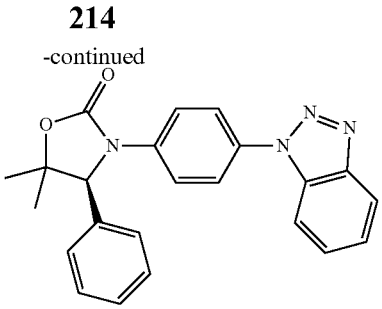

Example 69

A glass microwave reaction vessel was charged with (S)-3-(4-bromophenyl)-5,5-dimethyl-4-phenyloxazolidin-2-one (100 mg, 0.289 mmol), benzotriazole (25.3 μL, 0.289 mmol, commercially available from Sigma-Aldrich, Milwaukee, Wis.), copper (I) iodide (5.50 mg, 0.029 mmol, commercially available from Sigma-Aldrich, Milwaukee, Wis.), 3,4,7,8-tetramethyl-1,10-phenanthroline (27.3 mg, 0.116 mmol, commercially available from Sigma-Aldrich, Milwaukee, Wis.) and cesium carbonate (188 mg, 0.578 mmol) in DMSO (578 μL). The reaction mixture was stirred and heated in a heating block at 140° C. for 4 hours. LC-MS indicated complete conversion to the desired product. After cooling to room temperature, the reaction mixture was passed through a syringe filter. The material thus obtained was purified by reverse-phase preparative HPLC using 0.1% TFA in ACN/H$_2$O, gradient 20% to 90% over 20 minutes. The pure fractions were combined and diluted with 30% ammonium hydroxide, and the aqueous layer was extracted with DCM (3×20 mL) to provide (S)-3-(4-(1H-benzo[d][1,2,3]triazol-1-yl)phenyl)-5,5-dimethyl-4-phenyloxazolidin-2-one (10 mg, 0.026 mmol, 9.01% yield) as a white solid. $^1$H NMR (500 MHz, DMSO-d$_6$) δ 8.15 (d, J=8.33 Hz, 1H), 7.85 (d, J=8.33 Hz, 1H), 7.77-7.84 (m, 4H), 7.62 (dd, J=7.16, 7.91 Hz, 1H), 7.50 (d, J=7.48 Hz, 1H), 7.38-7.44 (m, J=7.60 Hz, 2H), 7.29-7.37 (m, 3H), 5.57 (s, 1H), 1.68 (s, 3H), 0.94 (s, 3H). m/z (ESI) 385.2 (M+H)$^+$.

Example 70

Synthesis of (S)-3-(4-(2-aminopyrimidin-5-yl)phenyl)-5,5-dimethyl-4-phenyloxazolidin-2-one

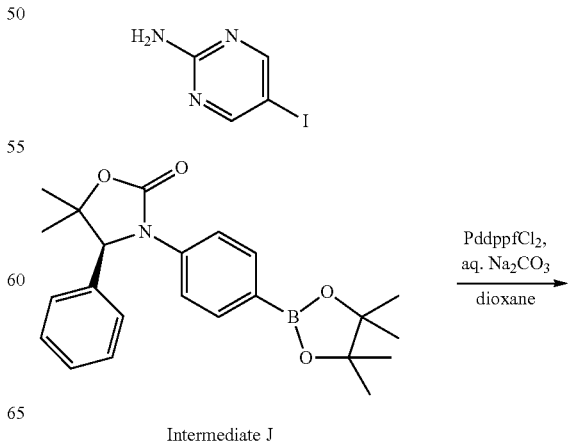

Intermediate J

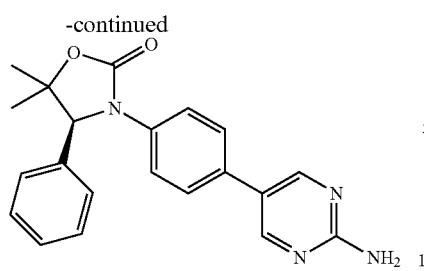

Example 70

5-Iodopyrimidin-2-amine (84 mg, 0.381 mmol, commercially available from Sigma-Aldrich, Milwaukee, Wis.), sodium carbonate (2M, 254 μL, 0.509 mmol), (S)-5,5-dimethyl-4-phenyl-3-(4-(4,4,5,5-tetramethyl-1,3,2-dioxaborolan-2-yl)phenyl)oxazolidin-2-one (100 mg, 0.254 mmol), and dichloro(1,1-bis(diphenylphosphinoferrocene))palladium (II) (20.76 mg, 0.025 mmol, commercially available from Sigma-Aldrich, Milwaukee, Wis.) were combined in dioxane (848 μL) and stirred at 130° C. for 2 hours. LC-MS indicated complete conversion to the desired product. The reaction mixture was passed through a syringe filter, and the material thus obtained was purified by reverse-phase preparative HPLC using 0.1% TFA in ACN/H$_2$O, gradient 15% to 90% over 20 minutes to provide (S)-3-(4-(2-aminopyrimidin-5-yl)phenyl)-5,5-dimethyl-4-phenyloxazolidin-2-one as a tan solid. $^1$H NMR (500 MHz, DMSO-d$_6$) δ 8.50 (s, 2H), 7.53 (s, 4H), 7.34-7.41 (m, 2H), 7.22-7.33 (m, 3H), 6.70 (s, 2H), 5.47 (s, 1H), 1.64 (s, 3H), 0.91 (s, 3H). m/z (ESI) 361.2 (M+H)$^+$.

Example 71

Synthesis of (S)-3-(3-((1,5-naphthyridin-4-yl)amino)-[1,2,4]triazolo[4,3-a]pyridin-7-yl)-5,5-dimethyl-4-phenyloxazolidin-2-one

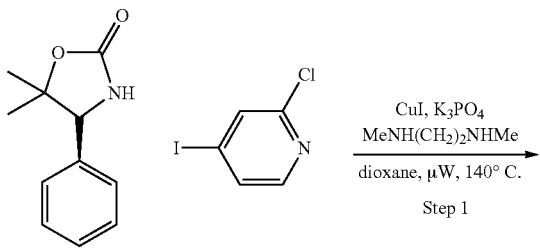

Step 1

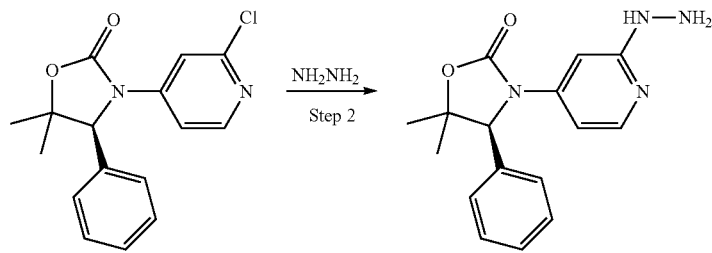

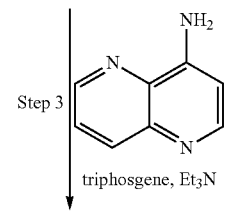

Step 3 triphosgene, Et$_3$N

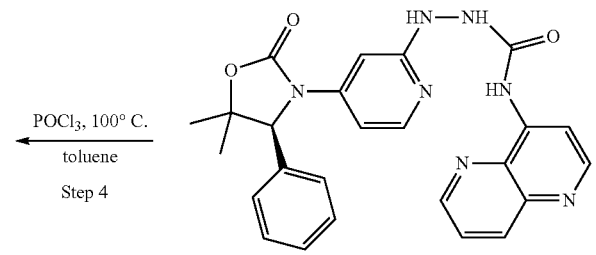

Example 71

Step 1

(S)-3-(2-Chloropyridin-4-yl)-5,5-dimethyl-4-phenyloxazolidin-2-one

To a microwave vial were added (S)-5,5-dimethyl-4-phenyloxazolidin-2-one (1 g, 5.23 mmol), 2-chloro-4-iodopyridine (1.878 g, 7.84 mmol) (commercially available from Frontier Scientific, Inc., Logan Utah), and dioxane (10.46 mL). Tribasic potassium phosphate (5.55 g, 26.1 mmol) and copper (I) iodide (0.996 g, 5.23 mmol, commercially available from Sigma-Aldrich, Milwaukee, Wis.) were then added to the vial. The vessel was purged with argon and then N,N'-dimethylethylenediamine (1.126 mL, 10.46 mmol, commercially available from Sigma-Aldrich, Milwaukee, Wis.) was added. The vessel was then irradiated at 140° C. for 40 minutes, and LC-MS indicated complete conversion to the desired product. After cooling to room temperature, the reaction mixture was passed through a syringe filtered, and the material thus obtained was absorbed onto a plug of silica gel and purified by chromatography through a Redi-Sep pre-packed silica gel column (40 g), eluting with a gradient of 0% to 10% MeOH in DCM, to provide (S)-3-(2-chloropyridin-4-yl)-5,5-dimethyl-4-phenyloxazolidin-2-one. m/z (ESI) 303.3 (M+H)+.

Step 2

(S)-3-(2-Hydrazinylpyridin-4-yl)-5,5-dimethyl-4-phenyloxazolidin-2-one

A mixture of (S)-3-(2-chloropyridin-4-yl)-5,5-dimethyl-4-phenyloxazolidin-2-one (1.44 g, 4.76 mmol) and anhydrous hydrazine (7.46 mL, 238 mmol, commercially available from Sigma-Aldrich, Milwaukee, Wis.) was heated at 140° C. for 15 minutes. LC-MS indicated complete consumption of starting material with the desired product as the major product. After cooling to room temperature, the solution was concentrated under reduced pressure. The residue thus obtained was absorbed onto a plug of silica gel and purified by chromatography through a Redi-Sep pre-packed silica gel column (12 g), eluting with a gradient of 0% to 10% MeOH in DCM, to provide (S)-3-(2-hydrazinylpyridin-4-yl)-5,5-dimethyl-4-phenyloxazolidin-2-one. m/z (ESI) 299.2 (M+H)+.

Step 3

(S)-2-(4-(5,5-Dimethyl-2-oxo-4-phenyloxazolidin-3-yl)pyridin-2-yl)-N-(1,5-naphthyridin-4-yl)hydrazinecarboxamide To a 10 mL round-bottomed flask was added triphosgene (109 mg, 0.369 mmol, commercially available from Sigma-Aldrich, Milwaukee, Wis.) in DCM (1.117 mL). The solution was cooled to 0° C., and 1,5-naphthyridin-4-amine (53.5 mg, 0.369 mmol) was added in one portion. Under argon, TEA (0.466 mL, 3.35 mmol) was then added dropwise. After stirring at room temperature for 15 minutes, (S)-3-(2-hydrazinylpyridin-4-yl)-5,5-dimethyl-4-phenyloxazolidin-2-one (100 mg, 0.335 mmol) in 6 mL of DCM was added to the reaction mixture. After stirring at room temperature overnight, LC-MS indicated good conversion to the desired product. The reaction mixture was concentrated under reduced pressure to give the product as a black solid which was used directly in the next step without further purification. m/z (ESI) 470.1 (M+H)+.

Step 4

(S)-3-(3-((1,5-Naphthyridin-4-yl)amino)-[1,2,4]triazolo[4,3-a]pyridin-7-yl)-5,5-dimethyl-4-phenyloxazolidin-2-one A mixture of (S)-2-(4-(5,5-dimethyl-2-oxo-4-phenyloxazolidin-3-yl)pyridin-2-yl)-N-(1,5-naphthyridin-4-yl)hydrazinecarboxamide (150 mg, 0.319 mmol) and POCl$_3$ (292 μL, 3.19 mmol, commercially available from Sigma-Aldrich, Milwaukee, Wis.) in toluene (6.390 mL) was heated at 100° C. After stirring for 1 hour, an additional 1.5 mL of POCl$_3$ was added to the reaction solution. After stirring for another 3 hours, the reaction mixture was concentrated under reduced pressure. The residue thus obtained was purified by reverse-phase preparative HPLC using 0.1% TFA in ACN/H$_2$O, gradient 20% to 90% over 20 minutes to provide a material which was further purified by chromatography through a Redi-Sep pre-packed silica gel column (12 g), eluting with a gradient of 0% to 10% MeOH in DCM, to provide (S)-3-(3-((1,5-naphthyridin-4-yl)amino)-[1,2,4]triazolo[4,3-a]pyridin-7-yl)-5,5-dimethyl-4-phenyloxazolidin-2-one (2.41 mg, 5.34 μmol, 1.671% yield) as greenish solid. $^1$H NMR (500 MHz, DMSO-d$_6$) δ 10.06-10.13 (m, 1H), 8.95-9.00 (m, 1H), 8.64 (br. s, 1H), 8.34-8.39 (m, 1H), 8.28 (d, J=6.09 Hz, 1H), 7.81-7.87 (m, 1H), 7.55 (d, J=9.62 Hz, 1H), 7.46-7.51 (m, 1H), 7.38-7.44 (m, 3H), 7.31-7.37 (m, 3H), 5.63 (s, 1H), 1.67 (s, 3H), 0.95 (s, 3H). m/z (ESI) 452.2 (M+H)+.

Examples 72, 73 and 131

Synthesis of (+/−)(S)-3-((1s,4R)-4-(6-amino-5-(pyrimidin-2-yl)pyridin-3-yl)cyclohexyl)-5,5-dimethyl-4-phenyloxazolidin-2-one, (+/−)(S)-3-((1 r,4S)-4-(6-amino-5-(pyrimidin-2-yl)pyridin-3-yl)cyclohexyl)-5,5-dimethyl-4-phenyloxazolidin-2-one and 3-(4-(6-amino-5-(pyrimidin-2-yl)pyridin-3-yl)cyclohex-3-en-1-yl)-5,5-dimethyl-4-phenyloxazolidin-2-one Example 72

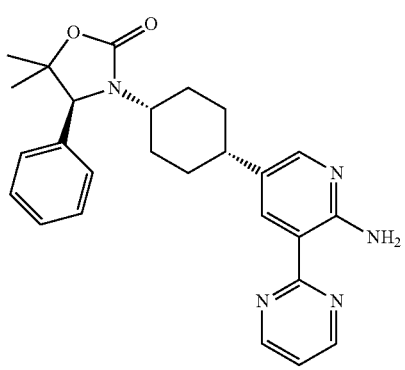

50% ee

-continued
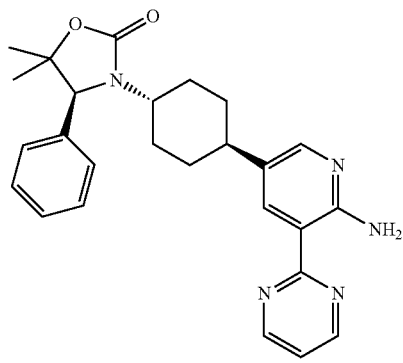
50% ee
Example 73
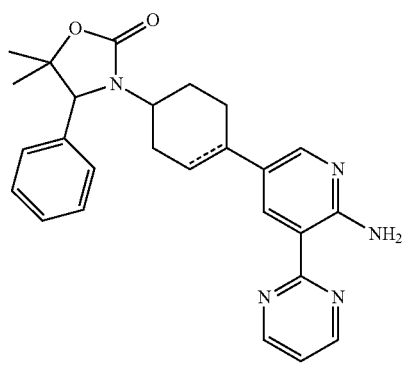
isomeric mixture (4 isomers)
Example 131
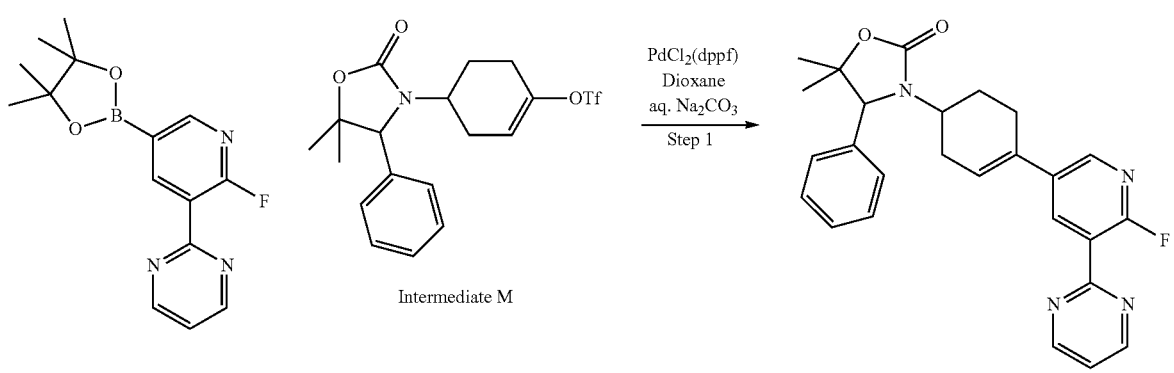
Intermediate M
Step 2 | NH₃ / DMSO

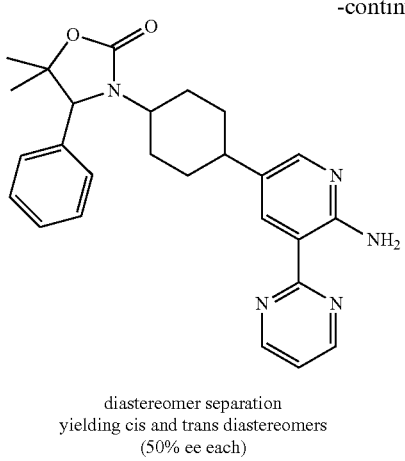

diastereomer separation
yielding cis and trans diastereomers
(50% ee each)

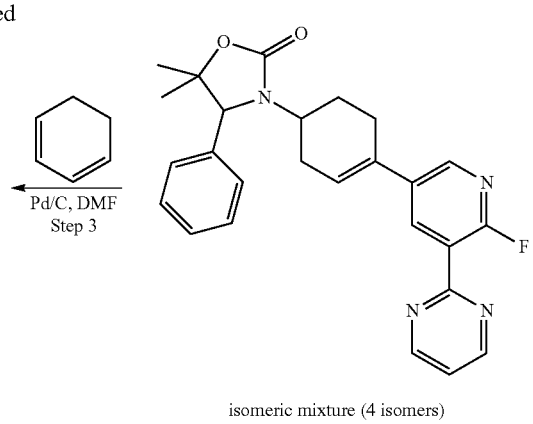

isomeric mixture (4 isomers)

Step 1

3-((R/S)-4-(6-Fluoro-5-(pyrimidin-2-yl)pyridin-3-yl)
cyclohex-3-en-1-yl)-5,5-dimethyl-4-phenyloxazolidin-2-one A microwave vial was charged with a mixture of (4R)-4-(5,5-dimethyl-2-oxo-4-phenyloxazolidin-3-yl)cyclohex-1-en-1-yl trifluoromethanesulfonate and (4S)-4-(5,5-dimethyl-2-oxo-4-phenyloxazolidin-3-yl)cyclohex-1-en-1-yl trifluoromethanesulfonate (Intermediate M) (730 mg, 1.741 mmol), 2-(2-fluoro-5-(4,4,5,5-tetramethyl-1,3,2-dioxaborolan-2-yl)pyridin-3-yl)pyrimidine (Intermediate H) (577 mg, 1.915 mmol), sodium carbonate (2 M, 2.611 mL, 5.22 mmol), and tetrakis(triphenylphosphine)palladium(0) (201 mg, 0.174 mmol) (commercially available from Strem Chemicals Inc., Newburyport, Mass.). Dioxane (8.703 mL) was added, the system was purged with argon, and the tube was sealed. The mixture was then stirred at 100° C. in the microwave for 1 hour. LC-MS indicated clean and good conversion to the desired product. The reaction mixture was filtered through Celite® brand filter aid and the filtrate was concentrated to afford a yellow oil. The oil was purified using column chromatography on silica gel (RediSep 40 g column, gradient elution with 0 to 60% EtOAc-heptane) to afford a mixture of 3-((S)-4-(6-fluoro-5-(pyrimidin-2-yl)pyridin-3-yl)cyclohex-3-en-1-yl)-5,5-dimethyl-4-phenyloxazolidin-2-one and 3-((R)-4-(6-fluoro-5-(pyrimidin-2-yl)pyridin-3-yl)cyclohex-3-en-1-yl)-5,5-dimethyl-4-phenyloxazolidin-2-one (370 mg, 0.832 mmol, 47.8% yield) as a white solid. m/z (ESI) 445.2 (M+H)$^+$.

Step 2

3-((R/S)-4-(6-Amino-5-(pyrimidin-2-yl)pyridin-3-yl)
cyclohex-3-en-1-yl)-5,5-dimethyl-4-phenyloxazolidin-2-one A 2-mL glass microwave reaction vessel was charged with ammonia, (2 M solution in 2-propanol) (1.806 mL, 83 mmol, commercially available from Sigma-Aldrich, Milwaukee, Wis.) and a mixture of 3-((S)-4-(6-fluoro-5-(pyrimidin-2-yl)pyridin-3-yl)cyclohex-3-en-1-yl)-5,5-dimethyl-4-phenyloxazolidin-2-one and 3-((R)-4-(6-fluoro-5-(pyrimidin-2-yl)pyridin-3-yl)cyclohex-3-en-1-yl)-5,5-dimethyl-4-phenyloxazolidin-2-one (370 mg, 0.832 mmol) in DMSO (8.324 mL). The reaction mixture was stirred and heated at 130° C. for 3 days. LC-MS indicated clean and good conversion to the desired product with a small amount of starting material present. After cooling to room temperature, the reaction mixture was diluted with water and extracted with EtOAc (3×). The combined organic layers were washed with water and brine and dried over MgSO$_4$. The solution was filtered and concentrated under reduced pressure. The material thus obtained was absorbed onto a plug of silica gel and purified by chromatography through a Redi-Sep pre-packed silica gel column (40 g), eluting with a gradient of 0% to 100% EtOAc in heptane, to provide Example 131 (3-(4-(6-amino-5-(pyrimidin-2-yl)pyridin-3-yl)cyclohex-3-en-1-yl)-5,5-dimethyl-4-phenyloxazolidin-2-one) (210 mg, 0.476 mmol, 57.1% yield) as yellow solid. $^1$H NMR (500 MHz, DMSO-d$_6$) δ 8.87-8.92 (m, 4H), 8.60-8.64 (m, 2H), 8.20 (d, J=2.56 Hz, 1H), 8.17 (d, J=2.46 Hz, 1H), 7.34-7.46 (m, 9H), 7.25-7.34 (m, 4H), 5.95-5.98 (m, 1H), 5.83-5.89 (m, 1H), 4.70 (s, 1H), 4.67 (s, 1H), 3.59-3.77 (m, 2H), 2.60-2.75 (m, 1H), 1.90-2.43 (m, 8H), 1.71-1.80 (m, 1H), 1.47-1.53 (m, 8H), 0.78-0.87 (m, 6H). m/z (ESI) 442.2 (M+H)$^+$.

Step 3

(+/−)(S)-3-((1 r,4S)-4-(6-Amino-5-(pyrimidin-2-yl)
pyridin-3-yl)cyclohexyl)-5,5-dimethyl-4-phenyloxazolidin-2-one A glass microwave reaction vessel was charged with (4S)-3-(4-(6-amino-5-(pyrimidin-2-yl)pyridin-3-yl)cyclohex-3-en-1-yl)-5,5-dimethyl-4-phenyloxazolidin-2-one (100 mg, 0.226 mmol), 1,3-cyclohexadiene (0.216 mL, 2.265 mmol, commercially available from Sigma-Aldrich, Milwaukee, Wis.) and palladium (10% wt. on activated carbon) (24.10 mg, 0.023 mmol, commercially available from Alfa Aesar, Ward Hill, Mass.) in DMF (1.132 mL). The reaction mixture was stirred and heated in a Initiator microwave reactor (Personal Chemistry, Biotage AB, Inc., Upssala, Sweden) at 100° C. Portions of 1,3-cyclohexadiene (0.216 mL, 2.265 mmol) and palladium (10% wt. on activated carbon) (24.10 mg, 0.023 mmol) were added to the reaction mixture at intervals of 30 minutes until the reaction was complete as indicated by LC-MS. The reaction mixture was allowed to cool to room temperature, and was passed through a syringe filter. The material thus obtained was purified by reverse-phase preparative HPLC using 0.1% TFA in ACN/H$_2$O, gradient 20% to 75% over min to provide Example 72 (3-((1s,4s)-4-(6-amino-5-(pyrimidin-2-yl)pyridin-3-yl)cyclohexyl)-5,5-dimethyl-4- phenyloxazolidin-2-one) as a yellow solid and Example 73 (3-((1r,4r)-4-(6-amino-5-(pyrimidin-2-yl)pyridin-3-yl)cyclohexyl)-5,5-dimethyl-4-phenyloxazolidin-2-one) as a yellow solid.

Data for Example 72: $^1$H NMR (500 MHz, DMSO-d$_6$) δ 8.88 (d, J=4.81 Hz, 2H), 8.45 (d, J=2.35 Hz, 1H), 7.97 (d, J=2.46 Hz, 1H), 7.39-7.46 (m, 3H), 7.33-7.39 (m, 3H), 7.20-7.33 (m, 2H), 4.64 (s, 1H), 3.47-3.59 (m, 1H), 2.32 (tt, J=3.21, 12.18 Hz, 1H), 1.81-1.92 (m, 3H), 1.58-1.73 (m, 2H), 1.48 (overlap s, 4H), 1.34-1.44 (m, 1H), 1.18-1.29 (m, 1H), 0.80 (s, 3H). m/z (ESI) 444.2 (M+H)$^+$.

Data for Example 73: $^1$H NMR (500 MHz, DMSO-d$_6$) δ 8.91 (d, J=5.13 Hz, 2H), 8.50 (d, J=2.46 Hz, 1H), 8.00 (d, J=2.14 Hz, 1H), 7.44-7.60 (m, 1H), 7.40 (t, J=4.59 Hz, 1H), 7.22-7.30 (m, 2H), 7.05-7.18 (m, 1H), 4.61 (s, 1H), 3.49-3.59 (m, 1H), 2.69-2.78 (m, 1H), 2.23-2.34 (m, 1H), 1.88-1.97 (m, 1H), 1.55-1.82 (m, 4H), 1.52 (s, 3H), 1.35-1.44 (m, 2H), 0.78 (s, 3H). m/z (ESI) 444.2 (M+H)$^+$.

Examples 74 and 75

Synthesis of (S)-3-((1r,4S)-4-(6-amino-5-(pyrimidin-2-yl)pyridin-3-yl)cyclohexyl)-5,5-dimethyl-4-phenyloxazolidin-2-one and (R)-3-((1r,4R)-4-(6-amino-5-(pyrimidin-2-yl)pyridin-3-yl)cyclohexyl)-5,5-dimethyl-4-phenyloxazolidin-2-one

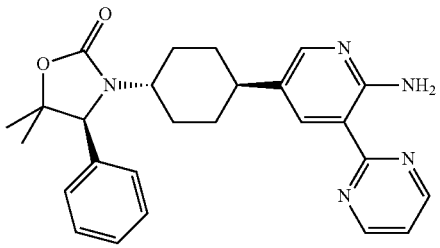

Example 74

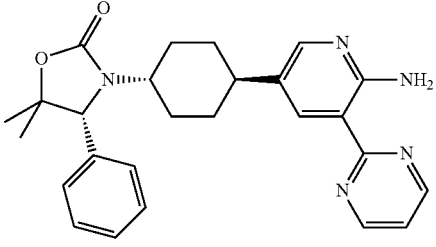

Example 75

The racemic material (Example 73) was subjected to chiral separation (Column: Chiralpak AD, 5 micron, 2 cm id×15 cm length, Mobile Phase: 40% MeOH w/0.2% diethylamine/60% CO2, Flowrate: 80 mL/min, sample dissolved in 8 mL of 1:1 MeOH:DCM, sample processed with ~8 mg/injection) to provide (S)-3-((1r,4S)-4-(6-amino-5-(pyrimidin-2-yl)pyridin-3-yl)cyclohexyl)-5,5-dimethyl-4-phenyloxazolidin-2-one (first eluting) and (R)-3-((1r,4R)-4-(6-amino-5-(pyrimidin-2-yl)pyridin-3-yl)cyclohexyl)-5,5-dimethyl-4-phenyloxazolidin-2-one (second eluting) in high optical purity (>98% ee). 3-((1s,4s)-4-(6-Fluoro-5-(pyrimidin-2-yl)pyridin-3-yl)cyclohexyl)-5,5-dimethyl-4-phenyloxazolidin-2-one was obtained as yellow solid. $^1$H NMR (500 MHz, DMSO-d$_6$) δ 8.91 (d, J=5.13 Hz, 2H), 8.50 (d, J=2.46 Hz, 1H), 8.00 (d, J=2.14 Hz, 1H), 7.44-7.60 (m, 1H), 7.40 (t, J=4.59 Hz, 1H), 7.22-7.30 (m, 2H), 7.05-7.18 (m, 1H), 4.61 (s, 1H), 3.49-3.59 (m, 1H), 2.69-2.78 (m, 1H), 2.23-2.34 (m, 1H), 1.88-1.97 (m, 1H), 1.55-1.82 (m, 4H), 1.52 (s, 3H), 1.35-1.44 (m, 2H), 0.78 (s, 3H). m/z (ESI) 444.2 (M+H)$^+$.

Examples 76 and 77

Synthesis of (S)-3-((1s,4R)-4-(6-amino-5-(1,4,5,6-tetrahydropyrimidin-2-yl)pyridin-3-yl)cyclohexyl)-5,5-dimethyl-4-phenyloxazolidin-2-one and (S)-3-((1r,4S)-4-(6-amino-5-(1,4,5,6-tetrahydropyrimidin-2-yl)pyridin-3-yl)cyclohexyl)-5,5-dimethyl-4-phenyloxazolidin-2-one To a 50 mL high pressure round-bottomed flask were added (S)-3-((S)-4-(6-amino-5-(pyrimidin-2-yl)pyridin-3-yl)cyclohex-3-en-1-yl)-5,5-dimethyl-4-phenyloxazolidin-2-one (130 mg, 0.294 mmol) and palladium (10% wt. on activated carbon) (31.3 mg, 0.029 mmol, commercially available from Alfa Aesar, Ward Hill, Mass.) in MeOH (5.889 mL). The reaction mixture was stirred at 50° C. under 45 psi of hydrogen for 3 days. After cooling to room temperature, the reaction mixture was filtered and concentrated in vacuo. Diastereomer separation was accomplished using preparative SFC using the following conditions: Column: (S, S) Whelk-O, 5 micron, 2 cm id×25 cm length, Mobile Phase: 35% MeOH w/0.2% diethylamine/65% $CO_2$, flowrate: 80 mL/min, 130 mg dissolved to 13 mg/mL in 1:1 DCM:MeOH, sample processed with ~5 mg/injection provided a first eluting peak, Example 76, and a second eluting peak, Example 77.

Example 76

(S)-3-((1 s,4R)-4-(6-Amino-5-(1,4,5,6-tetrahydropyrimidin-2-yl)pyridin-3-yl)cyclohexyl)-5,5-dimethyl-4-phenyloxazolidin-2-one: $^1$H NMR (500 MHz, DMSO-$d_6$) δ 7.78 (d, J=2.14 Hz, 1H), 7.50 (d, J=2.14 Hz, 1H), 7.21-7.45 (m, 5H), 4.61 (s, 1H), 3.45-3.55 (m, 1H), 3.34-3.41 (m, 4H), 2.58-2.67 (m, 1H), 2.21-2.34 (m, 1H), 1.90-2.01 (m, 1H), 1.53-1.83 (m, 6H), 1.51 (s, 3H), 1.32-1.42 (m, 2H), 0.78 (s, 3H). m/z (ESI) 448.2 (M+H)$^+$.

Example 77

(S)-3-((1 r,4S)-4-(6-Amino-5-(1,4,5,6-tetrahydropyrimidin-2-yl)pyridin-3-yl)cyclohexyl)-5,5-dimethyl-4-phenyloxazolidin-2-one: $^1$H NMR (500 MHz, DMSO-$d_6$) δ 7.73 (d, J=2.14 Hz, 1H), 7.54 (d, J=2.14 Hz, 1H), 7.31-7.48 (m, 5H), 4.64 (s, 1H), 3.43-3.52 (m, 1H), 3.31 (m, 4H, hidden under solvent peak), 2.15-2.24 (m, 1H), 1.85 (br. s., 3H), 1.57-1.71 (m, 4H), 1.43-1.55 (m, 4H), 1.32-1.43 (m, 1H), 1.13-1.26 (m, 1H), 0.77-0.83 (m, 3H). m/z (ESI) 448.2 (M+H)$^+$.

Example 78

Synthesis of 4-((4S)-5,5-dimethyl-2-oxo-4-phenyl-1,3-oxazolidin-3-yl)-N-8-quinolinylbenzamide

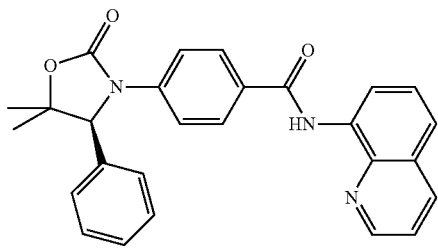 [SMILES: CC1(C)OC(=O)N(c2ccc(C(=O)Nc3cccc4cccnc34)cc2)[C@H]1c1ccccc1]

The title compound was prepared as described in General Scheme A using (S)-5,5-dimethyl-4-phenyloxazolidin-2-one (commercially available from Sigma-Aldrich, Milwaukee, Wis.). Purification was performed using preparative LC/MS with 0.1% NH$_4$OH in ACN and water as the mobile phase. The pure fractions were dried under reduced pressure to afford ((4S)-5,5-dimethyl-2-oxo-4-phenyl-1,3-oxazolidin-3-yl)-N-8-quinolinylbenzamide as a brown solid (82 mg, 0.187 mmol, 35% yield). $^1$H NMR (400 MHz, DMSO-$d_6$) δ=10.55 (s, 1H), 8.95 (dd, J=1.6, 4.2 Hz, 1H), 8.67 (dd, J=1.2, 7.6 Hz, 1H), 8.45 (dd, J=1.6, 8.3 Hz, 1H), 7.96 (d, J=8.8 Hz, 2H), 7.81-7.56 (m, 5H), 7.48-7.17 (m, 5H), 5.57 (s, 1H), 3.17 (d, J=5.1 Hz, 1H), 1.66 (s, 3H), 0.93 (s, 3H). m/z (ESI) 438.3 (M+H)$^+$.

Example 79

Synthesis of 4-((4R)-5,5-dimethyl-2-oxo-4-phenyl-1,3-oxazolidin-3-yl)-N-8-quinolinylbenzamide

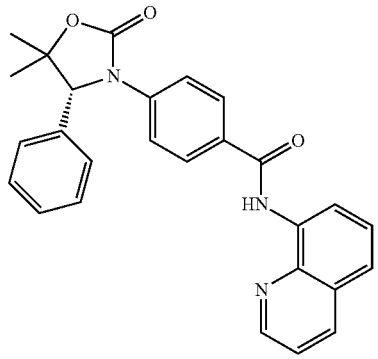 [SMILES: CC1(C)OC(=O)N(c2ccc(C(=O)Nc3cccc4cccnc34)cc2)[C@@H]1c1ccccc1]

The title compound was prepared as described in General Scheme A using (R)-5,5-dimethyl-4-phenyloxazolidin-2-one (commercially available from Sigma-Aldrich, Milwaukee, Wis.). Purification was performed using preparative LC/MS with 0.1% NH$_4$OH in ACN and water as the mobile phase. The pure fractions were concentrated under reduced pressure to afford 4-((4R)-5,5-dimethyl-2-oxo-4-phenyl-1,3-oxazolidin-3-yl)-N-8-quinolinylbenzamide as a white solid (122 mg, 0.279 mmol, 52% yield). $^1$H NMR (400 MHz, DMSO-$d_6$) δ=10.53 (s, 1H), 8.94 (dd, J=1.6, 4.3 Hz, 1H), 8.66 (dd, J=1.2, 7.5 Hz, 1H), 8.44 (dd, J=1.5, 8.3 Hz, 1H), 7.95 (d, J=8.8 Hz, 2H), 7.77-7.56 (m, 5H), 7.44-7.21 (m, 5H), 5.55 (s, 1H), 1.66 (s, 3H), 0.93 (s, 3H). m/z (ESI) 438.2 (M+H)$^+$.

Example 80

Synthesis of (4S)-5,5-dimethyl-3-(4-(2-oxo-4-phenyl-2,3-dihydro-1H-imidazol-1-yl)phenyl)-4-phenyl-1,3-oxazolidin-2-one

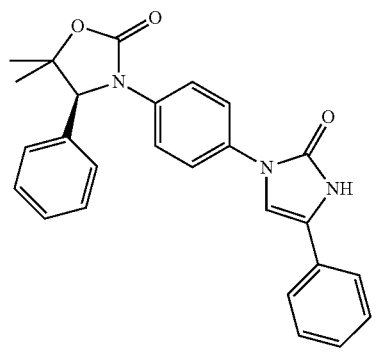 [SMILES: CC1(C)OC(=O)N(c2ccc(-n3cc(-c4ccccc4)[nH]c3=O)cc2)[C@H]1c1ccccc1]

The title compound was prepared as described in General Scheme B using intermediate C in place of intermediate B and 4-phenyl-1H-imidazol-2(3H)-one (commercially available from Sigma-Aldrich, Milwaukee, Wis.). Purification was performed using preparative LC/MS with 0.1% NH₄OH in ACN and water as the mobile phase. The pure fractions were dried under reduced pressure to afford (4S)-5,5-dimethyl-3-(4-(2-oxo-4-phenyl-2,3-dihydro-1H-imidazol-1-yl)phenyl)-4-phenyl-1,3-oxazolidin-2-one as a white solid (15 mg, 0.055 mmol, 9% yield). ¹H NMR (400 MHz, DMSO-d₆) δ=11.01 (br. s., 1H), 7.71-7.65 (m, 2H), 7.62-7.50 (m, 4H), 7.41-7.34 (m, 4H), 7.34-7.20 (m, 4H), 5.49 (s, 1H), 1.65 (s, 3H), 0.92 (s, 3H). m/z (ESI) 426.2 (M+H)⁺.

Examples 81 and 82

Synthesis of 3-(trans-4-((4S)-5,5-dimethyl-2-oxo-4-phenyl-1,3-oxazolidin-3-yl)cyclohexyl)-5-(2-pyrimidinyl)-2(1H)-pyridinone and 3-(trans-4-((4R)-5,5-dimethyl-2-oxo-4-phenyl-1,3-oxazolidin-3-yl)cyclohexyl)-5-(2-pyrimidinyl)-2(1H)-pyridinone

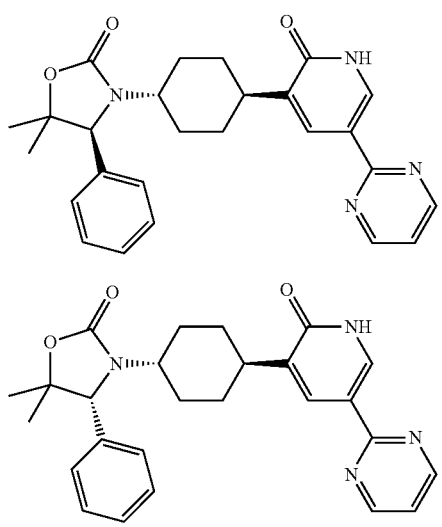

Example 81

Example 82

A racemic mixture of (+/−)-3-(trans-4-((4S/R)-5,5-dimethyl-2-oxo-4-phenyl-1,3-oxazolidin-3-yl)cyclohexyl)-5-(2-pyrimidinyl)-2(1H)-pyridinone (0.100 g, 0.225 mmol) (Example 7) was purified via SFC separation (Chiralpak Iowa column (2×25 cm), eluting with 70/30 CO₂/MeOH with 0.2% DEA; flow rate: 80 mL/min) to afford Example 81 (3-(trans-4-((4S)-5,5-dimethyl-2-oxo-4-phenyl-1,3-oxazolidin-3-yl)cyclohexyl)-5-(2-pyrimidinyl)-2(1H)-pyridinone) (0.023 g, 0.052 mmol, 23% yield) as an off-white solid (first eluting peak) and Example 82 (3-(trans-4-((4R)-5,5-dimethyl-2-oxo-4-phenyl-1,3-oxazolidin-3-yl)cyclohexyl)-5-(2-pyrimidinyl)-2(1H)-pyridinone) (0.010 g, 0.022 mmol, 10% yield) as an off-white solid (second eluting peak).

Example 81

¹H NMR (400 MHz, DMSO-d₆) δ ppm 0.80 (s, 3H), 1.01-1.45 (m, 3H), 1.48 (s, 3H), 1.60 (d, J=12.13 Hz, 1H), 1.66-1.77 (m, 1H), 1.78-1.97 (m, 3H), 2.56-2.66 (m, 1H), 3.46-3.67 (m, 1H), 4.66 (s, 1H), 6.92-7.69 (m, 6H), 8.08 (d, J=2.25 Hz, 1H), 8.20 (d, J=2.45 Hz, 1H), 8.76 (d, J=4.79 Hz, 2H), 11.76 (s, 1H). m/z (ESI) 445 (M+H)⁺.

Example 82

¹H NMR (400 MHz, DMSO-d₆) δ 0.80 (s, 3H), 1.08-1.41 (m, 4H), 1.48 (s, 3H), 1.55-1.76 (m, 2H), 1.77-1.94 (m, 3H), 3.45-3.66 (m, 1H), 4.66 (s, 1H), 7.10-7.55 (m, 6H), 8.08 (d, J=2.25 Hz, 1H), 8.20 (d, J=2.45 Hz, 1H), 8.76 (d, J=4.89 Hz, 2H), 11.88 (s, 1H). m/z (ESI) 445 (M+H)⁺.

Example 83

Synthesis of (S)-5,5-dimethyl-3-((1r,4S)-4-(2-oxo-1H-imidazo[4,5-c]pyridin-3(2H)-yl)cyclohexyl)-4-phenyloxazolidin-2-one

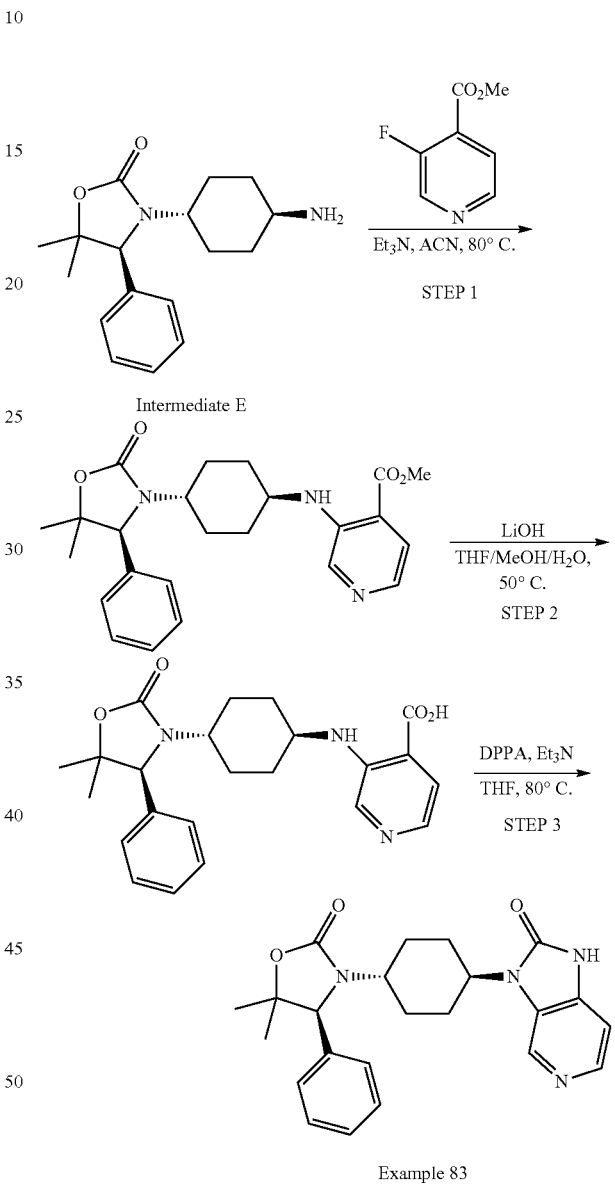

Example 83

Step 1

Methyl 3-(((1S,4r)-4-((S)-5,5-dimethyl-2-oxo-4-phenyloxazolidin-3-yl)cyclohexyl)amino)isonicotinate To a vial charged with (S)-3-((1r,4S)-4-aminocyclohexyl)-5,5-dimethyl-4-phenyloxazolidin-2-one (0.181 g, 0.628 mmol) were added ACN (2.51 mL), TEA (0.262 mL, 1.883 mmol) and methyl 3-fluoroisonicotinate (commercially available from Biogene Organics, Inc., Spring Tex.) (0.107 g, 0.690 mmol). The vessel was sealed and shaken at 80° C. for 72 hours. The mixture was dried under reduced pressure and purified with a 25 g SNAP column ramping DCM:MeOH (90:10) in DCM (0-25%, then isocratic at 25%, detection at 215 nm) providing methyl 3-(((1S,4r)-4-((S)-5,5-dimethyl-2-oxo-4-phenyloxazolidin-3-yl)cyclohexyl)amino)isonicotinate (0.184 g, 0.434 mmol, 69.2% yield) with minor impurities as a light brown oil. m/z (ESI) 424.4 (M+H)+.

Step 2

3-(((1S,4r)-4-((S)-5,5-Dimethyl-2-oxo-4-phenyloxazolidin-3-yl)cyclohexyl)amino)isonicotinic acid To a vial charged with methyl 3-(((1 S,4r)-4-((S)-5,5-dimethyl-2-oxo-4-phenyloxazolidin-3-yl)cyclohexyl)amino)isonicotinate (0.182 g, 0.430 mmol) were added THF (2.51 mL), MeOH (2.51 mL), water (2.51 mL) and LiOH (0.051 g, 2.149 mmol) respectively. The mixture was heated at 50° C. for 2 hours. The light brown solution was diluted with water, and acidified with 2 N HCl and extracted with EtOAc (2×) and DCM (2×). The organic layers were combined, dried with Na$_2$SO$_4$, filtered, and dried under reduced pressure providing 3-(((1 S,4r)-4-((S)-5,5-dimethyl-2-oxo-4-phenyloxazolidin-3-yl)cyclohexyl)amino)isonicotinic acid (0.132 g, 0.322 mmol, 75% yield) as an off-white solid. m/z (ESI) 410.3 (M+H)+.

Step 3

(S)-5,5-Dimethyl-3-((1r,4S)-4-(2-oxo-1H-imidazo[4,5-c]pyridin-3 (2H)-yl)cyclohexyl)-4-phenyloxazolidin-2-one To a flask charged with 3-(((1S,4r)-4-((S)-5,5-dimethyl-2-oxo-4-phenyloxazolidin-3-yl)cyclohexyl)amino)isonicotinic acid (0.128 g, 0.313 mmol) were added THF (1.563 mL), TEA (0.061 mL, 0.438 mmol) and diphenyl phosphoryl azide (0.094 mL, 0.438 mmol) respectively. The mixture was heated and shaken at 80° C. overnight. The mixture was then dried under reduced pressure and purified with a 25 g SNAP column ramping DCM:MeOH (90:10) in DCM 0-100% providing product eluting at 100% polar eluent which had coeluted with phosphitic acid side product from DPPA (~20%). Repurification with a HP spherical silica column (25 g, 15 μm spherical, Interchim) was only able to partially separate the impurity (had ~70 mg with ~5% impurity by LC-MS). The material was dissolved in DMSO:MeOH and purified with Gilson RP-HPLC ramping ACN in H$_2$O (25-80%, 0.1% TFA throughout). Product eluents were directly free-based with a 5 g SCX-2 column washing with MeOH then 2 M NH$_3$ in MeOH. The basic wash was dried under reduced pressure, then lyophilized from MeOH/H$_2$O yielding (S)-5,5-dimethyl-3-((1r,4S)-4-(2-oxo-1H-imidazo[4,5-c]pyridin-3(2H)-yl)cyclohexyl)-4-phenyloxazolidin-2-one (0.015 g, 0.037 mmol, 11.81% yield) as a white solid. $^1$H NMR (500 MHz, DMSO-d$_6$) δ=11.43-11.22 (m, 1H), 8.56 (s, 1H), 8.13 (d, J=5.3 Hz, 1H), 7.51-7.06 (m, 5H), 7.01 (d, J=5.1 Hz, 1H), 4.66 (s, 1H), 4.06 (t, J=12.1 Hz, 1H), 3.76-3.65 (m, 1H), 2.26-2.04 (m, 2H), 2.03-1.85 (m, 2H), 1.76 (d, J=11.9 Hz, 1H), 1.71-1.53 (m, 3H), 1.48 (s, 2H), 1.39-1.20 (m, 1H), 0.80 (s, 3H). m/z (ESI) 407.4 (M+H)+.

Examples 84, 85 and 86

Synthesis of 5,5-dimethyl-4-phenyl-3-((1 r,4r)-4-(5-phenyl-1,3,4-oxadiazol-2-yl)cyclohexyl)oxazolidin-2-one, (S)-5,5-dimethyl-4-phenyl-3-((1r,4S)-4-(5-phenyl-1,3,4-oxadiazol-2-yl)cyclohexyl)oxazolidin-2-one, and (R)-5,5-dimethyl-4-phenyl-3-((1r,4R)-4-(5-phenyl-1,3,4-oxadiazol-2-yl)cyclohexyl)oxazolidin-2-one

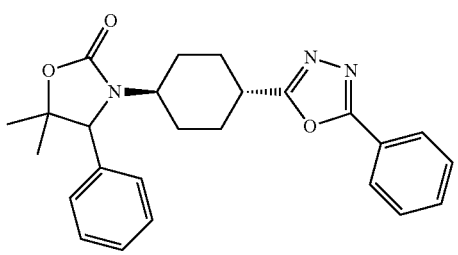

Example 84

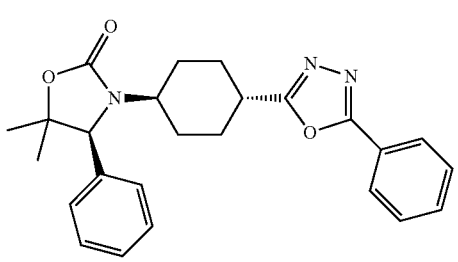

Example 85

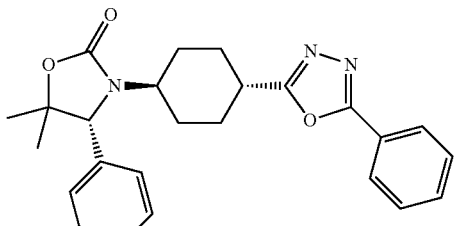

Example 86

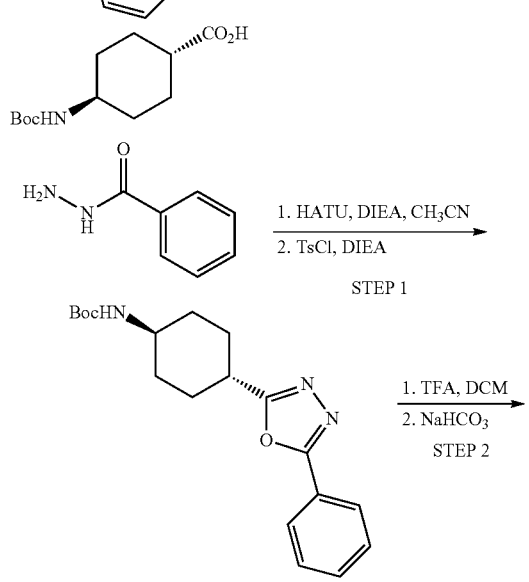

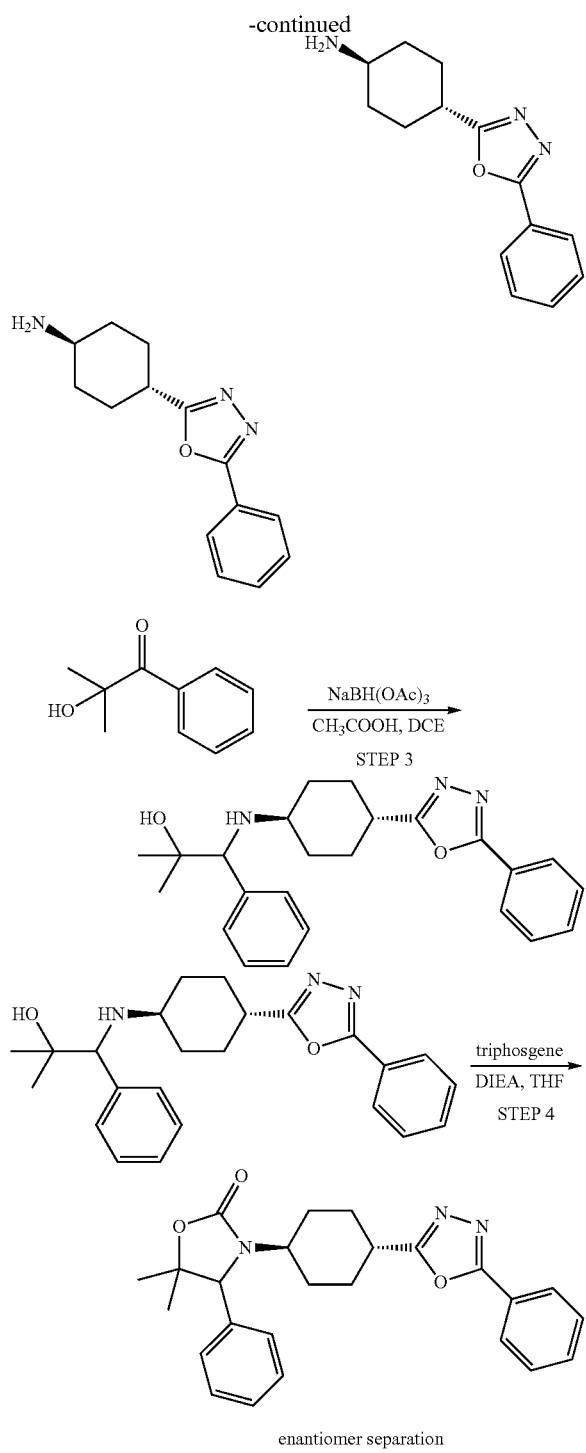

enantiomer separation

Step 1 tert-Butyl ((1r,4r)-4-(5-phenyl-1,3,4-oxadiazol-2-yl)cyclohexyl)carbamate

A 22 L three-neck flask was charged with (1r,4r)-4-((tert-butoxycarbonyl)amino)cyclohexanecarboxylic acid (commercially available from Albany Molecular Research, Inc., Albany, N.Y.) (227 g, 0.933 mol), benzohydrazide (127 g, 0.933 mol) and ACN (9 L). DIEA (488 mL, 2.799 mol) was added to the solution and the resulting mixture was stirred at room temperature for 10 minutes. HATU (390 g, 1.026 mol) was added in portions over 10 minutes and the resulting yellow mixture was stirred at room temperature for 23 hours. DIEA (325 mL, 1.866 mol) was added, followed by p-TsCl (534 g, 2.799 mol) over 5 minutes. The resulting orange suspension was then stirred at room temperature under nitrogen for 23 hours and the mixture turned dark brown. To the mixture was added DCM (2.5 L), followed by 15% ammonium hydroxide (2.5 L) and the mixture was stirred at room temperature for 1 hour. After separation, the aqueous layer was extracted with DCM (2.5 L) and the combined organic layers were dried over $MgSO_4$, filtered and concentrated under reduced pressure. The resulting residue was purified by column chromatography (eluting with hexanes/EtOAc=4:1 to 2:1) to yield 575 g of tert-butyl ((1r,4r)-4-(5-phenyl-1,3,4-oxadiazol-2-yl)cyclohexyl)carbamate which was still contaminated with p-toluene sulfonamide (as evident by $^1$H NMR) and was used in the next step without further purification.

Step 2

(1r,4r)-4-(5-Phenyl-1,3,4-oxadiazol-2-yl)cyclohexanamine

To a suspension of ((1r,4r)-4-(5-phenyl-1,3,4-oxadiazol-2-yl)cyclohexyl)carbamate (575 g) in DCM (10 L) was added TFA (1 L, 13.46 mol). The resulting mixture was stirred at room temperature for 2 hours. The mixture was concentrated under reduced pressure and the resulting solid was stirred in diethyl ether (5 L) for 1 hour. The suspension was filtered and the solid was put back in the flask and stirred in diethyl ether (5 L) for 1 hour. The operation was repeated three times and the solid thus obtained was dried to give 299 g of TFA salt with ~97% purity. The TFA salt was added to aqueous $NaHCO_3$ (prepared from 700 g of $NaHCO_3$ and 8 L of water), and the resulting suspension was stirred at room temperature for 2 hours. The white solid was filtered and then stirred in water (4 L) for 30 minutes. The solid was filtered and azeotroped with toluene to give 204 g of (1r,4r)-4-(5-phenyl-1,3,4-oxadiazol-2-yl)cyclohexanamine with >99% purity. Yield: 90% for two steps. $^1$H NMR (300 MHz, $d_6$-DMSO) δ ppm 8.05-7.90 (m, 2H), 7.65-7.50 (m, 3H), 4.80 (br, 2H), 3.35-3.20 (m, 1H), 3.00-2.80 (m, 1H), 2.13 (d, J=12.3 Hz, 2H), 1.91 (d, J=12.3 Hz, 2H), 1.60 (q, J=12.3 Hz, 2H), 1.30 (q, J=12.3 Hz, 2H). m/z (ESI) 244.0 (M+H)$^+$.

Step 3

2-Methyl-1-phenyl-1-(((1r,4r)-4-(5-phenyl-1,3,4-oxadiazol-2-yl)cyclohexyl)amino)propan-2-ol To 1-phenyl-2-hydroxy-2-methyl-1-propanone (149 μL, 0.981 mmol) in DCE (4.671 mL) at room temperature was added AcOH (53.5 μL, 0.934 mmol) followed by (1r,4r)-4-(5-phenyl-1,3,4-oxadiazol-2-yl)cyclohexanamine (227 mg, 0.934 mmol). The resulting mixture was stirred at room temperature for 5 minutes, followed by the addition of sodium triacetoxyborohydride (495 mg, 2.336 mmol). The resulting mixture was stirred at room temperature for 4 hours and an additional 0.5 eq 1-phenyl-2-hydroxy-2-methyl-1-propanone and 1 eq sodium triacetoxyborohydride were added. The mixture was stirred overnight at room temperature. The mixture was quenched with water, diluted with DCM, transferred to a separatory funnel and extracted with DCM (2×). The combined organic layers were dried with $Na_2SO_4$, filtered, and concentrated under reduced pressure. The material thus obtained was purified with MPLC (0 to 70 to 90% 90/10 DCM-MeOH in DCM) providing product (308 mg, 84%). m/z (ESI) 392.4 (M+H)$^+$.

Step 4

5,5-Dimethyl-4-phenyl-3-((1r,4r)-4-(5-phenyl-1,3,4-oxadiazol-2-yl)cyclohexyl)oxazolidin-2-one To a flask charged with 2-methyl-1-phenyl-1-((((1r,4r)-4-(5-phenyl-1,3,4-oxadiazol-2-yl)cyclohexyl)amino)propan-2-ol (308.4 mg, 0.788 mmol) were added THF (3.151 mL) and DIEA (288 μL, 1.654 mmol). The resulting mixture was cooled to 0° C. and then triphosgene (351 mg, 1.182 mmol) was added. The mixture was stirred at 0° C. for 70 minutes. The resulting mixture was diluted with DCM and water, transferred to a separatory funnel and extracted with DCM. The combined organic layers were dried with Na$_2$SO$_4$, filtered, and concentrated under reduced pressure. The material thus obtained was purified with MPLC ramping 0 to 70% EtOAc-heptane providing Example 84 (5,5-dimethyl-4-phenyl-3-((1r,4r)-4-(5-phenyl-1,3,4-oxadiazol-2-yl)cyclohexyl)oxazolidin-2-one) (232 mg, 71%). Chiral separation: Column: Chiralpak AD-H, 2×15 cm; Mobile Phase: 45% MeOH w/0.2% diethylamine/55% CO$_2$; Flowrate: 80 mL/min; Sample dissolution: 22.5 mg/mL in 1:1 DCM/MeOH, processed with 1.0 mL injections. Peak 1 was (S) isomer (Example 85: (S)-5,5-dimethyl-4-phenyl-3-((1r,4S)-4-(5-phenyl-1,3,4-oxadiazol-2-yl)cyclohexyl)oxazolidin-2-one), Peak 2 was (R) isomer (assigned on the basis of biological activity with (S) more potent than the (R) (Example 86: (R)-5,5-dimethyl-4-phenyl-3-((1r,4R)-4-(5-phenyl-1,3,4-oxadiazol-2-yl)cyclohexyl)oxazolidin-2-one). $^1$H NMR (400 MHz, DMSO-d$_6$) δ=7.99-7.92 (m, 2H), 7.65-7.53 (m, 3H), 7.48-7.14 (m, 5H), 4.65 (s, 1H), 3.56-3.43 (m, 1H), 2.91-2.76 (m, 1H), 2.24-2.14 (m, 1H), 2.09-1.99 (m, 1H), 1.96-1.86 (m, 2H), 1.71-1.56 (m, 2H), 1.55-1.45 (m, 4H), 1.33-1.18 (m, 1H), 0.80 (s, 3H). m/z (ESI) 418.2 (M+H)$^+$.

Examples 87 and 88

Synthesis of (4S)-5,5-dimethyl-3-(4-(2-oxo-1,2-dihydro-1,7-naphthyridin-3-yl)cyclohex-3-en-1-yl)-4-phenyloxazolidin-2-one and (S)-5,5-dimethyl-3-(4-(2-oxo-1,2-dihydro-1,7-naphthyridin-3-yl)phenyl)-4-phenyloxazolidin-2-one

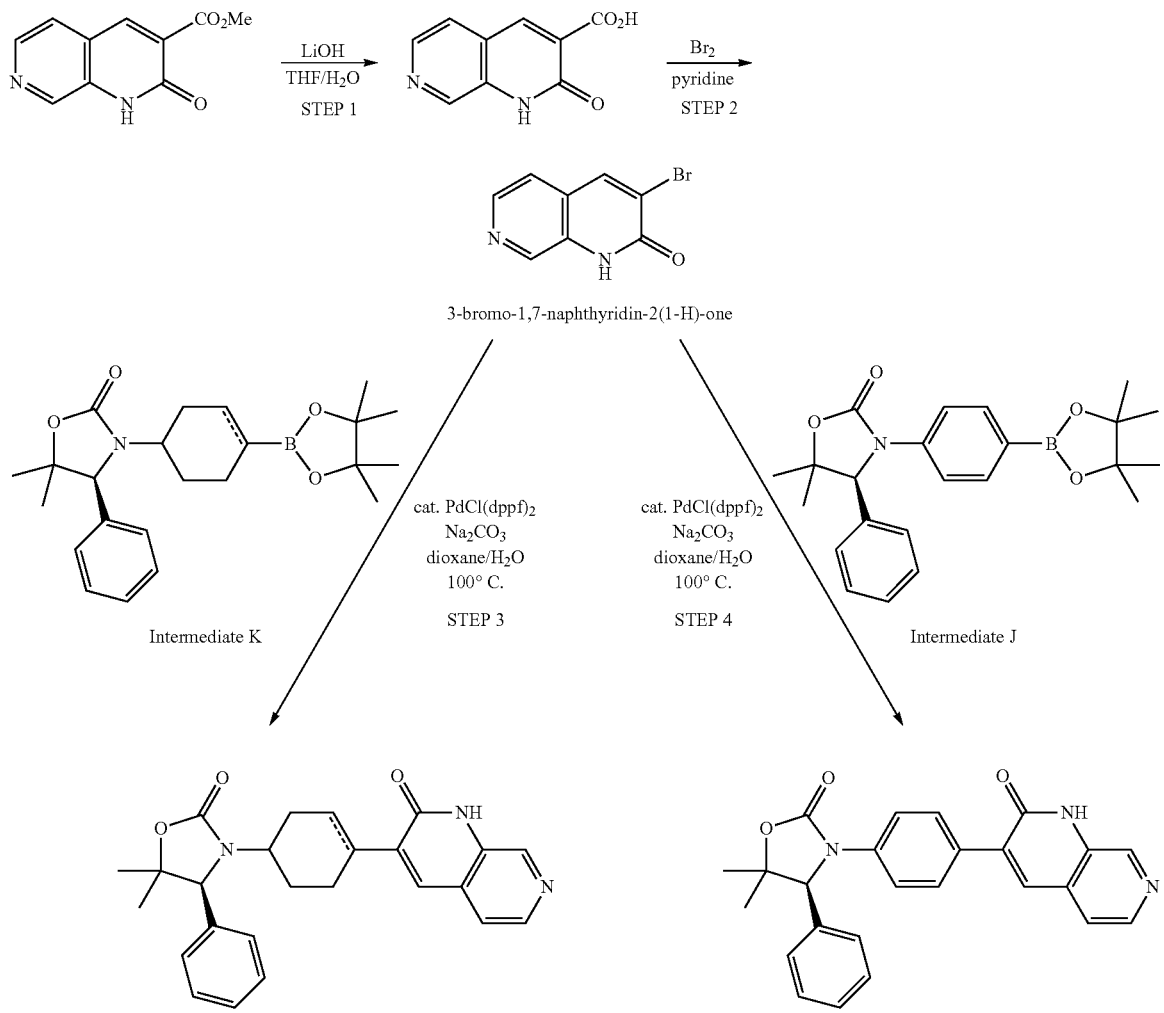

Example 87

Example 88

Step 1

1:2-Oxo-1,2-Dihydro-1,7-naphthyridine-3-carboxylic acid

A mixture of methyl 2-oxo-1,2-dihydro-1,7-naphthyridine-3-carboxylate (prepared as described in WO 2010/016846) (4.22 g, 20.67 mmol) and lithium hydroxide (2.475 g, 103 mmol) in THF (50 mL) and water (50 mL) was heated at 65° C. for 1 hour. The white precipitate was filtered, washed with water, and dried to afford a white solid. The filtrate was concentrated, dissolved in water and neutralized to pH=7 with concentrated HCl to afford a white solid. The white precipitate was filtered, washed with water, and dried. The solids were combined to afford 2-oxo-1,2-dihydro-1,7-naphthyridine-3-carboxylic acid (3.482 g, 18.31 mmol, 89% yield) as an off-white solid. m/z (ESI) 191.2 $(M+H)^+$.

Step 2

3-Bromo-1,7-naphthyridin-2(1H)-one

Bromine (0.539 mL, 10.52 mmol) was added dropwise to a 0° C. mixture of 2-oxo-1,2-dihydro-1,7-naphthyridine-3-carboxylic acid (1.00 g, 5.26 mmol) in pyridine (25.0 mL). The mixture stirred at 0° C. for 20 minutes and then at room temperature for 18 hours. The reaction was then heated at 50° C. for 18 hours. The reaction mixture was then concentrated to afford a brown solid. This material was partitioned between DCM and saturated aqueous sodium thiosulfate solution. The aqueous phase was separated and extracted with DCM. The combined organic phases were washed with water and brine, dried over anhydrous $Na_2SO_4$, filtered, and concentrated to afford a brown solid. The resulting material was purified using column chromatography on silica gel (RediSep 40 g column, gradient elution with 0-10% MeOH in DCM to afford 3-bromo-1,7-naphthyridin-2(1H)-one (0.562 g, 2.497 mmol, 47.5% yield) as a tan solid. m/z (ESI) 225.0, 227.0 $(M+H)^+$.

Step 3

(4S)-5,5-Dimethyl-3-(4-(2-oxo-1,2-dihydro-1,7-naphthyridin-3-yl)cyclohex-3-en-1-yl)-4-phenyloxazolidin-2-one A microwave vial was charged with (4S)-5,5-dimethyl-4-phenyl-3-(4-(4,4,5,5-tetramethyl-1,3,2-dioxaborolan-2-yl)cyclohex-3-en-1-yl)oxazolidin-2-one (0.124 g, 0.312 mmol), 3-bromo-1,7-naphthyridin-2(1H)-one (0.105 g, 0.468 mmol), sodium carbonate (0.099 g, 0.936 mmol), dioxane (3.0 mL), and water (0.600 mL). Dichloro[1,1'-bis(diphenylphosphino)ferrocene]palladium (II) (DCM adduct) (0.026 g, 0.031 mmol) was added, the system was purged with argon, and the tube was sealed. The mixture was irradiated at 100° C. in the microwave for 1.5 hours. The reaction mixture was then filtered through Celite® brand filter aid and the filtrate was concentrated to afford a brown oil. The oil thus obtained was purified using column chromatography on silica gel (RediSep 40 g column, gradient elution with 0-10% MeOH-EtOAc) to afford Example 87 ((4S)-5,5-dimethyl-3-(4-(2-oxo-1,2-dihydro-1,7-naphthyridin-3-yl)cyclohex-3-en-1-yl)-4-phenyloxazolidin-2-one) (50 mg, 39%) as an off-white solid as a mixture of diastereomers. m/z (ESI) 416.4 $(M+H)^+$.

Step 4

(S)-5,5-Dimethyl-3-(4-(2-oxo-1,2-dihydro-1,7-naphthyridin-3-yl)phenyl)-4-phenyloxazolidin-2-one A microwave vial was charged with (S)-5,5-dimethyl-4-phenyl-3-(4-(4,4,5,5-tetramethyl-1,3,2-dioxaborolan-2-yl)phenyl)oxazolidin-2-one (0.100 g, 0.254 mmol), 3-bromo-1,7-naphthyridin-2(1H)-one (0.063 g, 0.280 mmol), sodium carbonate (0.081 g, 0.763 mmol), dioxane (2.0 mL), and water (0.400 mL). Dichloro[1,1'-bis(diphenylphosphino)ferrocene]palladium (II) (DCM adduct) (0.021 g, 0.025 mmol) was added, the system was purged with argon, and the tube was sealed. The mixture was irradiated at 100° C. in the microwave for 1 hour. The reaction mixture was then filtered through Celite® brand filter aid, and the filtrate was concentrated to afford a brown oil. The oil thus obtained was purified using column chromatography on silica gel (RediSep 40 g column, gradient elution with 0-10% MeOH-EtOAc) to afford Example 88 ((S)-5,5-dimethyl-3-(4-(2-oxo-1,2-dihydro-1,7-naphthyridin-3-yl)phenyl)-4-phenyloxazolidin-2-one) (0.020 g, 0.049 mmol, 19.12% yield) as a white solid. $^1$H NMR (400 MHz, DMSO-$d_6$) δ ppm 0.92 (br. s., 3H), 1.65 (br. s., 3H), 5.52 (br. s., 1H), 7.09-7.49 (m, 5H), 7.49-7.93 (m, 5H), 8.08 (br. s., 1H), 8.20-8.50 (m, 1H), 8.50-8.83 (m, 1H), 12.18 (br. s., 1H). m/z (ESI) 412.3 $(M+H)^+$.

Example 89

Synthesis of (R+S)-5-methyl-3-((1r,4R)-4-(2-oxo-2,3-dihydro-1H-imidazo[4,5-c]pyridin-1-yl)cyclohexyl)-5-phenyloxazolidin-2-one

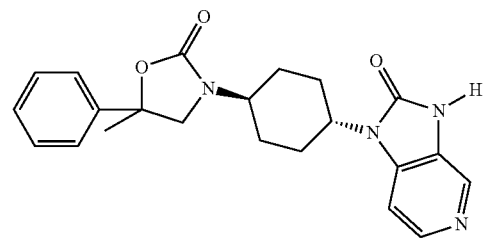 [SMILES: CC1(c2ccccc2)CN([C@H]2CC[C@H](n3c(=O)[nH]c4cnccc43)CC2)C(=O)O1]

Step 1

(4-Amino-cyclohexyl)-carbamic acid tert-butyl ester

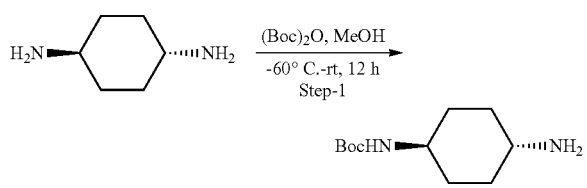

To a solution of trans-1,4-diaminocyclohexane (5 g, 43.78 mmol) in MeOH (100 mL), was added di-tert-butyl dicarbonate (4.77 g, 21.89 mmol) with MeOH (50 mL) at −60° C. over 90 minutes. The temperature was slowly raised to room temperature. The reaction mixture was then stirred for 12 hours at room temperature. After completion of reaction (monitored by TLC (TLC eluent: 10% MeOH in $CHCl_3$, Ninhydrin stain active)), the reaction mixture was concentrated to remove MeOH. Water was then added to afford a white precipitate. The resulting slurry was stirred for 10 minutes, and then the precipitate was filtered and washed with water. The filtrate (aqueous layer) was extracted with EtOAc (2×150 mL). The combined organic layers were washed with saturated NaCl solution and dried over anhydrous $Na_2SO_4$. The organic layer was concentrated under reduced pressure to afford (4-amino-cyclohexyl)-carbamic acid tert-butyl ester as a white solid, 2.6 g (27.70%). $^1$H NMR (400 MHz, DMSO-$d_6$): δ 6.67 (d, J=7.6 Hz, 1H), 3.12 (m, 1H), 2.44 (m, 1H), 1.71 (m, 4H), 1.36 (s, 9H), 1.17 (m, 2H), 1.04 (m, 2H). The filtered solid (3 g) product was the bisboc protected compound as confirmed by $^1$HNMR, and unreacted starting material remained in the aqueous layer.

Step 2 tert-Butyl ((1 r,4r)-4-((3-nitropyridin-4-yl)amino) cyclohexyl)carbamate

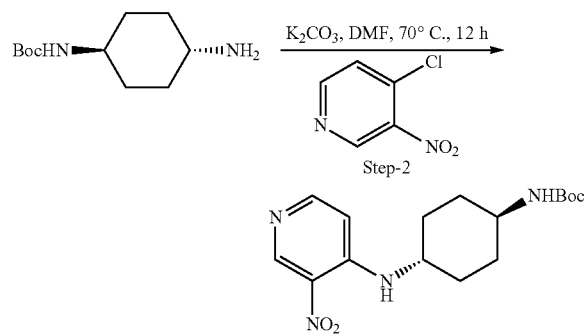

To a solution of (4-amino-cyclohexyl)-carbamic acid tert-butyl ester (2.5 g, 1.16 mmol) and 4-chloro-3-nitropyridine (2.2 g, 1.40 mmol) in DMF (15 mL), was added potassium carbonate (3.2 g, 2.32 mmol) at room temperature. The resulting reaction mixture was stirred for 12 hours at 70° C. After completion of reaction (monitored by TLC (TLC eluent: 50% EtOAc in petroleum ether, uv active)), the reaction mixture was cooled to room temperature and water was added to obtain a yellow precipitate. The slurry was stirred for 10 minutes, filtered, and then washed with water. The yellow solid was dried under vacuum to afford tert-butyl ((1r, 4r)-4-((3-nitropyridin-4-yl)amino)cyclohexyl)carbamate as a yellow solid, 2 g (90.9%), which was used in the next step without further purification. MS (ESI, pos. ion) m/z: 337.3 $^1$H NMR (300 MHz, CDCl$_3$) δ 9.21 (s, 1H), 8.28 (d, J=8.6 Hz, 1H), 8.11 (d, J=7.6 Hz, 1H), 6.70 (d, J=8.6 Hz, 1H), 4.50-4.40 (m, 1H), 3.49-3.47 (m, 2H), 2.17 (d, J=8.6 Hz, 4H), 1.45 (s, 9H), 1.31-1.28 (m, 2H). Note: The intermediate $^1$H NMR contained one proton less that it should, but the signal could be merged in the DMSO peak in aliphatic region.

Step 3 tert-Butyl ((1 r,4r)-4-((3-aminopyridin-4-yl)amino) cyclohexyl)carbamate

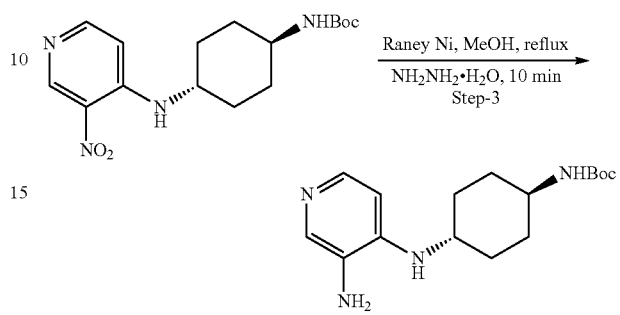

To a stirred suspension of Raney nickel (2 g) in MeOH (20 mL), was added tert-butyl ((1r,4r)-4-((3-nitropyridin-4-yl) amino)cyclohexyl)carbamate (2 g, 5.9 mmol) at room temperature. The temperature was then raised to 56° C. Hydrazine hydrate (1 mL) was added very slowly over 10 minutes, and the reaction mixture was stirred for 10 minutes at room temperature. After completion of the reaction (monitored by TLC (TLC eluent: 10% MeOH in DCM, Ninhydrin active), the reaction mixture was cooled to room temperature, filtered through Celite® brand filter aid and concentrated. Then high vacuum was applied to remove excess hydrazine hydrate. The product thus obtained was washed with diethyl ether to afford tert-butyl ((1r,4r)-4-((3-aminopyridin-4-yl)amino)cyclohexyl)carbamate as a grey solid (1 g) which was used in the next step without further purification. MS (ESI, pos. ion) m/z: 307.3 $^1$H NMR (300 MHz, DMSO-$d_6$): 7.60 (s, 1H), 7.55 (d, J=5.4 Hz, 1H), 6.82 (d, J=7.5 Hz, 1H), 6.35 (d, J=5.1 Hz, 1H), 5.00 (d, J=7.5 Hz, 1H), 4.54 (bs, 2H), 3.21-3.18 (m, 2H), 2.0-1.98 (m, 2H), 1.81-1.77 (m, 2H), 1.38 (s, 10H), 1.31-1.28 (m, 3H).

Step 4 tert-Butyl ((1r,4r)-4-(2-oxo-2,3-dihydro-1H-imidazo [4,5-c]pyridin-1-yl)cyclohexyl)carbamate

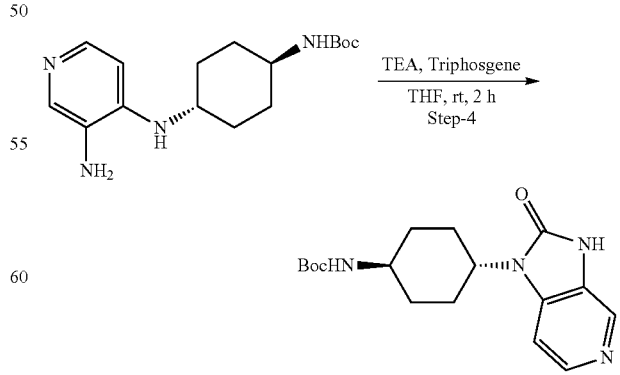

To a solution of tert-butyl ((1r,4r)-4-((3-aminopyridin-4-yl)amino)cyclohexyl)carbamate (8 g, 26.1 mmol) in THF (180 mL), were added TEA (2.6 g, 26.10 mmol) and triphosgene (7.7 g, 26.1 mmol) at 0° C. The reaction mixture was then stirred for 2 hours at room temperature. After completion of the reaction (monitored by TLC (TLC eluent: TLC eluent: 5% MeOH in DCM, UV active)), the reaction mixture was quenched with saturated NaHCO$_3$ solution and then extracted with 20% THF in EtOAc (3×200 mL). The combined organic layers were washed with brine and dried over anhydrous Na$_2$SO$_4$. The organic volatiles were removed under reduced pressure. The material thus obtained was purified by column chromatography using silica gel (60-120 mesh) eluting with 2-5% MeOH in DCM to afford [tert-butyl((1r,4r)-4-(2-oxo-2,3-dihydro-1H-imidazo[4,5-c]pyridin-1-yl)cyclohexyl)carbamate as an off white solid (5 g, 57.6%), which was used in the next step without further purification. MS (ESI, pos. ion) m/z: 332.9. $^1$H NMR (400 MHz, DMSO-d$_6$): δ 11.2 (bs, 1H), 8.18 (s, 1H), 8.14 (d, J=5.2 Hz, 1H), 7.43 (d, J=5.2 Hz, 1H), 6.83 (d, J=8 Hz, 1H), 4.13 (m, 1H), 2.18-2.12 (m, 2H), 1.91 (d, J=10.8 Hz, 3H), 1.69 (d, J=10.8 Hz, 3H), 1.39 (s, 10H).

Step 5

1-((1r,4r)-4-Aminocyclohexyl)-1H-imidazo[4,5-c]pyridin-2(3H)-one hydrochloride

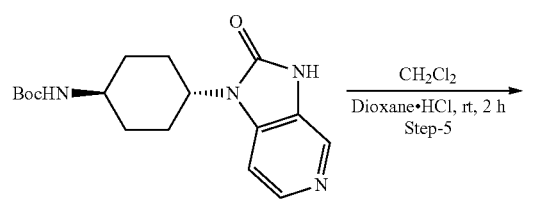

To a solution of [[tert-butyl((1r,4r)-4-(2-oxo-2,3-dihydro-1H-imidazo[4,5-c]pyridin-1-yl)cyclohexyl)carbamate (7 g, 21.0 mmol) in DCM (30 mL), was added saturated dioxane HCl (30 mL) at room temperature. The reaction mixture was then stirred for 2 hours at room temperature. After completion of the reaction (monitored by TLC (TLC eluent: 10% MeOH in DCM, uv active)), the reaction mixture was concentrated and diethyl ether (50 mL) was added to precipitate a solid. The resulting slurry was stirred for 10 minutes and then the diethyl ether was decanted away to afford solid 1-((1r,4r)-4-aminocyclohexyl)-1H-imidazo[4,5-c]pyridin-2(3H)-one hydrochloride (4.2 g, 75%), which was used in the next step without further purification. MS (ESI, pos. ion) m/z: 233.0. $^1$H NMR (400 MHz, DMSO-d$_6$): δ 12.43 (bs, 1H), 8.53-8.50 (m, 2H), 8.27 (bs, 2H), 8.08 (d, J=6.4 Hz, 1H), 4.30 (m, 1H), 3.23 (m, 1H), 2.24-2.21 (m, 2H), 2.12 (d, J=11.2 Hz, 2H), 1.85 (d, J=10.8 Hz, 2H), 1.58 (m, 2H).

Step 6

2-Phenylpropane-1,2-diol

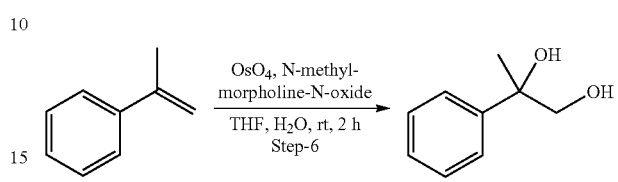

To a solution of in prop-1-en-2-ylbenzene (commercially available from Sigma-Aldrich, Milwaukee, Wis.)(5 g, 42.3 mmol) in a THF (70 mL): and H$_2$O (25 mL) mixture, were added N-methylmorpholine N-oxide (4.95 g, 42.3 mmol) and osmium tetroxide (1.0 mg, 4.2 mmol) at 0° C. The resulting reaction mixture was stirred for 2 hours at room temperature. After completion of the reaction (monitored by TLC (TLC eluent: 50% EtOAc in petroleum ether, UV active)), the reaction mixture was diluted with water and extracted with EtOAc. The combined organic layers were washed with water, saturated NaCl solution, and dried over anhydrous Na$_2$SO$_4$. The solvents were removed under reduced pressure to provide an initial product which was purified by column chromatography using silica gel (60-120 mesh) and eluting with 30-60% EtOAc in hexane to afford 2-phenylpropane-1,2-diol (3.2 g, 50%) as a colorless liquid. $^1$H NMR (300 MHz, CDCl$_3$): δ 7.47-7.44 (m, 2H), 7.44-7.35 (m, 2H), 7.30-7.26 (m, 1H), 3.81 (d, J=11.1 Hz, 1H), 3.64 (d, J=11.1 Hz, 1H), 1.38 (s, 3H).

Step 7

2-Hydroxy-2-phenylpropanal

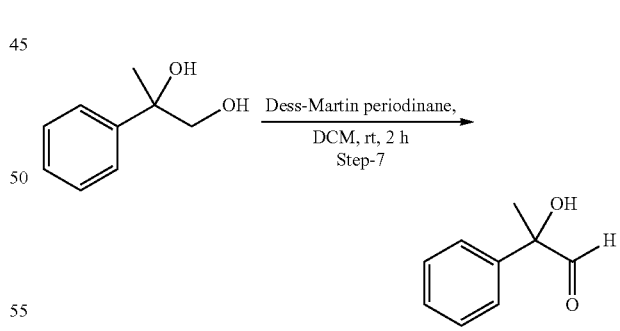

To a solution of 2-phenylpropane-1,2-diol (300 mg, 1.972 mmol) in DCM (60 mL) was added Dess-Martin periodinane (836 mg, 1.972 mmol) at 0° C. The reaction mixture was then stirred for 2 hours at room temperature. After completion of reaction (monitored by TLC (TLC eluent: 50% EtOAc in petroleum ether, UV active)), the reaction mixture was quenched with saturated NaHCO$_3$ solution and extracted with EtOAc. The combined organic layers were washed with water, saturated NaCl solution and dried over anhydrous Na$_2$SO$_4$. The solvents were removed under reduced pressure providing 2-hydroxy-2-phenylpropanal (250 g) as a colorless liquid, which was used without further purification.

Step 8

1-((1r,4r)-4-((2-Hydroxy-2-phenylpropyl)amino)cyclohexyl)-1H-imidazo[4,5-c]pyridin-2(3H)-one

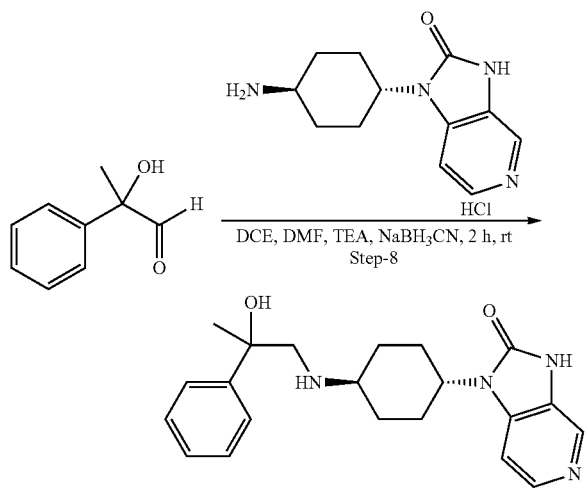

To a suspension of 2-hydroxy-2-phenylpropanal (4 g, 0.0266 mol) and 1-((1r,4r)-4-aminocyclohexyl)-1H-imidazo[4,5-c]pyridin-2(3H)-one hydrochloride (7.1 g, 0.0266 mol) in DCM:DMF (1:1), was added TEA (0.0532 mol). The reaction mixture was stirred for 30 minutes at room temperature. Next, NaBH₃CN (0.0532 mol) was added, and the reaction mixture was stirred for 2 hours at room temperature. After completion of the reaction (monitored by TLC (TLC eluent: 5% MeOH in DCM, KMnO₄ active)), the reaction mixture was quenched with saturated NaHCO₃ solution and extracted with EtOAc (5 times). The combined organic layers were washed with water, saturated NaCl solution and dried over anhydrous Na₂SO₄. Solvents were removed under reduced pressure to provide an initial product which was purified by column chromatography using silica gel (60-120 mesh) and eluting with 2-5% MeOH in DCM to afford 1-((1r,4r)-4-((2-hydroxy-2-phenylpropyl)amino)cyclohexyl)-1H-imidazo[4,5-c]pyridin-2(3H)-one as an off white solid (1.5 g, 0.0266 mol). MS (ESI, pos.ion) m/z: 367.1.

Step 9

(R+S)-5-Methyl-3-((1r,4R)-4-(2-oxo-2,3-dihydro-1H-imidazo[4,5-c]pyridin-1-yl)cyclohexyl)-5-phenyloxazolidin-2-one

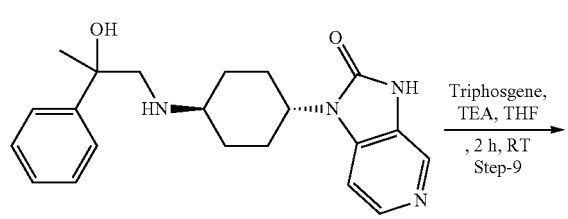

Triphosgene, TEA, THF, 2 h, RT
Step-9

-continued

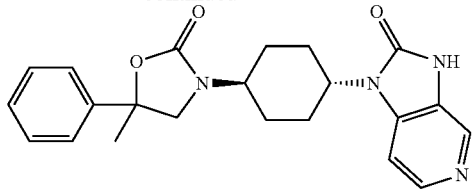

To a solution of 1-((1r,4r)-4-((2-hydroxy-2-phenylpropyl)amino)cyclohexyl)-1H-imidazo[4,5-c]pyridin-2(3H)-one (3 g, 0.0081 mol) in THF (9 mL) were added TEA (0.0081 mol) and triphosgene (0.820 g, 0.0081 mol) at 0° C. The reaction mixture was stirred for 2 hours at room temperature. After completion of the reaction (monitored by TLC (TLC eluent: 5% MeOH in DCM, UV active)), the reaction mixture was quenched with saturated NaHCO₃ solution and extracted with EtOAc. The combined organic layers were washed with water, saturated NaCl solution, and dried over anhydrous Na₂SO₄. Solvent was removed under reduced pressure and the resulting product was purified using column chromatography using 60-120 mesh silica gel and triturated with EtOAc to afford (R+S)-5-methyl-3-((1r,4R)-4-(2-oxo-2,3-dihydro-1H-imidazo[4,5-c]pyridin-1-yl)cyclohexyl)-5-phenyloxazolidin-2-one (270 mg, 8.4%). MS (ESI, pos.ion) m/z: 393.1. ¹H-NMR (400 MHz, DMSO-d₆): δ 11.83 (s, 1H), 8.20 (d, J=6.4 Hz, 1H), 8.11 (s, 1H), 7.88 (d, J=6.4 Hz, 1H), 7.42-7.41 (m, 4H), 7.34-7.33 (m, 1H), 4.23-4.11 (m, 1H), 3.80-3.73 (m, 2H), 3.76 (m, 1H), 3.63 (m, 1H), 2.22-2.18 (m, 2H), 1.90-1.80 (m, 2H), 1.80-1.70 (m, 2H), 1.68 (s, 3H), 1.61-1.60 (m, 1H).

Example 90

Synthesis of (R)-5-methyl-3-((1r,4R)-4-(2-oxo-2,3-dihydro-1H-imidazo[4,5-c]pyridin-1-yl)cyclohexyl)-5-phenyloxazolidin-2-one

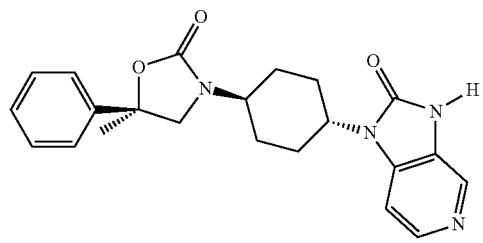 [SMILES: C[C@@]1(c2ccccc2)CN([C@H]2CC[C@H](n3c(=O)[nH]c4cnccc43)CC2)C(=O)O1]

The title compound was isolated as peak no. 1 in >99% ee by chiral resolution of Example 89 using SFC preparative column chromatography with a Chiralpak AS 5 micron, 2 cm id×15 cm length column with 25% MeOH with 0.2% DEA at 80 mL/min as the eluent. Absolute configuration was assigned arbitrarily. See Example 89 analytical data.

Example 91

Synthesis of (S)-5-methyl-3-((1r,4S)-4-(2-oxo-2,3-dihydro-1H-imidazo[4,5-c]pyridin-1-yl)cyclohexyl)-5-phenyloxazolidin-2-one

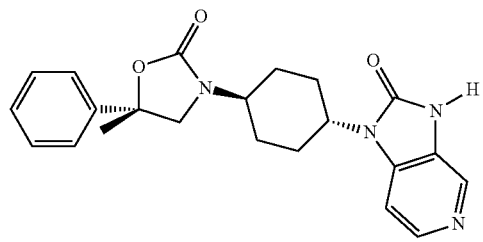 [SMILES: C[C@]1(c2ccccc2)CN([C@H]2CC[C@H](n3c(=O)[nH]c4cnccc43)CC2)C(=O)O1]

Example 92

Synthesis of 1-((1R,4r)-4-((R+S)-5-methyl-2-oxo-5-phenyloxazolidin-3-yl)cyclohexyl)-2-oxo-2,3-dihydro-1H-benzo[d]imidazole-5-carbonitrile

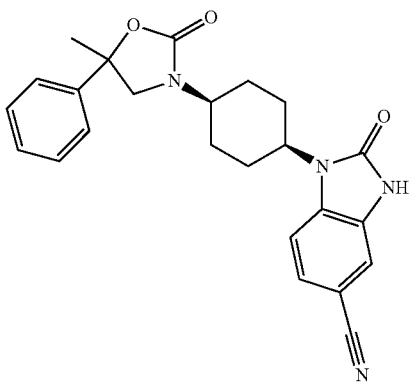 [SMILES: CC1(c2ccccc2)CN([C@H]2CC[C@@H](n3c(=O)[nH]c4cc(C#N)ccc43)CC2)C(=O)O1]

The title compound was isolated as peak no. 2 in >99% ee by chiral resolution of Example 89 using SFC preparative column chromatography with a Chiralpak AS 5 micron, 2 cm id×15 cm length column with 25% MeOH with 0.2% DEA at 80 mL/min as the eluent. Absolute configuration was assigned arbitrarily. See Example 89 analytical data.

Step 1

(4-Amino-cyclohexyl)-carbamic acid tert-butyl ester

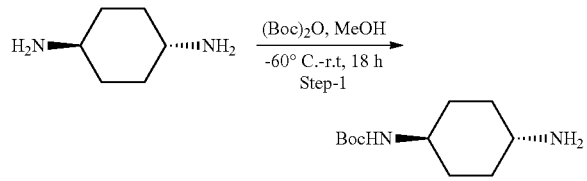

To a solution of trans-1,4-diaminocyclohexane (25.0 g, 218.93 mmol) in MeOH (500 mL), was added di-tert-butyl dicarbonate (4.77 g, 21.89 mmol) with MeOH (50 mL) at −60° C. over 3 hours. The temperature was slowly raised to ambient temperature, and the reaction mixture was stirred for 18 hours. After completion of reaction (monitored by TLC (TLC eluent: 10% MeOH in CHCl$_3$, Ninhydrin stain active)), the reaction mixture was concentrated to remove MeOH. Water (500 mL) was then added to afford a white precipitate. The mixture was further stirred for 10 minutes and then the precipitate was filtered and washed with water. The filtrate (aqueous layer) was extracted with EtOAc (3×600 mL). The combined organic layers were washed with saturated NaCl solution (2×300 mL), and separated and further dried on anhydrous Na$_2$SO$_4$. The organic layer was concentrated under reduced pressure to afford (4-amino-cyclohexyl)-carbamic acid tert-butyl ester as a white solid (10.5 g, 22.34%). The filtered solid product was bisboc protected compound and unreacted starting material remained in the aqueous layer. $^1$H NMR (300 MHz, DMSO-d$_6$) δ 6.65 (d, J=8.2 Hz, 1H), 3.12 (br, 1H), 2.47-2.36 (m, 1H), 1.73-1.65 (m, 4H), 1.37 (s, 9H), 1.18-0.96 (m, 4H). MS (ESI, pos. ion) m/z: 215.1 Two protons were missing in the $^1$H NMR and are due to the H$_2$O peak overlap in the NMR. The amine proton got exchanged with a water peak.

Step 2 tert-Butyl((1R,4R)4((4cyano2nitrophenyl)amino)-cyclohexyl)carbamate

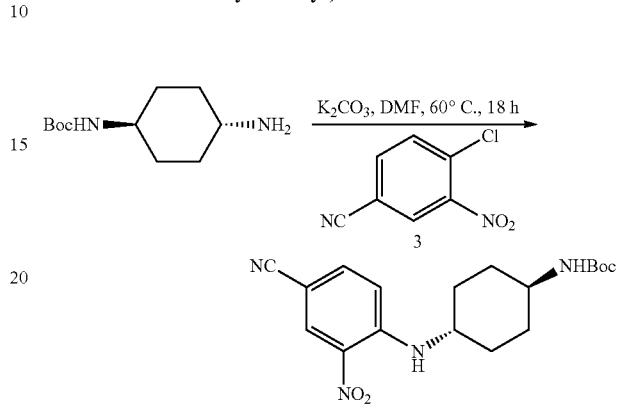

To a solution of (4-amino-cyclohexyl)-carbamic acid tert-butyl ester (10.5 g, 48.99 mmol) and 4-chloro-3-nitrobenzonitrile (commercially available from Sigma-Aldrich, Milwaukee, Wis.)(9.0 g, 49.29 mmol) in DMF (100 mL), was added potassium carbonate (13.6 g, 98.55 mmol) at ambient temperature. The resulting reaction mixture was stirred for 18 hours at 60° C. After completion of reaction (monitored by TLC (TLC eluent: 30% EtOAc in petroleum ether, UV active, Ninhydrin stain active)), the reaction mixture was cooled to ambient temperature and water (300 mL) was added providing a yellow precipitate. The resulting mixture was stirred for 10 minutes, filtered and washed with water (1000 mL). The material thus obtained was dried under vacuum affording tert-butyl ((1Rr, 4R)-4-((3-nitropyridin-4-yl)amino)cyclohexyl)carbamate as a yellow solid (16 g, 89.88%). This solid was directly used in the next step without further purification.

Step 3 tert-Butyl((1R,4R)4((2amino4cyanophenyl)amino) cyclohexyl)-carbamate

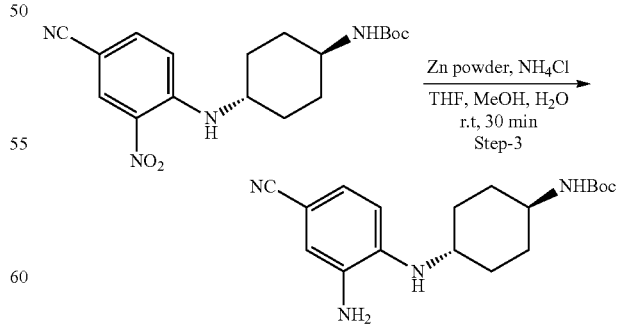

To a solution of tert-butyl ((1R,4R)-4-((4-cyano-2-nitrophenyl)amino)cyclohexyl)carbamate (16.0 g, 44.44 mmol) in MeOH (200 mL) and THF (200 mL), was added aqueous NH$_4$Cl (11.88 g, 222.11 mmol, in 200 mL of water) followed by zinc powder (14.52 g, 221.81 mmol) at ambient temperature. The resulting reaction mixture was stirred for 30 minutes at ambient temperature. After completion of reaction (monitored by TLC (TLC eluent: 50% EtOAc in petroleum ether, uv active, Ninhydrin stain active)). The reaction mixture was concentrated under reduced pressure to remove solvents and then water (500 mL) was added and the mixture was stirred for 10 minutes. Water was added, and the resulting precipitate was filtered and washed with water (300 mL). The material thus obtained was dried under vacuum to afford tert-butyl ((1r,4r)-4-((2-amino-4-cyanophenyl)amino)cyclohexyl)carbamate as brown solid (13.0 g, 88.61%). $^1$H NMR (300 MHz, DMSO-$d_6$) δ 6.89 (dd, J=8.3, 2.1 Hz, 1H), 6.81 (d, J=7.9 Hz, 1H), 6.75 (d, J=2.0 Hz, 1H), 6.49 (d, J=8.3 Hz, 1H), 5.09 (d, J=7.4 Hz, 1H), 4.98 (s, 1H), 3.29-3.18 (m, 3H), 1.97 (d, J=10.2 Hz, 2H), 1.81 (s, 2H), 1.38 (s, 9H), 1.28 (t, J=10.1 Hz, 4H). MS (ESI, pos. ion) m/z: 331.1.

Step 4 tert-Butyl ((1R,4R)-4-(5-cyano-2-oxo-2,3-dihydro-1H-benzo[d]imidazol-1-yl)cyclohexyl)carbamate

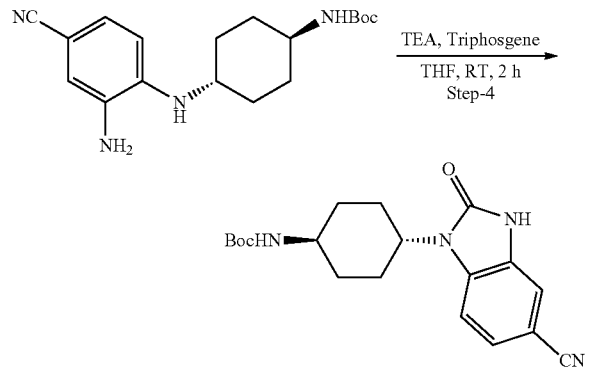

To a solution of tert-butyl ((1r,4r)-4-((2-amino-4-cyanophenyl)amino)cyclohexyl)carbamate (13 g, 39.39 mmol) in THF (250 mL), were added TEA (3.986 g, 39.39 mmol) and triphosgene (11.69 g, 39.39 mmol) at 0° C. The reaction mixture was then stirred for 2 hours at ambient temperature. After completion of reaction (monitored by TLC (TLC eluent: TLC eluent: 50% EtOAc in petroleum ether, UV active)), the reaction was quenched with saturated NaHCO$_3$ solution (250 mL) at 0° C. and concentrated under reduced pressure to remove solvent. Water was added, and the resulting precipitate was filtered and washed with water. The mixture was dried under vacuum affording tert-butyl ((1r,4r)-4-(5-cyano-2-oxo-2,3-dihydro-1H-benzo[d]imidazol-1-yl)cyclohexyl) carbamate as an off-white solid (13 g, 92.85%). $^1$H NMR (400 MHz, DMSO-$d_6$) δ 7.52 (d, J=8.5 Hz, 1H), 7.40 (d, J=8.4 Hz, 1H), 7.34 (s, 1H), 6.82 (d, J=8.2 Hz, 1H), 4.19-4.09 (m, 1H), 2.20 (q, J=12.9 Hz, 2H), 1.89 (d, J=12.0 Hz, 2H), 1.67 (d, J=12.6 Hz, 2H), 1.47-1.27 (m, 11H). MS (ESI, pos. ion) m/z: 357.1 Note: two protons under H$_2$O peak.

Step 5

1-((1R,4R)-4-Aminocyclohexyl)-2-oxo-2,3-dihydro-1H-benzo[d]imidazole-5-carbonitrile

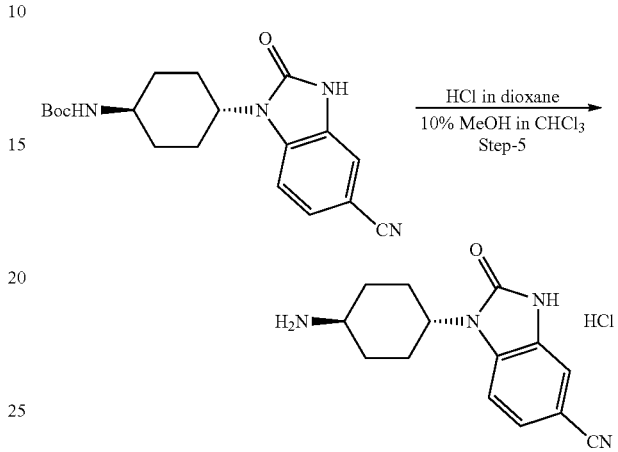

To a solution of tert-butyl ((1R,4R)-4-(5-cyano-2-oxo-2,3-dihydro-1H-benzo[d]imidazol-1-yl)cyclohexyl)carbamate (13 g, 36.473 mmol) in 10% MeOH in CHCl$_3$ (250 mL), was added saturated dioxane HCl (50 mL) at 0° C. The reaction mixture was then stirred for 2 hours at ambient temperature. After completion of reaction (monitored by TLC (TLC eluent: 10% MeOH in DCM, UV active)), the reaction mixture was concentrated and diethyl ether (100 mL) was added providing a precipitate. The mixture was stirred for 10 minutes and then the diethyl ether was decanted away. The solid was dried under reduced pressure to afford 1-((1r,4r)-4-aminocyclohexyl)-2-oxo-2,3-dihydro-1H-benzo[d]imidazole-5-carbonitrile hydrochloride as an off white solid (11 g). $^1$H NMR (400 MHz, DMSO-$d_6$) δ 11.41 (s, 1H), 8.06 (d, J=5.2 Hz, 2H), 7.60 (d, J=8.3 Hz, 1H), 7.47 (dd, J=8.6, 1.5 Hz, 1H), 7.38 (d, J=1.7 Hz, 1H), 4.20 (m, 1H), 3.28-3.18 (m, 1H), 2.25-2.23 (m, 2H), 2.12-2.04 (m, 2H), 1.76 (dd, J=13.1, 3.9 Hz, 2H), 1.55-1.52 (m, 2H). MS (ESI, pos. ion) m/z: 257.1.

Step 6

1-((1r,4r)-4-((2-Hydroxy-2-phenylpropyl)amino)cyclohexyl)-2-oxo-2,3-dihydro-1H-benzo[d]imidazole-5-carbonitrile

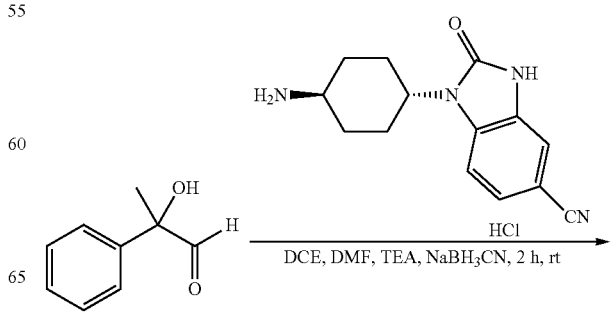

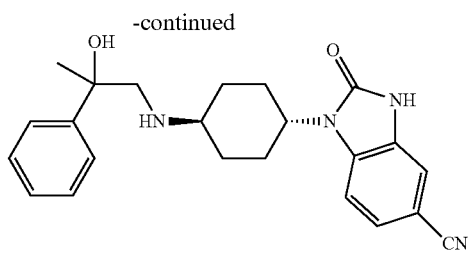

To a suspension of 2-hydroxy-2-phenylpropanal (200 mg, 1.332 mmol) and 1-((1 r,4r)-4-aminocyclohexyl)-2-oxo-2,3-dihydro-1H-benzo[d]imidazole-5-carbonitrile hydrochloride (341 mg, 1.332 mmol) in DCM:DMF (1:1), was added TEA (1.332 mmol). The reaction mixture was stirred for 30 minutes at room temperature. NaBH$_3$CN (2 equiv) was then added and the reaction mixture was stirred for 2 hours at room temperature. After completion of the reaction (monitored by TLC (TLC eluent: 5% MeOH in DCM, KMnO$_4$ active)), the reaction mixture was quenched with saturated NaHCO$_3$ solution and extracted with EtOAc (5 times). The combined organic layers were washed with water, saturated NaCl solution and dried over anhydrous Na$_2$SO$_4$. The organic layer was concentrated under reduced pressure to afford an initial product which was purified by column chromatography using silica gel (60-120 mesh) eluting with 2-5% MeOH in DCM to afford 1-((1r,4r)-4-((2-hydroxy-2-phenylpropyl)amino)cyclohexyl)-2-oxo-2,3-dihydro-1H-benzo[d]imidazole-5-carbonitrile as an off white solid (100 mg). MS (ESI, pos.ion) m/z: 391.2.

Step 7

1-((1R,4r)-4-((R+S)-5-Methyl-2-oxo-5-phenyloxazolidin-3-yl)cyclohexyl)-2-oxo-2,3-dihydro-1H-benzo[d]imidazole-5-carbonitrile

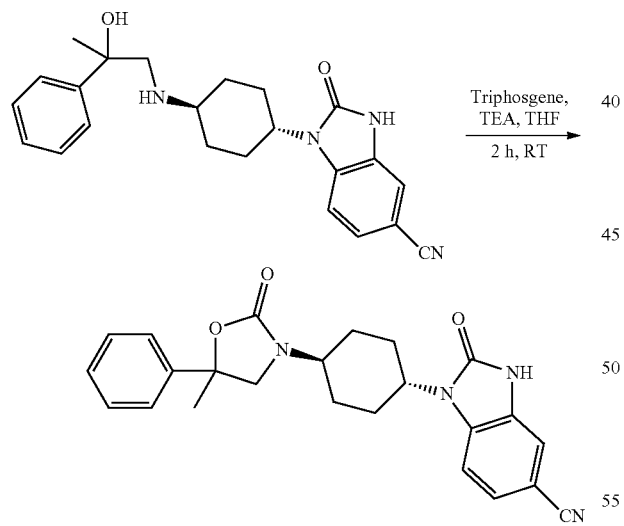

To a solution of 1-((1r,4r)-4-((2-hydroxy-2-phenylpropyl)amino)cyclohexyl)-2-oxo-2,3-dihydro-1H-benzo[d]imidazole-5-carbonitrile (1.3 g, 0.0033 mol) in THF (9 mL) were added TEA (0.0033 mol) and triphosgene (0.988 g, 0.0033 mol) at 0° C. The reaction mixture was then stirred for 2 hours at room temperature. After completion of the reaction (monitored by TLC (TLC eluent: 5% MeOH in DCM, UV active)), the reaction mixture was quenched with saturated NaHCO$_3$ solution and extracted with EtOAc. The combined organic layers were washed with water, saturated NaCl solution, and dried over anhydrous Na$_2$SO$_4$. The organic layer was concentrated under reduced pressure providing an initial product which was purified by preparative HPLC using a 21.2×150×5 µm Zorbax XDB C-18 column, eluting with a gradient mobile phase A: 0.01% TFA in water, B: 1:1/MeOH:CAN at 20 mL/min to afford Example 92 (1-((1R,4r)-4-((R+S)-5-methyl-2-oxo-5-phenyloxazolidin-3-yl)cyclohexyl)-2-oxo-2,3-dihydro-1H-benzo[d]imidazole-5-carbonitrile) (350 mg, 25.3%). MS (ESI, pos.ion) m/z: 417.1. $^1$H-NMR (400 MHz, DMSO-d$_6$): δ 11.34 (s, 1H), 7.62 (d, J=8.4 Hz, 1H), 7.45-7.42 (m, 5H), 7.36-7.34 (m, 2H), 4.23-4.11 (m, 1H), 3.80-3.73 (m, 2H), 3.63 (d, J=9.2 Hz, 1H), 2.42-2.24 (m, 2H), 1.88-1.85 (m, 1H), 1.77-1.71 (m, 2H), 1.68 (s, 4H), 1.61-1.60 (m, 2H).

Example 93

Synthesis of 1-((1R,4r)-4-((R)-5-methyl-2-oxo-5-phenyloxazolidin-3-yl)cyclohexyl)-2-oxo-2,3-dihydro-1H-benzo[d]imidazole-5-carbonitrile

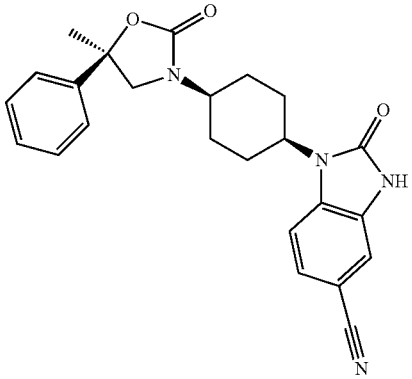 [SMILES: C[C@@]1(c2ccccc2)CN([C@H]2CC[C@@H](n3c(=O)[nH]c4cc(C#N)ccc43)CC2)C(=O)O1]

The title compound was isolated as peak no. 1 in >99% ee by chiral resolution of Example 92 using SFC preparative column chromatography with a Chiralpak AD-H 5 micron, 2 cm id×15 cm length column with 40% MeOH with 0.2% DEA at 60 mL/min as the eluent. Absolute configuration was assigned arbitrarily.

Example 94

Synthesis of 1-((1S,4r)-4-((S)-5-methyl-2-oxo-5-phenyloxazolidin-3-yl)cyclohexyl)-2-oxo-2,3-dihydro-1H-benzo[d]imidazole-5-carbonitrile

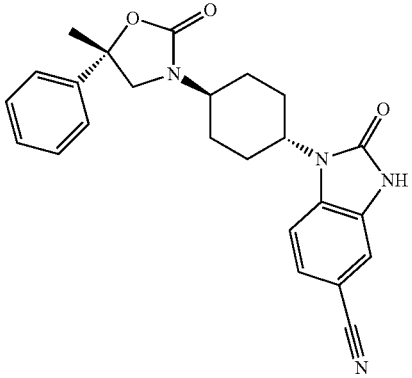 [SMILES: C[C@]1(c2ccccc2)CN([C@H]2CC[C@H](n3c(=O)[nH]c4cc(C#N)ccc43)CC2)C(=O)O1]

The title compound was isolated as peak no. 2 in >99% ee by chiral resolution of example Example 92 using SFC preparative column chromatography with a Chiralpak AD-H 5 micron, 2 cm id×15 cm length column with 40% MeOH with 0.2% DEA at 60 mL/min as the eluent. Absolute configuration was assigned arbitrarily.

Example 95

Synthesis of 2-amino-5-((1S,4r)-4-((S)-5,5-dimethyl-2-oxo-4-phenyloxazolidin-3-yl)cyclohexyl)nicotinonitrile

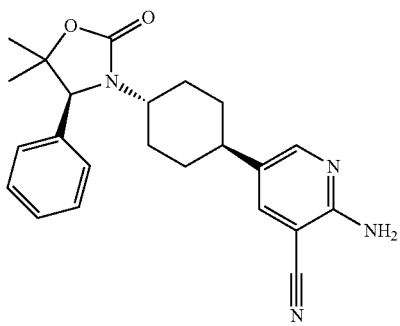 [SMILES: CC1(C)OC(=O)N([C@H]2CC[C@H](c3cnc(N)c(C#N)c3)CC2)[C@H]1c1ccccc1]

To a 2 mL sealable tube were added (S)-3-((1r,4S)-4-(6-amino-5-bromopyridin-3-yl)cyclohexyl)-5,5-dimethyl-4-phenyloxazolidin-2-one (50 mg, 0.113 mmol), dicyanozinc (13.21 mg, 0.113 mmol, commercially available from Sigma-Aldrich, Milwaukee, Wis.) and Pd(PPh$_3$)$_4$ (13.00 mg, 0.011 mmol) (commercially available from Strem Chemicals Inc., Newburyport, Mass.) in DMF (375 μL). The tube was purged with nitrogen for 5 minutes and then sealed. The vessel was heated at 85° C. in a microwave oven for 1 hour. LC-MS indicated that there was complete conversion to the desired product. The reaction mixture was then passed through a syringe filter, and the material thus obtained was purified by reverse-phase preparative HPLC using 0.1% TFA in ACN/H$_2$O, gradient 50% to 95% over 20 minutes to provide 2-amino-5-((1 S,4r)-4-((S)-5,5-dimethyl-2-oxo-4-phenyloxazolidin-3-yl)cyclohexyl)nicotinonitrile as a white solid. $^1$H NMR (500 MHz, DMSO-d$_6$) δ 8.06 (d, J=2.46 Hz, 1H), 7.70 (d, J=2.35 Hz, 1H), 7.39-7.47 (m, 2H), 7.35-7.38 (m, 1H), 7.26 (br. s, 1H), 6.58-6.61 (m, 2H), 4.62-4.64 (m, 1H), 3.43-3.53 (m, 1H), 2.21-2.31 (m, 1H), 1.80-1.87 (m, 2H), 1.71-1.79 (m, 1H), 1.56-1.65 (m, 2H), 1.43-1.54 (m, 4H), 1.29-1.42 (m, 1H), 1.11-1.23 (m, 1H), 0.78-0.82 (m, 3H). m/z (ESI) 391.2 (M+H)$^+$.

Examples 96 and 97

Synthesis of (S)-5,5-dimethyl-3-((1s,4R)-4-(6-oxo-5-(pyrimidin-2-yl)-1,6-dihydropyridin-3-yl)cyclohexyl)-4-phenyloxazolidin-2-one and (S)-5,5-dimethyl-3-((1r,4S)-4-(6-oxo-5-(pyrimidin-2-yl)-1,6-dihydropyridin-3-yl)cyclohexyl)-4-phenyloxazolidin-2-one

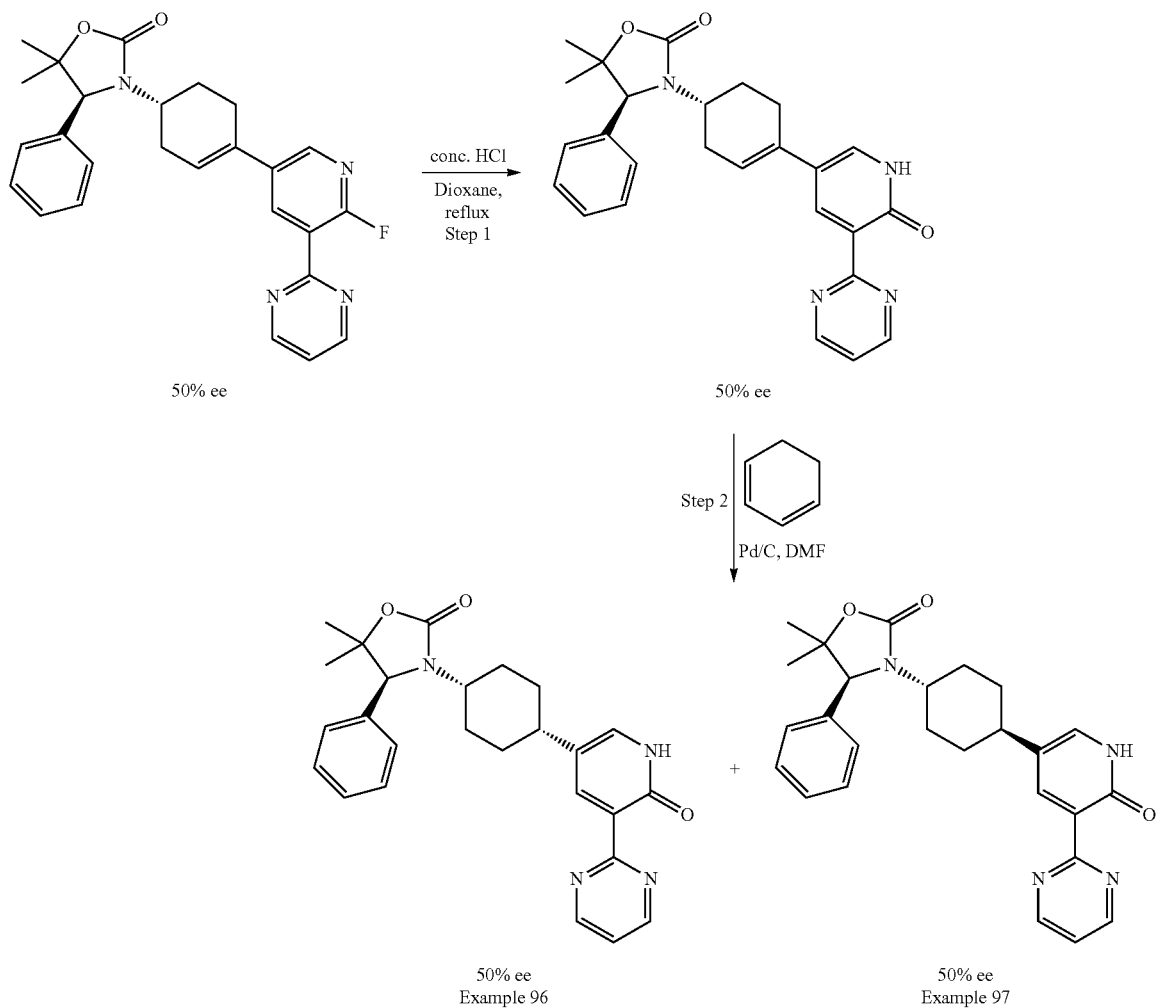

Step 1

(4S)-5,5-Dimethyl-3-(4-(6-oxo-5-(pyrimidin-2-yl)-1,6-dihydropyridin-3-yl)cyclohex-3-en-1-yl)-4-phenyloxazolidin-2-one A resealable tube was charged with (4S)-3-(4-(6-fluoro-5-(pyrimidin-2-yl)pyridin-3-yl)cyclohex-3-en-1-yl)-5,5-dimethyl-4-phenyloxazolidin-2-one (See Step 1 in the synthesis of Examples 72 and 73)(50 mg, 0.112 mmol, 50% ee), dioxane (2.647 mL), and water (882 μL). Concentrated HCl (37%) (221 μL) was added, the system was flushed with argon, and the tube was sealed. The reaction mixture was then stirred at 100° C. for 2 hours. LC-MS indicated a clean and complete reaction. After cooling to room temperature, the reaction mixture was partitioned between EtOAc and saturated aqueous NaHCO$_3$ solution. The aqueous phase was extracted with EtOAc. The organic phase was concentrated under reduced pressure. The material thus obtained was absorbed onto a plug of silica gel and purified by chromatography through a Redi-Sep pre-packed silica gel column (12 g), eluting with a gradient of 0% to 100% MeOH in DCM. The resulting product was then washed with 10% ammonium hydroxide in MeOH. The solution was concentrated under reduced pressure providing (4S)-5,5-dimethyl-3-(4-(6-oxo-5-(pyrimidin-2-yl)-1,6-dihydropyridin-3-yl)cyclohex-3-en-1-yl)-4-phenyloxazolidin-2-one (44 mg, 0.099 mmol, 88% yield, 50% ee) as yellow solid. m/z (ESI) 443.1 (M+H)$^+$.

Step 2

(S)-5,5-Dimethyl-3-((1 s,4R)-4-(6-oxo-5-(pyrimidin-2-yl)-1,6-dihydropyridin-3-yl)cyclohexyl)-4-phenyloxazolidin-2-one and (S)-5,5-dimethyl-3-((1r,4S)-4-(6-oxo-5-(pyrimidin-2-yl)-1,6-dihydropyridin-3-yl)cyclohexyl)-4-phenyloxazolidin-2-one A glass microwave reaction vessel was charged with (4S)-5,5-dimethyl-3-(4-(6-oxo-5-(pyrimidin-2-yl)-1,6-dihydropyridin-3-yl)cyclohex-3-en-1-yl)-4-phenyloxazolidin-2-one (44 mg, 0.099 mmol, 50% ee)), 1,3-cyclohexadiene (0.095 mL, 0.994 mmol, commercially available from Sigma-Aldrich, Milwaukee, Wis.) and palladium (10% wt. on activated carbon) (10.58 mg, 9.94 μmol, commercially available from Sigma-Aldrich, Milwaukee, Wis.) in DMF (1.132 mL). The reaction mixture was stirred and heated in a Initiator microwave reactor (Personal Chemistry, Biotage AB, Inc., Upssala, Sweden) at 100° C. for 30 minutes. Another portion of 1,3-cyclohexadiene (0.095 mL, 0.994 mmol) and palladium (10% wt. on activated carbon) (10.58 mg, 9.94 μmol) were added at intervals of 30 minutes until the reaction was complete as indicated by LC-MS. The resulting mixture was then passed through a syringe filter and concentrated under reduced pressure. The reaction mixture was purified by HPLC providing Examples 96 and 97.

Example 96

(S)-5,5-Dimethyl-3-((1s,4R)-4-(6-oxo-5-(pyrimidin-2-yl)-1,6-dihydropyridin-3-yl)cyclohexyl)-4-phenyloxazolidin-2-one.

$^1$H NMR (500 MHz, DMSO-d$_6$) δ 9.00 (br. s., 2H), 8.30 (br. s, 1H), 7.69 (br. s, 1H), 7.58 (br. s, 1H), 7.17-7.47 (m, J=7.60 Hz, 4H), 4.62 (s, 1H), 2.67-2.80 (m, 1H), 2.17-2.31 (m, 1H), 1.83-1.98 (m, 1H), 1.76 (s, 2H), 1.55-1.67 (m, 2H), 1.50 (s, 3H), 1.39-1.46 (m, 1H), 1.29-1.38 (m, 1H), 0.79 (s, 3H). m/z (ESI) 445.2 (M+H)$^+$.

Example 97

(S)-5,5-Dimethyl-3-((1r,4S)-4-(6-oxo-5-(pyrimidin-2-yl)-1,6-dihydropyridin-3-yl)cyclohexyl)-4-phenyloxazolidin-2-one. $^1$H NMR (500 MHz, DMSO-d$_6$) δ 8.94 (br. s, 2H), 8.21 (br. s, 1H), 7.68 (br. s, 1H), 7.47-7.55 (m, 1H), 7.38-7.45 (m, 2H), 7.32-7.38 (m, 1H), 7.20-7.32 (m, 2H), 4.63 (s, 1H), 2.25-2.41 (m, 1H), 1.86 (br. s., 3H), 1.58-1.72 (m, 2H), 1.47 (s, 4H), 1.31-1.44 (m, 1H), 1.14-1.28 (m, 1H), 0.79 (s, 3H). m/z (ESI) 445.2 (M+H)$^+$.

Example 98

Synthesis of (S)-5,5-dimethyl-3-((1r,4S)-4-(2-oxo-1-(pyrimidin-2-yl)-2,3-dihydro-1H-imidazo[4,5-b]pyridin-6-yl)cyclohexyl)-4-phenyloxazolidin-2-one

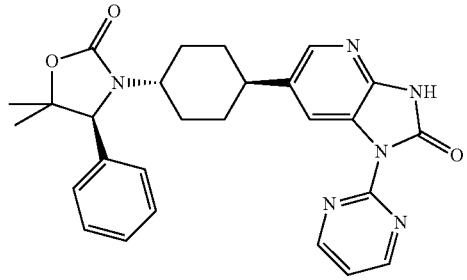 [SMILES: CC1(C)OC(=O)N([C@H]2CC[C@H](c3cnc4[nH]c(=O)n(-c5ncccn5)c4c3)CC2)[C@H]1c1ccccc1]

The title compound was prepared according to the procedure described in General Method HH-2 affording (S)-5,5-dimethyl-3-((1r,4S)-4-(2-oxo-1-(pyrimidin-2-yl)-2,3-dihydro-1H-imidazo[4,5-b]pyridin-6-yl)cyclohexyl)-4-phenyloxazolidin-2-one as a yellow solid. $^1$H NMR (500 MHz, DMSO-d$_6$) δ 11.74 (br. s, 1H), 8.94 (d, J=6.20 Hz, 2H), 7.86 (dd, J=1.50, 13.68 Hz, 2H), 7.49 (t, J=4.81 Hz, 1H), 7.34-7.46 (m, 3H), 7.25 (br. s, 2H), 4.63 (s, 1H), 3.45-3.63 (m, 1H), 2.36-2.47 (m, 1H), 1.78-1.92 (m, 3H), 1.59-1.72 (m, 2H), 1.52-1.59 (m, 1H), 1.47 (s, 3H), 1.38-1.46 (m, 1H), 1.16-1.28 (m, 1H), 0.80 (s, 3H). m/z (ESI) 485.2 (M+H)$^+$.

Example 99

Synthesis of (S)-2-(2-amino-5-(4-(5,5-dimethyl-2-oxo-4-phenyloxazolidin-3-yl)phenyl)pyridin-3-yl)pyrimidine-4-carboximidamide

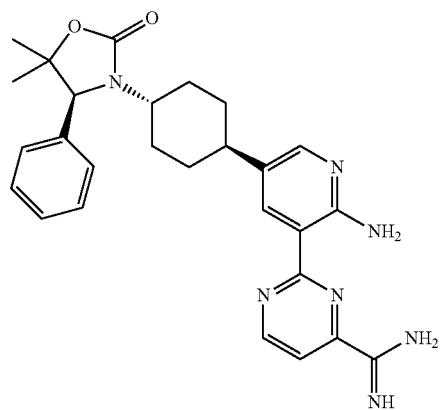 [SMILES: CC1(C)OC(=O)N([C@H]2CC[C@H](c3cnc(N)c(-c4nccc(C(=N)N)n4)c3)CC2)[C@H]1c1ccccc1]

The title compound was prepared from 2-chloropyrimidine-4-carbonitrile (commercially available from Synthonix, Wake Forest, N.C.) according to the procedure described in General Method HH-1 to afford (S)-2-(2-amino-5-(4-(5,5-dimethyl-2-oxo-4-phenyloxazolidin-3-yl)phenyl)pyridin-3-yl)pyrimidine-4-carboximidamide as yellow solid. $^1$H NMR (500 MHz, DMSO-$d_6$) δ 9.01 (dd, J=5.13, 10.26 Hz, 2H), 8.44 (d, J=1.71 Hz, 1H), 7.99 (d, J=5.98 Hz, 1H), 7.65 (d, J=8.76 Hz, 2H), 7.56 (d, J=8.76 Hz, 2H), 7.36-7.41 (m, 2H), 7.26-7.35 (m, 3H), 5.48 (s, 1H), 1.65 (s, 3H), 0.92 (s, 3H) m/z (ESI) 480.3 (M+H)$^+$.

Examples 100 and 101

Synthesis of (S)-3-(4-(6-amino-5-(5-chloropyridazin-3-yl)pyridin-3-yl)phenyl)-5,5-dimethyl-4-phenyloxazolidin-2-one and (S)-3-(4-(6-amino-5-(6-chloropyridazin-4-yl)pyridin-3-yl)phenyl)-5,5-dimethyl-4-phenyloxazolidin-2-one (structures arbitrarily assigned)

Examples 100 and 101

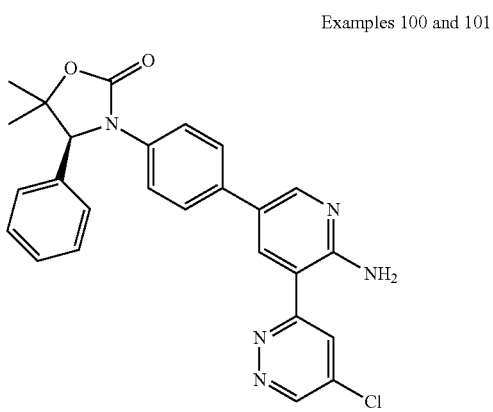

The title compounds were prepared from 3,5-dichloropyridazine (commercially available from ACES Pharma, Inc., Princeton, N.J.) according to the procedure described in General Method HH-1 to afford (S)-3-(4-(6-amino-5-(5-chloropyridazin-3-yl)pyridin-3-yl)phenyl)-5,5-dimethyl-4-phenyloxazolidin-2-one and (S)-3-(4-(6-amino-5-(6-chloropyridazin-4-yl)pyridin-3-yl)phenyl)-5,5-dimethyl-4-phenyloxazolidin-2-one.

(S)-3-(4-(6-amino-5-(5-chloropyridazin-3-yl)pyridin-3-yl)phenyl)-5,5-dimethyl-4-phenyloxazolidin-2-one. $^1$H NMR (500 MHz, DMSO-$d_6$) δ 8.37 (d, J=2.35 Hz, 1H), 8.09 (d, J=1.82 Hz, 1H), 8.06 (br. s, 1H), 7.64 (d, J=9.08 Hz, 2H), 7.56 (d, J=8.87 Hz, 2H), 7.36 (s, 2H), 7.23-7.33 (m, 3H), 5.50 (s, 1H), 1.64 (s, 3H), 0.92 (s, 3H). m/z (ESI) 471.8 (M+H)$^+$ (S)-3-(4-(6-amino-5-(6-chloropyridazin-4-yl)pyridin-3-yl)phenyl)-5,5-dimethyl-4-phenyloxazolidin-2-one $^1$H NMR (500 MHz, DMSO-$d_6$) δ 9.32 (d, J=2.03 Hz, 1H), 8.74 (d, J=2.24 Hz, 1H), 8.44 (d, J=2.35 Hz, 1H), 8.34 (d, J=2.24 Hz, 1H), 7.68 (d, J=8.87 Hz, 2H), 7.59 (br. s, 2H), 7.55 (d, J=8.98 Hz, 2H), 7.34-7.41 (m, 2H), 7.25-7.33 (m, 3H), 5.50 (s, 1H), 1.65 (s, 3H), 0.91 (s, 3H). m/z (ESI) 471.8 (M+H)$^+$.

Example 102

Synthesis of (S)-2-(2-amino-5-(4-(5,5-dimethyl-2-oxo-4-phenyloxazolidin-3-yl)phenyl)pyridin-3-yl)pyrimidine-4-carbonitrile

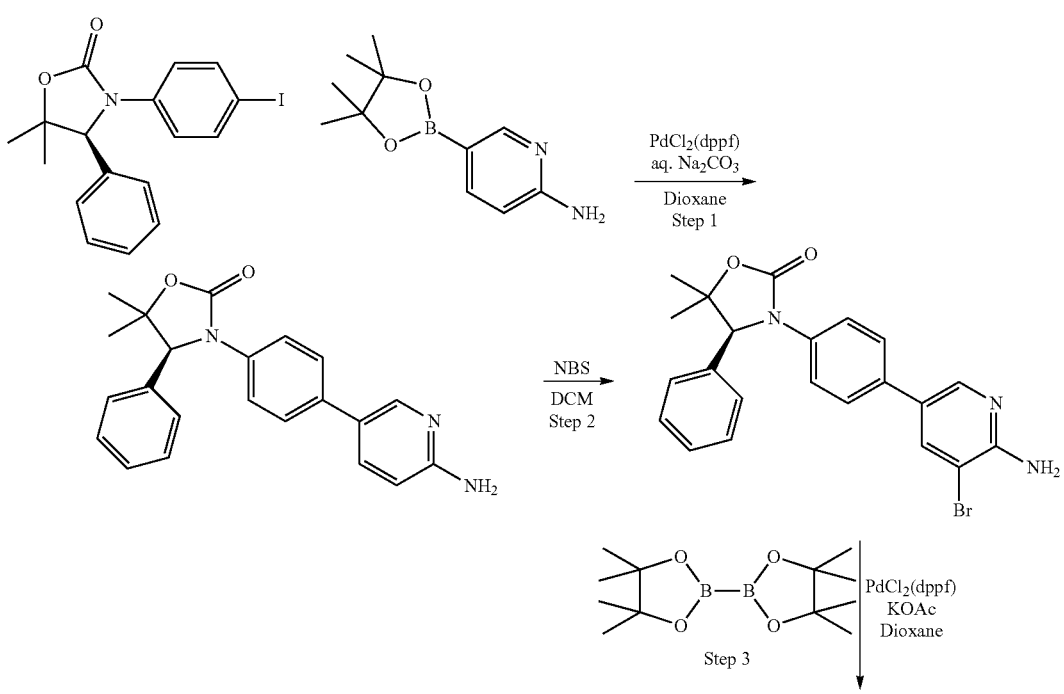

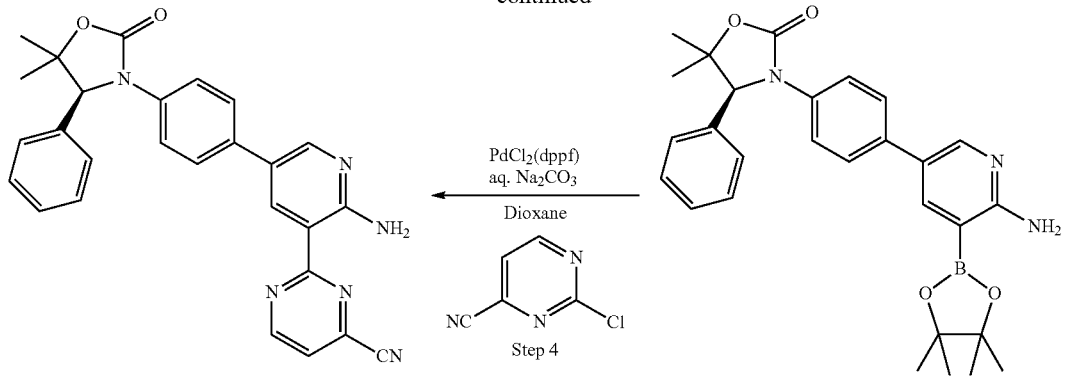

Example 102

Step 1

(S)-3-(4-(6-Aminopyridin-3-yl)phenyl)-5,5-dimethyl-4-phenyloxazolidin-2-one

2-Amino-5-bromopyridine (commercially available from Sigma-Aldrich, Milwaukee, Wis.)(0.114 mL, 5.09 mmol), sodium carbonate (5.09 mL, 10.17 mmol), (S)-5,5-dimethyl-4-phenyl-3-(4-(4,4,5,5-tetramethyl-1,3,2-dioxaborolan-2-yl)phenyl)oxazolidin-2-one (Intermediate J)(2.0 g, 5.09 mmol), and dichloro(1,1-bis(diphenylphosphinoferrocene)) palladium(II) (415 mg, 0.509 mmol) were combined in dioxane (10.200 mL) and stirred at 115° C. overnight. LC-MS indicated good conversion to desired product. After cooling to room temperature, the reaction mixture was absorbed onto a plug of silica gel and purified by chromatography through a Redi-Sep pre-packed silica gel column (12 g), eluting with a gradient of 0% to 100% EtOAc in hexane, to provide (S)-3-(4-(6-aminopyridin-3-yl)phenyl)-5,5-dimethyl-4-phenyloxazolidin-2-one (1 g, 2.78 mmol, 54.7% yield) as an off-white solid. m/z (ESI) 360.0 (M+H)$^+$.

Step 2

(S)-3-(4-(6-Amino-5-bromopyridin-3-yl)phenyl)-5,5-dimethyl-4-phenyloxazolidin-2-one To a solution of (S)-3-(4-(6-aminopyridin-3-yl)phenyl)-5,5-dimethyl-4-phenyloxazolidin-2-one (1 g, 2.78 mmol) in DCM (13.91 mL) at 0° C., was added NBS (0.545 g, 3.06 mmol). The reaction mixture was then stirred for 1 hour at the same temperature. LC-MS indicated clean and complete conversion to desired product. The solution was concentrated and water was added. The solid was filtered and washed with water three times. The solid was then air-dried affording (S)-3-(4-(6-amino-5-bromopyridin-3-yl)phenyl)-5,5-dimethyl-4-phenyloxazolidin-2-one (1.26 g, 2.87 mmol, 103% yield) as a tan solid. The material was used without further purification. m/z (ESI) 439.8 (M+2)$^+$.

Step 3

(S)-3-(4-(6-Amino-5-(4,4,5,5-tetramethyl-1,3,2-dioxaborolan-2-yl)pyridin-3-yl)phenyl)-5,5-dimethyl-4-phenyloxazolidin-2-one To a solution of (S)-3-(4-(6-amino-5-bromopyridin-3-yl)phenyl)-5,5-dimethyl-4-phenyloxazolidin-2-one (100 mg, 0.228 mmol) and dioxane (456 µL) were added potassium acetate (112 mg, 1.141 mmol), 4,4,4',4',5,5,5',5'-octamethyl-2,2'-bi(1,3,2-dioxaborolane) (63.7 mg, 0.251 mmol) and 1,1'-bis(diphenylphosphino)ferrocene-palladium(II)dichloride (DCM complex) (18.63 mg, 0.023 mmol). The reaction vessel was flushed with argon, sealed and heated at 100° C. for 1 hour in a microwave oven. LC-MS showed complete conversion to the desired products. The reaction was cooled to room temperature and filtered through a syringe filter. The material thus obtained was absorbed onto a plug of silica gel and purified by chromatography through a Redi-Sep pre-packed silica gel column (40 g), eluting with a gradient of 0% to 50% EtOAc in hexane, to provide (S)-3-(4-(6-amino-5-(4,4,5,5-tetramethyl-1,3,2-dioxaborolan-2-yl)pyridin-3-yl)phenyl)-5,5-dimethyl-4-phenyloxazolidin-2-one (65 mg, 0.134 mmol, 58.7% yield). m/z (ESI) 404.1 (M-C$_5$H$_{10}$)$^+$.

Step 4

(S)-2-(2-Amino-5-(4-(5,5-dimethyl-2-oxo-4-phenyloxazolidin-3-yl)phenyl)pyridin-3-yl)pyrimidine-4-carbonitrile 2-Chloropyrimidine-4-carbonitrile (22.42 mg, 0.161 mmol), Na$_2$CO$_3$ (134 µL, 0.268 mmol), (S)-3-(4-(6-amino-5-(4,4,5,5-tetramethyl-1,3,2-dioxaborolan-2-yl)pyridin-3-yl)phenyl)-5,5-dimethyl-4-phenyloxazolidin-2-one (65 mg, 0.134 mmol), and dichloro(1,1-bis(diphenylphosphinoferrocene))palladium(II) (10.94 mg, 0.013 mmol) were combined in dioxane (268 µL) and stirred at 100° C. in a microwave oven for 1 hour. LC-MS indicated good conversion to desired product. After cooling to room temperature, the reaction mixture was absorbed onto a plug of silica gel and purified by chromatography through a Redi-Sep pre-packed silica gel column (12 g), eluting with a gradient of 0% to 10% MeOH in DCM, to provide (S)-2-(2-amino-5-(4-(5,5-dimethyl-2-oxo-4-phenyloxazolidin-3-yl)phenyl)pyridin-3-yl)pyrimidine-4-carbonitrile as yellow solid. $^1$H NMR (500 MHz, DMSO-d$_6$) δ 10.56 (s, 1H), 8.83 (d, J=4.70 Hz, 1H), 8.59 (d, J=2.67 Hz, 1H), 8.13 (d, J=8.44 Hz, 1H), 8.06 (dd, J=2.14, 6.30 Hz, 1H), 7.66 (d, J=8.66 Hz, 2H), 7.58 (d, J=8.87

Hz, 2H), 7.49 (d, J=4.49 Hz, 1H), 7.35-7.42 (m, 2H), 7.23-7.35 (m, 3H), 5.49 (s, 1H), 1.66 (s, 3H), 0.92 (s, 3H). m/z (ESI) 463.8 (M+H)$^+$.

Example 103

Synthesis of 1-((1S,4r)-4-((S)-5,5-dimethyl-2-oxo-4-phenyloxazolidin-3-yl)cyclohexyl)-6-fluoro-2-oxo-2,3-dihydro-1H-benzo[d]imidazole-5-carbonitrile

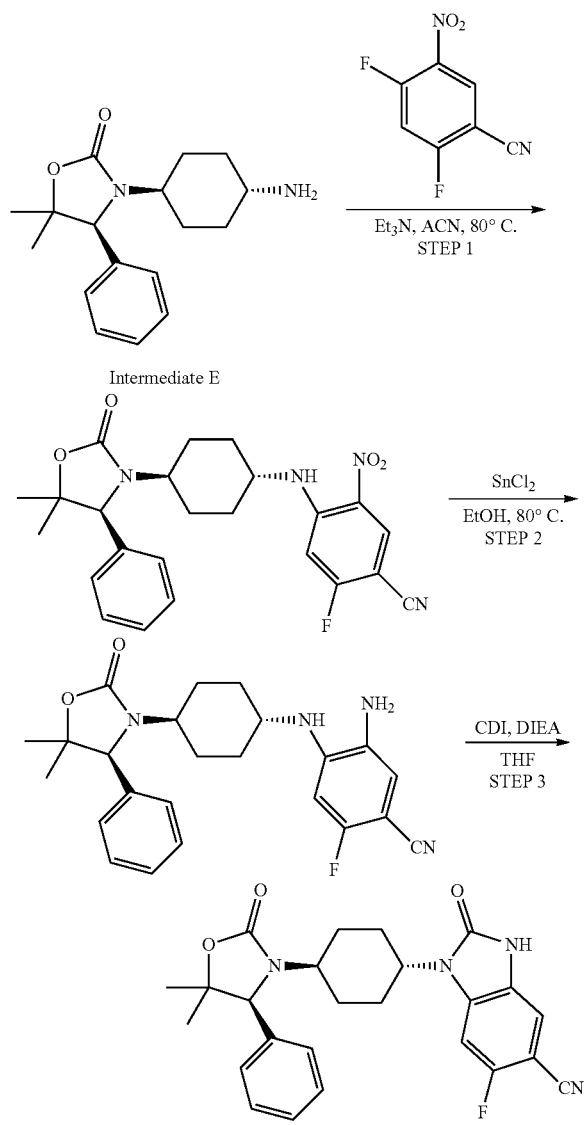

Example 103

Step 1

4-(((1S,4r)-4-((S)-5,5-Dimethyl-2-oxo-4-phenyloxazolidin-3-yl)cyclohexyl)amino)-2-fluoro-5-nitrobenzonitrile A vial charged with (S)-3-((1r,4S)-4-aminocyclohexyl)-5,5-dimethyl-4-phenyloxazolidin-2-one (0.184 g, 0.638 mmol), ACN (1.734 mL), and DIEA (0.181 mL, 1.04 mmol) was cooled to 0° C. and 2,4-difluoro-5-nitrobenzonitrile (commercially available from Sigma-Aldrich, Milwaukee, Wis.) (0.078 g, 0.342 mmol) was added. The vial was sealed and the temperature was slowly raised to room temperature over 16 hours providing a brown solution with product as the main species according to LC-MS. The solution was dried under reduced pressure and purified with a 25 g SNAP column (Biotage) ramping DCM:MeOH (90:10) in DCM (0-25%, then isocratic at 30%, 215 nm detection) providing 4-(((1S,4r)-4-((S)-5,5-dimethyl-2-oxo-4-phenyloxazolidin-3-yl)cyclohexyl)amino)-2-fluoro-5-nitrobenzonitrile (0.282 g, 0.623 mmol, 98% yield) as a yellow solid. m/z (ESI) 453.3 (M+H)$^+$.

Step 2

5-Amino-4-(((1S,4r)-4-((S)-5,5-dimethyl-2-oxo-4-phenyloxazolidin-3-yl)cyclohexyl)amino)-2-fluorobenzonitrile To a flask charged with 4-(((1S,4r)-4-((S)-5,5-dimethyl-2-oxo-4-phenyloxazolidin-3-yl)cyclohexyl)amino)-2-fluoro-5-nitrobenzonitrile (0.282 g, 0.623 mmol) were added EtOH (6.23 mL) and tin(II) chloride (0.019 mL, 0.405 mmol). The resulting yellow suspension was shaken for 3 hours at 80° C. LC-MS indicated complete conversion. The solution was dried under reduced pressure and purified with a 25 g SNAP column (Biotage) ramping DCM:MeOH (90:10) in DCM from 0-30%, then isocratic at 30% to provide 5-amino-4-(((1S,4r)-4-((S)-5,5-dimethyl-2-oxo-4-phenyloxazolidin-3-yl)cyclohexyl)amino)-2-fluorobenzonitrile (0.258 g, 0.611 mmol, 98% yield) as a yellow brown solid. m/z (ESI) 423.3 (M+H)$^+$.

Step 3

1-((1S,4r)-4-((S)-5,5-Dimethyl-2-oxo-4-phenyloxazolidin-3-yl)cyclohexyl)-6-fluoro-2-oxo-2,3-dihydro-1H-benzo[d]imidazole-5-carbonitrile To a flask charged 5-amino-4-(((1S,4r)-4-((S)-5,5-dimethyl-2-oxo-4-phenyloxazolidin-3-yl)cyclohexyl)amino)-2-fluorobenzonitrile (0.258 g, 0.611 mmol) were added THF (2.043 mL), DIEA (0.372 mL, 2.137 mmol) and CDI (0.347 g, 2.137 mmol). The mixture was then stirred at room temperature for 16 hours. LC-MS indicated complete reaction. Solvents were removed under reduced pressure and the residue was purified with a 25 g SNAP column (Biotage) ramping DCM:MeOH (90:10) in DCM from 0-40%, then isocratic at 40% to provide 1-((1S,4r)-4-((S)-5,5-dimethyl-2-oxo-4-phenyloxazolidin-3-yl)cyclohexyl)-6-fluoro-2-oxo-2,3-dihydro-1H-benzo[d]imidazole-5-carbonitrile as a light yellow solid (0.151 g, 0.337 mmol, 55% yield). $^1$H NMR (400 MHz, DMSO-d$_6$) δ=11.34 (br. s, 1H), 7.73 (d, J=10.5 Hz, 1H), 7.45-7.2 (m, 6H), 4.65 (s, 1H), 4.13-4.03 (m, 1H), 3.77-3.68

(m, 1H), 2.28-2.07 (m, 2H), 2.02-1.83 (m, 2H), 1.75-1.55 (m, 2H), 1.48 (s, 3H), 1.38-1.25 (m, 1H), 0.80 (s, 3H). m/z (ESI) 449.1 (M+H)+.

Example 104

Synthesis of (S)-3-((1r,4S)-4-(4,6-difluoro-2-oxo-2,3-dihydro-1H-benzo[d]imidazol-1-yl)cyclohexyl)-5,5-dimethyl-4-phenyloxazolidin-2-one

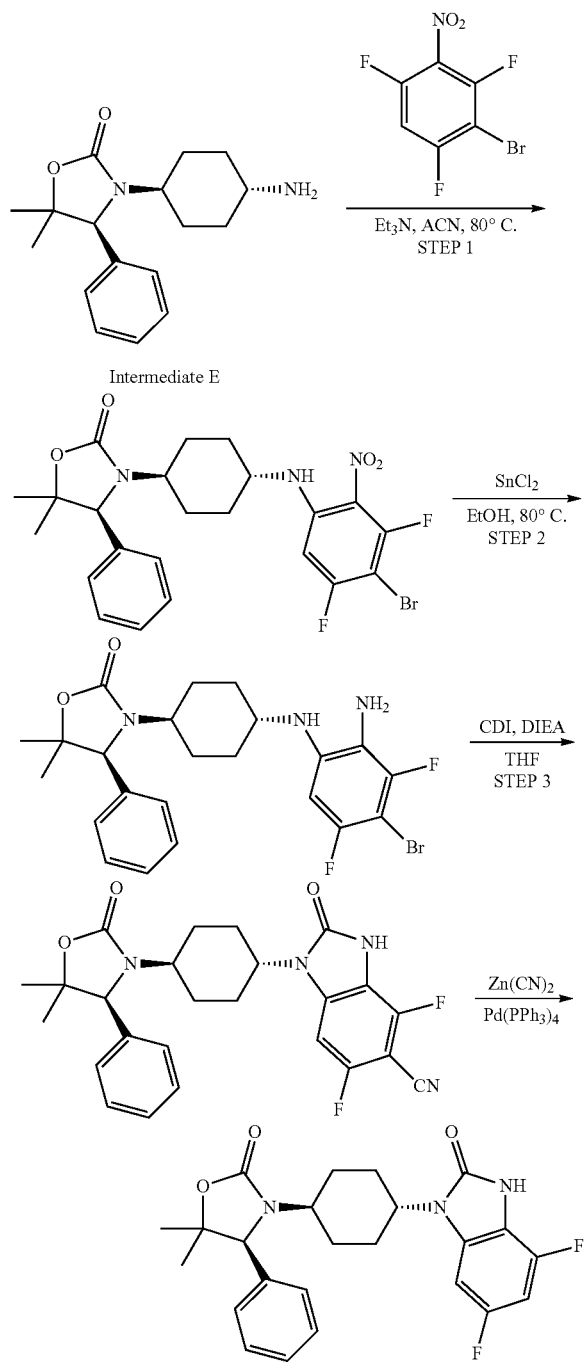

Example 104

Step 1

(S)-3-((1r,4S)-4-((4-Bromo-3,5-difluoro-2-nitrophenyl)amino)cyclohexyl)-5,5-dimethyl-4-phenyloxazolidin-2-one A vial charged with (S)-3-((1r,4S)-4-aminocyclohexyl)-5,5-dimethyl-4-phenyloxazolidin-2-one (0.154 g, 0.534 mmol), ACN (2 mL), and DIEA (0.279 mL, 1.602 mmol) was cooled to 0° C. Next, 2-bromo-1,3,5-trifluoro-4-nitrobenzene (HDH Pharma) (0.137 g, 0.534 mmol) was added. The vial was sealed and the temperature was slowly raised to room temperature over 16 hours providing a brown solution with product as the main species according to LC-MS. The solution was dried under reduced pressure and purified with a 25 g SNAP column (Biotage) ramping DCM:MeOH (90:10) in DCM (0-60, 215 nm detection) providing (S)-3-((1r,4S)-4-((4-bromo-3,5-difluoro-2-nitrophenyl)amino)cyclohexyl)-5,5-dimethyl-4-phenyloxazolidin-2-one (0.198 g, 0.378 mmol, 71% yield) as a yellow solid. m/z (ESI) 524.1 (M+H)+.

Step 2

(S)-3-((1r,4S)-4-((2-Amino-4-bromo-3,5-difluorophenyl)amino)cyclohexyl)-5,5-dimethyl-4-phenyloxazolidin-2-one To a flask charged with (S)-3-((1r,4S)-4-((4-bromo-3,5-difluoro-2-nitrophenyl)amino)cyclohexyl)-5,5-dimethyl-4-phenyloxazolidin-2-one (0.198 g, 0.378 mmol) were added EtOH (3.78 mL) and tin(II) chloride (0.054 mL, 1.133 mmol). The resulting yellow suspension was shaken for 16 hours at 80° C. LC-MS indicated complete conversion. The solution was dried under reduced pressure and purified with a 25 g SNAP column (Biotage) ramping DCM:MeOH (90:10) in DCM from 0-60% providing (S)-3-((1 r,4S)-4-((2-amino-4-bromo-3,5-difluorophenyl)amino)cyclohexyl)-5,5-dimethyl-4-phenyloxazolidin-2-one (0.168 g, 0.340 mmol, 90% yield) as a brown oil. m/z (ESI) 496.3 (M+H)+.

Step 3

(S)-3-((1 r,4S)-4-(5-Bromo-4,6-difluoro-2-oxo-2,3-dihydro-1H-benzo[d]imidazol-1-yl)cyclohexyl)-5,5-dimethyl-4-phenyloxazolidin-2-one To a flask charged with 5 (S)-3-((1r,4S)-4-((2-amino-4-bromo-3,5-difluorophenyl)amino)cyclohexyl)-5,5-dimethyl-4-phenyloxazolidin-2-one (0.168 g, 0.340 mmol) were added THF (1.133 mL), DIEA (0.207 mL, 1.189 mmol) and CDI (0.193 g, 1.189 mmol). The mixture was then stirred at room temperature for 16 hours. LC-MS indicated complete conversion. Solvents were removed under reduced pressure and the residue was purified with a 25 g SNAP column (Biotage) ramping DCM:MeOH (90:10) in DCM from 0-70% providing (S)-3-((1r,4S)-4-(5-bromo-4,6-difluoro-2-oxo-2,3-dihydro-1H-benzo[d]imidazol-1-yl)cyclohexyl)-5,5-dimethyl-4-phenyloxazolidin-2-one as a brown oil (0.16 g, 0.307 mmol, 90% yield). m/z (ESI) 520.2 (M+H)+.

Step 4

(S)-3-((1r,4S)-4-(4,6-Difluoro-2-oxo-2,3-dihydro-1H-benzo[d]imidazol-1-yl)cyclohexyl)-5,5-dimethyl-4-phenyloxazolidin-2-one To a flask charged with (S)-3-((1r,4S)-4-(5-bromo-4,6-difluoro-2-oxo-2,3-dihydro-1H-benzo[d]imidazol-1-yl)cyclohexyl)-5,5-dimethyl-4-phenyloxazolidin-2-one (0.057 g, 0.110 mmol) were added dioxane (1.095) and zinc cyanide (0.021 mL, 0.329 mmol) respectively. The flask was purged with nitrogen and tetrakis(triphenylphosphine)palladium (0.013 g, 0.0110 mmol) was added. The flask was sealed and shaken for 16 hours at 120° C. LC-MS indicated debromination as the only product. Solvents were removed under reduced pressure, and the resulting precipitate was dissolved in DCM (10 mL) and water (20 mL). The organic layer was separated and the solvent was removed under reduced pressure. The resulting residue was purified with a 25 g SNAP column (Biotage) ramping DCM:MeOH (90:10) in DCM (0-70%, 215 nm detection) providing (S)-3-((1r,4S)-4-(4,6-difluoro-2-oxo-2,3-dihydro-1H-benzo[d]imidazol-1-yl)cyclohexyl)-5,5-dimethyl-4-phenyloxazolidin-2-one (0.008 g, 13% yield) as light brown needles. $^1$H NMR (400 MHz, DMSO-d$_6$) δ=11.34 (br. s, 1H), 7.67-7.54 (m, 2H), 7.43-7.15 (m, 5H), 4.59 (s, 1H), 3.83-3.79 (m, 1H), 2.69-2.51 (m, 2H), 2.35-2.32 (m, 1H), 1.87-1.60 (m, 2H), 1.52-1.45 (m, 2H), 1.43 (s, 3H), 1.28-1.25 (m, 1H), 0.78 (s, 3H). m/z (ESI) 441.3 (M+H)$^+$.

Example 105

Synthesis of (+/−)-(R/S)-4-(4-(3-methoxyphenyl)-5,5-dimethyl-2-oxooxazolidin-3-yl)-N-(quinolin-8-yl)benzamide

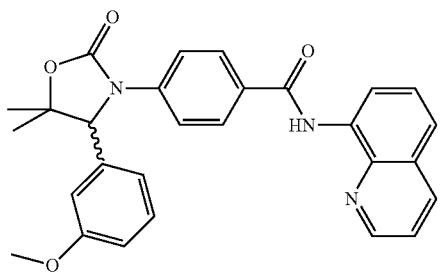 [SMILES: COc1cccc(C2N(c3ccc(C(=O)Nc4cccc5cccnc45)cc3)C(=O)OC2(C)C)c1]

The title compound was prepared from (+/−)-2-amino-2-(3-methoxyphenyl)acetic acid (commercially available from Life Chemicals, Orange, Conn.) according to the procedure described in General Method MM-1 to afford (+/−)-(R/S)-4-(4-(3-methoxyphenyl)-5,5-dimethyl-2-oxooxazolidin-3-yl)-N-(quinolin-8-yl)benzamide (0.137 g, 0.293 mmol, 86% yield) as a white solid. $^1$H NMR (400 MHz, DMSO-d$_6$) δ ppm 0.97 (s, 3H), 1.66 (s, 3H), 3.74 (s, 3H), 5.51 (s, 1H), 6.81 (br. s., 2H), 6.90 (dd, J=7.97, 2.10 Hz, 1H), 7.31 (t, J=7.78 Hz, 1H), 7.60-7.70 (m, 2H), 7.70-7.76 (m, 3H), 7.91-8.10 (m, 2H), 8.45 (dd, J=8.41, 1.66 Hz, 1H), 8.67 (dd, J=7.63, 1.27 Hz, 1H), 8.95 (dd, J=4.21, 1.66 Hz, 1H), 10.56 (s, 1H). m/z (ESI) 468 (M+H)$^+$.

Examples 106 and 107

Synthesis of (R)-4-(4-(3-methoxyphenyl)-5,5-dimethyl-2-oxooxazolidin-3-yl)-N-(quinolin-8-yl)benzamide and (S)-4-(4-(3-methoxyphenyl)-5,5-dimethyl-2-oxooxazolidin-3-yl)-N-(quinolin-8-yl)benzamide Example 106

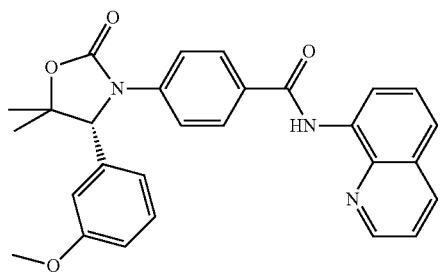

Example 107

A racemic mixture of (+/−)-(R/S)-4-(4-(3-methoxyphenyl)-5,5-dimethyl-2-oxooxazolidin-3-yl)-N-(quinolin-8-yl)benzamide (Example 105)(0.112 g, 0.240 mmol) was purified via SFC separation (Chiralpak AD-H column (2×15 cm), eluting with 50/50 CO$_2$/MeOH with 0.2% DEA; flow rate: 75 mL/min; 11 mg sample/injection) to afford Example 106 ((R)-4-(4-(3-Methoxyphenyl)-5,5-dimethyl-2-oxooxazolidin-3-yl)-N-(quinolin-8-yl)benzamide) (0.050 g, 0.107 mmol, 89% yield) as an off-white solid (first eluting peak). Example 107 ((S)-4-(4-(3-Methoxyphenyl)-5,5-dimethyl-2-oxooxazolidin-3-yl)-N-(quinolin-8-yl)benzamide) (0.050 g, 0.107 mmol, 89% yield) was also obtained as an off-white solid (second eluting peak).

Example 106

((R)-4-(4-(3-Methoxyphenyl)-5,5-dimethyl-2-oxooxazolidin-3-yl)-N-(quinolin-8-yl)benzamide). $^1$H NMR (400 MHz, DMSO-d$_6$) δ ppm 0.97 (s, 3H), 1.66 (s, 3H), 3.74 (s, 3H), 5.51 (s, 1H), 6.82 (br. s., 2H), 6.90 (dd, J=8.31, 1.76 Hz, 1H), 7.31 (t, J=7.82 Hz, 1H), 7.59-7.69 (m, 2H), 7.69-7.76 (m, 3H), 7.91-8.06 (m, 2H), 8.45 (dd, J=8.36, 1.61 Hz, 1H), 8.67 (dd, J=7.63, 1.37 Hz, 1H), 8.95 (dd, J=4.21, 1.66 Hz, 1H), 10.56 (s, 1H). m/z (ESI) 468 (M+H)$^+$.

Example 107

(S)-4-(4-(3-Methoxyphenyl)-5,5-dimethyl-2-oxooxazolidin-3-yl)-N-(quinolin-8-yl)benzamide. $^1$H NMR (400 MHz, DMSO-d$_6$) δ ppm 0.97 (s, 3H), 1.66 (s, 3H), 3.74 (s, 3H), 5.51 (s, 1H), 6.82 (br. s., 2H), 6.90 (dd, J=8.31, 1.76 Hz, 1H), 7.31 (t, J=7.73 Hz, 1H), 7.60-7.69 (m, 2H), 7.69-7.77 (m, 3H), 7.88-8.04 (m, 2H), 8.45 (dd, J=8.36, 1.61 Hz, 1H), 8.67 (dd, J=7.63, 1.37 Hz, 1H), 8.95 (dd, J=4.30, 1.66 Hz, 1H), 10.56 (s, 1H). m/z (ESI) 468 (M+H)$^+$.

Example 108

Synthesis of (+/−)-(R/S)-4-(4-(3-fluorophenyl)-5,5-dimethyl-2-oxooxazolidin-3-yl)-N-(quinolin-8-yl)benzamide The title compound was prepared from DL-3-fluorophenylglycine (commercially available from Alfa Aesar, Ward Hill, Mass.) according to the procedure described in General Method MM-1 to afford (+/−)-(R/S)-4-(4-(3-fluorophenyl)-5,5-dimethyl-2-oxooxazolidin-3-yl)-N-(quinolin-8-yl)benzamide (0.191 g, 0.419 mmol, 88% yield) as a white solid. $^1$H NMR (400 MHz, DMSO-$d_6$) δ ppm 0.97 (s, 3H), 1.67 (s, 3H), 5.61 (s, 1H), 7.04-7.25 (m, 3H), 7.44 (d, J=6.06 Hz, 1H), 7.60-7.69 (m, 2H), 7.69-7.78 (m, 3H), 7.92-8.04 (m, 2H), 8.45 (dd, J=8.36, 1.61 Hz, 1H), 8.67 (dd, J=7.63, 1.37 Hz, 1H), 8.95 (dd, J=4.21, 1.66 Hz, 1H), 10.56 (s, 1H). m/z (ESI) 456 (M+H)$^+$.

Examples 109 and 110

Synthesis of (R)-4-(4-(3-fluorophenyl)-5,5-dimethyl-2-oxooxazolidin-3-yl)-N-(quinolin-8-yl)benzamide and (S)-4-(4-(3-fluorophenyl)-5,5-dimethyl-2-oxooxazolidin-3-yl)-N-(quinolin-8-yl)benzamide

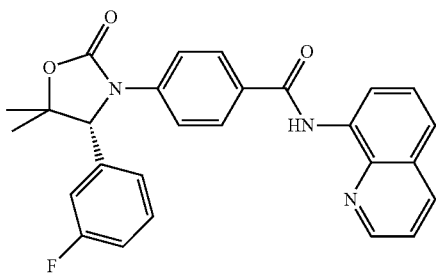 [SMILES: CC1(C)OC(=O)N(c2ccc(C(=O)Nc3cccc4cccnc34)cc2)C1c1cccc(F)c1]

Example 109

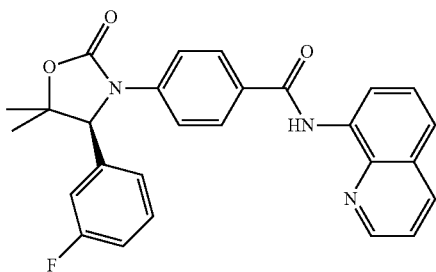

Example 110

A racemic mixture of (+/−)-(R/S)-4-(4-(3-fluorophenyl)-5,5-dimethyl-2-oxooxazolidin-3-yl)-N-(quinolin-8-yl)benzamide (Example 108)(0.160 mg, 0.351 mmol) was purified via SFC separation (Chiralpak AD-H column (2×15 cm), eluting with 40% MeOH (0.2% DEA)/CO$_2$; flow rate: 65 mL/min; injection volume 2 mL, 8 mg/mL MeOH) to afford Example 109 ((R)-4-(4-(3-fluorophenyl)-5,5-dimethyl-2-oxooxazolidin-3-yl)-N-(quinolin-8-yl)benzamide) (0.078 g, 0.171 mmol, 98% yield) as an off-white solid (first eluting peak). Example 110 ((S)-4-(4-(3-fluorophenyl)-5,5-dimethyl-2-oxooxazolidin-3-yl)-N-(quinolin-8-yl)benzamide) (0.079 g, 0.173 mmol, 99% yield) was also obtained as an off-white solid (second eluting peak).

Example 109

((R)-4-(4-(3-fluorophenyl)-5,5-dimethyl-2-oxooxazolidin-3-yl)-N-(quinolin-8-yl)benzamide). $^1$H NMR (400 MHz, DMSO-$d_6$) δ ppm 0.97 (s, 3H), 1.67 (s, 3H), 5.61 (s, 1H), 6.94-7.34 (m, 3H), 7.40-7.50 (m, 1H), 7.60-7.70 (m, 2H), 7.70-7.76 (m, 3H), 7.93-8.04 (m, 2H), 8.45 (dd, J=8.36, 1.61 Hz, 1H), 8.67 (dd, J=7.58, 1.32 Hz, 1H), 8.95 (dd, J=4.21, 1.66 Hz, 1H), 10.56 (s, 1H). m/z (ESI) 456 (M+H)$^+$.

Example 110

((S)-4-(4-(3-fluorophenyl)-5,5-dimethyl-2-oxooxazolidin-3-yl)-N-(quinolin-8-yl)benzamide). $^1$H NMR (400 MHz, DMSO-$d_6$) δ ppm 0.97 (s, 3H), 1.67 (s, 3H), 5.61 (s, 1H), 7.01-7.32 (m, 3H), 7.39-7.52 (m, 1H), 7.60-7.69 (m, 2H), 7.69-7.75 (m, 3H), 7.91-8.05 (m, 3H), 8.45 (dd, J=8.36, 1.61 Hz, 1H), 8.67 (dd, J=7.58, 1.32 Hz, 1H), 8.95 (dd, J=4.30, 1.66 Hz, 1H), 10.56 (s, 1H). m/z (ESI) 456 (M+H)$^+$.

Example 111

Synthesis of (+/−)-(R/S)-4-(4-(4-methoxyphenyl)-5,5-dimethyl-2-oxooxazolidin-3-yl)-N-(quinolin-8-yl)benzamide

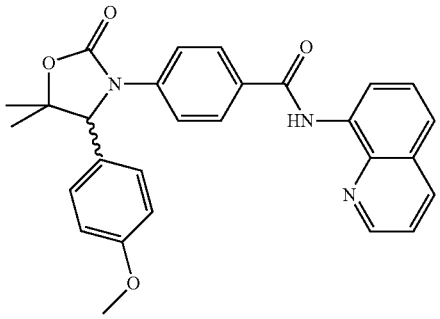

The title compound was prepared from (+/−)-4-methoxyphenylglycine (commercially available from Tyger Scientific, Inc., Ewing, N.J.) according to the procedure described in General Method MM-1 to afford (+/−)-(R/S)-4-(4-(4-methoxyphenyl)-5,5-dimethyl-2-oxooxazolidin-3-yl)-N-(quinolin-8-yl)benzamide (0.137 g, 0.293 mmol, 86% yield) as a white solid. $^1$H NMR (400 MHz, DMSO-$d_6$) δ ppm 0.95 (s, 3H), 1.64 (s, 3H), 3.73 (d, J=2.45 Hz, 3H), 5.49 (s, 1H), 6.95 (d, J=7.83 Hz, 2H), 7.21 (br. s., 2H), 7.56-7.79 (m, 5H), 7.96 (dd, J=8.80, 2.15 Hz, 2H), 8.37-8.52 (m, 1H), 8.67 (d, J=7.63 Hz, 1H), 8.87-9.04 (m, 1H), 10.55 (s, 1H). m/z (ESI) 468 (M+H)$^+$.

Examples 112 and 113

Synthesis of (R)-4-(4-(4-methoxyphenyl)-5,5-dimethyl-2-oxooxazolidin-3-yl)-N-(quinolin-8-yl)benzamide and (S)-4-(4-(4-methoxyphenyl)-5,5-dimethyl-2-oxooxazolidin-3-yl)-N-(quinolin-8-yl)benzamide

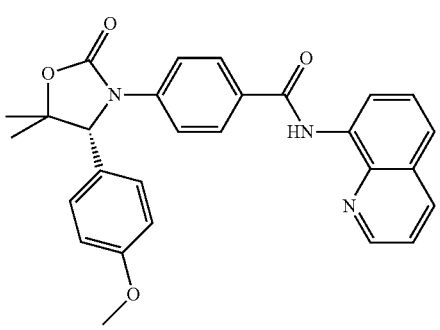 [SMILES: COc1ccc(C2N(c3ccc(C(=O)Nc4cccc5cccnc45)cc3)C(=O)OC2(C)C)cc1]

Example 112

Example 113

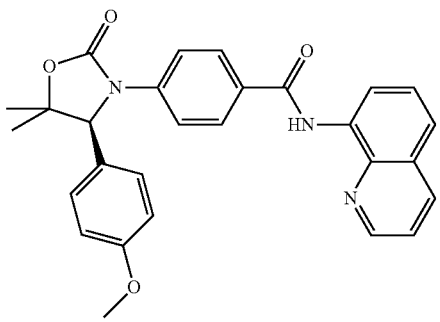

A racemic mixture of (+/−)-(R/S)-4-(4-(4-methoxyphenyl)-5,5-dimethyl-2-oxooxazolidin-3-yl)-N-(quinolin-8-yl)benzamide (Example 111)(0.112 g, 0.240 mmol) was purified via SFC separation (Chiralpak AD-H column (2×15 cm), eluting with 50/50 CO$_2$/MeOH with 0.2% DEA; flow rate: 80 mL/min; 7 mg sample/injection) to afford Example 112 ((R)-4-(4-(4-methoxyphenyl)-5,5-dimethyl-2-oxooxazolidin-3-yl)-N-(quinolin-8-yl)benzamide) (0.052 g, 0.111 mmol, 93% yield) as an off-white solid (first eluting peak). Example 113 ((S)-4-(4-(4-methoxyphenyl)-5,5-dimethyl-2-oxooxazolidin-3-yl)-N-(quinolin-8-yl)benzamide) (0.054 g, 0.116 mmol, 96% yield) was also obtained as an off-white solid (second eluting peak).

Example 112

((R)-4-(4-(4-methoxyphenyl)-5,5-dimethyl-2-oxooxazolidin-3-yl)-N-(quinolin-8-yl)benzamide). $^1$H NMR (400 MHz, DMSO-d$_6$) δ ppm 0.95 (s, 3H), 1.64 (s, 3H), 3.72 (s, 3H), 5.49 (s, 1H), 6.94 (d, J=8.80 Hz, 2H), 7.08-7.37 (m, 2H), 7.54-7.80 (m, 5H), 7.89-8.03 (m, 2H), 8.45 (dd, J=8.31, 1.56 Hz, 1H), 8.67 (dd, J=7.63, 1.37 Hz, 1H), 8.95 (dd, J=4.30, 1.66 Hz, 1H), 10.55 (s, 1H). m/z (ESI) 468 (M+H)$^+$.

Example 113

((S)-4-(4-(4-methoxyphenyl)-5,5-dimethyl-2-oxooxazolidin-3-yl)-N-(quinolin-8-yl)benzamide). $^1$H NMR (400 MHz, DMSO-d$_6$) δ ppm 0.95 (s, 3H), 1.64 (s, 3H), 3.72 (s, 3H), 5.49 (s, 1H), 6.94 (d, J=8.80 Hz, 2H), 7.22 (br. s., 2H), 7.54-7.82 (m, 5H), 7.89-8.04 (m, 2H), 8.45 (dd, J=8.36, 1.61 Hz, 1H), 8.67 (dd, J=7.63, 1.37 Hz, 1H), 8.95 (dd, J=4.21, 1.66 Hz, 1H), 10.55 (s, 1H). m/z (ESI) 468 (M+H)$^+$.

Example 114

Synthesis of (S)-3-(4-(6'-fluoro-[2,3'-bipyridin]-5'-yl)phenyl)-5,5-dimethyl-4-phenyloxazolidin-2-one

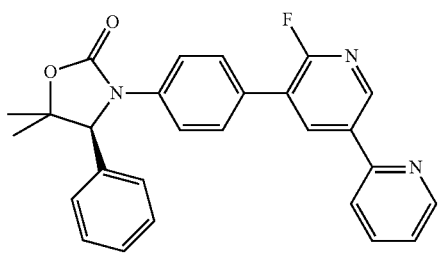 [SMILES: CC1(C)OC(=O)N(c2ccc(-c3cc(-c4ccccn4)cnc3F)cc2)[C@H]1c1ccccc1]

The title compound was prepared as described in General Method MM-2 using 2-(tributylstannyl)pyridine (commercially available from Sigma-Aldrich, Milwaukee, Wis.) in Step 2 to afford (S)-3-(4-(6'-fluoro-[2,3'-bipyridin]-5'-yl)phenyl)-5,5-dimethyl-4-phenyloxazolidin-2-one (0.015 g, 0.034 mmol, 38% yield) as a white solid. $^1$H NMR (400 MHz, DMSO-d$_6$) δ ppm 0.93 (s, 3H), 1.66 (s, 3H), 5.53 (s, 1H), 7.22-7.48 (m, 6H), 7.65 (s, 4H), 7.93 (td, J=7.78, 1.86 Hz, 1H), 8.13 (dt, J=8.00, 0.99 Hz, 1H), 8.63 (dd, J=9.78, 2.45 Hz, 1H), 8.68-8.74 (m, 1H), 8.87 (dd, J=2.40, 1.32 Hz, 1H). m/z (ESI) 440 (M+H)$^+$.

Example 115

Synthesis of (S)-5,5-dimethyl-3-(4-(6'-oxo-1',6'-dihydro-[2,3'-bipyridin]-5'-yl)phenyl)-4-phenyloxazolidin-2-one

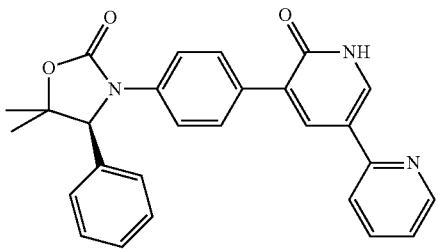 [SMILES: CC1(C)OC(=O)N(c2ccc(-c3cc(-c4ccccn4)c[nH]c3=O)cc2)[C@H]1c1ccccc1]

The title compound was prepared from Example 114 as described in General Method MM-2 to afford (S)-5,5-dimethyl-3-(4-(6'-oxo-1',6'-dihydro-[2,3'-bipyridin]-5'-yl)phenyl)-4-phenyloxazolidin-2-one (0.014 g, 0.032 mmol, 70% yield) as a white solid. $^1$H NMR (400 MHz, DMSO-d$_6$) δ ppm 0.92 (s, 3H), 1.65 (s, 3H), 5.49 (s, 1H), 7.18-7.45 (m, 6H), 7.47-7.58 (m, 2H) 7.67-7.76 (m, 2H), 7.76-7.84 (m, 1H), 7.86-7.95 (m, 1H), 8.11 (d, J=2.54 Hz, 1H), 8.29 (d, J=2.74 Hz, 1H), 8.56 (ddd, J=4.84, 1.81, 0.88 Hz, 1H), 12.09 (br. s., 1H). m/z (ESI) 438 (M+H)$^+$.

Example 116

Synthesis of (S)-5,5-dimethyl-3-(4-(5-(oxazol-2-yl)-2-oxo-1,2-dihydropyridin-3-yl)phenyl)-4-phenyloxazolidin-2-one

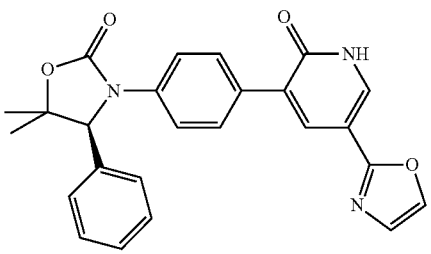 [SMILES: CC1(C)OC(=O)N(c2ccc(-c3cc(-c4ncco4)c[nH]c3=O)cc2)[C@H]1c1ccccc1]

The title compound was prepared as described in General Method MM-2 using 2-(tri-n-butylstannyl)oxazole (commercially available from Sigma-Aldrich, Milwaukee, Wis.) in Step 2 to afford (S)-5,5-dimethyl-3-(4-(5-(oxazol-2-yl)-2-oxo-1,2-dihydropyridin-3-yl)phenyl)-4-phenyloxazolidin-2-one (0.012 g, 0.028 mmol, 64% yield) as an off-white solid.

¹H NMR (400 MHz, DMSO-d₆) δ ppm 0.91 (s, 3H), 1.64 (s, 3H), 5.49 (s, 1H), 7.03-8.23 (m, 13H), 12.23 (br.s., 1H). m/z (ESI) 443 (M+H)⁺.

Example 117

Synthesis of (S)-3-(4-(6-fluoro-[3,3'-bipyridin]-5-yl)phenyl)-5,5-dimethyl-4-phenyloxazolidin-2-one

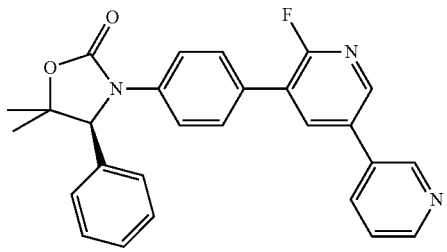 [SMILES: CC1(C)OC(=O)N(c2ccc(-c3cc(-c4cccnc4)cnc3F)cc2)[C@H]1c1ccccc1]

A microwave vial was charged with (S)-3-(4-(5-bromo-2-fluoropyridin-3-yl)phenyl)-5,5-dimethyl-4-phenyloxazolidin-2-one (Example 3)(0.040 g, 0.091 mmol), 3-pyridylboronic acid (commercially available from Sigma-Aldrich, Milwaukee, Wis., 0.022 g, 0.181 mmol), sodium carbonate (0.029 g, 0.272 mmol), dioxane (2.0 mL), and water (0.40 mL). Tetrakis(triphenylphosphine)-palladium(0) (10.47 mg, 9.06 mol) was added, the system was purged with argon, and the tube was sealed. The mixture was then stirred at 100° C. in the microwave for 1 hour. The reaction mixture was next filtered through Celite® brand filter aid and the filtrate was concentrated to afford a yellow oil. The oil thus obtained was purified using column chromatography on silica gel (RediSep 40 g column, gradient elution with 50-100% EtOAc-hexane) to afford (S)-3-(4-(6-fluoro-[3,3'-bipyridin]-5-yl)phenyl)-5,5-dimethyl-4-phenyloxazolidin-2-one (0.033 g, 0.075 mmol, 83% yield) as a white solid. ¹H NMR (400 MHz, DMSO-d₆) δ ppm 0.93 (s, 3H), 1.65 (s, 3H), 5.53 (s, 1H), 7.24-7.45 (m, 5H), 7.51 (ddd, J=8.00, 4.82, 0.88 Hz, 1H), 7.60-7.75 (m, 4H), 8.23 (ddd, J=8.00, 2.42, 1.61 Hz, 1H), 8.41 (dd, J=9.63, 2.49 Hz, 1H), 8.56 (dd, J=2.40, 1.32 Hz, 1H), 8.62 (dd, J=4.74, 1.61 Hz, 1H), 9.02 (dd, J=2.45, 0.78 Hz, 1H). m/z (ESI) 440 (M+H)⁺.

Example 118

Synthesis of (S)-5,5-dimethyl-3-(4-(6-oxo-1,6-dihydro-[3,3'-bipyridin]-5-yl)phenyl)-4-phenyloxazolidin-2-one

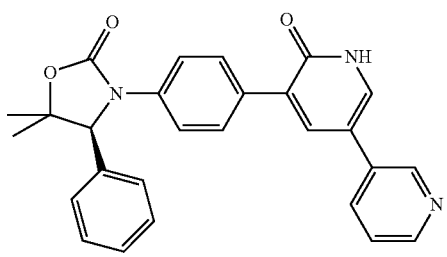 [SMILES: CC1(C)OC(=O)N(c2ccc(-c3cc(-c4cccnc4)c[nH]c3=O)cc2)[C@H]1c1ccccc1]

The title compound was prepared as described in General Method MM-2 using 3-pyridylboronic acid (commercially available from Sigma-Aldrich, Milwaukee, Wis.) to afford (S)-5,5-dimethyl-3-(4-(6-oxo-1,6-dihydro-[3,3'-bipyridin]-5-yl)phenyl)-4-phenyloxazolidin-2-one (0.012 g, 0.027 mmol, 48.2% yield) as a white solid. ¹H NMR (400 MHz, DMSO-d₆) δ ppm 0.92 (s, 3H), 1.65 (s, 3H), 5.49 (s, 1H), 7.14-7.45 (m, 6H), 7.51 (d, J=8.90 Hz, 2H), 7.72-7.87 (m, 3H), 7.98 (d, J=2.64 Hz, 1H), 8.05 (dt, J=7.92, 1.96 Hz, 1H), 8.48 (dd, J=4.74, 1.52 Hz, 1H), 8.87 (d, J=1.86 Hz, 1H), 12.08 (br. s., 1H). m/z (ESI) 438 (M+H)⁺.

Example 119

Synthesis of (S)-5,5-dimethyl-3-(4-(2-oxo-1,2-dihydropyridin-3-yl)phenyl)-4-phenyloxazolidin-2-one

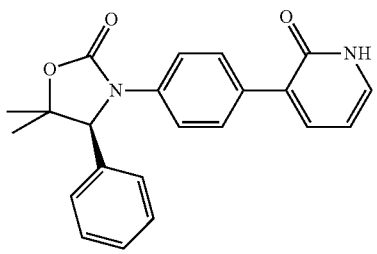 [SMILES: CC1(C)OC(=O)N(c2ccc(-c3ccc[nH]c3=O)cc2)[C@H]1c1ccccc1]

A resealable tube was charged with (S)-5,5-dimethyl-4-phenyl-3-(4-(4,4,5,5-tetramethyl-1,3,2-dioxaborolan-2-yl)phenyl)oxazolidin-2-one (Intermediate J)(0.100 g, 0.254 mmol), 5-bromo-3-iodopyridin-2(1H)-one (commercially available from Adesis, Inc., New Castle, Del.)(0.153 g, 0.509 mmol), sodium carbonate (0.108 g, 1.017 mmol), dioxane (2.0 mL), and water (0.40 mL). Tetrakis(triphenylphosphine) palladium(0) (0.147 g, 0.127 mmol) was added, the system was purged with argon, and the tube was sealed. The mixture was then stirred at 100° C. for 16 hours. The reaction mixture was filtered through Celite® brand filter aid. The filtrate was then concentrated to afford a black oil. The oil thus obtained was purified using column chromatography on silica gel (RediSep 40 g column, gradient elution with 0-100% EtOAc-hexane) to afford (S)-5,5-dimethyl-3-(4-(2-oxo-1,2-dihydropyridin-3-yl)phenyl)-4-phenyloxazolidin-2-one (0.021 g, 0.058 mmol, 23% yield) as an off-white solid. ¹H NMR (400 MHz, DMSO-d₆) δ ppm 0.91 (s, 3H), 1.64 (s, 3H), 5.46 (s, 1H), 6.24 (t, J=6.70 Hz, 1H), 7.20-7.43 (m, 6H), 7.48 (d, J=8.90 Hz, 2H), 7.58 (dd, J=6.94, 2.05 Hz, 1H), 7.65 (d, J=8.80 Hz, 2H), 11.72 (br. s., 1H). m/z (ESI) 361 (M+H)⁺.

Example 120

Synthesis of (S)-2-(5-(4-(5,5-dimethyl-2-oxo-4-phenyloxazolidin-3-yl)phenyl)-6-oxo-1,6-dihydropyridin-3-yl)pyrimidine-4-carbonitrile

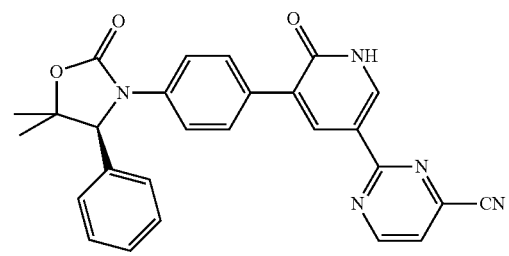 [SMILES: CC1(C)OC(=O)N(c2ccc(-c3cc(-c4nccc(C#N)n4)c[nH]c3=O)cc2)[C@H]1c1ccccc1]

Step 1

(S)-3-(4-(2-Fluoro-5-(4,4,5,5-tetramethyl-1,3,2-dioxaborolan-2-yl)pyridin-3-yl)phenyl)-5,5-dimethyl-4-phenyloxazolidin-2-one A microwave vial was charged with (S)-3-(4-(5-bromo-2-fluoropyridin-3-yl)phenyl)-5,5-dimethyl-4-phenyloxazolidin-2-one (Example 3)(0.100 g, 0.227 mmol), bis(pinacolato)diboron (commercially available from Sigma-Aldrich, Milwaukee, Wis.)(0.063 g, 0.249 mmol), potassium acetate (0.111 g, 1.133 mmol), and dioxane (2.0 mL). Dichloro[1,1'-bis(diphenylphosphino)ferrocene]palladium (II) (DCM adduct)(0.019 g, 0.023 mmol) was added, the system was purged with argon, and the tube was sealed. The mixture was then stirred at 100° C. in the microwave for 1 hour. The reaction mixture was filtered through Celite® brand filter aid, and the filtrate was concentrated to afford a brown solid. The solid thus obtained was purified via column chromatography on silica gel (RediSep 40 g column, gradient elution with 0-50% EtOAc-hexane) to afford (S)-3-(4-(2-fluoro-5-(4,4,5,5-tetramethyl-1,3,2-dioxaborolan-2-yl)pyridin-3-yl)phenyl)-5,5-dimethyl-4-phenyloxazolidin-2-one (0.074 g, 0.152 mmol, 66.9% yield) as a white solid. $^1$H NMR (400 MHz, DMSO-$d_6$) δ ppm 0.92 (s, 3H), 1.30 (s, 12H), 1.65 (s, 3H), 5.51 (s, 1H), 7.20-7.46 (m, 5H), 7.51-7.58 (m, 2H), 7.58-7.66 (m, 2H), 8.09 (dd, J=10.76, 1.96 Hz, 1H), 8.37 (d, J=1.27 Hz, 1H). m/z (ESI) 489 (M+H)$^+$.

Step 2

(S)-2-(5-(4-(5,5-Dimethyl-2-oxo-4-phenyloxazolidin-3-yl)phenyl)-6-fluoropyridin-3-yl)pyrimidine-4-carbonitrile A microwave vial was charged with (S)-3-(4-(2-fluoro-5-(4,4,5,5-tetramethyl-1,3,2-dioxaborolan-2-yl)pyridin-3-yl)phenyl)-5,5-dimethyl-4-phenyloxazolidin-2-one (0.074 g, 0.152 mmol), 2-chloropyrimidine-4-carbonitrile (commercially available from Synthonix, Wake Forest, N.C.)(0.023 g, 0.167 mmol), sodium carbonate (0.048 g, 0.455 mmol), dioxane (2.0 mL), and water (0.400 mL). Dichloro[1,1'-bis(diphenylphosphino)ferrocene]palladium (II) DCM adduct (0.012 g, 0.015 mmol) was added, the system was purged with argon, and the tube was sealed. The mixture was then stirred at 100° C. in a microwave for 1 hour. The resulting reaction mixture was filtered through Celite® brand filter aid and the filtrate was concentrated to afford a brown solid. The resulting solid was purified using column chromatography on silica gel (RediSep 40 g column, gradient elution with 0-50% EtOAc-hexane) to afford (S)-2-(5-(4-(5,5-dimethyl-2-oxo-4-phenyloxazolidin-3-yl)phenyl)-6-fluoropyridin-3-yl)pyrimidine-4-carbonitrile (0.051 g, 0.110 mmol, 72.3% yield) as a white solid. $^1$H NMR (400 MHz, DMSO-$d_6$) δ ppm 0.93 (s, 3H), 1.66 (s, 3H), 5.53 (s, 1H), 7.14-7.50 (m, 5H), 7.59-7.78 (m, 4H), 8.17 (d, J=4.99 Hz, 1H), 8.78 (dd, J=9.68, 2.35 Hz, 1H), 9.09 (dd, J=2.30, 0.93 Hz, 1H), 9.29 (d, J=4.89 Hz, 1H). m/z (ESI) 466 (M+H)$^+$.

Step 3

(S)-2-(5-(4-(5,5-Dimethyl-2-oxo-4-phenyloxazolidin-3-yl)phenyl)-6-oxo-1,6-dihydropyridin-3-yl)pyrimidine-4-carbonitrile A resealable tube was charged with (S)-2-(5-(4-(5,5-dimethyl-2-oxo-4-phenyloxazolidin-3-yl)phenyl)-6-fluoropyridin-3-yl)pyrimidine-4-carbonitrile (0.055 g, 0.12 mmol), dioxane (3.0 mL) and water (1.00 mL). Concentrated hydrochloric acid (37%)(0.25 mL) was added, the system was flushed with argon, the tube was sealed, and the reaction mixture stirred at 100° C. for 1 hour. The reaction mixture was then partitioned between EtOAc and saturated aqueous NaHCO$_3$ solution. The aqueous phase was extracted with EtOAc. The combined organic phases were washed with brine, dried over anhydrous Na$_2$SO$_4$, filtered, and concentrated to afford (S)-2-(5-(4-(5,5-dimethyl-2-oxo-4-phenyloxazolidin-3-yl)phenyl)-6-oxo-1,6-dihydropyridin-3-yl)pyrimidine-4-carbonitrile (0.044 g, 0.095 mmol, 80% yield) as an off-white solid. $^1$H NMR (400 MHz, DMSO-$d_6$) δ ppm 0.92 (s, 3H), 1.65 (s, 3H), 5.49 (s, 1H), 7.22-7.45 (m, 5H), 7.50-7.61 (m, 2H), 7.63-7.76 (m, 2H), 7.93 (d, J=4.89 Hz, 1H), 8.28-8.47 (m, 2H), 9.11 (d, J=4.99 Hz, 1H), 12.33 (br.s., 1H). m/z (ESI) 464 (M+H)$^+$.

Example 121

Synthesis of (+/−)-(R/S)-4-(5,5-dimethyl-2-oxo-4-(pyridin-2-yl)oxazolidin-3-yl)-N-(quinolin-8-yl)benzamide

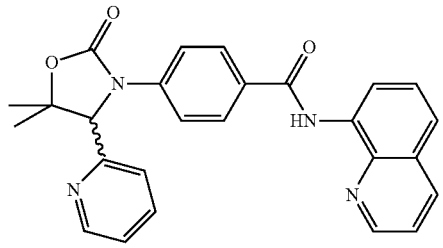 [SMILES: CC1(C)OC(=O)N(c2ccc(C(=O)Nc3cccc4cccnc34)cc2)C1c1ccccn1]

The title compound was prepared from methyl (+/−)-2-amino-2-(pyridin-2-yl)acetate (commercially available from Small Molecules, Inc., Hoboken, N.J.) according to the procedure described in General Method MM-4 to afford (+/−)-(R/S)-4-(5,5-dimethyl-2-oxo-4-(pyridin-2-yl)oxazolidin-3-yl)-N-(quinolin-8-yl)benzamide (0.125 g, 0.285 mmol, 73% yield) as an off-white solid. $^1$H NMR (400 MHz, DMSO-$d_6$) δ ppm 0.92 (s, 3H), 1.68 (s, 3H), 5.59 (s, 1H), 7.35 (ddd, J=7.60, 4.82, 1.17 Hz, 1H), 7.52 (d, J=7.92 Hz, 1H), 7.59-7.77 (m, 5H), 7.85 (td, J=7.70, 1.81 Hz, 1H), 7.91-8.01 (m, 2H), 8.45 (dd, J=8.41, 1.57 Hz, 1H), 8.52-8.62 (m, 1H), 8.67 (dd, J=7.63, 1.27 Hz, 1H), 8.95 (dd, J=4.25, 1.71 Hz, 1H), 10.54 (s, 1H). m/z (ESI) 439 (M+H)$^+$.

Examples 122 and 123

Synthesis of (R)-4-(5,5-dimethyl-2-oxo-4-(pyridin-2-yl)oxazolidin-3-yl)-N-(quinolin-8-yl)benzamide and (S)-4-(5,5-dimethyl-2-oxo-4-(pyridin-2-yl)oxazolidin-3-yl)-N-(quinolin-8-yl)benzamide Example 122

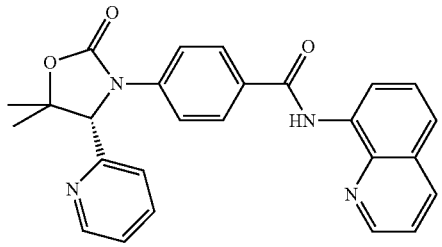

Example 123

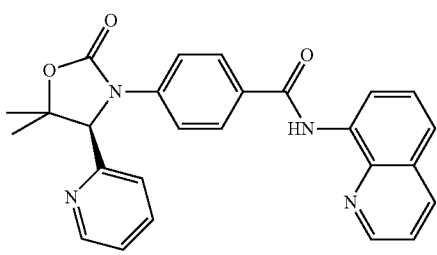

A racemic mixture of (+/−)-(R/S)-4-(5,5-dimethyl-2-oxo-4-(pyridin-2-yl)oxazolidin-3-yl)-N-(quinolin-8-yl)benzamide (Example 121)(0.093 g, 0.212 mmol) was purified via SFC separation (Chiralpak AD-H column (2×15 cm), eluting with 50/50 $CO_2$/MeOH with 0.2% DEA; flow rate: 75 mL/min; 5 mg sample/injection) to afford Example 122 ((R)-4-(5,5-dimethyl-2-oxo-4-(pyridin-2-yl)oxazolidin-3-yl)-N-(quinolin-8-yl)benzamide) (0.044 g, 0.100 mmol, 95% yield) as an off-white solid (first eluting peak). Example 123 ((S)-4-(5,5-dimethyl-2-oxo-4-(pyridin-2-yl)oxazolidin-3-yl)-N-(quinolin-8-yl)benzamide) (0.044 g, 0.100 mmol, 95% yield) was also obtained as an off-white solid (second eluting peak).

Example 122

((R)-4-(5,5-dimethyl-2-oxo-4-(pyridin-2-yl)oxazolidin-3-yl)-N-(quinolin-8-yl)benzamide). $^1$H NMR (400 MHz, DMSO-$d_6$) δ ppm 0.92 (s, 3H), 1.68 (s, 3H), 5.59 (s, 1H), 7.35 (ddd, J=7.58, 4.79, 1.12 Hz, 1H), 7.52 (d, J=7.82 Hz, 1H), 7.59-7.69 (m, 2H), 7.69-7.77 (m, 3H), 7.85 (td, J=7.70, 1.81 Hz, 1H), 7.91-7.98 (m, 2H), 8.45 (dd, J=8.36, 1.61 Hz, 1H), 8.54-8.63 (m, 1H), 8.67 (dd, J=7.63, 1.27 Hz, 1H), 8.95 (dd, J=4.30, 1.66 Hz, 1H), 10.54 (s, 1H). m/z (ESI) 439 (M+H)$^+$.

Example 123

((S)-4-(5,5-dimethyl-2-oxo-4-(pyridin-2-yl)oxazolidin-3-yl)-N-(quinolin-8-yl)benzamide). $^1$H NMR (400 MHz, DMSO-$d_6$) δ ppm 0.92 (s, 3H), 1.68 (s, 3H) 5.59 (s, 1H) 7.35 (ddd, J=7.56, 4.82, 1.12 Hz, 1H), 7.52 (d, J=7.83 Hz, 1H), 7.59-7.69 (m, 2H), 7.69-7.77 (m, 3H), 7.85 (td, J=7.70, 1.81 Hz, 1H),7.91-8.01 (m, 2H), 8.45 (dd, J=8.31, 1.56 Hz, 1H), 8.53-8.62 (m, 1H), 8.67 (dd, J=7.63, 1.37 Hz, 1H), 8.95 (dd, J=4.21, 1.66 Hz, 1H), 10.54 (s, 1H). m/z (ESI) 439 (M+H)$^+$.

Example 124

Synthesis of (+/−)-(R/S)-4-(5,5-dimethyl-2-oxo-4-(pyridin-4-yl)oxazolidin-3-yl)-N-(quinolin-8-yl)benzamide

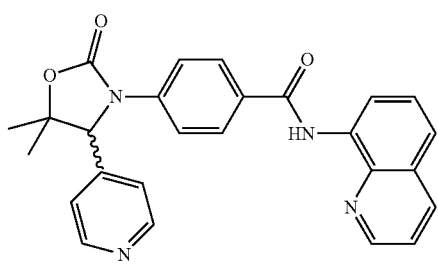 [SMILES: CC1(C)OC(=O)N(c2ccc(C(=O)Nc3cccc4cccnc34)cc2)C1c1ccncc1]

The title compound was prepared from (+/−)-ethyl 2-amino-2-(pyridin-4-yl)acetate dihydrochloride (commercially available from Accela Chemicals, Inc., San Diego, Calif.) according to the procedure described in General Method MM-4 to afford (+/−)-(R/S)-4-(5,5-dimethyl-2-oxo-4-(pyridin-4-yl)oxazolidin-3-yl)-N-(quinolin-8-yl)benzamide (0.128 g, 0.292 mmol, 76% yield) as an off-white solid.
$^1$H NMR (400 MHz, DMSO-$d_6$) δ ppm 0.92 (s, 3H), 1.68 (s, 3H), 5.59 (s, 1H), 7.35 (ddd, J=7.60, 4.82, 1.17 Hz, 1H), 7.52 (d, J=7.92 Hz, 1H), 7.59-7.77 (m, 5H), 7.85 (td, J=7.70, 1.81 Hz, 1H), 7.91-8.01 (m, 2H), 8.45 (dd, J=8.41, 1.57 Hz, 1H), 8.52-8.62 (m, 1H), 8.67 (dd, J=7.63, 1.27 Hz, 1H), 8.95 (dd, J=4.25, 1.71 Hz, 1H), 10.54 (s, 1H). m/z (ESI) 439 (M+H)$^+$.

Examples 125 and 126

Synthesis of (R)-4-(5,5-dimethyl-2-oxo-4-(pyridin-4-yl)oxazolidin-3-yl)-N-(quinolin-8-yl)benzamide and (S)-4-(5,5-dimethyl-2-oxo-4-(pyridin-4-yl)oxazolidin-3-yl)-N-(quinolin-8-yl)benzamide Example 125

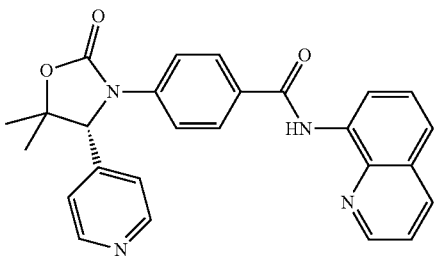

Example 126

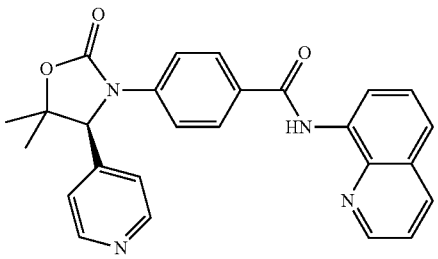

A racemic mixture of (+/−)-(R/S)-4-(5,5-dimethyl-2-oxo-4-(pyridin-4-yl)oxazolidin-3-yl)-N-(quinolin-8-yl)benzamide (Example 124)(0.109 g, 0.249 mmol) was purified via SFC separation (Chiralpak AD-H column (2×15 cm), eluting with 50/50 $CO_2$/MeOH with 0.2% DEA; flow rate: 80 mL/min; 11 mg sample/injection) to afford Example 125 ((R)-4-(5,5-dimethyl-2-oxo-4-(pyridin-4-yl)oxazolidin-3-yl)-N-(quinolin-8-yl)benzamide) (0.049 g, 0.112 mmol, 90% yield) as a pale yellow solid (first eluting peak). Example 126 ((S)-4-(5,5-dimethyl-2-oxo-4-(pyridin-4-yl)oxazolidin-3-yl)-N-(quinolin-8-yl)benzamide) (0.048 g, 0.109 mmol, 88% yield) was also obtained as a pale yellow solid (second eluting peak).

Example 125

((R)-4-(5,5-dimethyl-2-oxo-4-(pyridin-4-yl)oxazolidin-3-yl)-N-(quinolin-8-yl)benzamide). $^1$H NMR (400 MHz, DMSO-$d_6$) δ ppm 0.97 (s, 3H), 1.69 (s, 3H), 5.65 (s, 1H), 7.33 (br. s., 2H), 7.55-7.81 (m, 5H), 7.90-8.08 (m, 2H), 8.45 (dd, J=8.31, 1.66 Hz, 1H), 8.59 (d, J=5.38 Hz, 2H), 8.67 (dd, J=7.63, 1.37 Hz, 1H), 8.95 (dd, J=4.21, 1.66 Hz, 1H), 10.56 (s, 1H). m/z (ESI) 439 (M+H)$^+$.

Example 126

((S)-4-(5,5-dimethyl-2-oxo-4-(pyridin-4-yl)oxazolidin-3-yl)-N-(quinolin-8-yl)benzamide). $^1$H NMR (400 MHz, DMSO-d$_6$) δ ppm 0.97 (s, 3H), 1.69 (s, 3H), 5.65 (s, 1H), 7.34 (br. s., 2H), 7.54-7.80 (m, 5H), 7.92-8.07 (m, 2H), 8.45 (dd, J=8.36, 1.61 Hz, 1H), 8.59 (d, J=5.38 Hz, 2H), 8.67 (dd, J=7.63, 1.27 Hz, 1H), 8.95 (dd, J=4.21, 1.66 Hz, 1H), 10.56 (s, 1H). m/z (ESI) 439 (M+H)$^+$.

Example 127

Synthesis of (S)-5,5-dimethyl-3-(4-(2-oxo-5-(pyrimidin-2-yl)pyridin-1(2H)-yl)phenyl)-4-phenyloxazolidin-2-one

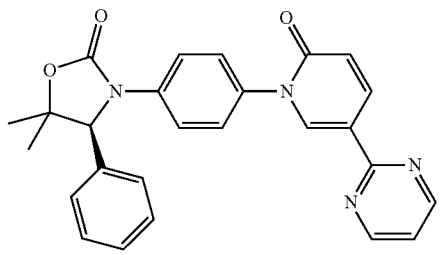 [SMILES: CC1(C)OC(=O)N(c2ccc(-n3cc(-c4ncccn4)ccc3=O)cc2)[C@H]1c1ccccc1]

Step 1

2-(6-Fluoropyridin-3-yl)pyrimidine

A microwave vial was charged with 5-bromo-2-fluoropyridine (commercially available from Acros, Pittsburgh, Pa.) (0.200 mL, 1.738 mmol), 2-(tributylstannyl)pyrimidine (commercially available from Frontier Scientific, Inc., Logan Utah) (0.718 mL, 2.173 mmol), lithium chloride (0.147 g, 3.48 mmol), copper (I) iodide (0.033 g, 0.174 mmol), and DMF (5.0 mL). Tetrakis(triphenylphosphine)palladium(0) (0.201 g, 0.174 mmol) was added, the system was purged with argon, and the tube was sealed. The resulting mixture was stirred at 120° C. in a microwave for 1 hour. The reaction mixture was then concentrated to afford a brown oil. The resulting oil was purified using column chromatography on silica gel (RediSep 40 g column, gradient elution with 0-25% EtOAc-heptane) to afford 2-(6-fluoropyridin-3-yl)pyrimidine (0.150 g, 0.856 mmol, 49% yield) as a pale yellow solid. $^1$H NMR (400 MHz, DMSO-d$_6$) δ ppm 7.35 (dddd, J=8.51, 7.65, 2.91, 0.59 Hz, 1H), 7.54 (t, J=4.89 Hz, 1H), 8.28-8.43 (m, 1H), 8.78-8.89 (m, 1H), 8.96 (d, J=4.89 Hz, 2H). m/z (ESI) 176(M+H)$^+$.

Step 2

5-(Pyrimidin-2-yl)pyridin-2(1H)-one

A resealable tube was charged with 2-(6-fluoropyridin-3-yl)pyrimidine (0.150 g, 0.856 mmol), dioxane (3.0 mL), and water (1.00 mL). Concentrated hydrochloric acid (37%)(0.25 mL) was added, the system was flushed with argon, the tube was sealed, and the reaction mixture stirred at 100° C. for 1.5 hours. The reaction mixture was then partitioned between EtOAc and saturated aqueous NaHCO$_3$ solution. The aqueous phase was extracted with EtOAc. The combined organic phases were washed with brine, dried over anhydrous Na$_2$SO$_4$, filtered, and concentrated to afford 5-(pyrimidin-2-yl)pyridin-2(1H)-one (0.079 g, 0.456 mmol, 53% yield) as an off-white solid. $^1$H NMR (400 MHz, DMSO-d$_6$) δ ppm 6.45 (dd, J=9.59, 0.78 Hz, 1H), 7.33 (t, J=4.89 Hz, 1H), 8.32 (td, J=10.07, 2.35 Hz, 2H), 8.79 (d, J=4.89 Hz, 2H), 11.96 (br. s., 1H). m/z (ESI) 174 (M+H)$^+$.

Step 3

(S)-5,5-Dimethyl-3-(4-(2-oxo-5-(pyrimidin-2-yl) pyridin-1(2H)-yl)phenyl)-4-phenyloxazolidin-2-one A microwave vial was charged with (S)-3-(4-iodophenyl)-5,5-dimethyl-4-phenyloxazolidin-2-one (Intermediate C)(0.100 g, 0.254 mmol), 5-(pyrimidin-2-yl)pyridin-2(1H)-one (0.048 g, 0.280 mmol), tribasic potassium phosphate (0.270 g, 1.272 mmol) and dioxane (2.5 mL). The mixture was purged with argon and then copper (I) iodide (0.048 g, 0.254 mmol) and N,N'-dimethylethylenediamine (0.055 mL, 0.509 mmol) were added. The system was purged with argon, the tube was sealed, and the reaction mixture was heated at 140° C. for 4 hours in the microwave. The reaction mixture was then filtered through Celite® brand filter aid and the filtrate was concentrated to afford a green solid. The resulting green solid was purified using column chromatography on silica gel (RediSep 40 g column, gradient elution with 50-100% EtOAc-hexane) to afford (S)-5,5-dimethyl-3-(4-(2-oxo-5-(pyrimidin-2-yl)pyridin-1 (2H)-yl)phenyl)-4-phenyloxazolidin-2-one (0.078 g, 0.178 mmol, 70% yield) as a white solid. $^1$H NMR (400 MHz, DMSO-d$_6$) δ ppm 0.93 (s, 3H), 1.66 (s, 3H), 5.52 (s, 1H), 6.60 (dd, J=9.59, 0.59 Hz, 1H), 7.21-7.53 (m, 8H), 7.59-7.71 (m, 2H), 8.36 (dd, J=9.63, 2.59 Hz, 1H), 8.43-8.53 (m, 1H), 8.79 (d, J=4.89 Hz, 2H). m/z (ESI) 439 (M+H)$^+$.

Example 128

Synthesis of (S)-4-(5,5-dimethyl-2-oxo-4-phenyloxazolidin-3-yl)-2-methyl-N-(1,5-naphthyridin-4-yl) benzamide

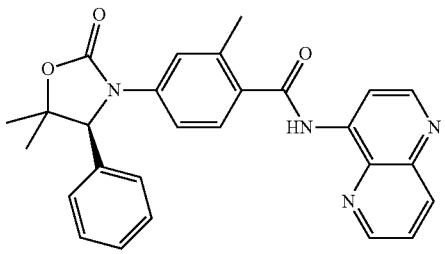 [SMILES: Cc1cc(N2C(=O)OC(C)(C)[C@@H]2c2ccccc2)ccc1C(=O)Nc1ccnc2cccnc12]

Step 1

(S)-Methyl 4-(5,5-dimethyl-2-oxo-4-phenyloxazolidin-3-yl)-2-methylbenzoate

A microwave vial was charged with (S)-5,5-dimethyl-4-phenyloxazolidin-2-one (commercially available from Sigma-Aldrich, Milwaukee, Wis., 0.100 g, 0.523 mmol), methyl 4-bromo-2-methylbenzoate (commercially available from Sigma-Aldrich, Milwaukee, Wis., 0.132 g, 0.575 mmol), tribasic potassium phosphate (0.555 g, 2.61 mmol) and dioxane (3.50 mL). The mixture was purged with argon and then copper (I) iodide (0.100 g, 0.523 mmol) and N,N'-dimethylethylenediamine (0.113 mL, 1.046 mmol) were added. The system was purged with argon, the tube was sealed, and the reaction mixture was heated at 140° C. for 1 hour in a microwave. The reaction mixture was filtered through Celite® brand filter aid and the filtrate was concentrated to afford an orange brown solid. The solid thus obtained was purified using column chromatography on silica gel (RediSep 40 g column, gradient elution with 0-50% EtOAc-hexane) to afford (S)-methyl 4-(5,5-dimethyl-2-oxo-4-phenyloxazolidin-3-yl)-2-methylbenzoate (0.159 g, 0.468 mmol, 90% yield) as a white solid. $^1$H NMR (400 MHz, DMSO-d$_6$) δ ppm 0.90 (s, 3H), 1.63 (s, 3H), 2.43 (s, 3H), 3.75 (s, 3H), 5.52 (s, 1H), 7.03-7.46 (m, 6H), 7.50 (d, J=2.35 Hz, 1H), 7.75 (d, J=8.71 Hz, 1H). m/z (ESI) 340 (M+H)$^+$.

Step 2

(S)-4-(5,5-Dimethyl-2-oxo-4-phenyloxazolidin-3-yl)-2-methylbenzoic acid

Lithium hydroxide (0.053 g, 2.210 mmol) was added to a solution of (S)-methyl 4-(5,5-dimethyl-2-oxo-4-phenyloxazolidin-3-yl)-2-methylbenzoate (0.150 g, 0.442 mmol) in THF (2.5 mL), MeOH (2.50 mL), and water (2.50 mL). The mixture was heated at 50° C. for 16 hours. The reaction mixture was then cooled in an ice bath and adjusted to pH~2 by the addition of 1 N aqueous HCl solution. Water was added, leading to the formation of a white precipitate. The precipitated material was filtered away and dried to afford (S)-4-(5,5-dimethyl-2-oxo-4-phenyloxazolidin-3-yl)-2-methylbenzoic acid (0.132 g, 0.406 mmol, 92% yield) as a white solid. $^1$H NMR (400 MHz, DMSO-d$_6$) δ ppm 0.91 (s, 3H), 1.63 (s, 3H), 2.44 (s, 3H), 5.51 (s, 1H), 7.18-7.44 (m, 6H), 7.48 (d, J=2.15 Hz, 1H), 7.75 (d, J=8.70 Hz, 1H), 12.57 (br. s., 1H). m/z (ESI) 326 (M+H)$^+$.

Step 3

(S)-4-(5,5-Dimethyl-2-oxo-4-phenyloxazolidin-3-yl)-2-methyl-N-(1,5-naphthyridin-4-yl)benzamide Thionyl chloride (0.287 mL, 3.93 mmol) was added to a solution of (S)-4-(5,5-dimethyl-2-oxo-4-phenyloxazolidin-3-yl)-2-methylbenzoic acid (0.128 g, 0.393 mmol) in DCM (2.5 mL) and the mixture was heated at 40° C. for 1 hour. The reaction mixture was concentrated to afford (S)-4-(5,5-dimethyl-2-oxo-4-phenyloxazolidin-3-yl)-2-methylbenzoyl chloride as a yellow-orange solid. The yellow-orange solid was dissolved in DCM (2.5 mL) and the solution was cooled to 0° C. 1,5-Naphthyridin-4-amine (commercially available from Astatech Inc., Bristol, Pa.) (0.063 g, 0.433 mmol) and N,N-diisopropylethylamine (0.144 mL, 0.826 mmol) were added and the ice bath was removed. The resulting reaction mixture was stirred at room temperature for 2 hours. The reaction mixture was then concentrated and the residue was purified using column chromatography on silica gel (RediSep 40 g column, gradient elution with 50-100% EtOAc-hexane) to afford (S)-4-(5,5-dimethyl-2-oxo-4-phenyloxazolidin-3-yl)-2-methyl-N-(1,5-naphthyridin-4-yl)benzamide (0.070 g, 0.155 mmol, 39% yield) as a tan solid. $^1$H NMR (400 MHz, DMSO-d$_6$) δ ppm 0.93 (s, 3H), 1.65 (s, 3H), 2.44 (s, 3H), 5.54 (s, 1H), 7.17-7.51 (m, 6H), 7.61 (d, J=2.15 Hz, 1H), 7.67 (d, J=8.51 Hz, 1H), 7.86 (dd, J=8.56, 4.16 Hz, 1H), 8.44 (dd, J=8.56, 1.61 Hz, 1H), 8.54 (d, J=5.09 Hz, 1H), 8.81-9.09 (m, 2H), 10.31 (s, 1H). m/z (ESI) 453 (M+H)$^+$.

Example 129

Synthesis of (S)-3-(4-(5-fluoro-2-(pyrimidin-2-yl)pyridin-4-yl)phenyl)-5,5-dimethyl-4-phenyloxazolidin-2-one

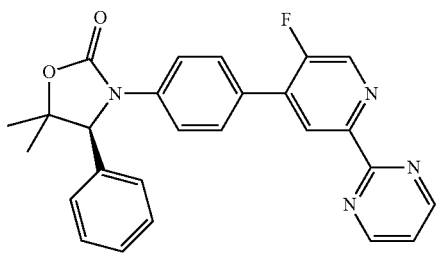 [SMILES: CC1(C)OC(=O)N(c2ccc(-c3cc(-c4ncccn4)ncc3F)cc2)[C@H]1c1ccccc1]

Step 1

(S)-3-(4-(2-Bromo-5-fluoropyridin-4-yl)phenyl)-5,5-dimethyl-4-phenyloxazolidin-2-one A microwave vial was charged with (S)-3-(4-iodophenyl)-5,5-dimethyl-4-phenyloxazolidin-2-one (Intermediate C)(0.200 g, 0.509 mmol), 2-bromo-5-fluoropyridine-4-boronic acid (commercially available from Combi Blocks, San Diego, Calif.) (0.224 g, 1.017 mmol), sodium carbonate (0.162 g, 1.526 mmol), dioxane (3.0 mL), and water (0.60 mL). Dichloro[1,1'-bis(diphenylphosphino)ferrocene]palladium (II) (DCM adduct)(0.042 g, 0.051 mmol) was added, the system was purged with argon, and the tube was sealed. The mixture was then stirred at 100° C. in the microwave for 1 hour. Additional 2-bromo-5-fluoropyridine-4-boronic acid (0.224 g, 1.017 mmol) and dichloro[1,1'-bis(diphenylphosphino)ferrocene]palladium (II) DCM adduct (0.042 g, 0.051 mmol) were added, the system was purged with argon, and the tube was sealed. The resulting mixture was then stirred at 100° C. in a microwave for 1 hour. Additional 2-bromo-5-fluoropyridine-4-boronic acid (0.224 g, 1.017 mmol) and dichloro[1,1'-bis(diphenylphosphino)ferrocene]palladium (II) DCM adduct (0.042 g, 0.051 mmol) were added, the system was purged with argon, and the tube was sealed. The resulting mixture was stirred at 100° C. in a microwave for 1 hour. The reaction mixture was then filtered through Celite® brand filter aid and the filtrate was concentrated to afford a dark brown oil. The oil thus obtained was purified using column chromatography on silica gel (RediSep 40 g column, gradient elution with 0-50% EtOAc-hexane) to afford (S)-3-(4-(2-bromo-5-fluoropyridin-4-yl)phenyl)-5,5-dimethyl-4-phenyloxazolidin-2-one (0.062 g, 0.140 mmol, 28% yield) as an off-white solid. $^1$H NMR (400 MHz, DMSO-d$_6$) δ ppm 0.92 (s, 3H), 1.65 (s, 3H), 5.53 (s, 1H), 7.17-7.49 (m, 5H), 7.59-7.73 (m, 4H), 7.83 (d, J=5.97 Hz, 1H), 8.48 (d, J=2.35 Hz, 1H). m/z (ESI) 441 (M+H)$^+$.

Step 2

2: (S)-3-(4-(5-Fluoro-2-(pyrimidin-2-yl)pyridin-4-yl)phenyl)-5,5-dimethyl-4-phenyloxazolidin-2-one A microwave vial was charged with (S)-3-(4-(2-bromo-5-fluoropyridin-4-yl)phenyl)-5,5-dimethyl-4-phenyloxazolidin-2-one (0.060 g, 0.136 mmol), 2-(tributylstannyl)pyrimidine (commercially available from Frontier Scientific, Inc., Logan Utah) (0.067 mL, 0.204 mmol), lithium chloride (0.012 g, 0.272 mmol), copper (I) iodide (2.59 mg, 0.014 mmol), and DMF (2.0 mL). Tetrakis(triphenylphosphine)palladium(0) (0.016 g, 0.014 mmol) was added, the system was purged with argon, and the tube was sealed. The resulting mixture was stirred at 120° C. in a microwave for 1 hour. The reaction mixture was then concentrated to afford an orange oil which was purified using column chromatography on silica gel (RediSep 40 g column, gradient elution with 0-10% MeOH-EtOAc) to afford (S)-3-(4-(5-fluoro-2-(pyrimidin-2-yl)pyridin-4-yl)phenyl)-5,5-dimethyl-4-phenyloxazolidin-2-one (0.012 g, 0.027 mmol, 20% yield) as a tan solid. $^1$H NMR (400 MHz, DMSO-d$_6$) δ ppm 0.93 (s, 3H), 1.66 (s, 3H), 5.53 (s, 1H), 7.10-7.54 (m, 6H), 7.56-7.89 (m, 5H), 8.10-9.41 (m, 3H). m/z (ESI) 441 (M+H)$^+$.

Example 130

Synthesis of (S)-5,5-dimethyl-3-((1r,4S)-4-(2-oxo-5-(1,4,5,6-tetrahydropyrimidin-2-yl)-1,2-dihydropyridin-3-yl)cyclohexyl)-4-phenyloxazolidin-2-one

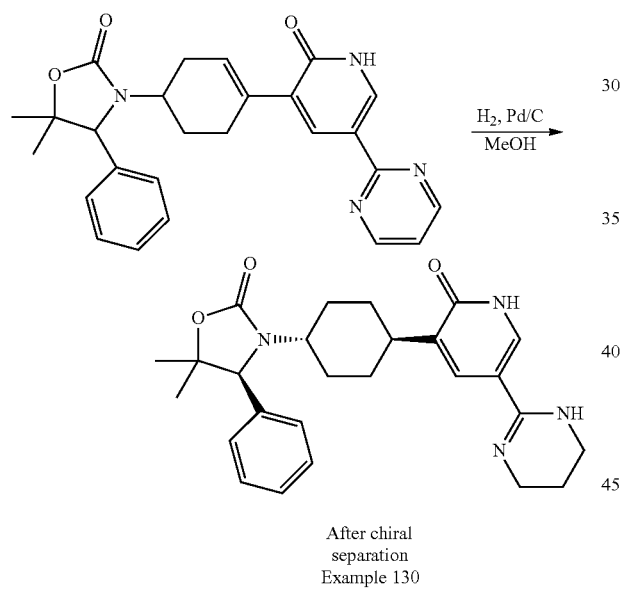

After chiral separation
Example 130

Palladium (10 wt % on activated carbon) (0.020 g, 0.188 mmol) was added to a solution of 5,5-dimethyl-3-(4-(2-oxo-5-(pyrimidin-2-yl)-1,2-dihydropyridin-3-yl)cyclohex-3-en-1-yl)-4-phenyloxazolidin-2-one (Examples 5 and 6)(0.100 g, 0.226 mmol) in MeOH (2.5 mL) and DCM (0.5 mL). The system was evacuated and purged with H$_2$ (g), and then stirred under a H$_2$ (g) atmosphere at 50° C. for 24 hours. Mostly starting material remained, so more palladium (10 wt % on activated carbon)(0.020 g, 0.188 mmol) was added as well as a few drops of AcOH. The system was evacuated and purged with H$_2$ (g), and then stirred under a H$_2$ (g) atmosphere at 50° C. for 6 hours. The reaction mixture was filtered through Celite® brand filter aid and the filtrate was concentrated to afford 161 mg of an off-white solid (33 mg, 32% after isomer separation). SFC separation (Chiralpak AS-H column (2×15 cm), eluting with 70/30 CO$_2$/MeOH with 0.1% DEA; flow rate: 70 mL/min; 0.5-1.0 mL per sample/injection, 16 mg/mL dissolved in 3:1 MeOH:DCM), first eluting peak. $^1$H NMR analysis confirmed that the compound had the trans configuration. The (S) phenyl stereocenter was assigned due to the enrichment of the starting material in (S) on the basis of recovery. $^1$H NMR (400 MHz, DMSO-d$_6$) δ=7.67-7.53 (m, 2H), 7.48-7.14 (m, 6H), 4.65 (s, 1H), 3.50 (t, J=11.3 Hz, 1H), 2.46-2.38 (m, 1H), 1.89-1.73 (m, 3H), 1.73-1.50 (m, 6H), 1.46 (s, 3H), 1.37-1.02 (m, 4H), 0.80 (s, 4H). m/z (ESI) 449.2 (M+H)$^+$.

Example 131

Synthesis of 3-(4-(6-amino-5-(pyrimidin-2-yl)pyridin-3-yl)cyclohex-3-en-1-yl)-5,5-dimethyl-4-phenyloxazolidin-2-one

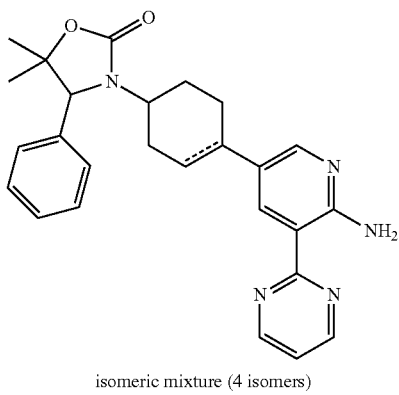

isomeric mixture (4 isomers)

The synthesis of Example 131 is provided in Examples 72 and 73.

Examples 132 and 133

Synthesis of (S)-5,5-dimethyl-4-phenyl-3-((1s,4r)-4-(pyridin-3-yl)cyclohexyl)oxazolidin-2-one and (S)-5,5-dimethyl-4-phenyl-3-((1r,4s)-4-(pyridin-3-yl)cyclohexyl)oxazolidin-2-one

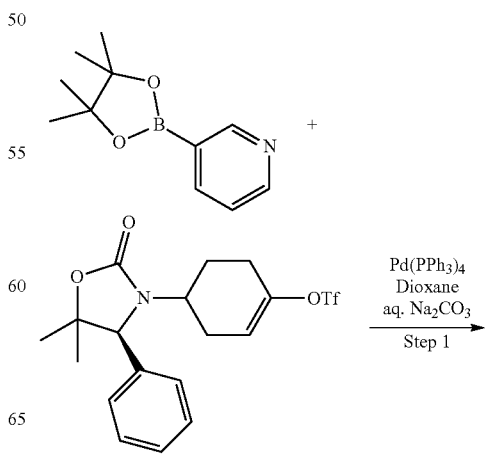

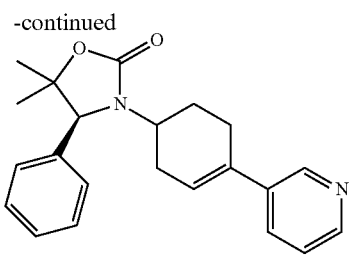

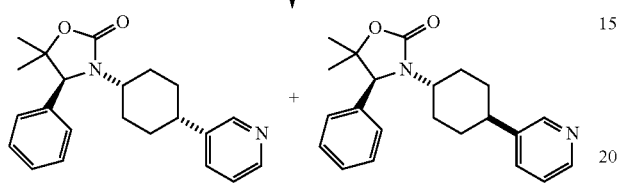

Example 132                    Example 133

Step 1: A microwave tube was charged with (S)-4-((S)-5,5-dimethyl-2-oxo-4-phenyloxazolidin-3-yl)cyclohex-1-en-1-yl trifluoromethanesulfonate (0.205 g, 0.489 mmol), 3-(4,4,5,5-tetramethyl-1,3,2-dioxaborolan-2-yl)pyridine (0.120 g, 0.587 mmol), tetrakis(triphenylphosphine)palladium(0) (0.085 g, 0.073 mmol) and sodium carbonate (0.155 g, 1.466 mmol). Dioxane (1.70 mL) and water (0.25 mL) were added and the vial was charged with argon. The reaction mixture was heated to 100° C. with microwave for 1 h. The reaction mixture was purified via column chromatography on silica gel (RediSep 12 g column, gradient elution with 0% to 50% (90:10 CH$_2$Cl$_2$—MeOH—CH$_2$Cl$_2$) to afford (S)-5,5-dimethyl-4-phenyl-3-((S)-4-(pyridin-3-yl)cyclohex-3-en-1-yl)oxazolidin-2-one (0.128 g, 0.367 mmol, 75% yield) as a yellow oil.

Step 2: A mixture of (S)-5,5-dimethyl-4-phenyl-3-((S)-4-(pyridin-3-yl)cyclohex-3-en-1-yl)oxazolidin-2-one (0.127 g, 0.364 mmol) and palladium 10 wt. % on activated carbon (0.078 g, 0.073 mmol) in EtOAc-MeOH (1:1, 2.0 mL) was stirred under hydrogen overnight. The mixture was filtered through a short pad of Celite® brand filter aid, concentrated and purified with Chiralpak AD-H (4.6×100 mm) column, eluting with 25% isopropanol with 0.2% diethylamine to afford (S)-5,5-dimethyl-4-phenyl-3-((1s,4r)-4-(pyridin-3-yl)cyclohexyl)oxazolidin-2-one (0.038 g, 29.7% yield) and (S)-5,5-dimethyl-4-phenyl-3-((1 r,4s)-4-(pyridin-3-yl)cyclohexyl)oxazolidin-2-one (0.020 g, 15.7% yield).

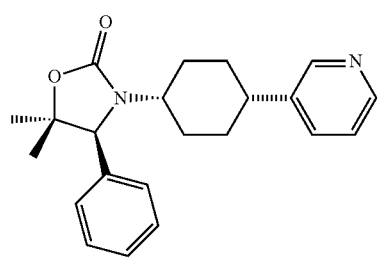

Example 132

(S)-5,5-dimethyl-4-phenyl-3-((1s,4r)-4-(pyridin-3-yl)cyclohexyl)oxazolidin-2-one. $^1$H NMR (400 MHz, DMSO-d$_6$) δ ppm 8.21 (s, 1H) 8.15 (d, J=3.81 Hz, 1H) 7.27-7.38 (m, 1H) 6.99-7.23 (m, 5H) 6.88 (br. s., 1H) 4.42 (s, 1H) 3.31 (tt, J=7.31, 3.84 Hz, 1H) 3.08 (s, 2H) 2.49-2.61 (m, 1H) 2.00-2.15 (m, 1H) 1.61-1.77 (m, 1H) 1.31-1.61 (m, 4H) 1.29 (s, 3H) 1.07-1.26 (m, 2H) 0.55 (s, 3H). m/z (ESI) 351.2 (M+H)$^+$.

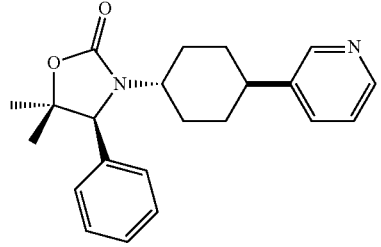

Example 133

(S)-5,5-dimethyl-4-phenyl-3-((1r,4s)-4-(pyridin-3-yl)cyclohexyl)oxazolidin-2-one. $^1$H NMR (400 MHz, DMSO-d$_6$) δ ppm 8.43 (br. s., 1H) 8.37 (d, J=4.21 Hz, 1H) 7.62 (dt, J=7.92, 1.86 Hz, 1H) 7.32-7.51 (m, 4H) 7.27 (dd, J=7.82, 4.60 Hz, 2H) 4.66 (s, 1H) 3.47-3.65 (m, 1H) 2.41 (tt, J=12.24, 3.02 Hz, 1H) 1.75-1.98 (m, 3H) 1.52-1.73 (m, 3H) 1.46-1.52 (m, 4H) 1.13-1.32 (m, 1H) 0.81 (s, 3H). m/z (ESI) 351.2 (M+H)$^+$.

Examples 134 and 135

Synthesis of (S)-5,5-dimethyl-3-((1s,4r)-4-(6-methylpyridin-3-yl)cyclohexyl)-4-phenyloxazolidin-2-one and (S)-5,5-dimethyl-3-((1r,4s)-4-(6-methylpyridin-3-yl)cyclohexyl)-4-phenyloxazolidin-2-one Examples 134 and 135 were prepared as described in Example 132 using 2-methyl-5-pyridinyl boronic acid as the boronic acid and 25% isopropanol w/0.2% diethylamine as eluent for Chiralpak AD-H column purification.

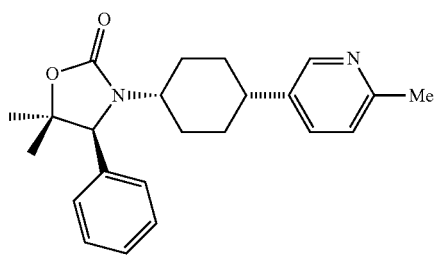

Example 134

(S)-5,5-dimethyl-3-((1 s,4r)-4-(6-methylpyridin-3-yl)cyclohexyl)-4-phenyloxazolidin-2-one. $^1$H NMR (400 MHz, DMSO-d$_6$) δ ppm 8.30 (br. s., 1H) 7.26-7.55 (m, 5H) 7.15 (d, J=7.04 Hz, 3H) 4.66 (br. s., 1H) 3.53 (br. s., 1H) 2.75 (br. s., 1H) 2.43 (br. s., 3H) 2.10-2.35 (m, 1H) 1.83-2.04 (m, 1H) 1.67-1.83 (m, 2H) 1.62 (br. s., 3H) 1.52 (br. s., 3H) 1.29-1.47 (m, 2H) 0.79 (br. s., 3H). m/z (ESI) 365.2 (M+H)$^+$.

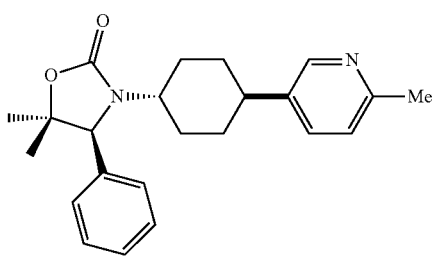

Example 135

(S)-5,5-dimethyl-3-((1r,4s)-4-(6-methylpyridin-3-yl)cyclohexyl)-4-phenyloxazolidin-2-one. $^1$H NMR (400 MHz, DMSO-$d_6$) δ ppm 8.08 (s, 1H) 7.31 (d, J=6.26 Hz, 1H) 7.03-7.27 (m, 5H) 6.93 (d, J=7.92 Hz, 1H) 4.46 (s, 1H) 3.24-3.46 (m, 1H) 2.20 (s, 3H) 2.10-2.19 (m, 1H) 1.55-1.74 (m, 3H) 1.39-1.55 (m, 2H) 1.31-1.39 (m, 1H) 1.30 (s, 3H) 1.15-1.28 (m, 2H) 0.96-1.12 (m, 1H) 0.62 (s, 3H). m/z (ESI) 365.2 (M+H)$^+$.

Examples 136 and 137

Synthesis of (S)-3-((1s,4r)-4-(1H-pyrrolo[2,3-b]pyridin-5-yl)cyclohexyl)-5,5-dimethyl-4-phenyloxazolidin-2-one and (S)-3-((1r,4s)-4-(1H-pyrrolo[2,3-b]pyridin-5-yl)cyclohexyl)-5,5-dimethyl-4-phenyloxazolidin-2-one Step 1: A mixture of 5-(4,4,5,5-tetramethyl-[1,3,2]dioxaborolan-2-yl)-1h-pyrrolo[2,3-b]pyridine (0.477 g, 1.955 mmol), 4-((S)-5,5-dimethyl-2-oxo-4-phenyloxazolidin-3-yl)cyclohex-1-en-1-yl trifluoromethanesulfonate (0.82 g, 1.955 mmol) and 2.0 M sodium carbonate (4.89 mL) in dioxane (6.52 mL) was flushed with nitrogen. Tetrakis(triphenylphosphine)palladium(0) (0.226 g, 0.196 mmol) was added and the mixture was stirred at 100° C. overnight. The reaction mixture was diluted with CH$_2$Cl$_2$ and extracted with CH$_2$Cl$_2$. The combined organic layers were concentrated. The material thus obtained was absorbed onto a plug of silica gel and purified by chromatography through a Redi-Sep pre-packed silica gel column (40 g), eluting with a gradient of 0% to 50% 1M NH$_3$.MeOH in CH$_2$Cl$_2$, to provide (4S)-3-(4-(1H-pyrrolo[2,3-b]pyridin-5-yl)cyclohex-3-en-1-yl)-5,5-dimethyl-4-phenyloxazolidin-2-one (0.76 g, 1.961 mmol, 100% yield) as light-yellow solid.

Step 2: A mixture of (4S)-3-(4-(1H-pyrrolo[2,3-b]pyridin-5-yl)cyclohex-3-en-1-yl)-5,5-dimethyl-4-phenyloxazolidin-2-one (0.76 g, 1.961 mmol) and palladium 10 wt. % on activated carbon (0.313 g, 0.294 mmol) in EtOAc-MeOH (1:1, 10 mL) was stirred under hydrogen at room temperature overnight. The mixture was filtered through a short pad of Celite® brand filter aid and concentrated. The material thus obtained was absorbed onto a plug of silica gel and purified by chromatography first through a Redi-Sep pre-packed silica gel column (40 g), eluting with a gradient of 0% to 50% 1M NH$_3$.MeOH in CH$_2$Cl$_2$, and then a Chiralpak AD-H (4.6×100 mm) column, eluting with % MeOH w/0.2% diethylamine to provide (S)-3-((1r,4s)-4-(1H-pyrrolo[2,3-b]pyridin-5-yl)cyclohexyl)-5,5-dimethyl-4-phenyloxazolidin-2-one (0.168 g, 0.431 mmol, 21.99% yield) and (S)-3-((1s,4r)-4-(1H-pyrrolo[2,3-b]pyridin-5-yl)cyclohexyl)-5,5-dimethyl-4-phenyloxazolidin-2-one (0.317 g, 0.814 mmol, 41.5% yield) as off-white solid.

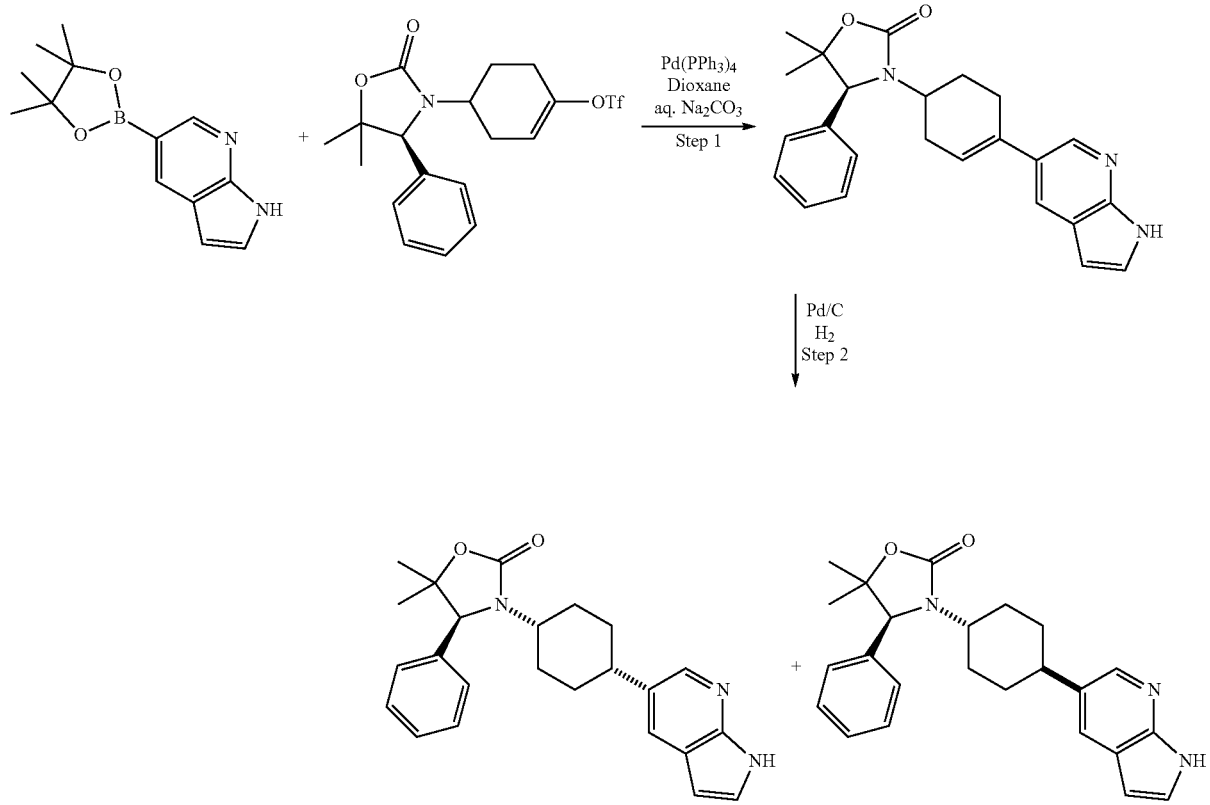

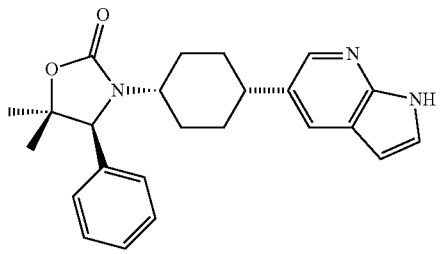

Example 136

(S)-3-((1s,4r)-4-(1H-pyrrolo[2,3-b]pyridin-5-yl)cyclohexyl)-5,5-dimethyl-4-phenyloxazolidin-2-one. $^{1}$H NMR (400 MHz, DMSO-$d_6$) δ ppm 11.48 (br. s., 1H) 8.08 (d, J=2.05 Hz, 1H) 7.69 (d, J=2.15 Hz, 1H) 7.39-7.52 (m, 2H) 7.36 (d, J=5.97 Hz, 3H) 7.13 (br. s., 1H) 6.38 (dd, J=3.42, 1.86 Hz, 1H) 4.70 (s, 1H) 3.51-3.66 (m, 1H) 2.77-2.92 (m, 1H) 2.30-2.47 (m, 1H) 1.87-2.07 (m, 1H) 1.58-1.87 (m, 4H) 1.55 (s, 3H) 1.47 (q, J=5.77 Hz, 2H) 0.80 (s, 3H). m/z (ESI) 390.2 (M+H)$^{+}$.

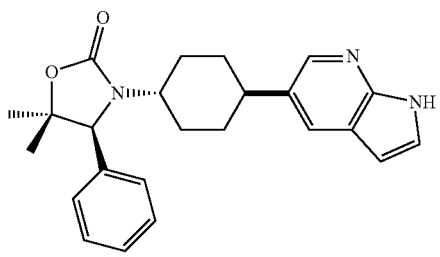

Example 137

(S)-3-((1r,4s)-4-(1H-pyrrolo[2,3-b]pyridin-5-yl)cyclohexyl)-5,5-dimethyl-4-phenyloxazolidin-2-one, $^{1}$H NMR (400 MHz, DMSO-$d_6$) δ ppm 11.45 (br. s., 1H) 8.06 (d, J=2.05 Hz, 1H) 7.74 (d, J=1.96 Hz, 1H) 7.19-7.48 (m, 7H) 6.34 (dd, J=3.42, 1.86 Hz, 1H) 4.67 (s, 1H) 3.50-3.68 (m, 1H) 2.41-2.48 (m, 1H) 1.82-1.96 (m, 3H) 1.58-1.80 (m, 3H) 1.50-1.58 (m, 1H) 1.49 (s, 3H) 1.15-1.32 (m, 2H) 0.81 (s, 3H). m/z (ESI) 390.2 (M+H)$^{+}$.

Examples 138 and 139

Synthesis of (S)-5,5-dimethyl-3-((1s,4r)-4-(2-oxo-1,2-dihydro-1,7-naphthyridin-3-yl)cyclohexyl)-4-phenyloxazolidin-2-one and (S)-5,5-dimethyl-3-((1r,4s)-4-(2-oxo-1,2-dihydro-1,7-naphthyridin-3-yl)cyclohexyl)-4-phenyloxazolidin-2-one

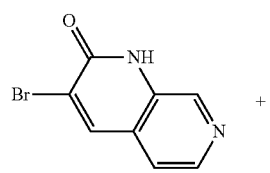

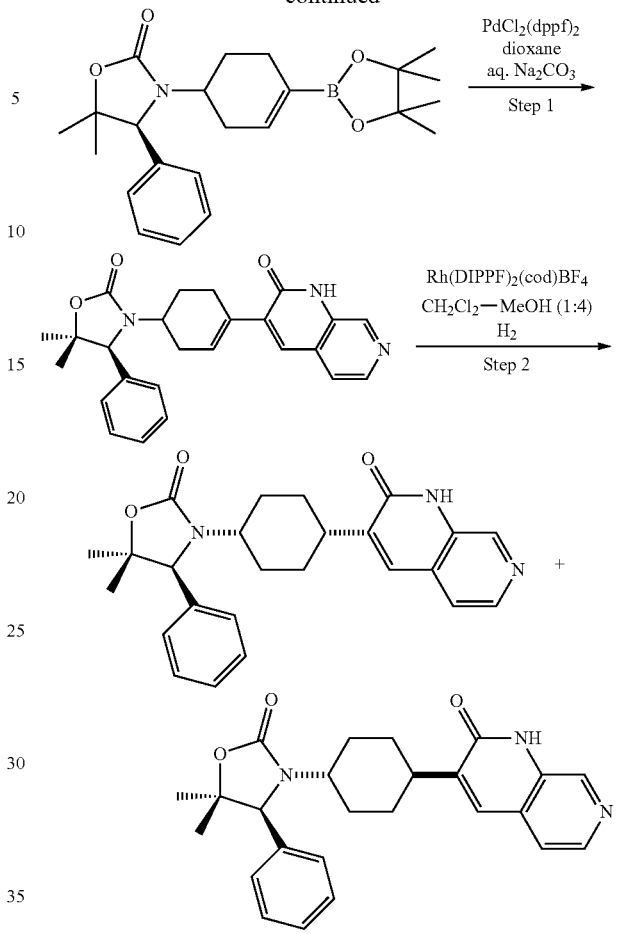

Step 1: A microwave vial was charged with (4S)-5,5-dimethyl-4-phenyl-3-(4-(4,4,5,5-tetramethyl-1,3,2-dioxaborolan-2-yl)cyclohex-3-en-1-yl)oxazolidin-2-one (0.124 g, 0.312 mmol), 3-bromo-1,7-naphthyridin-2(1H)-one (0.105 g, 0.468 mmol), sodium carbonate (0.099 g, 0.936 mmol), dioxane (3.0 mL), and water (0.600 mL). Dichloro[1,1'-bis(diphenylphosphino)ferrocene]palladium (II) dichloromethane adduct (0.026 g, 0.031 mmol) was added, the system was purged with argon, and the tube was sealed. The mixture stirred at 100° C. in the microwave for 1.5 h. The reaction mixture was filtered through Celite® brand filter aid and the filtrate was concentrated to afford a brown oil. This oil was purified via column chromatography on silica gel (RediSep 40 g column, gradient elution with 0-10% methanol-ethyl acetate) to afford (4S)-5,5-dimethyl-3-(4-(2-oxo-1,2-dihydro-1,7-naphthyridin-3-yl)cyclohex-3-en-1-yl)-4-phenyloxazolidin-2-one (0.050 g, 38.6% yield) as an off-white solid.

Step 2: 1,1'-bis(di-i-propylphosphino)ferrocene(1,5-cyclooctadiene)rhodium(I)tetrafluoroborate (0.013 g, 0.018 mmol) was added to a solution of (4S)-5,5-dimethyl-3-(4-(2-oxo-1,2-dihydro-1,7-naphthyridin-3-yl)cyclohex-3-en-1-yl)-4-phenyloxazolidin-2-one (0.073 g, 0.176 mmol) in MeOH (2.81 mL)-CH$_2$Cl$_2$ (0.70 mL). The mixture was stirred under an atmosphere of hydrogen at room temperature for 2 days. The mixture was concentrated and absorbed onto a plug of silica gel and purified by chromatography through a RediSep pre-packed silica gel column (12 g), eluting with a gradient of 0% to 50% 1M NH$_3$.MeOH in CH$_2$Cl$_2$, and then a Chiralpak AD-H (4.6×100 mm) column, eluting with 50% MeOH with 0.2% diethylamine to provide (S)-5,5-dimethyl-3-((1s,4r)-4-(2-oxo-1,2-dihydro-1,7-naphthyridin-3-yl)cyclohexyl)-4-phenyloxazolidin-2-one (0.009 g, 12.3% yield) and (S)-5,5-dimethyl-3-((1r,4s)-4-(2-oxo-1,2-dihydro-1,7-naphthyridin-3-yl)cyclohexyl)-4-phenyloxazolidin-2-one (0.005 g, 6.8% yield).

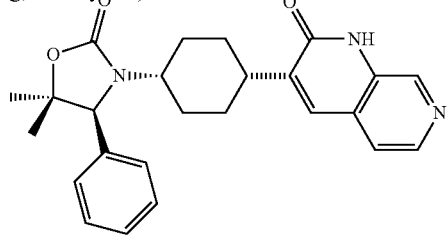

Example 138

(S)-5,5-dimethyl-3-((1s,4r)-4-(2-oxo-1,2-dihydro-1,7-naphthyridin-3-yl)cyclohexyl)-4-phenyloxazolidin-2-one, $^1$H NMR (400 MHz, DMSO-d$_6$) δ ppm 11.95 (br. s., 1H) 8.60 (s, 1H) 8.32 (d, J=5.09 Hz, 1H) 7.60 (s, 1H) 7.57 (d, J=4.99 Hz, 1H) 7.40 (br. s., 1H) 7.32 (br. s., 3H) 7.11 (br. s., 1H) 4.67 (s, 1H) 3.49-3.60 (m, 1H) 2.91 (t, J=6.50 Hz, 1H) 2.34-2.46 (m, 1H) 1.84-1.97 (m, 1H) 1.56-1.77 (m, 4H) 1.53 (s, 3H) 1.33-1.49 (m, 2H) 1.19-1.27 (m, 2H) 0.80 (s, 3H). m/z (ESI) 418.2 (M+H)$^+$.

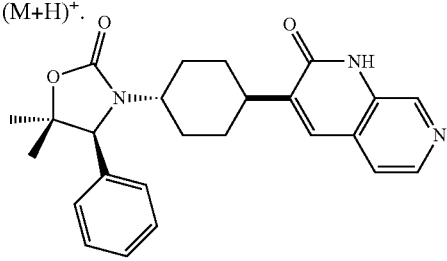

Example 139

(S)-5,5-dimethyl-3-((1r,4s)-4-(2-oxo-1,2-dihydro-1,7-naphthyridin-3-yl)cyclohexyl)-4-phenyloxazolidin-2-one, $^1$H NMR (400 MHz, DMSO-d$_6$) δ ppm 8.59 (s, 1H) 8.28 (d, J=5.18 Hz, 1H) 7.72 (s, 1H) 7.54 (d, J=5.18 Hz, 1H) 7.30-7.50 (m, 4H) 7.25 (br. s., 1H) 4.68 (s, 1H) 3.47-3.63 (m, 1H) 2.58-2.72 (m, 1H) 1.89 (d, J=5.67 Hz, 3H) 1.74 (d, J=12.42 Hz, 1H) 1.62 (d, J=9.78 Hz, 1H) 1.53 (d, J=3.33 Hz, 1H) 1.49 (s, 3H) 1.28-1.39 (m, 2H) 0.82 (s, 3H). m/z (ESI) 418.2 (M+H)$^+$.

Example 140

Synthesis of (S)-5,5-dimethyl-4-phenyl-3-(1-(1-(pyrimidin-2-yl)-1H-pyrrolo[3,2-b]pyridin-6-yl)piperidin-4-yl)oxazolidin-2-one

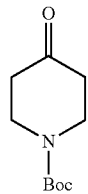

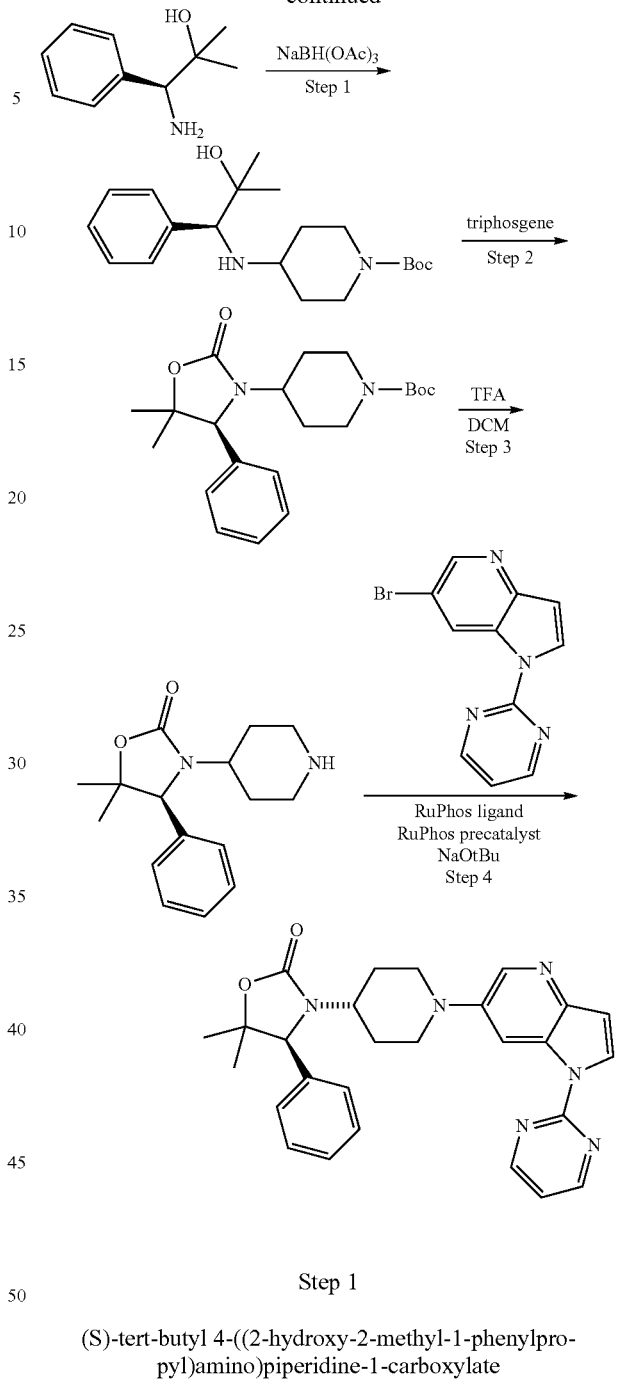

Step 1

(S)-tert-butyl 4-((2-hydroxy-2-methyl-1-phenylpropyl)amino)piperidine-1-carboxylate To a flask charged with boc-4-piperidone (2.412 g, 12.10 mmol, Alfa-Aesar) was added DCM (60.5 mL), acetic acid (0.901 mL, 15.74 mmol), (S)-1-amino-2-methyl-1-phenylpropan-2-ol (2 g, 12.10 mmol, BOC Scientific) and sodium triacetoxyborohydride (3.59 g, 16.95 mmol) respectively. The resulting orange suspension was stirred at room temperature for 3 h. LCMS indicated good conversion to desired product. To the mixture was added saturated NaHCO$_3$ and K$_2$CO$_3$ pellets. The mixture was transferred to a separatory funnel and extracted with DCM (2×). The combined organics were dried with Na$_2$SO$_4$, filtered, and dried under reduced pressure. The material thus obtained was used without further purification.

Step 2

(S)-tert-butyl 4-(5,5-dimethyl-2-oxo-4-phenyloxazolidin-3-yl)piperidine-1-carboxylate To a flask charged with (S)-tert-butyl 4-((2-hydroxy-2-methyl-1-phenylpropyl)amino)piperidine-1-carboxylate (4.22 g, 12.11 mmol) was added THF (40.4 mL) followed by DIEA (10.58 mL, 60.5 mmol). The resulting suspension was cooled in an ice water bath. Triphosgene (3.59 g, 12.11 mmol) was added portionwise affording an immediate evolution of HCl gas. The reaction mixture remained as clear yellow solution. After stirring the reaction for 1 h, saturated aqueous $NH_4Cl$ was added to the reaction mixture. The resulting mixture was transferred to a separatory funnel and extracted with EtOAc (2×). The combined organics were dried with $Na_2SO_4$, filtered, and dried under reduced pressure. The material was used without further purification.

Step 3

(S)-5,5-dimethyl-4-phenyl-3-(piperidin-4-yl)oxazolidin-2-one

To a 250-mL round-bottomed flask were added (S)-tert-butyl 4-(5,5-dimethyl-2-oxo-4-phenyloxazolidin-3-yl)piperidine-1-carboxylate (4530 mg, 12.10 mmol) and 2,2,2-trifluoroacetic acid (23.16 mL, 302 mmol) in DCM (24.200 mL). The mixture was then stirred at rt overnight. The reaction mixture was concentrated in vacuo. The material thus obtained was dissolved in DCM, and extracted with water (3×). The aqueous layers were combined and the pH of the solution was adjusted to above 8 by adding 35% $NH_4OH$ water solution. The solution was then extracted with EtOAc (3×). The organic extract was dried over $MgSO_4$. The solution was filtered and concentrated in vacuo to give the residual material as a yellow solid. The material was used without further purification.

Step 4

(S)-5,5-dimethyl-4-phenyl-3-(1-(1-(pyrimidin-2-yl)-1H-pyrrolo[3,2-b]pyridin-6-yl)piperidin-4-yl)oxazolidin-2-one A glass microwave reaction vessel was charged with (S)-5,5-dimethyl-4-phenyl-3-(piperidin-4-yl)oxazolidin-2-one (50 mg, 0.182 mmol), 6-bromo-1-(pyrimidin-2-yl)-1H-pyrrolo[3,2-b]pyridine (50.1 mg, 0.182 mmol), 2-dicyclohexylphosphino-2',6'-di-i-propoxy-1,1'-biphenyl (8.50 mg, 0.018 mmol, Sigma-Aldrich), chloro(2-dicyclohexylphosphino-2',6'-dimethoxy-1,1'-biphenyl)[2-(2-aminoethylphenyl)]palladium(II)-dichloromethane (13.81 mg, 0.018 mmol, Sigma-Aldrich) and sodium tert-butoxide (26.3 mg, 0.273 mmol). The vessel was capped and evacuated and refilled with argon three times. Dioxane (364 μl) was then added to the reaction mixture. The mixture was stirred and heated at 100° C. overnight. After cooling to room temperature, the material was purified by Waters Auto purification HPLC (Column: Xbridge 19×100 mm; Flow rate: 40 mL/min; Mobile phase: 0.1% $NH_4OH$ in ACN and water; Gradient: 20-75% B in 8 min with total run time of 10 min) to provide (S)-5,5-dimethyl-4-phenyl-3-(1-(1-(pyrimidin-2-yl)-1H-pyrrolo[3,2-b]pyridin-6-yl)piperidin-4-yl)oxazolidin-2-one as a white solid. $^1$H NMR (500 MHz, DMSO-$d_6$) δ 8.73 (d, J=5.56 Hz, 2H), 8.52-8.60 (m, 1H), 8.32 (d, J=4.49 Hz, 1H), 8.07-8.20 (m, 1H), 7.26-7.42 (m, 3H), 7.15-7.25 (m, 4H), 6.63 (d, J=3.53 Hz, 1H), 4.59 (s, 1H), 3.70 (d, J=11.22 Hz, 1H), 3.51-3.64 (m, 2H), 2.76 (qt, J=2.89, 12.50 Hz, 1H), 2.04-2.18 (m, 1H), 1.83-1.94 (m, 1H), 1.59-1.70 (m, 1H), 1.48-1.58 (m, 1H), 1.46 (s, 3H), 0.80 (s, 3H). m/z (ESI) 469.2 (M+H)$^+$.

Example 141

Synthesis of N-((1S,4r)-4-((S)-5,5-dimethyl-2-oxo-4-phenyloxazolidin-3-yl)cyclohexyl)benzamide

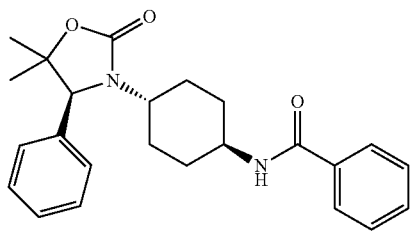 [SMILES: CC1(C)OC(=O)N([C@H]2CC[C@H](NC(=O)c3ccccc3)CC2)[C@H]1c1ccccc1]

Example 141 was prepared from Intermediate E according to the procedure of Example 25 using benzoic acid providing N-((1 S,4r)-4-((S)-5,5-dimethyl-2-oxo-4-phenyloxazolidin-3-yl)cyclohexyl)benzamide as a light yellow solid, (34.88 mg, 89 mmol, 36% yield). $^1$H NMR (400 MHz, DMSO-$d_6$) δ ppm 8.14 (d, J=7.79 Hz, 1H), 8.14 (d, J=7.79 Hz, 1H), 7.79 (d, J=7.27 Hz, 2H), 7.45-7.51 (m, 1H), 7.30-7.44 (m, 6H), 3.56-3.64 (m, 1H), 4.64 (s, 1H), 3.38-3.49 (m, 1H), 1.88 (d, J=12.26 Hz, 1H), 1.67-1.85 (m, 3H), 1.53 (d, J=10.02 Hz, 1H), 1.46 (s, 3H), 1.23-1.44 (m, 2H), 1.12 (dtd, J=12.80, 12.69, 12.69, 3.52 Hz, 1H), 0.80 (s, 3H). m/z (ESI) 393.2 (M+H)$^+$.

Example 142

Synthesis of N-((1S,4r)-4-((S)-5,5-dimethyl-2-oxo-4-phenyloxazolidin-3-yl)cyclohexyl)isonicotinamide

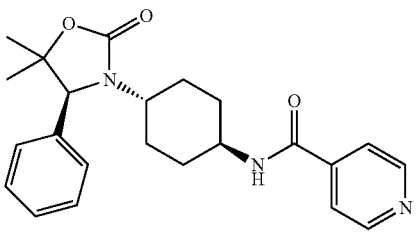 [SMILES: CC1(C)OC(=O)N([C@H]2CC[C@H](NC(=O)c3ccncc3)CC2)[C@H]1c1ccccc1]

Example 142 was prepared from Intermediate E according to the procedure of Example 25 using isonicotinic acid providing N-((1 S,4r)-4-((S)-5,5-dimethyl-2-oxo-4-phenyloxazolidin-3-yl)cyclohexyl)isonicotinamide as a light yellow solid (53.87 mg, 137 mmol, 55% yield). $^1$H NMR (400 MHz, DMSO-$d_6$) δ ppm 8.46 (d, J=7.85 Hz, 1H) 8.65-8.71 (m, 2H), 7.66-7.72 (m, 2H), 7.27-7.44 (m, 4H), 4.64 (s, 1H), 3.55-3.65 (m, 1H), 3.38-3.50 (m, 1H), 1.89 (d, J=12.54 Hz, 1H), 1.68-

1.86 (m, 3H), 1.45-1.56 (m, 4H), 1.23-1.44 (m, 2H), 1.08-1.19 (m, 1H), 0.76-0.84 (m, 3H). m/z (ESI) 394.2 (M+H)⁺.

Example 143

Synthesis of N-((1R,4r)-4-((R)-5,5-dimethyl-2-oxo-4-phenyloxazolidin-3-yl)cyclohexyl)-1-methyl-1H-indole-3-carboxamide

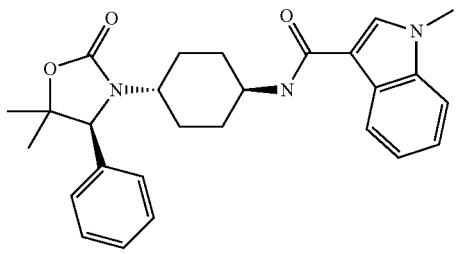

Example 143 was prepared from Intermediate E according to the procedure of Example 25 using 1-methyl-1H-indole-3-carboxylic acid providing N-((1R,4r)-4-((R)-5,5-dimethyl-2-oxo-4-phenyloxazolidin-3-yl)cyclohexyl)-1-methyl-1H-indole-3-carboxamide as a light yellow solid, (39.3 mg, 89 mmol, 35% yield). ¹H NMR (400 MHz, DMSO-d₆) δ ppm 0.80 (s, 3H), 1.06-1.16 (m, 1H), 1.19-1.30 (m, 1H), 1.30-1.43 (m, 1H), 1.47 (s, 3H), 1.53 (d, J=12.60 Hz, 1H), 1.70-1.86 (m, 3H), 1.91 (d, J=12.66 Hz, 1H), 3.39-3.51 (m, 1H), 3.54-3.65 (m, 1H), 3.79 (s, 3H), 4.65 (s, 1H), 7.07-7.15 (m, 1H), 7.18 (t, J=7.13 Hz, 2H), 7.27-7.46 (m, 5H), 7.56 (d, J=7.96 Hz, 1H), 7.94 (s, 1H) 8.08 (d, J=7.90 Hz, 1H). m/z (ESI). m/z (ESI) 446.2 (M+H)⁺.

Example 144

Synthesis of N-((1R,4r)-4-((R)-5,5-dimethyl-2-oxo-4-phenyloxazolidin-3-yl)cyclohexyl)-2-methyl-2H-indazole-4-carboxamide

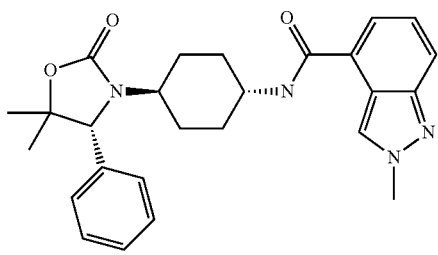 [SMILES: Cn1cc2c(C(=O)N[C@H]3CC[C@H](N4C(=O)OC(C)(C)[C@H]4c4ccccc4)CC3)cccc2n1]

Example 144 was prepared from Intermediate E according to the procedure of Example 25 using 2-methyl-2H-indazole-4-carboxylic acid providing N-((1R,4r)-4-((R)-5,5-dimethyl-2-oxo-4-phenyloxazolidin-3-yl)cyclohexyl)-2-methyl-2H-indazole-4-carboxamide as a light yellow solid, (18.99 mg, 89 mmol, 43% yield). ¹H NMR (400 MHz, DMSO-d₆) δ ppm 0.81 (s, 3H), 1.11-1.20 (m, 1H), 1.23-1.37 (m, 1H), 1.37-1.50 (m, 4H), 1.51-1.60 (m, 1H), 1.75 (d, J=12.20 Hz, 1H), 1.83 (d, J=2.69 Hz, 2H), 1.87-1.96 (m, 1H), 3.17 (d, J=5.27 Hz, 1H), 3.4-3.5 (m, 1H), 3.64 (d, J=7.68 Hz, 1H), 4.18 (s, 3H), 4.65 (s, 1H), 7.25 (dd, J=8.51, 7.13 Hz, 2H), 7.31-7.45 (m, 4H), 7.49 (d, J=7.05 Hz, 1H), 7.72 (d, J=8.53 Hz, 1H), 8.16 (d, J=7.79 Hz, 1H), 8.50 (s, 1H). m/z (ESI) 447.2 (M+H)⁺.

Example 145

Synthesis of N-((1S,4r)-4-((S)-5,5-dimethyl-2-oxo-4-phenyloxazolidin-3-yl)cyclohexyl)-2-methyl-2H-indazole-7-carboxamide

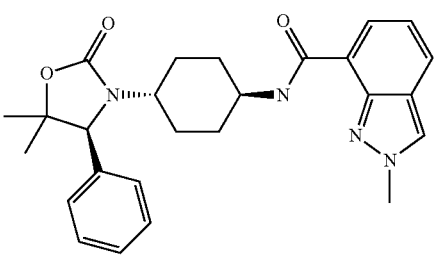 [SMILES: Cn1cc2cccc(C(=O)N[C@H]3CC[C@H](N4C(=O)OC(C)(C)[C@@H]4c4ccccc4)CC3)c2n1]

Example 145 was prepared from Intermediate E according to the procedure of Example 25 using 2-methyl-2H-indazole-7-carboxylic acid providing N-((1S,4r)-4-((S)-5,5-dimethyl-2-oxo-4-phenyloxazolidin-3-yl)cyclohexyl)-2-methyl-2H-indazole-7-carboxamide as a light yellow solid, (15.89 mg, 89 mmol, 36% yield). ¹H NMR (400 MHz, DMSO-d₆) δ ppm 0.81 (s, 3H) 1.16-1.25 (m, 1H) 1.25-1.31 (m, 1H) 1.39 (dd, J=11.80, 4.64 Hz, 1H) 1.47 (s, 3H) 1.57 (d, J=12.14 Hz, 1H) 1.83-1.91 (m, 3H) 2.04 (br. s., 1H) 3.68 (br. s., 2H) 4.22 (s, 3H) 4.66 (s, 1H) 7.14-7.26 (m, 2H) 7.26-7.45 (m, 4H) 7.90-7.96 (m, 2H) 8.55 (s, 1H) 8.97 (d, J=8.02 Hz, 1H). m/z (ESI) 447.2 (M+H)⁺.

Example 146

Synthesis of N-((1S,4r)-4-((S)-5,5-dimethyl-2-oxo-4-phenyloxazolidin-3-yl)cyclohexyl)pyrazolo[1,5-a]pyrimidine-3-carboxamide

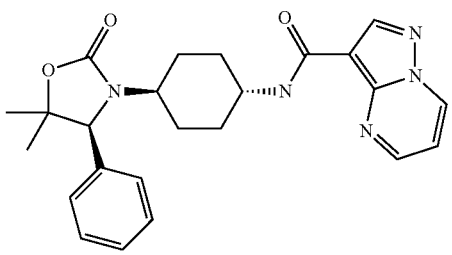 [SMILES: CC1(C)OC(=O)N([C@H]2CC[C@H](NC(=O)c3cnn4cccnc34)CC2)[C@H]1c1ccccc1]

Example 146 was prepared from Intermediate E according to the procedure of Example 25 using pyrazolo[1,5-a]pyrimidine-3-carboxylic acid providing N-((1S,4r)-4-((S)-5,5-dimethyl-2-oxo-4-phenyloxazolidin-3-yl)cyclohexyl)pyrazolo[1,5-a]pyrimidine-3-carboxamide as a light yellow solid, (18.73 mg, 43 mmol, 17% yield). ¹H NMR (400 MHz, DMSO-d₆) δ ppm 0.80 (s, 3H), 1.11-1.20 (m, 1H), 1.23-1.44 (m, 2H), 1.46 (s, 3H), 1.53 (d, J=11.28 Hz, 1H), 1.77-1.92 (m, 3H), 1.99 (d, J=12.03 Hz, 1H), 3.64 (dd, J=7.90, 3.89 Hz, 2H), 4.65 (s, 1H), 7.24 (dd, J=6.99, 4.30 Hz, 3H), 7.30-7.44 (m, 4H), 7.68 (d, J=7.90 Hz, 1H), 8.53 (s, 1H), 8.78 (dd, J=4.21, 1.58 Hz, 1H), 9.27 (dd, J=7.02, 1.58 Hz, 1H). m/z (ESI) 434.2 (M+H)+.

Example 147

Synthesis of N-((1S,4r)-4-((S)-5,5-dimethyl-2-oxo-4-phenyloxazolidin-3-yl)cyclohexyl)-1H-pyrrolo[2,3-b]pyridine-6-carboxamide

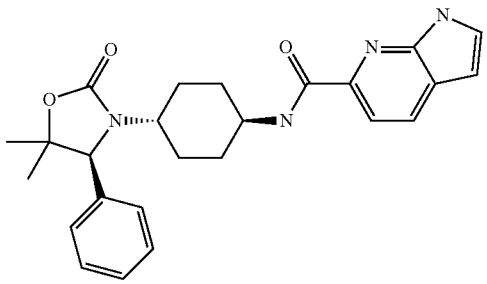 [SMILES: CC1(C)OC(=O)N([C@H]2CC[C@H](NC(=O)c3ccc4cc[nH]c4n3)CC2)[C@H]1c1ccccc1]

Example 147 was prepared from Intermediate E according to the procedure of Example 25 using 1H-pyrrolo[2,3-b]pyridine-6-carboxylic acid providing N-((1 S,4r)-4-((S)-5,5-dimethyl-2-oxo-4-phenyloxazolidin-3-yl)cyclohexyl)-1H-pyrrolo[2,3-b]pyridine-6-carboxamide as a light yellow solid, (11.94 mg, 28 mmol, 11% yield). $^1$H NMR (400 MHz, DMSO-$d_6$) δ ppm 8.39 (br. s., 1H), 7.81 (d, J=7.50 Hz, 1H), 7.72 (d, J=7.45 Hz, 1H), 7.34-7.44 (m, 4H), 7.30 (t, J=7.62 Hz, 3H), 4.66 (s, 1H), 3.68 (br. s., 1H), 3.55 (br. s., 1H), 2.07 (br. s., 1H), 1.82-1.90 (m, 3H), 1.55 (d, J=13.63 Hz, 1H), 1.50-1.38 (m, 4H), 1.29 (d, J=13.06 Hz, 1H), 0.80 (s, 3H) 1.18 (br. s., 1H). m/z (ESI) 433.2 (M+H)+.

Example 148

Synthesis of N-((1S,4r)-4-((S)-5,5-dimethyl-2-oxo-4-phenyloxazolidin-3-yl)cyclohexyl)-2-phenylpyrimidine-4-carboxamide

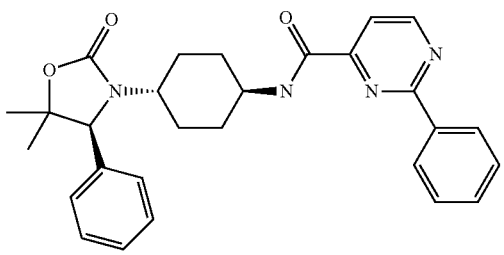 [SMILES: CC1(C)OC(=O)N([C@H]2CC[C@H](NC(=O)c3ccnc(-c4ccccc4)n3)CC2)[C@H]1c1ccccc1]

Example 148 was prepared from Intermediate E according to the procedure of Example 25 using 2-phenylpyrimidine-4-carboxylic acid providing N-((1 S,4r)-4-((S)-5,5-dimethyl-2-oxo-4-phenyloxazolidin-3-yl)cyclohexyl)-2-phenylpyrimidine-4-carboxamide as a light yellow solid, (70.12 mg, 150 mmol, 60% yield). $^1$H NMR (400 MHz, DMSO-$d_6$) δ ppm 9.10 (d, J=4.98 Hz, 1H), 8.73 (d, J=8.71 Hz, 1H), 8.58 (dd, J=7.65, 1.86 Hz, 2H), 7.87 (d, J=4.93 Hz, 1H), 7.48-7.60 (m, 3H), 7.45-7.29 (m, 4H), 7.24 (br. s., 1H), 4.66 (s, 1H), 3.76-3.66 (m, 1H), 3.52-3.42 (m, 1H), 1.92-1.78 (m, 3H), 1.72 (d, J=12.37 Hz, 1H), 1.67-1.45 (m, 6H), 1.27-1.11 (m, 1H), 0.81 (s, 3H). m/z (ESI) 472.2 (M+H)+.

Example 149

Synthesis of N-((1S,4r)-4-((S)-5,5-dimethyl-2-oxo-4-phenyloxazolidin-3-yl)cyclohexyl)-1H-pyrrolo[2,3-c]pyridine-2-carboxamide

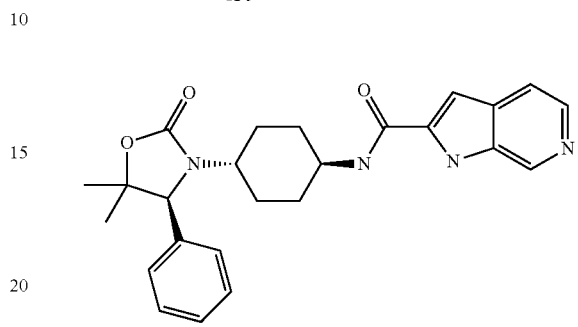

Example 149 was prepared from Intermediate E according to the procedure of Example 25 using 1H-pyrrolo[2,3-c]pyridine-2-carboxylic acid providing N-((1 S,4r)-4-((S)-5,5-dimethyl-2-oxo-4-phenyloxazolidin-3-yl)cyclohexyl)-1H-pyrrolo[2,3-c]pyridine-2-carboxamide as light yellow solid, (24.04 mg, 56 mmol, 22% yield). $^1$H NMR (400 MHz, DMSO-$d_6$) δ ppm 11.98 (br. s., 1H), 8.76 (s, 1H), 8.42 (d, J=7.90 Hz, 1H), 8.09 (d, J=5.50 Hz, 1H), 7.56 (d, J=5.50 Hz, 1H), 7.45-7.28 (m, 4H), 7.21 (br. s., 1H), 7.13 (s, 1H), 4.65 (s, 1H), 3.68-3.54 (m, 1H), 1.95-1.72 (m, 4H), 1.54 (d, J=12.09 Hz, 1H), 1.47 (s, 3H), 1.45-1.26 (m, 2H), 1.20-1.09 (m, 1H), 0.80 (s, 3H). m/z (ESI) 433.2 (M+H)+.

Example 150

Synthesis of N-((1S,4r)-4-((S)-5,5-dimethyl-2-oxo-4-phenyloxazolidin-3-yl)cyclohexyl)benzo[d]thiazole-5-carboxamide

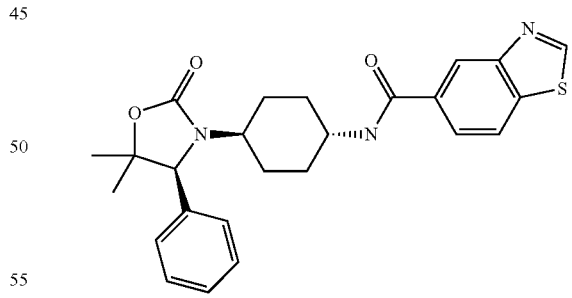

Example 150 was prepared from Intermediate E according to the procedure of Example 25 using benzo[d]thiazole-5-carboxylic acid providing N-((1 S,4r)-4-((S)-5,5-dimethyl-2-oxo-4-phenyloxazolidin-3-yl)cyclohexyl)benzo[d]thiazole-5-carboxamide as a light yellow solid, (24.46 mg, 46 mmol, 18% yield). $^1$H NMR (400 MHz, DMSO-$d_6$) δ ppm 8.44 (s, 1H), 8.38 (d, J=8.65 Hz, 1H), 7.90 (d, J=7.90 Hz, 1H), 7.78 (dd, J=8.16, 2.03 Hz, 1H), 7.44-7.27 (m, 3H), 7.20 (br. s., 1H), 4.64 (s, 1H), 3.61 (d, J=8.13 Hz, 1H), 2.65 (t, J=7.59 Hz, 2H), 1.85-1.78 (m, 2H), 1.65 (d, J=12.83 Hz, 1H), 1.59-1.37 (m, 7H), 1.23-1.33 (m, 2H), 1.18-1.09 (m, 1H), 0.88 (t, J=7.36 Hz, 2H), 0.79 (s, 2H). m/z (ESI) 450.2 (M+H)⁺.

Example 151

Synthesis of N-((1S,4r)-4-((S)-5,5-dimethyl-2-oxo-4-phenyloxazolidin-3-yl)cyclohexyl)-1-methyl-1H-imidazole-5-carboxamide

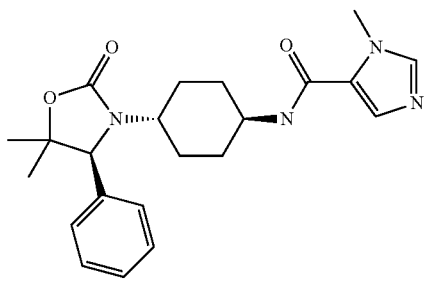 [SMILES: Cn1cncc1C(=O)N[C@H]1CC[C@H](N2C(=O)OC(C)(C)[C@@H]2c2ccccc2)CC1]

Example 151 was prepared from Intermediate E according to the procedure of Example 25 using 1-methyl-1H imidazole-5-carboxylic acid providing N-((1 S,4r)-4-((S)-5,5-dimethyl-2-oxo-4-phenyloxazolidin-3-yl)cyclohexyl)-1-methyl-1H-imidazole-5-carboxamide as a light yellow solid, (62.44 mg, 158 mmol, 63% yield). $^1$H NMR (400 MHz, DMSO-d$_6$) δ ppm 0.79 (s, 3H), 1.05-1.15 (m, 1H), 1.18-1.40 (m, 2H), 1.46 (s, 3H), 1.52 (d, J=12.37 Hz, 1H), 1.68 (d, J=12.66 Hz, 1H), 1.73-1.88 (m, 3H), 3.17 (s, 2H), 3.39-3.57 (m, 2H), 3.76 (s, 2H), 4.63 (s, 1H), 7.20 (br. s., 1H), 7.27-7.44 (m, 4H), 7.51 (s, 1H), 7.68 (s, 1H), 7.95 (d, J=7.96 Hz, 1H). m/z (ESI) 397.2 (M+H)⁺.

Example 152

Synthesis of N-((1S,4r)-4-((S)-5,5-dimethyl-2-oxo-4-phenyloxazolidin-3-yl)cyclohexyl)-1H-pyrrolo[2,3-b]pyridine-4-carboxamide

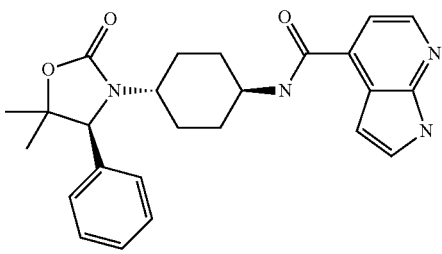 [SMILES: CC1(C)OC(=O)N([C@H]2CC[C@H](NC(=O)c3ccnc4[nH]ccc34)CC2)[C@H]1c1ccccc1]

Example 152 was prepared from Intermediate E according to the procedure of Example 25 using 1H-pyrrolo[2,3-b]pyridine-4-carboxylic acid providing N-((1 S,4r)-4-((S)-5,5-dimethyl-2-oxo-4-phenyloxazolidin-3-yl)cyclohexyl)-1-methyl-1H-imidazole-5-carboxamide as a light yellow solid, (24.74 mg, 57 mmol, 23% yield). $^1$H NMR (400 MHz, DMSO-d$_6$) δ ppm 0.81 (s, 3H), 1.14 (qd, J=12.76, 3.12 Hz, 1H), 1.23-1.45 (m, 2H), 1.47 (s, 3H), 1.50-1.64 (m, 1H), 1.72-1.88 (m, 3H), 1.88-1.98 (m, 1H), 3.5-3.3 (m, 1H), 3.17 (d, J=4.12 Hz, 1H), 3.54-3.69 (m, 1H), 4.08 (br. s., 1H), 4.65 (s, 1H), 6.69 (d, J=3.38 Hz, 1H), 7.28 (d, J=4.93 Hz, 2H), 7.32-7.45 (m, 3H), 7.54 (d, J=3.32 Hz, 1H), 8.22-8.29 (m, 2H), 11.78 (br. s., 1H). m/z (ESI) 433.2 (M+H)⁺.

Example 153

Synthesis of N-((1S,4r)-4-((S)-5,5-dimethyl-2-oxo-4-phenyloxazolidin-3-yl)cyclohexyl)-1H-indazole-4-carboxamide

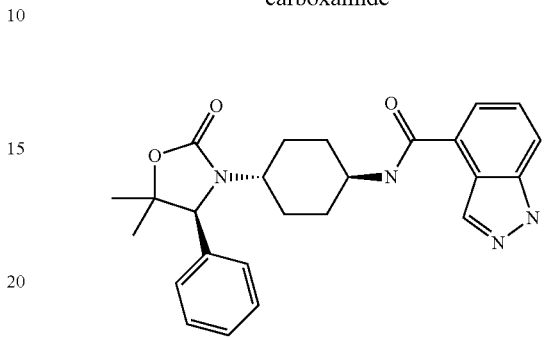

Example 153 was prepared from Intermediate E according to Example 25 using 1H-indazole-4-carboxylic acid providing N-((1 S,4r)-4-((S)-5,5-dimethyl-2-oxo-4-phenyloxazolidin-3-yl)cyclohexyl)-1H-indazole-4-carboxamide as a light yellow solid, (58.34 mg, 135 mmol, 54% yield). $^1$H NMR (400 MHz, DMSO-d$_6$) δ ppm 0.81 (s, 3H), 1.09-1.19 (m, 1H), 1.26-1.35 (m, 1H), 1.38-1.50 (m, 4H), 1.51-1.60 (m, 1H), 1.73-1.88 (m, 3H), 1.93 (d, J=12.66 Hz, 1H), 3.39-3.49 (m, 1H), 3.62-3.70 (m, 1H), 4.65 (s, 1H), 7.21 (br. s., 1H), 7.29-7.45 (m, 5H), 7.50 (d, J=7.05 Hz, 1H), 7.66 (d, J=8.19 Hz, 1H), 8.23 (d, J=8.02 Hz, 1H), 8.29 (s, 1H), 13.19 (br. s., 1H). m/z (ESI) 433.2 (M+H)⁺.

Example 154

Synthesis of N-((1S,4r)-4-((S)-5,5-dimethyl-2-oxo-4-phenyloxazolidin-3-yl)cyclohexyl)-3-isopropyl-1H-pyrazole-5-carboxamide

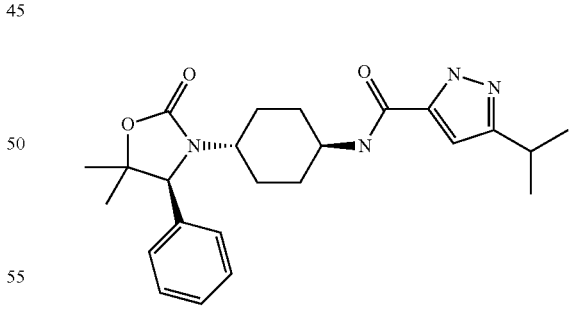

Example 154 was prepared from Intermediate E according to the procedure of Example 25 using 3-isopropyl-1H-pyrazole-5-carboxylic acid providing N-((1 S,4r)-4-((S)-5,5-dimethyl-2-oxo-4-phenyloxazolidin-3-yl)cyclohexyl)-3-isopropyl-1H-pyrazole-5-carboxamide as light yellow solid, (38.23 mg, 90 mmol, 36% yield). $^1$H NMR (400 MHz, DMSO-d$_6$) δ ppm 0.79 (s, 3H), 1.05-1.14 (m, 1H), 1.17-1.33 (m, 7H), 1.35-1.52 (m, 5H), 1.63 (d, J=10.31 Hz, 1H), 1.77-1.89 (m, 3H), 2.88-2.97 (m, 1H), 3.53-3.64 (m, 1H), 4.63 (s, 1H), 6.37

(br. s., 1H), 7.19 (br. s., 1H), 7.26-7.44 (m, 4H), 7.70 (br. s., 1H), 12.84 (br. s., 1H). m/z (ESI) 425.2 (M+H)⁺.

Example 155

Synthesis of N-((1R,4r)-4-((R)-5,5-dimethyl-2-oxo-4-phenyloxazolidin-3-yl)cyclohexyl)quinoline-3-carboxamide

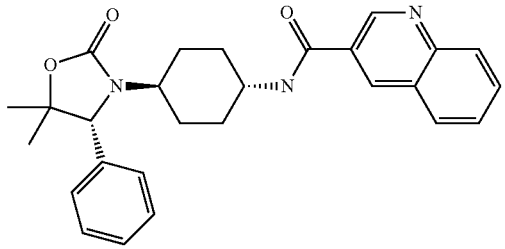 [SMILES: CC1(C)OC(=O)N([C@H]2CC[C@H](NC(=O)c3cnc4ccccc4c3)CC2)[C@@H]1c1ccccc1]

Example 155 was prepared from Intermediate E according to the procedure of Example 25 using quinoline-3-carboxylic acid providing N-((1R,4r)-4-((R)-5,5-dimethyl-2-oxo-4-phenyloxazolidin-3-yl)cyclohexyl)quinoline-3-carboxamide as a light yellow solid, (55.22 mg, 124 mmol, 50% yield). a ¹H NMR (400 MHz, DMSO-d₆) δ ppm 0.80 (s, 3H), 1.10-1.23 (m, 1H), 1.28-1.37 (m, 1H), 1.38-1.57 (m, 5H), 1.75-1.88 (m, 3H), 1.92-2.00 (m, 1H), 3.43-3.54 (m, 1H), 3.64-3.72 (m, 1H), 4.66 (s, 1H), 7.21 (br. s., 1H), 7.28-7.45 (m, 4H), 7.67 (t, J=7.45 Hz, 1H), 7.81-7.87 (m, 1H), 8.07 (dd, J=7.88, 4.73 Hz, 2H), 8.56 (d, J=7.73 Hz, 1H), 8.76 (d, J=1.78 Hz, 1H), 9.23 (d, J=2.12 Hz, 1H). m/z (ESI) 444.2 (M+H)⁻

Example 156

Synthesis of N-((1S,4r)-4-((S)-5,5-dimethyl-2-oxo-4-phenyloxazolidin-3-yl)cyclohexyl)-2-phenylthiazole-4-carboxamide

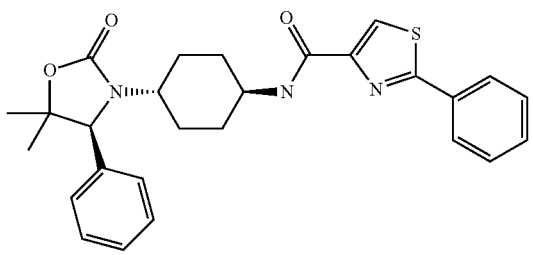 [SMILES: CC1(C)OC(=O)N([C@H]2CC[C@H](NC(=O)c3csc(-c4ccccc4)n3)CC2)[C@H]1c1ccccc1]

Example 156 was prepared from Intermediate E according to the procedure of Example 25 using 2-phenylthiazole-4-carboxylic acid providing N-((1 S,4r)-4-((S)-5,5-dimethyl-2-oxo-4-phenyloxazolidin-3-yl)cyclohexyl)-2-phenylthiazole-4-carboxamide as a light yellow solid, (65.07 mg, 137 mmol, 55% yield). ¹H NMR (400 MHz, DMSO-d₆) δ ppm 0.79 (s, 3H), 1.13 (qd, J=12.72, 3.44 Hz, 1H), 1.37-1.56 (m, 6H), 1.70 (d, J=12.49 Hz, 1H), 1.74-1.90 (m, 3H), 3.41-3.52 (m, 1H), 3.60-3.69 (m, 1H), 4.64 (s, 1H), 7.10-7.27 (m, 1H), 7.27-7.44 (m, 4H), 7.46-7.56 (m, 3H), 7.99-8.09 (m, 2H), 8.15 (d, J=8.53 Hz, 1H), 8.25 (s, 1H). m/z (ESI) 475.2 (M+H)⁺.

Example 157

Synthesis of N-((1S,4r)-4-((S)-5,5-dimethyl-2-oxo-4-phenyloxazolidin-3-yl)cyclohexyl)-1H-benzo[d]imidazole-2-carboxamide

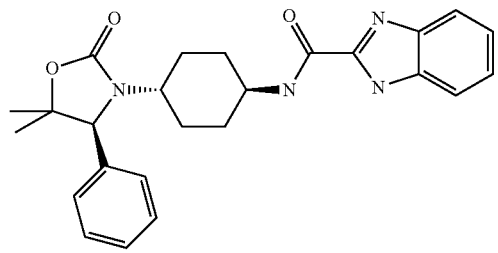 [SMILES: CC1(C)OC(=O)N([C@H]2CC[C@H](NC(=O)c3nc4ccccc4[nH]3)CC2)[C@H]1c1ccccc1]

Example 157 was prepared from Intermediate E according to the procedure of Example 25 using 1H-benzo[d]imidazole-2-carboxylic acid providing N-((1 S,4r)-4-((S)-5,5-dimethyl-2-oxo-4-phenyloxazolidin-3-yl)cyclohexyl)-1H-benzo[d]imidazole-2-carboxamide as a light yellow solid, (65.07 mg, 137 mmol, 55% yield). ¹H NMR (400 MHz, DMSO-d₆) δ ppm 0.80 (s, 3H), 1.11-1.23 (m, 1H), 1.40-1.50 (m, 4H), 1.50-1.61 (m, 2H), 1.65-1.76 (m, 1H), 1.79-1.89 (m, 3H), 3.66 (d, J=8.25 Hz, 1H), 4.64 (s, 1H), 7.26 (dd, J=6.01, 3.09 Hz, 4H), 7.31-7.45 (m, 4H), 7.59 (br. s., 2H), 8.67 (d, J=8.59 Hz, 1H). m/z (ESI) 433.2 (M+H)⁺.

Example 158

Synthesis of N-((1S,4r)-4-((S)-5,5-dimethyl-2-oxo-4-phenyloxazolidin-3-yl)cyclohexyl)-1H-pyrrole-2-carboxamide

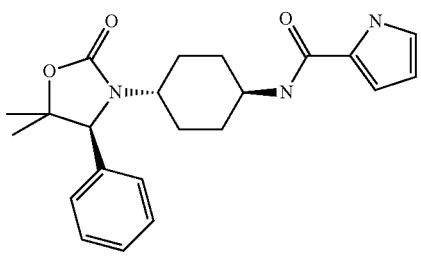 [SMILES: CC1(C)OC(=O)N([C@H]2CC[C@H](NC(=O)c3ccc[nH]3)CC2)[C@H]1c1ccccc1]

Example 158 was prepared from Intermediate E according to the procedure of Example 25 using 1H-pyrrole-2-carboxylic acid providing N-((1 S,4r)-4-((S)-5,5-dimethyl-2-oxo-4-phenyloxazolidin-3-yl)cyclohexyl)-1H-benzo[d]imidazole-2-carboxamide as a light yellow solid, (18.3 mg, 48 mmol, 19% yield). ¹H NMR (400 MHz, DMSO-d₆) δ ppm 0.79 (s, 3H), 1.10 (td, J=12.66, 3.09 Hz, 1H), 1.18-1.28 (m, 1H), 1.29-1.39 (m, 1H), 1.43-1.58 (m, 4H), 1.67 (d, J=12.49 Hz, 1H), 1.73-1.89 (m, 3H), 3.17 (d, J=5.21 Hz, 1H), 3.53-3.58 (m, 1H), 4.64 (s, 1H), 6.00-6.04 (m, 1H), 6.72 (br. s., 1H), 6.79 (br. s., 1H), 7.19 (br. s., 1H), 7.27-7.43 (m, 4H), 7.65 (d, J=8.19 Hz, 1H), 11.32 (br. s., 1H). m/z (ESI) 382.2 (M+H)$^+$.

Example 159

Synthesis of N-((1S,4r)-4-((S)-5,5-dimethyl-2-oxo-4-phenyloxazolidin-3-yl)cyclohexyl)imidazo[1,2-a]pyridine-6-carboxamide

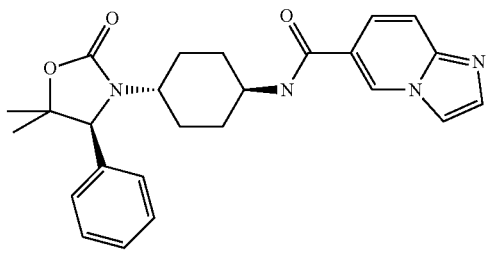 [SMILES: CC1(C)OC(=O)N([C@H]2CC[C@H](NC(=O)c3ccc4nccn4c3)CC2)[C@H]1c1ccccc1]

Example 159 was prepared from Intermediate E according to the procedure of Example 25 using imidazo[1,2-a]pyridine-6-carboxylic acid providing N-((1S,4r)-4-((S)-5,5-dimethyl-2-oxo-4-phenyloxazolidin-3-yl)cyclohexyl)imidazo[1,2-a]pyridine-6-carboxamide as a light yellow solid, (25.84 mg, 60 mmol, 24% yield). $^1$H NMR (400 MHz, DMSO-d$_6$) δ ppm 0.80 (s, 3H), 1.08-1.18 (m, 1H), 1.23-1.44 (m, 2H) 1.46 (s, 3H), 1.53 (d, J=12.83 Hz, 1H), 1.71-1.86 (m, 3H), 1.91 (d, J=12.43 Hz, 1H), 3.3-3.5 (m, 1H), 3.54-3.65 (m, 1H), 4.65 (s, 1H), 7.21 (br. s., 1H), 7.28-7.44 (m, 4H), 7.54-7.64 (m, 3H), 8.03 (s, 1H), 8.29 (d, J=7.79 Hz, 1H), 9.04 (s, 1H). m/z (ESI) 433.2 (M+H)$^+$.

Example 160

Synthesis of N-((1S,4r)-4-((S)-5,5-dimethyl-2-oxo-4-phenyloxazolidin-3-yl)cyclohexyl)thiazole-2-carboxamide

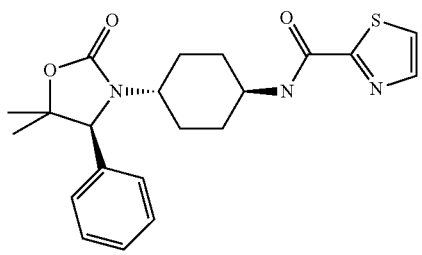 [SMILES: CC1(C)OC(=O)N([C@H]2CC[C@H](NC(=O)c3nccs3)CC2)[C@H]1c1ccccc1]

Example 160 was prepared from Intermediate E according to the procedure of Example 25 using thiazole-2-carboxylic acid providing N-((1S,4r)-4-((S)-5,5-dimethyl-2-oxo-4-phenyloxazolidin-3-yl)cyclohexyl)thiazole-2-carboxamide as a light yellow solid, (50.61 mg, 127 mmol, 51% yield). $^1$H NMR (400 MHz, DMSO-d$_6$) δ ppm 0.79 (s, 3H), 1.13 (qd, J=12.70, 3.49 Hz, 1H), 1.32-1.43 (m, 1H), 1.46 (s, 3H), 1.51 (d, J=9.34 Hz, 2H), 1.65 (d, J=11.57 Hz, 1H), 1.75-1.86 (m, 3H), 3.36-3.46 (m, 1H), 3.51-3.65 (m, 1H), 4.63 (s, 1H), 7.20 (br. s., 1H), 7.27-7.45 (m, 4H), 7.99 (d, J=3.09 Hz, 1H), 7.96 (d, J=3.04 Hz, 1H), 8.59 (d, J=8.53 Hz, 1H). m/z (ESI) 400 (M+H)$^+$.

Example 161

Synthesis of N-((1S,4r)-4-((S)-5,5-dimethyl-2-oxo-4-phenyloxazolidin-3-yl)cyclohexyl)-1-phenyl-1H-pyrazole-4-carboxamide

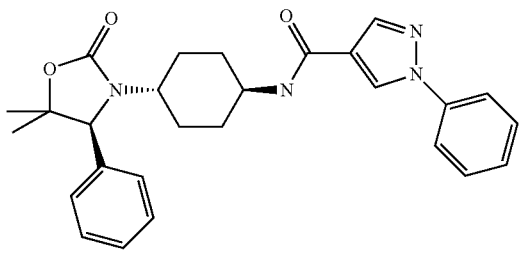 [SMILES: CC1(C)OC(=O)N([C@H]2CC[C@H](NC(=O)c3cnn(-c4ccccc4)c3)CC2)[C@H]1c1ccccc1]

Example 161 was prepared from Intermediate E according to the procedure of Example 25 using 1-phenyl-1H-pyrazole-4-carboxylic acid providing N-((1S,4r)-4-((S)-5,5-dimethyl-2-oxo-4-phenyloxazolidin-3-yl)cyclohexyl)-1-phenyl-1H-pyrazole-4-carboxamide as a light yellow solid, (47.76 mg, 105 mmol, 42% yield). $^1$H NMR (400 MHz, DMSO-d$_6$) δ ppm 0.80 (s, 3H), 1.06-1.16 (m, 1H), 1.19-1.39 (m, 2H), 1.42-1.56 (m, 4H), 1.69-1.86 (m, 3H), 1.86-1.94 (m, 1H), 3.45-3.57 (m, 2H), 4.64 (s, 1H), 7.19 (br. s., 1H), 7.27-7.44 (m, 5H), 7.51 (t, J=7.96 Hz, 2H), 7.82 (d, J=7.73 Hz, 2H), 7.92 (d, J=7.85 Hz, 1H), 8.09 (s, 1H) 8.86 (s, 1H). m/z (ESI) 459.2 (M+H)$^+$.

Example 162

Synthesis of N-((1R,4r)-4-((R)-5,5-dimethyl-2-oxo-4-phenyloxazolidin-3-yl)cyclohexyl)imidazo[1,2-a]pyridine-2-carboxamide

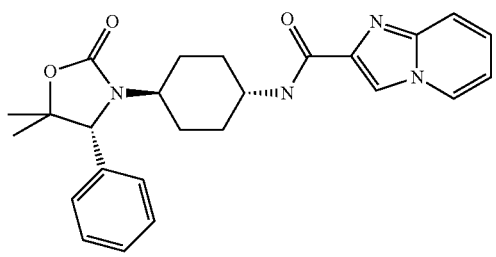 [SMILES: CC1(C)OC(=O)N([C@H]2CC[C@H](NC(=O)c3cn4ccccc4n3)CC2)[C@@H]1c1ccccc1]

Example 162 was prepared from Intermediate E according to the procedure of Example 25 using imidazo[1,2-a]pyridine-2-carboxylic acid providing N-((1R,4r)-4-((R)-5,5-dimethyl-2-oxo-4-phenyloxazolidin-3-yl)cyclohexyl)imidazo[1,2-a]pyridine-2-carboxamide as a light yellow solid, (7.14 mg, 17 mmol, 7% yield). $^1$H NMR (400 MHz, DMSO-d$_6$) δ ppm 0.80 (s, 3H), 1.08-1.28 (m, 1H), 1.35-1.48 (m, 5H), 1.50 (br. s., 2H), 1.66 (d, J=13.52 Hz, 1H), 1.75-1.86 (m, 3H), 3.4-3.5 (m, 1H), 3.57-3.65 (m, 1H), 4.64 (s, 1H), 6.95 (t, J=6.73 Hz, 1H), 7.21 (br. s., 1H), 7.26-7.45 (m, 5H), 7.55 (d, J=9.16 Hz, 1H), 8.02 (d, J=8.65 Hz, 1H), 8.31 (s, 1H), 8.55 (d, J=6.76 Hz, 1H). m/z (ESI) 433.2 (M+H)⁻

Example 163

Synthesis of N-((1S,4r)-4-((S)-5,5-dimethyl-2-oxo-4-phenyloxazolidin-3-yl)cyclohexyl)-2-methoxybenzamide

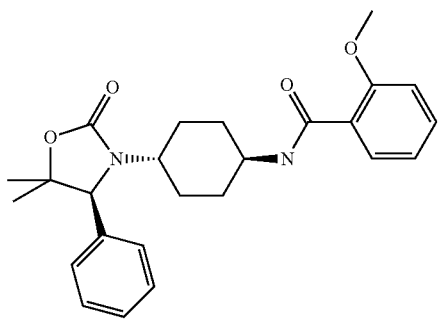 [SMILES: COc1ccccc1C(=O)N[C@H]1CC[C@H](N2C(=O)OC(C)(C)[C@@H]2c2ccccc2)CC1]

Example 163 was prepared from Intermediate E according to the procedure of Example 25 using 2-methoxy benzoic acid providing N-((1 S,4r)-4-((S)-5,5-dimethyl-2-oxo-4-phenyloxazolidin-3-yl)cyclohexyl)-2-methoxybenzamide as a light yellow solid, (60.45 mg, 144 mmol, 58% yield). ¹H NMR (400 MHz, DMSO-d₆) δ ppm 0.80 (s, 3H), 1.09-1.30 (m, 2H), 1.30-1.42 (m, 1H), 1.46 (s, 3H), 1.49-1.59 (m, 1H), 1.74 (d, J=11.74 Hz, 1H), 1.78-1.86 (m, 2H), 1.87-1.93 (m, 1H), 3.37-3.47 (m, 1H), 3.52-3.62 (m, 1H), 3.83 (s, 3H), 4.64 (s, 1H), 6.99 (t, J=7.22 Hz, 1H), 7.09 (d, J=8.25 Hz, 1H), 7.25 (br. s., 1H), 7.29-7.47 (m, 5H), 7.64 (dd, J=7.68, 1.72 Hz, 1H), 7.86 (d, J=7.90 Hz, 1H). m/z (ESI) 423.2 (M+H)⁺.

Example 164

Synthesis of N-((1S,4r)-4-((S)-5,5-dimethyl-2-oxo-4-phenyloxazolidin-3-yl)cyclohexyl)-2-phenyloxazole-4-carboxamide

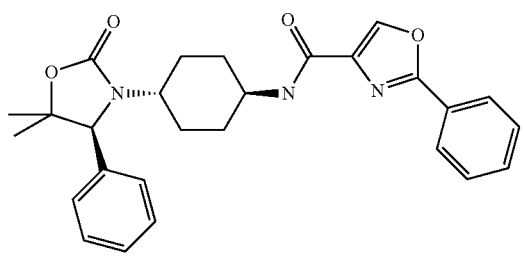 [SMILES: CC1(C)OC(=O)N([C@H]2CC[C@H](NC(=O)c3coc(-c4ccccc4)n3)CC2)[C@H]1c1ccccc1]

Example 164 was prepared from Intermediate E according to Example 25 using 2-phenyloxazole-4-carboxylic acid providing N-((1 S,4r)-4-((S)-5,5-dimethyl-2-oxo-4-phenyloxazolidin-3-yl)cyclohexyl)-2-phenyloxazole-4-carboxamide as a light yellow solid, (115.0 mg, 98 mmol, 39% yield). ¹H NMR (400 MHz, DMSO-d₆) δ ppm 8.66 (s, 1H), 8.00-8.06 (m, 3H), 7.58 (s, 3H), 7.47-7.17 (m, 6H), 4.65 (s, 1H), 3.57-3.70 (m, 1H), 3.52-3.41 (m, 1H), 1.90-1.76 (m, 3H), 1.74-1.63 (m, 1H), 1.47 (s, 6H), 1.07-1.16 (m, 1H), 0.81 (s, 3H), m/z (ESI) 460.5 (M+H)⁺.

Example 165

Synthesis of N-((1S,4r)-4-((S)-5,5-dimethyl-2-oxo-4-phenyloxazolidin-3-yl)cyclohexyl)pyrimidine-4-carboxamide

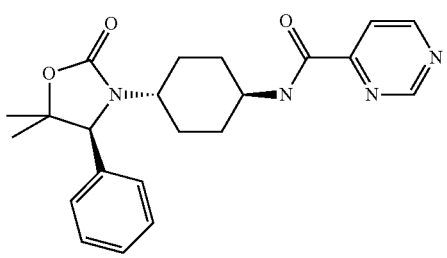 [SMILES: CC1(C)OC(=O)N([C@H]2CC[C@H](NC(=O)c3ccncn3)CC2)[C@H]1c1ccccc1]

Example 165 was prepared from Intermediate E according to the procedure of Example 25 using pyrimidine-4-carboxylic acid providing N-((1 S,4r)-4-((S)-5,5-dimethyl-2-oxo-4-phenyloxazolidin-3-yl)cyclohexyl)pyrimidine-4-carboxamide as a light yellow solid, (50.0 mg, 126 mmol, 51% yield). ¹H NMR (400 MHz, DMSO-d₆) δ ppm=9.30 (d, J=1.27 Hz, 1H), 9.04 (d, J=5.18 Hz, 1H), 8.78-8.72 (m, 1H), 7.98 (dd, J=5.04, 1.42 Hz, 1H), 7.48-7.13 (m, 5H), 4.65 (s, 1H), 3.71-3.58 (m, 1H), 3.46-3.40 (m, 1H), 3.31 (s, 3H) 2.70 (s, 1H) 1.82, (br. s., 1H), 1.71-1.64 (m, 1H) 1.58-1.37 (s, 4H), 0.80 (s, 3H), m/z (ESI) 395.5 (M+H)⁻

Example 166

Synthesis of N-((1S,4r)-4-((S)-5,5-dimethyl-2-oxo-4-phenyloxazolidin-3-yl)cyclohexyl)-2-methylthiazole-4-carboxamide

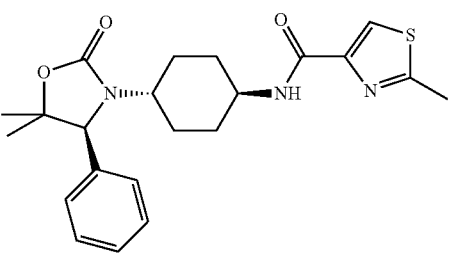

Example 166 was prepared from Intermediate E according to the procedure of Example 25 using 2-methylthiazole-4-carboxylic acid providing N-((1S,4r)-4-((S)-5,5-dimethyl-2-oxo-4-phenyloxazolidin-3-yl)cyclohexyl)-2-methylthiazole-4-carboxamide as a light yellow solid, (61.25 mg, 149 mmol, 59% yield). ¹H NMR (400 MHz, DMSO-d₆) δ ppm=0.79 (s, 3H), 1.06-1.16 (m, 1H), 1.23-1.43 (m, 1H) 1.43-1.53 (m, 5H), 1.63 (d, J=12.20 Hz, 1H), 1.74-1.84 (m, 3H), 2.67 (s, 3H), 3.17 (d, J=5.27 Hz, 1H), 3.37-3.47 (m, 1H), 3.53-3.62 (m, 1H), 4.63 (s, 1H), 7.19 (br. s., 1H), 7.26-7.46 (m, 4H), 7.97 (d, J=8.53 Hz, 1H), 8.03 (s, 1H), m/z (ESI) 414.2 (M+H)⁺.

Example 167

Synthesis of N-((1S,4r)-4-((S)-5,5-dimethyl-2-oxo-4-phenyloxazolidin-3-yl)cyclohexyl)-2-(pyridin-4-yl)thiazole-4-carboxamide

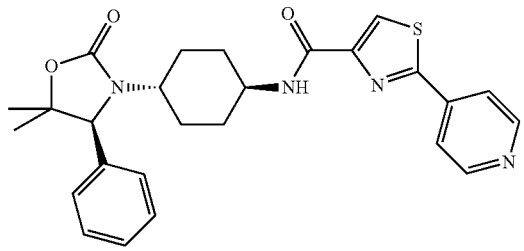 [SMILES: CC1(C)OC(=O)N([C@H]2CC[C@H](NC(=O)c3csc(-c4ccncc4)n3)CC2)[C@H]1c1ccccc1]

Example 167 was prepared from Intermediate E according to the procedure of Example 25 using 2-(pyridin-4-yl)thiazole-4-carboxylic acid providing N-((1 S,4r)-4-((S)-5,5-dimethyl-2-oxo-4-phenyloxazolidin-3-yl)cyclohexyl)-2-(pyridin-4-yl)thiazole-4-carboxamide as a light yellow solid, (85.06 mg, 177 mmol, 72% yield). $^1$H NMR (400 MHz, DMSO-d$_6$) δ ppm=0.80 (s, 3H), 1.13 (qd, J=12.66, 3.21 Hz, 1H), 1.34-1.44 (m, 1H), 1.45-1.56 (m, 2H), 1.67-1.75 (m, 1H), 1.78-1.92 (m, 3H), 3.17 (d, J=5.04 Hz, 2H), 3.40-3.53 (m, 1H), 3.60-3.69 (m, 1H), 4.08 (q, J=5.06 Hz, 1H), 4.65 (s, 1H), 7.22 (br. s., 1H), 7.28-7.46 (m, 4H), 8.00 (d, J=6.01 Hz, 2H), 8.24 (d, J=8.53 Hz, 1H), 8.39-8.44 (m, 1H), 8.74 (d, J=6.01 Hz, 2H), m/z (ESI) 477.2 (M+H).

Example 168

Synthesis of N-((1S,4r)-4-((S)-5,5-dimethyl-2-oxo-4-phenyloxazolidin-3-yl)cyclohexyl)thiazole-4-carboxamide

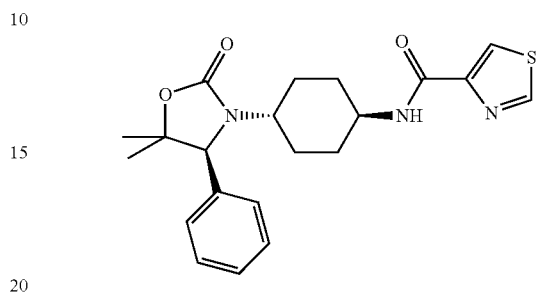

Example 168 was prepared from Intermediate E according to the procedure of Example 25 using thiazole-4-carboxylic acid providing -((1 S,4r)-4-((S)-5,5-dimethyl-2-oxo-4-phenyloxazolidin-3-yl)cyclohexyl)thiazole-4-carboxamide as a light yellow solid, (61.01 mg, 153 mmol, 61% yield). $^1$H NMR (400 MHz, DMSO-d$_6$) δ ppm=0.79 (s, 3H), 1.12 (qd, J=12.75, 3.55 Hz, 1H), 1.37 (dtd, J=12.83, 12.57, 12.57, 3.44 Hz, 1H), 1.44-1.53 (m, 5H), 1.65 (d, J=12.14 Hz, 1H), 1.80 (t, J=7.45 Hz, 3H), 3.37-3.47 (m, 1H), 3.56-3.65 (m, 1H), 4.63 (s, 1H), 7.19 (br. s., 1H), 7.26-7.46 (m, 4H), 8.14 (d, J=8.53 Hz, 1H), 8.26 (d, J=2.01 Hz, 1H), 9.13 (d, J=1.95 Hz, 1H), m/z (ESI) 400.1 (M+H)⁺.

Examples 169, 170, 171, 172

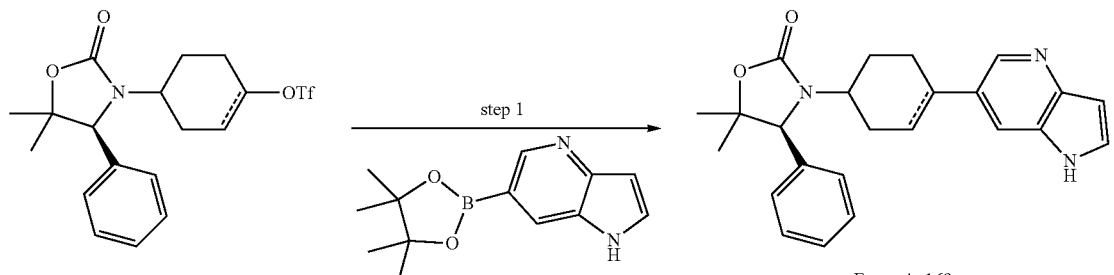

Example 169

Pd/C, balloon
step 2

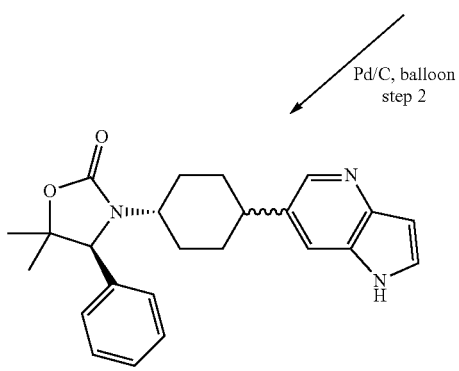

Example 170

303

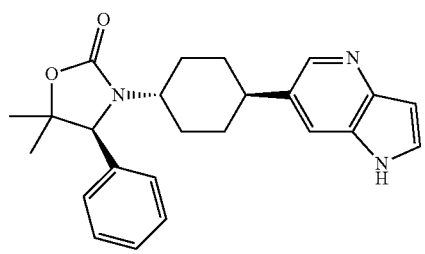

Example 171

304

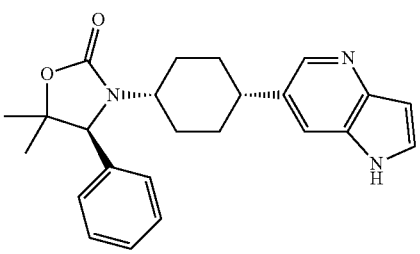

Example 172

1H), 8.38 (s, 1H), 7.61-7.65 (m, 1H), 7.56-7.60 (m, 1H), 7.25-7.50 (m, 5H), 6.47-6.51 (m, 1H), 6.05-6.09 (m, 0.5H), 5.94-5.98 (m, 0.5H), 4.72-4.75 (s, 0.5H), 4.69-4.72 (s, 0.5H), 3.67-3.81 (m, 1H), 2.56-2.69 (m, 2H), 1.93-2.23 (m, 2H), 1.51 (s, 4H), 0.83 (s, 3H), one proton was found to over lap with DMSO peak. m/z (ESI) 388.2 (M+H)$^+$.

Example 169

Synthesis of mixture of (S)-3-((S)-4-(1H-pyrrolo[3,2-b]pyridin-6-yl)cyclohex-3-en-1-yl)-5,5-dimethyl-4-phenyloxazolidin-2-one and (S)-3-((R)-4-(1H-pyrrolo[3,2-b]pyridin-6-yl)cyclohex-3-en-1-yl)-5,5-dimethyl-4-phenyloxazolidin-2-one

Example 170

Synthesis of (S)-3-((1r,4S)-4-(1H-pyrrolo[3,2-b]pyridin-6-yl)cyclohexyl)-5,5-dimethyl-4-phenyloxazolidin-2-one and (R)-3-((1r,4R)-4-(1H-pyrrolo[3,2-b]pyridin-6-yl)cyclohexyl)-5,5-dimethyl-4-phenyloxazolidin-2-one

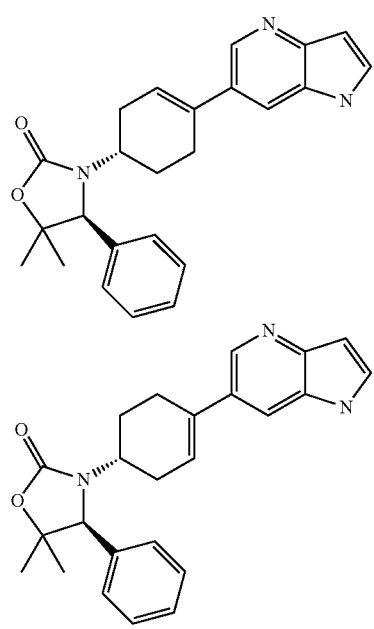

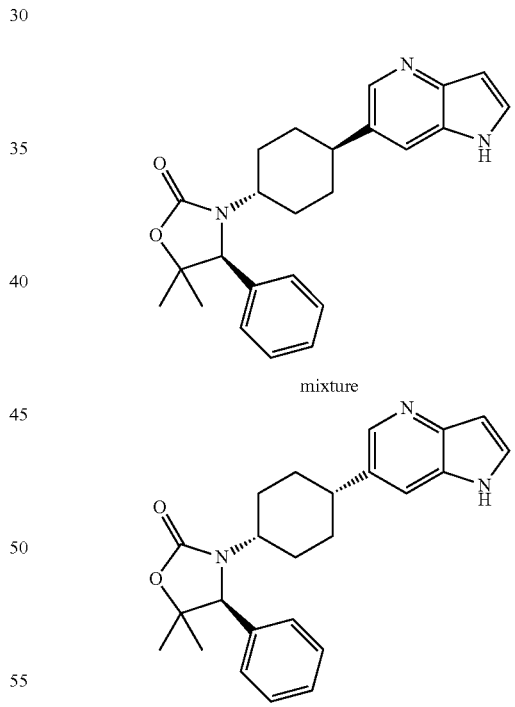

mixture

A vial containing a solution of Intermediate MM-1 (0.250 g, 0.596 mmol), 6-(4,4,5,5-tetramethyl-1,3,2-dioxaborolan-2-yl)-1H-pyrrolo[3,2-b]pyridine (0.145 g, 0.596 mmol) and sodium carbonate (1.490 mL, 2.98 mmol) in dioxane (1.987 mL) was purged with nitrogen and tetrakis(triphenylphosphine)palladium (0.069 g, 0.060 mmol) was added. The vial was sealed and shaken on shaker for 16 h at 100° C. LC-MS showed clean conversion. The reaction mixture was concentrated and diluted with DCM (12 mL). The organic layer was then passed through a phase separator, concentrated and purified with a 100 g SNAP column ramping DCM:MeOH (90:10) up to 75% providing a (1:1) diasteomeric mixture (S)-3-((S)-4-(1H-pyrrolo[3,2-b]pyridin-6-yl)cyclohex-3-en-1-yl)-5,5-dimethyl-4-phenyloxazolidin-2-one and (S)-3-((R)-4-(1H-pyrrolo[3,2-b]pyridin-6-yl)cyclohex-3-en-1-yl)-5,5-dimethyl-4-phenyloxazolidin-2-one (0.168 g, 0.434 mmol, 73% yield) as an oily white solid. $^1$H NMR (400 MHz, DMSO-d$_6$) δ ppm=11.19-11.24 (m, 1H), 8.38 (t, J=1.00 Hz, To a flask containing a solution of (S)-3-((S)-4-(1H-pyrrolo[3,2-b]pyridin-6-yl)cyclohex-3-en-1-yl)-5,5-dimethyl-4-phenyloxazolidin-2-one (0.05 g, 0.129 mmol) and (S)-3-((R)-4-(1H-pyrrolo[3,2-b]pyridin-6-yl)cyclohex-3-en-1-yl)-5,5-dimethyl-4-phenyloxazolidin-2-one (0.050 g, 0.129 mmol) in EtOAc (0.331 mL) and DCM (0.099 mL) was added palladium 10 wt. % on activated carbon (2.75 µl, 0.026 mmol). The resulting mixture was hydrogenated at atmospheric pressure (using a balloon) for 16 h. LC-MS showed complete conversion. The organic layer was filtered through Celite® brand filter aid plug, concentrated and purified with a 100 g SNAP column ramping DCM:MeOH (90:10) up to 100% to obtain (S)-3-((1r,4S)-4-(1H-pyrrolo[3,2-b]pyridin-6-yl)cyclohexyl)-5,5-dimethyl-4-phenyloxazolidin-2-one and (R)-3-((1r,4R)-4-(1H-pyrrolo[3,2-b]pyridin-6-yl)cyclohexyl)-5,5-dimethyl-4-phenyloxazolidin-2-one (35 mg, 95 mmol, 70% yield) as an off white solid. $^1$H NMR (400 MHz, CDCl$_3$) δ ppm=8.38 (d, J=1.86 Hz, 1H), 7.50-7.51 (m, 1H), 7.37-7.45 (m, 2H), 7.37-7.45 (m, 2H), 7.29-7.37 (m, 3H), 6.98-7.05 (m, 1H), 6.74-6.76 (m, 1H), 4.37 (s, 1H), 3.71-3.79 (m, 1H), 2.97-3.05 (m, 1H), 2.36-2.46 (m, 1H), 2.10-2.20 (m, 1H), 1.68-1.97 (m, 6H) 1.58 (s, 4H) 0.93 (s, 3H). m/z (ESI) 390.3 (M+H)$^+$.

Example 171

Synthesis of (S)-3-((1r,4S)-4-(1H-pyrrolo[3,2-b]pyridin-6-yl)cyclohexyl)-5,5-dimethyl-4-phenyloxazolidin-2-one

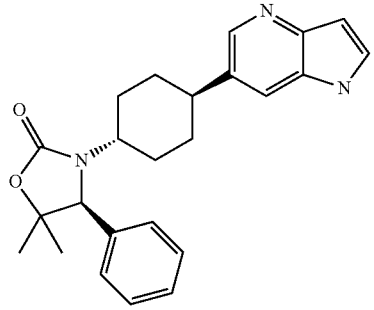 [SMILES: CC1(C)OC(=O)N([C@H]2CC[C@H](c3cnc4cc[nH]c4c3)CC2)[C@H]1c1ccccc1]

Achiral purification using the mixture of Example 170 and reverse phase HPLC with 0.1% NH$_4$OH in ACN and water as the mobile phase allowed the separation of the cis and trans isomers providing Examples 171 and 172.

Example 171

$^1$H NMR (400 MHz, CDCl$_3$) δ ppm=8.30 (s, 2H), 7.37-7.49 (m, 7H), 6.72 (dt, J=2.05, 1.03 Hz, 1H), 4.43 (s, 1H), 3.65-3.79 (m, 1H), 2.51-2.62 (m, 1H), 1.26-2.11 (m, 11H), 0.95 (s, 3H). m/z (ESI) 390.3 (M+H)$^+$.

Example 172

Synthesis of (S)-3-((1s,4R)-4-(1H-pyrrolo[3,2-b]pyridin-6-yl)cyclohexyl)-5,5-dimethyl-4-phenyloxazolidin-2-one

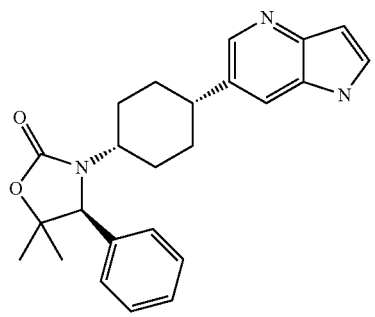 [SMILES: CC1(C)OC(=O)N([C@H]2CC[C@@H](c3cnc4cc[nH]c4c3)CC2)[C@H]1c1ccccc1]

The title compound was obtained as described in Example 171 from the mixture of Example 170. However, not enough of the compound was obtained to fully characterize it so this other isomer was assumed to be the trans isomer as shown. m/z (ESI) 390.3 (M+H)$^+$.

Examples 173 and 174

Synthesis of (S)-5,5-dimethyl-4-phenyl-3-((R)-4-(1-(pyrimidin-2-yl)-1H-pyrrolo[3,2-b]pyridin-6-yl)cyclohex-3-en-1-yl)oxazolidin-2-one and (S)-5,5-dimethyl-4-phenyl-3-(4-(1-(pyrimidin-2-yl)-1H-pyrrolo[3,2-b]pyridin-6-yl)cyclohexyl)oxazolidin-2-one

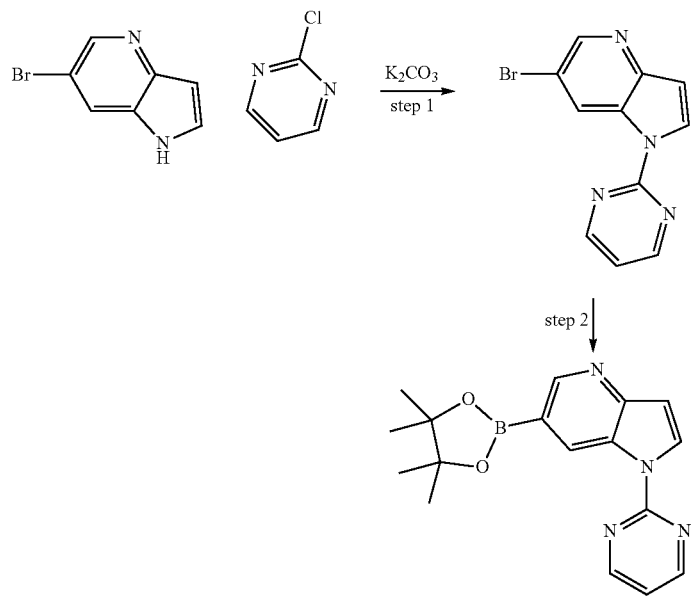

Example 173

307

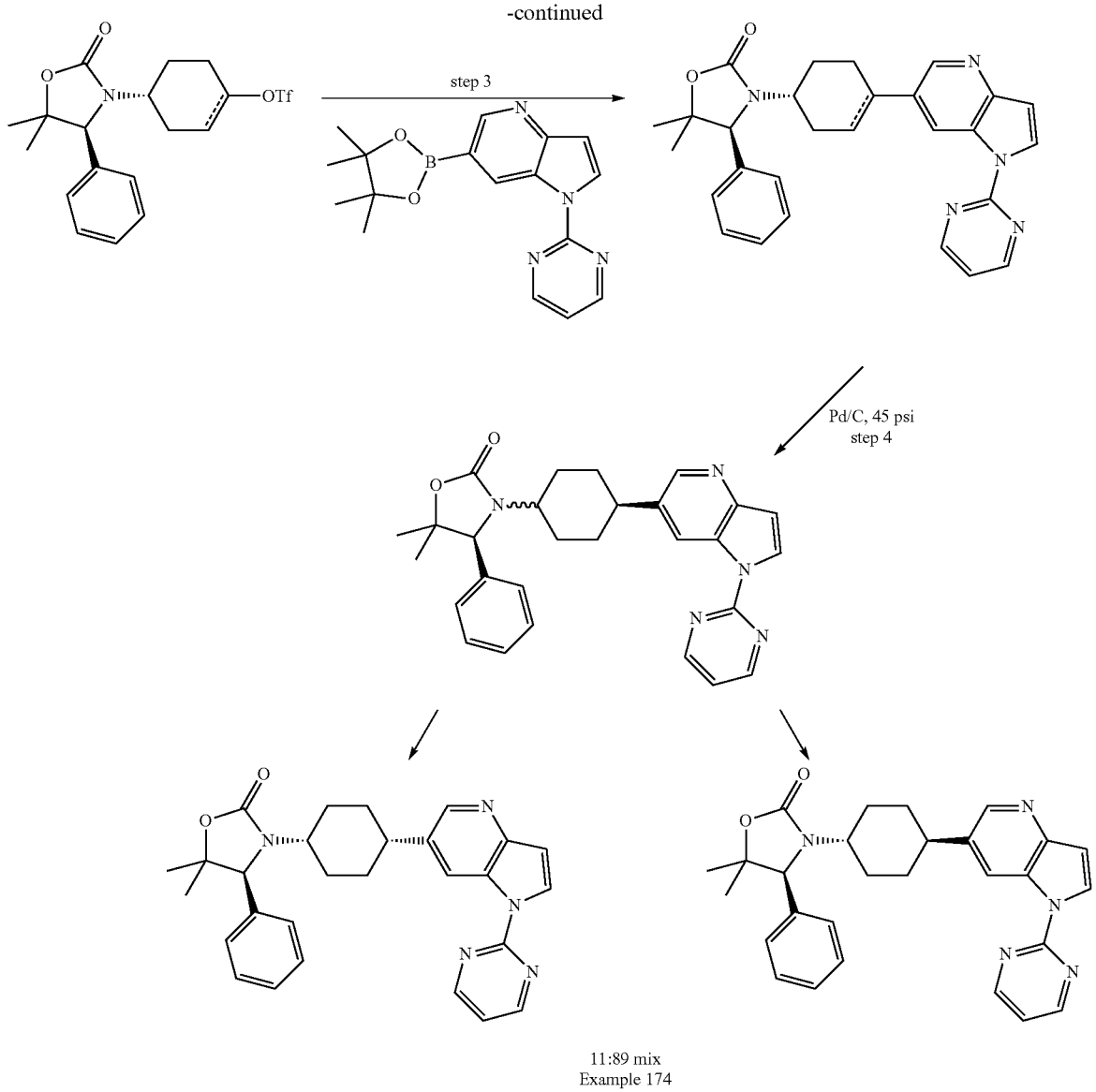

11:89 mix
Example 174

Step 1

Synthesis of 6-bromo-1-(pyrimidin-2-yl)-1H-pyrrolo[3,2-b]pyridine

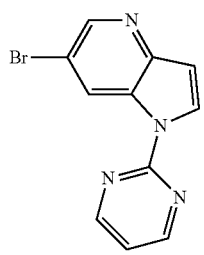 [SMILES: Brc1cnc2ccn(-c3ncccn3)c2c1]

To a flask charged with 6-bromo-1H-pyrrolo[3,2]pyrridine (Ark Pharm) (1 g, 5.08 mmol) and 2-chloropyrimidine (0.581 g, 5.08 mmol) in ACN (25 mL) was added anhydrous potassium carbonate (0.919 mL, 15.23 mmol). The resulting mixture was then stirred for 16 h at 40° C. LC-MS showed the product as the major peak. The reaction mixture was then concentrated and the residue was purified with a 100 g SNAP column ramping DCM:MeOH (90:10) providing 6-bromo-1-(pyrimidin-2-yl)-1H-pyrrolo[3,2-b]pyridine (1.15 g, 4.18 mmol, 82% yield) as a light yellow solid. m/z (ESI) 276.1/278.1.

Step 2

1-(pyrimidin-2-yl)-6-(4,4,5,5-tetramethyl-1,3,2-dioxaborolan-2-yl)-1H-pyrrolo[3,2-b]pyridine

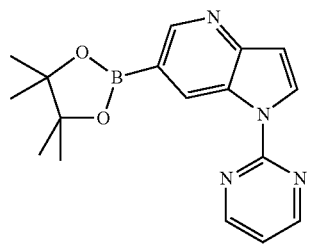 [SMILES: CC1(C)OB(c2cnc3ccn(-c4ncccn4)c3c2)OC1(C)C]

A vial containing a solution of 6-bromo-1-(pyrimidin-2-yl)-1H-pyrrolo[3,2-b]pyridine (0.511 g, 1.857 mmol) and bis(pinacolato)diboron (Sigma Aldrich) (0.542 g, 2.136 mmol) in dioxane (14 mL) was purged with nitrogen and to it was added potassium acetate (Sigma Aldrich) (0.581 mL, 9.29 mmol) followed by (1,1'-bis(diphenylphosphino)ferrocene)dichloropalladium(ii) (Strem Chemicals) (0.152 g, 0.186 mmol). The via was then purged again with nitrogen. The vial was sealed and shaken for 18 h at 100° C. The reaction mixture was diluted with DCM (50 mL) and saturated aqueous NH₄Cl solution (10 mL) and water (50 mL) were added. The product was then extracted with DCM (2×50 mL). The combined organic extracts were passed through SCX and concentrated to obtain 1-(pyrimidin-2-yl)-6-(4,4,5,5-tetramethyl-1,3,2-dioxaborolan-2-yl)-1H-pyrrolo[3,2-b]pyridine as a black oil. LC-MS (showed the acid as the major peak) and the NMR looked clean enough to use. The material was taken to to the next step without further purification assuming quantitative yield. m/z (ESI) 241.2 (M+H)⁺ (of boronic acid).

Step 3

Example 173

Mixture of (S)-5,5-dimethyl-4-phenyl-3-((S)-4-(1-(pyrimidin-2-yl)-1H-pyrrolo[3,2-b]pyridin-6-yl)cyclohex-3-en-1-yl)oxazolidin-2-one and (S)-5,5-dimethyl-4-phenyl-3-((R)-4-(1-(pyrimidin-2-yl)-1H-pyrrolo[3,2-b]pyridin-6-yl)cyclohex-3-en-1-yl)oxazolidin-2-one

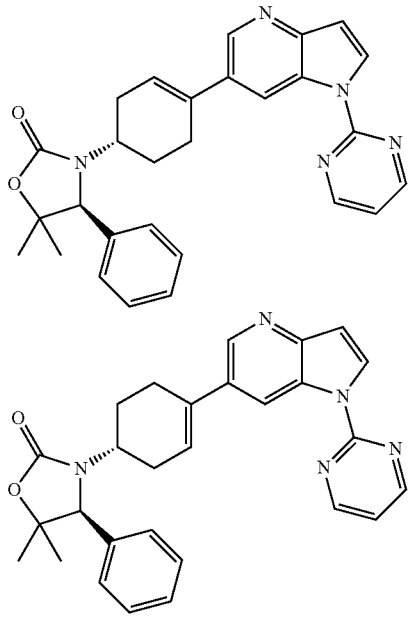

A vial containing a mixture of sodium carbonate (1.490 mL, 2.98 mmol), intermediate MM-1 (0.250 g, 0.596 mmol) and 1-(pyrimidin-2-yl)-6-(4,4,5,5-tetramethyl-1,3,2-dioxaborolan-2-yl)-1H-pyrrolo[3,2-b]pyridine (0.192 g, 0.596 mmol) in dioxane (1.987 mL) was purged with nitrogen and tetrakis(triphenylphosphine)palladium (0.069 g, 0.060 mmol) was added. The reaction mixture was then heated at 100° C. for 16 h. LC-MS showed the product as the major peak. The reaction mixture was concentrated and diluted with water (40 mL) and DCM (60 mL). The organic layer was passed through a phase separator, concentrated, and purified with a 100 g SNAP column ramping DCM:MeOH (90:10) up to 100%. NMR showed some impurity. Further achiral purification using 0.1% NH₄OH in ACN and water as the mobile phase provided (S)-5,5-dimethyl-4-phenyl-3-((S)-4-(1-(pyrimidin-2-yl)-1H-pyrrolo[3,2-b]pyridin-6-yl)cyclohex-3-en-1-yl)oxazolidin-2-one and (S)-5,5-dimethyl-4-phenyl-3-((R)-4-(1-(pyrimidin-2-yl)-1H-pyrrolo[3,2-b]pyridin-6-yl)cyclohex-3-en-1-yl)oxazolidin-2-one as a (1:1) diasteromeric mixture. ¹H NMR (400 MHz, DMSO-d₆) δ ppm=8.90 (m, 3H) 8.48-8.58 (m, 2H) 7.22-7.53 (m, 6H) 6.84-6.92 (m, 1H) 6.11-6.18 (m, 0.5H) 6.00-6.07 (m, 0.5H) 4.74 (s, 0.5H) 4.71 (m, 0.5H) 3.68-3.84 (m, 1H) 2.57-2.81 (m, 2H) 2.02-2.46 (m, 2H) 1.74-1.86 (m, 1H) 1.52 (s, 4H) 1.07 (s, 1H) 0.83 (s, 3H). NMR shows a (1:1) diasteromeric mixture. m/z (ESI) 466.2 (M+H)⁺.

Step 4

Example 174

Mixture of (S)-5,5-dimethyl-4-phenyl-3-((1r,4S)-4-(1-(pyrimidin-2-yl)-1H-pyrrolo[3,2-b]pyridin-6-yl)cyclohexyl)oxazolidin-2-one compound and (S)-5,5-dimethyl-4-phenyl-3-((1s,4R)-4-(1-(pyrimidin-2-yl)-1H-pyrrolo[3,2-b]pyridin-6-yl)cyclohexyl)oxazolidin-2-one (86:14)

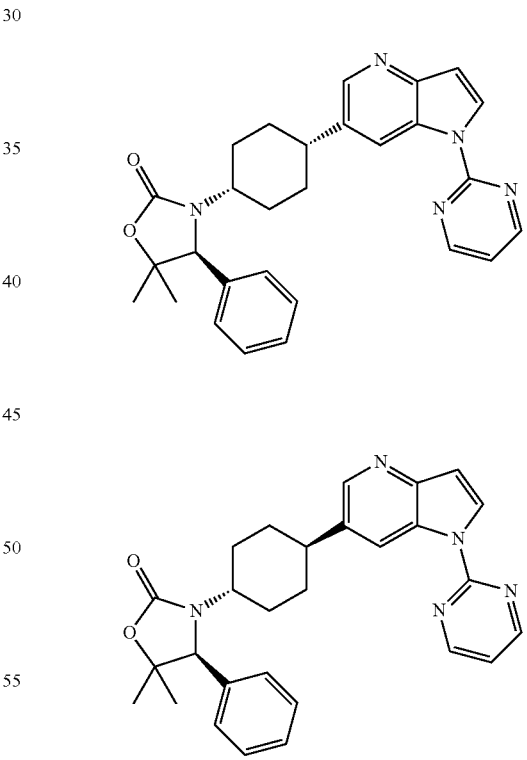

A suspension of (S)-5,5-dimethyl-4-phenyl-3-((S)-4-(1-(pyrimidin-2-yl)-1H-pyrrolo[3,2-b]pyridin-6-yl)cyclohex-3-en-1-yl)oxazolidin-2-one (0.23 g, 0.494 mmol) and palladium 10 wt. % on activated carbon (0.053 mL, 0.494 mmol) in EtOAc (3.29 mL), DCM (3.29 mL) and MeOH (3.29 mL) was hydrogenated at 50 psi at room temperature overnight for 2 days. LC-MS showed some desired product formation. The reaction mixture was filtered through Celite® brand filter aid and concentrated. Achiral purification using 0.1% NH₄OH in ACN and water as the mobile phase provided a mixture of (S)-5,5-dimethyl-4-phenyl-3-((1r,4S)-4-(1-(pyrimidin-2-yl)-1H-pyrrolo[3,2-b]pyridin-6-yl)cyclohexyl)oxazolidin-2-one compound and (S)-5,5-dimethyl-4-phenyl-3-((1s,4R)-4-(1-(pyrimidin-2-yl)-1H-pyrrolo[3,2-b]pyridin-6-yl) cyclohexyl)oxazolidin-2-one (14:86 mixture) as a white solid (33 mg, 71 mmol, 14% yield). The major isomer was arbitrarily assigned to be the cis isomer. ¹H NMR (400 MHz, CDCl₃) δ ppm=8.84 (d, J=1.86 Hz, 1H), 8.75 (s, 1H), 8.74 (s, 1H), 8.47 (d, J=3.81 Hz, 1H), 8.34 (d, J=1.96 Hz, 1H), 7.39-7.43 (m, 1H), 7.13 (s, 1H), 6.84-6.84 (m, 5H), 6.84 (s, 1H), 4.44 (s, 1H), 3.75-3.85 (m, 1H) 2.57-2.68 (m, 1H) 1.56-2.13 (m, 7H) 1.27-1.40 (m, 2H) 0.96 (s, 3H). m/z (ESI) 468.2 (M+H)⁺.

Examples 175, 176, and 177

Examples 175, 176, and 177 were synthesized following the procedure described in Examples 84, 85 and 86. However, in step 1, trans-3-(tert-butoxycarbonylamino)cyclobutanecarboxylic acid (Pharma Sys) was used instead of (1 r,4r)-4-((tert-butoxycarbonyl)amino)cyclohexanecarboxylic acid.

Example 175

Mixture of (R)-5,5-dimethyl-4-phenyl-3-((1r,3R)-3-(5-phenyl-1,3,4-oxadiazol-2-yl)cyclobutyl)oxazolidin-2-one compound and (S)-5,5-dimethyl-4-phenyl-3-((1 r,3 S)-3-(5-phenyl-1,3,4-oxadiazol-2-yl)cyclobutyl)oxazolidin-2-one (1:1)

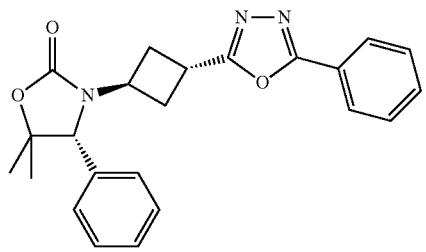

Example 175

¹H NMR (400 MHz, CDCl₃-d) δ ppm 7.97-8.02 (m, 2H), 7.45-7.55 (m, 3H), 7.33-7.44 (m, 3H), 7.17 (d, J=6.36 Hz, 2H), 4.48 (s, 1H), 4.20-4.31 (m, 1H), 3.67 (d, J=1.08 Hz, 1H), 3.31 (d, J=10.27 Hz, 1H), 2.98-3.09 (m, 1H), 2.52-2.65 (m, 2H), 1.59 (s, 4H) 0.94 (s, 3H). m/z (ESI) 390.4 (M+H)⁺.

Achiral purification of the mixture of Example 175 was performed using 0.1% NH₄OH in ACN and water as the mobile phase which allowed the separation of R and S isomers providing Example 176: ((R)-5,5-dimethyl-4-phenyl-3-((1r,3R)-3-(5-phenyl-1,3,4-oxadiazol-2-yl)cyclobutyl)oxazolidin-2-one) and Example 177: ((S)-5,5-dimethyl-4-phenyl-3-((1r,3 S)-3-(5-phenyl-1,3,4-oxadiazol-2-yl)cyclobutyl)oxazolidin-2-one). The stereochemistry was arbitrarily assigned for the R and S isomers.

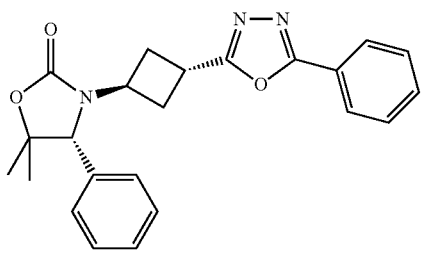 [SMILES: CC1(C)OC(=O)N([C@H]2C[C@H](c3nnc(-c4ccccc4)o3)C2)[C@@H]1c1ccccc1]

Example 176

¹H NMR (400 MHz, DMSO-d₆) δ ppm 7.94 (m, 2H), 7.54-7.64 (m, 3H), 7.43 (m, 3H), 7.15-7.30 (m, 2H), 4.82 (s, 1H), 4.26-4.37 (m, 1H), 3.56-3.64 (m, 1H), 2.97-3.06 (m, 1H), 2.51-2.68 (m, 3H), 2.25-2.34 (m, 1H), 1.52 (s, 3H), 0.82 (s, 3H). m/z (ESI) 390.2 (M+H)⁺.

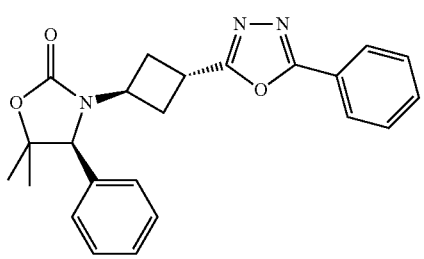

Example 177

¹H NMR (400 MHz, CDCl₃-d) δ=8.02-7.97 (m, 2H), 7.55-7.45 (m, 3H), 7.43-7.34 (m, 3H), 7.17 (d, J=6.3 Hz, 2H), 4.48 (s, 1H), 4.30-4.20 (m, 1H), 3.71-3.63 (m, 1H), 3.50 (s, 1H), 3.36-3.26 (m, 1H), 3.08-2.99 (m, 1H), 2.65-2.52 (m, 2H), 0.94 (s, 3H). m/z (ESI) 390.2.

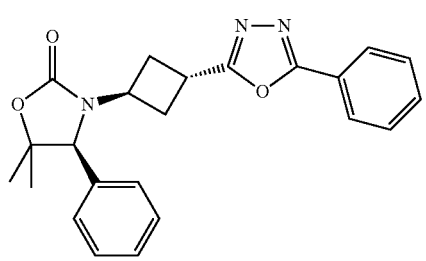 [SMILES: CC1(C)OC(=O)N([C@H]2C[C@H](c3nnc(-c4ccccc4)o3)C2)[C@H]1c1ccccc1]

Examples 178 and 179

Synthesis of 1-((1R,4s)-4-((4S,5R)-5-methyl-2-oxo-4-phenyloxazolidin-3-yl)cyclohexyl)-2-oxo-2,3-dihydro-1H-benzo[d]imidazole-5-carbonitrile and 1-((1R,4r)-4-((4R,5S)-5-methyl-2-oxo-4-phenyloxazolidin-3-yl)cyclohexyl)-2-oxo-2,3-dihydro-1H-benzo[d]imidazole-5-carbonitrile (arbitrarily assigned)

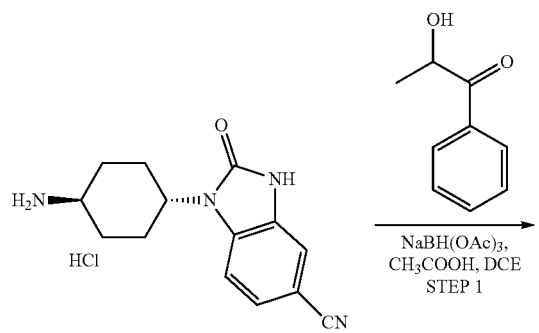

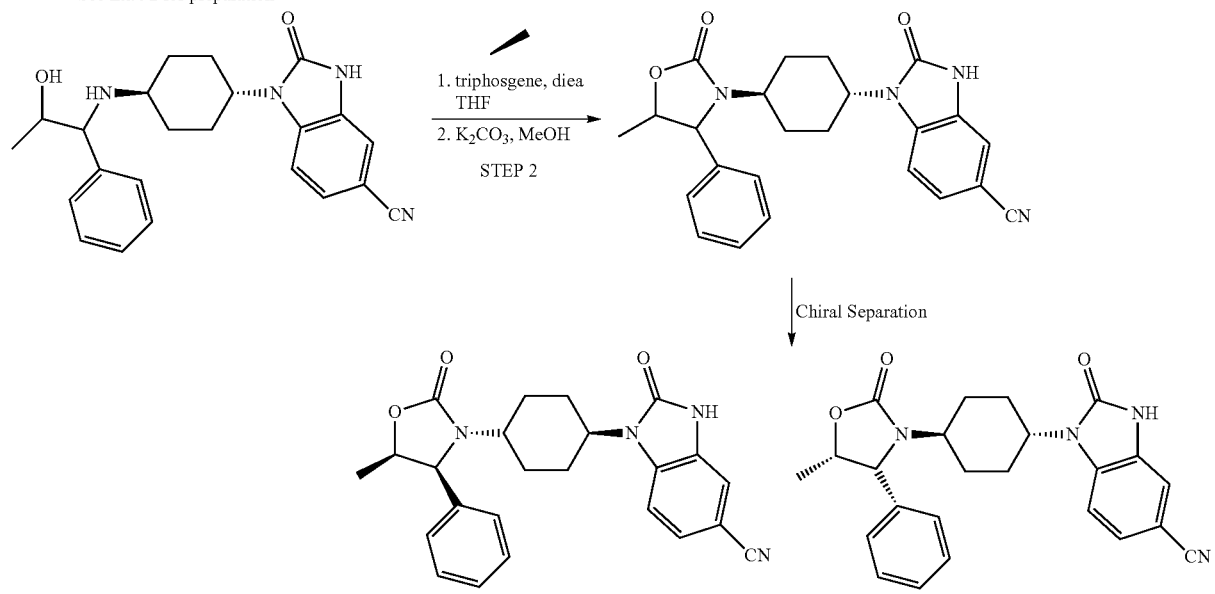

Example 178    Example 179

Step 1

1-((1r,4r)-4-((2-hydroxy-1-phenylpropyl)amino)cyclohexyl)-2-oxo-2,3-dihydro-1H-benzo[d]imidazole-5-carbonitrile To a flask charged with 2-hydroxy-1-phenylpropan-1-one (HDH Pharma) (0.141 g, 0.939 mmol) was added DCE (3.42 mL), acetic acid (0.054 mL, 0.939 mmol) and 1-((1r,4r)-4-aminocyclohexyl)-2-oxo-2,3-dihydro-1H-benzo[d]imidazole-5-carbonitrile hydrochloride (0.250 g, 0.854 mmol). The resulting suspension was stirred 15 mins prior to the addition of sodium triacetoxyborohydride (0.362 g, 1.708 mmol). The resulting mixture was stirred at room temperature overnight. LC-MS indicated 10-20% conversion to the desired product with starting amine present as the major species. Additional 2-hydroxy-1-phenylpropan-1-one (2 eq) and sodium triacetoxyborohydride (0.362 g, 1.708 mmol) were added, and the mixture was heated to 60° C. Additional starting keto-alcohol (1 eq) and NaBH(OAc)$_3$ were added and the mixture was stirred at 60° C. overnight. To the resulting orange turbid solution, were added water (~5 mL) and MeOH (~5 mL). The resulting solution was purified with a 10 g SCX-2 column washing with MeOH, and then with 2M NH$_3$ in MeOH. The basic wash was dried under reduced pressure and the material obtained was purified with a 25 g SNAP column (Biotage) ramping DCM:MeOH (90:10) in DCM from 0-30%. The mixture of product isomers was obtained as a yellow film 1-((1r,4r)-4-((2-hydroxy-1-phenylpropyl)amino)cyclohexyl)-2-oxo-2,3-dihydro-1H-benzo[d]imidazole-5-carbonitrile (0.132 g, 0.338 mmol, 39.6% yield). m/z (ESI) 391.3 (M+H)$^+$.

Step 2

1-((1r,4r)-4-(5-methyl-2-oxo-4-phenyloxazolidin-3-yl)cyclohexyl)-2-oxo-2,3-dihydro-1H-benzo[d]imidazole-5-carbonitrile To a flask charged with 1-((1 r,4r)-4-((2-hydroxy-1-phenylpropyl)amino)cyclohexyl)-2-oxo-2,3-dihydro-1H-benzo[d]imidazole-5-carbonitrile (0.132 g, 0.338 mmol) was added THF (1.352 mL) and DIEA (0.177 mL, 1.014 mmol). The solution was cooled in a dry ice/acetone bath. In a separate vial was added triphosgene (0.100 g, 0.338 mmol) and THF (200 μL). The triphosgene solution was added dropwise to the solution of starting material at −78° C. After 10 mins, the mixture had become a yellow suspension. LC-MS indicated ~80 conversion to a mono-acylated intermediate (methyl 6-cyano-3-((1r,4r)-4-(5-methyl-2-oxo-4-phenyloxazolidin-3-yl)cyclohexyl)-2-oxo-2,3-dihydro-1H-benzo[d]imidazole-1-carboxylate) observed. The bath was removed, and the mixture was stirred at room temperature overnight. EtOAc and water were then added to the mixture. The resulting 1H), 2.33-2.11 (m, 2H), 2.11-1.83 (m, 4H), 1.82-1.75 (m, 1H), 1.40-1.26 (m, 1H), 0.96 (d, J=6.5 Hz, 3H). m/z (ESI) 417.2 (M+H)+.

Examples 180 and 181

Synthesis of 1-((1R,4r)-4-((R)-5,5-dimethyl-2-oxo-4-phenyloxazolidin-3-yl)cyclohexyl)-1H-indazole-5-carbonitrile and 1-((1S,4r)-4-((S)-5,5-dimethyl-2-oxo-4-phenyloxazolidin-3-yl)cyclohexyl)-1H-indazole-5-carbonitrile

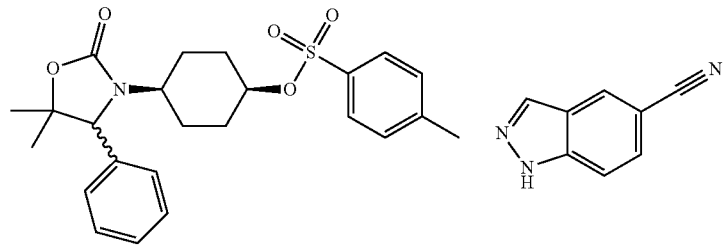

(2:1 S:R enantiomer)
See Ex. 49 for preparation

Cs2CO3, DMF
60° C.

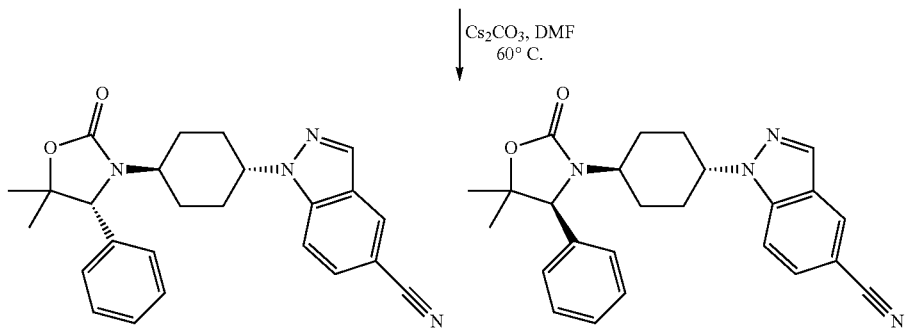

Example 180                    Example 181 mixture was transferred to a separatory funnel and extracted 2× with EtOAc. The combined organics were dried with Na2SO4, filtered, and dried under reduced pressure providing (136 mg) of a yellow solid. To the mixture was added MeOH (5 mL) and K2CO3 (690 mg) (1M). The mixture was shaken at 90° C. for 90 mins and LC-MS indicated cleavage of acyl group. The solvent was decanted and dried under reduced pressure. The material thus obtained was triturated with MeOH and the solid was collected with vacuum filtration. The filtrate contained product as a mixture of diastereomers and was obtained as a white film (48 mg). m/z (ESI) 417.2 (M+H)+.

Isomer Separation: Column: ChiralPak AD-H (2×15 cm); 20% MeOH (0.1% DEA)/CO2, 100 bar, 70 mL/min, 220 nm. Injection Volume: 0.6 mL, 4 mg/mL EtOH. These conditions provided isolation of the two major species which had identical NMR spectra, indicating that they were enantiomers. Example 178 was assigned as the first eluting peak and Example 179 was assigned as the second. ROESY experiments indicated that these compounds were cis isomers. The absolute stereochemistries were arbitrarily assigned. 1H NMR (400 MHz, CDCl3) δ=9.13 (br. s., 1H), 7.47-7.39 (m, 5H), 7.34 (d, J=1.3 Hz, 1H), 7.25-7.16 (m, 2H), 4.93-4.83 (m, 1H), 4.74 (d, J=7.9 Hz, 1H), 4.20-4.09 (m, 1H), 3.80-3.68 (m, To a vial charged with (1s,4s)-4-(5,5-dimethyl-2-oxo-4-phenyloxazolidin-3-yl)cyclohexyl 4-methylbenzenesulfonate (0.350 g, 0.789 mmol) were added DMF (3.16 mL), cesium carbonate (0.257 g, 0.789 mmol) and 1H-indazole-5-carbonitrile (ArkPharm) (0.113 g, 0.789 mmol). The resulting mixture was shaken at room temperature for 2 hrs and then was heated at 60° C. for 72 hr. The material thus obtained was dried under reduced pressure and purified with a 25 g HP spherical silica column (15 μm spherical, Interchim) (two rounds of chromatography) ramping DCM:MeOH (90:10) in DCM (0-20%) providing the product (55 mg) as an oil with minor aliphatic impurities. The product was submitted for chiral separation yielding 11 mg of the minor (R) first eluting enantiomer (Example 180) and 24 mg of the major (S), second eluting enantiomer (Example 181). Chiral separation conditions: ChiralPak IC (4.6×100 mm), 35% MeOH w/0.2% DEA, CO2, 5 mL/min, 100 bar, sample dissolved in 20 mL, 1:1 DCM:MeOH, inj. vol.: 1.0 mL, 6.8 min process time. 1H NMR (400 MHz, DMSO-d6) δ=8.62 (d, J=0.8 Hz, 1H), 8.38 (dd, J=0.9, 1.5 Hz, 1H), 7.74 (td, J=0.8, 9.0 Hz, 1H), 7.48-7.40 (m, 3H), 7.40-7.15 (m, 3H), 4.67 (s, 1H), 4.51-4.39 (m, 1H), 3.63-3.52 (m, 1H), 2.16 (d, J=2.4 Hz, 1H), 2.08-1.82 (m, 5H), 1.75-1.66 (m, 1H), 1.49 (s, 3H), 1.36 (dq, J=3.7, 12.8 Hz, 1H), 0.81 (s, 3H). m/z (ESI) 415.2 (M+H)+.

Example 182

Synthesis of 2-bromo-N-((1S,4r)-4-((S)-5,5-dimethyl-2-oxo-4-phenyloxazolidin-3-yl)cyclohexyl)thiazole-4-carboxamide

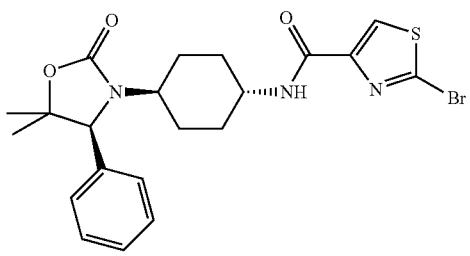 [SMILES: CC1(C)OC(=O)N([C@H]2CC[C@H](NC(=O)c3csc(Br)n3)CC2)[C@H]1c1ccccc1]

Exampled 182 was prepared from Intermediate E according to the procedure of Example 25 using 2-bromo-4-thiazolecarboxylic acid (Combi-blocks) providing the product as a white solid, 2-bromo-N-((1S,4r)-4-((S)-5,5-dimethyl-2-oxo-4-phenyloxazolidin-3-yl)cyclohexyl)thiazole-4-carboxamide (1.098 g, 2.295 mmol, 66.2% yield). $^1$H NMR (400 MHz, DMSO-$d_6$) δ=8.25-8.17 (m, 2H), 7.46-7.38 (m, 2H), 7.38-7.10 (m, 3H), 4.63 (s, 1H), 3.64-3.53 (m, 1H), 3.47-3.36 (m, 1H), 1.84-1.74 (m, 3H), 1.61 (d, J=11.3 Hz, 1H), 1.53-1.43 (m, 5H), 1.38 (d, J=12.5 Hz, 1H), 1.15-1.02 (m, 1H), 0.79 (s, 3H). m/z (ESI) 478.4/480.4 (M+H)$^+$.

Example 183

Synthesis of N-((1S,4r)-4-((S)-5,5-dimethyl-2-oxo-4-phenyloxazolidin-3-yl)cyclohexyl)-2-(pyrimidin-2-yl)thiazole-4-carboxamide

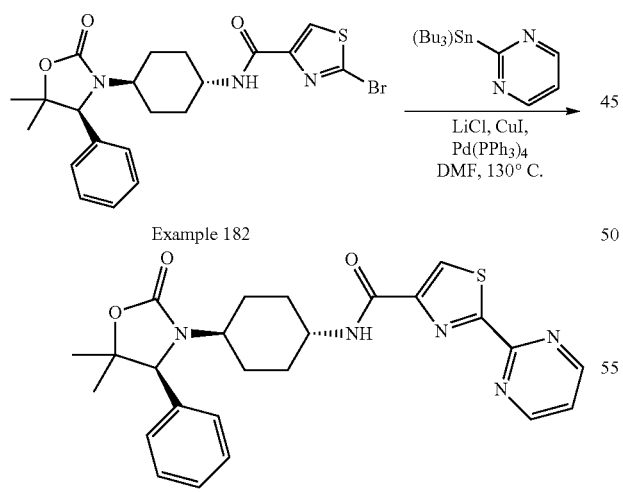

To a vial charged with 2-bromo-N-((1 S,4r)-4-((S)-5,5-dimethyl-2-oxo-4-phenyloxazolidin-3-yl)cyclohexyl)thiazole-4-carboxamide (0.05 g, 0.105 mmol) were added lithium chloride (8.86 mg, 0.209 mmol), copper(I) iodide (1.990 mg, 10.45 μmol), and DMF (0.348 mL) respectively. The mixture was purged with argon prior to the addition of 2-(tributylstannyl)pyrimidine (Frontier Scientific) (0.058 mL, 0.157 mmol). The vessel was sealed and shaken overnight at 130° C. The mixture was dried under reduced pressure and purified with a 25 g HP spherical silica column ramping DCM:MeOH (90:10) in DCM (0-100%) to provide the product which had coeluted with a minor impurity. The material was dissolved in MeOH and purified with RP-HPLC ramping ACN in H$_2$O (15-85%, 0.1% TFA throughout) yielding separation of impurities. The product containing eluents were dried under reduced pressure, free-based with a 2 g SCX-2 column by washing with MeOH, then 2M NH$_3$ in MeOH. The basic wash was dried under reduced pressure to provide a film which was lyophilized from MeOH/H$_2$O affording product (7 mg, 14%) as a white solid. $^1$H NMR (500 MHz, DMSO-$d_6$) δ=8.97 (d, J=4.9 Hz, 2H), 8.45 (s, 1H), 8.06 (d, J=8.5 Hz, 1H), 7.62 (t, J=4.9 Hz, 1H), 7.46-7.39 (m, 2H), 7.39-7.13 (m, 3H), 4.65 (s, 1H), 3.65 (d, J=8.5 Hz, 1H), 3.46 (s, 1H), 1.83 (d, J=9.5 Hz, 3H), 1.67 (br. s., 1H), 1.61-1.50 (m, 2H), 1.49-1.40 (m, 4H), 1.13 (d, J=9.2 Hz, 1H), 0.80 (s, 3H). m/z (ESI) 478.4 (M+H)$^+$.

Example 184

Synthesis of N-((1S,4r)-4-((S)-5,5-dimethyl-2-oxo-4-phenyloxazolidin-3-yl)cyclohexyl)-2-(pyrimidin-5-yl)thiazole-4-carboxamide

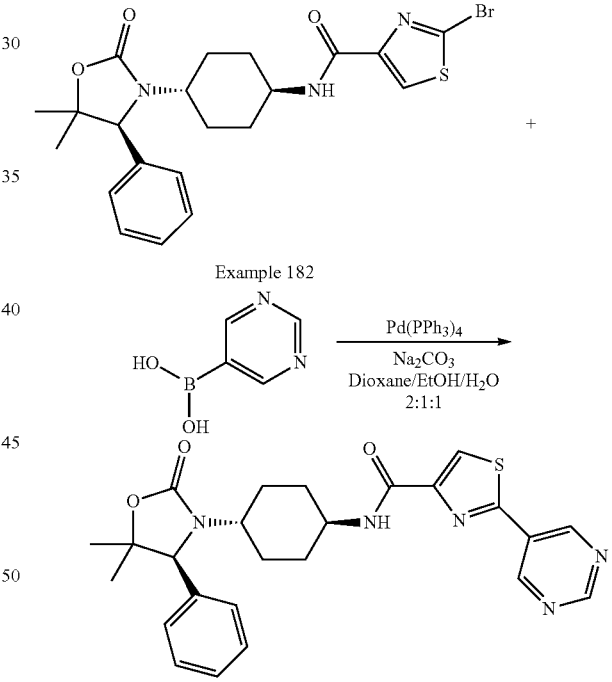

To a vial charged with 5-(4,4,5,5-tetramethyl-1,3,2-dioxaborolan-2-yl)pyrimidine (0.031 g, 0.25 mmol) was added 2-bromo-N-((1S,4r)-4-((S)-5,5-dimethyl-2-oxo-4-phenyloxazolidin-3-yl)cyclohexyl)thiazole-4-carboxamide (0.092 g, 0.192 mmol), sodium carbonate (0.061 g, 0.577 mmol), Pd(Ph$_3$P)$_4$ (0.022 g, 0.019 mmol), 1,4-dioxane (0.385 mL), EtOH (0.192 mL), and H$_2$O (0.192 mL). The vessel was sealed and shaken overnight at 130° C. The mixture was cooled to room temperature and filtered through a frit and the filtrate dried under reduced pressure. The material thus obtained was purified with reverse phase HPLC ramping CH$_3$CN in H$_2$O (0.1% NH$_4$OH modifier) to provide the final product (56 mg, 61%). $^1$H NMR (500 MHz, DMSO-d$_6$) δ ppm=9.29 (s, 1H), 8.40 (s, 1H), 8.29 (d, J=8.5 Hz, 1H), 7.47-7.13 (m, 6H), 4.65 (s, 1H), 3.65 (dd, J=3.7, 8.0 Hz, 1H), 3.54-3.41 (m, 1H), 1.94-1.79 (m, 3H), 1.71 (d, J=13.2 Hz, 1H), 1.58-1.44 (m, 5H), 1.44-1.34 (m, 1H), 1.23-1.07 (m, 1H), 0.80 (s, 3H). m/z (ESI) 478.2 (M+H)$^+$.

Example 185

Synthesis of N-((1S,4r)-4-((S)-5,5-dimethyl-2-oxo-4-phenyloxazolidin-3-yl)cyclohexyl)-[2,4'-bithiazole]-4-carboxamide

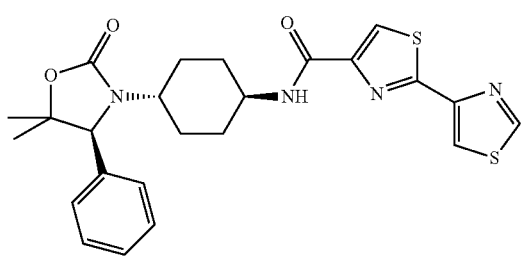 [SMILES: CC1(C)OC(=O)N([C@H]2CC[C@H](NC(=O)c3csc(-c4cscn4)n3)CC2)[C@H]1c1ccccc1]

Example 185 was prepared according to the protocol described for Example 183 using 4-(4,4,5,5-tetramethyl-1,3,2-dioxaborolan-2-yl)-1,3-thiazole affording N-((1 S,4r)-4-((S)-5,5-dimethyl-2-oxo-4-phenyloxazolidin-3-yl)cyclohexyl)-[2,4'-bithiazole]-4-carboxamide (18 mg, 19%). $^1$H NMR (500 MHz, DMSO-d$_6$) δ ppm 0.80 (s, 3H) 1.08-1.24 (m, 1H) 1.34-1.45 (m, 1H) 1.47 (s, 3H) 1.49-1.57 (m, 2H) 1.68-1.75 (m, 1H) 1.78-1.91 (m, 3H) 3.43-3.53 (m, 1H) 3.58-3.67 (m, 1H) 4.65 (s, 1H) 7.22 (br. s., 1H) 7.28-7.44 (m, 4H) 8.07 (d, J=8.31 Hz, 1H) 8.25 (s, 1H) 8.37 (d, J=1.89 Hz, 1H) 9.25 (d, J=1.95 Hz, 1H). m/z (ESI) 482.1 (M+H)$^+$.

Example 186

Synthesis of N-((1S,4r)-4-((S)-5,5-dimethyl-2-oxo-4-phenyloxazolidin-3-yl)cyclohexyl)-2-(6-fluoropyridin-3-yl)thiazole-4-carboxamide

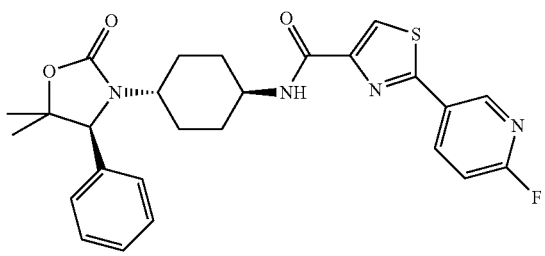 [SMILES: CC1(C)OC(=O)N([C@H]2CC[C@H](NC(=O)c3csc(-c4ccc(F)nc4)n3)CC2)[C@H]1c1ccccc1]

Example 186 was prepared according to the protocol described for Example 184 using (6-fluoropyridin-3-yl)boronic acid affording N-((1 S,4r)-4-((S)-5,5-dimethyl-2-oxo-4-phenyloxazolidin-3-yl)cyclohexyl)-2-(6-fluoropyridin-3-yl)thiazole-4-carboxamide (64 mg, 67%). $^1$H NMR (500 MHz, DMSO-d$_6$) δ ppm 0.80 (s, 3H) 1.09-1.23 (m, 1H) 1.35-1.56 (m, 6H) 1.70 (d, J=12.26 Hz, 1H) 1.84 (d, J=8.36 Hz, 2H) 1.89 (br. s., 1H) 3.39-3.52 (m, 1H) 3.57-3.69 (m, 1H) 4.65 (s, 1H) 7.21 (br. s., 1H) 7.27-7.44 (m, 5H) 8.15-8.27 (m, 1H) 8.30-8.34 (m, 1H) 8.61 (td, J=8.08, 2.46 Hz, 1H) 8.95 (d, J=2.29 Hz, 1H). m/z (ESI) 495.2 (M+H)$^+$.

Example 187

Synthesis of N-((1S,4r)-4-((S)-5,5-dimethyl-2-oxo-4-phenyloxazolidin-3-yl)cyclohexyl)-2-(1H-pyrazol-5-yl)thiazole-4-carboxamide

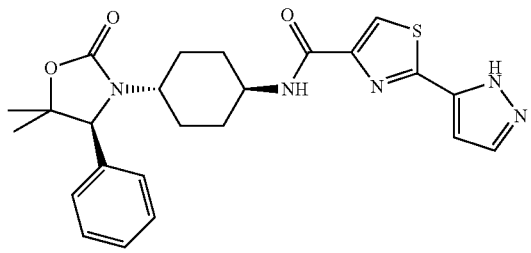 [SMILES: CC1(C)OC(=O)N([C@H]2CC[C@H](NC(=O)c3csc(-c4ccn[nH]4)n3)CC2)[C@H]1c1ccccc1]

Example 187 was prepared according to the protocol described for Example 184 using 1H-pyrazole-5-boronic acid affording N-((1 S,4r)-4-((S)-5,5-dimethyl-2-oxo-4-phenyloxazolidin-3-yl)cyclohexyl)-2-(1H-pyrazol-5-yl)thiazole-4-carboxamide (34 mg, 38%). $^1$H NMR (500 MHz, DMSO-d$_6$) δ ppm=8.13 (s, 1H), 7.98 (d, J=8.6 Hz, 1H), 7.88 (d, J=2.2 Hz, 1H), 7.47-7.09 (m, 5H), 6.82 (d, J=2.3 Hz, 1H), 4.68-4.59 (m, 1H), 3.68-3.57 (m, 1H), 3.52-3.45 (m, 1H), 1.92-1.75 (m, 3H), 1.69 (d, J=12.1 Hz, 1H), 1.57-1.30 (m, 6H), 1.19-1.05 (m, 1H), 0.80 (s, 3H). m/z (ESI) 466.2 (M+H)$^+$.

Example 188

Synthesis of N-((1S,4r)-4-((S)-5,5-dimethyl-2-oxo-4-phenyloxazolidin-3-yl)cyclohexyl)-2-(5-fluoropyridin-3-yl)thiazole-4-carboxamide

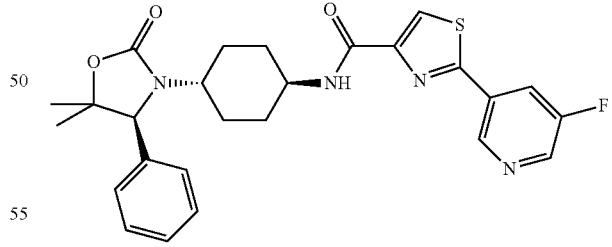

Example 188 was prepared according to the protocol described for Example 184 using 3-fluoropyridine-5-boronic acid pinacol ester affording N-((1S,4r)-4-((S)-5,5-dimethyl-2-oxo-4-phenyloxazolidin-3-yl)cyclohexyl)-2-(5-fluoropyridin-3-yl)thiazole-4-carboxamide (59 mg, 62%). $^1$H NMR (500 MHz, DMSO-d$_6$) δ ppm=0.80 (s, 3H) 1.14 (qd, J=12.65, 3.24 Hz, 1H) 1.34-1.56 (m, 6H) 1.71 (d, J=12.31 Hz, 1H) 1.78-1.91 (m, 3H) 3.39-3.51 (m, 1H) 3.60-3.69 (m, 1H). 4.65 (s, 1H) 7.21 (br. s., 1H) 7.28-7.46 (m, 4H) 8.28 (d, J=8.48 Hz, 1H) 8.37 (s, 1H) 8.39-8.47 (m, 1H) 8.72 (d, J=2.63 Hz, 1H) 9.14 (s, 1H). m/z (ESI) 495.2 (M+H)+.

Example 189

Synthesis of N-((1S,4r)-4-((S)-5,5-dimethyl-2-oxo-4-phenyloxazolidin-3-yl)cyclohexyl)-2-(1-methyl-1H-pyrazol-4-yl)thiazole-4-carboxamide

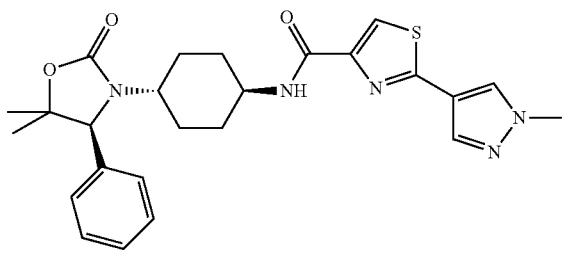

Example 189 was prepared according to the protocol described for Example 184 using 1-methyl-1H-pyrazole-4-boronic acid pinacol ester to afford N-((1 S,4r)-4-((S)-5,5-dimethyl-2-oxo-4-phenyloxazolidin-3-yl)cyclohexyl)-2-(1-methyl-1H-pyrazol-4-yl)thiazole-4-carboxamide (71 mg, 77%). $^1$H NMR (500 MHz, DMSO-d$_6$) δ ppm=8.35 (s, 1H), 8.06 (s, 1H), 7.98-7.89 (m, 2H), 7.48-7.39 (m, 2H), 7.38-7.13 (m, 3H), 4.64 (s, 1H), 3.89 (s, 3H), 3.66-3.55 (m, 1H), 3.52-3.42 (m, 1H), 1.91-1.77 (m, 3H), 1.69 (d, J=12.0 Hz, 1H), 1.56-1.48 (m, 2H), 1.46 (s, 3H), 1.42-1.32 (m, 1H), 1.17-1.06 (m, 1H), 0.80 (s, 3H). m/z (ESI) 480.2 (M+H)+.

Example 190

Synthesis of N-((1S,4r)-4-((S)-5,5-dimethyl-2-oxo-4-phenyloxazolidin-3-yl)cyclohexyl)-2-(pyridin-3-yl)thiazole-4-carboxamide

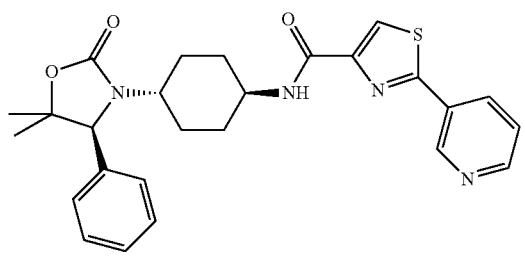

Example 190 was prepared according to the protocol described for Example 184 using pyridin-3-yl-boranediol affording N-((1 S,4r)-4-((S)-5,5-dimethyl-2-oxo-4-phenyloxazolidin-3-yl)cyclohexyl)-2-(pyridin-3-yl)thiazole-4-carboxamide (43 mg, 47%). $^1$H NMR (500 MHz, DMSO-d$_6$) δ ppm=0.80 (s, 3H) 1.09-1.19 (m, 1H) 1.35-1.45 (m, 1H) 1.45-1.59 (m, 5H) 1.70 (d, J=12.43 Hz, 1H) 1.75-1.93 (m, 3H) 3.39-3.52 (m, 1H) 3.55-3.69 (m, 1H) 4.65 (s, 1H) 7.21 (br. s., 1H) 7.28-7.45 (m, 4H) 7.56 (dd, J=7.93, 4.78 Hz, 1H) 8.24 (d, J=8.59 Hz, 1H) 8.33 (s, 1H) 8.40 (dt, J=7.96, 1.89 Hz, 1H) 8.69 (dd, J=4.78, 1.46 Hz, 1H) 9.27 (d, J=1.72 Hz, 1H). m/z (ESI) 477.2 (M+H)+.

The following table provides the name and structure of the Example compounds.

TABLE 1

| | Names and Structures of Example Compounds | |
|---|---|---|
| Example | Name | Structure |
| 1 | (S)-4-(5,5-dimethyl-2-oxo-4-phenyloxazolidin-3-yl)-N-(1,5-naphthyridin-4-yl)benzamide | |
| 2 | (S)-4-(4-(4-fluorophenyl)-5,5-dimethyl-2-oxooxazolidin-3-yl)-N-(quinolin-8-yl)benzamide | |

TABLE 1-continued

Names and Structures of Example Compounds

| Example | Name | Structure |
|---|---|---|
| 3 | (S)-3-(4-(2-fluoro-5-(pyrimidin-2-yl)pyridin-3-yl)phenyl)-5,5-dimethyl-4-phenyloxazolidin-2-one | 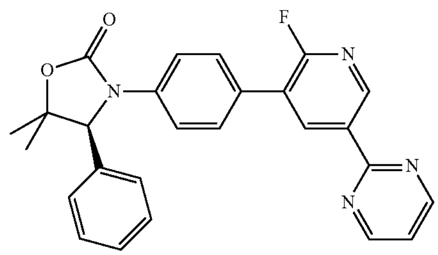 |
| 4 | (S)-5,5-dimethyl-3-(4-(2-oxo-5-(pyrimidin-2-yl)-1,2-dihydropyridin-3-yl)phenyl)-4-phenyloxazolidin-2-one | 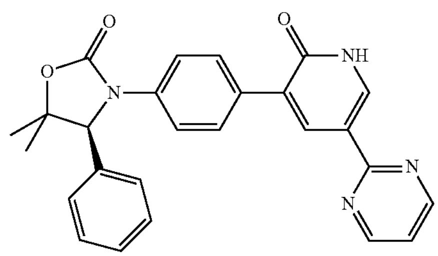 [SMILES: CC1(C)OC(=O)N(c2ccc(-c3cc(-c4ncccn4)c[nH]c3=O)cc2)[C@H]1c1ccccc1] |
| 5 | (S)-5,5-dimethyl-3-((S)-4-(2-oxo-5-(pyrimidin-2-yl)-1,2-dihydropyridin-3-yl)cyclohex-3-en-1-yl)-4-phenyloxazolidin-2-one<br>or<br>(S)-5,5-dimethyl-3-((R)-4-(2-oxo-5-(pyrimidin-2-yl)-1,2-dihydropyridin-3-yl)cyclohex-3-en-1-yl)-4-phenyloxazolidin-2-one | |
| 6 | The isomer of 5 | The isomer of 5 |
| 7 | (+/−)-3-(trans-4-((4S/R)-5,5-dimethyl-2-oxo-4-phenyl-1,3-oxazolidin-3-yl)cyclohexyl)-5-(2-pyrimidinyl)-2(1H)-pyridinone | 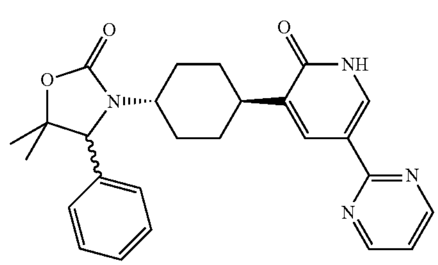 [SMILES: CC1(C)OC(=O)N([C@H]2CC[C@H](c3cc(-c4ncccn4)c[nH]c3=O)CC2)C1c1ccccc1] |

TABLE 1-continued

Names and Structures of Example Compounds

| Example | Name |
|---|---|
| 8 | (+/−)-3-(cis-4-((4S/R)-5,5-dimethyl-2-oxo-4-phenyl-1,3-oxazolidin-3-yl)cyclohexyl)-5-(2-pyrimidinyl)-2(1H)-pyridinone |
| 9 | (+/−)-(R/S)-4-(5,5-dimethyl-2-oxo-4-(pyridin-3-yl)oxazolidin-3-yl)-N-(quinolin-8-yl)benzamide |
| 10 | (R)-4-(5,5-dimethyl-2-oxo-4-(pyridin-3-yl)oxazolidin-3-yl)-N-(quinolin-8-yl)benzamide |
| 11 | (S)-4-(5,5-dimethyl-2-oxo-4-(pyridin-3-yl)oxazolidin-3-yl)-N-(quinolin-8-yl)benzamide |
| 12 | (S)-3-(4-(5-([1,2,4]triazolo[4,3-b]pyridazin-6-yl)-6-aminopyridin-3-yl)phenyl)-5,5-dimethyl-4-phenyloxazolidin-2-one |

TABLE 1-continued

Names and Structures of Example Compounds

| Example | Name | Structure |
|---|---|---|
| 13 | (S)-3-((1r,4S)-4-(6-amino-5-(pyrimidin-2-ylamino)pyridin-3-yl)cyclohexyl)-5,5-dimethyl-4-phenyloxazolidin-2-one | 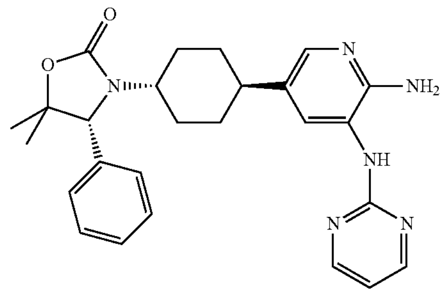 [SMILES: CC1(C)OC(=O)N([C@H]2CC[C@H](c3cnc(N)c(Nc4ncccn4)c3)CC2)[C@@H]1c1ccccc1] |
| 14 | (R)-5,5-dimethyl-3-((1r,4R)-4-(2-oxo-1-(pyrimidin-2-yl)-2,3-dihydro-1H-imidazo[4,5-b]pyridin-6-yl)cyclohexyl)-4-phenyloxazolidin-2-one | 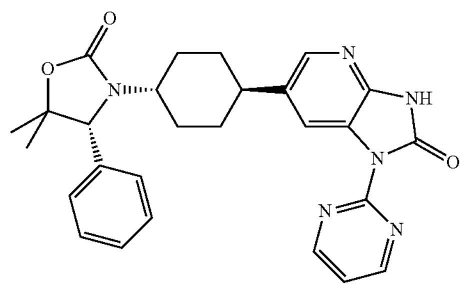 [SMILES: CC1(C)OC(=O)N([C@H]2CC[C@H](c3cnc4[nH]c(=O)n(-c5ncccn5)c4c3)CC2)[C@@H]1c1ccccc1] |
| 15 | (S)-5,5-dimethyl-3-(4-(2-oxo-1H-imidazo[4,5-c]pyridin-3(2H)-yl)phenyl)-4-phenyloxazolidin-2-one or (S)-5,5-dimethyl-3-(4-(2-oxo-2,3-dihydro-1H-imidazo[4,5-c]pyridin-1-yl)phenyl)-4-phenyloxazolidin-2-one | or |
| 16 | The isomer of 15 | The isomer of 15 |
| 17 | (S)-3-(4-(5,5-dimethyl-2-oxo-4-phenyloxazolidin-3-yl)phenyl)benzo[d]oxazol-2(3H)-one | 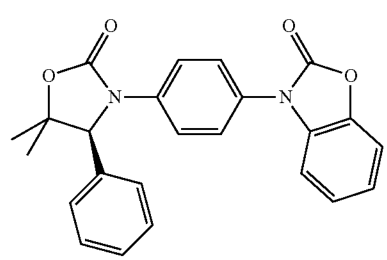 |

TABLE 1-continued

Names and Structures of Example Compounds

| Example | Name | Structure |
|---|---|---|
| 18 | (S)-5,5-dimethyl-3-(4-(2-oxoindolin-1-yl)phenyl)-4-phenyloxazolidin-2-one | 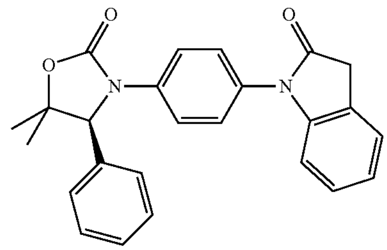 |
| 19 | (S)-5,5-dimethyl-3-(4-(2-oxo-2,3-dihydro-1H-benzo[d]imidazol-1-yl)phenyl)-4-phenyloxazolidin-2-one | 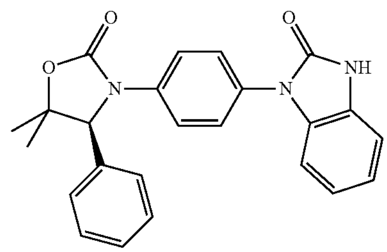 [SMILES: CC1(C)OC(=O)N(c2ccc(-n3c(=O)oc4ccccc43)cc2)[C@H]1c1ccccc1] |
| 20 | (S)-4-(5,5-dimethyl-2-oxo-4-phenyloxazolidin-3-yl)-N-(1,7-naphthyridin-8-yl)benzamide | 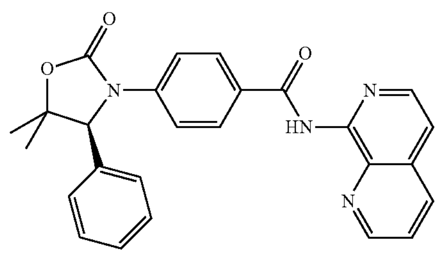 [SMILES: CC1(C)OC(=O)N(c2ccc(C(=O)Nc3nccc4cccnc34)cc2)[C@H]1c1ccccc1] |
| 21 | (S)-4-(5,5-dimethyl-2-oxo-4-phenyloxazolidin-3-yl)-N-(4-hydroxypyridin-3-yl)benzamide | 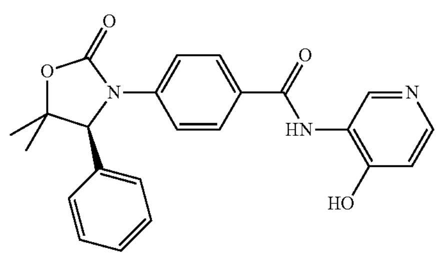 [SMILES: CC1(C)OC(=O)N(c2ccc(C(=O)Nc3cnccc3O)cc2)[C@H]1c1ccccc1] |
| 22 | (S)-5,5-dimethyl-3-(6-(2-oxo-2,3-dihydro-1H-yl)pyridin-3-yl)-4-benzo[d]imidazol-1-phenyloxazolidin-2-one | 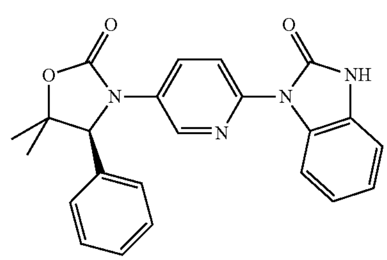 [SMILES: CC1(C)OC(=O)N(c2ccc(-n3c(=O)[nH]c4ccccc43)nc2)[C@H]1c1ccccc1] |
| 23 | (S)-5,5-dimethyl-3-((1r,4S)-4-(2-oxo-2,3-dihydro-1H-imidazo[4,5-c]pyridin-1-yl)cyclohexyl)-4-phenyloxazolidin-2-one | 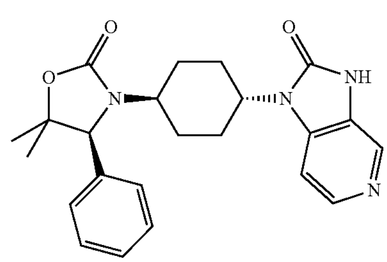 |

TABLE 1-continued

Names and Structures of Example Compounds

| Example | Name |
|---|---|
| 24 | (R)-5,5-dimethyl-3-((1r,4R)-4-(2-oxo-2,3-dihydro-1H-imidazo[4,5-c]pyridin-1-yl)cyclohexyl)-4-phenyloxazolidin-2-one |
| 25 | N-((1S,4r)-4-((S)-5,5-dimethyl-2-oxo-4-phenyloxazolidin-3-yl)cyclohexyl)-1,5-naphthyridine-4-carboxamide |
| 26 | N-((1S,4r)-4-((S)-5,5-dimethyl-2-oxo-4-phenyloxazolidin-3-yl)cyclohexyl)quinoline-8-carboxamide |
| 27 | (R + S) N-((1S,4r)-4-((S)-5,5-dimethyl-2-oxo-4-phenyloxazolidin-3-yl)cyclohexyl)quinoline-8-carboxamide |

~3:1 S:R

TABLE 1-continued

Names and Structures of Example Compounds

| Example | Name |
|---|---|
| 28 | N-((1R,4r)-4-((R)-5,5-dimethyl-2-oxo-4-phenyloxazolidin-3-yl)cyclohexyl)quinoline-8-carboxamide |
| 29 | (S)-3-((1r,4S)-4-(5-chloro-2-oxo-2,3-dihydro-1H-benzo[d]imidazol-1-yl)cyclohexyl)-5,5-dimethyl-4-phenyloxazolidin-2-one |
| 30 | (S)-5,5-dimethyl-3-((1r,4S)-4-(2-oxo-2,3-dihydro-1H-imidazo[4,5-b]pyridin-1-yl)cyclohexyl)-4-phenyloxazolidin-2-one |
| 31 | (R)-5,5-dimethyl-3-((1r,4R)-4-(2-oxo-2,3-dihydro-1H-imidazo[4,5-b]pyridin-1-yl)cyclohexyl)-4-phenyloxazolidin-2-one |
| 32 | (1S,4r)-4-((S)-5,5-dimethyl-2-oxo-4-phenyloxazolidin-3-yl)-N-(quinolin-8-yl)cyclohexanecarboxamide |
| 33 | (1R,4s)-4-((S)-5,5-dimethyl-2-oxo-4-phenyloxazolidin-3-yl)-N-(quinolin-8-yl)cyclohexanecarboxamide |

TABLE 1-continued

Names and Structures of Example Compounds

| Example | Name | Structure |
|---|---|---|
| 34 | (R + S) 5-methyl-3-((1r,4r)-4-(2-oxo-2,3-dihydro-1H-benzo[d]imidazol-1-yl)cyclohexyl)-5-phenyloxazolidin-2-one | 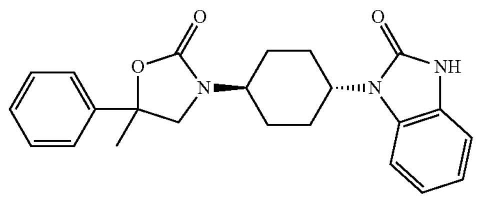 [SMILES: CC1(c2ccccc2)CN([C@H]2CC[C@H](n3c(=O)[nH]c4ccccc43)CC2)C(=O)O1] |
| 35 | (R + S) 5,5-dimethyl-3-((1r,4r)-4-(2-oxo-2,3-dihydro-1H-benzo[d]imidazol-1-yl)cyclohexyl)-4-phenyloxazolidin-2-one | 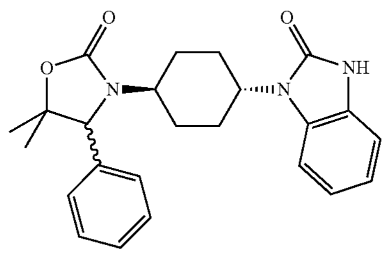 [SMILES: CC1(C)OC(=O)N([C@H]2CC[C@H](n3c(=O)[nH]c4ccccc43)CC2)C1c1ccccc1] |
| 36 | (R + S) 5,5-dimethyl-3-((1r,4r)-4-(2-oxo-1H-imidazo[4,5-b]pyridin-3(2H)-yl)cyclohexyl)-4-phenyloxazolidin-2-one | 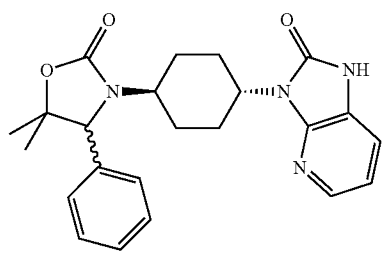 |
| 37 | (S)-5,5-dimethyl-3-((1r,4S)-4-(2-oxo-1H-imidazo[4,5-b]pyridin-3(2H)-yl)cyclohexyl)-4-phenyloxazolidin-2-one | 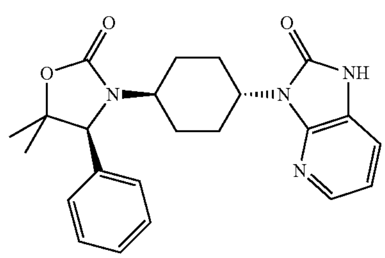 |
| 38 | (R)-5,5-dimethyl-3-((1r,4R)-4-(2-oxo-1H-imidazo[4,5-b]pyridin-3(2H)-yl)cyclohexyl)-4-phenyloxazolidin-2-one | 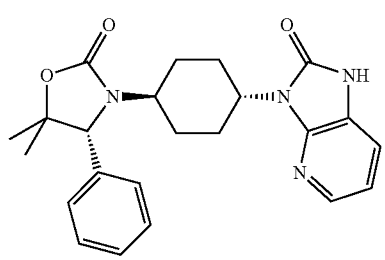 [SMILES: CC1(C)OC(=O)N([C@H]2CC[C@H](n3c(=O)[nH]c4cccnc43)CC2)[C@@H]1c1ccccc1] |
| 39 | (S)-3-((1r,4S)-4-(3-(2,2-difluoroethyl)-2-oxo-2,3-dihydro-1H-imidazo[4,5-c]pyridin-1-yl)cyclohexyl)-5,5-dimethyl-4-phenyloxazolidin-2-one | 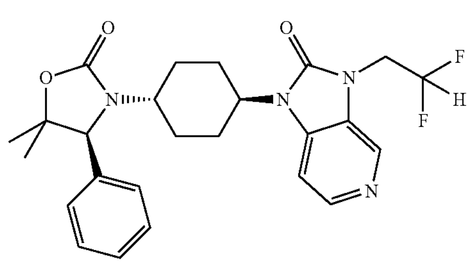 [SMILES: CC1(C)OC(=O)N([C@H]2CC[C@H](n3c(=O)n(CC(F)F)c4cnccc43)CC2)[C@H]1c1ccccc1] |

TABLE 1-continued

Names and Structures of Example Compounds

| Example | Name | Structure |
|---|---|---|
| 40 | (S)-5,5-dimethyl-4-phenyl-3-(4-(5-(pyridin-2-yl)pyridazin-3-yl)phenyl)oxazolidin-2-one | 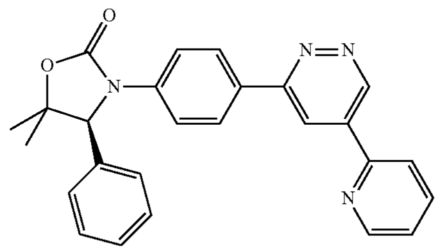 [SMILES: CC1(C)OC(=O)N(c2ccc(-c3cc(-c4ccccn4)cnn3)cc2)[C@H]1c1ccccc1] |
| 41 | (S)-4-(5,5-dimethyl-2-oxo-4-(o-tolyl)oxazolidin-3-yl)-N-(quinolin-8-yl)benzamide | 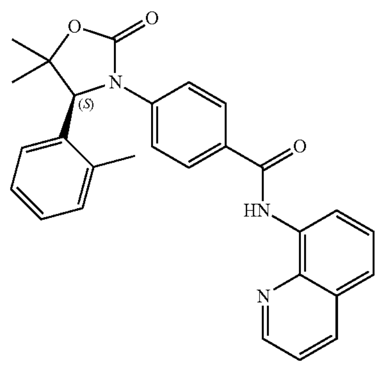 |
| 42 | (R + S) 4-(4-(2-fluorophenyl)-5,5-dimethyl-2-oxooxazolidin-3-yl)-N-(quinolin-8-yl)benzamide | 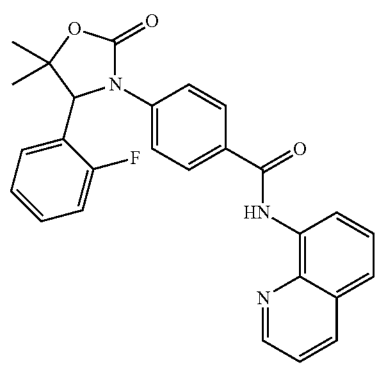 [SMILES: CC1(C)OC(=O)N(c2ccc(C(=O)Nc3cccc4cccnc34)cc2)C1c1ccccc1F] |
| 43 | (S)-4-(5,5-diethyl-2-oxo-4-phenyloxazolidin-3-yl)-N-(quinolin-8-yl)benzamide | 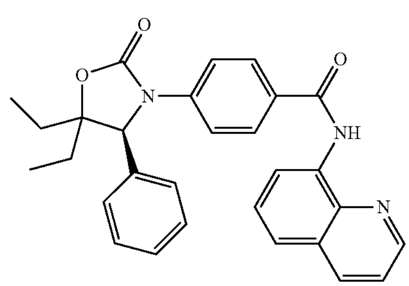 [SMILES: CCC1(CC)OC(=O)N(c2ccc(C(=O)Nc3cccc4cccnc34)cc2)[C@H]1c1ccccc1] |
| 44 | (R + S) 4-(6-oxo-8-phenyl-5-oxa-7-azaspiro[3.4]octan-7-yl)-N-(quinolin-8-yl)benzamide | 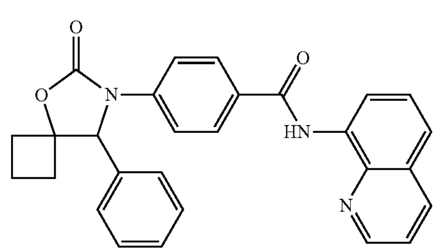 [SMILES: O=C(Nc1cccc2cccnc12)c1ccc(N2C(=O)OC3(CCC3)C2c2ccccc2)cc1] |

TABLE 1-continued

Names and Structures of Example Compounds

| Example | Name |
|---------|------|
| 45 | (R + S) 4-(2-oxo-4-phenyl-1-oxa-3-azaspiro[4.4]nonan-3-yl)-N-(quinolin-8-yl)benzamide |
| 46 | (R + S) 4-(2-oxo-4-phenyl-1-oxa-3-azaspiro[4.5]decan-3-yl)-N-(quinolin-8-yl)benzamide |
| 47 | 1-((1S,4r)-4-((S)-5,5-dimethyl-2-oxo-4-phenyloxazolidin-3-yl)cyclohexyl)-2-oxo-2,3-dihydro-1H-benzo[d]imidazole-5-carbonitrile |
| 48 | (S)-3-((1s,4R)-4-(3,3-difluoro-2-oxoindolin-1-yl)cyclohexyl)-5,5-dimethyl-4-phenyloxazolidin-2-one |
| 49 | '3-(trans-4-((4S)-5,5-dimethyl-2-oxo-4-phenyl-1,3-oxazolidin-3-yl)cyclohexyl)[1,3]oxazolo[4,5-b]pyridin-2(3H)-one |
| 50 | (S)-5,5-dimethyl-3-((1r,4S)-4-(8-oxo-7H-purin-9(8H)-yl)cyclohexyl)-4-phenyloxazolidin-2-one |

TABLE 1-continued

Names and Structures of Example Compounds

| Example | Name | Structure |
|---|---|---|
| 51 | 1-((1S,4r)-4-((S)-5,5-dimethyl-2-oxo-4-phenyloxazolidin-3-yl)cyclohexyl)-2-oxo-2,3-dihydro-1H-benzo[d]imidazole-4-carbonitrile | 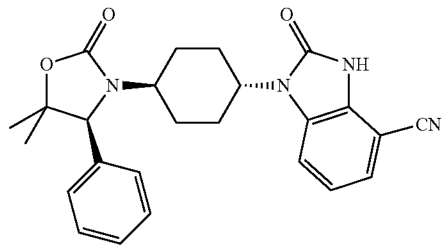 [SMILES: CC1(C)OC(=O)N([C@H]2CC[C@H](n3c(=O)[nH]c4c(C#N)cccc43)CC2)[C@H]1c1ccccc1] |
| 52 | (S)-5,5-dimethyl-3-((1r,4S)-4-(2-oxo-6-(trifluoromethyl)-2,3-dihydro-1H-imidazo[4,5-c]pyridin-1-yl)cyclohexyl)-4-phenyloxazolidin-2-one | 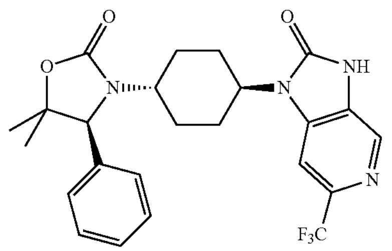 [SMILES: CC1(C)OC(=O)N([C@H]2CC[C@H](n3c(=O)[nH]c4cnc(C#N)cc43)CC2)[C@H]1c1ccccc1] |
| 53 | (S)-3-((1r,4S)-4-(6-chloro-2-oxo-2,3-dihydro-1H-imidazo[4,5-c]pyridin-1-yl)cyclohexyl)-5,5-dimethyl-4-phenyloxazolidin-2-one | 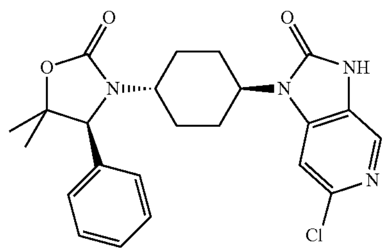 |
| 54 | 1-((1S,4r)-4-((S)-5,5-dimethyl-2-oxo-4-phenyloxazolidin-3-yl)cyclohexyl)-2-oxo-2,3-dihydro-1H-imidazo[4,5-c]pyridine-6-carbonitrile | 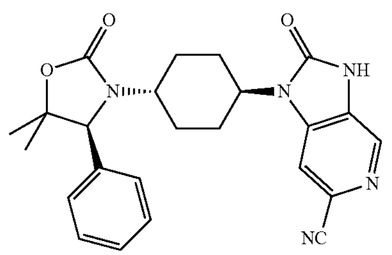 |
| 55 | (S)-4-(4-fluorophenyl)-5,5-dimethyl-3-((1r,4S)-4-(2-oxo-2,3-dihydro-1H-imidazo[4,5-c]pyridin-1-yl)cyclohexyl)oxazolidin-2-one | 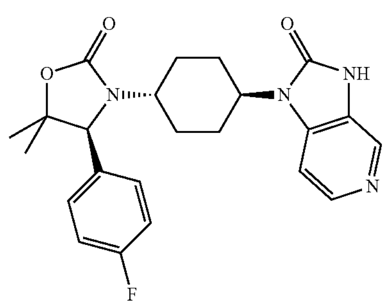 [SMILES: CC1(C)OC(=O)N([C@H]2CC[C@H](n3c(=O)[nH]c4cnccc43)CC2)[C@H]1c1ccc(F)cc1] |
| 56 | (S)-3-((1r,4S)-4-(6-bromo-2-oxo-1H-imidazo[4,5-b]pyridin-3(2H)-yl)cyclohexyl)-5,5-dimethyl-4-phenyloxazolidin-2-one | 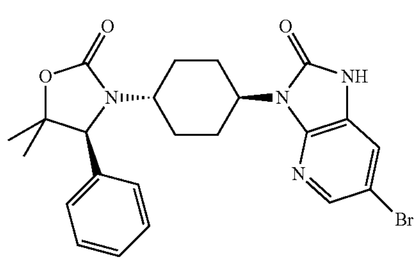 [SMILES: CC1(C)OC(=O)N([C@H]2CC[C@H](n3c(=O)[nH]c4cc(Br)cnc43)CC2)[C@H]1c1ccccc1] |

TABLE 1-continued

Names and Structures of Example Compounds

| Example | Name |
|---|---|
| 57 | 3-((1S,4r)-4-((S)-5,5-dimethyl-2-oxo-4-phenyloxazolidin-3-yl)cyclohexyl)-2-oxo-2,3-dihydro-1H-imidazo[4,5-b]pyridine-6-carbonitrile |
| 58 | N-(trans-4-((4S)-5,5-dimethyl-2-oxo-4-phenyl-1,3-oxazolidin-3-yl)cyclohexyl)-1H-pyrrolo[2,3-b]pyridine-1-carboxamide |
| 59 | N-((1S,4r)-4-((S)-5,5-dimethyl-2-oxo-4-phenyloxazolidin-3-yl)cyclohexyl)-7-fluoro-1,5-naphthyridine-4-carboxamide |
| 60 | 1-((1S,4r)-4-((S)-5,5-dimethyl-2-oxo-4-phenyloxazolidin-3-yl)cyclohexyl)-4-fluoro-2-oxo-2,3-dihydro-1H-benzo[d]imidazole-5-carbonitrile |
| 61 | 1-((1S,4r)-4-((S)-4-(4-fluorophenyl)-5,5-dimethyl-2-oxooxazolidin-3-yl)cyclohexyl)-2-oxo-2,3-dihydro-1H-benzo[d]imidazole-5-carbonitrile |

TABLE 1-continued

Names and Structures of Example Compounds

| Example | Name | Structure |
|---|---|---|
| 62 | 3-((1S,4r)-4-((S)-5,5-dimethyl-2-oxo-4-phenyloxazolidin-3-yl)cyclohexyl)-2-oxo-1,2,3,4-tetrahydroquinazoline-6-carbonitrile | 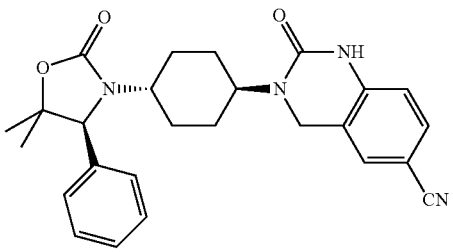 [SMILES: CC1(C)OC(=O)N([C@H]2CC[C@H](N3Cc4cc(C#N)ccc4NC3=O)CC2)[C@H]1c1ccccc1] |
| 63 | (S)-5,5-dimethyl-3-(1-oxo-2-(quinolin-8-yl)-1,2,3,4-tetrahydroisoquinolin-6-yl)-4-phenyloxazolidin-2-one | 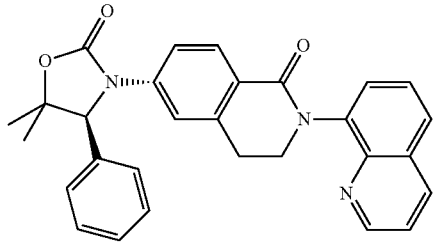 |
| 64 | (S)-3-(4-(6-amino-5-(5-fluoropyrimidin-2-yl)pyridin-3-yl)phenyl)-5,5-dimethyl-4-phenyloxazolidin-2-one | 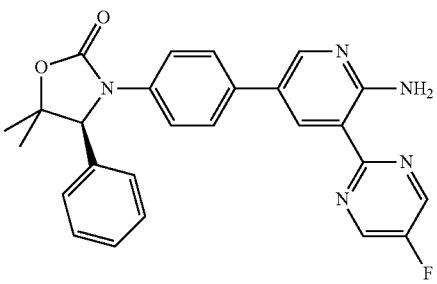 [SMILES: CC1(C)OC(=O)N(c2ccc(-c3cnc(N)c(-c4ncc(F)cn4)c3)cc2)[C@H]1c1ccccc1] |
| 65 | (S)-3-(4-(6-amino-5-(pyrimidin-2-yl)pyridin-3-yl)phenyl)-5,5-dimethyl-4-phenyloxazolidin-2-one | 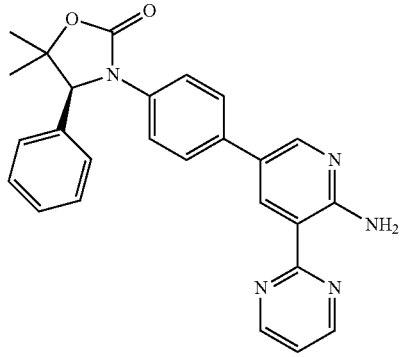 [SMILES: CC1(C)OC(=O)N(c2ccc(-c3cnc(N)c(-c4ncccn4)c3)cc2)[C@H]1c1ccccc1] |
| 66 | (S)-5,5-dimethyl-4-phenyl-3-(4-(7-(pyrimidin-5-yl)-[1,2,4]triazolo[4,3-a]pyridin-3-yl)phenyl)oxazolidin-2-one | 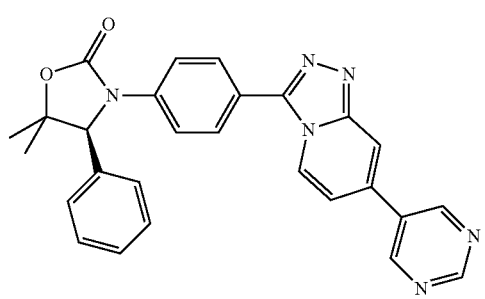 [SMILES: CC1(C)OC(=O)N(c2ccc(-c3nnc4cc(-c5cncnc5)ccn34)cc2)[C@H]1c1ccccc1] |

TABLE 1-continued

Names and Structures of Example Compounds

| Example | Name | Structure |
|---|---|---|
| 67 | (S)-3-(4-(5,5-dimethyl-2-oxo-4-phenyloxazolidin-3-yl)phenyl)-[1,2,4]triazolo[4,3-a]pyridine-7-carbonitrile | 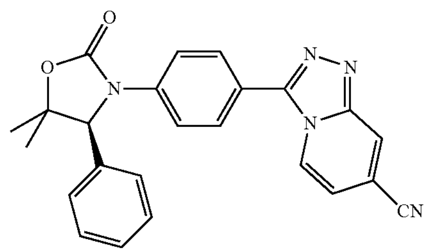 [SMILES: CC1(C)OC(=O)N(c2ccc(-c3nnc4cc(C#N)ccn34)cc2)[C@H]1c1ccccc1] |
| 68 | (S)-3-(4-(6-chloro-[1,2,4]triazolo[4,3-b]pyridazin-3-yl)phenyl)-5,5-dimethyl-4-phenyloxazolidin-2-one | 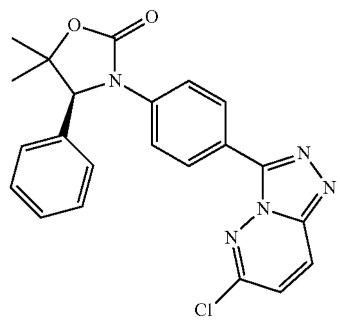 [SMILES: CC1(C)OC(=O)N(c2ccc(-c3nnc4ccc(Cl)nn34)cc2)[C@H]1c1ccccc1] |
| 69 | (S)-3-(4-(1H-benzo[d][1,2,3]triazol-1-yl)phenyl)-5,5-dimethyl-4-phenyloxazolidin-2-one | 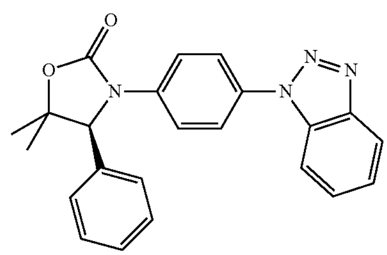 [SMILES: CC1(C)OC(=O)N(c2ccc(-n3nnc4ccccc43)cc2)[C@H]1c1ccccc1] |
| 70 | (S)-3-(4-(2-aminopyrimidin-5-yl)phenyl)-5,5-dimethyl-4-phenyloxazolidin-2-one | 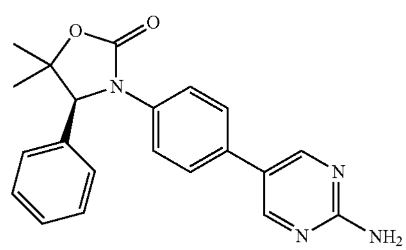 [SMILES: CC1(C)OC(=O)N(c2ccc(-c3cnc(N)nc3)cc2)[C@H]1c1ccccc1] |
| 71 | (S)-3-(3-((1,5-naphthyridin-4-yl)amino)-[1,2,4]triazolo[4,3-a]pyridin-7-yl)-5,5-dimethyl-4-phenyloxazolidin-2-one | 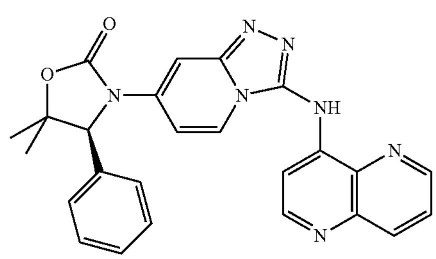 [SMILES: CC1(C)OC(=O)N(c2ccn3c(Nc4ccnc5cccnc45)nnc3c2)[C@H]1c1ccccc1] |

TABLE 1-continued

Names and Structures of Example Compounds

| Example | Name |
|---|---|
| 72 | (+/−)(S)-3-((1s,4R)-4-(6-amino-5-(pyrimidin-2-yl)pyridin-3-yl)cyclohexyl)-5,5-dimethyl-4-phenyloxazolidin-2-one<br><br>50% ee |
| 73 | (+/−)(S)-3-((1r,4S)-4-(6-amino-5-(pyrimidin-2-yl)pyridin-3-yl)cyclohexyl)-5,5-dimethyl-4-phenyloxazolidin-2-one<br><br>50% ee |
| 74 | (S)-3-((1r,4S)-4-(6-amino-5-(pyrimidin-2-yl)pyridin-3-yl)cyclohexyl)-5,5-dimethyl-4-phenyloxazolidin-2-one |
| 75 | (R)-3-((1r,4R)-4-(6-amino-5-(pyrimidin-2-yl)pyridin-3-yl)cyclohexyl)-5,5-dimethyl-4-phenyloxazolidin-2-one |
| 76 | (S)-3-((1s,4R)-4-(6-amino-5-(1,4,5,6-tetrahydropyrimidin-2-yl)pyridin-3-yl)cyclohexyl)-5,5-dimethyl-4-phenyloxazolidin-2-one |

TABLE 1-continued

Names and Structures of Example Compounds

| Example | Name |
|---|---|
| 77 | (S)-3-((1r,4S)-4-(6-amino-5-(1,4,5,6-tetrahydropyrimidin-2-yl)pyridin-3-yl)cyclohexyl)-5,5-dimethyl-4-phenyloxazolidin-2-one |
| 78 | 4-((4S)-5,5-dimethyl-2-oxo-4-phenyl-1,3-oxazolidin-3-yl)-N-8-quinolinylbenzamide |
| 79 | 4-((4R)-5,5-dimethyl-2-oxo-4-phenyl-1,3-oxazolidin-3-yl)-N-8-quinolinylbenzamide |
| 80 | (4S)-5,5-dimethyl-3-(4-(2-oxo-4-phenyl-2,3-dihydro-1H-imidazol-1-yl)phenyl)-4-phenyl-1,3-oxazolidin-2-one |
| 81 | 3-(trans-4-((4S)-5,5-dimethyl-2-oxo-4-phenyl-1,3-oxazolidin-3-yl)cyclohexyl)-5-(2-pyrimidinyl)-2(1H)-pyridinone |

TABLE 1-continued

Names and Structures of Example Compounds

| Example | Name | Structure |
|---------|------|-----------|
| 82 | 3-(trans-4-((4R)-5,5-dimethyl-2-oxo-4-phenyl-1,3-oxazolidin-3-yl)cyclohexyl)-5-(2-pyrimidinyl)-2(1H)-pyridinone | 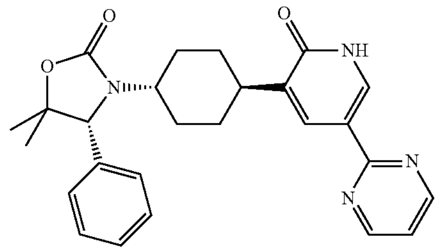 [SMILES: CC1(C)OC(=O)N([C@H]2CC[C@H](c3cc(-c4ncccn4)c[nH]c3=O)CC2)[C@@H]1c1ccccc1] |
| 83 | (S)-5,5-dimethyl-3-((1r,4S)-4-(2-oxo-1H-imidazo[4,5-c]pyridin-3(2H)-yl)cyclohexyl)-4-phenyloxazolidin-2-one | 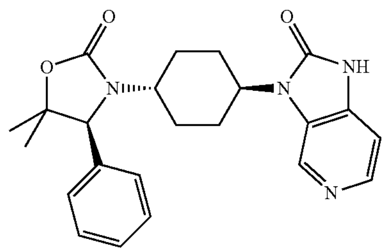 [SMILES: CC1(C)OC(=O)N([C@H]2CC[C@H](n3c(=O)[nH]c4ccncc43)CC2)[C@H]1c1ccccc1] |
| 84 | 5,5-dimethyl-4-phenyl-3-((1r,4r)-4-(5-phenyl-1,3,4-oxadiazol-2-yl)cyclohexyl)oxazolidin-2-one | 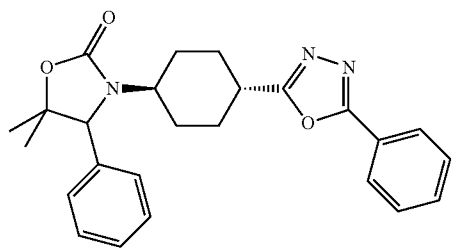 [SMILES: CC1(C)OC(=O)N([C@H]2CC[C@H](c3nnc(-c4ccccc4)o3)CC2)C1c1ccccc1] |
| 85 | (S)-5,5-dimethyl-4-phenyl-3-((1r,4S)-4-(5-phenyl-1,3,4-oxadiazol-2-yl)cyclohexyl)oxazolidin-2-one | 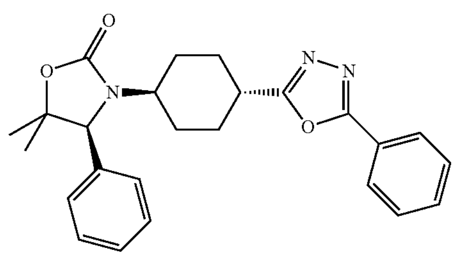 [SMILES: CC1(C)OC(=O)N([C@H]2CC[C@H](c3nnc(-c4ccccc4)o3)CC2)[C@H]1c1ccccc1] |
| 86 | (R)-5,5-dimethyl-4-phenyl-3-((1r,4R)-4-(5-phenyl-1,3,4-oxadiazol-2-yl)cyclohexyl)oxazolidin-2-one | 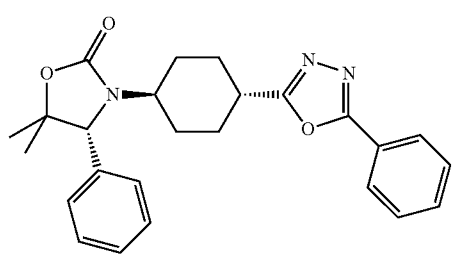 [SMILES: CC1(C)OC(=O)N([C@H]2CC[C@H](c3nnc(-c4ccccc4)o3)CC2)[C@@H]1c1ccccc1] |
| 87 | (4S)-5,5-dimethyl-3-(4-(2-oxo-1,2-dihydro-1,7-naphthyridin-3-yl)cyclohex-3-en-1-yl)-4-phenyloxazolidin-2-one | 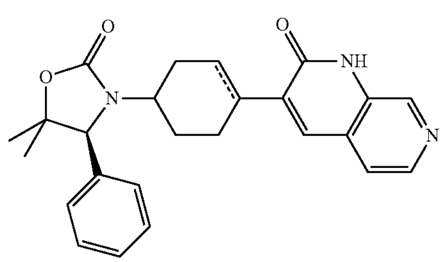 |

TABLE 1-continued

Names and Structures of Example Compounds

| Example | Name | Structure |
|---|---|---|
| 88 | (S)-5,5-dimethyl-3-(4-(2-oxo-1,2-dihydro-1,7-naphthyridin-3-yl)phenyl)-4-phenyloxazolidin-2-one | 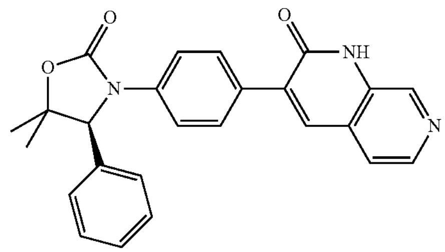 [SMILES: CC1(C)OC(=O)N(c2ccc(-c3cc4ccncc4[nH]c3=O)cc2)[C@H]1c1ccccc1] |
| 89 | (R + S)-5-methyl-3-((1r,4R)-4-(2-oxo-2,3-dihydro-1H-imidazo[4,5-c]pyridin-1-yl)cyclohexyl)-5-phenyloxazolidin-2-one | 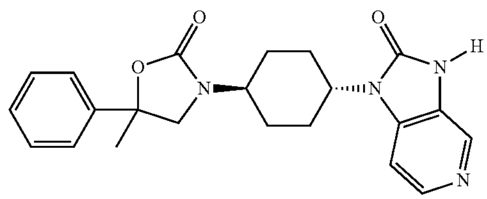 [SMILES: CC1(c2ccccc2)CN([C@H]2CC[C@H](n3c(=O)[nH]c4cnccc43)CC2)C(=O)O1] |
| 90 | (R)-5-methyl-3-((1r,4R)-4-(2-oxo-2,3-dihydro-1H-imidazo[4,5-c]pyridin-1-yl)cyclohexyl)-5-phenyloxazolidin-2-one | 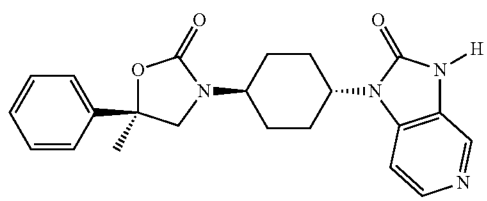 [SMILES: C[C@@]1(c2ccccc2)CN([C@H]2CC[C@H](n3c(=O)[nH]c4cnccc43)CC2)C(=O)O1] |
| 91 | (S)-5-methyl-3-((1r,4S)-4-(2-oxo-2,3-dihydro-1H-imidazo[4,5-c]pyridin-1-yl)cyclohexyl)-5-phenyloxazolidin-2-one | 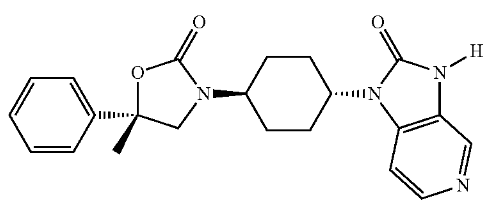 [SMILES: C[C@]1(c2ccccc2)CN([C@H]2CC[C@H](n3c(=O)[nH]c4cnccc43)CC2)C(=O)O1] |
| 92 | 1-((1R,4r)-4-((R + S)-5-methyl-2-oxo-5-phenyloxazolidin-3-yl)cyclohexyl)-2-oxo-2,3-dihydro-1H-benzo[d]imidazole-5-carbonitrile | 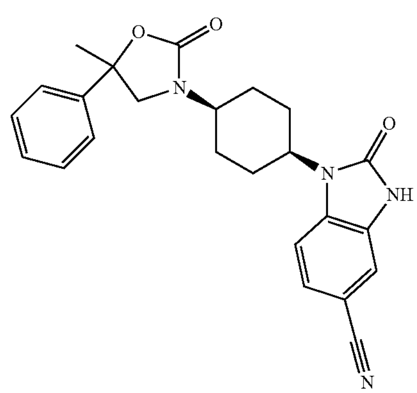 [SMILES: CC1(c2ccccc2)CN([C@H]2CC[C@@H](n3c(=O)[nH]c4cc(C#N)ccc43)CC2)C(=O)O1] |

TABLE 1-continued

Names and Structures of Example Compounds

| Example | Name |
|---|---|
| 93 | 1-((1R,4r)-4-((R)-5-methyl-2-oxo-5-phenyloxazolidin-3-yl)cyclohexyl)-2-oxo-2,3-dihydro-1H-benzo[d]imidazole-5-carbonitrile |
| 94 | 1-((1S,4r)-4-((S)-5-methyl-2-oxo-5-phenyloxazolidin-3-yl)cyclohexyl)-2-oxo-2,3-dihydro-1H-benzo[d]imidazole-5-carbonitrile |
| 95 | 2-amino-5-((1S,4r)-4-((S)-5,5-dimethyl-2-oxo-4-phenyloxazolidin-3-yl)cyclohexyl)nicotinonitrile |
| 96 | (S)-5,5-dimethyl-3-((1s,4R)-4-(6-oxo-5-(pyrimidin-2-yl)-1,6-dihydropyridin-3-yl)cyclohexyl)-4-phenyloxazolidin-2-one |

TABLE 1-continued

Names and Structures of Example Compounds

| Example | Name |
|---|---|
| 97 | (S)-5,5-dimethyl-3-((1r,4S)-4-(6-oxo-5-(pyrimidin-2-yl)-1,6-dihydropyridin-3-yl)cyclohexyl)-4-phenyloxazolidin-2-one |
| 98 | (S)-5,5-dimethyl-3-((1r,4S)-4-(2-oxo-1-(pyrimidin-2-yl)-2,3-dihydro-1H-imidazo[4,5-b]pyridin-6-yl)cyclohexyl)-4-phenyloxazolidin-2-one |
| 99 | (S)-2-(2-amino-5-(4-(5,5-dimethyl-2-oxo-4-phenyloxazolidin-3-yl)phenyl)pyridin-3-yl)pyrimidine-4-carboximidamide |
| 100 | (S)-3-(4-(6-amino-5-(5-chloropyridazin-3-yl)pyridin-3-yl)phenyl)-5,5-dimethyl-4-phenyloxazolidin-2-one or (S)-3-(4-(6-amino-5-(6-chloropyridazin-4-yl)pyridin-3-yl)phenyl)-5,5-dimethyl-4-phenyloxazolidin-2-one | or

TABLE 1-continued

Names and Structures of Example Compounds

| Example | Name | Structure |
|---|---|---|
| 101 | The isomer of 100 | The isomer of 100 |
| 102 | (S)-2-(2-amino-5-(4-(5,5-dimethyl-2-oxo-4-phenyloxazolidin-3-yl)phenyl)pyridin-3-yl)pyrimidine-4-carbonitrile | 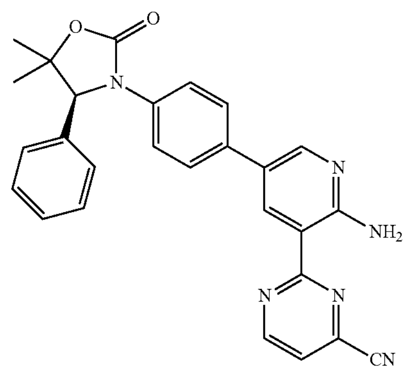 [SMILES: CC1(C)OC(=O)N(c2ccc(-c3cnc(N)c(-c4nccc(C#N)n4)c3)cc2)[C@H]1c1ccccc1] |
| 103 | 1-((1S,4r)-4-((S)-5,5-dimethyl-2-oxo-4-phenyloxazolidin-3-yl)cyclohexyl)-6-fluoro-2-oxo-2,3-dihydro-1H-benzo[d]imidazole-5-carbonitrile | 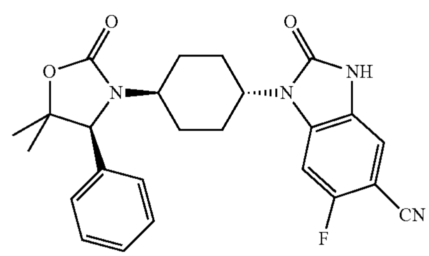 [SMILES: CC1(C)OC(=O)N([C@H]2CC[C@H](n3c(=O)[nH]c4cc(C#N)c(F)cc43)CC2)[C@H]1c1ccccc1] |
| 104 | (S)-3-((1r,4S)-4-(4,6-difluoro-2-oxo-2,3-dihydro-1H-benzo[d]imidazol-1-yl)cyclohexyl)-5,5-dimethyl-4-phenyloxazolidin-2-one | 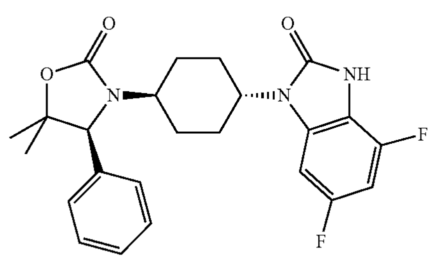 [SMILES: CC1(C)OC(=O)N([C@H]2CC[C@H](n3c(=O)[nH]c4c(F)cc(F)cc43)CC2)[C@H]1c1ccccc1] |
| 105 | (+/−)-(R/S)-4-(4-(3-methoxyphenyl)-5,5-dimethyl-2-oxooxazolidin-3-yl)-N-(quinolin-8-yl)benzamide | 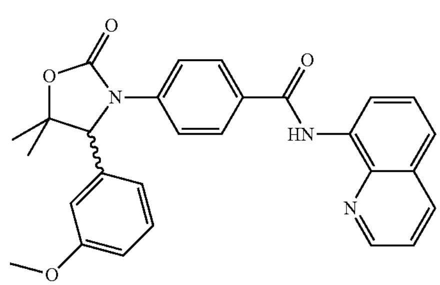 [SMILES: COc1cccc(C2N(c3ccc(C(=O)Nc4cccc5cccnc45)cc3)C(=O)OC2(C)C)c1] |

TABLE 1-continued

Names and Structures of Example Compounds

| Example | Name |
|---|---|
| 106 | (R)-4-(4-(3-methoxyphenyl)-5,5-dimethyl-2-oxooxazolidin-3-yl)-N-(quinolin-8-yl)benzamide |
| 107 | (S)-4-(4-(3-methoxyphenyl)-5,5-dimethyl-2-oxooxazolidin-3-yl)-N-(quinolin-8-yl)benzamide |
| 108 | (+/−)-(R/S)-4-(4-(3-fluorophenyl)-5,5-dimethyl-2-oxooxazolidin-3-yl)-N-(quinolin-8-yl)benzamide |
| 109 | (R)-4-(4-(3-fluorophenyl)-5,5-dimethyl-2-oxooxazolidin-3-yl)-N-(quinolin-8-yl)benzamide |
| 110 | (S)-4-(4-(3-fluorophenyl)-5,5-dimethyl-2-oxooxazolidin-3-yl)-N-(quinolin-8-yl)benzamide |

TABLE 1-continued

Names and Structures of Example Compounds

| Example | Name | Structure |
|---|---|---|
| 111 | (+/−)-(R/S)-4-(4-methoxyphenyl)-5,5-dimethyl-2-oxooxazolidin-3-yl)-N-(quinolin-8-yl)benzamide | 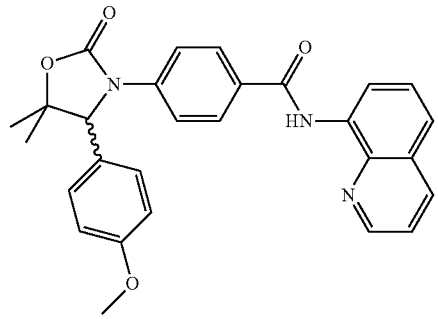 [SMILES: COc1ccc(C2N(c3ccc(C(=O)Nc4cccc5cccnc45)cc3)C(=O)OC2(C)C)cc1] |
| 112 | (R)-4-(4-(4-methoxyphenyl)-5,5-dimethyl-2-oxooxazolidin-3-yl)-N-(quinolin-8-yl)benzamide | 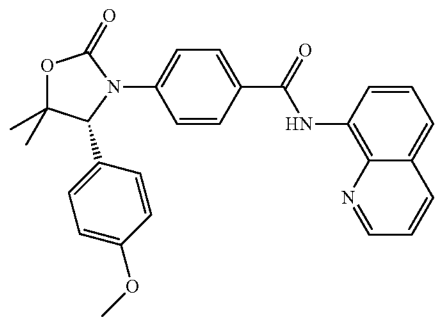 [SMILES: COc1ccc([C@H]2N(c3ccc(C(=O)Nc4cccc5cccnc45)cc3)C(=O)OC2(C)C)cc1] |
| 113 | (S)-4-(4-(4-methoxyphenyl)-5,5-dimethyl-2-oxooxazolidin-3-yl)-N-(quinolin-8-yl)benzamide | 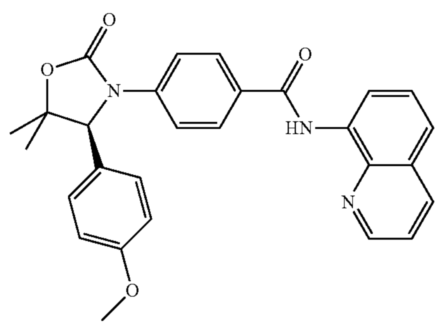 [SMILES: COc1ccc([C@@H]2N(c3ccc(C(=O)Nc4cccc5cccnc45)cc3)C(=O)OC2(C)C)cc1] |
| 114 | (S)-3-(4-(6'-fluoro-[2,3'-bipyridin]-5'-yl)phenyl)-5,5-dimethyl-4-phenyloxazolidin-2-one | 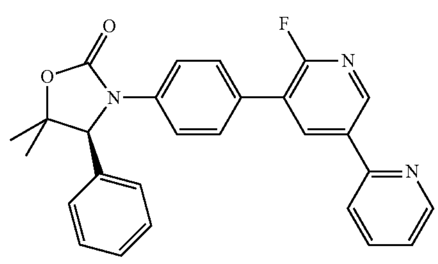 |
| 115 | (S)-5,5-dimethyl-3-(4-(6'-oxo-1',6'-dihydro-[2,3'-bipyridin]-5'-yl)phenyl)-4-phenyloxazolidin-2-one | 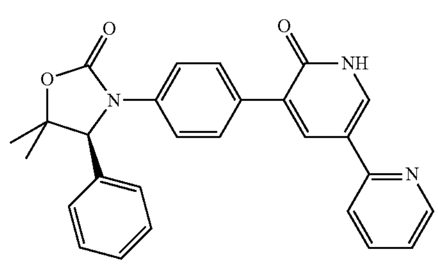 [SMILES: CC1(C)OC(=O)N(c2ccc(-c3cc(-c4ccccn4)c[nH]c3=O)cc2)[C@H]1c1ccccc1] |

TABLE 1-continued

Names and Structures of Example Compounds

| Example | Name |
|---|---|
| 116 | (S)-5,5-dimethyl-3-(4-(5-(oxazol-2-yl)-2-oxo-1,2-dihydropyridin-3-yl)phenyl)-4-phenyloxazolidin-2-one |
| 117 | (S)-3-(4-(6-fluoro-[3,3'-bipyridin]-5-yl)phenyl)-5,5-dimethyl-4-phenyloxazolidin-2-one |
| 118 | (S)-5,5-dimethyl-3-(4-(6-oxo-1,6-dihydro-[3,3'-bipyridin]-5-yl)phenyl)-4-phenyloxazolidin-2-one |
| 119 | (S)-5,5-dimethyl-3-(4-(2-oxo-1,2-dihydropyridin-3-yl)phenyl)-4-phenyloxazolidin-2-one |
| 120 | (S)-2-(5-(4-(5,5-dimethyl-2-oxo-4-phenyloxazolidin-3-yl)phenyl)-6-oxo-1,6-dihydropyridin-3-yl)pyrimidine-4-carbonitrile |
| 121 | (+/−)-(R/S)-4-(5,5-dimethyl-2-oxo-4-(pyridin-2-yl)oxazolidin-3-yl)-N-(quinolin-8-yl)benzamide |

TABLE 1-continued

Names and Structures of Example Compounds

| Example | Name |
|---|---|
| 122 | (R)-4-(5,5-dimethyl-2-oxo-4-(pyridin-2-yl)oxazolidin-3-yl)-N-(quinolin-8-yl)benzamide |
| 123 | (S)-4-(5,5-dimethyl-2-oxo-4-(pyridin-2-yl)oxazolidin-3-yl)-N-(quinolin-8-yl)benzamide |
| 124 | (+/−)-(R/S)-4-(5,5-dimethyl-2-oxo-4-(pyridin-4-yl)oxazolidin-3-yl)-N-(quinolin-8-yl)benzamide |
| 125 | (R)-4-(5,5-dimethyl-2-oxo-4-(pyridin-4-yl)oxazolidin-3-yl)-N-(quinolin-8-yl)benzamide |
| 126 | (S)-4-(5,5-dimethyl-2-oxo-4-(pyridin-4-yl)oxazolidin-3-yl)-N-(quinolin-8-yl)benzamide |
| 127 | (S)-5,5-dimethyl-3-(4-(2-oxo-5-(pyrimidin-2-yl)pyridin-1(2H)-yl)phenyl)-4-phenyloxazolidin-2-one |

TABLE 1-continued

Names and Structures of Example Compounds

| Example | Name | Structure |
|---|---|---|
| 128 | (S)-4-(5,5-dimethyl-2-oxo-4-phenyloxazolidin-3-yl)-2-methyl-N-(1,5-naphthyridin-4-yl)benzamide | 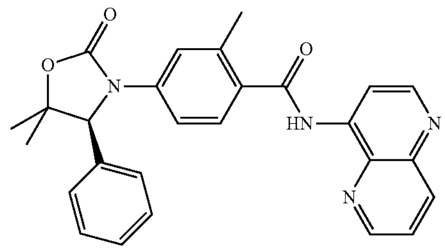 [SMILES: Cc1cc(N2C(=O)OC(C)(C)[C@@H]2c2ccccc2)ccc1C(=O)Nc1ccnc2cccnc12] |
| 129 | (S)-3-(4-(5-fluoro-2-(pyrimidin-2-yl)pyridin-4-yl)phenyl)-5,5-dimethyl-4-phenyloxazolidin-2-one | 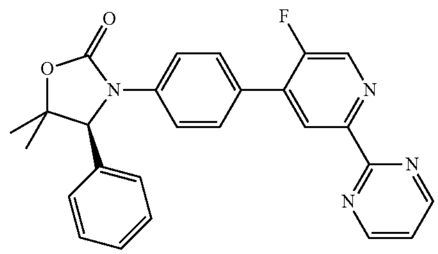 [SMILES: CC1(C)OC(=O)N(c2ccc(-c3cc(-c4ncccn4)ncc3F)cc2)[C@H]1c1ccccc1] |
| 130 | (S)-5,5-dimethyl-3-((1r,4S)-4-(2-oxo-5-(1,4,5,6-tetrahydropyrimidin-2-yl)-1,2-dihydropyridin-3-yl)cyclohexyl)-4-phenyloxazolidin-2-one | 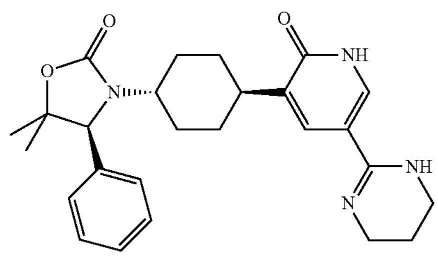 [SMILES: CC1(C)OC(=O)N([C@H]2CC[C@H](c3cc(C4=NCCCN4)c[nH]c3=O)CC2)[C@H]1c1ccccc1] |
| 131 | 3-(4-(6-amino-5-(pyrimidin-2-yl)pyridin-3-yl)cyclohex-3-en-1-yl)-5,5-dimethyl-4-phenyloxazolidin-2-one | 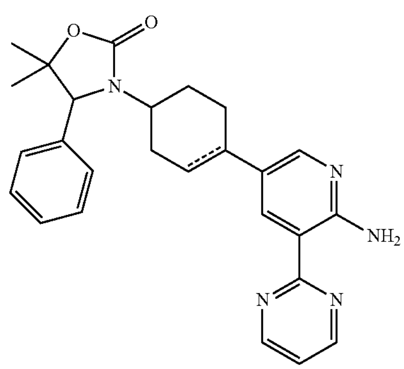 |
| | | isomeric mixture (4 isomers) |
| 132 | (S)-5,5-dimethyl-4-phenyl-3-((1s,4r)-4-(pyridin-3-yl)cyclohexyl)oxazolidin-2-one | 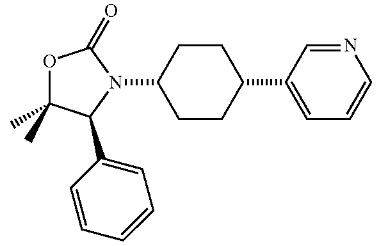 |

TABLE 1-continued

Names and Structures of Example Compounds

| Example | Name |
|---|---|
| 133 | (S)-5,5-dimethyl-4-phenyl-3-((1r,4s)-4-(pyridin-3-yl)cyclohexyl)oxazolidin-2-one |
| 134 | (S)-5,5-dimethyl-3-((1s,4r)-4-(6-methylpyridin-3-yl)cyclohexyl)-4-phenyloxazolidin-2-one |
| 135 | (S)-5,5-dimethyl-3-((1r,4s)-4-(6-methylpyridin-3-yl)cyclohexyl)-4-phenyloxazolidin-2-one |
| 136 | (S)-3-((1s,4r)-4-(1H-pyrrolo[2,3-b]pyridin-5-yl)cyclohexyl)-5,5-dimethyl-4-phenyloxazolidin-2-one |
| 137 | (S)-3-((1r,4s)-4-(1H-pyrrolo[2,3-b]pyridin-5-yl)cyclohexyl)-5,5-dimethyl-4-phenyloxazolidin-2-one |
| 138 | (S)-5,5-dimethyl-3-((1s,4r)-4-(2-oxo-1,2-dihydro-1,7-naphthyridin-3-yl)cyclohexyl)-4-phenyloxazolidin-2-one |

TABLE 1-continued

Names and Structures of Example Compounds

| Example | Name | Structure |
|---------|------|-----------|
| 139 | (S)-5,5-dimethyl-3-((1r,4s)-4-(2-oxo-1,2-dihydro-1,7-naphthyridin-3-yl)cyclohexyl)-4-phenyloxazolidin-2-one | 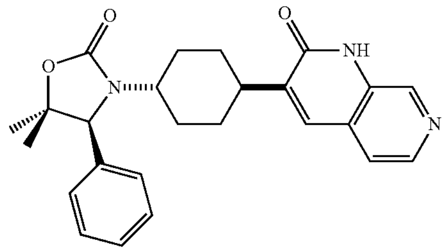 |
| 140 | (S)-5,5-dimethyl-4-phenyl-3-(1-(1-(pyrimidin-2-yl)-1H-pyrrolo[3,2-b]pyridin-6-yl)piperidin-4-yl)oxazolidin-2-one | 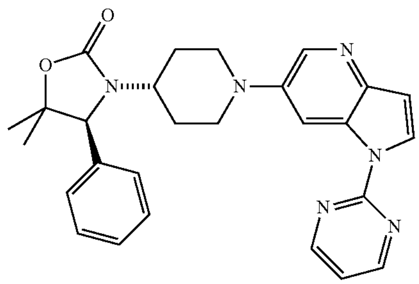 |
| 141 | N-((1S,4r)-4-((S)-5,5-dimethyl-2-oxo-4-phenyloxazolidin-3-yl)cyclohexyl)benzamide | 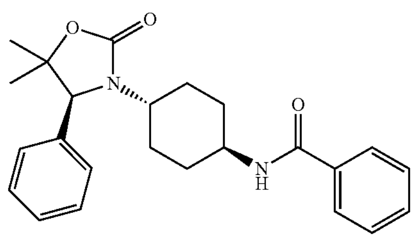 [SMILES: CC1(C)OC(=O)N([C@H]2CC[C@H](NC(=O)c3ccccc3)CC2)[C@H]1c1ccccc1] |
| 142 | N-((1S,4r)-4-((S)-5,5-dimethyl-2-oxo-4-phenyloxazolidin-3-yl)cyclohexyl)isonicotinamide | 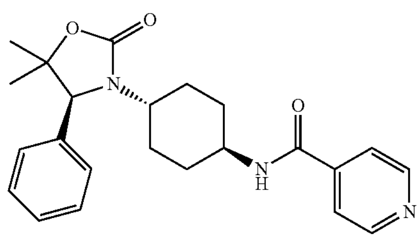 [SMILES: CC1(C)OC(=O)N([C@H]2CC[C@H](NC(=O)c3ccncc3)CC2)[C@H]1c1ccccc1] |
| 143 | N-((1R,4r)-4-((R)-5,5-dimethyl-2-oxo-4-phenyloxazolidin-3-yl)cyclohexyl)-1-methyl-1H-indole-3-carboxamide | 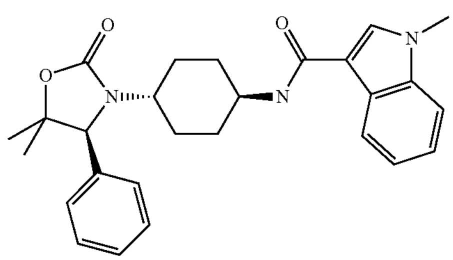 |
| 144 | N-((1R,4r)-4-((R)-5,5-dimethyl-2-oxo-4-phenyloxazolidin-3-yl)cyclohexyl)-2-methyl-2H-indazole-4-carboxamide | 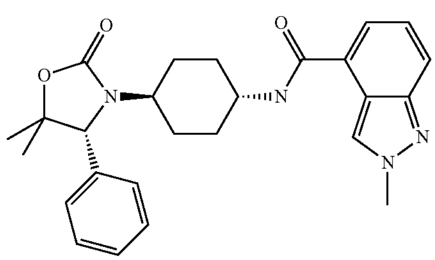 [SMILES: Cn1cc2c(C(=O)N[C@H]3CC[C@H](N4C(=O)OC(C)(C)[C@H]4c4ccccc4)CC3)cccc2n1] |

TABLE 1-continued

Names and Structures of Example Compounds

| Example | Name |
|---|---|
| 145 | N-((1S,4r)-4-((S)-5,5-dimethyl-2-oxo-4-phenyloxazolidin-3-yl)cyclohexyl)-2-methyl-2H-indazole-7-carboxamide |
| 146 | 146: N-((1S,4r)-4-((S)-5,5-dimethyl-2-oxo-4-phenyloxazolidin-3-yl)cyclohexyl)pyrazolo[1,5-a]pyrimidine-3-carboxamide |
| 147 | N-((1S,4r)-4-((S)-5,5-dimethyl-2-oxo-4-phenyloxazolidin-3-yl)cyclohexyl)-1H-pyrrolo[2,3-b]pyridine-6-carboxamide |
| 148 | N-((1S,4r)-4-((S)-5,5-dimethyl-2-oxo-4-phenyloxazolidin-3-yl)cyclohexyl)-2-phenylpyrimidine-4-carboxamide |
| 149 | N-((1S,4r)-4-((S)-5,5-dimethyl-2-oxo-4-phenyloxazolidin-3-yl)cyclohexyl)-1H-pyrrolo[2,3-c]pyridine-2-carboxamide |

TABLE 1-continued

Names and Structures of Example Compounds

| Example | Name | Structure |
|---|---|---|
| 150 | N-((1S,4r)-4-((S)-5,5-dimethyl-2-oxo-4-phenyloxazolidin-3-yl)cyclohexyl)benzo[d]thiazole-5-carboxamide | 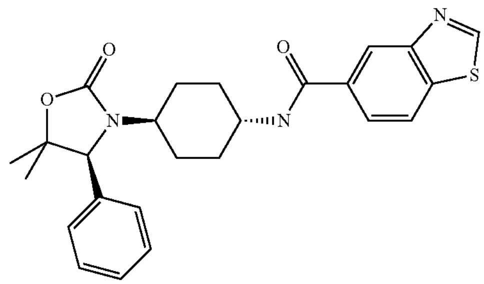 [SMILES: CC1(C)OC(=O)N([C@H]2CC[C@H](NC(=O)c3ccc4scnc4c3)CC2)[C@H]1c1ccccc1] |
| 151 | N-((1S,4r)-4-((S)-5,5-dimethyl-2-oxo-4-phenyloxazolidin-3-yl)cyclohexyl)-1-methyl-1H-imidazole-5-carboxamide | 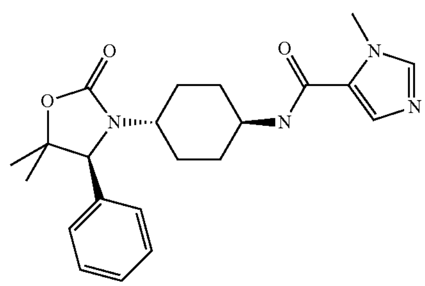 [SMILES: Cn1cncc1C(=O)N[C@H]1CC[C@H](N2C(=O)OC(C)(C)[C@@H]2c2ccccc2)CC1] |
| 152 | N-((1S,4r)-4-((S)-5,5-dimethyl-2-oxo-4-phenyloxazolidin-3-yl)cyclohexyl)-1H-pyrrolo[2,3-b]pyridine-4-carboxamide | 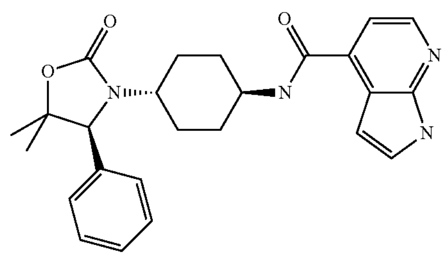 [SMILES: CC1(C)OC(=O)N([C@H]2CC[C@H](NC(=O)c3ccnc4[nH]ccc34)CC2)[C@H]1c1ccccc1] |
| 153 | N-((1S,4r)-4-((S)-5,5-dimethyl-2-oxo-4-phenyloxazolidin-3-yl)cyclohexyl)-1H-indazole-4-carboxamide | 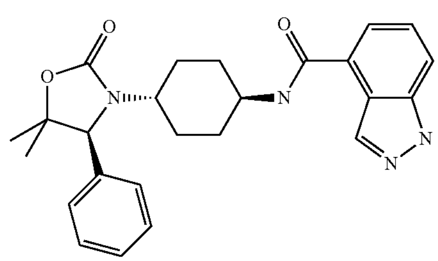 [SMILES: CC1(C)OC(=O)N([C@H]2CC[C@H](NC(=O)c3cccc4[nH]ncc34)CC2)[C@H]1c1ccccc1] |
| 154 | N-((1S,4r)-4-((S)-5,5-dimethyl-2-oxo-4-phenyloxazolidin-3-yl)cyclohexyl)-3-isopropyl-1H-pyrazole-5-carboxamide | 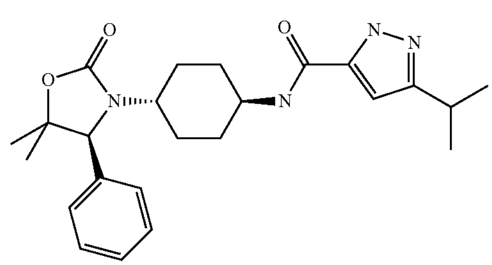 [SMILES: CC(C)c1cc(C(=O)N[C@H]2CC[C@H](N3C(=O)OC(C)(C)[C@@H]3c3ccccc3)CC2)[nH]n1] |

TABLE 1-continued

Names and Structures of Example Compounds

| Example | Name |
|---|---|
| 155 | N-((1R,4r)-4-((R)-5,5-dimethyl-2-oxo-4-phenyloxazolidin-3-yl)cyclohexyl)quinoline-3-carboxamide |
| 156 | N-((1S,4r)-4-((S)-5,5-dimethyl-2-oxo-4-phenyloxazolidin-3-yl)cyclohexyl)-2-phenylthiazole-4-carboxamide |
| 157 | N-((1S,4r)-4-((S)-5,5-dimethyl-2-oxo-4-phenyloxazolidin-3-yl)cyclohexyl)-1H-benzo[d]imidazole-2-carboxamide |
| 158 | N-((1S,4r)-4-((S)-5,5-dimethyl-2-oxo-4-phenyloxazolidin-3-yl)cyclohexyl)-1H-pyrrole-2-carboxamide |
| 159 | N-((1S,4r)-4-((S)-5,5-dimethyl-2-oxo-4-phenyloxazolidin-3-yl)cyclohexyl)imidazo[1,2-a]pyridine-6-carboxamide |
| 160 | N-((1S,4r)-4-((S)-5,5-dimethyl-2-oxo-4-phenyloxazolidin-3-yl)cyclohexyl)thiazole-2-carboxamide |

TABLE 1-continued

Names and Structures of Example Compounds

| Example | Name | Structure |
|---|---|---|
| 161 | N-((1S,4r)-4-((S)-5,5-dimethyl-2-oxo-4-phenyloxazolidin-3-yl)cyclohexyl)-1-phenyl-1H-pyrazole-4-carboxamide | 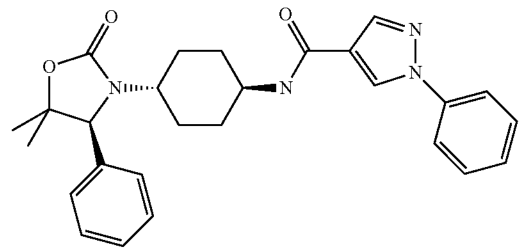 [SMILES: CC1(C)OC(=O)N([C@H]2CC[C@H](NC(=O)c3cnn(-c4ccccc4)c3)CC2)[C@H]1c1ccccc1] |
| 162 | N-((1R,4r)-4-((R)-5,5-dimethyl-2-oxo-4-phenyloxazolidin-3-yl)cyclohexyl)imidazo[1,2-a]pyridine-2-carboxamide | 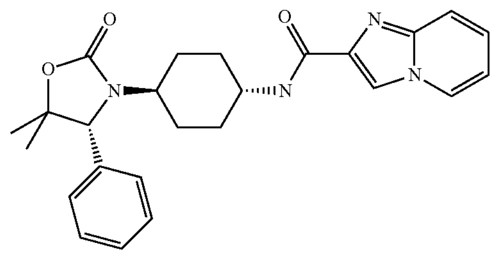 [SMILES: CC1(C)OC(=O)N([C@H]2CC[C@H](NC(=O)c3cn4ccccc4n3)CC2)[C@@H]1c1ccccc1] |
| 163 | N-((1S,4r)-4-((S)-5,5-dimethyl-2-oxo-4-phenyloxazolidin-3-yl)cyclohexyl)-2-methoxybenzamide | 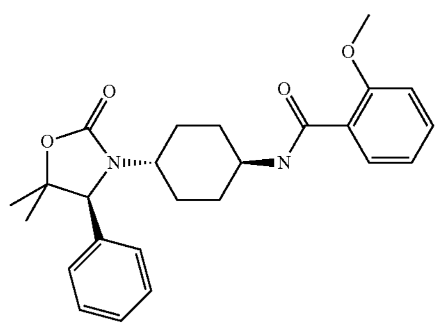 [SMILES: COc1ccccc1C(=O)N[C@H]1CC[C@H](N2C(=O)OC(C)(C)[C@@H]2c2ccccc2)CC1] |
| 164 | N-((1S,4r)-4-((S)-5,5-dimethyl-2-oxo-4-phenyloxazolidin-3-yl)cyclohexyl)-2-phenyloxazole-4-carboxamide | 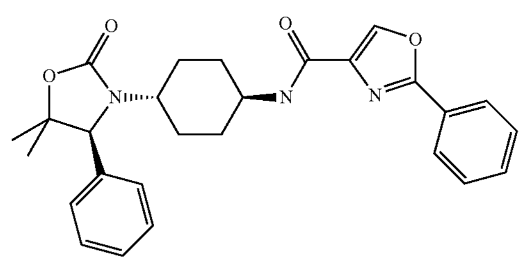 |
| 165 | N-((1S,4r)-4-((S)-5,5-dimethyl-2-oxo-4-phenyloxazolidin-3-yl)cyclohexyl)pyrimidine-4-carboxamide | 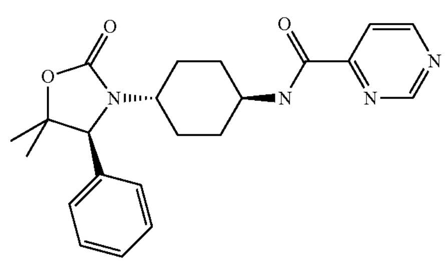 [SMILES: CC1(C)OC(=O)N([C@H]2CC[C@H](NC(=O)c3ccncn3)CC2)[C@H]1c1ccccc1] |

TABLE 1-continued

Names and Structures of Example Compounds

| Example | Name | Structure |
|---|---|---|
| 166 | N-((1S,4r)-4-((S)-5,5-dimethyl-2-oxo-4-phenyloxazolidin-3-yl)cyclohexyl)-2-methylthiazole-4-carboxamide | 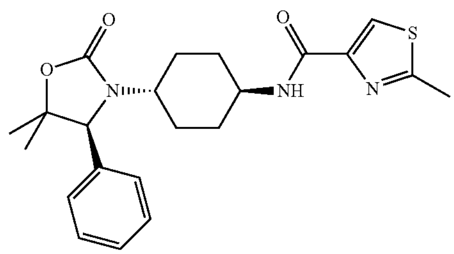 |
| 167 | N-((1S,4r)-4-((S)-5,5-dimethyl-2-oxo-4-phenyloxazolidin-3-yl)cyclohexyl)-2-(pyridin-4-yl)thiazole-4-carboxamide | 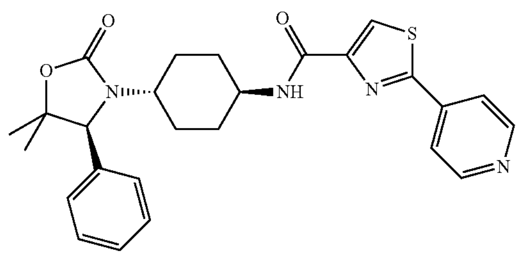 [SMILES: CC1(C)OC(=O)N([C@H]2CC[C@H](NC(=O)c3csc(-c4ccncc4)n3)CC2)[C@H]1c1ccccc1] |
| 168 | N-((1S,4r)-4-((S)-5,5-dimethyl-2-oxo-4-phenyloxazolidin-3-yl)cyclohexyl)thiazole-4-carboxamide | 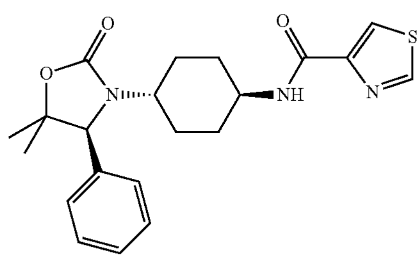 [SMILES: CC1(C)OC(=O)N([C@H]2CC[C@H](NC(=O)c3cscn3)CC2)[C@H]1c1ccccc1] |
| 169 | Mixture of (S)-3-((S)-4-(1H-pyrrolo[3,2-b]pyridin-6-yl)cyclohex-3-en-1-yl)-5,5-dimethyl-4-phenyloxazolidin-2-one and (S)-3-((R)-4-(1H-pyrrolo[3,2-b]pyridin-6-yl)cyclohex-3-en-1-yl)-5,5-dimethyl-4-phenyloxazolidin-2-one | |

TABLE 1-continued

Names and Structures of Example Compounds

| Example | Name | Structure |
|---------|------|-----------|
| 170 | Mixture (S)-3-((1r,4S)-4-(1H-pyrrolo[3,2-b]pyridin-6-yl)cyclohexyl)-5,5-dimethyl-4-phenyloxazolidin-2-one and (R)-3-((1r,4R)-4-(1H-pyrrolo[3,2-b]pyridin-6-yl)cyclohexyl)-5,5-dimethyl-4-phenyloxazolidin-2-one | 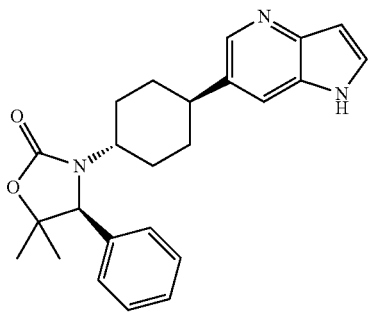 [SMILES: CC1(C)OC(=O)N([C@H]2CC[C@H](c3cnc4cc[nH]c4c3)CC2)[C@H]1c1ccccc1]<br>mixture |
| 171 | (S)-3-((1r,4S)-4-(1H-pyrrolo[3,2-b]pyridin-6-yl)cyclohexyl)-5,5-dimethyl-4-phenyloxazolidin-2-one | 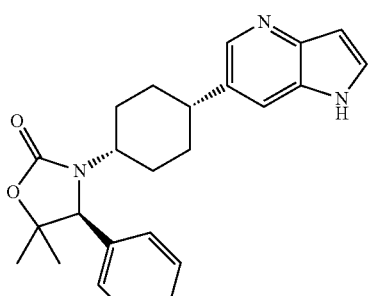 |
| 172 | (S)-3-((1s,4R)-4-(1H-pyrrolo[3,2-b]pyridin-6-yl)cyclohexyl)-5,5-dimethyl-4-phenyloxazolidin-2-one | 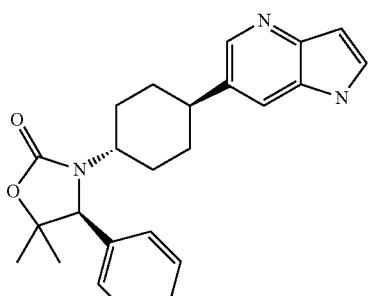 |

TABLE 1-continued

Names and Structures of Example Compounds

| Example | Name | Structure |
|---|---|---|
| 173 | Mixture of (S)-5,5-dimethyl-4-phenyl-3-((S)-4-(1-(pyrimidin-2-yl)-1H-pyrrolo[3,2-b]pyridin-6-yl)cyclohex-3-en-1-yl)oxazolidin-2-one and (S)-5,5-dimethyl-4-phenyl-3-((R)-4-(1-(pyrimidin-2-yl)-1H-pyrrolo[3,2-b]pyridin-6-yl)cyclohex-3-en-1-yl)oxazolidin-2-one | 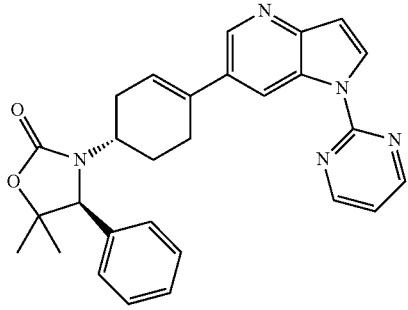 [SMILES: CC1(C)OC(=O)N([C@@H]2CC=C(c3cnc4ccn(-c5ncccn5)c4c3)CC2)[C@H]1c1ccccc1]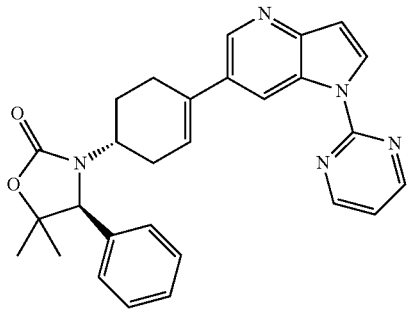 [SMILES: CC1(C)OC(=O)N([C@H]2CC=C(c3cnc4ccn(-c5ncccn5)c4c3)CC2)[C@H]1c1ccccc1] |
| 174 | Mixture of (S)-5,5-dimethyl-4-phenyl-3-((1r,4S)-4-(1-(pyrimidin-2-yl)-1H-pyrrolo[3,2-b]pyridin-6-yl)cyclohexyl)oxazolidin-2-one compound and (S)-5,5-dimethyl-4-phenyl-3-((1s,4R)-4-(1-(pyrimidin-2-yl)-1H-pyrrolo[3,2-b]pyridin-6-yl)cyclohexyl)oxazolidin-2-one (86:14) | 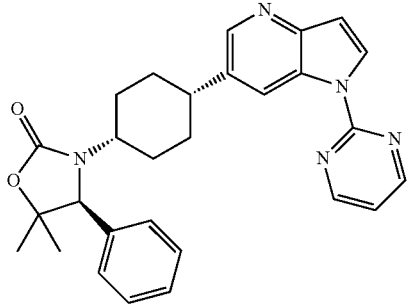 [SMILES: CC1(C)OC(=O)N([C@H]2CC[C@@H](c3cnc4ccn(-c5ncccn5)c4c3)CC2)[C@H]1c1ccccc1]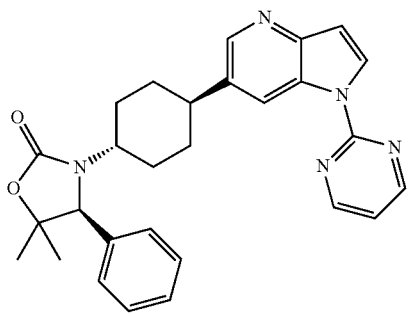 [SMILES: CC1(C)OC(=O)N([C@H]2CC[C@H](c3cnc4ccn(-c5ncccn5)c4c3)CC2)[C@H]1c1ccccc1] |
| 175 | Mixture of (R)-5,5-dimethyl-4-phenyl-3-((1r,3R)-3-(5-phenyl-1,3,4-oxadiazol-2-yl)cyclobutyl)oxazolidin-2-one compound and (S)-5,5-dimethyl-4-phenyl-3-((1r,3S)-3-(5-phenyl-1,3,4-oxadiazol-2-yl)cyclobutyl)oxazolidin-2-one (1:1) | 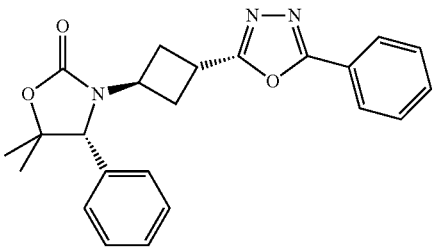 |

TABLE 1-continued

Names and Structures of Example Compounds

| Example | Name | Structure |
|---|---|---|
| | | |
| 176 | (R)-5,5-dimethyl-4-phenyl-3-((1r,3R)-3-(5-phenyl-1,3,4-oxadiazol-2-yl)cyclobutyl)oxazolidin-2-one | 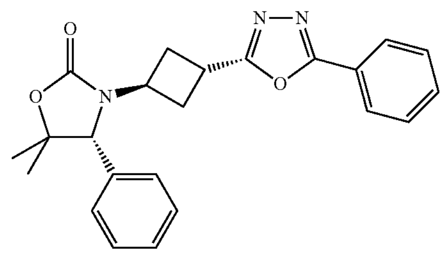 |
| 177 | (S)-5,5-dimethyl-4-phenyl-3-((1r,3S)-3-(5-phenyl-1,3,4-oxadiazol-2-yl)cyclobutyl)oxazolidin-2-one | 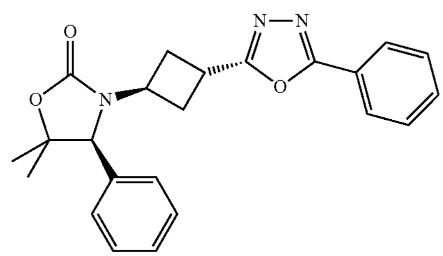 |
| 178 | 1-((1R,4s)-4-((4S,5R)-5-methyl-2-oxo-4-phenyloxazolidin-3-yl)cyclohexyl)-2-oxo-2,3-dihydro-1H-benzo[d]imidazole-5-carbonitrile | 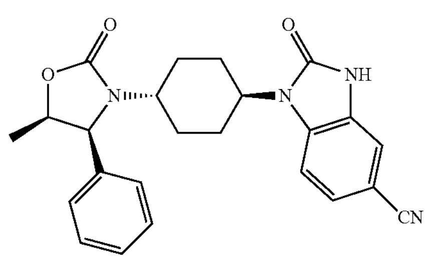 [SMILES: C[C@H]1OC(=O)N([C@H]2CC[C@H](n3c(=O)[nH]c4cc(C#N)ccc43)CC2)[C@H]1c1ccccc1] |
| 179 | 1-((1R,4r)-4-((4R,5S)-5-methyl-2-oxo-4-phenyloxazolidin-3-yl)cyclohexyl)-2-oxo-2,3-dihydro-1H-benzo[d]imidazole-5-carbonitrile | 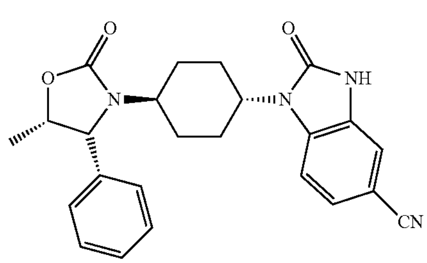 |
| 180 | 1-((1R,4r)-4-((R)-5,5-dimethyl-2-oxo-4-phenyloxazolidin-3-yl)cyclohexyl)-1H-indazole-5-carbonitrile | 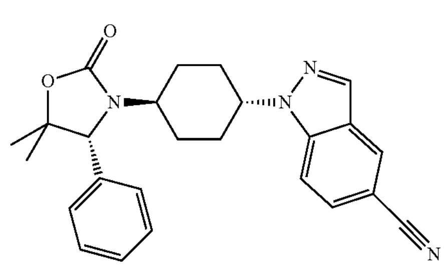 [SMILES: CC1(C)OC(=O)N([C@H]2CC[C@H](n3ncc4cc(C#N)ccc43)CC2)[C@@H]1c1ccccc1] |

TABLE 1-continued

Names and Structures of Example Compounds

| Example | Name | Structure |
|---|---|---|
| 181 | 1-((1S,4r)-4-((S)-5,5-dimethyl-2-oxo-4-phenyloxazolidin-3-yl)cyclohexyl)-1H-indazole-5-carbonitrile | 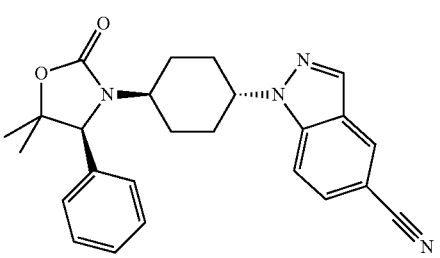 |
| 182 | 2-bromo-N-((1S,4r)-4-((S)-5,5-dimethyl-2-oxo-4-phenyloxazolidin-3-yl)cyclohexyl)thiazole-4-carboxamide | 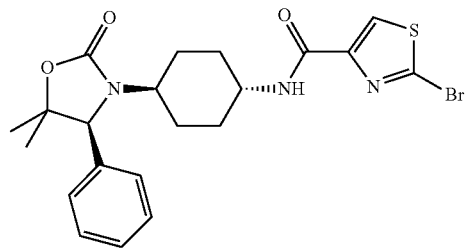 [SMILES: CC1(C)OC(=O)N([C@H]2CC[C@H](NC(=O)c3csc(Br)n3)CC2)[C@H]1c1ccccc1] |
| 183 | N-((1S,4r)-4-((S)-5,5-dimethyl-2-oxo-4-phenyloxazolidin-3-yl)cyclohexyl)-2-(pyrimidin-2-yl)thiazole-4-carboxamide | 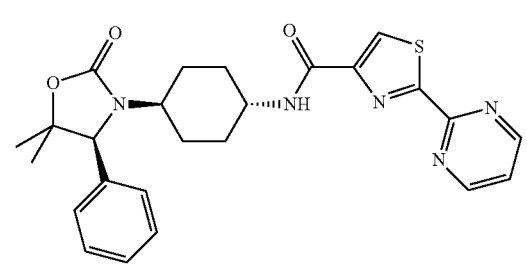 [SMILES: CC1(C)OC(=O)N([C@H]2CC[C@H](NC(=O)c3csc(-c4ncccn4)n3)CC2)[C@H]1c1ccccc1] |
| 184 | N-((1S,4r)-4-((S)-5,5-dimethyl-2-oxo-4-phenyloxazolidin-3-yl)cyclohexyl)-2-(pyrimidin-5-yl)thiazole-4-carboxamide | 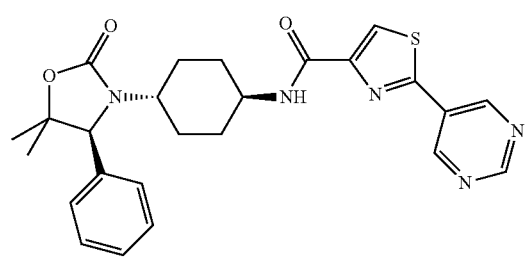 [SMILES: CC1(C)OC(=O)N([C@H]2CC[C@H](NC(=O)c3csc(-c4cncnc4)n3)CC2)[C@H]1c1ccccc1] |
| 185 | N-((1S,4r)-4-((S)-5,5-dimethyl-2-oxo-4-phenyloxazolidin-3-yl)cyclohexyl)-[2,4'-bithiazole]-4-carboxamide | 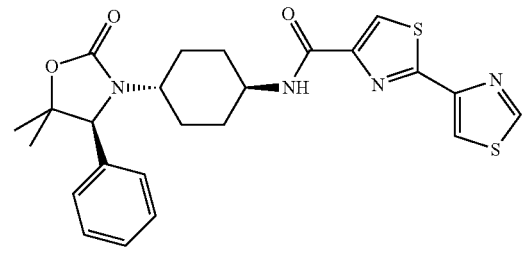 [SMILES: CC1(C)OC(=O)N([C@H]2CC[C@H](NC(=O)c3csc(-c4cscn4)n3)CC2)[C@H]1c1ccccc1] |
| 186 | N-((1S,4r)-4-((S)-5,5-dimethyl-2-oxo-4-phenyloxazolidin-3-yl)cyclohexyl)-2-(6-fluoropyridin-3-yl)thiazole-4-carboxamide | 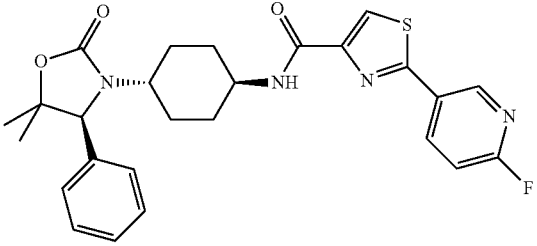 [SMILES: CC1(C)OC(=O)N([C@H]2CC[C@H](NC(=O)c3csc(-c4ccc(F)nc4)n3)CC2)[C@H]1c1ccccc1] |

TABLE 1-continued

Names and Structures of Example Compounds

| Example | Name | Structure |
|---|---|---|
| 187 | N-((1S,4r)-4-((S)-5,5-dimethyl-2-oxo-4-phenyloxazolidin-3-yl)cyclohexyl)-2-(1H-pyrazol-5-yl)thiazole-4-carboxamide | 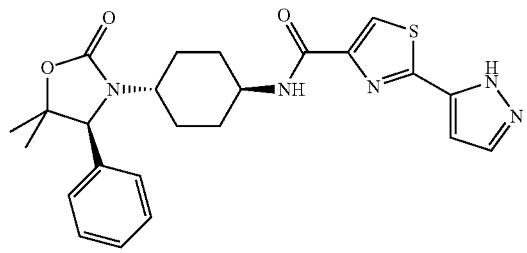 [SMILES: CC1(C)OC(=O)N([C@H]2CC[C@H](NC(=O)c3csc(-c4ccn[nH]4)n3)CC2)[C@H]1c1ccccc1] |
| 188 | N-((1S,4r)-4-((S)-5,5-dimethyl-2-oxo-4-phenyloxazolidin-3-yl)cyclohexyl)-2-(5-fluoropyridin-3-yl)thiazole-4-carboxamide | 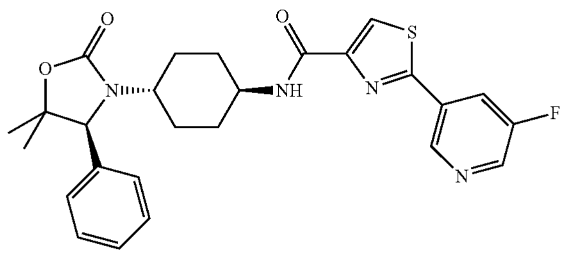 [SMILES: CC1(C)OC(=O)N([C@H]2CC[C@H](NC(=O)c3csc(-c4cncc(F)c4)n3)CC2)[C@H]1c1ccccc1] |
| 189 | N-((1S,4r)-4-((S)-5,5-dimethyl-2-oxo-4-phenyloxazolidin-3-yl)cyclohexyl)-2-(1-methyl-1H-pyrazol-4-yl)thiazole-4-carboxamide | 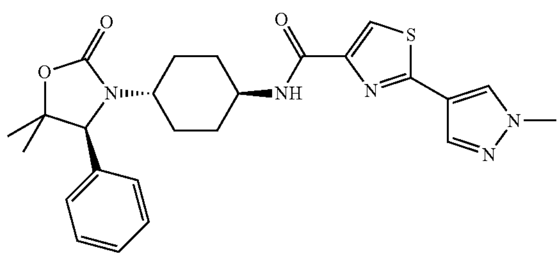 |
| 190 | N-((1S,4r)-4-((S)-5,5-dimethyl-2-oxo-4-phenyloxazolidin-3-yl)cyclohexyl)-2-(pyridin-3-yl)thiazole-4-carboxamide | 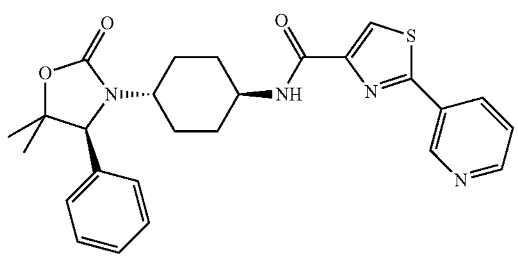 [SMILES: CC1(C)OC(=O)N([C@H]2CC[C@H](NC(=O)c3csc(-c4cccnc4)n3)CC2)[C@H]1c1ccccc1] |

Biological Activity
Axin2 384 Immunofluorescence Protocol

SW480 cells were grown in RPMI 1640 (Invitrogen, 72400-047), 10% HI FBS (Invitrogen, 16140-071), 1× sodium pyruvate (Invitrogen, 11360-070), 750 ug/mL Geneticin® antibiotic (Invitrogen, 10131-027) and 10 µg/mL Blasticidin S antibiotic (Invitrogen, R210-01). On the day of the assay, cells were trypsinized (Invitrogen, 25200-056) to remove cells from flask and media was added. The cells were then centrifuged at 300 RCF for 5 minutes, and the media was removed and replaced with assay media (RPMI 1640 (Invitrogen, 72400-047), 10% HI FBS (Invitrogen, 16140-071), and 1× sodium pyruvate (Invitrogen, 11360-070)). The cells were then counted using a ViCell and plated at 2,500 cells per well in 60 µL of assay media in Perkin Elmer Black 384 ViewPlates (Fisher, 509052489). Compounds (0.5 µL in 100% DMSO) were diluted using a FlexDrop by adding 13.8 µL of assay media to columns 1-22 (resulting in 3.5% DMSO). Control compound was added to column 23 at a concentration of 14 M, and 3.5% DMSO (HI). DMSO in assay media (3.5%) was added to column 24 (LO). Using a VPrep, 10 µL of compound/controls was transferred from the compound plate to 60 µL in the cell plate (final 0.5% DMSO, 70 µL). The mixture was incubated for 24 hours at 37° C. at 5% $CO_2$.

The assay media was aspirated off the cells using a BioTek plate washer, and the cells were then washed with 50 µL of PBS (Invitrogen, 14040-117). The extra media was tapped out. 50 µL of 4% paraformaldehyde (Fisher, AA433689M), 0.1% Triton (Sigma, X100-100 ML) in PBS were added, and the mixture was incubated for 15 minutes at room temperature. The cels were then washed with PBS, 0.1% Tween-20 (BioRad, 1610781), and 1% Normal Goat Serum (Fisher, NC9270494). The extra media was tapped out and to this was added 50 µL of buffer containing Axin2 Antibody (Sigma, SAB1100677-200 UL) at 1:10000 in PBS, 0.1% Tween-20, 1% Normal Goat Serum. The mixture was incubated for 2 hours at room temperature or overnight at 4° C. The cells were then washed twice with PBS, 0.1% Tween-20, and 1% Normal Goat Serum. To the cells was added 50 μL Secondary Alexa 488 Antibody (Invitrogen, A11008) at 0.5 μg/mL and Hoechst (Invitrogen, H3570) at 1 g/mL in PBS, 0.1% Tween-20, and 1% Normal Goat Serum. The mixture was then incubated for 30 minutes at room temperature. The cells were then washed twice with PBS, 0.1% Tween-20, and 1% Normal Goat Serum. 50-100 μL PBS was added, and the mixture was covered with a plate seal (Fisher, NC9425162). An ArrayScan (a variation of the compartmental analysis protocol was optimized) was used to scan the plates, and data was analyzed using MEAN_RingSpotAvgIntenCh2). The Axin2 accumulation POC was calculated, and the EC50 was determined using Genedata Screener software to report Axin2 activity.

Total β-Catenin MSD 96-Well Plate Assay for SW480 Cells

SW480 colorectal cells were seeded at a density of 10,000/well in CellBIND 96-well plates (Corning catalog no. 3300) in 60 μL of normal growth medium (MEM alpha supplemented with 10% heat inactivated FBS, GlutaMAX, pyruvate, and 10 mM HEPES).

A 10-point, 3-fold dilution series for each TNKS inhibitor was constructed in a 96-well "stock" plate. Twenty microliters of each diluted compound was transferred from the "stock" plate into the plate containing the SW-480 cells resulting in a 1:4 dilution of the compounds and resulted in final vehicle (DMSO) concentration of 0.1%. The top concentration of TNKS inhibitors tested was 10 μM. DMSO alone (0.1%) served as the "HI" control and a potent tankyrase inhibitor at a final concentration of 20 M served as the "LO" control for $IC_{50}$ calculations. The plates were incubated at 37° C. for 40 to 48 hours. The media was removed from the CellBIND plate via plate inversion and gentle shaking and the inverted plate was touched to a paper towel and immediately placed on ice. Cell lysis was achieved with 75 μL/well MSD lysis buffer containing following protease and phosphatase inhibitors (Protease inhibitor tablet, Roche catalog no. 11836153001; PhosSTOP phosphatase inhibitor tablet, Roche cat. No. 04906845001; 10 mM NaF) as well as 1 mM EDTA and 1 mM EGTA. Plates containing cell lysates were sealed and shaken for one hour at 4° C. and then quickly frozen in a −80° C. for approximately 15 to 30 minutes followed by gradually thawing at 4° C. Finally, lysate containing plates were centrifuged @1000×g (2073 rpm) for 10 minutes at 4° C.

A goat anti-rabbit MSD plate (catalog no. L41RA-1) was coated with 25 μL of 5 μg/mL of Cell Signaling anti-total β-catenin polyclonal (catalog no. 9562, lyophilized, carrier-free special order) which had been reconstituted with TBS. The sealed MSD plate was incubated overnight in a cold room with gentle shaking. The MSD plate was then blocked with 150 μL of Blocker "A" per well and incubated overnight at 4° C. with vigorous shaking. The blocked MSD plate was washed 4 times with 150 μL/well TBS-T wash buffer (150 mM NaCl, 50 mM Tris, pH 7.5, 0.02% Tween-20). Cell lysates (75 μL) were transferred to prepared MSD plates and incubated at 4° C. ON with gentle shaking. The next day MSD plates were washed 4 times with TBS-T wash buffer and 25 μL/well of detection antibody at a concentration of 1 μg/mL BD Biosciences anti-total β-catenin mAb (catalog no. 610153) conjugated to SULFO-TAG in MSD Antibody Diluent (catalog no. R50AA-2) was added. The detection antibody was incubated for 1 hour at room temperature with vigorous shaking after which plates were washed 3 times with 150 μL/well TBS-T wash buffer. Plates were processed for analysis by the addition of 150 μL/well MSD Read 4× Buffer T with surfactant (catalog no. R92TC-2; diluted 1:3 in deionized water) and were read on the SECTOR Imager 6000.

Colony Formation Assays

Colorectal cell lines grown under normal logarithmic growth conditions in 10% FBS were trypsinized, counted in a Vi-CELL Cell Viability Analyzer and diluted to 400 cells/mL in RPMI media containing 0.5% FBS. Cells were plated in 12 well plates using 0.5 mL of diluted cells for a total of 200 cells/well. Tankyrase inhibitors were diluted in RPMI (0.5% FBS) at 2× final concentration. Ten concentrations of compound were prepared starting at 20 μM and serially diluted by 2 fold and 0.5 mL of diluted compound was added to each well. The final concentration range tested was thus 10 μM down to 20 nM. Two additional wells per plate were treated with the vehicle control (0.1% DMSO). The cells were grown for 12 days with the media and the compounds changed at day 6. Colonies were visualized by fixing and staining with Crystal Violet dye diluted in 1× fixation solution (2% formaldehyde, 0.2%, glutaraldehyde in 1×PBS) for 30 minutes at room temperature. The plates were washed extensively and air dried. Images of plates were captured and the colony counts were performed using the Bioreader® (Biosys) reader.

Tankyrase 1 and 2 Assays

The tankyrase 1 biochemical activity of the compounds was assayed in the following assay buffer (50 mM MOPS pH7.5, 100 mM NaCl, 2.5 mM $MgCl_2$, 0.01% Tween-20, 0.05% BSA, and 1 mM DTT) as follows: 0.25 nM of 6×HIS-tankyrase 1 (1091-1325) was incubated in the presence of compound (DMSO 1.85% final) in a Perkin Elmer 384 well Proxiplate Plus™ (cat. no. 6008289) with 400 nM of NAD for 60 minutes at room temperature. The assay was then stopped with the above assay buffer containing a 0.6 M inhibitor and the following detection components: 0.05 g/mL monoclonal anti-PAR antibody (Trevigen cat. no. 4335-MC-01K-AC) prebound for 60 minutes with 0.63 μg/mL protein G Alpha-Lisa® acceptor bead (Perkin Elmer cat. no. AL102M) and 5 μg/mL AlphaLisa® nickel chelate donor bead (Perkin Elmer cat. no. AS101M). The assay was incubated for 16 hours at room temperature in the dark and read on a Perkin Elmer Envision® multi label reader using the default program set with laser excitation at 680 nM and emission at 615 nM.

The tankyrase 2 biochemical assay was performed using the procedure set forth above with respect to tankyrase 1 except that 4 nM 6×HIS-tankyrase 2 (946-1162) and 250 nM NAD were used.

2H9-STF Assay. Wnt Ligand Activated HEK-293 Assay in WT APC Cellular Context

HEK-293 cells engineered with an 8×TCF promoter-driven Firefly (FF) luciferase gene (Wnt reporter) along with an SV40 promoter-driven Renilla (RN) luciferase gene (control reporter) were used to measure the potency of tankyrase compounds in the context of Wnt ligand activation in a wild-type (non-APC mutated) cellular background. The engineered HEK-293 cells were plated (25 μL) at a density of 40,000 cells/well in black, clear-bottom, 96-well View plates (PerkinElmer) in normal growth medium (DMEM with 10% FBS with no antibiotics). Tankyrase inhibitors (5 μL) were transferred to cells from a three-fold serially diluted compound plate. A 10-point dilution series was tested starting at a concentration (10 μM final concentration in assay). Column 6 contained only DMSO and served as the "HI" control. Cells and compounds were incubated together for 1 hour at 37° C. after which the Wnt3a ligand (pathway inducer) was added to all wells except column 12 which served as the "LO" control. Twenty microliters of diluted recombinant mouse Wnt3a (R & D Systems) was added to the cells for a final concentration of 200 ng/mL (5 nM which is the Wnt3a~EC80) and the plates were incubated at 37° C. for 18 to 24 hours. The Dual-Glo Reagents (Promega) were added as directed by manufacturer to assay the FF and RN luciferase activity. Luciferase activity was measures using the EnVision multilabel plate reader (PerkinElmer).

DLD-1-STF Assay. Constitutively Activated Wnt Pathway Assay in Mutant APC Cancer Cell Context DLD-1 colorectal cells engineered with an 8×TCF promoter-driven Firefly (FF) luciferase gene (Wnt reporter) along with an EF1a promoter-driven Renilla (RN) luciferase gene (control reporter) were used to measure the potency of tankyrase compounds in the context of the constitutively activated Wnt pathway due to mutated APC in colorectal cancer cells. The engineered DLD-1 cells were plated (45 μL) at a density of 10,000 cells/well in black, clear-bottom, 96-well View plates (PerkinElmer) in normal growth medium (RPMI with 10% FBS with no antibiotics). Tankyrase inhibitors (5 μL) were transferred to cells from a three-fold serially diluted compound plate. A 10-point dilution series was tested starting at a concentration (10 μM final concentration in assay). Column 6 contained only DMSO and served as the "HI" control. A potent Tankyrase inhibitor was used at a final concentration of 10 uM in column 12 which served as the "LO" control. The plates were incubated at 37° C. for 40 to 48 hours. The Dual-Glo Reagents (Promega) were added as directed by manufacturer to assay the FF and RN luciferase activity. Luciferase activity was measures using the EnVision multilabel plate reader (PerkinElmer).

The following tables includes biological activity data obtained using the procedures and assays set forth above for the Example compounds described herein.

TABLE 2

Biological Activity Information for Example Compounds in TNKS1, TNKS2, SW480-TBC, and Axin2 384 IF Assays.

| Example | TNKS1 IP $IC_{50}$ (μM) | TNKS2 IP $IC_{50}$ (μM) | SW480-Total β-Catenin $IC_{50}$ IP (μM) | Axin2 384 IF $EC_{50}$ IP (μM) |
|---|---|---|---|---|
| 1 | 0.0183 | 0.011 | 0.189 | 1.01 |
| 2 | 0.307 | — | 1.96 | 5.48 |
| 3 | 0.378 | — | 1.75 | >25.0 |
| 4 | 0.0769 | 0.0659 | 0.75 | 2.84 |
| 5 | 0.0241 | — | 0.447 | 0.816 |
| 6 | 0.0468 | — | 0.585 | 2.66 |
| 7 | 0.0318 | — | 0.695 | 1.46 |
| 8 | 12.8 | — | >10.0 | >25.0 |
| 9 | 1.16 | — | 2.48 | — |
| 10 | 4.45 | — | — | >25.0 |
| 11 | 0.392 | — | 1.52 | 7.06 |
| 12 | 0.0521 | 0.0493 | 0.212 | — |
| 13 | 2.06 | — | >10.0 | >25.0 |
| 14 | 0.0268 | — | 0.923 | 1.03 |
| 15 | 0.105 | — | 0.992 | 4.15 |
| 16 | 0.114 | — | 2.54 | 8.19 |
| 17 | 2.82 | — | >10.0 | >25.0 |
| 18 | 0.973 | — | >10.0 | >25.0 |
| 19 | 0.863 | — | 8.63 | — |
| 20 | 1.48 | — | 5.33 | — |
| 21 | 1.34 | — | — | — |
| 22 | 1.43 | — | >10.0 | >25.0 |
| 23 | 0.00304 | — | 0.143 | 0.231 |
| 24 | 0.249 | — | 1.48 | 4.64 |
| 25 | 0.00456 | 0.00546 | 0.0463 | 0.231 |
| 26 | 0.0103 | 0.00478 | 0.148 | 0.562 |
| 27 | 0.022 | 0.0201 | — | 1.15 |
| 28 | 0.323 | 0.185 | 0.423 | 5.78 |
| 29 | 0.00533 | 0.00498 | 0.536 | 2.56 |
| 30 | 0.0107 | — | 1.12 | 1.98 |
| 31 | 0.371 | — | 2.66 | 17.5 |
| 32 | 0.0168 | 0.0109 | 0.33 | 0.637 |
| 33 | 5.2 | — | — | >25.0 |
| 34 | 0.0428 | — | 0.829 | 2.72 |
| 35 | 0.0118 | — | 1.33 | 6.69 |
| 36 | 0.0201 | — | 1.24 | 4.4 |
| 37 | 0.0118 | — | 0.517 | 3.58 |
| 38 | 0.47 | — | 4.74 | — |
| 39 | 0.457 | — | 6.75 | — |
| 40 | 0.621 | — | 9.47 | >25.0 |
| 41 | 0.116 | — | 1.98 | 4.37 |
| 42 | 0.263 | — | 4.87 | 9.4 |
| 43 | 0.786 | — | >10.0 | >25.0 |
| 44 | 0.822 | — | 8.8 | >25.0 |
| 45 | 1.25 | — | >10.0 | >25.0 |
| 46 | 5.17 | — | — | >25.0 |
| 47 | 0.00112 | — | 0.0537 | 0.0729 |
| 48 | 0.617 | — | >10.0 | >25.0 |
| 49 | 3.46 | — | 0.949 | >25.0 |
| 50 | 0.00511 | — | 0.292 | 0.391 |
| 51 | 0.00356 | — | 0.274 | 0.454 |
| 52 | 0.0258 | — | 0.693 | 1.03 |
| 53 | 0.00652 | — | 0.284 | 0.291 |
| 54 | 0.00742 | — | 0.605 | 0.725 |
| 55 | 0.00295 | — | 0.145 | 0.1 |
| 56 | 0.00148 | — | 0.651 | 0.676 |
| 57 | 0.143 | — | 0.172 | 0.795 |
| 58 | 0.00746 | — | 0.979 | 0.828 |
| 59 | 0.00386 | — | 0.18 | 0.19 |
| 60 | 0.00109 | — | 0.0754 | 0.0614 |
| 61 | 0.00342 | — | 0.148 | 0.238 |
| 62 | 0.00763 | — | 0.438 | 0.147 |
| 63 | 7.05 | — | >10.0 | >25.0 |
| 64 | 0.085 | 0.0483 | 0.293 | 3.23 |
| 65 | 0.049 | 0.0259 | 0.233 | 1.44 |
| 66 | 1.97 | — | 9.27 | >25.0 |
| 67 | 5.23 | — | >10.0 | >25.0 |
| 68 | 1.98 | — | >10.0 | >25.0 |
| 69 | 2.1 | — | >10.0 | >25.0 |
| 70 | 1.49 | — | >10.0 | >25.0 |
| 71 | 0.503 | — | — | >25.0 |
| 72 | 0.37 | — | 6.55 | 5.81 |
| 73 | 0.0083 | — | 0.0952 | 0.202 |
| 74 | 0.00147 | — | 0.0908 | 0.0519 |
| 75 | 0.174 | — | 1.58 | 2.68 |
| 76 | 9.84 | — | >10.0 | >25.0 |
| 77 | 1.65 | — | >10.0 | >25.0 |
| 78 | 0.198 | 0.189 | 2.09 | 10.5 |
| 79 | 6.85 | — | >10.0 | >25.0 |
| 80 | 3.08 | — | 1.36 | >12.5, >25.0 |
| 81 | 0.0114 | — | 0.767 | 0.84 |
| 82 | 0.195 | — | 1.34 | 7.13 |
| 83 | 0.00407 | — | — | — |
| 84 | 0.473 | — | 4.94 | 7.6 |
| 85 | 0.0452 | — | 2.41 | — |
| 86 | 0.0322 | — | >10.0 | 1.66 |
| 87 | 0.00691 | — | — | — |
| 88 | 0.0118 | — | 0.473 | 0.285 |
| 89 | 0.0172 | — | 3.44 | 7.03 |
| 90 | 0.772 | — | >10.0 | >25.0 |
| 91 | 0.00901 | — | 3.61 | 4.43 |
| 92 | 0.0049 | — | 0.177 | 0.183 |
| 93 | 0.003 | — | 0.125 | — |
| 94 | 0.27 | — | 3.01 | — |
| 95 | 0.00698 | — | 0.468 | 0.474 |
| 96 | 0.511 | — | >10.0 | >25.0 |
| 97 | 0.267 | — | 4.43 | >25.0 |
| 98 | 0.000316 | — | 0.0482 | 0.0357 |
| 99 | 0.0143 | — | 0.62 | — |
| 100 | 0.22 | — | 3.38 | — |
| 101 | 0.0162 | — | 0.21 | 0.197 |
| 102 | 0.92 | — | >10.0 | — |
| 103 | 0.00348 | — | 0.0672 | 0.116 |
| 104 | 0.093 | — | >10.0 | — |

TABLE 2-continued

Biological Activity Information for Example Compounds in TNKS1, TNKS2, SW480-TBC, and Axin2 384 IF Assays.

| Example | TNKS1 IP IC$_{50}$ (μM) | TNKS2 IP IC$_{50}$ (μM) | SW480-Total β-Catenin IC$_{50}$ IP (μM) | Axin2 384 IF EC$_{50}$ IP (μM) |
|---|---|---|---|---|
| 105 | 0.152 | — | 3.25 | 8.93 |
| 106 | 1.88 | — | 6.65 | >25.0 |
| 107 | 0.0899 | — | 2.36 | — |
| 108 | 0.551 | — | >10.0 | — |
| 109 | 5.53 | — | — | >25.0 |
| 110 | 0.193 | — | 1.69 | 2.7 |
| 111 | 0.631 | — | 2.44 | 7.26 |
| 112 | 2.75 | — | — | >25.0 |
| 113 | 0.13 | — | 2.11 | 5.22 |
| 114 | 0.447 | — | 1.78 | — |
| 115 | 0.0953 | — | 1.01 | 4.38 |
| 116 | 0.167 | — | 0.906 | >6.25 |
| 117 | 0.193 | — | 1.05 | 5.74 |
| 118 | 0.15 | — | >10.0 | >25.0 |
| 119 | 1.35 | — | >10.0 | >25.0 |
| 120 | 0.0758 | — | 2.36 | 0.825 |
| 121 | 0.31 | — | 5.64 | — |
| 122 | 1.53 | — | 8.56 | — |
| 123 | 0.228 | — | 3.44 | — |
| 124 | 0.767 | — | 1.5 | — |
| 125 | 7.91 | — | — | >25.0 |
| 126 | 0.272 | — | 0.761 | 4.62 |
| 127 | 0.28 | — | 1.1 | 6.27 |
| 128 | 0.693 | — | 4.35 | — |
| 129 | 1.83 | — | >10.0 | >25.0 |
| 130 | 0.783 | — | >10.0 | >25.0 |
| 131 | 0.016 | — | 0.362 | 1.03 |
| 132 | Undefined | — | — | — |
| 133 | 1.38 | — | — | — |
| 134 | >46.3 | — | — | — |
| 135 | 1.38 | — | — | — |
| 136 | 0.00517 | — | — | — |
| 137 | 0.218 | — | — | — |
| 138 | 1.25 | — | — | — |
| 139 | 0.0115 | — | — | — |
| 140 | 0.0243 | — | 1.83 | — |
| 141 | 0.755 | — | — | — |
| 142 | 0.205 | — | — | — |
| 143 | 0.225 | — | — | — |
| 144 | 0.222 | — | — | — |
| 145 | 0.0137 | — | — | — |
| 146 | 0.00918 | — | — | — |
| 147 | 0.0264 | — | — | — |
| 148 | 0.0114 | — | — | — |
| 149 | 0.034 | — | — | — |
| 150 | 1.54 | — | — | — |
| 151 | 16.6 | — | — | — |
| 152 | 0.228 | — | — | — |
| 153 | 0.848 | — | — | — |
| 154 | 2.32 | — | — | — |
| 155 | 0.548 | — | — | — |
| 156 | 0.00518 | — | — | — |
| 157 | 0.0768 | — | — | — |
| 158 | 0.142 | — | — | — |
| 159 | 1.56 | — | — | — |
| 160 | 1.46 | — | — | — |
| 161 | 0.35 | — | — | — |
| 162 | 0.101 | — | — | — |
| 163 | 0.22 | — | — | — |
| 164 | 0.0519 | — | — | — |
| 165 | 0.26 | — | — | — |
| 166 | >46.3 | — | — | — |
| 167 | >46.3 | — | — | — |
| 168 | >46.3 | — | — | — |
| 169 | 0.0886 | — | 3.18 | — |
| 170 | — | — | — | — |
| 171 | 0.019 | — | — | — |
| 172 | 1.25 | — | — | — |
| 173 | 0.00926 | — | 1.12 | — |
| 174 | 0.00101 | — | — | — |
| 175 | 1.47 | — | — | — |
| 176 | 3.13 | — | — | — |
| 177 | 1.02 | — | — | — |
| 178 | 0.000375 | — | — | — |
| 179 | 0.129 | — | — | — |
| 180 | 0.915 | — | — | — |
| 181 | 0.714 | — | — | — |
| 182 | 0.0321 | — | — | — |
| 183 | 0.00394 | — | — | — |
| 184 | — | — | — | — |
| 185 | — | — | — | — |
| 186 | — | — | — | — |
| 187 | — | — | — | — |
| 188 | — | — | — | — |
| 189 | — | — | — | — |
| 190 | — | — | — | — |

TABLE 3

Biological Activity Information for Example Compounds in 2H9-Wnt3a-STF-FF/RL * 100, DLD1-STF-FF/RL * 100, and Colony Formation Inhibition Assays.

| Example | 2H9-Wnt3a-STF-FF/RL * 100 IC$_{50}$ (μM) | DLD1-STF-FF/RL * 100 IC$_{50}$ (μM) | SW480 Colony Inhibition IC$_{50}$ (μM) |
|---|---|---|---|
| 4 | 0.29 | — | — |
| 23 | — | 0.044 | — |
| 26 | 0.055 | — | 1.3 |
| 28 | 0.113 | — | — |
| 32 | 0.0928 | — | — |
| 35 | 0.543 | — | — |
| 37 | 0.183 | — | — |
| 47 | — | 0.012 | — |
| 65 | 0.0959 | 0.107 | 1.3 |
| 78 | 1.26 | — | — |

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound of Formula I:

or a pharmaceutically acceptable salt thereof, a tautomer thereof, a pharmaceutically acceptable salt of the tautomer, a stereoisomer of any of the foregoing, or a mixture thereof, wherein:

$R^1$ and $R^2$ are $(C_1-C_6)$alkyl;

$R^3$ is —H;

W is selected from pyridyl, phenyl, or phenyl substituted with 1, 2, or 3 substituents independently selected from —F, —Cl, —Br, —I, —C≡N, —NO$_2$, —OH, —O—$(C_1-C_6)$alkyl, —OCF$_3$, —CF$_3$, —$(C_1-C_6)$alkyl, —NH$_2$, —NH$((C_1-C_4)$alkyl), —N$((C_1-C_4)$alkyl)$_2$, —NHSO$_2$—$(C_1-C_6)$alkyl, —NHC(=O)—$(C_1-C_6)$alkyl, —C(=O)NH$_2$, —C(=O)NH$((C_1-C_6)$alkyl), —C(=O)N$((C_1-C_6)$alkyl)$_2$, —C(=O)—$(C_1-C_6)$alkyl, —CO$_2$H, —C(=O)—O—$(C_1-C_6)$alkyl, —SO$_2$NH$_2$, —SO$_2$N$((C_1-C_6)$alkyl), —SO$_2$N$((C_1-C_6)$alkyl)$_2$, —SO$_2$—$(C_1-C_6)$alkyl, or —SO—$(C_1-C_6)$alkyl;

X is O;

Y is selected from unsubstituted $(C_4-C_7)$cycloalkyl, substituted $(C_4-C_7)$cycloalkyl, unsubstituted $(C_4-C_7)$cycloalkenyl, substituted $(C_4-C_7)$cycloalkenyl, unsubstituted $(C_6-C_{10})$aryl, substituted $(C_6-C_{10})$aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 4 to 10 membered heterocyclyl comprising 1, 2, or 3 heteroatoms independently selected from O, S, or N, or substituted 4 to 10 membered heterocyclyl comprising 1, 2, or 3 heteroatoms independently selected from O, S, or N, wherein the substituted $(C_4-C_7)$cycloalkyl and substituted $(C_4-C_7)$cycloalkenyl are substituted with 1 or 2 substituents independently selected from —F, —Cl, —Br, —I, —C≡N, —NO$_2$, —OH, —O—$(C_1-C_6)$alkyl, —OCF$_3$, —OCHF$_2$, —CF$_3$, —$(C_1-C_6)$alkyl, —NH$_2$, —NH$((C_1-C_4)$alkyl), —N$((C_1-C_4)$alkyl)$_2$, —C(=O)NH$_2$, —C(=O)NH$((C_1-C_6)$alkyl), —C(=O)N$((C_1-C_6)$alkyl)$_2$, —C(=O)—$(C_1-C_6)$alkyl, —CO$_2$H, or —C(=O)—O—$(C_1-C_6)$alkyl, and wherein the substituted $(C_6-C_{10})$aryl, substituted 5 to 10 membered heteroaryl, and substituted 4 to 10 membered heterocyclyl are substituted with 1, 2, or 3 substituents independently selected from —F, —Cl, —Br, —I, —C≡N, —NO$_2$, —OH, —O—$(C_1-C_6)$alkyl, —OCF$_3$, —OCHF$_2$, —CF$_3$, —$(C_1-C_6)$alkyl, —NH$_2$, —NH$((C_1-C_4)$alkyl), —N$((C_1-C_4)$alkyl)$_2$, —C(=O)NH$_2$, —C(=O)NH$((C_1-C_6)$alkyl), —C(=O)N$((C_1-C_6)$alkyl)$_2$, —C(=O)—$(C_1-C_6)$alkyl, —CO$_2$H, or —C(=O)—O—$(C_1-C_6)$alkyl, and further wherein the substituted 4 to 10 membered heterocyclyl may also be substituted with a =O;

Z is selected from unsubstituted $(C_6-C_{10})$aryl, substituted $(C_6-C_{10})$aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 5 to 10 membered heterocyclyl comprising 1, 2, 3 or 4 heteroatoms independently selected from O, S, or N, or substituted 5 to 10 membered heterocyclyl comprising 1, 2, 3, or 4 heteroatoms independently selected from O, S, or N, or Z is selected from —NR$^b$—Z', —NR$^c$—C(=O)—Z', or —C(=O)—NR$^d$—Z', wherein the substituted $(C_6-C_{10})$aryl, substituted 5 to 10 membered heteroaryl, and the substituted 5 to 10 membered heterocyclyl are substituted with 1, 2, or 3 Q substituents and may additionally be substituted with 0 or 1 of Z' or —NR$^e$—Z', and further wherein the substituted 5 to 10 membered heterocyclyl may also be substituted with a =O;

each Q is independently selected from —F, —Cl, —Br, —I, —C≡N, —NO$_2$, —OH, —O—$(C_1-C_6)$alkyl, —SH, —S—$(C_1-C_6)$alkyl, —OCF$_3$, —OCHF$_2$, —CH$_2$CHF$_2$, —CF$_3$, —$(C_1-C_6)$alkyl, —NH$_2$, —NH$((C_1-C_4)$alkyl), —N$((C_1-C_4)$alkyl)$_2$, —NHSO$_2$—$(C_1-C_6)$alkyl, —NHC(=O)—$(C_1-C_6)$alkyl, —C(=O)NH$_2$, —C(=O)NH$((C_1-C_6)$alkyl), —C(=O)N$((C_1-C_6)$alkyl)$_2$, —C(=O)NH—OH, —C(=O)NH—O—$(C_1-C_6)$alkyl, —C(=O)—$(C_1-C_6)$alkyl, —CO$_2$H, —C(=O)—O—$(C_1-C_6)$alkyl, —SO$_2$NH$_2$, —SO$_2$NH$((C_1-C_6)$alkyl), —SO$_2$N$((C_1-C_6)$alkyl)$_2$, —SO$_2$—$(C_1-C_6)$alkyl, —SO—$(C_1-C_6)$alkyl, —$(C_1-C_4)$alkylene-OH, —$(C_1-C_4)$alkylene-O—$(C_1-C_6)$alkyl, unsubstituted $(C_3-C_7)$cycloalkyl, unsubstituted 5 to 10 membered heterocyclyl comprising 1, 2, 3, or 4 heteroatoms independently selected from O, S, or N, or unsubstituted 3 or 4 membered heterocyclyl comprising 1 heteroatom selected from O, S, or N;

$R^b$ is selected from —H or $(C_1-C_6)$alkyl;

$R^c$ is selected from —H or $(C_1-C_6)$alkyl;

$R^d$ is selected from —H or $(C_1-C_6)$alkyl;

$R^e$ is selected from —H or $(C_1-C_6)$alkyl;

Z' is selected from unsubstituted $(C_6-C_{10})$ aryl, substituted $(C_6-C_{10})$ aryl, unsubstituted 5 to 10 membered heteroaryl comprising 1, 2, 3, or 4 heteroatoms independently selected from O, S, or N, substituted 5 to 10 membered heteroaryl comprising 1, 2, 3, or 4 heteroatoms independently selected from O, S, or N, unsubstituted 5 to 10 membered heterocyclyl comprising 1, 2, 3 or 4 heteroatoms independently selected from O, S, or N, substituted 5 to 10 membered heterocyclyl comprising 1, 2, 3, or 4 heteroatoms independently selected from O, S, or N, unsubstituted 3 or 4 membered heterocyclyl comprising 1 heteroatom selected from O, S, or N, substituted 3 or 4 membered heterocyclyl comprising 1 heteroatom selected from O, S, or N, or unsubstituted $(C_3-C_7)$cycloalkyl, wherein, the substituted $(C_6-C_{10})$ aryl, the substituted 5 to 10 membered heteroaryl, the substituted 5 to 10 membered heterocyclyl, and the 3 or 4 membered heterocyclyl are substituted with 1, 2, or 3 substituents independently selected from —F, —Cl, —Br, —I, —C≡N, —NO$_2$, —C(=NH)—NH$_2$, —OH, —O—$(C_1-C_6)$alkyl, —SH, —S—$(C_1-C_6)$alkyl, —OCF$_3$, —OCHF$_2$, —CH$_2$CHF$_2$, —CF$_3$, —$(C_1-C_6)$alkyl, —NH$_2$, —NH$((C_1-C_4)$alkyl), —N$((C_1-C_4)$alkyl)$_2$, —NHSO$_2$—$(C_1-C_6)$alkyl, —NHC(=O)—$(C_1-C_6)$alkyl, —C(=O)NH$_2$, —C(=O)NH$((C_1-C_6)$alkyl), —C(=O)N$((C_1-C_6)$alkyl)$_2$, —C(=O)NH—OH, —C(=O)NH—O—$(C_1-C_6)$alkyl, —C(=O)—$(C_1-C_6)$alkyl, —CO$_2$H, —C(=O)—O—$(C_1-C_6)$alkyl, —SO$_2$NH$_2$, —SO$_2$NH$((C_1-C_6)$alkyl), —SO$_2$N$((C_1-C_6)$alkyl)$_2$, —SO$_2$—$(C_1-C_6)$alkyl, —SO—$(C_1-C_6)$alkyl, —$(C_1-C_4)$alkylene-OH, or —$(C_1-C_4)$alkylene-O—$(C_1-C_6)$alkyl, and further wherein the substituted 5 to 10 membered heterocyclyl and the 3 or 4 membered heterocyclyl may also be substituted with a =O.

2. The compound of claim 1, wherein $R^1$ and $R^2$ are independently selected from —CH$_3$ or —CH$_2$CH$_3$, or the pharmaceutically acceptable salt thereof, the tautomer thereof, the pharmaceutically acceptable salt of the tautomer, the stereoisomer of any of the foregoing, or the mixture thereof.

3. The compound of claim 1, wherein $R^1$ and $R^2$ are both —CH$_3$, or the pharmaceutically acceptable salt thereof, the tautomer thereof, the pharmaceutically acceptable salt of the tautomer, the stereoisomer of any of the foregoing, or the mixture thereof.

4. The compound of claim 1, wherein Y is selected from cyclohexyl, cyclohexenyl, phenyl, tolyl, pyridyl, [1,2,4]triazolo[4,3-a]pyridinyl, or 3,4-dihydroisoquinolin-1(2H)-onyl, or the pharmaceutically acceptable salt thereof, the tautomer thereof, the pharmaceutically acceptable salt of the tautomer, the stereoisomer of any of the foregoing, or the mixture thereof.

5. The compound of claim 4, wherein Y is cyclohexyl, or the pharmaceutically acceptable salt thereof, the tautomer thereof, the pharmaceutically acceptable salt of the tautomer, the stereoisomer of any of the foregoing, or the mixture thereof.

6. The compound of claim 1, wherein —Y—Z is selected from

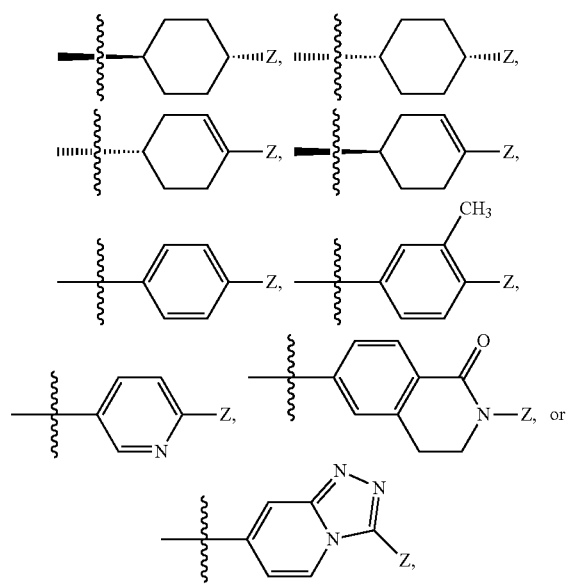

or the pharmaceutically acceptable salt thereof, the tautomer thereof, the pharmaceutically acceptable salt of the tautomer, the stereoisomer of any of the foregoing, or the mixture thereof, wherein the symbol ∼∼, when drawn across a bond, indicates the point of attachment to the rest of the molecule.

7. The compound of claim 1, wherein —Y—Z is selected from

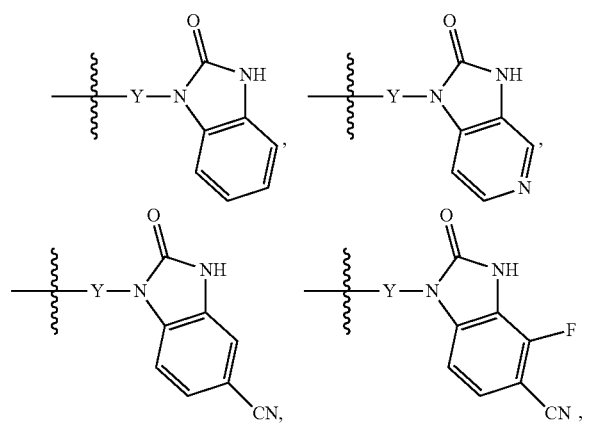

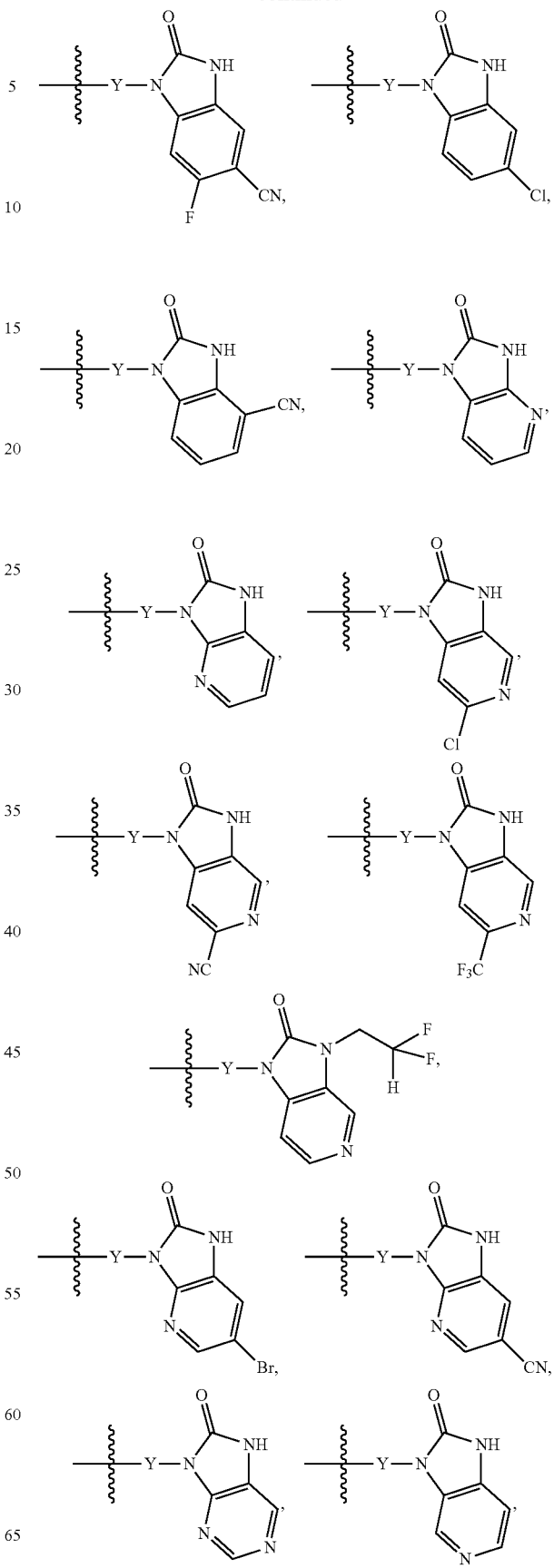

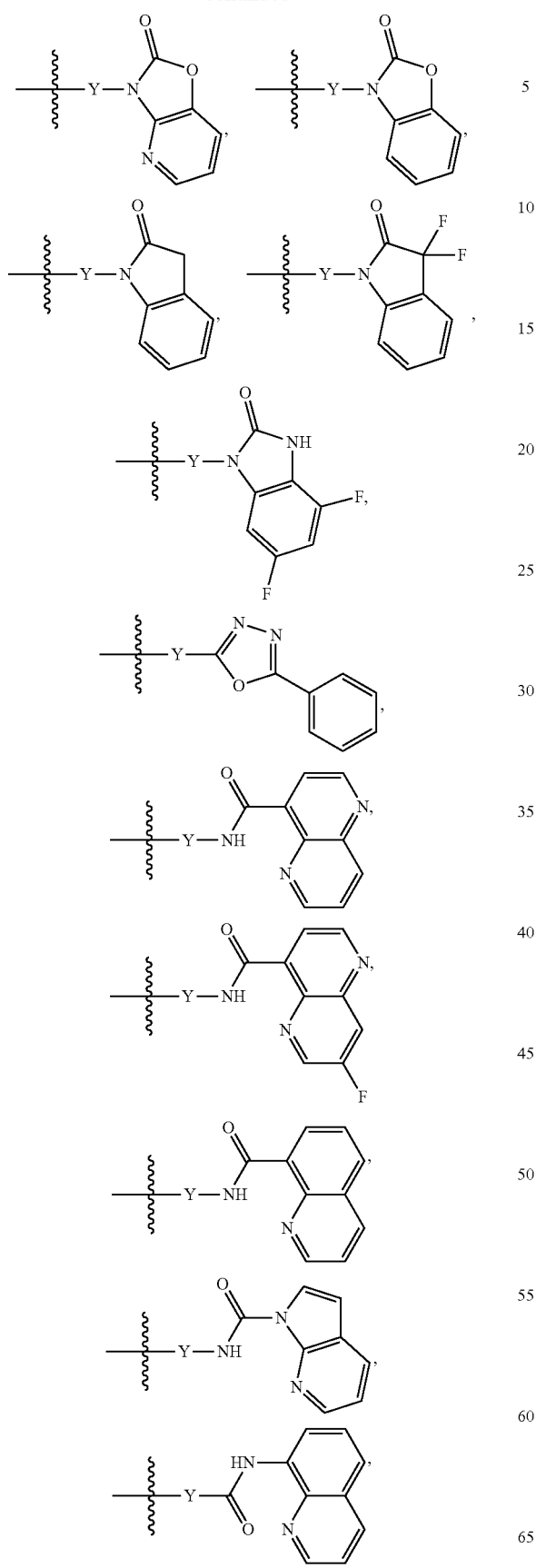
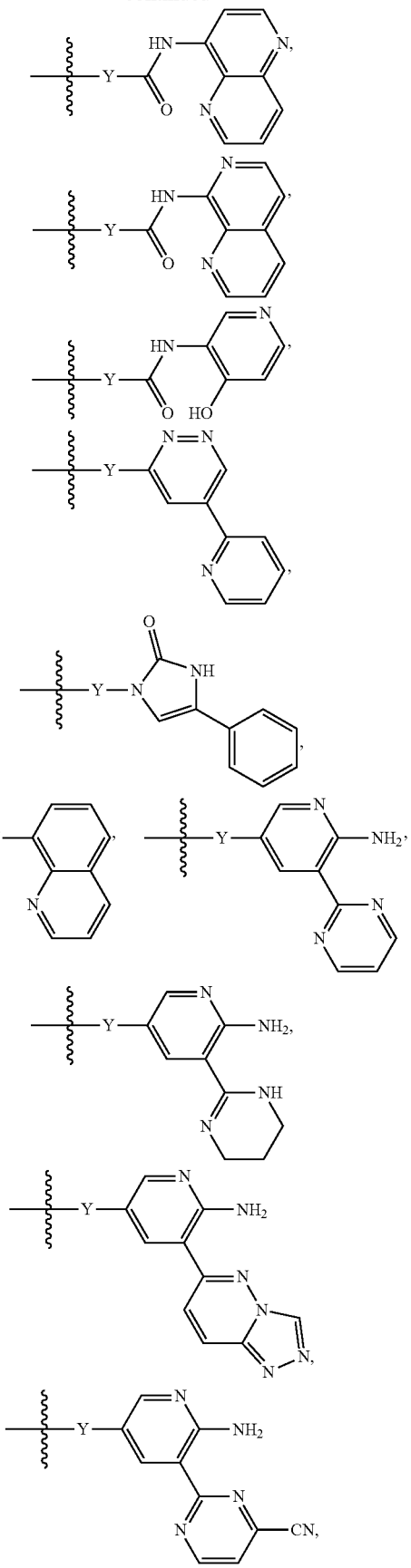

409
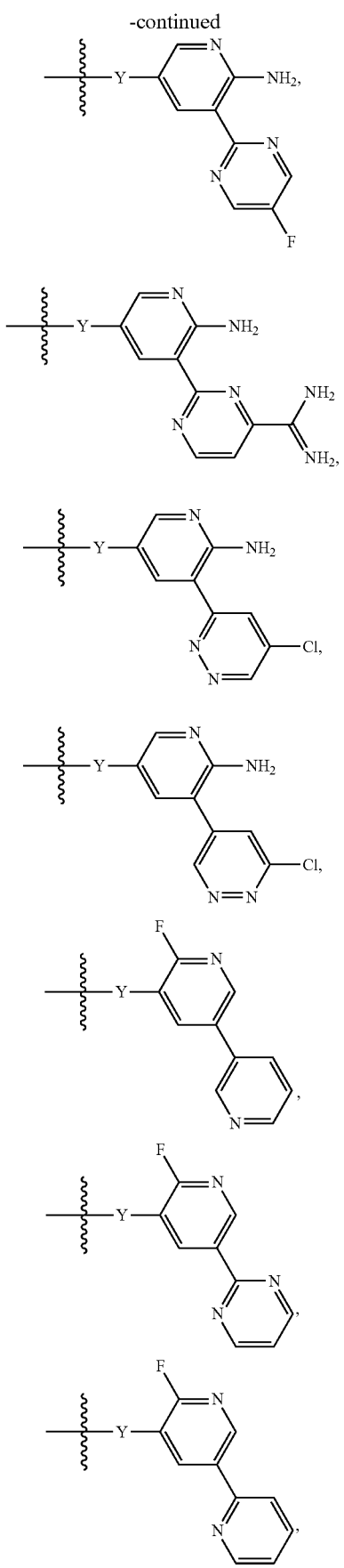
410
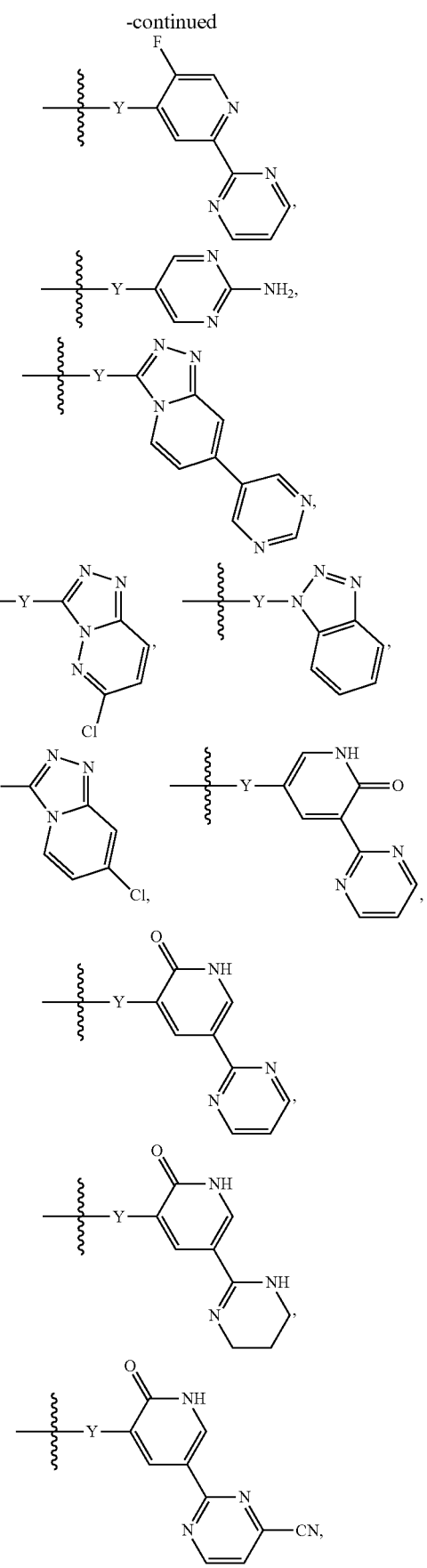

411
-continued
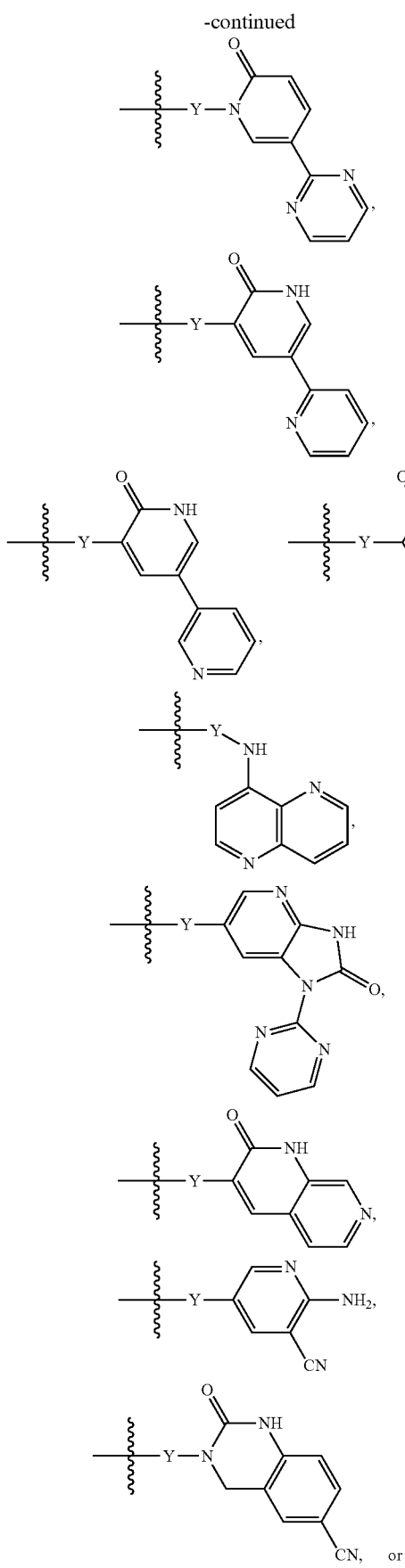
or,
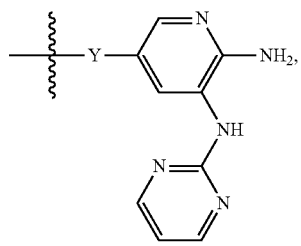
or the pharmaceutically acceptable salt thereof, the tautomer thereof, the pharmaceutically acceptable salt of the tautomer, the stereoisomer of any of the foregoing, or the mixture thereof, wherein the symbol ⌇, when drawn across a bond, indicates the point of attachment to the rest of the molecule.
8. The compound of claim 1, wherein —Y—Z is selected from
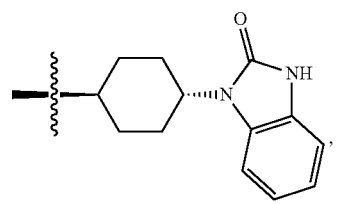
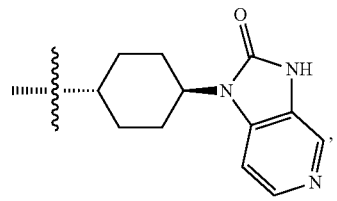
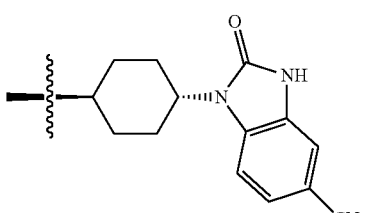
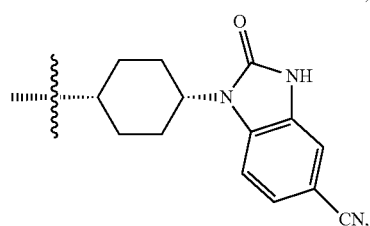
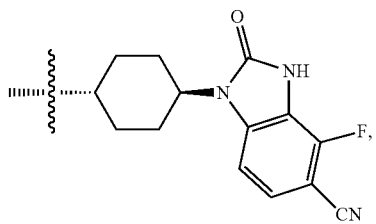

413
-continued
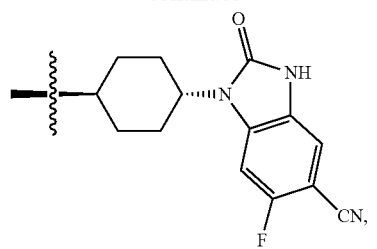
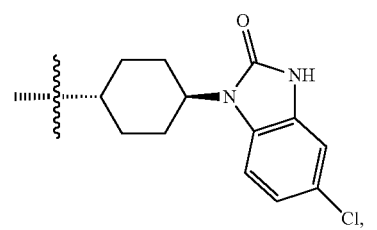
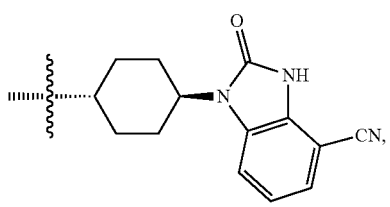
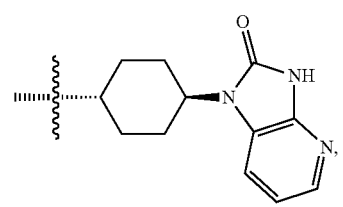
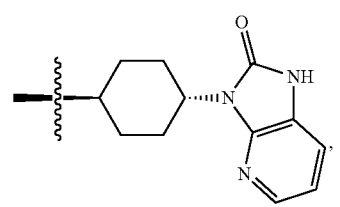
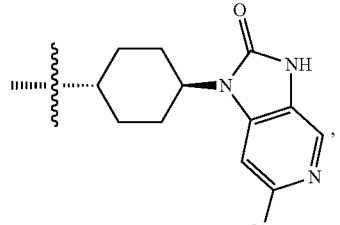
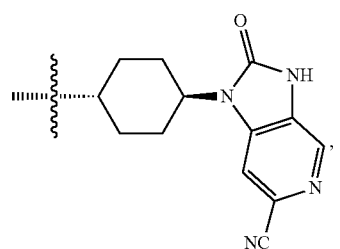
414
-continued
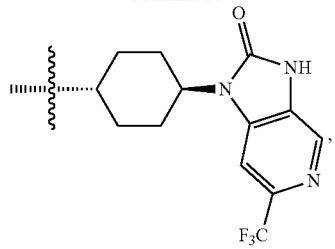
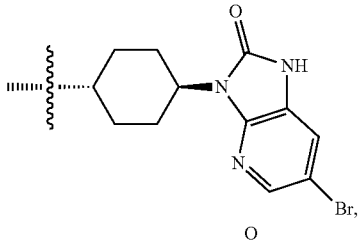
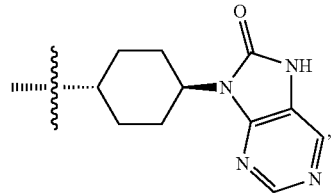
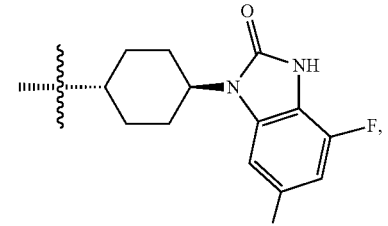
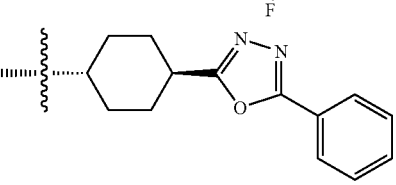
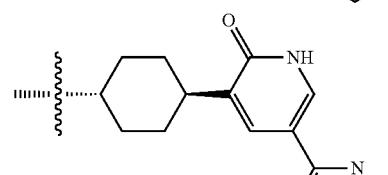
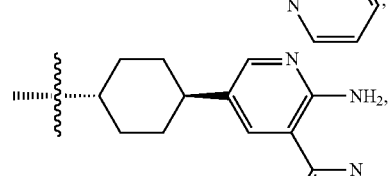
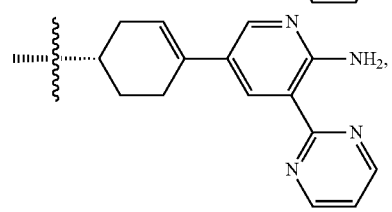

415
-continued
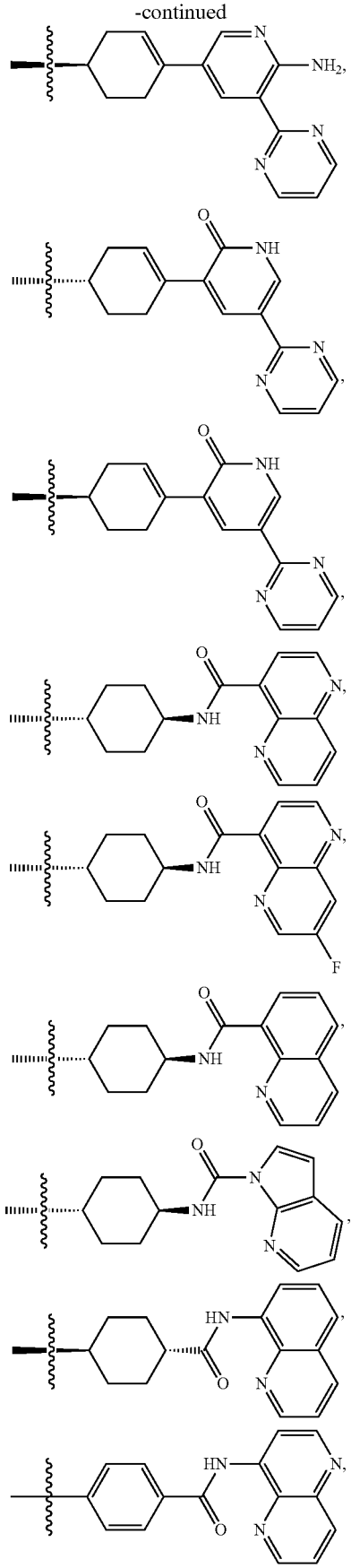
416
-continued
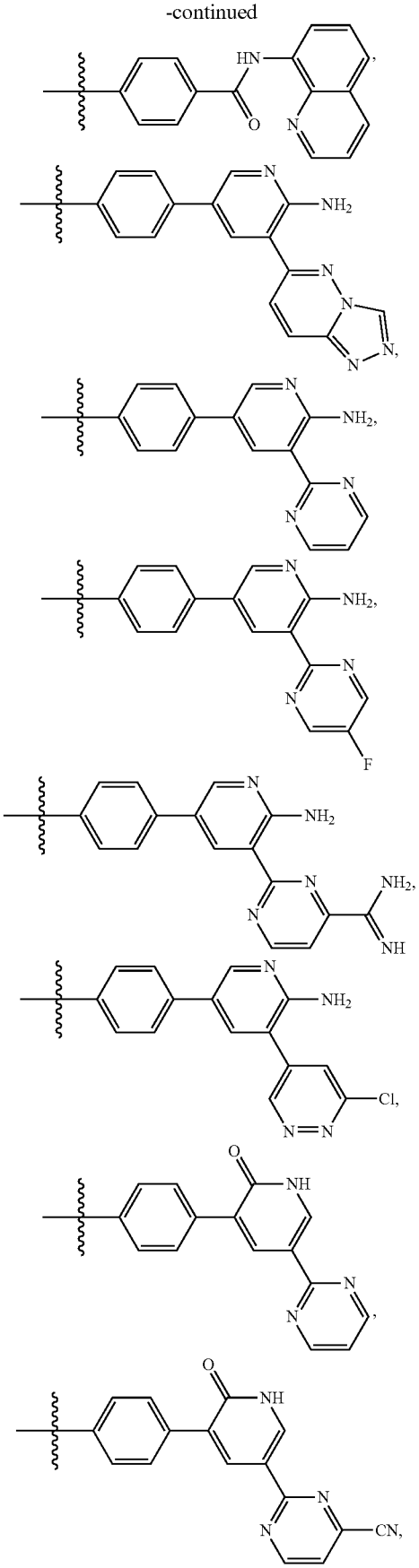

417
-continued

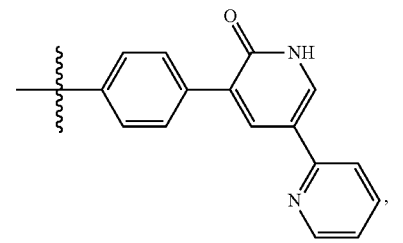

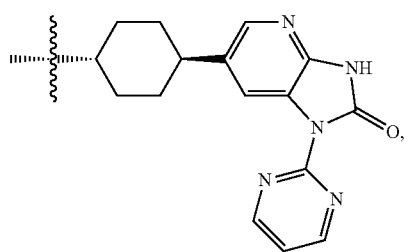

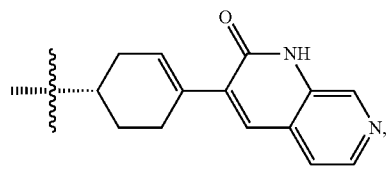

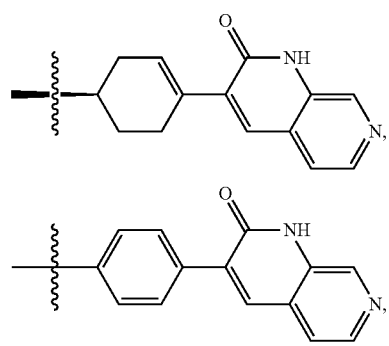

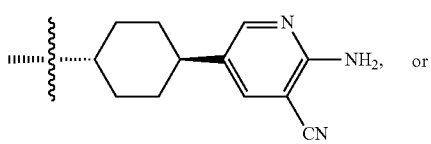 or

418
-continued

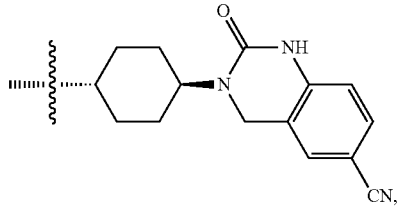

or the pharmaceutically acceptable salt thereof, the tautomer thereof, the pharmaceutically acceptable salt of the tautomer, the stereoisomer of any of the foregoing, or the mixture thereof, wherein the symbol ⌇, when drawn across a bond, indicates the point of attachment to the rest of the molecule.

9. The compound of claim 1, wherein W is selected from

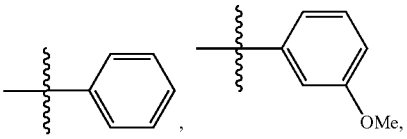

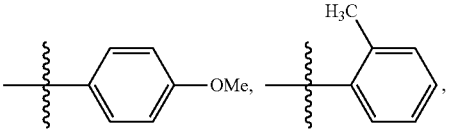

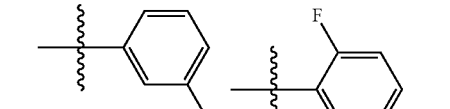

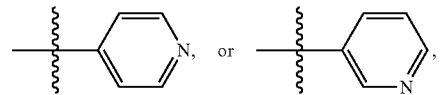

or the pharmaceutically acceptable salt thereof, the tautomer thereof, the pharmaceutically acceptable salt of the tautomer, the stereoisomer of any of the foregoing, or the mixture thereof, wherein the symbol ⌇, when drawn across a bond, indicates the point of attachment to the rest of the molecule.

10. A pharmaceutical composition, comprising the compound or the pharmaceutically acceptable salt thereof, the tautomer thereof, the pharmaceutically acceptable salt of the tautomer, the stereoisomer of any of the foregoing, or the mixture thereof according to claim 1 and at least one pharmaceutically acceptable excipient, carrier, or diluent.

* * * * *